United States Patent
Corkey et al.

(10) Patent No.: US 9,676,760 B2
(45) Date of Patent: *Jun. 13, 2017

(54) FUSED HETEROCYCLIC COMPOUNDS AS ION CHANNEL MODULATORS

(71) Applicant: Gilead Sciences, Inc., Foster City, CA (US)

(72) Inventors: Britton Kenneth Corkey, Redwood City, CA (US); Elfatih Elzein, Fremont, CA (US); Michael Graupe, Pacifica, CA (US); Juan Guerrero, Concord, CA (US); Robert H. Jiang, Cupertino, CA (US); Rao V. Kalla, Cupertino, CA (US); Dmitry Koltun, Foster City, CA (US); Xiaofen Li, Mountain View, CA (US); Ruben Martinez, San Diego, CA (US); Eric Q. Parkhill, San Francisco, CA (US); Thao Perry, San Jose, CA (US); Chandrasekar Venkataramani, Redwood City, CA (US); Jeff Zablocki, Los Altos, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/152,231

(22) Filed: May 11, 2016

(65) Prior Publication Data

US 2016/0347744 A1    Dec. 1, 2016

Related U.S. Application Data

(63) Continuation of application No. 14/872,787, filed on Oct. 1, 2015, which is a continuation of application
(Continued)

(51) Int. Cl.
| | |
|---|---|
| *C07D 413/06* | (2006.01) |
| *A61K 31/553* | (2006.01) |
| *A61K 31/5513* | (2006.01) |
| *C07D 267/08* | (2006.01) |
| *C07D 243/24* | (2006.01) |
| *C07D 267/14* | (2006.01) |
| *C07D 291/08* | (2006.01) |
| *C07D 403/06* | (2006.01) |
| *C07D 413/12* | (2006.01) |

(Continued)

(52) U.S. Cl.
CPC .......... *C07D 413/06* (2013.01); *A61K 31/553* (2013.01); *A61K 31/5513* (2013.01); *C07B 59/002* (2013.01); *C07D 243/14* (2013.01); *C07D 243/24* (2013.01); *C07D 267/08* (2013.01); *C07D 267/14* (2013.01); *C07D 291/08* (2013.01); *C07D 403/06* (2013.01); *C07D 413/04* (2013.01); *C07D 413/12* (2013.01); *C07D 413/14* (2013.01); *C07D 417/14* (2013.01); *C07D 419/06* (2013.01); *C07D 471/04* (2013.01); *C07D 487/04* (2013.01); *C07D 498/04* (2013.01); *C07B 2200/05* (2013.01)

(58) Field of Classification Search
None
See application file for complete search history.

(56) References Cited

U.S. PATENT DOCUMENTS

| 2,826,575 A | 3/1958 | Rigterink |
| 2,867,618 A | 1/1959 | Rigterink |

(Continued)

FOREIGN PATENT DOCUMENTS

| CA | 2068255 | 11/1992 |
| CN | 1735605 | 2/2006 |

(Continued)

OTHER PUBLICATIONS

Abate et al., "Effects of bretylium tosylate on the atrio ventricular and intra ventricular conduction in man", Bollettino Della Societa Italiana di Cardiologia, Pensiero Scientifico, vol. 21, No. 4, 1975, pp. 601-608.
Agag et al., "Primary Amine-Functional Benzoxazine Monomers and Their Use for Amide-Containing Monomeric Benzoxazines," Macromolecules, 2010, 43(6):2748-2758.
Antoons, et al., "Late Na+ Current Inhibition by Ranolazine Reduces Torsades de Pointes in the Chronic Atrioventricular Block Dog Model," Journal of the American College of Cardiology, 55(8), 2010, pp. 801-809.
Baldwin et al., Kinase array design, back to front: Biaryl amides, Bioorganic & Medicinal Chemistry Letters, 18(2008), pp. 5285-5289.
Banchs, et al., "Efficacy and safety of dofetillide in patients with atrial fibrillation and atrial flutter," J. Interv. Card. Electrophysiol, 23, 2008, pp. 111-115.
(Continued)

*Primary Examiner* — Theodore R West
(74) *Attorney, Agent, or Firm* — Francis O. Ginah

(57) ABSTRACT

The present disclosure relates to compounds that are sodium channel inhibitors and to their use in the treatment of various disease states, including cardiovascular diseases and diabetes. In particular embodiments, the structure of the compounds is given by Formula I:

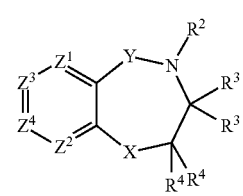

wherein $Z^1$, $Z^2$, $Z^3$, $Z^4$, X, Y, $R^2$, $R^3$ and $R^4$ are as described herein, to methods for the preparation and use of the compounds and to pharmaceutical compositions containing the same.

2 Claims, No Drawings

Related U.S. Application Data

No. 14/038,646, filed on Sep. 26, 2013, now Pat. No. 9,193,694, which is a continuation of application No. 13/789,469, filed on Mar. 7, 2013, now Pat. No. 8,697,863, which is a continuation of application No. 13/538,847, filed on Jun. 29, 2012, now Pat. No. 8,586,732.

(60) Provisional application No. 61/582,160, filed on Dec. 30, 2011, provisional application No. 61/503,980, filed on Jul. 1, 2011.

(51) Int. Cl.

| | | |
|---|---|---|
| C07D 413/14 | (2006.01) | |
| C07D 419/06 | (2006.01) | |
| C07D 471/04 | (2006.01) | |
| C07D 487/04 | (2006.01) | |
| C07D 498/04 | (2006.01) | |
| C07D 243/14 | (2006.01) | |
| C07B 59/00 | (2006.01) | |
| C07D 413/04 | (2006.01) | |
| C07D 417/14 | (2006.01) | |

(56) References Cited

U.S. PATENT DOCUMENTS

| | | |
|---|---|---|
| 3,441,649 A | 4/1969 | Bacaner |
| 3,483,193 A | 12/1969 | Gall et al. |
| 3,594,372 A | 7/1971 | Santilli et al. |
| 4,062,881 A | 12/1977 | Kugele |
| 4,230,705 A | 10/1980 | Allen, Jr. et al. |
| 4,242,515 A | 12/1980 | Trust et al. |
| 4,244,953 A | 1/1981 | Trust et al. |
| 4,326,525 A | 4/1982 | Swanson et al. |
| 4,654,343 A | 3/1987 | Albright et al. |
| 4,746,655 A | 5/1988 | Cale, Jr. |
| 4,812,565 A | 3/1989 | Cale, Jr. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,565,449 A | 10/1996 | Blackburn et al. |
| 5,616,345 A | 4/1997 | Geoghegan et al. |
| 5,773,186 A | 6/1998 | Takashima |
| 5,939,412 A | 8/1999 | Bondinell et al. |
| 6,011,150 A | 1/2000 | Iwasaki et al. |
| 6,579,875 B1 | 6/2003 | Carling et al. |
| 6,908,917 B2 | 6/2005 | Ortwine |
| 6,998,408 B2 | 2/2006 | Pinto |
| 7,005,523 B2 | 2/2006 | Dombroski et al. |
| 7,122,677 B2 | 10/2006 | Reichard et al. |
| 7,157,490 B2 | 1/2007 | Colandrea et al. |
| 7,306,631 B2 | 12/2007 | Glenn, Jr. et al. |
| 7,456,187 B2 | 11/2008 | Ford et al. |
| 7,572,807 B2 | 8/2009 | Li et al. |
| 7,579,348 B2 | 8/2009 | Wang et al. |
| 7,790,741 B2 | 9/2010 | Calderwood et al. |
| 8,212,041 B2 | 7/2012 | Albrecht et al. |
| 8,252,810 B2 | 8/2012 | Ozaki et al. |
| 8,389,500 B2 | 3/2013 | Abelman et al. |
| 8,586,732 B2 * | 11/2013 | Corkey ............... C07D 243/24 540/484 |
| 8,697,863 B2 * | 4/2014 | Elzein ............... C07D 243/24 540/484 |
| 8,703,759 B2 | 4/2014 | Kobayashi et al. |
| 8,952,034 B2 | 2/2015 | Corkey et al. |
| 8,962,610 B2 | 2/2015 | Corkey et al. |
| 9,079,901 B2 | 7/2015 | Kobayashi et al. |
| 9,115,096 B2 | 8/2015 | Corkey et al. |
| 9,193,694 B2 | 11/2015 | Corkey et al. |
| 9,371,329 B2 | 6/2016 | Corkey et al. |
| 9,403,782 B2 | 8/2016 | Corkey et al. |
| 2004/0038974 A1 | 2/2004 | Ortwine |
| 2004/0063580 A1 | 4/2004 | Kuragano et al. |
| 2004/0204404 A1 | 10/2004 | Zelle et al. |
| 2004/0224959 A1 | 11/2004 | Ohkura et al. |
| 2004/0242572 A1 | 12/2004 | Stenkamp et al. |
| 2005/0239767 A1 | 10/2005 | Chan et al. |
| 2007/0066584 A1 | 3/2007 | Yao et al. |
| 2007/0066617 A1 | 3/2007 | Mita et al. |
| 2007/0142376 A1 | 6/2007 | Fleenor et al. |
| 2007/0249598 A1 | 10/2007 | Wang et al. |
| 2008/0176830 A1 | 7/2008 | Adams et al. |
| 2008/0293939 A1 | 11/2008 | Culshaw et al. |
| 2009/0012095 A1 | 1/2009 | Zelle et al. |
| 2009/0069300 A1 | 3/2009 | Zhou et al. |
| 2009/0124612 A1 | 5/2009 | Albrecht et al. |
| 2009/0131402 A1 | 5/2009 | Shirai et al. |
| 2009/0203707 A1 | 8/2009 | Rajamani et al. |
| 2009/0221555 A1 | 9/2009 | Ahmed et al. |
| 2009/0253689 A1 | 10/2009 | Baeschlin et al. |
| 2010/0056536 A1 | 3/2010 | Antzelevitch et al. |
| 2010/0099676 A1 | 4/2010 | Endoh et al. |
| 2010/0113449 A1 | 5/2010 | Abelman et al. |
| 2010/0113461 A1 | 5/2010 | Koltun et al. |
| 2010/0144715 A1 | 6/2010 | Hoyt et al. |
| 2010/0174065 A1 | 7/2010 | Heer et al. |
| 2010/0197684 A1 | 8/2010 | Abelman et al. |
| 2010/0240635 A1 | 9/2010 | Cordi et al. |
| 2011/0021521 A1 | 1/2011 | Corkey et al. |
| 2011/0076292 A1 | 3/2011 | Blaquiere et al. |
| 2011/0183990 A1 | 7/2011 | Antzelevitch et al. |
| 2012/0010192 A1 | 1/2012 | Kobayashi et al. |
| 2012/0289493 A1 | 11/2012 | Corkey et al. |
| 2013/0005706 A1 | 1/2013 | Corkey et al. |
| 2013/0012492 A1 | 1/2013 | Corkey et al. |
| 2013/0184255 A1 | 7/2013 | Corkey et al. |
| 2014/0135317 A1 | 5/2014 | Corkey et al. |
| 2014/0221286 A1 | 8/2014 | Belardinelli et al. |
| 2014/0303158 A1 | 10/2014 | Corkey et al. |
| 2015/0045305 A1 | 2/2015 | Belardinelli et al. |
| 2015/0080370 A1 | 3/2015 | Kobayashi et al. |
| 2015/0225383 A1 | 8/2015 | Chiu et al. |
| 2015/0225384 A1 | 8/2015 | Chiu et al. |
| 2015/0239904 A1 | 8/2015 | Corkey et al. |
| 2015/0329558 A1 | 11/2015 | Corkey et al. |

FOREIGN PATENT DOCUMENTS

| | | |
|---|---|---|
| DE | 4010488 | 10/1991 |
| DE | 10317526 | 11/2004 |
| EP | 0017438 | 10/1980 |
| EP | 0464572 | 1/1992 |
| EP | 0477789 | 4/1992 |
| EP | 0540334 | 5/1993 |
| EP | 0597423 | 5/1994 |
| EP | 0635488 | 1/1995 |
| EP | 0999208 | 5/2000 |
| EP | 1182195 | 2/2002 |
| EP | 1333031 | 8/2003 |
| EP | 1354602 | 10/2003 |
| EP | 1803748 | 7/2007 |
| JP | 5675428 | 6/1981 |
| JP | 06-001779 | 1/1994 |
| JP | 06107647 | 4/1994 |
| JP | 09157262 | 6/1997 |
| JP | 11100394 | 4/1999 |
| JP | 2003277384 | 10/2003 |
| JP | 2003321461 | 11/2003 |
| JP | 2006-503875 | 2/2006 |
| JP | 2006063064 | 3/2006 |
| JP | 04209692 | 1/2009 |
| JP | 5271069 | 8/2013 |
| JP | 2014-509611 | 4/2014 |
| TW | 200726765 | 7/2007 |
| WO | WO-93/00095 | 1/1993 |
| WO | WO-93/08174 | 4/1993 |
| WO | WO-94/13272 | 6/1994 |
| WO | WO-94/13292 | 6/1994 |
| WO | WO-97/03975 | 2/1997 |
| WO | WO-98/11890 | 3/1998 |
| WO | WO-98/47885 | 10/1998 |

(56) References Cited

FOREIGN PATENT DOCUMENTS

| | | |
|---|---|---|
| WO | WO-98/54135 | 12/1998 |
| WO | WO-99/13038 | 3/1999 |
| WO | WO-99/41246 | 8/1999 |
| WO | WO-99/42456 | 8/1999 |
| WO | WO-99/65904 | 12/1999 |
| WO | WO-00/23451 | 4/2000 |
| WO | WO-01/16110 | 3/2001 |
| WO | WO-01/16263 | 3/2001 |
| WO | WO-01/16274 | 3/2001 |
| WO | WO-01/16275 | 3/2001 |
| WO | WO-01/16276 | 3/2001 |
| WO | WO-01/16277 | 3/2001 |
| WO | WO-01/16278 | 3/2001 |
| WO | WO-01/87883 | 11/2001 |
| WO | WO-02/10135 | 2/2002 |
| WO | WO-02/18377 | 3/2002 |
| WO | WO-02/38562 | 5/2002 |
| WO | WO-02/072579 | 9/2002 |
| WO | WO-02/096873 | 12/2002 |
| WO | WO-03/024941 | 3/2003 |
| WO | WO-03/033480 | 4/2003 |
| WO | WO-03/075858 | 9/2003 |
| WO | WO-2004/014866 | 2/2004 |
| WO | WO-2004/020440 | 3/2004 |
| WO | WO-2004/024702 | 3/2004 |
| WO | WO-2004/026292 | 4/2004 |
| WO | WO-2004/037192 | 5/2004 |
| WO | WO-2004/043940 | 5/2004 |
| WO | WO-2004/062616 | 7/2004 |
| WO | WO-2004/083190 | 9/2004 |
| WO | WO-2004/094371 | 11/2004 |
| WO | WO-2004/096767 | 11/2004 |
| WO | WO-2004/101509 | 11/2004 |
| WO | WO-2005/002520 | 1/2005 |
| WO | WO-2005/011690 | 2/2005 |
| WO | WO-2005/014558 | 2/2005 |
| WO | WO-2005/060967 | 7/2005 |
| WO | WO-2005/097052 | 10/2005 |
| WO | WO-2006/002470 | 1/2006 |
| WO | WO-2006/011669 | 2/2006 |
| WO | WO-2006/020959 | 2/2006 |
| WO | WO-2006/021544 | 3/2006 |
| WO | WO-2006/023750 | 3/2006 |
| WO | WO-2006/031676 | 3/2006 |
| WO | WO-2006/032518 | 3/2006 |
| WO | WO-2006/048727 | 5/2006 |
| WO | WO-2006/091897 | 8/2006 |
| WO | WO-2006/095014 | 9/2006 |
| WO | WO-2006/113864 | 10/2006 |
| WO | WO-2006/125119 | 11/2006 |
| WO | WO-2006/125972 | 11/2006 |
| WO | WO-2006/138549 | 12/2006 |
| WO | WO-2006/138657 | 12/2006 |
| WO | WO-2006/138695 | 12/2006 |
| WO | WO-2007/004028 | 1/2007 |
| WO | WO-2007/023750 | 3/2007 |
| WO | WO-2007/038209 | 4/2007 |
| WO | WO-2007/047604 | 4/2007 |
| WO | WO-2007/058583 | 5/2007 |
| WO | WO-2007/061677 | 5/2007 |
| WO | WO-2007/061696 | 5/2007 |
| WO | WO-2007/069986 | 6/2007 |
| WO | WO-2007/070866 | 6/2007 |
| WO | WO-2007/113226 | 10/2007 |
| WO | WO-2007/146284 | 12/2007 |
| WO | WO-2008/005338 | 1/2008 |
| WO | WO-2008/005457 | 1/2008 |
| WO | WO-2008/006540 | 1/2008 |
| WO | WO-2008/007661 | 1/2008 |
| WO | WO-2008/023336 | 2/2008 |
| WO | WO-2008/055068 | 5/2008 |
| WO | WO-2008/079570 | 7/2008 |
| WO | WO-2008/080012 | 7/2008 |
| WO | WO-2008/094909 | 8/2008 |
| WO | WO-2008/108445 | 9/2008 |
| WO | WO-2008/117061 | 10/2008 |
| WO | WO-2008/118141 | 10/2008 |
| WO | WO-2008/128086 | 10/2008 |
| WO | WO-2008/134553 | 11/2008 |
| WO | WO-2008/144483 | 11/2008 |
| WO | WO-2009/005675 | 1/2009 |
| WO | WO-2009/016462 | 2/2009 |
| WO | WO-2009/026444 | 2/2009 |
| WO | WO-2009/036144 | 3/2009 |
| WO | WO-2009/045753 | 4/2009 |
| WO | WO-2009/085980 | 7/2009 |
| WO | WO-2009/089027 | 7/2009 |
| WO | WO-2009/091374 | 7/2009 |
| WO | WO-2009/101917 | 8/2009 |
| WO | WO-2009/112275 | 9/2009 |
| WO | WO-2009/137462 | 11/2009 |
| WO | WO-2009/137499 | 11/2009 |
| WO | WO-2009/141026 | 11/2009 |
| WO | WO-2009/148452 | 12/2009 |
| WO | WO-2009/153589 | 12/2009 |
| WO | WO-2010/006292 | 1/2010 |
| WO | WO-2010/018686 | 2/2010 |
| WO | WO-2010/022001 | 2/2010 |
| WO | WO-2010/053757 | 5/2010 |
| WO | WO-2010/056865 | 5/2010 |
| WO | WO-2010/068461 | 6/2010 |
| WO | WO-2010/074807 | 7/2010 |
| WO | WO-2010/077680 | 7/2010 |
| WO | WO-2010/077686 | 7/2010 |
| WO | WO-2010/106249 | 9/2010 |
| WO | WO-2010/111534 | 9/2010 |
| WO | WO-2010/118208 | 10/2010 |
| WO | WO-2011/014462 | 2/2011 |
| WO | WO-2011/036280 | 3/2011 |
| WO | WO-2011/042920 | 4/2011 |
| WO | WO-2011/056985 | 5/2011 |
| WO | WO-2011/075607 | 6/2011 |
| WO | WO-2011/084733 | 7/2011 |
| WO | WO-2012/003392 | 1/2012 |
| WO | WO-2012/019071 | 2/2012 |
| WO | WO-2012/019076 | 2/2012 |
| WO | WO-2012/036233 | 3/2012 |
| WO | WO-2012/037105 | 3/2012 |
| WO | WO-2012/038813 | 3/2012 |
| WO | WO-2012/050918 | 4/2012 |
| WO | WO-2012/071509 | 5/2012 |
| WO | WO-2012/154760 | 11/2012 |
| WO | WO-2012/167212 | 12/2012 |
| WO | WO-2013/004551 | 1/2013 |
| WO | WO-2013/006400 | 1/2013 |
| WO | WO-2013/006463 | 1/2013 |
| WO | WO-2013/006485 | 1/2013 |
| WO | WO-2013/043925 | 3/2013 |
| WO | WO-2013/097052 | 7/2013 |
| WO | WO-2013/098375 | 7/2013 |
| WO | WO-2013/112932 | 8/2013 |
| WO | WO-2013/185764 | 12/2013 |
| WO | WO-2014/134419 | 9/2014 |
| WO | WO-2015/123519 | 8/2015 |

OTHER PUBLICATIONS

Banker, et al., "Modern Pharmaceutics, 3ed.," Marcel Dekker, 1996, pp. 451 and 596.

Barsky et al., "Hypoglycemic Cyclic Amidines", J. Med. Chem., vol. 14, No. 1, 1971, pp. 40-44.

Belardinelli et al., "A Novel, Potent, and Selective Inhibitor of Cardiac Late Sodium Current Suppresses Experimental Arrhythmias," J. Pharm. Exp. Ther., 344(1), pp. 23-32, 2013.

Benson et al., "SUMO modification regulates inactivation of the voltage-gated potassium channel Kv1.5" Proc. Nat. Acad. Sci., 104(6), pp. 1805-1810, 2007.

Brady, et al., "Synthesis of Conformationally Constrained Benzoylureas as BH3-mimetics," Organic and Biomolecular Chemistry 10(27), 2012, pp. 5230-5237.

Burashnikov et al., "Role of late sodium channel current block in the management of atrial fibrillation," Cardiovascular Drugs and Therapy / Sponsored by the International Society of Cardiovascular Pharmacotherapy, 27(1), pp. 79-89, 2013.

(56) References Cited

OTHER PUBLICATIONS

Caira, "Crystalline Polymorphism of Organic Compounds," Topics in Current Chemistry Springer, 198, 1998, pp. 163-208.
Chiu et al., "Cycloaddition of Alpha-Chloroformylarylhydrazines with Pyridines Afford 2ryl-2H-[1,2,4]triazolo[4,3]pyridine-3-ones", Journal of the Chinese Chemical Society, Chinese Electronic Periodical Services, China, vol. 48, 2001, pp. 1135-1142.
Chouhan et al., "Domino Ring-Opening/Carboxamidation Reactions of N-Tosyl Aziridines and 2-Halophenols/Pyridinol: Efficient Synthesis of 1,4-Benzo- and Pyrido-oxazepinones", Organic Letters, vol. 12. No. 1, pp. 192-195, 2010.
Chylinska et al., "Dihydro-1,3-oxazine Derivatives and Their Antitumor Activity," Journal of Medicinal Chemistry, 1963, vol. 6:484-487.
Clare et al, Drug Discovery Today 2000, vol. 5, No. 11, 506-520.
Cleator et al., "Synthesis of Novel Benzoxathiazepine-1,1-dioxides by Means of a One-pot Multicomponent Reaction", Tetrahedron Letters, 51, pp. 1079-1082, 2010.
Curran, "Potassium ion channels and human disease: phenotypes to drug targets?", Current Opinion in Biotechnology, vol. 9. No. 6, 1998, pp. 565-572.
Database WPI, Week 198132, Thomson Scientific, London, abstract, 1981, XP-002690413, JP56075428 (1 page).
Database WPI, Week 199346, Thomson Scientific, London, abstract, 1993, XP-002690414, JP5271069 (2 pages).
Dermer et al., Bio/Technology, 1994, 12:320.
Drici et al., "The bee venom peptide tertiapin underlines the role of IKACh in acetylcholine-induced artrioventricular blocks", British Journal of Pharmacology, vol. 131, No. 3, 2000, pp. 569-577.
Ege et al., "6-Fulor-Sowie 6-Nitro-3-phenyl-3,4-dihydro-1,2,3-benzo-triazin-4-on und deren Photolyse; nucleophile Substitution zur Erprobung der Fluor-Markierungsmethode von Suschitzky," Liabigs Ann. Chem. 1976, 946-968.
Elzein et al., "Novel 1,3-dipropyl-8-(1-heteroarylmethyl-1 H-pyrazol-4-yl)-xanthine derivatives as high affinity and selective A2B adenosine receptor antagonists," *Bioorganic & Medicinal Chemistry Letters*, 16:302-306 (2006).
Examination Report for Australian Application No. 2012279236, dated Apr. 1, 2014.
Examination Report for Australian Application No. 2013201608, dated Apr. 1, 2014.
Examination Report for Australian Application No. 2013201608, dated Apr. 27, 2015.
Examination Report for New Zealand Application No. 716245 dated Feb. 12, 2016.
Examination Report for Australian Application No. 2015224425 dated Feb. 2, 2016.
Examination Report for New Zealand Application No. 618691 dated Oct. 15, 2014.
Extended European Search Report for European Application No. 16169306.4 dated Jul. 18, 2016. (12 pages).
Extended European Search Report for European Application No. 16169333.8 dated Jul. 14, 2016. (12 pages).
Extended European Search Report for European Application No. 16169386.6 dated Jul. 18, 2016. (12 pages).
Extended European Search Report for European Application No. 16169320.5, dated Sep. 9, 2016. (11 pages).
Extended European Search Report for European Application No. 16169314.8, dated Sep. 9, 2016. (11 pages).
Examination Report for New Zealand Application No. 618691 dated Feb. 12, 2016. (2 pages).
Examination Report for Pakistan Application No. 423/2012 dated Oct. 26, 2015. (1 page).
Foster, "Deuterium Isotope Effects in Studies of Drug Metabolism", Trends Pharmacol. Sci., 5(12):524-527, 1984.
Freshney et al., Culture of Animal Cells, A Manual of Basic Technique, Alan R. Liss, Inc., 1983, New York, pp. 1-6.
Guidelines for Drug Treatment of Arrhythmias (JCS 2009), 2009, p. 16-24.
Hale et al., "Late sodium current inhibition as a new cardioprotective approach", Journal of Molecular and Cellular Cardiology, vol. 44 (2008), pp. 954-967.
Ilyin, et al., "One-step assembly of carbamoyl substituted annulated 1,4-oxazepines", Tetrahedron Letters, (2006), 47(15):2649-2653, Supplementary Data 3 pages.
International Search Report and Written Opinion for PCT/US2011/042700 dated Aug. 17, 2011. (10 pages).
International Search Report and Written Opinion for PCT/US2012/036976, dated Jul. 2, 2012. (11 pages).
International Search Report and Written Opinion for PCT/US2012/045021 dated Oct. 9, 2012. (6 pages).
International Search Report and Written Opinion for PCT/US2012/045086, dated Sep. 19, 2012. (10 pages).
International Search Report and Written Opinion for PCT/US2012/056419, dated Jan. 30, 2013. (10 pages).
International Search Report and Written Opinion for PCT/US2010/043264, dated Oct. 4, 2010. (12 pages).
International Search Report and Written Opinion for PCT/US2013/023291, dated Mar. 13, 2013. (14 pages).
International Search Report and Written Opinion for PCT/US2015/015652 dated Apr. 22, 2015. (8 pages).
International Search Report and Written Opinion for PCT/US2015/015814, dated Aug. 17, 2015. (20 pages).
International Preliminary Report on Patentability for International Application No. PCT/US2012/045021 dated Jan. 7, 2014. (4 pages).
International Preliminary Report on Patentability for International Application No. PCT/US2012/045086 dated Jan. 7, 2014. (6 pages).
International Preliminary Report on Patentability for International Application No. PCT/US2010/043264 dated Jan. 31, 2012. (8 pages).
International Preliminary Report on Patentability for International Application No. PCT/US2011/042700 dated Jan. 8, 2013. (7 pages).
International Preliminary Report on Patentability for International Application No. PCT/US2012/036976 dated Nov. 12, 2013. (8 pages).
International Preliminary Report on Patentability for International Application No. PCT/US2015/015814 dated Aug. 16, 2016. (14 pages).
International Preliminary Report on Patentability for International Application No. PCT/US2013/023291 dated Jul. 29, 2014. (10 pages).
International Preliminary Report on Patentability for International Application No. PCT/US2012/056419 dated Mar. 25, 2014. (7 pages).
Invitation to Respond to Written Opinion for Singapore Application No. 201309133-5 dated Oct. 5, 2015. (10 pages).
Kamei, et al, "Synthesis, SAR Studies, and Evaluation of 1,4-benzoxazepine Derivatives as Selective 5-HT1A Receptor Agonists with Neuroprotective Effect: Discovery of Piclozotan," Bioorganic & Medicinal Chemistry, 14(6), 2006, pp. 1978-1992.
Kerr et al., "Efficacy of azimilide for the maintenance of sinus rhythm in patients with paroxysmal atrial fibrillation in the presence and absence of structural heart disease", American Journal of Cardiology, vol. 98, No. 2, 2006, pp. 215-218.
Kirk-Othmer, "Encyclopedia of Chemical Technology," 2002, pp. 1-7.
Krafte et al., Current Opinion in Pharmacology 2008, 8:50-56.
Kumar et al., "New and emerging antiarrhythmic drugs for atrial fibrillation: what may become available to the clinician in the near future", Curr. Treat. Options Cardiovasc. Med., pp. 373-380 11(55), 2009.
Manikannan et al., "Chemoselective Reaction of Formalin with 2-(5-Substituted-2-hydroxybenzylamino)phenols: Synthesis of 6-Substituted 3-(2-hydroxyphenyl)-3,4-dihydro-2H-benzo[e][1,3]oxazines," Journal of Heterocyclic Chemistry, 2008, vol. 45:1207-1210.
Marc et al., "High Yield Phase Transfer Nlkylation of Some Benzodiazepines by Esters of omega-Halo Acids," Syn. Comm. 1998, 28, pp. 1143-1157.
Murdock et al, "The Use of Oral Ranolazine to Convert New or Paroxysmal Atrial Fibrillation: A Review of Experience with Impli-

(56) References Cited

OTHER PUBLICATIONS cations for Possible 'Pill in the Pocket' Approach to Atrial Fibrillation," Indian Pacing and Electrophysiology Journal, 9(5), 2009, pp. 260-267.
Nagashima et al., "Dual effects of disopyramide to the glycemic control in patients with diabetes mellitus", Diabetes, American Diabetes Association, vol. 53, No. Suppl. 2, 2004 (1 page).
Neumayr et al., "Ibutilide and sinus arrest", Herz Kardiovaskulare Erkrankungen, Urban & Vogel, vol. 32, No. 4, 2007, p. 342.
Ning et al., "Ranolazine Increases Beta-Cell Survival and Improves Glucose Homeostasis in Low-Dose Streptozotocin-induced Diabetes in Mice", J. Pharmacol. Exp. Ther., 337(1), 50-58, 2011.
Office Action for Chile Application No. 2013-03598 dated Feb. 19, 2016. (19 pages).
Office Action, U.S. Appl. No. 13/538,847, dated May 3, 2013. (6 pages).
Office Action, U.S. Appl. No. 13/789,469, dated May 2, 2013. (6 pages).
Office Action for Chinese Application No. 201280042528.4, dated Jun. 4, 2015. (9 pages).
Office Action for Chinese Application No. 201280042528.4, dated Dec. 1, 2014. (15 pages).
Office Action for Chinese Application No. 201280042528.4 dated Dec. 3, 2015. (8 pages).
Office Action for Colombian Application No. 13-291981, dated Sep. 17, 2015. (6 pages).
Office Action for European Application No. 12735402.5, dated Mar. 23, 2015. (5 pages).
Office Action for Korean Application No. 2013-7033295 dated Sep. 22, 2015. (5 pages).
Office Action, Moldova Application No. A 20130095, dated Jan. 6, 2015. (2 pages).
Office Action, Moldova Application No. A 20130095, dated Jun. 22, 2015. (2 pages).
Office Action for Mexico Application No. MX/a/2013/014846 dated Sep. 18, 2015. (3 pages).
Office Action for Eurasian Application No. 201391639, dated Jan. 26, 2015. (4 pages).
Official Action for Eurasian Application No. 201391639 dated Sep. 29, 2015. (3 pages).
Office Action for Taiwan Application No. 101123291, dated May 2, 2014. (12 pages).
Office Action and Search Report for Taiwan Application No. 104100530 dated Oct. 15, 2015. (6 pages).
Office Action for Chinese Application No. 201280042528.4 dated Jun. 6, 2016. (4 pages).
Office Action for Thailand Application No. 1301006981 dated Aug. 15, 2016. (1 page).
Office Action for Israel Application No. 230022, dated Feb. 17, 2015. (7 pages).
Office Action for Colombia Application No. 13-291981, dated Nov. 28, 2013. (8 pages).
Office Action for Chilean Application No. 2013-03598 dated Aug. 30, 2016. (7 pages).
Office Action for Colombia Application No. 15-265.006 dated Oct. 11, 2016. (12 pages).
Official Action for Eurasian Application No. 201391639 dated Aug. 24, 2016. (2 pages).
Official Action for Japanese Application No. 2014-519190 dated Oct. 1, 2015. (3 pages).
Official Action in Ukraine Application No. a 2013 14145, dated Nov. 16, 2016. (3 pages).
Official Notification for Israel Application No. 230022 dated Jun. 20, 2016. (2 pages).
Opposition for Costa Rican Application No. 2013-0658, Aug. 25, 2014. (11 pages).
Opposition for Ecuadorian Application No. SP-13-13083 dated Feb. 23, 2015. (8 pages).
Opposition Notice for Bolivia Application No. SP-0212-2012 dated Mar. 25, 2014. (5 pages).

Rudolph et al., "Quinazolinone Derivatives as Orally Available Ghrelin Receptor Antagonists for the Treatment of Diabetes and Obesity", Journal of Medicinal Chemistry, vol. 50, No. 21, 2007, pp. 5202-5216.
Rush et al., Molecular Interventions 2007, vol. 4, issue 7, 192-195.
Seto, et al., "Design, synthesis, and evaluation of novel 2-substituted-4ryl-6,7,8,9-tetrahydro-5H-pyrimido[4,5-b][1,5]oxazocin-5-ones as NK1 antagonists", Bioorganic & Medicinal Chemistry, (2005), 13(20):5717-5732.
Shin et al., "New Synthesis of Highly Potential Efficient Bluish-Green Electroluminescent Materials Based on 1,3,4-Oxadiazole Triazolopyridinone Carbazole Derivatives for Single-Layer Devices", Heteroatom Chemistry, Wiley Periodicals, Inc., vol. 17, No. 2, 2006, pp. 160-165.
Shin et al., "Synthesis and Characterization of New Bluish-Green Electroluminescent Materials Based on 1,3,4-Oxadiazole Triazolopyridinone Hybrids", Heteroatom Chemistry, Wiley Periodicals, Inc., vol. 10, No. 3, 2007, pp. 212-219.
Scirica, "Ranolazine in patients with coronary artery disease", Expert Opinion Pharmacother (2007), 8(13): 2149-2157.
Sircar, "Synthesis of new 1,2,4-triazolo[4,3-b]pyridazines and related compounds" Journal of Heterocyclic Chemistry 22(1):1045-1048 (1985). ISSN: 0022-152X.
Skidmore et al., "Optimization of Sphingosine-1-phosphate-1 Receptor Agonists: Effects of Acidic, Basic, and Zwitterionic Chemotypes on Pharmacokinetic and Pharmacodynamic Profiles," J. Med. Chem., 2014, 57 (24), pp. 10424-10442.
Takahara et al., "Analysis of Arrhythmogenic profile in a canine model of chronic atrioventricular block by comparing in vitro effects of the class III antiarrhythmic drug nifekalant on the ventricular action potential indices between normal heart and atrioventricular block heart", Journal of Pharmacological Sciences, vol. 103, No. 2, Feb. 1, 2007 (Feb. 1, 2007), pp. 181-188.
Toussaint et al., "Late sodium current as a promising antiarrhythmic drug target for treatment of atrial fibrilolation?" Naunyn-Schmiedeberg's Archives of Pharmacology, 383(1), p. 61, 20117 77th Annual Meeting on German-Society-for Experimentalnd-Clinical-Pharmacologynd Toxicology; Frankfurt, Germany; Mar. 30Apr. 2, 2011.
Toyofuku et al. JP 06001779, Jan. 11, 1995; CA 122;10048, 1995. Abstract provided. JP06001779 (2 pages).
Vadnais, et al., "Emerging Clinical Role of Ranolazine in the Management of Angina," Ther. Clin. Risk Management, 6, 2010, pp. 517-530.
Vippagunta et al., "Crystalline solids", Advanced Drug Delivery Reviews 48, pp. 3-26, (2001).
Wang et al., "Influence of Electronic Effects from Bridging Groups on Synthetic Reaction and Thermally Activated Polymerization of Bisphenol-Based Benzoxazines," Journal of Polymer Science: Part A: Polymer Chemistry, 2011, vol. 49(6):1443-1452.
Witty et al., Discovery of potent and stable conformationally constrained analogues of the MCH R1 antagonist SB-568849, Bioorganic & Medicinal Chemistry Letters 16 (2006), pp. 4872-4878.
Wolff, 1995, Burger's Medicinal Chemistry and Drug Discovery, 5th ed., pp. 172-178, 950-982.
Wu, et al., "Late Sodium Current Contributes to the Reverse Rate-Dependent Effect of I-KR Inhibition on Ventricular Repolarization", Circulation, 123(16), pp. 1713-1720, 2011.
Wunsche et al., "Skelettumlagerungen unter elektronenbeschuss-III : Benzotriazinone und 1,3-diphenyltriazene," Tetrahedron, 1969, 25: 5869-5877.
Yamada, "The role of muscarinic K+ channels in the negative chronotropic effect of a muscarinic agonist", Journal of Pharmacology and Experimental Therapeutics, vol. 300, No. 1, 2002, pp. 681-687.
Yamazaki et al., "Negative chronotropic and dromotropic effects of E-4031, an I-Kr blocker, on the atrioventricular node in anesthetized dog hearts", European Journal of Pharmacology, vol. 297, No. 3, 1996, pp. 233-239.

(56) References Cited

OTHER PUBLICATIONS

Yang, et al., "Synthesis of Dibenzo[b,f][1,4]oxazepin-11(10H)-ones via Intramolecular Cyclocarbonylation Reactions Using pfl2/Cytop 292 as the Catalytic System", Journal of Organic Chemistry, 75(18), 2010, pp. 6297-6299, S1-S12.

Zaza et al., "Pathophysiology and Pharmacology of the Cardiac "Late Sodium Current"," *Pharmacology and Therapeutics*, 119, pp. 326-339, 2008.

\* cited by examiner

FUSED HETEROCYCLIC COMPOUNDS AS ION CHANNEL MODULATORS

CROSS-REFERENCE TO RELATED APPLICATIONS

This application is a continuation of U.S. application Ser. No. 14/872,787, filed Oct. 1, 2015 which is a continuation of U.S. application Ser. No. 14/038,646, filed Sep. 26, 2013, now U.S. Pat. No. 9,193,694, which is a continuation of U.S. application Ser. No. 13/789,469, filed Mar. 7, 2013, now U.S. Pat. No. 8,697,863, which is a continuation of U.S. application Ser. No. 13/538,847, filed Jun. 29, 2012, now U.S. Pat. No. 8,586,732, which claims the benefit under 35 U.S.C. §119(e) to U.S. Provisional Application Ser. No. 61/503,980, filed on Jul. 1, 2011 and 61/582,160, filed on Dec. 30, 2011, the entirety of which are incorporated herein by reference.

FIELD

The present disclosure relates to novel compounds and to their use in the treatment of various diseases, including cardiovascular diseases and diabetes. The disclosure also relates to methods for preparation of the compounds and to pharmaceutical compositions comprising such compounds.

BACKGROUND

The late sodium current (INaL) is a sustained component of the fast Na+ current of cardiac myocytes and neurons. Many common neurological and cardiac conditions are associated with abnormal (INaL) enhancement, which contributes to the pathogenesis of both electrical and contactile dysfunction in mammals. See, for example, Pathophysiology and Pharmacology of the Cardiac "Late Sodium Current", Pharmacology and Therapeutics 119 (2008) 326-339. Accordingly, compounds that selectively inhibit (INaL) in mammals are useful in treating such disease states.

One example of a selective inhibitor of (INaL) is RANEXA®, a compound approved by the FDA for the treatment of chronic stable angina pectoris. RANEXA® has also been shown to be useful for the treatment of a variety of cardiovascular diseases, including ischemia-reperfusion injury, arrhythmia and unstable angina, and also for the treatment of diabetes. It would be desirable to provide novel compounds that selectively inhibit (INaL) in mammals and that have the similar or improved selectivity over peak INa inhibition of the cardiac sodium channel as RANEXA®.

SUMMARY

Accordingly, typical embodiments the present disclosure provide novel compounds that function as late sodium channel blockers. In one embodiment, the disclosure provides compounds of Formula I:

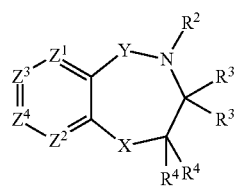

I wherein:

$Z^1$ and $Z^2$ are each independently selected from the group consisting of $CR^7$ and N;

$Z^3$ and $Z^4$ are each independently selected from the group consisting of $CR^7$, $C$-Q-$R^1$ and N, provided that one of $Z^3$ and $Z^4$ is C-Q-$R^1$ and the other of $Z^3$ and $Z^4$ is $CR^7$ or N and further provided that only one of $Z^1$, $Z^2$ and $Z^4$ is N;

X is —O— or —$NR^6$—;

Y is —C(O)—, —C($R^{11}$)$_2$— or —S(O)$_2$—;

Q is a covalent bond, —O—$C_{0-2}$ alkylene, —$NR^{11}$—$C_{0-2}$ alkylene, $C_2$ alkylene, $C_2$ alkenylene or $C_2$ alkynylene;

$R^1$ is aryl, cycloalkyl, cycloalkenyl, heterocyclyl or heteroaryl;

wherein said aryl, cycloalkyl, cycloalkenyl, heterocyclyl or heteroaryl are optionally substituted with one, two or three substituents independently selected from the group consisting of halo, —$NO_2$, —CN, —$SF_5$, —Si($CH_3$)$_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—S(O)$_2$—$R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;

wherein each —$C_{1-6}$ alkylene is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—$OR^{26}$, —C(O)—N($R^{20}$)($R^{22}$), —N($R^{20}$)—S(O)$_2$—$R^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

L is —O—, —S—, —C(O)—, —NHS(O)$_2$—, —S(O)$_2$NH—, —C(O)NH—, or —NHC(O)—; provided that when Y is —C($R^{11}$)$_2$—, then $R^2$ is -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$ and L is not —C(O)—; and when $R^2$ is -L-$R^5$ or -L-$C_{1-6}$ alkylene-$R^5$, then L is not —O—, —S—, —NHS(O)$_2$— or —NHC(O)—;

each $R^3$ is independently hydrogen, deuterium, $C_{1-6}$ alkyl, cycloalkyl, aryl, heteroaryl or heterocyclyl;

wherein said $C_{1-6}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$, wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, aralkyl, cycloalkyl, aryl, heterocyclyl or heteroaryl, are optionally further substituted with one, two or three substituents independently selected from the group consisting of halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

or when Y is —C(O)—, then R$^2$ and one of R$^3$ can join together with the atom to which they are attached to form a heterocyclyl;

wherein said heterocyclyl is optionally substituted with one, two or three substituents independently selected from the group consisting of C$_{1-6}$ alkyl, —O—R$^{20}$, —N(R$^{20}$)(R$^{22}$), —N(R$^{20}$)—C(O)—OR$^{20}$ and —C(O)—OR$^{20}$; and wherein said C$_{1-6}$ alkyl is optionally substituted with one, two or three substituents independently selected from the group consisting of halo and heteroaryl;

each R$^4$ is independently hydrogen, deuterium, C$_{1-6}$ alkyl, —C(O)—OR$^{26}$, —C(O)—N(R$^{26}$)(R$^{26}$), cycloalkyl, aryl, heteroaryl or heterocyclyl;

wherein said C$_{1-6}$ alkyl is optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$, wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, aralkyl, cycloalkyl, aryl, heterocyclyl, heteroaryl, are optionally further substituted with one, two or three substituents independently selected from the group consisting of hydroxyl, halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

or two R$^3$ or two R$^4$ together with the carbon atom to which they are attached form an oxo;

R$^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN, oxo and —O—R$^{20}$;

wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —S(O)$_2$—R$^{20}$ and —O—R$^{20}$;

R$^6$ is hydrogen, C$_{1-6}$ alkyl or cycloalkyl;

wherein said C$_{1-6}$ alkyl is optionally substituted with one, two or three substituents independently selected from the group consisting of halo, —NO$_2$, —N(R$^{20}$)(R$^{22}$), —C(O)R$^{20}$, —C(O)—OR$^{20}$, —C(O)—N(R$^{20}$)(R$^{22}$), —CN and —O—R$^{20}$;

R$^7$ is hydrogen, halo, —O—R$^{20}$ or C$_{1-6}$ alkyl;

R$^{11}$ is hydrogen or C$_{1-4}$ alkyl;

R$^{20}$ and R$^{22}$ are in each instance independently selected from the group consisting of hydrogen, C$_{1-6}$ alkyl, C$_{2-6}$ alkenyl, C$_{2-6}$ alkynyl, cycloalkyl, heterocyclyl, aryl and heteroaryl;

wherein the C$_{1-6}$ alkyl, C$_{2-6}$ alkenyl, C$_{2-6}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and wherein said heteroaryl is optionally further substituted with C$_{1-4}$ alkyl or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and each R$^{26}$ is independently selected from the group consisting of hydrogen, C$_{1-4}$ alkyl, aryl and cycloalkyl;

wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;

or a pharmaceutically acceptable salt, ester, stereoisomer, mixture of stereoisomers or tautomer thereof;

provided that when Y is —C(O)—, X is —O—, each R$^4$ is hydrogen, R$^2$ and R$^3$ together with the atom to which they are attached form a piperazine which is optionally substituted with tert-butoxycarbonyl and Q is a bond, then R$^1$ is not unsubstituted phenyl or morpholinyl; and that when Y is —S(O)$_2$—, X is —O—, R$^2$ is benzyl, each R$^3$ is hydrogen, Z$^4$ is C-Q-R$^1$, Q is a bond and R$^1$ is aryl or heteroaryl, then both R$^4$ are hydrogen.

In certain embodiments, the disclosure provides compounds of Formula IA:

$$IA$$

[Structure showing: $(R^{10})_n$—Cy—Q— attached to a bicyclic benzo-fused oxazepinone ring bearing $R^2$ on N, $R^3, R^3$ on one carbon, $R^4R^4$ on carbon adjacent to O, and $(R^{17})_m$ substituents on the benzo ring, with a C=O group]

wherein:
Cy is aryl, cycloalkyl, cycloalkenyl, heterocyclyl or heteroaryl;
Q is a covalent bond, —O—$C_{0-2}$ alkylene, —$NR^{11}$—$C_{0-2}$ alkylene, $C_2$ alkylene, $C_2$ alkenylene or $C_2$ alkynylene;
m is 0, 1, 2 or 3;
n is 0, 1, 2, 3, 4 or 5;
each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —$N(R^{20})(R^{22})$, —C(O)—$N(R^{20})(R^{22})$, —$N(R^{20})$—C(O)—$R^{22}$, —$N(R^{20})$—C(O)—$OR^{22}$, —$N(R^{20})$—$S(O)_2$—$R^{26}$, —$S(O)_2$—$R^{20}$, —O—$S(O)_2$—$R^{20}$, —$S(O)_2$—$N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and
  wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-6}$ alkyl, $C_{1-3}$ haloalkyl, cycloalkyl, —$N(R^{20})(R^{22})$, —C(O)—$R^{20}$, —C(O)—$OR^{20}$, —C(O)—$N(R^{20})(R^{22})$, —CN and —O—$R^{20}$;
$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;
  wherein each —$C_{1-6}$ alkylene is optionally substituted by one substituent independently selected from the group consisting of $C_{2-4}$ alkynyl, halo, —$NO_2$, —CN, —O—$R^{20}$, —$N(R^{20})(R^{22})$, —C(O)—$R^{20}$, —C(O)—$OR^{26}$, —C(O)—$N(R^{20})(R^{22})$, —$N(R^{20})$—$S(O)_2R^{20}$, cycloalkyl, aryl, heteroaryl or heterocyclyl; and
    wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$;
L is —O—, —S—, —C(O)—, —$NHS(O)_2$—, —$S(O)_2NH$—, —C(O)NH— or —NHC(O)—; provided that when $R^2$ is -L-$R^5$ or -L-$C_{1-6}$ alkylene-$R^5$, then L is not —O—, —S—, —$NHS(O)_2$— or —NHC(O)—; and
each $R^3$ is independently hydrogen, deuterium, $C_{1-6}$ alkyl, cycloalkyl, aryl, heteroaryl or heterocyclyl;
  wherein said $C_{1-6}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$;
  wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and
  wherein said $C_{1-6}$ alkyl, aralkyl, cycloalkyl, aryl, heterocyclyl or heteroaryl, are optionally further substituted with one, two or three substituents independently selected from the group consisting of halo, —$NO_2$, —$N(R^{20})(R^{22})$, —C(O)—$R^{20}$, —C(O)—$OR^{20}$, —C(O)—$N(R^{20})(R^{22})$, —CN and —O—$R^{20}$;
or $R^2$ and one of $R^3$ can join together with the atom to which they are attached to form a heterocyclyl;
  wherein said heterocyclyl is optionally substituted with one, two or three substituents independently selected from the group consisting of $C_{1-6}$ alkyl, —O—$R^{20}$, —$N(R^{20})(R^{22})$, —$N(R^{20})$—C(O)—$OR^{20}$ and —C(O)—$OR^{20}$; and
  wherein said $C_{1-6}$ alkyl is optionally substituted with one, two or three substituents independently selected from the group consisting of halo and heteroaryl;
each $R^4$ is independently hydrogen, deuterium, $C_{1-6}$ alkyl, —C(O)—$OR^{26}$, —C(O)—$N(R^{26})(R^{26})$, cycloalkyl, aryl, heteroaryl or heterocyclyl;
  wherein said $C_{1-6}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$,
    wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and
    wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —$N(R^{20})(R^{22})$, —C(O)—$R^{20}$, —C(O)—$OR^{20}$, —C(O)—$N(R^{20})(R^{22})$, —CN and —O—$R^{20}$,
$R^5$ is cycloalkyl, aryl, heteroaryl or heterocyclyl;
  wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —$N(R^{20})(R^{22})$, —$N(R^{20})$—$S(O)_2$—$R^{20}$, —$N(R^{20})$—C(O)—$R^{22}$, —C(O)—$R^{20}$, —C(O)—$OR^{20}$, —C(O)—$N(R^{20})(R^{22})$, —CN, oxo and —O—$R^{20}$;
    wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, $-NO_2$, $-CF_3$, $-N(R^{20})(R^{22})$, $-C(O)-R^{20}$, $-C(O)-OR^{20}$, $-C(O)-N(R^{20})(R^{22})$, $-S(O)_2-R^{20}$ and $-O-R^{20}$;

$R^{17}$ is halo, $-O-R^{20}$ or $C_{1-6}$ alkyl;

$R^{20}$ and $R^{22}$ are in each instance independently selected from the group consisting of hydrogen, $C_{1-6}$ alkyl, $C_{2-6}$ alkenyl, $C_{2-6}$ alkynyl, cycloalkyl, heterocyclyl, aryl and heteroaryl;

wherein the $C_{1-6}$ alkyl, $C_{2-6}$ alkenyl, $C_{2-6}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, $-NO_2$, $-S(O)_2R^{26}$, $-CN$, $C_{1-3}$ alkoxy, $-CF_3$, $-OCF_3$, $-OCH_2CF_3$, $-C(O)-NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, $-NO_2$, $-S(O)_2R^{26}$, $-CN$, alkoxy, $-CF_3$, $-OCF_3$, aryl, heteroaryl and cycloalkyl; and each $R^{26}$ is independently selected from the group consisting of hydrogen, $C_{1-4}$ alkyl, aryl and cycloalkyl;

wherein the $C_{1-4}$ alkyl, aryl and cycloalkyl may be further substituted with from 1 to 3 substituents independently selected from the group consisting of hydroxyl, halo, $C_{1-4}$ alkoxy, $-CF_3$ and $-OCF_3$;

or a pharmaceutically acceptable salt, ester, stereoisomer, mixture of stereoisomers or tautomer thereof;

provided that when each $R^4$ is hydrogen, $R^2$ and $R^3$ together with the atom to which they are attached form a piperazine which is optionally substituted with tert-butoxycarbonyl, Q is a bond and Cy is phenyl or morpholinyl, then n is 1, 2, 3, 4 or 5.

Some embodiments provide a method of using the compounds of Formula I, IA, IB, II, IIA, IIB, III, IIIA, IV, V, VI, VIII, VIIIA, IX, X, XII or XIII, or additional Formula(s) described throughout, in the treatment of a disease or condition in a mammal that is amenable to treatment by a late sodium channel blocker. Such diseases include cardiovascular diseases such as atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease and intermittent claudication. Such diseases may also include diabetes and conditions related to diabetes, e.g. diabetic peripheral neuropathy. Such diseases may also include conditions affecting the neuromuscular system resulting in pain, seizures or paralysis. Therefore, it is contemplated that the compounds of the disclosure and their pharmaceutically acceptable salt, ester, stereoisomer, mixture of stereoisomers and/or tautomer forms are potentially of use as medicaments for the treatment of the aforementioned diseases.

In certain embodiments, the disclosure provides pharmaceutical compositions comprising a therapeutically effective amount of a compound of the disclosure (e.g. a compound of Formula I or additional Formulas described throughout), and at least one pharmaceutically acceptable excipient.

In certain embodiments, the compound is:

4-((3-methyloxetan-3-yl)methyl)-7-(4-(trifluoromethoxy)phenyl)-3,4-dihydrobenzo[f][1,4]oxazepin-5(2H)-one (II-1);

4-(2-(pyrrolidin-1-yl)ethyl)-7-(4-(trifluoromethoxy)phenyl)-3,4-dihydrobenzo[f][1,4]oxazepin-5(2H)-one (II-3);

4-((5-cyclobutyl-1,3,4-oxadiazol-2-yl)methyl)-7-(4-(trifluoromethoxy)phenyl)-3,4-dihydrobenzo[f][1,4]oxazepin-5(2H)-one (II-4);

4-((2,3-dihydrobenzo[b][1,4]dioxin-6-yl)methyl)-7-(4-(trifluoromethoxy)phenyl)-3,4-dihydrobenzo[f][1,4]oxazepin-5(2H)-one (II-5);

4-(quinolin-2-ylmethyl)-7-(4-(trifluoromethoxy)phenyl)-3,4-dihydrobenzo[f][1,4]oxazepin-5(2H)-one (II-7);

(R)-2-(pyrimidin-2-ylmethyl)-8-(4-(trifluoromethyl)phenyl)-3,4,12,12a-tetrahydro-1H-benzo[f]pyrazino[2,1-c][1,4]oxazepin-6(2H)-one (II-8);

4-(cyclopropylmethyl)-7-(4-(trifluoromethoxy)phenyl)-3,4-dihydrobenzo[f][1,4]oxazepin-5(2H)-one (II-10);

(S)-3-methyl-4-(pyrimidin-2-ylmethyl)-7-(4-(trifluoromethyl)phenyl)-3,4-dihydrobenzo[f][1,4]oxazepin-5(2H)-one (II-12);

(R)-3-methyl-4-(pyrimidin-2-ylmethyl)-7-(4-(trifluoromethyl)phenyl)-3,4-dihydrobenzo[f][1,4]oxazepin-5(2H)-one (II-13);

6-((5-oxo-7-(4-(trifluoromethoxy)phenyl)-2,3-dihydrobenzo[f][1,4]oxazepin-4(5H)-yl)methyl)picolinonitrile (II-14);

7-(4-(trifluoromethoxy)phenyl)-4-((6-(trifluoromethyl)pyridin-2-yl)methyl)-3,4-dihydrobenzo[f][1,4]oxazepin-5(2H)-one (II-15);

7-(4-(trifluoromethoxy)phenyl)-4-((6-(trifluoromethyl)pyridin-3-yl)methyl)-3,4-dihydrobenzo[f][1,4]oxazepin-5(2H)-one (II-16);

4-((6-methylpyridin-2-yl)methyl)-7-(4-(trifluoromethoxy)phenyl)-3,4-dihydrobenzo[f][1,4]oxazepin-5(2H)-one (II-17);

(2R,11aS)-2-amino-7-(4-(trifluoromethyl)phenyl)-2,3,11,11a-tetrahydrobenzo[f]pyrrolo[2,1-c][1,4]oxazepin-5(1H)-one (II-21);

(R)-2-(2,2-difluoroethyl)-8-(4-(trifluoromethyl)phenyl)-3,4,12,12a-tetrahydro-1H-benzo[f]pyrazino[2,1-c][1,4]oxazepin-6(2H)-one (II-22);

(R)-2-ethyl-8-(4-(trifluoromethyl)phenyl)-3,4,12,12a-tetrahydro-1H-benzo[f]pyrazino[2,1-c][1,4]oxazepin-6(2H)-one (II-23);

(S)-2-(2,2-difluoroethyl)-8-(4-(trifluoromethyl)phenyl)-3,4,12,12a-tetrahydro-1H-benzo[f]pyrazino[2,1-c][1,4]oxazepin-6(2H)-one (II-24);

(S)-2-ethyl-8-(4-(trifluoromethyl)phenyl)-3,4,12,12a-tetrahydro-1H-benzo[f]pyrazino[2,1-c][1,4]oxazepin-6(2H)-one (II-25);

4-(pyrazin-2-ylmethyl)-7-(4-(trifluoromethoxy)phenyl)-3,4-dihydrobenzo[f][1,4]oxazepin-5(2H)-one (II-31);

4-((5-methyloxazol-2-yl)methyl)-7-(4-(trifluoromethoxy)phenyl)-3,4-dihydrobenzo[f][1,4]oxazepin-5(2H)-one (II-33);

7-(4-(trifluoromethoxy)phenyl)-4-(2-(2,5,5-trimethyl-1,3-dioxan-2-yl)ethyl)-3,4-dihydrobenzo[f][1,4]oxazepin-5(2H)-one (II-35);

tert-butyl (2R,11aR)-5-oxo-7-(4-(trifluoromethyl)phenyl)-1,2,3,5,11,11a-hexahydrobenzo[f]pyrrolo[2,1-c][1,4]oxazepin-2-ylcarbamate (II-39);

4-((5-(pyridin-2-yl)isoxazol-3-yl)methyl)-7-(4-(trifluoromethoxy)phenyl)-3,4-dihydrobenzo[f][1,4]oxazepin-5(2H)-one (II-41);

4-((4,6-dimethoxypyrimidin-2-yl)methyl)-7-(4-(trifluoromethoxy)phenyl)-3,4-dihydrobenzo[f][1,4]oxazepin-5(2H)-one (II-42);

ethyl 3-((5-oxo-7-(4-(trifluoromethoxy)phenyl)-2,3-dihydrobenzo[f][1,4]oxazepin-4(5H)-yl)methyl)benzoate (II-43);

4-(2-(pyrimidin-2-yl)ethyl)-7-(4-(trifluoromethoxy)phenyl)-3,4-dihydrobenzo[f][1,4]oxazepin-5(2H)-one (II-44);

4-(3,4-difluorobenzyl)-7-(4-(trifluoromethoxy)phenyl)-3,4-dihydrobenzo[f][1,4]oxazepin-5(2H)-one (II-45);

4-(2-chlorobenzyl)-7-(4-(trifluoromethoxy)phenyl)-3,4-dihydrobenzo[f][1,4]oxazepin-5(2H)-one (II-47);

4-(2,6-dichlorobenzyl)-7-(4-(trifluoromethoxy)phenyl)-3,4-dihydrobenzo[f][1,4]oxazepin-5(2H)-one (II-48);

4-(2,6-difluorobenzyl)-7-(4-(trifluoromethoxy)phenyl)-3,4-dihydrobenzo[f][1,4]oxazepin-5(2H)-one (II-49);

4-(2-(1H-pyrazol-1-yl)ethyl)-7-(4-(trifluoromethoxy)phenyl)-3,4-dihydrobenzo[f][1,4]oxazepin-5(2H)-one (II-50);

(2S,11aS)-2-amino-7-(4-(trifluoromethyl)phenyl)-2,3,11,11a-tetrahydrobenzo[f]pyrrolo[2,1-c][1,4]oxazepin-5(1H)-one (II-51);

4-(2-(pyridin-2-yl)ethyl)-7-(4-(trifluoromethoxy)phenyl)-3,4-dihydrobenzo[f][1,4]oxazepin-5(2H)-one (II-54);

4-(2-fluorobenzyl)-7-(4-(trifluoromethoxy)phenyl)-3,4-dihydrobenzo[f][1,4]oxazepin-5(2H)-one (II-57);

(R)-7-(4-(trifluoromethyl)phenyl)-2,3,11,11a-tetrahydrobenzo[f]pyrrolo[2,1-c][1,4]oxazepin-5(1H)-one (II-59);

4-(pyrimidin-2-ylmethyl)-7-(4-(trifluoromethyl)phenyl)-3,4-dihydrobenzo[f][1,4]oxazepin-5(2H)-one (II-61);

4-(4-fluorobenzyl)-7-(4-(trifluoromethoxy)phenyl)-3,4-dihydrobenzo[f][1,4]oxazepin-5(2H)-one (II-62);

4-((1-methyl-1H-pyrazol-3-yl)methyl)-7-(4-(trifluoromethoxy)phenyl)-3,4-dihydrobenzo[f][1,4]oxazepin-5(2H)-one (II-64);

4-((5-chloropyrimidin-2-yl)methyl)-7-(4-(trifluoromethoxy)phenyl)-3,4-dihydrobenzo[f][1,4]oxazepin-5(2H)-one (II-65);

4-(pyridin-4-ylmethyl)-7-(4-(trifluoromethoxy)phenyl)-3,4-dihydrobenzo[f][1,4]oxazepin-5(2H)-one (II-67);

4-((5-cyclopropyl-1,3,4-oxadiazol-2-yl)methyl)-7-(4-(trifluoromethoxy)phenyl)-3,4-dihydrobenzo[f][1,4]oxazepin-5(2H)-one (II-68);

4-(2-(pyrimidin-2-yloxy)ethyl)-7-(4-(trifluoromethoxy)phenyl)-3,4-dihydrobenzo[f][1,4]oxazepin-5(2H)-one (II-69);

4-(pyridin-3-ylmethyl)-7-(4-(trifluoromethoxy)phenyl)-3,4-dihydrobenzo[f][1,4]oxazepin-5(2H)-one (II-70);

4-(pyrimidin-2-ylmethyl)-7-(4-(trifluoromethyl)phenyl)-3,4-dihydrobenzo[f][1,4]oxazepin-5(2H)-one (II-72);

4-(pyrimidin-2-ylmethyl)-7-(4-(trifluoromethoxy)phenyl)-3,4-dihydrobenzo[f][1,4]oxazepin-5(2H)-one (II-73);

4-((3-methylpyridin-2-yl)methyl)-7-(4-(trifluoromethoxy)phenyl)-3,4-dihydrobenzo[f][1,4]oxazepin-5(2H)-one (II-75);

(R)-2-(2,2,2-trifluoroethyl)-8-(4-(trifluoromethyl)phenyl)-3,4,12,12a-tetrahydro-1H-benzo[f]pyrazino[2,1-c][1,4]oxazepin-6(2H)-one (II-83);

4-(pyrimidin-2-ylmethyl)-7-p-tolyl-3,4-dihydrobenzo[f][1,4]oxazepin-5(2H)-one (II-87);

7-(4-chlorophenyl)-4-(pyrimidin-2-ylmethyl)-3,4-dihydrobenzo[f][1,4]oxazepin-5(2H)-one (II-88);

7-(4-isopropylphenyl)-4-(pyrimidin-2-ylmethyl)-3,4-dihydrobenzo[f][1,4]oxazepin-5(2H)-one (II-89);

7-(4-ethylphenyl)-4-(pyrimidin-2-ylmethyl)-3,4-dihydrobenzo[f][1,4]oxazepin-5(2H)-one (II-91);

7-(4-cyclopropylphenyl)-4-(pyrimidin-2-ylmethyl)-3,4-dihydrobenzo[f][1,4]oxazepin-5(2H)-one (II-92);

(R)-4-(1-(pyrimidin-2-yl)ethyl)-7-(4-(trifluoromethyl)phenyl)-3,4-dihydrobenzo[f][1,4]oxazepin-5(2H)-one (II-95);

7-(4-isobutoxyphenyl)-4-(pyrimidin-2-ylmethyl)-3,4-dihydrobenzo[f][1,4]oxazepin-5(2H)-one (II-97);

7-(4-tert-butylphenyl)-4-(pyrimidin-2-ylmethyl)-3,4-dihydrobenzo[f][1,4]oxazepin-5(2H)-one (II-98);

7-(4-cyclopropoxyphenyl)-4-(pyrimidin-2-ylmethyl)-3,4-dihydrobenzo[f][1,4]oxazepin-5(2H)-one (II-102);

7-(4-fluorophenyl)-4-(pyrimidin-2-ylmethyl)-3,4-dihydrobenzo[f][1,4]oxazepin-5(2H)-one (II-104);

7-(2-fluoro-4-(trifluoromethyl)phenyl)-4-(pyrimidin-2-ylmethyl)-3,4-dihydrobenzo[f][1,4]oxazepin-5(2H)-one (II-105);

7-(3-fluoro-4-(2,2,2-trifluoroethoxy)phenyl)-4-(pyrimidin-2-ylmethyl)-3,4-dihydrobenzo[f][1,4]oxazepin-5(2H)-one (II-106);

4-(pyrimidin-2-ylmethyl)-7-(4-(2,2,2-trifluoroethoxy)phenyl)-3,4-dihydrobenzo[f][1,4]oxazepin-5(2H)-one (II-107);

7-(2-chloro-4-(trifluoromethyl)phenyl)-4-(pyrimidin-2-ylmethyl)-3,4-dihydrobenzo[f][1,4]oxazepin-5(2H)-one (II-110);

7-(4-(trifluoromethoxy)phenyl)-4-((4-(trifluoromethyl)pyrimidin-2-yl)methyl)-3,4-dihydrobenzo[f][1,4]oxazepin-5(2H)-one (II-113);

7-(4-(trifluoromethoxy)phenyl)-4-((5-(6-(trifluoromethyl)pyridin-3-yl)pyrimidin-2-yl)methyl)-3,4-dihydrobenzo[f][1,4]oxazepin-5(2H)-one (II-115);

7-(4-chloro-2-fluorophenyl)-4-(pyrimidin-2-ylmethyl)-3,4-dihydrobenzo[f][1,4]oxazepin-5(2H)-one (II-117);

1-(4-(5-oxo-4-(pyrimidin-2-ylmethyl)-2,3,4,5-tetrahydrobenzo[f][1,4]oxazepin-7-yl)phenyl)cyclopentanecarbonitrile (II-122);

7-(4-ethoxyphenyl)-4-(pyrimidin-2-ylmethyl)-3,4-dihydrobenzo[f][1,4]oxazepin-5(2H)-one (II-123);

7-(4-(difluoromethyl)phenyl)-4-(pyrimidin-2-ylmethyl)-3,4-dihydrobenzo[f][1,4]oxazepin-5(2H)-one (II-124);

4-(imidazo[1,2-a]pyridin-2-ylmethyl)-7-(4-(trifluoromethyl)phenyl)-3,4-dihydrobenzo[f][1,4]oxazepin-5(2H)-one (II-129);

4-((4-morpholinopyrimidin-2-yl)methyl)-7-(4-(trifluoromethoxy)phenyl)-3,4-dihydrobenzo[f][1,4]oxazepin-5(2H)-one (II-133);

4-benzyl-7-(4-(trifluoromethoxy)phenyl)-3,4-dihydrobenzo[f][1,4]oxazepin-5(2H)-one (II-134);

4-(imidazo[1,2-a]pyridin-2-ylmethyl)-7-(4-(trifluoromethyl)phenyl)-3,4-dihydrobenzo[f][1,4]oxazepin-5(2H)-one (II-135);

7-(3-fluoro-4-(trifluoromethyl)phenyl)-4-(pyrimidin-2-ylmethyl)-3,4-dihydrobenzo[f][1,4]oxazepin-5(2H)-one (II-136);

4-((4-methoxypyrimidin-2-yl)methyl)-7-(4-(trifluoromethoxy)phenyl)-3,4-dihydrobenzo[f][1,4]oxazepin-5(2H)-one (II-137);

4-(4-methylpyrimidin-2-yl)methyl)-7-(4-(trifluoromethoxy) phenyl)-3,4-dihydrobenzo[f][1,4]oxazepin-5(2H)-one (II-138);

4-((4-(piperidin-1-yl)pyrimidin-2-yl)methyl)-7-(4-(trifluoromethoxy)phenyl)-3,4-dihydrobenzo[f][1,4]oxazepin-5 (2H)-one (II-139);

4-((4-(dimethylamino)pyrimidin-2-yl)methyl)-7-(4-(trifluoromethoxy)phenyl)-3,4-dihydrobenzo[f][1,4]oxazepin-5 (2H)-one (II-140);

4-benzyl-7-(4-(trifluoromethyl)phenyl)-3,4-dihydrobenzo [f][1,4]oxazepin-5(2H)-one (II-141);

4-((3-methoxypyridin-2-yl)methyl)-7-(4-(trifluoromethoxy) phenyl)-3,4-dihydrobenzo[f][1,4]oxazepin-5(2H)-one (II-143);

7-(4-(cyclobutylmethoxy)phenyl)-4-(pyrimidin-2-ylmethyl)-3,4-dihydrobenzo[f][1,4]oxazepin-5(2H)-one (II-144);

7-(2-methyl-4-(trifluoromethyl)phenyl)-4-(pyrimidin-2-ylmethyl)-3,4-dihydrobenzo[f][1,4]oxazepin-5(2H)-one (II-145);

7-(2-methyl-4-(trifluoromethoxy)phenyl)-4-(pyrimidin-2-ylmethyl)-3,4-dihydrobenzo[f][1,4]oxazepin-5(2H)-one (II-146);

4-((1-(difluoromethyl)-1H-pyrazol-3-yl)methyl)-7-(4-(trifluoromethoxy)phenyl)-3,4-dihydrobenzo[f][1,4]oxazepin-5(2H)-one (II-147);

7-(4-(trifluoromethoxy)phenyl)-4-((3-(trifluoromethyl)-1H-pyrazol-1-yl)methyl)-3,4-dihydrobenzo[f][1,4]oxazepin-5(2H)-one (II-148);

4-(pyrimidin-2-ylmethyl)-7-(4-(2,2,2-trifluoroethyl)phenyl)-3,4-dihydrobenzo[f][1,4]oxazepin-5(2H)-one (II-150);

4-(pyridin-2-ylmethyl)-7-(4-(2,2,2-trifluoroethyl)phenyl)-3,4-dihydrobenzo[f][1,4]oxazepin-5(2H)-one (II-151);

4-((1-cyclopentyl-1H-pyrazol-3-yl)methyl)-7-(4-(trifluoromethoxy)phenyl)-3,4-dihydrobenzo[f][1,4]oxazepin-5 (2H)-one (II-152);

4-((1-ethyl-1H-pyrazol-3-yl)methyl)-7-(4-(trifluoromethoxy)phenyl)-3,4-dihydrobenzo[f][1,4]oxazepin-5 (2H)-one (II-153);

4-((1-methyl-1H-imidazol-4-yl)methyl)-7-(4-(trifluoromethoxy)phenyl)-3,4-dihydrobenzo[f][1,4]oxazepin-5 (2H)-one (II-154);

4-((4-methyl-1H-pyrazol-1-yl)methyl)-7-(4-(trifluoromethoxy)phenyl)-3,4-dihydrobenzo[f][1,4]oxazepin-5 (2H)-one (II-155);

4-((4-chloro-1H-pyrazol-1-yl)methyl)-7-(4-(trifluoromethoxy)phenyl)-3,4-dihydrobenzo[f][1,4]oxazepin-5 (2H)-one (II-156);

7-(4-(difluoromethyl)phenyl)-4-(pyridin-2-ylmethyl)-3,4-dihydrobenzo[f][1,4]oxazepin-5(2H)-one (II-157);

7-(4-chloro-3-fluorophenyl)-4-(pyridin-2-ylmethyl)-3,4-dihydrobenzo[f][1,4]oxazepin-5(2H)-one (II-158);

7-(4-(difluoromethoxy)phenyl)-4-(pyridin-2-ylmethyl)-3,4-dihydrobenzo[f][1,4]oxazepin-5(2H)-one (II-159);

4-((1-methyl-1H-pyrazol-4-yl)methyl)-7-(4-(trifluoromethoxy)phenyl)-3,4-dihydrobenzo[f][1,4]oxazepin-5 (2H)-one (II-160);

4-(pyrimidin-2-ylmethyl)-7-(2,3,4-trifluorophenyl)-3,4-dihydrobenzo[f][1,4]oxazepin-5(2H)-one (II-162);

7-(3,4-difluorophenyl)-4-(pyrimidin-2-ylmethyl)-3,4-dihydrobenzo[f][1,4]oxazepin-5 (2H)-one (II-163);

4-((3-fluoropyridin-2-yl)methyl)-7-(4-(trifluoromethoxy) phenyl)-3,4-dihydrobenzo[f][1,4]oxazepin-5(2H)-one (II-164);

4-benzyl-9-fluoro-7-(4-(trifluoromethoxy)phenyl)-3,4-dihydrobenzo[f][1,4]oxazepin-5(2H)-one (II-165);

4-benzyl-9-fluoro-7-(4-(trifluoromethyl)phenyl)-3,4-dihydrobenzo[f][1,4]oxazepin-5(2H)-one (II-166);

4-benzyl-8-fluoro-7-(4-(trifluoromethoxy)phenyl)-3,4-dihydrobenzo[f][1,4]oxazepin-5(2H)-one (II-167);

4-benzyl-8-fluoro-7-(4-(trifluoromethyl)phenyl)-3,4-dihydrobenzo[f][1,4]oxazepin-5(2H)-one (II-168);

7-(4-chloro-3-fluorophenyl)-4-((3-fluoropyridin-2-yl) methyl)-3,4-dihydrobenzo[f][1,4]oxazepin-5(2H)-one (II-169);

7-(2-fluoro-4-(trifluoromethyl)phenyl)-4-(3-fluoropyridin-2-yl)methyl)-3,4-dihydrobenzo[f][1,4]oxazepin-5(2H)-one (II-170);

4-(5-oxo-4-(pyrimidin-2-ylmethyl)-2,3,4,5-tetrahydrobenzo [f][1,4]oxazepin-7-yl)phenyl trifluoromethanesulfonate (II-171);

4-((5-methylpyrazin-2-yl)methyl)-7-(4-(trifluoromethoxy) phenyl)-3,4-dihydrobenzo[f][1,4]oxazepin-5(2H)-one (II-172);

2,2,3,3-tetradeutero-4-(pyrimidin-2-ylmethyl)-7-(4-(trifluoromethoxy)phenyl)-3,4-dihydrobenzo[f][1,4]oxazepin-5 (2H)-one (II-174);

4-((6-methylpyrazin-2-yl)methyl)-7-(4-(trifluoromethoxy) phenyl)-3,4-dihydrobenzo[f][1,4]oxazepin-5(2H)-one (II-175);

4-((3-fluoropyridin-2-yl)methyl)-7-(4-(trifluoromethyl)phenyl)-3,4-dihydrobenzo[f][1,4]oxazepin-5(2H)-one (II-176);

N-(2-(5-oxo-7-(4-(trifluoromethoxy)phenyl)-2,3-dihydrobenzo[f][1,4]oxazepin-4(5H)-yl)ethyl)benzenesulfonamide (II-177);

N-(2-(5-oxo-7-(4-(trifluoromethoxy)phenyl)-2,3-dihydrobenzo[f][1,4]oxazepin-4(5H)-yl)ethyl)cyclopropanesulfonamide (II-179);

4-((1-methyl-1H-imidazol-2-yl)methyl)-7-(4-(trifluoromethoxy)phenyl)-3,4-dihydrobenzo[f][1,4]oxazepin-5 (2H)-one (II-186);

4-((1-benzyl-1H-imidazol-2-yl)methyl)-7-(4-(trifluoromethoxy)phenyl)-3,4-dihydrobenzo[f][1,4]oxazepin-5 (2H)-one (II-187);

4-(imidazo[1,2-a]pyridin-2-ylmethyl)-7-(4-(trifluoromethoxy)phenyl)-3,4-dihydrobenzo[f][1,4]oxazepin-5 (2H)-one (II-189);

N-cyclopropyl-3-(5-oxo-7-(4-(trifluoromethoxy)phenyl)-2, 3-dihydrobenzo[f][1,4]oxazepin-4(5H)-yl)propane-1-sulfonamide (II-190);

N-(2-(5-oxo-7-(4-(trifluoromethoxy)phenyl)-2,3-dihydrobenzo[f][1,4]oxazepin-4(5H)-yl)ethyl)pyrimidine-2-carboxamide (II-192);

7-(4-(4-fluorophenoxy)phenyl)-4-(pyrimidin-2-ylmethyl)-3,4-dihydrobenzo[f][1,4]oxazepin-5(2H)-one (II-193);

7-(4-phenoxyphenyl)-4-(pyrimidin-2-ylmethyl)-3,4-dihydrobenzo[f][1,4]oxazepin-5(2H)-one (II-194);

7-(3-phenoxyphenyl)-4-(pyrimidin-2-ylmethyl)-3,4-dihydrobenzo[f][1,4]oxazepin-5(2H)-one (II-195);

7-(4-tert-butylcyclohex-1-enyl)-4-(pyrimidin-2-ylmethyl)-3,4-dihydrobenzo[f][1,4]oxazepin-5(2H)-one (V-1);

7-cyclohexenyl-4-(pyrimidin-2-ylmethyl)-3,4-dihydrobenzo[f][1,4]oxazepin-5(2H)-one (V-3);

7-(4-methylcyclohex-1-enyl)-4-(pyrimidin-2-ylmethyl)-3, 4-dihydrobenzo[f][1,4]oxazepin-5(2H)-one (V-5);

7-(2-tert-butoxypyridin-4-yl)-4-(pyridin-2-ylmethyl)-3,4-dihydrobenzo[f][1,4]oxazepin-5(2H)-one (VI-4);

7-(1-methyl-2-oxo-1,2-dihydropyridin-4-yl)-4-(pyridin-2-ylmethyl)-3,4-dihydrobenzo[f][1,4]oxazepin-5(2H)-one (VI-12);

4-(pyridin-2-ylmethyl)-7-(5-(trifluoromethyl)pyridin-2-yl)-3,4-dihydrobenzo[f][1,4]oxazepin-5(2H)-one (VI-26);

7-(2-isopropylthiazol-4-yl)-4-(pyridin-2-ylmethyl)-3,4-dihydrobenzo[f][1,4]oxazepin-5(2H)-one (VI-30);

4-(pyridin-2-ylmethyl)-7-(5-(trifluoromethyl)thiophen-2-yl)-3,4-dihydrobenzo[f][1,4]oxazepin-5(2H)-one (VI-31);

7-(5-cyclopropylthiophen-2-yl)-4-(pyridin-2-ylmethyl)-3,4-dihydrobenzo[f][1,4]oxazepin-5(2H)-one (VI-32);

7-(5-cyclopropylthiophen-2-yl)-4-(pyrimidin-2-ylmethyl)-3,4-dihydrobenzo[f][1,4]oxazepin-5(2H)-one (VI-36); and 4-(pyrimidin-2-ylmethyl)-7-(5-(trifluoromethyl)thiophen-2-yl)-3,4-dihydrobenzo[f][1,4]oxazepin-5(2H)-one (VI-37);

4-(pyrimidin-2-ylmethyl)-7-((4-(trifluoromethoxy)phenyl)ethynyl)-3,4-dihydrobenzo[f][1,4]oxazepin-5(2H)-one (VIII-4);

7-(phenylethynyl)-4-(pyrimidin-2-ylmethyl)-3,4-dihydrobenzo[f][1,4]oxazepin-5(2H)-one (VIII-5);

4-(pyrimidin-2-ylmethyl)-7-((4-(trifluoromethyl)phenyl)ethynyl)-3,4-dihydrobenzo[f][1,4]oxazepin-5(2H)-one (VIII-6);

4-(pyridin-2-ylmethyl)-7-(4-(trifluoromethyl)phenethyl)-3,4-dihydrobenzo[f][1,4]oxazepin-5(2H)-one (VIII-7);

4-(pyrimidin-2-ylmethyl)-7-(4-(trifluoromethyl)phenethyl)-3,4-dihydrobenzo[f][1,4]oxazepin-5(2H)-one (VIII-8);

4-((3-fluoropyridin-2-yl)methyl)-7-(4-(trifluoromethyl)phenethyl)-3,4-dihydrobenzo[f][1,4]oxazepin-5(2H)-one (VIII-9);

(E)-4-benzyl-7-(4-(trifluoromethyl)styryl)-3,4-dihydrobenzo[f][1,4]oxazepin-5(2H)-one (VIII-10); and 4-benzyl-7-(4-(trifluoromethyl)phenethyl)-3,4-dihydrobenzo[f][1,4]oxazepin-5(2H)-one (VIII-11);

2-((pyrimidin-2-yl)methyl)-8-(4-(trifluoromethyl)phenyl)-3,4-dihydro-2H-benzo[b][1,4,5]oxathiazepin-sulfone (IX-2);

2-((5-chloropyrimidin-2-yl)methyl)-8-(4-(trifluoromethyl)phenyl)-3,4-dihydro-2H-benzo[b][1,4,5]oxathiazepin-sulfone (IX-3);

4-(2-(benzyloxy)ethyl)-1-methyl-7-(4-(trifluoromethoxy)phenyl)-3,4-dihydro-1H-benzo[e][1,4]diazepine-2,5-dione (X-7);

4-benzyl-7-(4-(trifluoromethyl)phenyl)-3,4-dihydro-1H-benzo[e][1,4]diazepine-2,5-dione (X-8);

4-benzyl-1-methyl-7-(4-(trifluoromethyl)phenyl)-3,4-dihydro-1H-benzo[e][1,4]diazepine-2,5-dione (X-11);

5-benzyl-8-(4-(trifluoromethyl)phenyl)-4H-benzo[f]imidazo[1,2-a][1,4]diazepin-6(5H)-one (X-12);

4-benzyl-7-(4-(trifluoromethoxy)phenyl)-3,4-dihydropyrido[4,3-f][1,4]oxazepin-5(2H)-one (XII-1);

4-benzyl-7-(4-(trifluoromethoxy)phenyl)-3,4-dihydropyrido[2,3-f][1,4]oxazepin-5(2H)-one (XII-2);

4-benzyl-7-(4-(trifluoromethyl)phenyl)-3,4-dihydropyrido[2,3-f][1,4]oxazepin-5(2H)-one (XII-3);

4-(pyrimidin-2-ylmethyl)-7-(4-(trifluoromethoxy)phenyl)-3,4-dihydropyrido[4,3-f][1,4]oxazepin-5(2H)-one (XII-5);

4-((4-methylpyrimidin-2-yl)methyl)-7-(4-(trifluoromethoxy)phenyl)-3,4-dihydropyrido[4,3-f][1,4]oxazepin-5(2H)-one (XII-8);

4-(cyclopropylmethyl)-7-(4-(trifluoromethoxy)phenyl)-3,4-dihydropyrido[4,3-f][1,4]oxazepin-5(2H)-one (XII-9);

4-((3-methoxypyridin-2-yl)methyl)-7-(4-(trifluoromethoxy)phenyl)-3,4-dihydropyrido[4,3-f][1,4]oxazepin-5(2H)-one (XII-10);

4-((3-fluoropyridin-2-yl)methyl)-7-(4-(trifluoromethoxy)phenyl)-3,4-dihydropyrido[4,3-f][1,4]oxazepin-5(2H)-one (XII-11);

4-((4-methoxypyrimidin-2-yl)methyl)-7-(4-(trifluoromethoxy)phenyl)-3,4-dihydropyrido[4,3-f][1,4]oxazepin-5(2H)-one (XII-14);

4-(pyrimidin-2-ylmethyl)-7-(4-(trifluoromethoxy)phenylamino)-3,4-dihydrobenzo[f][1,4]oxazepin-5(2H)-one (XIII-1);

4-(pyrimidin-2-ylmethyl)-7-(4-(trifluoromethoxy)phenoxy)-3,4-dihydrobenzo[f][1,4]oxazepin-5(2H)-one (XIII-2);

4-(pyrimidin-2-ylmethyl)-7-(4-(trifluoromethyl)phenylamino)-3,4-dihydrobenzo[f][1,4]oxazepin-5(2H)-one (XIII-3);

4-(pyridin-2-ylmethyl)-7-(4-(trifluoromethoxy)phenylamino)-3,4-dihydrobenzo[f][1,4]oxazepin-5(2H)-one (XIII-4);

4-(pyridin-2-ylmethyl)-7-(4-(trifluoromethyl)phenylamino)-3,4-dihydrobenzo[f][1,4]oxazepin-5(2H)-one (XIII-6); or 7-(methyl(4-(trifluoromethoxy)phenyl)amino)-4-(pyrimidin-2-ylmethyl)-3,4-dihydrobenzo[f][1,4]oxazepin-5(2H)-one (XIII-10);

or a pharmaceutically acceptable salt, ester, stereoisomer, mixture of stereoisomers or tautomer thereof.

In other embodiments, the compound is:

4-(2,2-difluoroethyl)-7-(4-(trifluoromethoxy)phenyl)-3,4-dihydrobenzo[f][1,4]oxazepin-5(2H)-one (II-6);

4-(2-methoxyethyl)-7-(4-(trifluoromethoxy)phenyl)-3,4-dihydrobenzo[f][1,4]oxazepin-5(2H)-one (II-11);

(R)-3-methyl-7-(4-(trifluoromethyl)phenyl)-3,4-dihydrobenzo[f][1,4]oxazepin-5(2H)-one (II-19);

4-methyl-7-(4-(trifluoromethoxy)phenyl)-3,4-dihydrobenzo[f][1,4]oxazepin-5(2H)-one (II-46);

(S)-3-isopropyl-7-(4-(trifluoromethyl)phenyl)-3,4-dihydrobenzo[f][1,4]oxazepin-5(2H)-one (II-77);

3-(pyridin-2-ylmethyl)-7-(4-(trifluoromethoxy)phenyl)-3,4-dihydrobenzo[f][1,4]oxazepin-5(2H)-one (II-142);

N-(2-(5-oxo-7-(4-(trifluoromethoxy)phenyl)-2,3-dihydrobenzo[f][1,4]oxazepin-4(5H)-yl)ethyl)ethanesulfonamide (II-178); or 4-(3-(azetidin-1-ylsulfonyl)propyl)-7-(4-(trifluoromethoxy)phenyl)-3,4-dihydrobenzo[f][1,4]oxazepin-5(2H)-one (II-191);

or a pharmaceutically acceptable salt, ester, stereoisomer, mixture of stereoisomers or tautomer thereof.

In other embodiments, the compound is:

pyrimidin-2-yl(7-(4-(trifluoromethoxy)phenyl)-2,3-dihydrobenzo[f][1,4]oxazepin-4(5H)-yl)methanone (III-1);

phenyl(7-(4-(trifluoromethoxy)phenyl)-2,3-dihydrobenzo[f][1,4]oxazepin-4(5H)-yl)methanone (III-4);

(1-methylcyclopropyl)(7-(4-(trifluoromethoxy)phenyl)-2,3-dihydrobenzo[f][1,4]oxazepin-4(5H)-yl)methanone (III-10);

(3,3-difluorocyclobutyl)(7-(4-(trifluoromethoxy)phenyl)-2,3-dihydrobenzo[f][1,4]oxazepin-4(5H)-yl)methanone (III-11);

(1-methyl-1H-pyrazol-4-yl)(7-(4-(trifluoromethoxy)phenyl)-2,3-dihydrobenzo[f][1,4]oxazepin-4(5H)-yl)methanone (III-12);

(1H-pyrazol-3-yl)(7-(4-(trifluoromethoxy)phenyl)-2,3-dihydrobenzo[f][1,4]oxazepin-4(5H)-yl)methanone (III-15);

pyrazin-2-yl(7-(4-(trifluoromethoxy)phenyl)-2,3-dihydrobenzo[f][1,4]oxazepin-4(5H)-yl)methanone (III-23);

pyridazin-3-yl(7-(4-(trifluoromethoxy)phenyl)-2,3-dihydrobenzo[f][1,4]oxazepin-4(5H)-yl)methanone (III-24);
2-(pyridin-2-yl)-1-(7-(4-(trifluoromethyl)phenyl)-2,3-dihydrobenzo[f][1,4]oxazepin-4(5H)-yl)ethanone (III-29);
2-(pyrimidin-2-yl)-1-(7-(4-(trifluoromethyl)phenyl)-2,3-dihydrobenzo[f][1,4]oxazepin-4(5H)-yl)ethanone (III-30);
(1-methyl-1H-imidazol-5-yl)(7-(4-(trifluoromethyl)phenyl)-2,3-dihydrobenzo[f][1,4]oxazepin-4(5H)-yl)methanone (III-32);
(1H-imidazol-2-yl)(7-(4-(trifluoromethyl)phenyl)-2, 3-dihydrobenzo[f][1,4]oxazepin-4(5H)-yl)methanone (III-33);
(1-methyl-1H-imidazol-2-yl)(7-(4-(trifluoromethyl)phenyl)-2, 3-dihydrobenzo[f][1,4]oxazepin-4(5H)-yl)methanone (III-37);
(R)-(2-methyl-7-(4-(trifluoromethoxy)phenyl)-2,3-dihydrobenzo[f][1,4]oxazepin-4(5H)-yl)(pyrimidin-2-yl)methanone (III-38);
tert-butyl 2-(7-(4-(trifluoromethyl)phenyl)-2,3,4,5-tetrahydrobenzo[f][1,4]oxazepine-4-carbonyl)-5,6-dihydroimidazo[1,2-a]pyrazine-7(8H)-carboxylate (III-40);
(1H-1,2,4-triazol-3-yl)(7-(4-(trifluoromethyl)phenyl)-2,3-dihydrobenzo[f][1,4]oxazepin-4(5H)-yl)methanone (III-50); or
(1,5-dimethyl-1H-pyrazol-3-yl)(7-(4-(trifluoromethoxy)phenyl)-2,3-dihydrobenzo[f][1,4]oxazepin-4(5H)-yl)methanone (III-58);
or a pharmaceutically acceptable salt, ester, stereoisomer, mixture of stereoisomers or tautomer thereof.

The inventions of this disclosure are described throughout. In addition, specific embodiments of the invention are as disclosed herein.

DETAILED DESCRIPTION

1. Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)— heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or
2) an alkyl group as defined above that is interrupted by 1-10 atoms (e.g. 1, 2, 3, 4 or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or
3) an alkyl group as defined above that has both 1, 2, 3, 4 or 5 substituents as defined above and is also interrupted by 1-10 atoms (e.g. 1, 2, 3, 4 or 5 atoms) as defined above.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, in some embodiments, having 1, 2, 3, 4, 5 or 6 carbon atoms.

The term "substituted alkylene" refers to an alkylene group as defined above having 1 to 5 substituents (in some embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH=CH$_2$), 1-propylene (or allyl, i.e. —CH$_2$CH=CH$_2$), isopropylene (—C(CH$_3$)=CH$_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkenylene" refers to a diradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "alkynylene" refers to a diradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "C$_{1-3}$ haloalkyl" refers to an alkyl group having from 1 to 3 carbon atoms covalently bonded to from 1 to 7, or from 1 to 6, or from 1 to 3, halogen(s), where alkyl and halogen are defined herein. In some embodiments, C$_{1-3}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)— cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. In addition, a substituent on the heterocyclic group may be attached to the same carbon atom as, or is geminal to, the attachment of the substituted heterocyclic group to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, $CF_3$, amino, substituted amino, cyano or $—S(O)_nR^a$, in which $R^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_n R^a$, in which $R^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_n R^a$, in which $R^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_n R^a$, in which $R^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2.

The term "alkoxycarbonylamino" refers to the group $—N(R^d)C(O)OR$ in which R is alkyl and $R^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_n R^a$, in which $R^a$ is alkyl, aryl or heteroaryl and n is 0, 1 or 2.

The term "aminocarbonylamino" refers to the group $—NR^cC(O)NRR$, wherein $R^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_n R^a$, in which $R^a$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group $—S(O)_2R$, in which R is alkyl, cycloalkyl, heterocyclyl, aryl or heteroaryl. "Substituted sulfone" refers to a group $—S(O)_2R$, in which R is substituted alkyl, substituted cycloalkyl, substituted heterocyclyl, substituted aryl or substituted heteroaryl, as defined herein.

The term "aminosulfonyl" refers to the group $—S(O)_2$NRR, wherein each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and $—S(O)_nR^a$, in which $R^a$ is alkyl, aryl or heteroaryl and n is 0, 1 or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given formula (e.g. the compound of Formula I, which also includes Formula IA, IB, II, IIA, III, IIIA, IV, V, VI, VIII, VIIIA, IX, X, XI and XIII) is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers. Non-limiting examples of amide-comprising and imidic acid-comprising tautomers are shown below:

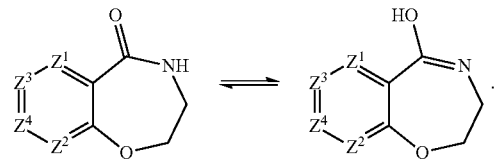

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of Formula I, IA, IB, II, IIA, BB, III, IIIA, IV, V, VI, VIII, VIIIA, IX, X, XII or XIII and a solvent.

The term "hydrate" refers to the complex formed by the combining of a compound of Formula I, IA, IB, II, IIA, IIB, III, IIIA, IV, V, VI, VIII, VIIIA, IX, X, XII or XIII and water.

The term "prodrug" refers to compounds of Formula I, IA, IB, II, IIA, IIB, III, IIIA, IV, V, VI, VIII, VIIIA, IX, X, XII or XIII that include chemical groups which, in vivo, can be converted and/or can be split off from the remainder of the molecule to provide for the active drug, a pharmaceutically acceptable salt thereof or a biologically active metabolite thereof.

Any formula or structure given herein, including Formula I, IA, IB, II, IIA, BB, III, IIIA, IV, V, VI, VIII, VIIIA, IX, X, XII or XIII compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, IA, IB, II, IIA, IIB, III, IIIA, IV, V, VI, VIII, VIIIA, IX, X, XII or XIII in which from 1 to n hydrogens attached to a carbon atom is/are replaced by deuterium, in which n is the number of hydrogens in the molecule. Such compounds exhibit increased resistance to metabolism and are thus useful for increasing the half life of any compound of Formula I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "treatment" or "treating" means administration of a compound of the invention, by or at the direction of a competent caregiver, to a mammal having a disease for purposes including:
 (i) preventing the disease, that is, causing the clinical symptoms of the disease not to develop;
 (ii) inhibiting the disease, that is, arresting the development of clinical symptoms; and/or
 (iii) relieving the disease, that is, causing the regression of clinical symptoms.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroayl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to $NH(heteroaryl)_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs or calves when walking, climbing stairs or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia and the ventricular tachycardias (VTs), including idiopathic ventricular tachycardia, ventricular fibrillation, pre-excitation syndrome and Torsade de Pointes (TdP).

2. Nomenclature

Names of compounds of the present disclosure are provided using ACD/Name software for naming chemical compounds (Advanced Chemistry Development, Inc., Toronto, Canada). Other compounds or radicals may be named with common names or systematic or non-systematic names. The naming and numbering of the compounds of the disclosure is illustrated with a representative compound of Formula I:

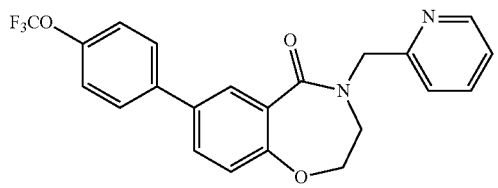

which is named 4-(pyridin-2-ylmethyl)-7-(4-(trifluoromethoxy)phenyl)-3,4-dihydrobenzo[f][1,4]oxazepin-5(2H)-one.

3. Compounds

Accordingly, typical embodiments the present disclosure provide novel compounds that function as late sodium channel blockers. In one embodiment, the disclosure provides compounds of Formula I:

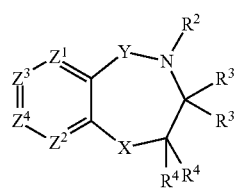

I wherein:

$Z^1$ and $Z^2$ are each independently selected from the group consisting of $CR^7$ and N;

$Z^3$ and $Z^4$ are each independently selected from the group consisting of $CR^7$, C-Q-$R^1$ and N, provided that one of $Z^3$ and $Z^4$ is C-Q-$R^1$ and the other of $Z^3$ and $Z^4$ is $CR^7$ or N and further provided that only one of $Z^1$, $Z^2$ and $Z^4$ is N;

X is —O— or —$NR^6$—;

Y is —C(O)—, —C($R^{11}$)$_2$— or —S(O)$_2$—;

Q is a covalent bond, —O—$C_{0-2}$ alkylene, —$NR^{11}$—$C_{0-2}$ alkylene, $C_2$ alkylene, $C_2$ alkenylene or $C_2$ alkynylene;

$R^1$ is aryl, cycloalkyl, cycloalkenyl, heterocyclyl or heteroaryl;
  wherein said aryl, cycloalkyl, cycloalkenyl, heterocyclyl or heteroaryl are optionally substituted with one, two or three substituents independently selected from the group consisting of halo, —$NO_2$, —CN, —$SF_5$, —Si($CH_3$)$_3$, —O—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—S(O)$_2$—$R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
  wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;
  wherein each —$C_{1-6}$ alkylene is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—$OR^{26}$, —C(O)—N($R^{20}$)($R^{22}$), —N($R^{20}$)—S(O)$_2R^{20}$, cycloalkyl, aryl, heteroaryl or heterocyclyl; and
  wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

L is —O—, —S—, —C(O)—, —NHS(O)$_2$—, —S(O)$_2$NH—, —C(O)NH—, or —NHC(O)—; provided that when Y is —C($R^{11}$)$_2$—, then $R^2$ is -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$ and L is not —C(O)—; and when $R^2$ is -L-$R^5$ or -L-$C_{1-6}$ alkylene-$R^5$, then L is not —O—, —S—, —NHS(O)$_2$— or —NHC(O)—;

each $R^3$ is independently hydrogen, deuterium, $C_{1-6}$ alkyl, cycloalkyl, aryl, heteroaryl or heterocyclyl;
  wherein said $C_{1-6}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;
  wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
wherein said C$_{1-6}$ alkyl, aralkyl, cycloalkyl, aryl, heterocyclyl or heteroaryl, are optionally further substituted with one, two or three substituents independently selected from the group consisting of halo, —NO$_2$, —N(R$^{20}$)(R$^{22}$), —C(O)R$^{20}$, —C(O)—OR$^{20}$, —C(O)—N(R$^{20}$)(R$^{22}$), —CN and —O—R$^{20}$;
or when Y is —C(O)—, then R$^2$ and one of R$^3$ can join together with the atom to which they are attached to form a heterocyclyl;
wherein said heterocyclyl is optionally substituted with one, two or three substituents independently selected from the group consisting of C$_{1-6}$ alkyl, —O—R$^{20}$, —N(R$^{20}$)(R$^{22}$), —N(R$^{20}$)—C(O)—OR$^{20}$ and —C(O)—OR$^{20}$; and
wherein said C$_{1-6}$ alkyl is optionally substituted with one, two or three substituents independently selected from the group consisting of halo and heteroaryl;
each R$^4$ is independently hydrogen, deuterium, C$_{1-6}$ alkyl, —C(O)—OR$^{26}$, —C(O)—N(R$^{26}$)(R$^{26}$), cycloalkyl, aryl, heteroaryl or heterocyclyl;
wherein said C$_{1-6}$ alkyl is optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
wherein said C$_{1-6}$ alkyl, aralkyl, cycloalkyl, aryl, heterocyclyl, heteroaryl, are optionally further substituted with one, two or three substituents independently selected from the group consisting of hydroxyl, halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
or two R$^3$ or two R$^4$ together with the carbon atom to which they are attached form an oxo;
R$^5$ is cycloalkyl, aryl, heteroaryl or heterocyclyl;
wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN, oxo and —O—R$^{20}$;
wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
wherein said C$_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —CN, —S(O)$_2$—R$^{20}$ and —O—R$^{20}$;

R$^6$ is hydrogen, C$_{1-6}$ alkyl or cycloalkyl;
wherein said C$_{1-6}$ alkyl is optionally substituted with one, two or three substituents independently selected from the group consisting of halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^7$ is hydrogen, halo, —O—R$^{20}$ or C$_{1-6}$ alkyl;
R$^{11}$ is hydrogen or C$_{1-4}$ alkyl;
R$^{20}$ and R$^{22}$ are in each instance independently selected from the group consisting of hydrogen, C$_{1-6}$ alkyl, C$_{2-6}$ alkenyl, C$_{2-6}$ alkynyl, cycloalkyl, heterocyclyl, aryl and heteroaryl;
wherein the C$_{1-6}$ alkyl, C$_{2-6}$ alkenyl, C$_{2-6}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and
wherein said heteroaryl is optionally further substituted with C$_{1-4}$ alkyl or cycloalkyl; or
when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and
each R$^{26}$ is independently selected from the group consisting of hydrogen, C$_{1-4}$ alkyl, aryl and cycloalkyl;
wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;
or a pharmaceutically acceptable salt, ester, stereoisomer, mixture of stereoisomers or tautomer thereof;
provided that when Y is —C(O)—, X is —O—, each R$^4$ is hydrogen, R$^2$ and R$^3$ together with the atom to which they are attached form a piperazine which is optionally substituted with tert-butoxycarbonyl and Q is a bond, then R$^1$ is not unsubstituted phenyl or morpholinyl; and that when Y is —S(O)$_2$—, X is —O—, R$^2$ is benzyl, each R$^3$ is hydrogen, Z$^4$ is C-Q-R$^1$, Q is a bond and R$^1$ is aryl or heteroaryl, then both R$^4$ are hydrogen.

In another embodiment, the disclosure provides compounds of Formula I:

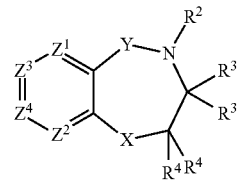

I wherein:

$Z^1$ and $Z^2$ are each independently selected from the group consisting of $CR^7$ and N; $Z^3$ and $Z^4$ are each independently selected from the group consisting of $CR^7$, C-Q-$R^1$ and N, provided that one of $Z^3$ and $Z^4$ is C-Q-$R^1$ and the other of $Z^3$ and $Z^4$ is $CR^7$ or N and further provided that only one of $Z^2$ and $Z^4$ is N;

X is —O— or —$NR^6$—;

Y is —C(O)—;

Q is a covalent bond, —O—$C_{0-2}$ alkylene, —$NR^{11}$—$C_{0-2}$ alkylene, $C_2$ alkylene, $C_2$ alkenylene or $C_2$ alkynylene;

$R^1$ is aryl, cycloalkyl, cycloalkenyl, heterocyclyl or heteroaryl;

wherein said aryl, cycloalkyl, cycloalkenyl, heterocyclyl or heteroaryl are optionally substituted with one, two, three, four or five substituents independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—$S(O)_2$—$R^{26}$, —$S(O)_2$—$R^{20}$, —O—$S(O)_2$—$R^{20}$, —$S(O)_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;

wherein each —$C_{1-6}$ alkylene is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—$OR^{26}$, —C(O)—N($R^{20}$)($R^{22}$), —N($R^{20}$)—$S(O)_2R^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

L is —O—, —S—, —C(O)—, —$NHS(O)_2$—, —$S(O)_2NH$—, —C(O)NH— or —NHC(O)—; provided that when $R^2$ is -L-$R^5$ or -L-$C_{1-6}$ alkylene-$R^5$, then L is not —O—, —S—, —$NHS(O)_2$— or —NHC(O)—; and each $R^3$ is independently hydrogen, deuterium, $C_{1-6}$ alkyl, cycloalkyl, aryl, heteroaryl or heterocyclyl;

wherein said $C_{1-6}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl or heteroaryl, are optionally further substituted with one, two or three substituents independently selected from the group consisting of halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

or $R^2$ and one of $R^3$ can join together with the atom to which they are attached to form a heterocyclyl;

wherein said heterocyclyl is optionally substituted with one, two or three substituents independently selected from the group consisting of $C_{1-6}$ alkyl, —O—$R^{20}$, —N($R^{20}$)($R^{22}$), —N($R^{20}$)—C(O)—$OR^{20}$ and —C(O)—$OR^{20}$; and wherein said $C_{1-6}$ alkyl is optionally substituted with one, two or three substituents independently selected from the group consisting of halo and heteroaryl;

each $R^4$ is independently hydrogen, deuterium, $C_{1-6}$ alkyl, —C(O)—$OR^{26}$, —C(O)—N($R^{26}$)($R^{26}$), cycloalkyl, aryl, heteroaryl or heterocyclyl;

wherein said $C_{1-6}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

or two $R^3$ or two $R^4$ together with the carbon atom to which they are attached form an oxo;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—$S(O)_2$—$R^{20}$, —N($R^{20}$)—C(O)—$R^{22}$, —C(O)—$R^{20}$, —C(O)—$OR^{20}$, —C(O)—N($R^{20}$)($R^{22}$), —CN, oxo and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —CN, —S(O)$_2$—R$^{20}$ and —O—R$^{20}$;

R$^6$ is hydrogen, C$_{1-6}$ alkyl or cycloalkyl;
wherein said C$_{1-6}$ alkyl is optionally substituted with one, two or three substituents independently selected from the group consisting of halo, —NO$_2$, —N(R$^{20}$)(R$^{22}$), —C(O)R$^{20}$, —C(O)—OR$^{20}$, —C(O)—N(R$^{20}$)(R$^{22}$), —CN and —O—R$^{20}$;

R$^7$ is hydrogen, halo, —O—R$^{20}$ or C$_{1-6}$ alkyl;
R$^{11}$ is hydrogen or C$_{1-4}$ alkyl;
R$^{20}$ and R$^{22}$ are in each instance independently selected from the group consisting of hydrogen, C$_{1-6}$ alkyl, C$_{2-6}$ alkenyl, C$_{2-6}$ alkynyl, cycloalkyl, heterocyclyl, aryl and heteroaryl;
wherein the C$_{1-6}$ alkyl, C$_{2-6}$ alkenyl, C$_{2-6}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and
wherein said heteroaryl is optionally further substituted with C$_{1-4}$ alkyl or cycloalkyl; or
when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and
each R$^{26}$ is independently selected from the group consisting of hydrogen, C$_{1-4}$ alkyl, aryl and cycloalkyl;
wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;

or a pharmaceutically acceptable salt, ester, stereoisomer, mixture of stereoisomers or tautomer thereof;
provided that when X is —O—, each R$^4$ is hydrogen, R$^2$ and R$^3$ together with the atom to which they are attached form a piperazine which is optionally substituted with tert-butoxycarbonyl and Q is a bond, then R$^1$ is not unsubstituted phenyl or morpholinyl.

In another embodiment, the disclosure provides compounds of Formula I:

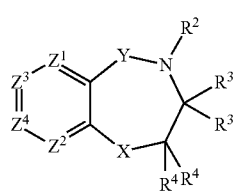

wherein Z$^1$, Z$^2$, Z$^3$, Z$^4$, X, R$^3$ and R$^4$ are as defined herein;
Y is —C(R$^{11}$)$_2$—;
R$^2$ is -L-R$^5$, -L-C$_{1-6}$ alkylene-R$^5$, —C$_{1-6}$ alkylene-L-R$^5$ or —C$_{1-6}$ alkylene-L-C$_{1-6}$ alkylene-R$^5$;

wherein each —C$_{1-6}$ alkylene is optionally substituted by one substituent independently selected from the group consisting of C$_{2-4}$ alkynyl, halo, —NO$_2$, —CN, —O—R$^{20}$, —N(R$^{20}$)(R$^{22}$), —C(O)—R$^{20}$, —C(O)—OR$^{26}$, —C(O)—N(R$^{20}$)(R$^{22}$), —N(R$^{20}$)—S(O)$_2$R$^{20}$, cycloalkyl, aryl, heteroaryl or heterocyclyl; and
wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

L is —O—, —S—, —NHS(O)$_2$—, —S(O)$_2$NH—, —C(O)NH— or —NHC(O)—; and
R$^{11}$ is hydrogen or C$_{1-4}$ alkyl.

In yet another embodiment, the disclosure provides compounds of Formula I:

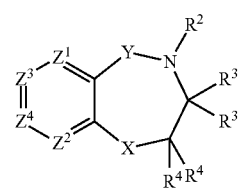

wherein Z$^1$, Z$^2$, Z$^3$, Z$^4$, X, R$^2$, R$^3$ and R$^4$ are as defined herein; and
Y is —S(O)$_2$—;
provided that when X is —O—, R$^2$ is benzyl, each R$^3$ is hydrogen, Z$^4$ is C-Q-R$^1$, Q is a bond and R$^1$ is aryl or heteroaryl, then both R$^4$ are hydrogen.

In some embodiments, R$^1$ is aryl, cycloalkyl, cycloalkenyl or heteroaryl;
wherein said aryl, cycloalkenyl or heteroaryl are optionally substituted with one, two or three substituents independently selected from the group consisting of halo, —O—R$^{20}$, —C(O)—R$^{20}$, —C(O)—OR$^{20}$, —N(R$^{20}$)(R$^{22}$), —N(R$^{20}$)—C(O)—R$^{22}$, —N(R$^{20}$)—C(O)—OR$^{22}$, —S(O)$_2$—R$^{20}$, —O—S(O)$_2$—R$^{20}$, C$_{1-6}$ alkyl, cycloalkyl and heterocyclyl; and
wherein said C$_{1-6}$ alkyl or cycloalkyl are optionally substituted with one, two or three substituents independently selected from the group consisting of halo, —CN and —O—R$^{20}$.

In some embodiments, each R$^3$ is independently hydrogen, deuterium or C$_{1-6}$ alkyl.
In some embodiments, each R$^4$ is independently hydrogen, deuterium or C$_{1-6}$ alkyl.
In some embodiments, R$^5$ is cycloalkyl, aryl, heteroaryl or heterocyclyl;
wherein said cycloalkyl, aryl, heteroaryl or heterocyclyl are optionally substituted with one, two or three substituents independently selected from the group consisting of C$_{1-6}$ alkyl, halo, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN, oxo and —O—R$^{20}$;
wherein said C$_{1-6}$ alkyl, cycloalkyl, aryl, heterocyclyl or heteroaryl are optionally further substituted with one, two or three substituents independently selected from the group consisting of halo, C$_{1-6}$ alkyl, aryl, heterocyclyl and heteroaryl; and wherein said C$_{1-6}$ alkyl is optionally further substituted with one, two or three halo.

In some embodiments, R$^2$ and one of R$^3$ can join together with the atom to which they are attached to form a heterocyclyl;
wherein said heterocyclyl is optionally substituted with one, two or three substituents independently selected from the group consisting of C$_{1-6}$ alkyl, —O—R$^{20}$, —N(R$^{20}$)(R$^{22}$) and —C(O)—OR$^{20}$; and
wherein said C$_{1-6}$ alkyl is optionally substituted with one, two or three substituents independently selected from the group consisting of halo and heteroaryl.

In certain embodiments of each of the formulas disclosed herein, each —C$_{1-6}$ alkylene of R$^2$ is unsubstituted —C$_{1-6}$ alkylene.

In certain embodiments, the compound is not tert-butyl 6-oxo-8-phenyl-3,4,12,12a-tetrahydro-1H-benzo[f]pyrazino[2,1-c][1,4]oxazepine-2(6H)-carboxylate, tert-butyl 6-oxo-9-phenyl-3,4,12,12a-tetrahydro-1H-benzo[f]pyrazino[2,1-c][1,4]oxazepine-2(6H)-carboxylate, 8-phenyl-3,4,12,12a-tetrahydro-1H-benzo[f]pyrazino[2,1-c][1,4]oxazepin-6(2H)-one, 9-phenyl-3,4,12,12a-tetrahydro-1H-benzo[f]pyrazino[2,1-c][1,4]oxazepin-6(2H)-one, 8-morpholino-1,2,3,4,12,12a-hexahydrobenzo[e]pyrazino[1,2-a]azepin-6(11H)-one, tert-butyl 8-morpholino-6-oxo-3,4,6,11,12,12a-hexahydrobenzo[e]pyrazino[1,2-a]azepine-2(1H)-carboxylate, tert-butyl 2-morpholino-12-oxo-5,6,6a,7,9,10-hexahydropyrazino[1,2-a]pyrido[3,2-e]azepine-8(12H)-carboxylate, 2-morpholino-6,6a,7,8,9,10-hexahydropyrazino[1,2-a]pyrido[3,2-e]azepin-12(5H)-one, 2-morpholino-8,9,10,10a,11,12-hexahydropyrazino[1,2-a]pyrido[2,3-e]azepin-5(7H)-one or tert-butyl 2-morpholino-5-oxo-7,8,10,10a,11,12-hexahydropyrazino[1,2-a]pyrido[2,3-e]azepine-9(5H)-carboxylate.

In alternative embodiments, the disclosure provides compounds of Formula I:

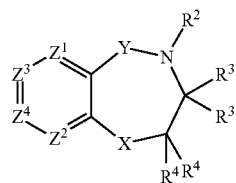

I wherein:
Z$^1$ and Z$^2$ are each independently selected from the group consisting of CR$^7$ and N;
Z$^3$ and Z$^4$ are each independently selected from the group consisting of CR$^7$, C-Q-R$^1$ and N, provided that one of Z$^3$ and Z$^4$ is C-Q-R$^1$ and the other of Z$^3$ and Z$^4$ is CR$^7$ or N and further provided that only one of Z$^1$, Z$^2$ and Z$^4$ is N;
X is —O— or —NR$^6$—;
Y is —C(O)—, —C(R$^{11}$)$_2$— or —S(O)$_2$—;
Q is a covalent bond, —O—C$_{0-2}$ alkylene, —NR$^{11}$—C$_{0-2}$ alkylene or C$_2$ alkynylene;
R$^1$ is aryl, cycloalkyl, cycloalkenyl, heterocyclyl or heteroaryl;
wherein said aryl, cycloalkyl, cycloalkenyl, heterocyclyl or heteroaryl are optionally substituted with one, two or three substituents independently selected from the group consisting of halo, —NO$_2$, —CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—C(O)—OR$^{22}$, —N(R$^{20}$)—S(O)$_2$—R$^{26}$, —S(O)$_2$—R$^{20}$, —O—S(O)$_2$—R$^{20}$, —S(O)$_2$—N(R$^{20}$)(R$^{22}$), C$_{1-6}$ alkyl, C$_{2-4}$ alkenyl, C$_{2-4}$ alkynyl, cycloalkyl, aryl, heteroaryl and heterocyclyl; and
wherein said C$_{1-6}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, C$_{1-6}$ alkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
R$^2$ is —C$_{1-6}$ alkylene-R$^5$, alkylene-R$^5$, —C$_{1-6}$ alkylene-L-R$^5$ or —C$_{1-6}$ alkylene-L-C$_{1-6}$ alkylene-R$^5$;
L is —O—, —S—, —C(O)—, —NHS(O)$_2$—, —S(O)$_2$NH—, —C(O)NH— or —NHC(O)—; provided that when Y is —C(R$^{11}$)$_2$—, then R$^2$ is -L-R$^5$, alkylene-R$^5$, —C$_{1-6}$ alkylene-L-R$^5$ or —C$_{1-6}$ alkylene-L-C$_{1-6}$ alkylene-R$^5$;
each R$^3$ is independently hydrogen, deuterium, C$_{1-15}$ alkyl, cycloalkyl, aryl, heteroaryl or heterocyclyl;
wherein said C$_{1-15}$ alkyl is optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
wherein said C$_{1-6}$ alkyl, aralkyl, cycloalkyl, aryl, heterocyclyl or heteroaryl, are optionally further substituted with one, two or three substituents independently selected from the group consisting of halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
or when Y is —C(O)—, then R$^2$ and one of R$^3$ can join together with the atom to which they are attached to form a heterocyclyl;
wherein said heterocyclyl is optionally substituted with one, two or three substituents independently selected from the group consisting of C$_{1-15}$ alkyl, —O—R$^{20}$, —N(R$^{20}$)(R$^{22}$), —N(R$^{20}$)—C(O)—OR$^{20}$ and —C(O)—OR$^{20}$; and
wherein said C$_{1-15}$ alkyl is optionally substituted with one, two or three substituents independently selected from the group consisting of halo and heteroaryl;
each R$^4$ is independently hydrogen, deuterium, C$_{1-15}$ alkyl, C$_{1-4}$ alkoxy, —C(O)—OR$^{26}$, —C(O)—N(R$^{26}$)(R$^{26}$), —N(R$^{20}$)—S(O)$_2$—R$^{20}$, cycloalkyl, aryl, heteroaryl or heterocyclyl;
wherein said C$_{1-15}$ alkyl is optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, aralkyl, cycloalkyl, aryl, heterocyclyl, heteroaryl, are optionally further substituted with one, two or three substituents independently selected from the group consisting of hydroxyl, halo, —NO$_2$, —N(R$^{20}$)(R$^{22}$), —C(O)—OR$^{20}$, —C(O)—OR$^{20}$, —C(O)—N(R$^{20}$)(R$^{22}$), —CN and —O—R$^{20}$;

or two R$^3$ or two R$^4$ together with the carbon atom to which they are attached form an oxo;

R$^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN and —O—R$^{20}$;

wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —S(O)$_2$—R$^{20}$ and —O—R$^{20}$;

R$^6$ is hydrogen, C$_{1-15}$ alkyl, —C(O)—R$^{20}$, —C(O)—OR$^{26}$, cycloalkyl, aryl, heteroaryl or heterocyclyl;

wherein said C$_{1-15}$ alkyl is optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

wherein said cycloalkyl, aryl, heterocyclyl or heteroaryl are optionally further substituted with one, two or three substituents independently selected from the group consisting of halo, —NO$_2$, C$_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, aralkyl, cycloalkyl, aryl, heterocyclyl or heteroaryl are optionally further substituted with one, two or three substituents independently selected from the group consisting of halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^7$ is hydrogen, halo or C$_{1-6}$ alkyl;

R$^{11}$ is hydrogen or C$_{1-4}$ alkyl;

R$^{20}$ and R$^{22}$ are in each instance independently selected from the group consisting of hydrogen, C$_{1-15}$ alkyl, C$_{2-15}$ alkenyl, C$_{2-15}$ alkynyl, cycloalkyl, heterocyclyl, aryl and heteroaryl;

wherein the C$_{1-15}$ alkyl, C$_{2-15}$ alkenyl, C$_{2-15}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and wherein said heteroaryl is optionally further substituted with C$_{1-4}$ alkyl or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and each R$^{26}$ is independently selected from the group consisting of hydrogen, C$_{1-4}$ alkyl, aryl and cycloalkyl; and wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;

or a pharmaceutically acceptable salt, ester, hydrate, solvate, stereoisomer, mixture of stereoisomers, tautomer, polymorph and/or prodrug thereof;

provided that when Y is —C(O)—, X is —O—, each R$^4$ is hydrogen, R$^2$ and R$^3$ together with the atom to which they are attached form a piperazine which is optionally substituted with tert-butoxycarbonyl and Q is a bond, then R$^1$ is not unsubstituted phenyl or morpholinyl; and that when Y is —S(O)$_2$—, X is —O—, R$^2$ is benzyl, each R$^3$ is hydrogen, Z$^4$ is C-Q-R$^1$, Q is a bond and R$^1$ is aryl or heteroaryl, then both R$^4$ are hydrogen.

In some embodiments, R$^1$ is aryl, cycloalkyl, cycloalkenyl or heteroaryl;

wherein said aryl, cycloalkenyl or heteroaryl are optionally substituted with one, two or three substituents independently selected from the group consisting of halo, —O—R$^{20}$, —C(O)—R$^{20}$, —C(O)—OR$^{20}$, —N(R$^{20}$)(R$^{22}$), —N(R$^{20}$)—C(O)—R$^{22}$, —N(R$^{20}$)—C(O)—OR$^{22}$, —S(O)$_2$—R$^{20}$, —O—S(O)$_2$—R$^{20}$, C$_{1-6}$ alkyl, cycloalkyl and heterocyclyl; and wherein said C$_{1-6}$ alkyl or cycloalkyl are optionally substituted with one, two or three substituents independently selected from the group consisting of halo, —CN and —O—R$^{20}$.

In some embodiments, each R$^3$ is independently hydrogen, deuterium or C$_{1-15}$ alkyl.

In some embodiments, each R$^4$ is independently hydrogen, deuterium or C$_{1-15}$ alkyl.

In some embodiments, R$^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of C$_{1-6}$ alkyl, halo, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

wherein said C$_{1-6}$ alkyl, cycloalkyl, aryl, heterocyclyl or heteroaryl are optionally further substituted with one, two or three substituents independently selected from the group consisting of halo, $C_{1-6}$ alkyl, aryl, heterocyclyl and heteroaryl; and
wherein said $C_{1-6}$ alkyl is optionally further substituted with one, two or three halo.

In some embodiments, Y is —C(O)— and $R^2$ and one of $R^3$ can join together with the atom to which they are attached to form a heterocyclyl;
wherein said heterocyclyl is optionally substituted with one, two or three substituents independently selected from the group consisting of $C_{1-15}$ alkyl, —O—$R^{20}$, —N($R^{20}$)($R^{22}$) and —C(O)—O$R^{20}$; and
wherein said $C_{1-15}$ alkyl is optionally substituted with one, two or three substituents independently selected from the group consisting of halo and heteroaryl.

In some embodiments, the disclosure provides compounds of Formula IA:

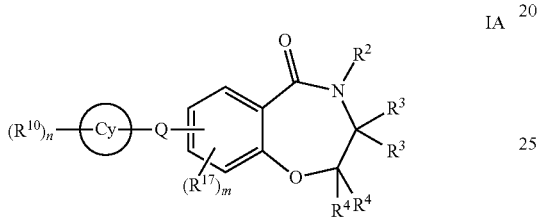

IA wherein:
Cy is aryl, cycloalkyl, cycloalkenyl, heterocyclyl or heteroaryl;
Q is a covalent bond, —O—$C_{0-2}$ alkylene, —N$R^{11}$—$C_{0-2}$ alkylene, $C_2$ alkylene, $C_2$ alkenylene or $C_2$ alkynylene;
m is 0, 1, 2 or 3;
n is 0, 1, 2, 3, 4 or 5;
each $R^{10}$ is independently selected from the group consisting of halo, —NO$_2$, —CN, —SF$_5$, —Si(CH$_3$)$_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—C(O)—O$R^{22}$, —N($R^{20}$)—S(O)$_2$—$R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —NO$_2$, aryl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$;
$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;
wherein each —$C_{1-6}$ alkylene is optionally substituted by one substituent independently selected from the group consisting of $C_{2-4}$ alkynyl, halo, —NO$_2$, —CN, —O—$R^{20}$, —N($R^{20}$)($R^{22}$), —C(O)—$R^{20}$, —C(O)—O$R^{26}$, —C(O)—N($R^{20}$)($R^{22}$), —N($R^{20}$)—S(O)$_2$—$R^{20}$, cycloalkyl, aryl, heteroaryl or heterocyclyl; and
wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —NO$_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
L is —O—, —S—, —C(O)—, —NHS(O)$_2$—, —S(O)$_2$NH—, —C(O)NH— or —NHC(O)—; provided that when $R^2$ is -L-$R^5$ or -L-$C_{1-6}$ alkylene-$R^5$, then L is not —O—, —S—, —NHS(O)$_2$— or —NHC(O)—; and
each $R^3$ is independently hydrogen, deuterium, $C_{1-6}$ alkyl, cycloalkyl, aryl, heteroaryl or heterocyclyl;
wherein said $C_{1-6}$ alkyl is optionally substituted with one, two or three substituents independently selected from the group consisting of halo, —NO$_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
wherein said cycloalkyl, aryl, heterocyclyl or heteroaryl are optionally further substituted with one, two or three substituents independently selected from the group consisting of halo, —NO$_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
wherein said $C_{1-6}$ alkyl, aralkyl, cycloalkyl, aryl, heterocyclyl or heteroaryl, are optionally further substituted with one, two or three substituents independently selected from the group consisting of halo, —NO$_2$, —N($R^{20}$)($R^{22}$), —C(O)—$R^{20}$, —C(O)—O$R^{20}$, —C(O)—N($R^{20}$)($R^{22}$), —CN and —O—$R^{20}$;
or $R^2$ and one of $R^3$ can join together with the atom to which they are attached to form a heterocyclyl;
wherein said heterocyclyl is optionally substituted with one, two or three substituents independently selected from the group consisting of $C_{1-6}$ alkyl, —O—$R^{20}$, —N($R^{20}$)($R^{22}$), —($R^{20}$)—C(O)—O$R^{20}$ and —C(O)—O$R^{20}$; and
wherein said $C_{1-6}$ alkyl is optionally substituted with one, two or three substituents independently selected from the group consisting of halo and heteroaryl;
each $R^4$ is independently hydrogen, deuterium, $C_{1-6}$ alkyl, —C(O)—O$R^{26}$, —C(O)—N($R^{26}$)($R^{26}$), cycloalkyl, aryl, heteroaryl or heterocyclyl;
wherein said $C_{1-6}$ alkyl is optionally substituted with one, two or three substituents independently selected from the group consisting of halo, —NO$_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
wherein said cycloalkyl, aryl, heterocyclyl or heteroaryl are optionally further substituted with one, two or three substituents independently selected from the group consisting of halo, —NO$_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —NO$_2$, —N($R^{20}$)($R^{22}$), —C(O)—$R^{20}$, —C(O)—O$R^{20}$, —C(O)—N($R^{20}$)($R^{22}$), —CN and —O—$R^{20}$;

R[5] is cycloalkyl, aryl, heteroaryl or heterocyclyl;
  wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—S(O)$_2$—$R^{20}$, —N($R^{20}$)—C(O)—$R^{22}$, —C(O)—$R^{20}$, —C(O)—O$R^{20}$, —C(O)—N($R^{20}$)($R^{22}$), —CN, oxo and —O—$R^{20}$;
    wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
      wherein said $C_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —N($R^{20}$)($R^{22}$), —C(O)—$R^{20}$, —C(O)—O$R^{20}$, —C(O)—N($R^{20}$)($R^{22}$), —S(O)$_2$—$R^{20}$ and —O—$R^{20}$;

$R^{17}$ is halo, —O—$R^{20}$ or $C_{1-6}$ alkyl;

$R^{20}$ and $R^{22}$ are in each instance independently selected from the group consisting of hydrogen, $C_{1-6}$ alkyl, $C_{2-6}$ alkenyl, $C_{2-6}$ alkynyl, cycloalkyl, heterocyclyl, aryl and heteroaryl;
  wherein the $C_{1-6}$ alkyl, $C_{2-6}$ alkenyl, $C_{2-6}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —S(O)$_2R^{26}$, —CN, $C_{1-3}$ alkoxy, —$CF_3$, —$OCF_3$, —$OCH_2CF_3$, —C(O)—$NH_2$, aryl, cycloalkyl and heterocyclyl; and
    wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —S(O)$_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl;
  wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, stereoisomer, mixture of stereoisomers or tautomer thereof;

provided that when each $R^4$ is hydrogen, $R^2$ and $R^3$ together with the atom to which they are attached form a piperazine which is optionally substituted with tert-butoxycarbonyl, Q is a bond and Cy is phenyl or morpholinyl, then n is 1, 2, 3, 4 or 5.

In certain embodiments, the disclosure provides compounds of Formula II:

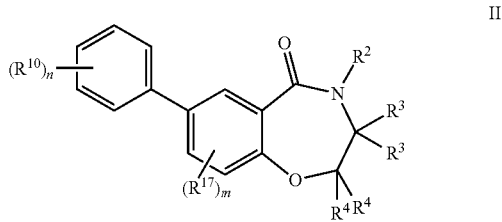

wherein:
m is 0, 1, 2 or 3;
n is 0, 1, 2, 3, 4 or 5;
each $R^{10}$ is independently selected from the group consisting of halo, —$NO_2$, —CN, —$SF_5$, —Si($CH_3$)$_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—C(O)—O$R^{22}$, —N($R^{20}$)—S(O)$_2$—$R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
  wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$;

$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;
  wherein each —$C_{1-6}$ alkylene is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—O$R^{26}$, —C(O)—N($R^{20}$)($R^{22}$), —N($R^{20}$)—S(O)$_2$—$R^{20}$, cycloalkyl, aryl, heteroaryl or heterocyclyl; and
    wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;

L is —O—, —S—, —C(O)—, —NHS(O)$_2$—, —S(O)$_2$NH—, —C(O)NH— or —NHC(O)—, provided that when $R^2$ is -L-$R^5$ or -L-$C_{1-6}$ alkylene-$R^5$, then L is not —O—, —S—, —NHS(O)$_2$— or —NHC(O)—;

each $R^3$ is independently hydrogen, deuterium, $C_{1-6}$ alkyl, cycloalkyl, aryl, heteroaryl or heterocyclyl;
  wherein said $C_{1-6}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
    wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl or heteroaryl, are optionally further substituted with one, two or three substituents independently selected from the group consisting of halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

or $R^2$ and one of $R^3$ can join together with the atom to which they are attached to form a heterocyclyl;

wherein said heterocyclyl is optionally substituted with one, two or three substituents independently selected from the group consisting of $C_{1-6}$ alkyl, —O—$R^{20}$, —N($R^{20}$)($R^{22}$), —N($R^{20}$)—C(O)—$OR^{20}$ and —C(O)—$OR^{20}$; and wherein said $C_{1-6}$ alkyl is optionally substituted with one, two or three substituents independently selected from the group consisting of halo and heteroaryl;

each $R^4$ is independently hydrogen, deuterium, $C_{1-6}$ alkyl, —C(O)—$OR^{26}$, —C(O)—N($R^{26}$)($R^{26}$), cycloalkyl, aryl, heteroaryl or heterocyclyl;

wherein said $C_{1-6}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—S(O)$_2$—$R^{20}$, —N($R^{20}$)—C(O)—$R^{22}$, —C(O)—$R^{20}$, —C(O)—$OR^{20}$, —C(O)—N($R^{20}$)($R^{22}$), —CN, oxo and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —N($R^{20}$)($R^{22}$), —C(O)—$R^{20}$, —C(O)—$OR^{20}$, —C(O)—N($R^{20}$)($R^{22}$), —S(O)$_2$—$R^{20}$ and —O—$R^{20}$;

$R^{17}$ is halo, —O—$R^{20}$ or $C_{1-6}$ alkyl;

$R^{20}$ and $R^{22}$ are in each instance independently selected from the group consisting of hydrogen, $C_{1-6}$ alkyl, $C_{2-6}$ alkenyl, $C_{2-6}$ alkynyl, cycloalkyl, heterocyclyl, aryl and heteroaryl;

wherein the $C_{1-6}$ alkyl, $C_{2-6}$ alkenyl, $C_{2-6}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —S(O)$_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —S(O)$_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl;

wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, stereoisomer, mixture of stereoisomers or tautomer thereof;

provided that when m is 0, each $R^4$ is hydrogen, $R^2$ and $R^3$ together with the atom to which they are attached form a piperazine which is optionally substituted with tert-butoxycarbonyl and Q is a bond, then n is 1, 2 or 3.

In some embodiments, $R^2$ is —$C_{1-6}$ alkylene-$R^5$ or —$C_{1-6}$ alkylene-L-$R^5$.

In some embodiments, each —$C_{1-6}$ alkylene of $R^2$ is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—$OR^{26}$, —C(O)—N($R^{20}$)($R^{22}$), —N($R^{20}$)—S(O)$_2$—$R^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$.

In some embodiments, each —$C_{1-6}$ alkylene of $R^2$ is unsubstituted.

In some embodiments, $R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, halo, cycloalkyl, heterocyclyl, heteroaryl, —N($R^{20}$)($R^{22}$), —C(O)—$OR^{20}$, —CN and —O—$R^{20}$;

wherein said $C_{1-6}$ alkyl or heteroaryl are optionally further substituted with one, two or three substituents independently selected from the group consisting of halo, $C_{1-6}$ alkyl and aryl; and wherein said $C_{1-6}$ alkyl is optionally further substituted with one, two or three halo.

In some embodiments, $R^2$ and one of $R^3$ can join together with the atom to which they are attached to form a heterocyclyl;

wherein said heterocyclyl is optionally substituted with one, two or three substituents independently selected from the group consisting of $C_{1-6}$ alkyl, —O—$R^{20}$, —N($R^{20}$)($R^{22}$) and —C(O)—O$R^{20}$; and wherein said $C_{1-6}$ alkyl is optionally substituted with one, two or three substituents independently selected from the group consisting of halo and heteroaryl.

In some embodiments, $R^2$ is

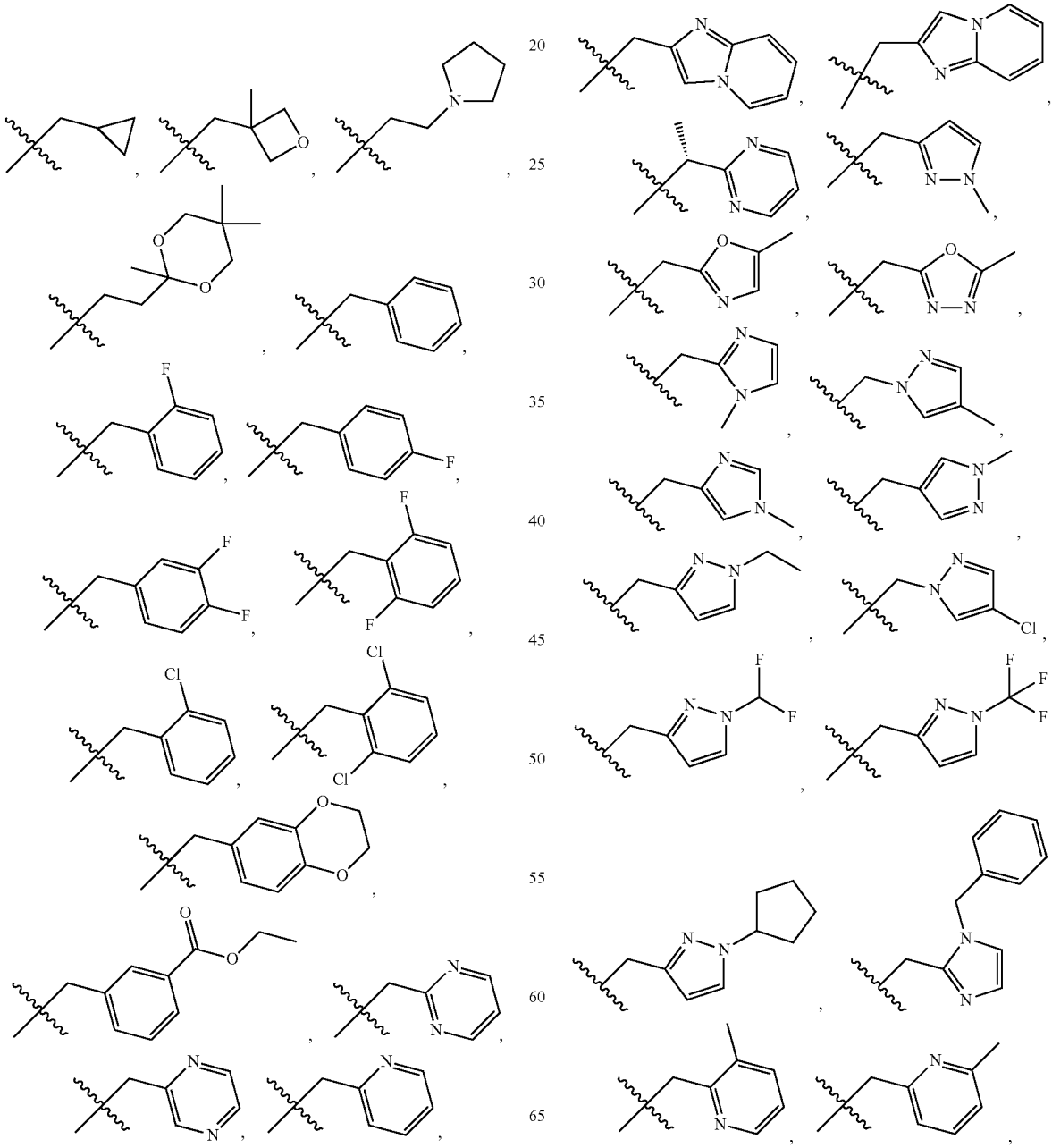

-continued
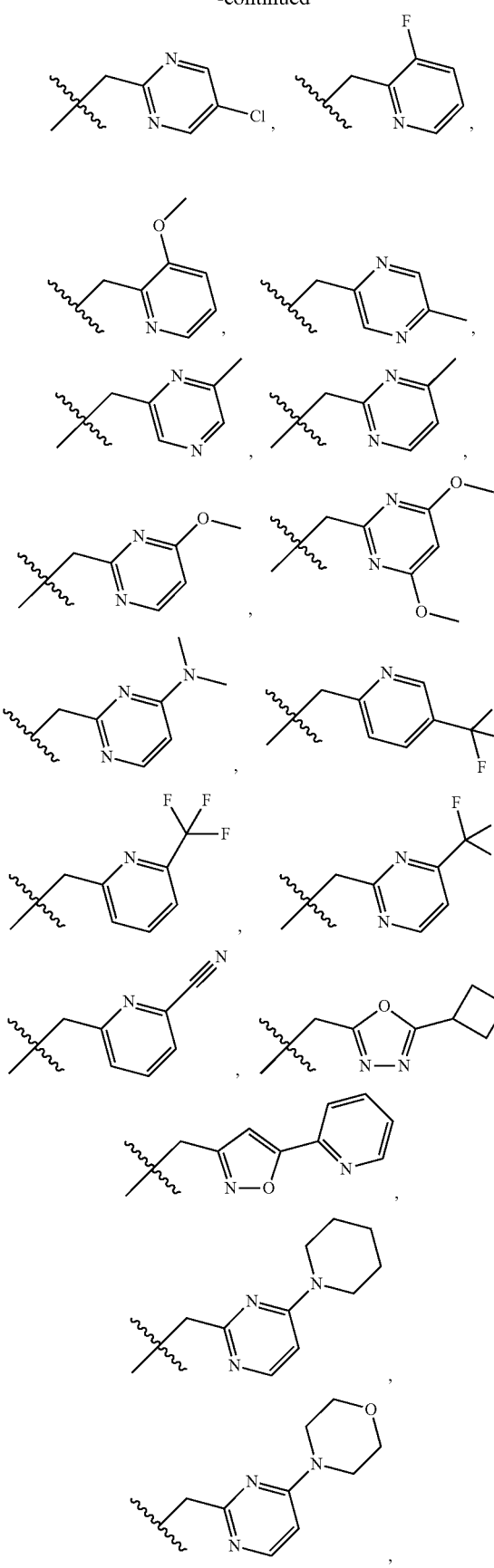
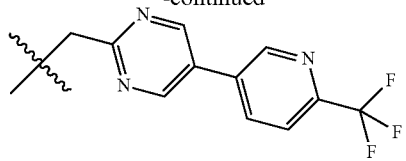
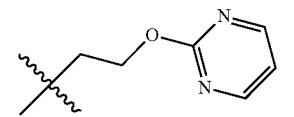
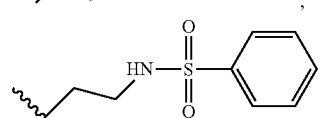
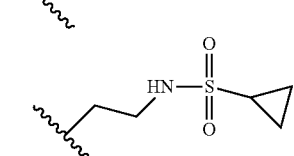
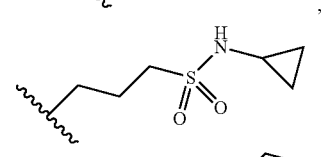
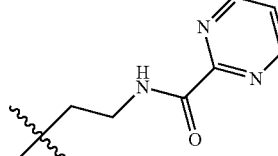
or
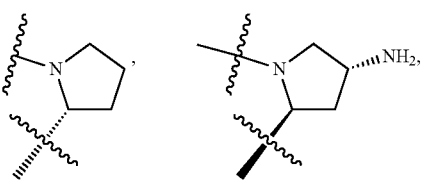
;
or $R^2$ and one of $R^3$ together with the carbon atoms to which they are attached form a
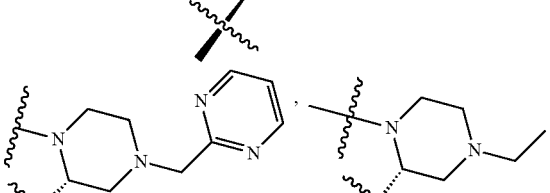
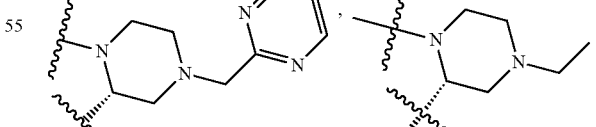
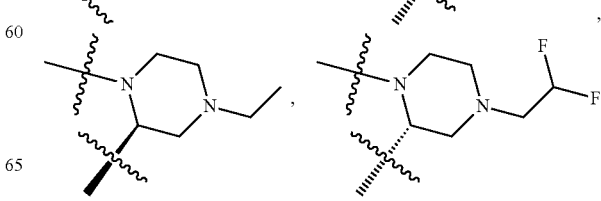

-continued

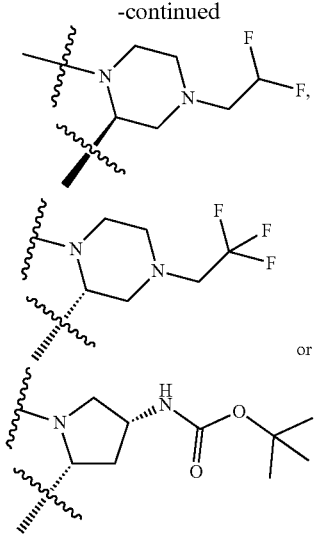

In some embodiments, n is 1, 2 or 3; and
each $R^{10}$ is independently selected from the group consisting of halo, —O—$R^{20}$, —O—S(O)$_2$—$R^{20}$, $C_{1-4}$ alkyl and cycloalkyl; and
wherein said alkyl and cycloalkyl are optionally substituted with one, two or three halo or —CN; and
$R^{20}$ is independently selected from the group consisting of $C_{1-6}$ alkyl, cycloalkyl and aryl; and
wherein the alkyl and aryl are optionally substituted with one, two or three halo or cycloalkyl.

In some embodiments, n is 1, 2 or 3; and each $R^{10}$ is independently 2-fluoro, 3-fluoro, 4-fluoro, 2-chloro, 4-chloro, 2-methyl, 4-methyl, 4-ethyl, 4-isopropyl, 4-tert-butyl, 4-difluoromethyl, 4-trifluoromethyl, 4-cyclopropyl, 4-isobutoxy, 4-difluoromethoxy, 4-trifluoromethoxy, 4-(2,2,2-trifluoroethoxy), 4-trifluoromethylsulfoxyl, 4-(2,2,2-trifluoroethyl), 4-cyclopropoxy, 4-cyclobutylmethoxy, 4-fluorophenoxy, 4-phenoxy or 3-phenoxy.

In some embodiments, each $R^3$ is independently hydrogen, deuterium or $C_{1-6}$ alkyl optionally substituted with heteroaryl;
or $R^2$ and one of $R^3$ can join together with the atom to which they are attached to form a heterocyclyl;
wherein said heterocyclyl is optionally substituted with one, two or three substituents independently selected from the group consisting of $C_{1-6}$ alkyl, —N($R^{20}$)($R^{22}$) and —N($R^{20}$)—C(O)—OR$^{20}$; and
wherein said $C_{1-6}$ alkyl is optionally substituted with one, two or three substituents independently selected from the group consisting of halo and heteroaryl; and
$R^{20}$ and $R^{22}$ are in each instance independently selected from the group consisting of hydrogen, $C_{1-6}$ alkyl and heteroaryl.

In some embodiments, each $R^3$ is independently hydrogen, deuterium or $C_{1-6}$ alkyl optionally substituted with heteroaryl; and
each $R^4$ is independently hydrogen, deuterium or $C_{1-6}$ alkyl optionally substituted with heteroaryl.

In some embodiments, each $R^3$ is independently hydrogen, deuterium or $C_{1-6}$ alkyl optionally substituted with heteroaryl;
m is 0 or 1; and
$R^{17}$ is halo.

In some embodiments, each $R^3$ is independently hydrogen, deuterium, methyl, isopropyl or pyridin-2-ylmethyl;
m is 0 or 1; and
$R^{17}$ is fluoro.

In some embodiments, each $R^4$ is independently hydrogen, deuterium or $C_{1-6}$ alkyl.

In some embodiments, each $R^3$ is independently hydrogen, deuterium or $C_{1-6}$ alkyl optionally substituted with heteroaryl;
or $R^2$ and one of $R^3$ can join together with the atom to which they are attached to form a heterocyclyl;
wherein said heterocyclyl is optionally substituted with one, two or three substituents independently selected from the group consisting of $C_{1-6}$ alkyl, —N($R^{20}$)($R^{22}$) and —N($R^{20}$)—C(O)—OR$^{20}$; and
wherein said $C_{1-6}$ alkyl is optionally substituted with one, two or three substituents independently selected from the group consisting of halo and heteroaryl; and
each $R^4$ is independently hydrogen, deuterium or $C_{1-6}$ alkyl optionally substituted with heteroaryl.

In certain embodiments, the disclosure provides compounds of Formula IIA:

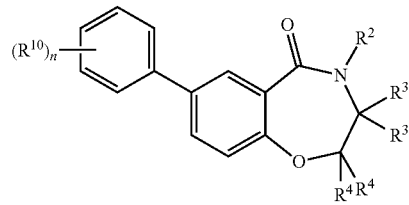

IIA wherein:
n is 0, 1, 2 or 3;
each $R^{10}$ is independently selected from the group consisting of halo, —NO$_2$, —CN, —SF$_5$, —Si(CH$_3$)$_3$, —O—$R^{20}$, —S—$R^{20}$, —C(O)—$R^{20}$, —C(O)—OR$^{20}$, —N($R^{20}$)($R^{22}$), —C(O)—N($R^{20}$)($R^{22}$), —N($R^{20}$)—C(O)—$R^{22}$, —N($R^{20}$)—C(O)—OR$^{22}$, —N($R^{20}$)—S(O)$_2$—$R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —NO$_2$, aryl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—OR$^{20}$, —C(O)—N($R^{20}$)($R^{22}$), —CN and —O—$R^{20}$;
$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;
L is —O—, —S—, —C(O)—, —NHS(O)$_2$—, —S(O)$_2$NH—, —C(O)NH— or —NHC(O)—, provided that when $R^2$ is -L-$R^5$ or -L-$C_{1-6}$ alkylene-$R^5$, then L is not —O—, —S—, —NHS(O)$_2$— or —NHC(O)—;
each $R^3$ is independently hydrogen or $C_{1-6}$ alkyl;
each $R^4$ is independently hydrogen or $C_{1-6}$ alkyl;
$R^5$ is cycloalkyl, aryl, heteroaryl or heterocyclyl;
wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —$N(R^{20})(R^{22})$, —$N(R^{20})$—$S(O)_2$—$R^{20}$, —$N(R^{20})$—$C(O)$—$R^{22}$, —$C(O)$—$R^{20}$, —$C(O)$—$OR^{20}$, —$C(O)$—$N(R^{20})(R^{22})$, —CN, oxo and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —$N(R^{20})(R^{22})$, —$C(O)$—$R^{20}$, —$C(O)$—$OR^{20}$, —$C(O)$—$N(R^{20})(R^{22})$, —$S(O)_2$—$R^{20}$ and —O—$R^{20}$;

$R^{20}$ and $R^{22}$ are in each instance independently selected from the group consisting of hydrogen, $C_{1-6}$ alkyl, $C_{2-6}$ alkenyl, $C_{2-6}$ alkynyl, cycloalkyl, heterocyclyl, aryl and heteroaryl;

wherein the $C_{1-6}$ alkyl, $C_{2-6}$ alkenyl, $C_{2-6}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —$S(O)_2R^{26}$, —CN, $C_{1-3}$ alkoxy, —$CF_3$, —$OCF_3$, —$OCH_2CF_3$, —$C(O)$—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl;

wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, stereoisomer, mixture of stereoisomers or tautomer thereof.

In certain embodiments, the disclosure provides compounds of Formula IIB:

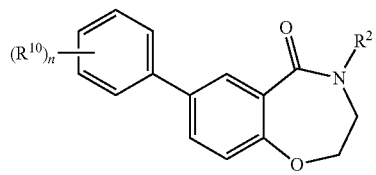

IIB wherein:

n is 0, 1, 2 or 3;

each $R^{10}$ is independently selected from the group consisting of halo, —$NO_2$, —CN, —$SF_5$, —$Si(CH_3)_3$, —O—$R^{20}$, —S—$R^{20}$, —$C(O)$—$R^{20}$, —$C(O)$—$OR^{20}$, —$N(R^{20})(R^{22})$, —$C(O)$—$N(R^{20})(R^{22})$, —$N(R^{20})$—$C(O)$—$R^{22}$, —$N(R^{20})$—$C(O)$—$OR^{22}$, —$N(R^{20})$—$S(O)_2$—$R^{26}$, —$S(O)_2$—$R^{20}$, —O—$S(O)_2$—$R^{20}$, —$S(O)_2$—$N(R^{20})(R^{22})$, $C_{1-6}$ alkyl, $C_{2-4}$ alkenyl, $C_{2-4}$ alkynyl, cycloalkyl, aryl, heteroaryl and heterocyclyl;

wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-6}$ alkyl, $C_{1-3}$ haloalkyl, cycloalkyl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$;

$R^2$ is —$C_{1-6}$ alkylene-$R^5$;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, —$N(R^{20})(R^{22})$, —$N(R^{20})$—$S(O)_2$—$R^{20}$, —$N(R^{20})$—$C(O)$—$R^{22}$, —$C(O)$—$R^{20}$, —$C(O)$—$OR^{20}$, —$C(O)$—$N(R^{20})(R^{22})$,) CN, oxo and —O—$R^{20}$; and wherein said $C_{1-6}$ alkyl is optionally further substituted with one, two or three substituents independently selected from the group consisting of halo, —$NO_2$, —$N(R^{20})(R^{22})$, —$C(O)$—$R^{20}$, —$C(O)$—$OR^{20}$, —$C(O)$—$N(R^{20})(R^{22})$, —CN and —O—$R^{20}$;

$R^{20}$ and $R^{22}$ are in each instance independently selected from the group consisting of hydrogen, $C_{1-6}$ alkyl, $C_{2-6}$ alkenyl, $C_{2-6}$ alkynyl, cycloalkyl, heterocyclyl, aryl and heteroaryl;

wherein the $C_{1-6}$ alkyl, $C_{2-6}$ alkenyl, $C_{2-6}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —$S(O)_2R^{26}$, —CN, $C_{1-3}$ alkoxy, —$CF_3$, —$OCF_3$, —$OCH_2CF_3$ and —$C(O)$—$NH_2$; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —$S(O)_2R^{26}$, —CN, $C_{1-3}$ alkoxy, —$CF_3$ and —$OCF_3$; and each $R^{26}$ is independently selected from the group consisting of hydrogen, $C_{1-4}$ alkyl, aryl and cycloalkyl;

wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, stereoisomer, mixture of stereoisomers or tautomer thereof.

In some embodiments, n is 1, 2 or 3; and each $R^{10}$ is independently selected from the group consisting of halo, —O—$R^{20}$, —O—$S(O)_2$—$R^{20}$, $C_{1-4}$ alkyl and cycloalkyl; and wherein said alkyl and cycloalkyl are optionally substituted with one, two or three halo or —CN; and R²⁰ is $C_{1-6}$ alkyl, cycloalkyl or aryl; and
  wherein the alkyl and aryl are optionally substituted with one, two or three halo or cycloalkyl.

In some embodiments, n is 1, 2 or 3; and each $R^{10}$ is independently 2-fluoro, 3-fluoro, 4-fluoro, 2-chloro, 4-chloro, 2-methyl, 4-methyl, 4-ethyl, 4-isopropyl, 4-tert-butyl, 4-difluoromethyl, 4-trifluoromethyl, 4-cyclopropyl, 4-isobutoxy, 4-difluoromethoxy, 4-trifluoromethoxy, 4-(2,2,2-trifluoroethoxy), 4-trifluoromethylsulfoxyl, 4-(2,2,2-trifluoroethyl), 4-cyclopropoxy, 4-cyclobutylmethoxy, 4-fluorophenoxy, 4-phenoxy or 3-phenoxy.

In some embodiments, the compound is selected from the group consisting of:
4-((3-methyloxetan-3-yl)methyl)-7-(4-(trifluoromethoxy) phenyl)-3,4-dihydrobenzo[f][1,4]oxazepin-5(2H)-one (II-1);
4-(2-(pyrrolidin-1-yl)ethyl)-7-(4-(trifluoromethoxy)phenyl)-3,4-dihydrobenzo[f][1,4]oxazepin-5(2H)-one (II-3);
4-((5-cyclobutyl-1,3,4-oxadiazol-2-yl)methyl)-7-(4-(trifluoromethoxy)phenyl)-3,4-dihydrobenzo[f][1,4]oxazepin-5(2H)-one (II-4);
4-((2,3-dihydrobenzo[b][1,4]dioxin-6-yl)methyl)-7-(4-(trifluoromethoxy)phenyl)-3,4-dihydrobenzo[f][1,4]oxazepin-5(2H)-one (II-5);
4-(quinolin-2-ylmethyl)-7-(4-(trifluoromethoxy)phenyl)-3,4-dihydrobenzo[f][1,4]oxazepin-5(2H)-one (II-7);
(R)-2-(pyrimidin-2-ylmethyl)-8-(4-(trifluoromethyl)phenyl)-3,4,12,12a-tetrahydro-1H-benzo[f]pyrazino[2,1-c][1,4]oxazepin-6(2H)-one (II-8);
4-cyclopropylmethyl)-7-(4-(trifluoromethoxy)phenyl)-3,4-dihydrobenzo[f][1,4]oxazepin-5(2H)-one (II-10);
(S)-3-methyl-4-(pyrimidin-2-ylmethyl)-7-(4-(trifluoromethyl)phenyl)-3,4-dihydrobenzo[f][1,4]oxazepin-5(2H)-one (II-12);
(R)-3-methyl-4-(pyrimidin-2-ylmethyl)-7-(4-(trifluoromethyl)phenyl)-3,4-dihydrobenzo[f][1,4]oxazepin-5(2H)-one (II-13);
6-((5-oxo-7-(4-(trifluoromethoxy)phenyl)-2,3-dihydrobenzo[f][1,4]oxazepin-4(5H)-yl)methyl)picolinonitrile (II-14);
7-(4-(trifluoromethoxy)phenyl)-4-((6-(trifluoromethyl)pyridin-2-yl)methyl)-3,4-dihydrobenzo[f][1,4]oxazepin-5(2H)-one (II-15);
7-(4-(trifluoromethoxy)phenyl)-4-((6-(trifluoromethyl)pyridin-3-yl)methyl)-3,4-dihydrobenzo[f][1,4]oxazepin-5(2H)-one (II-16);
4-((6-methylpyridin-2-yl)methyl)-7-(4-(trifluoromethoxy) phenyl)-3,4-dihydrobenzo[f][1,4]oxazepin-5(2H)-one (II-17);
(2R,11aS)-2-amino-7-(4-(trifluoromethyl)phenyl)-2,3,11,11a-tetrahydrobenzo[f]pyrrolo[2,1-c][1,4]oxazepin-5(1H)-one (II-21);
(R)-2-(2,2-difluoroethyl)-8-(4-(trifluoromethyl)phenyl)-3,4,12,12a-tetrahydro-1H-benzo[f]pyrazino[2,1-c][1,4]oxazepin-6(2H)-one (II-22);
(R)-2-ethyl-8-(4-(trifluoromethyl)phenyl)-3,4,12,12a-tetrahydro-1H-benzo[f]pyrazino[2,1-c][1,4]oxazepin-6(2H)-one (II-23);
(S)-2-(2,2-difluoroethyl)-8-(4-(trifluoromethyl)phenyl)-3,4,12,12a-tetrahydro-1H-benzo[f]pyrazino[2,1-c][1,4]oxazepin-6(2H)-one (II-24);
(S)-2-ethyl-8-(4-(trifluoromethyl)phenyl)-3,4,12,12a-tetrahydro-1H-benzo[f]pyrazino[2,1-c][1,4]oxazepin-6(2H)-one (II-25);
4-(pyrazin-2-ylmethyl)-7-(4-(trifluoromethoxy)phenyl)-3,4-dihydrobenzo[f][1,4]oxazepin-5(2H)-one (II-31);
4-((5-methyloxazol-2-yl)methyl)-7-(4-(trifluoromethoxy) phenyl)-3,4-dihydrobenzo[f][1,4]oxazepin-5(2H)-one (II-33);
7-(4-(trifluoromethoxy)phenyl)-4-(2-(2,5,5-trimethyl-1,3-dioxan-2-yl)ethyl)-3,4-dihydrobenzo[f][1,4]oxazepin-5(2H)-one (II-35);
tert-butyl (2R,11aR)-5-oxo-7-(4-(trifluoromethyl)phenyl)-1,2,3,5,11,11a-hexahydrobenzo[f]pyrrolo[2,1-c][1,4]oxazepin-2-ylcarbamate (II-39);
4-((5-(pyridin-2-yl)isoxazol-3-yl)methyl)-7-(4-(trifluoromethoxy)phenyl)-3,4-dihydrobenzo[f][1,4]oxazepin-5(2H)-one (II-41);
4-((4,6-dimethoxypyrimidin-2-yl)methyl)-7-(4-(trifluoromethoxy)phenyl)-3,4-dihydrobenzo[f][1,4]oxazepin-5(2H)-one (II-42);
ethyl 3-((5-oxo-7-(4-(trifluoromethoxy)phenyl)-2,3-dihydrobenzo[f][1,4]oxazepin-4(5H)-yl)methyl)benzoate (II-43);
4-(2-(pyrimidin-2-yl)ethyl)-7-(4-(trifluoromethoxy)phenyl)-3,4-dihydrobenzo[f][1,4]oxazepin-5(2H)-one (II-44);
4-(3,4-difluorobenzyl)-7-(4-(trifluoromethoxy)phenyl)-3,4-dihydrobenzo[f][1,4]oxazepin-5(2H)-one (II-45);
4-(2-chlorobenzyl)-7-(4-(trifluoromethoxy)phenyl)-3,4-dihydrobenzo[f][1,4]oxazepin-5(2H)-one (II-47);
4-(2,6-dichlorobenzyl)-7-(4-(trifluoromethoxy)phenyl)-3,4-dihydrobenzo[f][1,4]oxazepin-5(2H)-one (II-48);
4-(2,6-difluorobenzyl)-7-(4-(trifluoromethoxy)phenyl)-3,4-dihydrobenzo[f][1,4]oxazepin-5(2H)-one (II-49);
4-(2-(1H-pyrazol-1-yl)ethyl)-7-(4-(trifluoromethoxy)phenyl)-3,4-dihydrobenzo[f][1,4]oxazepin-5(2H)-one (II-50);
(2S,11aS)-2-amino-7-(4-(trifluoromethyl)phenyl)-2,3,11,11a-tetrahydrobenzo[f]pyrrolo[2,1-c][1,4]oxazepin-5(1H)-one (II-51);
4-(2-(pyridin-2-yl)ethyl)-7-(4-(trifluoromethoxy)phenyl)-3,4-dihydrobenzo[f][1,4]oxazepin-5(2H)-one (II-54);
4-(2-fluorobenzyl)-7-(4-(trifluoromethoxy)phenyl)-3,4-dihydrobenzo[f][1,4]oxazepin-5(2H)-one (II-57);
(R)-7-(4-(trifluoromethyl)phenyl)-2,3,11,11a-tetrahydrobenzo[f]pyrrolo[2,1-c][1,4]oxazepin-5(1H)-one (II-59);
4-(pyrimidin-2-ylmethyl)-7-(4-(trifluoromethyl)phenyl)-3,4-dihydrobenzo[f][1,4]oxazepin-5(2H)-one (II-61);
4-(4-fluorobenzyl)-7-(4-(trifluoromethoxy)phenyl)-3,4-dihydrobenzo[f][1,4]oxazepin-5(2H)-one (II-62);
4-((1-methyl-1H-pyrazol-3-yl)methyl)-7-(4-(trifluoromethoxy)phenyl)-3,4-dihydrobenzo[f][1,4]oxazepin-5(2H)-one (II-64);
4-((5-chloropyrimidin-2-yl)methyl)-7-(4-(trifluoromethoxy)phenyl)-3,4-dihydrobenzo[f][1,4]oxazepin-5(2H)-one (II-65);
4-(pyridin-4-ylmethyl)-7-(4-(trifluoromethoxy)phenyl)-3,4-dihydrobenzo[f][1,4]oxazepin-5(2H)-one (II-67);
4-((5-cyclopropyl-1,3,4-oxadiazol-2-yl)methyl)-7-(4-(trifluoromethoxy)phenyl)-3,4-dihydrobenzo[f][1,4]oxazepin-5(2H)-one (II-68);
4-(2-(pyrimidin-2-yloxy)ethyl)-7-(4-(trifluoromethoxy)phenyl)-3,4-dihydrobenzo[f][1,4]oxazepin-5(2H)-one (II-69);
4-(pyridin-3-ylmethyl)-7-(4-(trifluoromethoxy)phenyl)-3,4-dihydrobenzo[f][1,4]oxazepin-5(2H)-one (II-70);
4-(pyridin-2-ylmethyl)-7-(4-(trifluoromethoxy)phenyl)-3,4-dihydrobenzo[f][1,4]oxazepin-5(2H)-one (II-72);
4-(pyrimidin-2-ylmethyl)-7-(4-(trifluoromethoxy)phenyl)-3,4-dihydrobenzo[f][1,4]oxazepin-5(2H)-one (II-73);

4-((3-methylpyridin-2-yl)methyl)-7-(4-(trifluoromethoxy)phenyl)-3,4-dihydrobenzo[f][1,4]oxazepin-5(2H)-one (II-75);

(R)-2-(2,2,2-trifluoroethyl)-8-(4-(trifluoromethyl)phenyl)-3,4,12,12a-tetrahydro-1H-benzo[f]pyrazino[2,1-c][1,4]oxazepin-6(2H)-one (II-83);

4-(pyrimidin-2-ylmethyl)-7-p-tolyl-3,4-dihydrobenzo[f][1,4]oxazepin-5(2H)-one (II-87);

7-(4-chlorophenyl)-4-(pyrimidin-2-ylmethyl)-3,4-dihydrobenzo[f][1,4]oxazepin-5(2H)-one (II-88);

7-(4-isopropylphenyl)-4-(pyrimidin-2-ylmethyl)-3,4-dihydrobenzo[f][1,4]oxazepin-5(2H)-one (II-89);

7-(4-ethylphenyl)-4-(pyrimidin-2-ylmethyl)-3,4-dihydrobenzo[f][1,4]oxazepin-5(2H)-one (II-91);

7-(4-cyclopropylphenyl)-4-(pyrimidin-2-ylmethyl)-3,4-dihydrobenzo[f][1,4]oxazepin-5 (2H)-one (II-92);

(R)-4-(1-(pyrimidin-2-yl)ethyl)-7-(4-(trifluoromethyl)phenyl)-3,4-dihydrobenzo[f][1,4]oxazepin-5(2H)-one (II-95);

7-(4-isobutoxyphenyl)-4-(pyrimidin-2-ylmethyl)-3,4-dihydrobenzo[f][1,4]oxazepin-5 (2H)-one (II-97);

7-(4-tert-butylphenyl)-4-(pyrimidin-2-ylmethyl)-3,4-dihydrobenzo[f][1,4]oxazepin-5(2H)-one (II-98);

7-(4-cyclopropoxyphenyl)-4-(pyrimidin-2-ylmethyl)-3,4-dihydrobenzo[f][1,4]oxazepin-5(2H)-one (II-102);

7-(4-fluorophenyl)-4-(pyrimidin-2-ylmethyl)-3,4-dihydrobenzo[f][1,4]oxazepin-5(2H)-one (II-104);

7-(2-fluoro-4-(trifluoromethyl)phenyl)-4-(pyrimidin-2-ylmethyl)-3,4-dihydrobenzo[f][1,4]oxazepin-5(2H)-one (II-105);

7-(3-fluoro-4-(2,2,2-trifluoroethoxy)phenyl)-4-(pyrimidin-2-ylmethyl)-3,4-dihydrobenzo[f][1,4]oxazepin-5(2H)-one (II-106);

4-(pyrimidin-2-ylmethyl)-7-(4-(2,2,2-trifluoroethoxy)phenyl)-3,4-dihydrobenzo[f][1,4]oxazepin-5(2H)-one (II-107);

7-(2-chloro-4-(trifluoromethyl)phenyl)-4-(pyrimidin-2-ylmethyl)-3,4-dihydrobenzo[f][1,4]oxazepin-5(2H)-one (II-110);

7-(4-(trifluoromethoxy)phenyl)-4-((4-(trifluoromethyl)pyrimidin-2-yl)methyl)-3,4-dihydrobenzo[f][1,4]oxazepin-5(2H)-one (II-113);

7-(4-(trifluoromethoxy)phenyl)-4-((5-(6-(trifluoromethyl)pyridin-3-yl)pyrimidin-2-yl)methyl)-3,4-dihydrobenzo[f][1,4]oxazepin-5(2H)-one (II-115);

7-(4-chloro-2-fluorophenyl)-4-(pyrimidin-2-ylmethyl)-3,4-dihydrobenzo[f][1,4]oxazepin-5(2H)-one (II-117);

1-(4-(5-oxo-4-(pyrimidin-2-ylmethyl)-2,3,4,5-tetrahydrobenzo[f][1,4]oxazepin-7-yl)phenyl)cyclopentanecarbonitrile (II-122);

7-(4-ethoxyphenyl)-4-(pyrimidin-2-ylmethyl)-3,4-dihydrobenzo[f][1,4]oxazepin-5(2H)-one (II-123);

7-(4-(difluoromethyl)phenyl)-4-(pyrimidin-2-ylmethyl)-3,4-dihydrobenzo[f][1,4]oxazepin-5(2H)-one (II-124);

4-(imidazo[1,2-a]pyridin-2-ylmethyl)-7-(4-(trifluoromethyl)phenyl)-3,4-dihydrobenzo[f][1,4]oxazepin-5(2H)-one (II-129);

4-(4-morpholinopyrimidin-2-yl)methyl)-7-(4-(trifluoromethoxy)phenyl)-3,4-dihydrobenzo[f][1,4]oxazepin-5(2H)-one (II-133);

4-benzyl-7-(4-(trifluoromethoxy)phenyl)-3,4-dihydrobenzo[f][1,4]oxazepin-5(2H)-one (II-134);

4-(imidazo[1,2-a]pyridin-2-ylmethyl)-7-(4-(trifluoromethoxy)phenyl)-3,4-dihydrobenzo[f][1,4]oxazepin-5(2H)-one (II-135);

7-(3-fluoro-4-(trifluoromethyl)phenyl)-4-(pyrimidin-2-ylmethyl)-3,4-dihydrobenzo[f][1,4]oxazepin-5(2H)-one (II-136);

4-((4-methoxypyrimidin-2-yl)methyl)-7-(4-(trifluoromethoxy)phenyl)-3,4-dihydrobenzo[f][1,4]oxazepin-5(2H)-one (II-137);

4-((4-methylpyrimidin-2-yl)methyl)-7-(4-(trifluoromethoxy)phenyl)-3,4-dihydrobenzo[f][1,4]oxazepin-5(2H)-one (II-138);

4-((4-(piperidin-1-yl)pyrimidin-2-yl)methyl)-7-(4-(trifluoromethoxy)phenyl)-3,4-dihydrobenzo[f][1,4]oxazepin-5(2H)-one (II-139);

4-((4-(dimethylamino)pyrimidin-2-yl)methyl)-7-(4-(trifluoromethoxy)phenyl)-3,4-dihydrobenzo[f][1,4]oxazepin-5(2H)-one (II-140);

4-benzyl-7-(4-(trifluoromethyl)phenyl)-3,4-dihydrobenzo[f][1,4]oxazepin-5(2H)-one (II-141);

4-((3-methoxypyridin-2-yl)methyl)-7-(4-(trifluoromethoxy)phenyl)-3,4-dihydrobenzo[f][1,4]oxazepin-5(2H)-one (II-143);

7-(4-(cyclobutylmethoxy)phenyl)-4-(pyrimidin-2-ylmethyl)-3,4-dihydrobenzo[f][1,4]oxazepin-5(2H)-one (II-144);

7-(2-methyl-4-(trifluoromethyl)phenyl)-4-(pyrimidin-2-ylmethyl)-3,4-dihydrobenzo[f][1,4]oxazepin-5(2H)-one (II-145);

7-(2-methyl-4-(trifluoromethoxy)phenyl)-4-(pyrimidin-2-ylmethyl)-3,4-dihydrobenzo[f][1,4]oxazepin-5(2H)-one (II-146);

4-((1-(difluoromethyl)-1H-pyrazol-3-yl)methyl)-7-(4-(trifluoromethoxy)phenyl)-3,4-dihydrobenzo[f][1,4]oxazepin-5(2H)-one (II-147);

7-(4-(trifluoromethoxy)phenyl)-4-((3-(trifluoromethyl)-1H-pyrazol-1-yl)methyl)-3,4-dihydrobenzo[f][1,4]oxazepin-5(2H)-one (II-148);

4-(pyrimidin-2-ylmethyl)-7-(4-(2,2,2-trifluoroethyl)phenyl)-3,4-dihydrobenzo[f][1,4]oxazepin-5(2H)-one (II-150);

4-(pyridin-2-ylmethyl)-7-(4-(2,2,2-trifluoroethyl)phenyl)-3,4-dihydrobenzo[f][1,4]oxazepin-5(2H)-one (II-151);

4-((1-cyclopentyl-1H-pyrazol-3-yl)methyl)-7-(4-(trifluoromethoxy)phenyl)-3,4-dihydrobenzo[f][1,4]oxazepin-5(2H)-one (II-152);

4-((1-ethyl-1H-pyrazol-3-yl)methyl)-7-(4-(trifluoromethoxy)phenyl)-3,4-dihydrobenzo[f][1,4]oxazepin-5(2H)-one (II-153);

4-((1-methyl-1H-imidazol-4-yl)methyl)-7-(4-(trifluoromethoxy)phenyl)-3,4-dihydrobenzo[f][1,4]oxazepin-5(2H)-one (II-154);

4-((4-methyl-1H-pyrazol-1-yl)methyl)-7-(4-(trifluoromethoxy)phenyl)-3,4-dihydrobenzo[f][1,4]oxazepin-5(2H)-one (II-155);

4-((4-chloro-1H-pyrazol-1-yl)methyl)-7-(4-(trifluoromethoxy)phenyl)-3,4-dihydrobenzo[f][1,4]oxazepin-5(2H)-one (II-156);

7-(4-(difluoromethyl)phenyl)-4-(pyridin-2-ylmethyl)-3,4-dihydrobenzo[f][1,4]oxazepin-5(2H)-one (II-157);

7-(4-chloro-3-fluorophenyl)-4-(pyridin-2-ylmethyl)-3,4-dihydrobenzo[f][1,4]oxazepin-5(2H)-one (II-158);

7-(4-(difluoromethoxy)phenyl)-4-(pyridin-2-ylmethyl)-3,4-dihydrobenzo[f][1,4]oxazepin-5(2H)-one (II-159);

4-((1-methyl-1H-pyrazol-4-yl)methyl)-7-(4-(trifluoromethoxy)phenyl)-3,4-dihydrobenzo[f][1,4]oxazepin-5(2H)-one (II-160);

4-(pyrimidin-2-ylmethyl)-7-(2,3,4-trifluorophenyl)-3,4-dihydrobenzo[f][1,4]oxazepin-5(2H)-one (II-162);

7-(3,4-difluorophenyl)-4-(pyrimidin-2-ylmethyl)-3,4-dihydrobenzo[f][1,4]oxazepin-5 (2H)-one (II-163);

4-((3-fluoropyridin-2-yl)methyl)-7-(4-(trifluoromethoxy)phenyl)-3,4-dihydrobenzo[f][1,4]oxazepin-5(2H)-one (II-164);

4-benzyl-9-fluoro-7-(4-(trifluoromethoxy)phenyl)-3,4-dihydrobenzo[f][1,4]oxazepin-5(2H)-one (II-165);

4-benzyl-9-fluoro-7-(4-(trifluoromethyl)phenyl)-3,4-dihydrobenzo[f][1,4]oxazepin-5(2H)-one (II-166);

4-benzyl-8-fluoro-7-(4-(trifluoromethoxy)phenyl)-3,4-dihydrobenzo[f][1,4]oxazepin-5(2H)-one (II-167);

4-benzyl-8-fluoro-7-(4-(trifluoromethyl)phenyl)-3,4-dihydrobenzo[f][1,4]oxazepin-5(2H)-one (II-168);

7-(4-chloro-3-fluorophenyl)-4-((3-fluoropyridin-2-yl)methyl)-3,4-dihydrobenzo[f][1,4]oxazepin-5(2H)-one (II-169);

7-(2-fluoro-4-(trifluoromethyl)phenyl)-4-((3-fluoropyridin-2-yl)methyl)-3,4-dihydrobenzo[f][1,4]oxazepin-5(2H)-one (II-170);

4-(5-oxo-4-(pyrimidin-2-ylmethyl)-2,3,4,5-tetrahydrobenzo[f][1,4]oxazepin-7-yl)phenyl trifluoromethanesulfonate (II-171);

4-((5-methylpyrazin-2-yl)methyl)-7-(4-(trifluoromethoxy)phenyl)-3,4-dihydrobenzo[f][1,4]oxazepin-5(2H)-one (II-172);

2,2,3,3-tetradeutero-4-(pyrimidin-2-ylmethyl)-7-(4-(trifluoromethoxy)phenyl)-3,4-dihydrobenzo[f][1,4]oxazepin-5(2H)-one (II-174);

4-((6-methylpyrazin-2-yl)methyl)-7-(4-(trifluoromethoxy)phenyl)-3,4-dihydrobenzo[f][1,4]oxazepin-5(2H)-one (II-175);

4-((3-fluoropyridin-2-yl)methyl)-7-(4-(trifluoromethyl)phenyl)-3,4-dihydrobenzo[f][1,4]oxazepin-5(2H)-one (II-176);

N-(2-(5-oxo-7-(4-(trifluoromethoxy)phenyl)-2,3-dihydrobenzo[f][1,4]oxazepin-4(5H)-yl)ethyl)benzenesulfonamide (II-177);

N-(2-(5-oxo-7-(4-(trifluoromethoxy)phenyl)-2,3-dihydrobenzo[f][1,4]oxazepin-4(5H)-yl)ethyl)cyclopropanesulfonamide (II-179);

4-((1-methyl-1H-imidazol-2-yl)methyl)-7-(4-(trifluoromethoxy)phenyl)-3,4-dihydrobenzo[f][1,4]oxazepin-5(2H)-one (II-186);

4-(1-benzyl-1H-imidazol-2-yl)methyl)-7-(4-(trifluoromethoxy)phenyl)-3,4-dihydrobenzo[f][1,4]oxazepin-5(2H)-one (II-187);

4-(imidazo[1,2-a]pyridin-2-ylmethyl)-7-(4-(trifluoromethoxy)phenyl)-3,4-dihydrobenzo[f][1,4]oxazepin-5(2H)-one (II-189);

N-cyclopropyl-3-(5-oxo-7-(4-(trifluoromethoxy)phenyl)-2,3-dihydrobenzo[f][1,4]oxazepin-4(5H)-yl)propane-1-sulfonamide (II-190);

N-(2-(5-oxo-7-(4-(trifluoromethoxy)phenyl)-2,3-dihydrobenzo[f][1,4]oxazepin-4(5H)-yl)ethyl)pyrimidine-2-carboxamide (II-192);

7-(4-(4-fluorophenoxy)phenyl)-4-(pyrimidin-2-ylmethyl)-3,4-dihydrobenzo[f][1,4]oxazepin-5(2H)-one (II-193);

7-(4-phenoxyphenyl)-4-(pyrimidin-2-ylmethyl)-3,4-dihydrobenzo[f][1,4]oxazepin-5(2H)-one (II-194); and 7-(3-phenoxyphenyl)-4-(pyrimidin-2-ylmethyl)-3,4-dihydrobenzo[f][1,4]oxazepin-5(2H)-one (II-195);

or a pharmaceutically acceptable salt, ester, stereoisomer, mixture of stereoisomers or tautomer thereof.

In other embodiments, the disclosure provides compounds of Formula II:

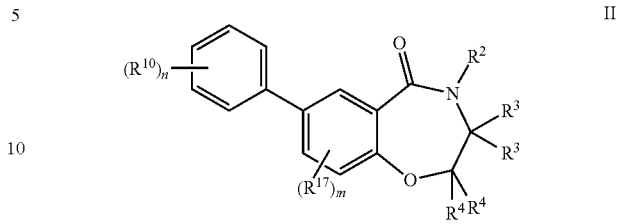

II wherein:

m is 0 or 1;

n is 0, 1, 2 or 3:

each $R^{10}$ is independently selected from the group consisting of halo, $-NO_2$, $-CN$, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $-N(R^{20})-C(O)-R^{22}$, $-N(R^{20})-C(O)-OR^{22}$, $-N(R^{20})-S(O)_2-R^{26}$, $-S(O)_2-R^{20}$, $-O-S(O)_2-R^{20}$, $-S(O)_2-N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, phenyl, heterocyclyl, heteroaryl, $C_{1-6}$ alkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;

$R^2$ is $-C_{1-6}$ alkylene-$R^5$, -L-$R^5$, alkylene-$R^5$, $-C_{1-6}$ alkylene-L-$R^5$ or $-C_{1-6}$ alkylene-L-$C_{1-6}$ alkylene-$R^5$;

L is $-O-$, $-S-$, $-C(O)-$, $-NHS(O)_2-$, $-S(O)_2NH-$, $-C(O)NH-$ or $-NHC(O)-$;

each $R^3$ is independently hydrogen, deuterium, $C_{1-15}$ alkyl, cycloalkyl, aryl, heteroaryl or heterocyclyl;

wherein said $C_{1-15}$ alkyl is optionally substituted with one, two or three substituents independently selected from the group consisting of halo, $-NO_2$, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;

wherein said cycloalkyl, aryl, heterocyclyl or heteroaryl are optionally further substituted with one, two or three substituents independently selected from the group consisting of halo, $-NO_2$, $C_{1-6}$ alkyl, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$; and wherein said $C_{1-6}$ alkyl, aralkyl, cycloalkyl, aryl, heterocyclyl or heteroaryl, are optionally further substituted with one, two or three substituents independently selected from the group consisting of halo, $-NO_2$, $-N(R^{20})(R^{22})$, $-C(O)-R^{20}$, $-C(O)-OR^{20}$, $-C(O)-N(R^{20})(R^{22})$, $-CN$ and $-O-R^{20}$;

or $R^2$ and one of $R^3$ can join together with the atom to which they are attached to form a heterocyclyl;

wherein said heterocyclyl is optionally substituted with one, two or three substituents independently selected from the group consisting of $C_{1-15}$ alkyl, $-O-R^{20}$, $-N(R^{20})(R^{22})$, $-N(R^{20})-C(O)-OR^{20}$ and $-C(O)-OR^{20}$; and wherein said $C_{1-15}$ alkyl is optionally substituted with one, two or three substituents independently selected from the group consisting of halo and heteroaryl;

each $R^4$ is independently hydrogen, deuterium, $C_{1-15}$ alkyl, $C_{1-4}$ alkoxy, —C(O)—OR$^{26}$, —C(O)—N(R$^{26}$)(R$^{26}$), —N(R$^{20}$)—S(O)$_2$—R$^{20}$, cycloalkyl, aryl, heteroaryl or heterocyclyl;

wherein said $C_{1-15}$ alkyl is optionally substituted with one, two or three substituents independently selected from the group consisting of halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

wherein said cycloalkyl, aryl, heterocyclyl or heteroaryl are optionally further substituted with one, two or three substituents independently selected from the group consisting of halo, —NO$_2$, $C_{1-6}$ alkyl, aralkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —NO$_2$, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

or two $R^3$ or two $R^4$ together with the carbon atom to which they are attached form an oxo;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN and —O—R$^{20}$;

wherein said $C_{1-6}$ alkyl, cycloalkyl, aryl, heterocyclyl or heteroaryl are optionally further substituted with one, two or three substituents independently selected from the group consisting of halo, —NO$_2$, $C_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said $C_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^2$)(R$^{22}$), —S(O)$_2$—R$^{20}$ and —O—R$^{20}$;

$R^{17}$ is halo or $C_{1-6}$ alkyl;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —NO$_2$, —S(O)$_2$R$^{26}$, —CN, $C_{1-3}$ alkoxy, —CF$_3$, —OCF$_3$, —OCH$_2$CF$_3$, —C(O)—NH$_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —NO$_2$, —S(O)$_2$R$^{26}$, —CN, $C_{1-3}$ alkoxy, —CF$_3$, —OCF$_3$, aryl, heteroaryl and cycloalkyl; and each $R^{26}$ is independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —CF$_3$ and —OCF$_3$;

or a pharmaceutically acceptable salt, ester, hydrate, solvate, stereoisomer, mixture of stereoisomers, tautomer, polymorph and/or prodrug thereof;

provided the compound is not tert-butyl 6-oxo-8-phenyl-3,4,12,12a-tetrahydro-1H-benzo[f]pyrazino[2,1-c][1,4]oxazepine-2(6H)-carboxylate, tert-butyl 6-oxo-9-phenyl-3,4,12,12a-tetrahydro-1H-benzo[f]pyrazino[2,1-c][1,4]oxazepine-2(6H)-carboxylate, 8-phenyl-3,4,12,12a-tetrahydro-1H-benzo[f]pyrazino[2,1-c][1,4]oxazepin-6(2H)-one, or 9-phenyl-3,4,12,12a-tetrahydro-1H-benzo[f]pyrazino[2,1-c][1,4]oxazepin-6(2H)-one.

In some embodiments, $R^2$ is —$C_{1-6}$ alkylene-$R^5$ or —$C_{1-6}$ alkylene-L-$R^5$.

In some embodiments, $R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, halo, cycloalkyl, heterocyclyl, heteroaryl, —N(R$^{20}$)(R$^{22}$), —C(O)—OR$^{20}$, —CN and —O—R$^{20}$;

wherein said $C_{1-6}$ alkyl or heteroaryl are optionally further substituted with one, two or three substituents independently selected from the group consisting of halo, $C_{1-6}$ alkyl and aryl; and wherein said $C_{1-6}$ alkyl is optionally further substituted with one, two or three halo.

In some embodiments, $R^2$ and one of $R^3$ can join together with the atom to which they are attached to form a heterocyclyl;

wherein said heterocyclyl is optionally substituted with one, two or three substituents independently selected from the group consisting of $C_{1-15}$ alkyl, —O—R$^{20}$, —N(R$^{20}$)(R$^{22}$) and —C(O)—OR$^{20}$; and wherein said $C_{1-15}$ alkyl is optionally substituted with one, two or three substituents independently selected from the group consisting of halo and heteroaryl.

In some embodiments, $R^2$ is

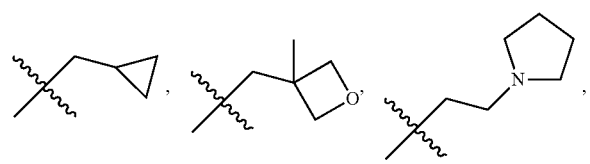

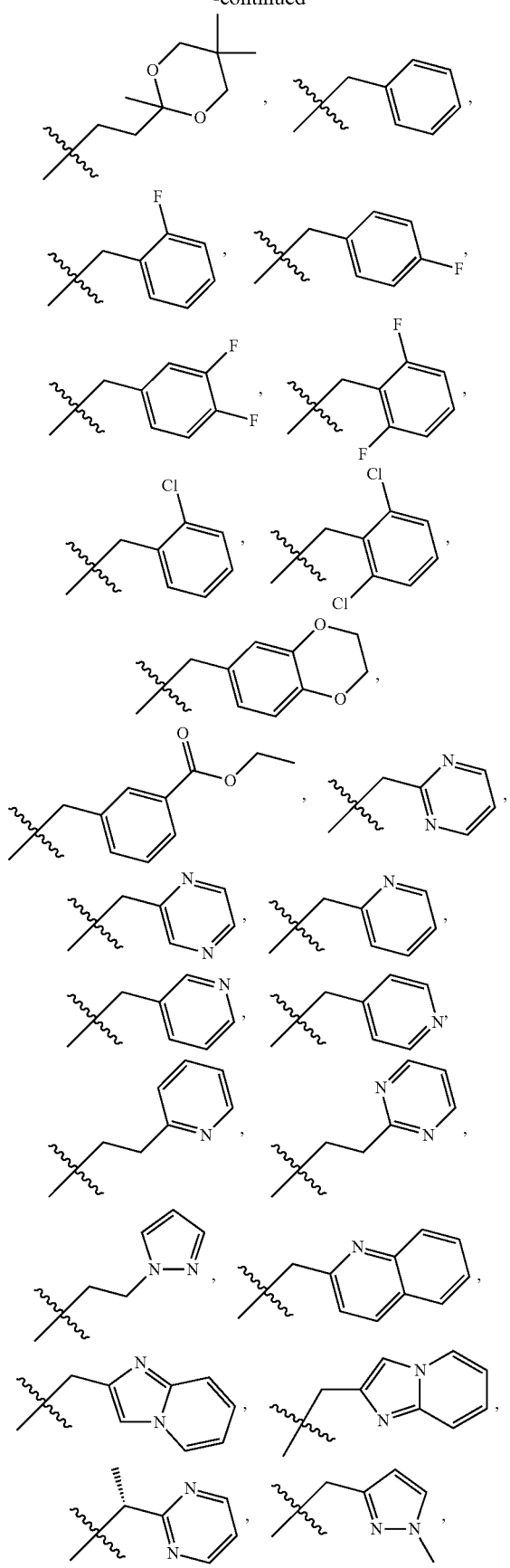
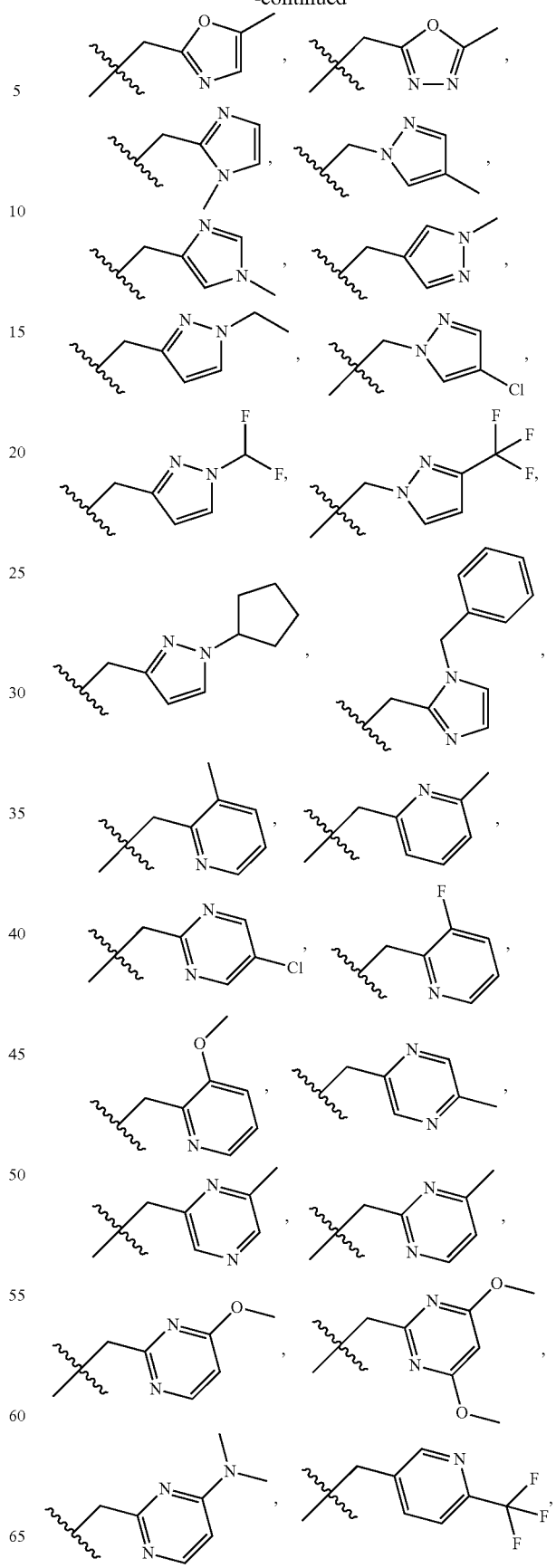

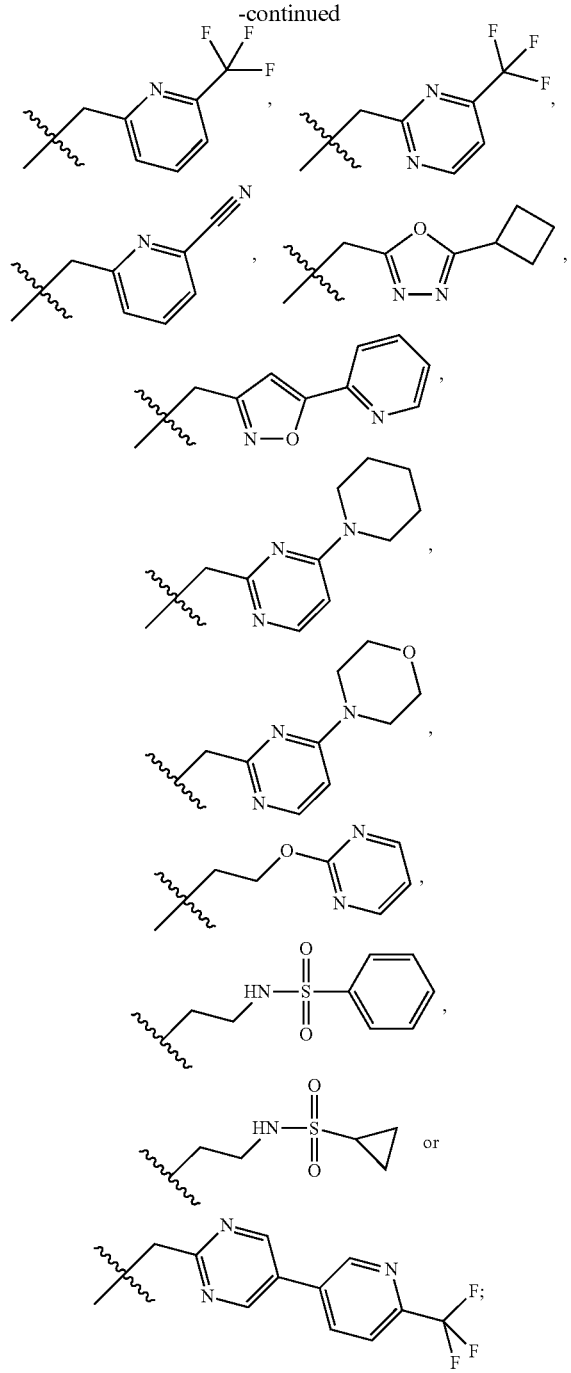

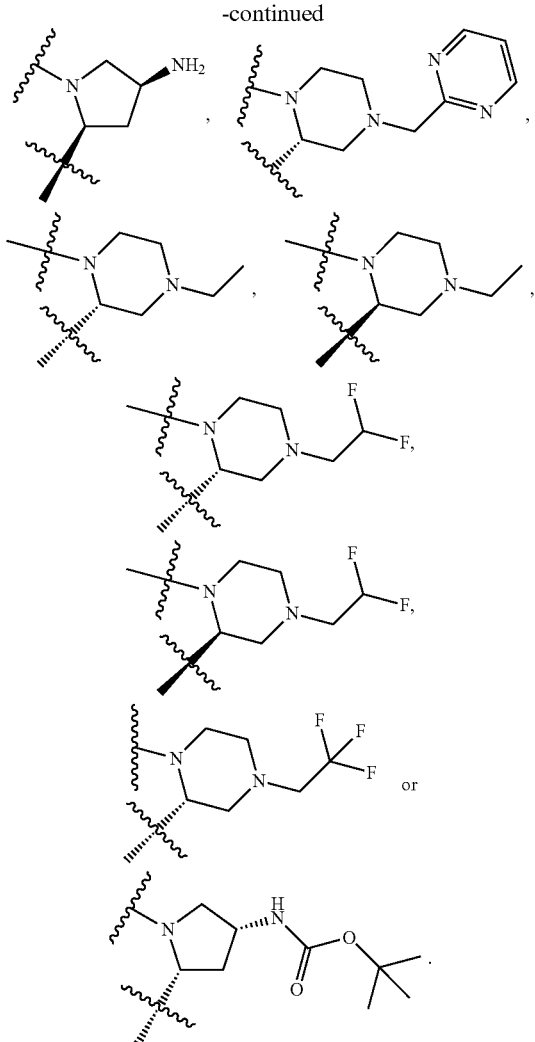

or

R² and one of R³ together with the carbon atoms to which they are attached form a

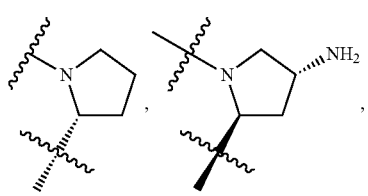

In some embodiments, n is 1, 2 or 3; and
each $R^{10}$ is independently selected from the group consisting of halo, $-O-R^{20}$, $-O-S(O)_2-R^{20}$, $C_{1-4}$ alkyl and cycloalkyl; and
wherein said alkyl is optionally substituted with one, two or three halo; and
$R^{20}$ is independently selected from the group consisting of $C_1$-$C_{15}$ alkyl and cycloalkyl; and
wherein the alkyl is optionally substituted with one, two or three halo or cycloalkyl.

In some embodiments, n is 1, 2 or 3; and each $R^{10}$ is independently 2-fluoro, 3-fluoro, 4-fluoro, 2-chloro, 4-chloro, 2-methyl, 4-methyl, 4-ethyl, 4-isopropyl, 4-tert-butyl, 4-difluoromethyl, 4-trifluoromethyl, 4-cyclopropyl, 4-isobutoxy, 4-difluoromethoxy, 4-trifluoromethoxy, 4-(2,2,2-trifluoroethoxy), 4-trifluoromethylsulfoxyl, 4-(2,2,2-trifluoroethyl), 4-cyclopropoxy or 4-cyclobutylmethoxy.

In some embodiments, each $R^3$ is independently hydrogen, deuterium or $C_{1-15}$ alkyl optionally substituted with heteroaryl;
or $R^2$ and one of $R^3$ can join together with the atom to which they are attached to form a heterocyclyl;
wherein said heterocyclyl is optionally substituted with one, two or three substituents independently selected from the group consisting of $C_{1-15}$ alkyl, $-N(R^{20})(R^{22})$ and $-N(R^{20})-C(O)-OR^{20}$; and wherein said $C_{1-15}$ alkyl is optionally substituted with one, two or three substituents independently selected from the group consisting of halo and heteroaryl; and $R^{20}$ and $R^{22}$ are in each instance independently selected from the group consisting of hydrogen, $C_1$-$C_{15}$ alkyl and heteroaryl.

In some embodiments, each $R^3$ is independently hydrogen, deuterium or $C_{1-15}$ alkyl optionally substituted with heteroaryl.

In some embodiments, each $R^3$ is independently hydrogen, deuterium, methyl, isopropyl or pyridin-2-ylmethyl.

In some embodiments, each $R^4$ is independently hydrogen, deuterium or $C_{1-15}$ alkyl.

In some embodiments, each $R^4$ is independently hydrogen, deuterium or methyl.

In some embodiments, m is 0.

In some embodiments, m is 1; and $R^{17}$ is halo.

In some embodiments, m is 1; and $R^{17}$ is fluoro.

In certain embodiments, the disclosure provides compounds of Formula III:

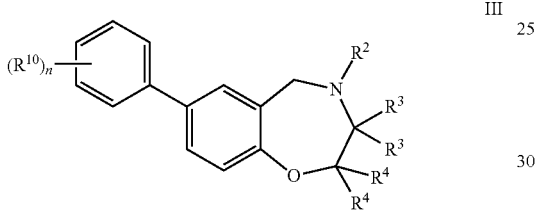

III wherein:

n is 0, 1, 2, 3, 4 or 5:

each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—$S(O)_2$—$R^{26}$, —$S(O)_2$—$R^{20}$, —O—$S(O)_2$—$R^{20}$, —$S(O)_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^2$ is -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;

wherein each —$C_{1-6}$ alkylene is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—$OR^{26}$, —C(O)—N($R^{20}$)($R^{22}$), —N($R^{20}$)—$S(O)_2$—$R^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

L is —O—, —S—, —$NHS(O)_2$—, —$S(O)_2NH$—, —C(O)NH— or —NHC(O)—, provided that when $R^2$ is -L-$R^5$ or -L-$C_{1-6}$ alkylene-$R^5$, then L is not —O—, —S—, —$NHS(O)_2$— or —NHC(O)—;

each $R^3$ is independently hydrogen, deuterium, $C_{1-15}$ alkyl, cycloalkyl, aryl, heteroaryl or heterocyclyl;

wherein said $C_{1-15}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl or heteroaryl, are optionally further substituted with one, two or three substituents independently selected from the group consisting of halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

each $R^4$ is independently hydrogen, deuterium, $C_{1-15}$ alkyl, $C_{1-4}$ alkoxy, —C(O)—$OR^{26}$, —C(O)—N($R^{26}$)($R^{26}$), —N($R^{20}$)—$S(O)_2$—$R^{20}$, cycloalkyl, aryl, heteroaryl or heterocyclyl;

wherein said $C_{1-15}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

or two $R^3$ or two $R^4$ together with the carbon atom to which they are attached form an oxo;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—$S(O)_2$—$R^{20}$, —N($R^{20}$)—C(O)—$R^{22}$, —C(O)—$R^{20}$, —C(O)—$OR^{20}$, —C(O)—N($R^{20}$)($R^{22}$), —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —NO₂, C₁₋₆ alkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰; and
wherein said C₁₋₆ alkyl, cycloalkyl, aryl, heterocyclyl or heteroaryl are optionally further substituted with one, two or three substituents independently selected from the group consisting of halo, aryl, —NO₂, —CF₃, —N(R²⁰)(R²²), —C(O)—R²⁰, —C(O)—OR²⁰, —C(O)—N(R²⁰)(R²²), —S(O)₂—R²⁰ and —O—R²⁰;

R²⁰ and R²² are in each instance independently selected from the group consisting of hydrogen, C₁₋₁₅ alkyl, C₂₋₁₅ alkenyl, C₂₋₁₅ alkynyl, cycloalkyl, heterocyclyl, aryl and heteroaryl;
wherein the C₁₋₁₅ alkyl, C₂₋₁₅ alkenyl, C₂₋₁₅ alkynyl, cycloalkyl, heterocyclyl, aryl and heteroaryl are optionally substituted with one, two or three substituents independently selected from the group consisting of hydroxyl, halo, C₁₋₄ alkyl, acylamino, oxo, —NO₂, —S(O)₂R²⁶, —CN, C₁₋₃ alkoxy, —CF₃, —OCF₃, —OCH₂CF₃, —C(O)—NH₂, aryl, cycloalkyl and heteroaryl; and
wherein said heteroaryl is optionally further substituted with C₁₋₄ alkyl or cycloalkyl; or
when R²⁰ and R²² are attached to a common nitrogen atom R²⁰ and R²² may join to form a heterocyclic or heteroaryl ring which is then optionally substituted with one, two or three substituents independently selected from the group consisting of hydroxyl, halo, C₁₋₄ alkyl, aralkyl, aryloxy, aralkyloxy, acylamino, —NO₂, —S(O)₂R²⁶, —CN, C₁₋₃ alkoxy, —CF₃, —OCF₃, aryl, heteroaryl and cycloalkyl; and
each R²⁶ is independently selected from the group consisting of hydrogen, C₁₋₄ alkyl, aryl and cycloalkyl; and
wherein the C₁₋₄ alkyl, aryl and cycloalkyl may be further substituted with from 1 to 3 substituents independently selected from the group consisting of hydroxyl, halo, C₁₋₄ alkoxy, —CF₃ and —OCF₃;

or a pharmaceutically acceptable salt, ester, stereoisomer, mixture of stereoisomers or tautomer thereof.

In other embodiments, the disclosure provides compounds of Formula III:

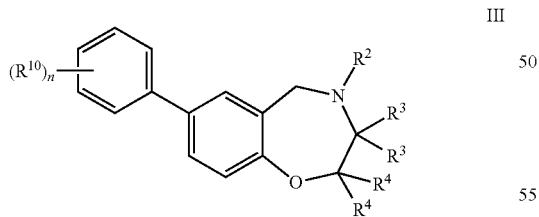

III wherein:
n is 0, 1, 2 or 3:
each R¹⁰ is independently selected from the group consisting of halo, —NO₂, —CN, —SF₅, —Si(CH₃)₃, —O—R²⁰, —S—R²⁰, —C(O)—R²⁰, —C(O)—OR²⁰, —N(R²⁰)(R²²), —C(O)—N(R²⁰)(R²²), —N(R²⁰)—C(O)—R²², —N(R²⁰)—C(O)—OR²², —N(R²⁰)—S(O)₂—R²⁶, —S(O)₂—R²⁰, —O—S(O)₂—R²⁰, —S(O)₂—N(R²⁰)(R²²), C₁₋₆ alkyl, C₂₋₄ alkenyl, C₂₋₄ alkynyl, cycloalkyl, aryl, heteroaryl and heterocyclyl; and wherein said C₁₋₆ alkyl, C₂₋₄ alkenyl, C₂₋₄ alkynyl, cycloalkyl, aryl, heteroaryl or heterocyclyl are optionally substituted with one, two or three substituents independently selected from the group consisting of halo, —NO₂, phenyl, heterocyclyl, heteroaryl, C₁₋₆ alkyl, cycloalkyl, —N(R²⁰)(R²²), —C(O)—R²⁰, —C(O)—OR²⁰, —C(O)—N(R²⁰)(R²²), —CN and —O—R²⁰;
R² is -L-R⁵, alkylene-R⁵, —C₁₋₆ alkylene-L-R⁵ or —C₁₋₆ alkylene-L-C₁₋₆ alkylene-R⁵;
L is —O—, —S—, —C(O)—, —NHS(O)₂—, —S(O)₂NH—, —C(O)NH— or —NHC(O)—;
each R³ is independently hydrogen, deuterium, C₁₋₁₅ alkyl, cycloalkyl, aryl, heteroaryl or heterocyclyl;
wherein said C₁₋₁₅ alkyl is optionally substituted with one, two or three substituents independently selected from the group consisting of halo, —NO₂, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰;
wherein said cycloalkyl, aryl, heterocyclyl or heteroaryl are optionally further substituted with one, two or three substituents independently selected from the group consisting of halo, —NO₂, C₁₋₆ alkyl, aralkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰; and
wherein said C₁₋₆ alkyl, aralkyl, cycloalkyl, aryl, heterocyclyl or heteroaryl, are optionally further substituted with one, two or three substituents independently selected from the group consisting of halo, —NO₂, —N(R²⁰)(R²²), —C(O)—R²⁰, —C(O)—OR²⁰, —C(O)—N(R²⁰)(R²²), —CN and —O—R²⁰;

each R⁴ is independently hydrogen, deuterium, C₁₋₁₅ alkyl, C₁₋₄ alkoxy, —C(O)—OR²⁶, —C(O)—N(R²⁶)(R²⁶), —N(R²⁰)—S(O)₂—R²⁰, cycloalkyl, aryl, heteroaryl or heterocyclyl;
wherein said C₁₋₁₅ alkyl is optionally substituted with one, two or three substituents independently selected from the group consisting of halo, —NO₂, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰;
wherein said cycloalkyl, aryl, heterocyclyl or heteroaryl are optionally further substituted with one, two or three substituents independently selected from the group consisting of halo, —NO₂, C₁₋₆ alkyl, aralkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰; and
wherein said C₁₋₆ alkyl, aralkyl, cycloalkyl, aryl, heterocyclyl, heteroaryl, are optionally further substituted with one, two or three substituents independently selected from the group consisting of hydroxyl, halo, —NO₂, —N(R²⁰)(R²²), —C(O)—R²⁰, —C(O)—OR²⁰, —C(O)—N(R²⁰)(R²²), —CN and —O—R²⁰;

or two R³ or two R⁴ together with the carbon atom to which they are attached form an oxo;
R⁵ is cycloalkyl, aryl, heteroaryl or heterocyclyl;
wherein said cycloalkyl, aryl, heteroaryl or heterocyclyl are optionally substituted with one, two or three substituents independently selected from the group consisting of C₁₋₆ alkyl, C₂₋₄ alkynyl, halo, —NO₂, cycloalkyl, aryl, heterocyclyl, heteroaryl, —N($R^{20}$)($R^{22}$), —N($R^{20}$)—S(O)$_2$—$R^{20}$, —N($R^{20}$)—C(O)—$R^{22}$, —C(O)—$R^{20}$, —C(O)—O$R^{20}$, —C(O)—N($R^{20}$)($R^{22}$), —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —NO$_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N($R^{20}$)($R^{22}$), —C(O)—$R^{20}$, —C(O)—O$R^{20}$, —C(O)—N($R^{20}$)($R^{22}$), —CN, —S(O)$_2$—$R^{20}$ and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —NO$_2$, —S(O)$_2$$R^{26}$, —CN, $C_{1-3}$ alkoxy, —CF$_3$, —OCF$_3$, —OCH$_2$CF$_3$, —C(O)—NH$_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —NO$_2$, —S(O)$_2$$R^{26}$, —CN, $C_{1-3}$ alkoxy, —CF$_3$, —OCF$_3$, aryl, heteroaryl and cycloalkyl; and each $R^{26}$ is independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —CF$_3$ and —OCF$_3$;

or a pharmaceutically acceptable salt, ester, hydrate, solvate, stereoisomer, mixture of stereoisomers, tautomer, polymorph and/or prodrug thereof.

In some embodiments, $R^2$ is —C(O)—$R^5$ or —C(O)—$C_{1-6}$ alkylene-$R^5$; and $R^5$ is cycloalkyl, aryl or heteroaryl;

wherein said cycloalkyl or heteroaryl are optionally substituted with one, two or three substituents independently selected from the group consisting of $C_{1-6}$ alkyl, halo and —C(O)—O$R^{20}$.

In some embodiments, $R^5$ is cycloalkyl, aryl or heteroaryl;

wherein said cycloalkyl or heteroaryl are optionally substituted with one, two or three substituents independently selected from the group consisting of $C_{1-6}$ alkyl, halo and —C(O)—O$R^{20}$.

In some embodiments, each —$C_{1-6}$ alkylene of $R^2$ is unsubstituted.

In some embodiments, $R^2$ is

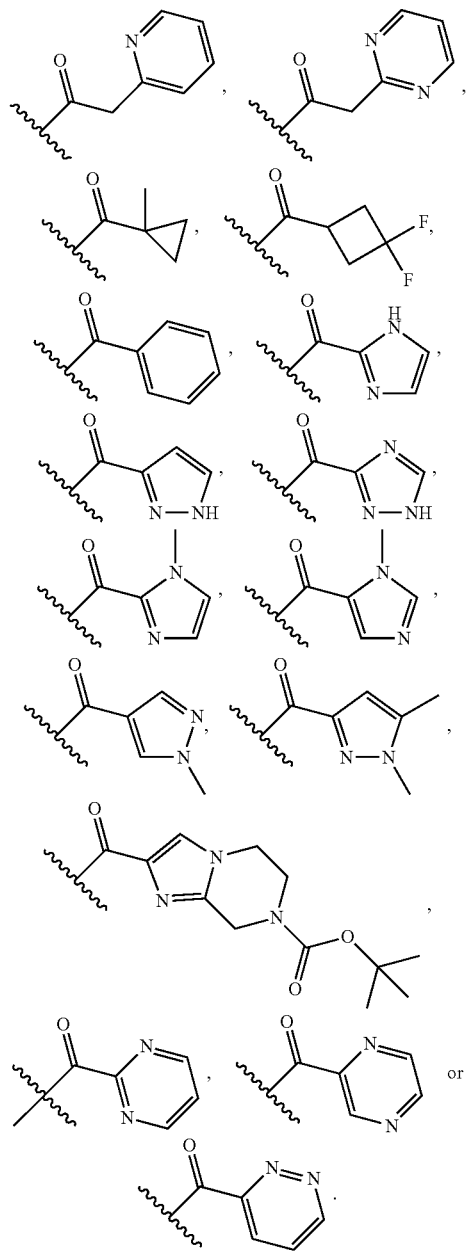

In some embodiments, n is 1; and $R^{10}$ is —O—$R^{20}$ or $C_{1-4}$ alkyl;

wherein said alkyl is optionally substituted with one, two or three halo; and $R^{20}$ is $C_1$-$C_{15}$ alkyl;

wherein the alkyl is optionally substituted with one, two or three halo.

In some embodiments, n is 1; and $R^{10}$ is 4-trifluoromethyl or 4-trifluoromethoxy.

In some embodiments, the compound is selected from the group consisting of:

pyrimidin-2-yl(7-(4-(trifluoromethoxy)phenyl)-2,3-dihydrobenzo[f][1,4]oxazepin-4(5H)-yl)methanone (III-1);

phenyl(7-(4-(trifluoromethoxy)phenyl)-2,3-dihydrobenzo[f][1,4]oxazepin-4(5H)-yl)methanone (III-4);

(1-methylcyclopropyl)(7-(4-(trifluoromethoxy)phenyl)-2,3-dihydrobenzo[f][1,4]oxazepin-4(5H)-yl)methanone (III-10);

(3,3-difluorocyclobutyl)(7-(4-(trifluoromethoxy)phenyl)-2,3-dihydrobenzo[f][1,4]oxazepin-4(5H)-yl)methanone (III-11);

(1-methyl-1H-pyrazol-4-yl)(7-(4-(trifluoromethoxy)phenyl)-2,3-dihydrobenzo[f][1,4]oxazepin-4(5H)-yl)methanone (III-12);

(1H-pyrazol-3-yl)(7-(4-(trifluoromethoxy)phenyl)-2,3-dihydrobenzo[f][1,4]oxazepin-4(5H)-yl)methanone (III-15);

pyrazin-2-yl(7-(4-(trifluoromethoxy)phenyl)-2,3-dihydrobenzo[f][1,4]oxazepin-4(5H)-yl)methanone (III-23);

pyridazin-3-yl(7-(4-(trifluoromethoxy)phenyl)-2,3-dihydrobenzo[f][1,4]oxazepin-4(5H)-yl)methanone (III-24);

2-(pyridin-2-yl)-1-(7-(4-(trifluoromethoxy)phenyl)-2,3-dihydrobenzo[f][1,4]oxazepin-4(5H)-yl)ethanone (III-29);

2-(pyrimidin-2-yl)-1-(7-(4-(trifluoromethyl)phenyl)-2,3-dihydrobenzo[f][1,4]oxazepin-4(5H)-yl)ethanone (III-30);

(1-methyl-1H-imidazol-5-yl)(7-(4-(trifluoromethyl)phenyl)-2,3-dihydrobenzo[f][1,4]oxazepin-4(5H)-yl)methanone (III-32);

(1H-imidazol-2-yl)(7-(4-(trifluoromethyl)phenyl)-2,3-dihydrobenzo[f][1,4]oxazepin-4(5H)-yl)methanone (III-33);

(1-methyl-1H-imidazol-2-yl)(7-(4-(trifluoromethyl)phenyl)-2,3-dihydrobenzo[f][1,4]oxazepin-4(5H)-yl)methanone (III-37);

(R)-(2-methyl-7-(4-(trifluoromethoxy)phenyl)-2,3-dihydrobenzo[f][1,4]oxazepin-4(5H)-yl)(pyrimidin-2-yl)methanone (III-38);

tert-butyl 2-(7-(4-(trifluoromethyl)phenyl)-2,3,4,5-tetrahydrobenzo[f][1,4]oxazepine-4-carbonyl)-5,6-dihydroimidazo[1,2-a]pyrazine-7(8H)-carboxylate (III-40);

(1H-1,2,4-triazol-3-yl)(7-(4-(trifluoromethyl)phenyl)-2,3-dihydrobenzo[f][1,4]oxazepin-4(5H)-yl)methanone (III-50); and (1,5-dimethyl-1H-pyrazol-3-yl)(7-(4-(trifluoromethoxy)phenyl)-2,3-dihydrobenzo[f][1,4]oxazepin-4(5H)-yl)methanone (III-58);

or a pharmaceutically acceptable salt, ester, stereoisomer, mixture of stereoisomers or tautomer thereof.

In certain embodiments, the disclosure provides compounds of Formula IV:

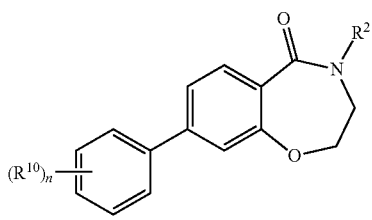

IV wherein:

n is 0, 1, 2, 3, 4 or 5:

each $R^{10}$ is independently selected from the group consisting of halo, $-NO_2$, $-CN$, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $-N(R^{20})-C(O)-R^{22}$, $-N(R^{20})-C(O)-OR^{22}$, $-N(R^{20})-S(O)_2-R^{26}$, $-S(O)_2-R^{20}$, $-O-S(O)_2-R^{20}$, $-S(O)_2-N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, phenyl, heterocyclyl, heteroaryl, $C_{1-6}$ alkyl, $C_{1-3}$ haloalkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;

$R^2$ is $-C_{1-6}$ alkylene-$R^5$, -L-$R^5$, alkylene-$R^5$, $-C_{1-6}$ alkylene-L-$R^5$ or $-C_{1-6}$ alkylene-L-$C_{1-6}$ alkylene-$R^5$;

wherein each $-C_{1-6}$ alkylene is optionally substituted by one substituent independently selected from the group consisting of $C_{2-4}$ alkynyl, halo, $-NO_2$, $-CN$, $-O-R^{20}$, $-N(R^{20})(R^{22})$, $-C(O)-R^{20}$, $-C(O)-OR^{26}$, $-C(O)-N(R^{20})(R^{22})$, $-N(R^{20})-S(O)_2-R^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, $-NO_2$, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;

L is $-O-$, $-S-$, $-C(O)-$, $-NHS(O)_2-$, $-S(O)_2NH-$, $-C(O)NH-$ or $-NHC(O)-$, provided that when $R^2$ is -L-$R^5$ or -L-$C_{1-6}$ alkylene-$R^5$, then L is not $-O-$, $-S-$, $-NHS(O)_2-$ or $-NHC(O)-$;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, $-NO_2$, cycloalkyl, aryl, heterocyclyl, heteroaryl, $-N(R^{20})(R^{22})$, $-N(R^{20})-S(O)_2-R^{20}$, $-N(R^{20})-C(O)-R^{22}$, $-C(O)-R^{20}$, $-C(O)-OR^{20}$, $-C(O)-N(R^{20})(R^{22})$, $-CN$ and $-O-R^{20}$;

wherein said $C_{1-6}$ alkyl, cycloalkyl, aryl, heterocyclyl or heteroaryl are optionally further substituted with one, two or three substituents independently selected from the group consisting of halo, $-NO_2$, $C_{1-6}$ alkyl, cycloalkyl, aryl, heterocyclyl, heteroaryl, $-N(R^{20})(R^{22})$, $-C(O)-OR^{20}$, $-C(O)-N(R^{20})(R^{22})$, $-CN$ and $-O-R^{20}$; and wherein said $C_{1-6}$ alkyl, cycloalkyl, aryl, heterocyclyl or heteroaryl are optionally further substituted with one, two or three substituents independently selected from the group consisting of halo, aryl, $-NO_2$, $-CF_3$, $-N(R^{20})(R^{22})$, $-C(O)-R^{20}$, $-C(O)-OR^{20}$, $-C(O)-N(R^{20})(R^{22})$, $-CN$, $-S(O)_2-R^{20}$ and $-O-R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, $-NO_2$, $-S(O)_2R^{26}$, $-CN$, $C_{1-3}$ alkoxy, $-CF_3$, $-OCF_3$, $-OCH_2CF_3$, $-C(O)-NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, stereoisomer, mixture of stereoisomers or tautomer thereof.

In other embodiments, the disclosure provides compounds of Formula IV:

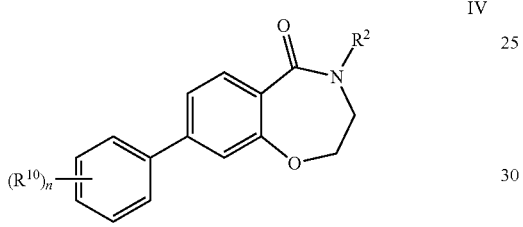

IV n is 0, 1, 2 or 3:

each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—$S(O)_2$—$R^{26}$, —$S(O)_2$—$R^{20}$, —O—$S(O)_2$—$R^{20}$, —$S(O)_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —N($R^{20}$)($R^{22}$), —C(O)$R^{20}$, —C(O)—$OR^{20}$, —C(O)—N($R^{20}$)($R^{22}$), —CN and —O—$R^{20}$;

$R^2$ is —$C_{1-6}$ alkylene-$R^5$, -L-$R^5$, alkylene-$R^5$, —$C_{1-6}$ alkylene-L-$R^5$ or —$C_{1-6}$ alkylene-L-$C_{1-6}$ alkylene-$R^5$;

L is —O—, —S—, —C(O)—, —NHS(O)$_2$—, —$S(O)_2$NH—, —C(O)NH— or —NHC(O)—;

$S(O)R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—$S(O)_2$—$R^{20}$, —N($R^{20}$)—C(O)—$R^{22}$, —C(O)—$R^{20}$, —C(O)—$OR^{20}$, —C(O)—N($R^{20}$)($R^{22}$), —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —N($R^{20}$)($R^{22}$), —C(O)—$R^{20}$, —C(O)—$OR^{20}$, —C(O)—N($R^{20}$)($R^{22}$), —$S(O)_2$—$R^{20}$ and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —$S(O)_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, mixture of stereoisomers, tautomer, polymorph and/or prodrug thereof.

In some embodiments, each —$C_{1-6}$ alkylene of $R^2$ is unsubstituted.

In certain embodiments, the disclosure provides compounds of Formula V:

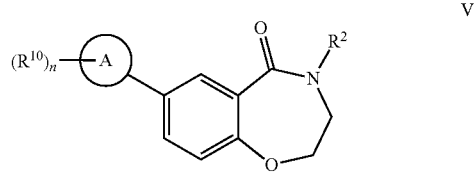

V wherein:

A is cycloalkenyl;

n is 0, 1, 2, 3, 4 or 5;

each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—$S(O)_2$—$R^{26}$, —$S(O)_2$—$R^{20}$, —O—$S(O)_2$—$R^{20}$, —$S(O)_2$—

N(R$^{20}$)(R$^{22}$), C$_{1-6}$ alkyl, C$_{2-4}$ alkenyl, C$_{2-4}$ alkynyl, cycloalkyl, aryl, heteroaryl and heterocyclyl; and wherein said C$_{1-6}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, C$_{1-6}$ alkyl, C$_{1-3}$ haloalkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^2$ is —C$_{1-6}$ alkylene-R$^5$, -L-R$^5$, -L-C$_{1-6}$ alkylene-R$^5$, —C$_{1-6}$ alkylene-L-R$^5$ or —C$_{1-6}$ alkylene-L-C$_{1-6}$ alkylene-R$^5$;

wherein each —C$_{1-6}$ alkylene is optionally substituted by one substituent independently selected from the group consisting of C$_{2-4}$ alkynyl, halo, —NO$_2$, —CN, —O—R$^{20}$, —N(R$^{20}$)(R$^{22}$), —C(O)—R$^{20}$, —C(O)—OR$^{26}$, —C(O)—N(R$^{20}$)(R$^{22}$), —N(R$^{20}$)—S(O)$_2$—R$^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

L is —O—, —S—, —C(O)—, —NHS(O)$_2$—, —S(O)$_2$NH—, —C(O)NH— or —NHC(O)—, provided that when R$^2$ is -L-R$^5$ or -L-C$_{1-6}$ alkylene-R$^5$, then L is not —O—, —S—, —NHS(O)$_2$— or —NHC(O)—;

R$^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN and —O—R$^{20}$;

wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —S(O)$_2$—R$^{20}$ and —O—R$^{20}$;

R$^{20}$ and R$^{22}$ are in each instance independently selected from the group consisting of hydrogen, C$_{1-15}$ alkyl, C$_{2-15}$ alkenyl, C$_{2-15}$ alkynyl, cycloalkyl, heterocyclyl, aryl and heteroaryl;

wherein the C$_{1-15}$ alkyl, C$_{2-15}$ alkenyl, C$_{2-15}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and wherein said heteroaryl is optionally further substituted with C$_{1-4}$ alkyl or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and each R$^{26}$ is independently selected from the group consisting of hydrogen, C$_{1-4}$ alkyl, aryl and cycloalkyl; and wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;

or a pharmaceutically acceptable salt, ester, stereoisomer, mixture of stereoisomers or tautomer thereof.

In other embodiments, the disclosure provides compounds of Formula V:

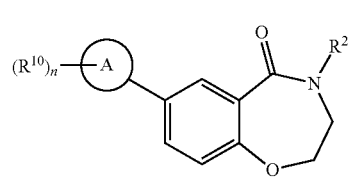

wherein:

A is cycloalkenyl;

n is 0, 1, 2 or 3:

each R$^{10}$ is independently selected from the group consisting of halo, —NO$_2$, —CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—C(O)—OR$^{22}$, —N(R$^{20}$)—S(O)$_2$—R$^{26}$, —S(O)$_2$—R$^{20}$, —O—S(O)$_2$—R$^{20}$, —S(O)$_2$—N(R$^{20}$)(R$^{22}$), C$_{1-6}$ alkyl, C$_{2-4}$ alkenyl, C$_{2-4}$ alkynyl, cycloalkyl, aryl, heteroaryl and heterocyclyl; and wherein said C$_{1-6}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, C$_{1-6}$ alkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^2$ is —C$_{1-6}$ alkylene-R$^5$, -L-R$^5$, alkylene-R$^5$, —C$_{1-6}$ alkylene-L-R$^5$ or —C$_{1-6}$ alkylene-L-C$_{1-6}$ alkylene-R$^5$;

L is —O—, —S—, —C(O)—, —NHS(O)$_2$—, —S(O)$_2$NH—, —C(O)NH— or —NHC(O)—;

R$^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN and —O—R$^{20}$;

wherein said C$_{1-6}$ alkyl, cycloalkyl, aryl, heterocyclyl or heteroaryl are optionally further substituted with one, two or three substituents independently selected from the group consisting of halo, —NO₂, $C_{1-6}$ alkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰; and wherein said $C_{1-6}$ alkyl, cycloalkyl, aryl, heterocyclyl or heteroaryl are optionally further substituted with one, two or three substituents independently selected from the group consisting of halo, aryl, —NO₂, —CF₃, —N(R²⁰)(R²²), —C(O)—R²⁰, —C(O)—OR²⁰, —C(O)—N(R²⁰)(R²²), —CN, —S(O)₂—R²⁰ and —O—R²⁰;

R²⁰ and R²² are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —NO₂, —S(O)₂R²⁶, —CN, $C_{1-3}$ alkoxy, —CF₃, —OCF₃, —OCH₂CF₃, —C(O)—NH₂, aryl, cycloalkyl and heteroaryl; and wherein said heteroaryl is optionally further substituted with $C_{1-4}$ alkyl or cycloalkyl; or when R²⁰ and R²² are attached to a common nitrogen atom R²⁰ and R²² may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —NO₂, —S(O)₂R²⁶, —CN, $C_{1-3}$ alkoxy, —CF₃, —OCF₃, aryl, heteroaryl and cycloalkyl; and each R²⁶ is independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —CF₃ and —OCF₃;

or a pharmaceutically acceptable salt, ester, hydrate, solvate, stereoisomer, mixture of stereoisomers, tautomer, polymorph and/or prodrug thereof.

In some embodiments, R² is —$C_{1-6}$ alkylene-R⁵.
In some embodiments, R⁵ is heteroaryl.
In some embodiments, each —$C_{1-6}$ alkylene of R² is unsubstituted.
In some embodiments, R² is

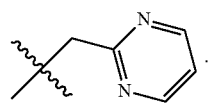

In some embodiments, A is cyclohex-1-enyl.
In some embodiments, A is cyclohex-1-enyl; n is 0 or 1; and R¹⁰ is 4-methyl or 4-tert-butyl.
In some embodiments, the compound is selected from the group consisting of:
7-(4-tert-butylcyclohex-1-enyl)-4-(pyrimidin-2-ylmethyl)-3,4-dihydrobenzo[f][1,4]oxazepin-5(2H)-one (V-1);
7-cyclohexenyl-4-(pyrimidin-2-ylmethyl)-3,4-dihydrobenzo[f][1,4]oxazepin-5(2H)-one (V-3); and
7-(4-methylcyclohex-1-enyl)-4-(pyrimidin-2-ylmethyl)-3,4-dihydrobenzo[f][1,4]oxazepin-5(2H)-one (V-5);
or a pharmaceutically acceptable salt, ester, stereoisomer, mixture of stereoisomers or tautomer thereof.

In certain embodiments, the disclosure provides compounds of Formula VI:

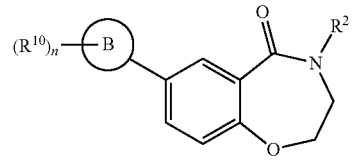

wherein:
B is heterocyclyl or heteroaryl;
n is 0, 1, 2, 3, 4 or 5:
each R¹⁰ is independently selected from the group consisting of halo, —NO₂, —CN, —SF₅, —Si(CH₃)₃, —O—R²⁰, —S—R²⁰, —C(O)—R²⁰, —C(O)—OR²⁰, —N(R²⁰)(R²²), —C(O)—N(R²⁰)(R²²), —N(R²⁰)—C(O)—R²², —N(R²⁰)—C(O)—OR²², —N(R²⁰)—S(O)₂—R²⁶, —S(O)₂—R²⁰, —O—S(O)₂—R²⁰, —S(O)₂—N(R²⁰)(R²²), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —NO₂, phenyl, heterocyclyl, heteroaryl, $C_{1-6}$ alkyl, $C_{1-3}$ haloalkyl, cycloalkyl, —N(R²⁰)(R²²), —C(O)—R²⁰, —C(O)—OR²⁰, —C(O)—N(R²⁰)(R²²), —CN and —O—R²⁰;

R² is —$C_{1-6}$ alkylene-R⁵, -L-R⁵, alkylene-R⁵, —$C_{1-6}$ alkylene-L-R⁵ or —$C_{1-6}$ alkylene-L-$C_{1-6}$ alkylene-R⁵;

wherein each —$C_{1-6}$ alkylene is optionally substituted by one substituent independently selected from the group consisting of $C_{2-4}$ alkynyl, halo, —NO₂, —CN, —O—R²⁰, —N(R²⁰)(R²²), —C(O)—R²⁰, —C(O)—OR²⁶, —C(O)—N(R²⁰)(R²²), —N(R²⁰)—S(O)₂—R²⁰, cycloalkyl, aryl, heteroaryl or heterocyclyl; and wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —NO₂, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰;

L is —O—, —S—, —C(O)—, —NHS(O)₂—, —S(O)₂NH—, —C(O)NH— or —NHC(O)—, provided that when R² is -L-R⁵ or -L-$C_{1-6}$ alkylene-R⁵, then L is not —O—, —S—, —NHS(O)₂— or —NHC(O)—;

R⁵ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —NO₂, cycloalkyl, aryl, heterocyclyl, heteroaryl, —N(R²⁰)(R²²), —N(R²⁰)—S(O)₂—R²⁰, —N(R²⁰)—C(O)—R²², —C(O)—R²⁰, —C(O)—OR²⁰, —C(O)—N(R²⁰)(R²²), —CN and —O—R²⁰;

wherein said $C_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —CN, —S(O)$_2$—R$^{20}$ and —O—R$^{20}$;

R$^{20}$ and R$^{22}$ are in each instance independently selected from the group consisting of hydrogen, C$_{1-15}$ alkyl, C$_{2-15}$ alkenyl, C$_{2-15}$ alkynyl, cycloalkyl, heterocyclyl, aryl and heteroaryl;

wherein the C$_{1-15}$ alkyl, C$_{2-15}$ alkenyl, C$_{2-15}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and wherein said heteroaryl is optionally further substituted with C$_{1-4}$ alkyl or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and each R$^{26}$ is independently selected from the group consisting of hydrogen, C$_{1-4}$ alkyl, aryl and cycloalkyl; and wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;

or a pharmaceutically acceptable salt, ester, stereoisomer, mixture of stereoisomers or tautomer thereof.

In other embodiments, the disclosure provides compounds of Formula VI:

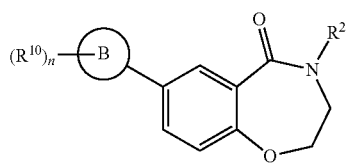

VI wherein:
B is heterocyclyl or heteroaryl;
n is 0, 1, 2 or 3:
each R$^{10}$ is independently selected from the group consisting of halo, —NO$_2$, —CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—C(O)—OR$^{22}$, —N(R$^{20}$)—S(O)$_2$—R$^{26}$, —S(O)$_2$—R$^{20}$, —O—S(O)$_2$—R$^{20}$, —S(O)$_2$—N(R$^{20}$)(R$^{22}$), C$_{1-6}$ alkyl, C$_{2-4}$ alkenyl, C$_{2-4}$ alkynyl, cycloalkyl, aryl, heteroaryl and heterocyclyl; and wherein said C$_{1-6}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, C$_{1-6}$ alkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^2$ is —C$_{1-6}$ alkylene-R$^5$, -L-R$^5$, alkylene-R$^5$, —C$_{1-6}$ alkylene-L-R$^5$ or —C$_{1-6}$ alkylene-L-C$_{1-6}$ alkylene-R$^5$;

L is —O—, —S—, —C(O)—, —NHS(O)$_2$—, —S(O)$_2$NH—, —C(O)NH— or —NHC(O)—;

R$^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN and —O—R$^{20}$;

wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —S(O)$_2$—R$^{20}$ and —O—R$^{20}$;

R$^{20}$ and R$^{22}$ are in each instance independently selected from the group consisting of hydrogen, C$_{1-15}$ alkyl, C$_{2-15}$ alkenyl, C$_{2-15}$ alkynyl, cycloalkyl, heterocyclyl, aryl and heteroaryl;

wherein the C$_{1-15}$ alkyl, C$_{2-15}$ alkenyl, C$_{2-15}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and wherein said heteroaryl is optionally further substituted with C$_{1-4}$ alkyl or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and each R$^{26}$ is independently selected from the group consisting of hydrogen, C$_{1-4}$ alkyl, aryl and cycloalkyl; and wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;

or a pharmaceutically acceptable salt, ester, hydrate, solvate, stereoisomer, mixture of stereoisomers, tautomer, polymorph and/or prodrug thereof.

In some embodiments, B is heteroaryl.

In some embodiments, B is 2-oxo-1,2-dihydropyridin-4-yl, pyridin-4-yl, pyridin-2-yl, thiazol-4-yl or thiophen-2-yl.

In some embodiments, each —$C_{1-6}$ alkylene of $R^2$ is unsubstituted.

In some embodiments, $R^2$ is —$C_{1-6}$ alkylene-$R^5$.

In some embodiments, $R^5$ is heteroaryl.

In some embodiments, $R^2$ is

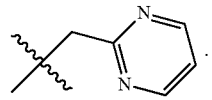

In some embodiments, n is 1;
$R^{10}$ is cycloalkyl, —O—$R^{20}$ or $C_{1-4}$ alkyl;
wherein said alkyl is optionally substituted with one, two or three halo; and
$R^{20}$ is $C_1$-$C_{15}$ alkyl.

In some embodiments, n is 1;
$R^{10}$ is —O—$R^{20}$ or $C_{1-4}$ alkyl;
wherein said alkyl is optionally substituted with one, two or three halo; and
$R^{20}$ is $C_1$-$C_{15}$ alkyl.

In some embodiments, B is 2-oxo-1,2-dihydropyridin-4-yl, pyridin-4-yl, 5-(trifluoromethyl)pyridin-2-yl, 2-isopropylthiazol-4-yl, 5-(trifluoromethyl)thiophen-2-yl or 5-cyclopropylthiophen-2-yl.

In some embodiments, the compound is selected from the group consisting of:

7-(2-tert-butoxypyridin-4-yl)-4-(pyridin-2-ylmethyl)-3,4-dihydrobenzo[f][1,4]oxazepin-5(2H)-one (VI-4);

7-(1-methyl-2-oxo-1,2-dihydropyridin-4-yl)-4-(pyridin-2-ylmethyl)-3,4-dihydrobenzo[f][1,4]oxazepin-5(2H)-one (VI-12);

4-(pyridin-2-ylmethyl)-7-(5-(trifluoromethyl)pyridin-2-yl)-3,4-dihydrobenzo[f][1,4]oxazepin-5(2H)-one (VI-26);

7-(2-isopropylthiazol-4-yl)-4-(pyridin-2-ylmethyl)-3,4-dihydrobenzo[f][1,4]oxazepin-5(2H)-one (VI-30);

4-(pyridin-2-ylmethyl)-7-(5-(trifluoromethyl)thiophen-2-yl)-3,4-dihydrobenzo[f][1,4]oxazepin-5(2H)-one (VI-31);

7-(5-cyclopropylthiophen-2-yl)-4-(pyridin-2-ylmethyl)-3,4-dihydrobenzo[f][1,4]oxazepin-5(2H)-one (VI-32);

7-(5-cyclopropylthiophen-2-yl)-4-(pyrimidin-2-ylmethyl)-3,4-dihydrobenzo[f][1,4]oxazepin-5(2H)-one (VI-36); and 4-(pyrimidin-2-ylmethyl)-7-(5-(trifluoromethyl)thiophen-2-yl)-3,4-dihydrobenzo[f][1,4]oxazepin-5(2H)-one (VI-37);

or a pharmaceutically acceptable salt, ester, stereoisomer, mixture of stereoisomers or tautomer thereof.

In certain embodiments, the disclosure provides compounds of Formula VIII:

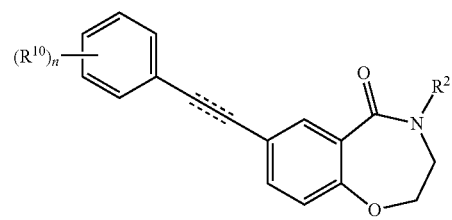

VIII wherein:
n is 0, 1, 2, 3, 4 or 5;
≡ represents a single, double or triple bond;
each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—S(O)$_2$—$R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;
$R^2$ is —$C_{1-6}$ alkylene-$R^5$, -L-$R^5$, alkylene-$R^5$, —$C_{1-6}$ alkylene-L-$R^5$ or —$C_{1-6}$ alkylene-L-$C_{1-6}$ alkylene-$R^5$;
wherein each —$C_{1-6}$ alkylene is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—$OR^{26}$, —C(O)—N($R^{20}$)($R^{22}$), —N($R^{20}$)—S(O)$_2$—$R^{20}$, cycloalkyl, aryl, heteroaryl or heterocyclyl; and
wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;
L is —O—, —S—, —C(O)—, —NHS(O)$_2$—, —S(O)$_2$NH—, —C(O)NH— or —NHC(O)—, provided that when $R^2$ is -L-$R^5$ or -L-$C_{1-6}$ alkylene-$R^5$, then L is not —O—, —S—, —NHS(O)$_2$— or —NHC(O)—;
$R^5$ is cycloalkyl, aryl, heteroaryl or heterocyclyl;
wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—S(O)$_2$—$R^{20}$, —N($R^{20}$)—C(O)—$R^{22}$, —C(O)—$R^{20}$, —C(O)—$OR^{20}$, —C(O)—N($R^{20}$)($R^{22}$), —CN, oxo and —O—$R^{20}$;
wherein said $C_{1-6}$ alkyl, cycloalkyl, aryl, heterocyclyl or heteroaryl are optionally further substituted with one, two or three substituents independently selected from the group consisting of halo, —NO₂, C₁₋₆ alkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰; and wherein said C₁₋₆ alkyl, cycloalkyl, aryl, heterocyclyl or heteroaryl are optionally further substituted with one, two or three substituents independently selected from the group consisting of halo, aryl, —NO₂, —CF₃, —N(R²⁰)(R²²), —C(O)—R²⁰, —C(O)—OR²⁰, —C(O)—N(R²⁰)(R²²), —S(O)₂—R²⁰ and —O—R²⁰;

R²⁰ and R²² are in each instance independently selected from the group consisting of hydrogen, C₁₋₆ alkyl, C₂₋₆ alkenyl, C₂₋₆ alkynyl, cycloalkyl, heterocyclyl, aryl and heteroaryl;

wherein the C₁₋₆ alkyl, C₂₋₆ alkenyl, C₂₋₆ alkynyl, cycloalkyl, heterocyclyl, aryl and heteroaryl are optionally substituted with one, two or three substituents independently selected from the group consisting of hydroxyl, halo, C₁₋₄ alkyl, acylamino, oxo, —NO₂, —S(O)₂R²⁶, —CN, C₁₋₃ alkoxy, —CF₃, —OCF₃, —OCH₂CF₃, —C(O)—NH₂, aryl, cycloalkyl and heteroaryl; and wherein said heteroaryl is optionally further substituted with C₁₋₄ alkyl or cycloalkyl; or when R²⁰ and R²² are attached to a common nitrogen atom R²⁰ and R²² may join to form a heterocyclic or heteroaryl ring which is then optionally substituted with one, two or three substituents independently selected from the group consisting of hydroxyl, halo, C₁₋₄ alkyl, aralkyl, aryloxy, aralkyloxy, acylamino, —NO₂, —S(O)₂R²⁶, —CN, C₁₋₃ alkoxy, —CF₃, —OCF₃, aryl, heteroaryl and cycloalkyl; and each R²⁶ is independently selected from the group consisting of hydrogen, C₁₋₄ alkyl, aryl and cycloalkyl;

wherein the C₁₋₄ alkyl, aryl and cycloalkyl may be further substituted with from 1 to 3 substituents independently selected from the group consisting of hydroxyl, halo, C₁₋₄ alkoxy, —CF₃ and —OCF₃;

or a pharmaceutically acceptable salt, ester, stereoisomer, mixture of stereoisomers or tautomer thereof.

In some embodiments, each —C₁₋₆ alkylene of R² is unsubstituted.

In some embodiments, R² is

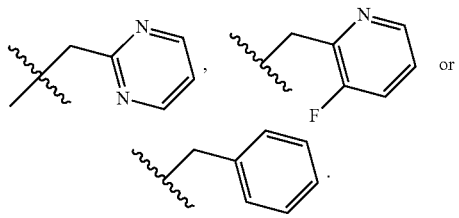

In some embodiments, n is 0 or 1; and R¹⁰ is 4-trifluoromethyl or 4-trifluoromethoxy.

In some embodiments, the compound is selected from the group consisting of:

4-(pyrimidin-2-ylmethyl)-7-((4-(trifluoromethoxy)phenyl)ethynyl)-3,4-dihydrobenzo[f][1,4]oxazepin-5(2H)-one (VIII-4);

7-(phenylethynyl)-4-(pyrimidin-2-ylmethyl)-3,4-dihydrobenzo[f][1,4]oxazepin-5(2H)-one (VIII-5);

4-(pyrimidin-2-ylmethyl)-7-((4-(trifluoromethyl)phenyl)ethynyl)-3,4-dihydrobenzo[f][1,4]oxazepin-5(2H)-one (VIII-6);

4-(pyridin-2-ylmethyl)-7-(4-(trifluoromethyl)phenethyl)-3,4-dihydrobenzo[f][1,4]oxazepin-5(2H)-one (VIII-7);

4-(pyrimidin-2-ylmethyl)-7-(4-(trifluoromethyl)phenethyl)-3,4-dihydrobenzo[f][1,4]oxazepin-5(2H)-one (VIII-8);

4-((3-fluoropyridin-2-yl)methyl)-7-(4-(trifluoromethyl)phenethyl)-3,4-dihydrobenzo[f][1,4]oxazepin-5(2H)-one (VIII-9);

(E)-4-benzyl-7-(4-(trifluoromethyl)styryl)-3,4-dihydrobenzo[f][1,4]oxazepin-5(2H)-one (VIII-10); and 4-benzyl-7-(4-(trifluoromethyl)phenethyl)-3,4-dihydrobenzo[f][1,4]oxazepin-5(2H)-one (VIII-11);

or a pharmaceutically acceptable salt, ester, stereoisomer, mixture of stereoisomers or tautomer thereof.

In other embodiments, the disclosure provides compounds of Formula VIIIA:

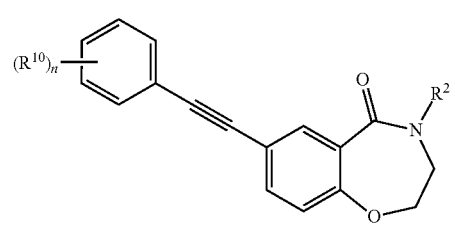

VIIIA wherein:
n is 0, 1, 2 or 3:
each R¹⁰ is independently selected from the group consisting of halo, —NO₂, —CN, —SF₅, —Si(CH₃)₃, —O—R²⁰, —S—R²⁰, —C(O)—R²⁰, —C(O)—OR²⁰, —N(R²⁰)(R²²), —C(O)—N(R²⁰)(R²²), —N(R²⁰)—C(O)—R²², —N(R²⁰)—C(O)—OR²², —N(R²⁰)—S(O)₂—R²⁶, —S(O)₂—R²⁰, —O—S(O)₂—R²⁰, —S(O)₂—N(R²⁰)(R²²), C₁₋₆ alkyl, C₂₋₄ alkenyl, C₂₋₄ alkynyl, cycloalkyl, aryl, heteroaryl and heterocyclyl; and wherein said C₁₋₆ alkyl, C₂₋₄ alkenyl, C₂₋₄ alkynyl, cycloalkyl, aryl, heteroaryl or heterocyclyl are optionally substituted with one, two or three substituents independently selected from the group consisting of halo, —NO₂, phenyl, heterocyclyl, heteroaryl, C₁₋₆ alkyl, cycloalkyl, —N(R²⁰)(R²²), —C(O)—R²⁰, —C(O)—OR²⁰, —C(O)—N(R²⁰)(R²²), —CN and —O—R²⁰;

R² is —C₁₋₆ alkylene-R⁵, -L-R⁵, alkylene-R⁵, —C₁₋₆ alkylene-L-R⁵ or —C₁₋₆ alkylene-L-C₁₋₆ alkylene-R⁵;

L is —O—, —S—, —C(O)—, —NHS(O)₂—, —S(O)₂NH—, —C(O)NH— or —NHC(O)—;

R⁵ is cycloalkyl, aryl, heteroaryl or heterocyclyl;

wherein said cycloalkyl, aryl, heteroaryl or heterocyclyl are optionally substituted with one, two or three substituents independently selected from the group consisting of C₁₋₆ alkyl, C₂₋₄ alkynyl, halo, —NO₂, cycloalkyl, aryl, heterocyclyl, heteroaryl, —N(R²⁰)(R²²), —N(R²⁰)—S(O)₂—R²⁰, —N(R²⁰)—C(O)—R²², —C(O)—R²⁰, —C(O)—OR²⁰, —C(O)—N(R²⁰)(R²²), —CN and —O—R²⁰;

wherein said C₁₋₆ alkyl, cycloalkyl, aryl, heterocyclyl or heteroaryl are optionally further substituted with one, two or three substituents independently selected from the group consisting of halo, —NO₂, C₁₋₆ alkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰; and
wherein said C₁₋₆ alkyl, cycloalkyl, aryl, heterocyclyl or heteroaryl are optionally further substituted with one, two or three substituents independently selected from the group consisting of halo, aryl, —NO₂, —CF₃, —N(R²⁰)(R²²), —C(O)—R²⁰, —C(O)—OR²⁰, —C(O)—N(R²⁰)(R²²), —S(O)₂—R²⁰ and —O—R²⁰;

R²⁰ and R²² are in each instance independently selected from the group consisting of hydrogen, C₁₋₁₅ alkyl, C₂₋₁₅ alkenyl, C₂₋₁₅ alkynyl, cycloalkyl, heterocyclyl, aryl and heteroaryl;
wherein the C₁₋₁₅ alkyl, C₂₋₁₅ alkenyl, C₂₋₁₅ alkynyl, cycloalkyl, heterocyclyl, aryl and heteroaryl are optionally substituted with one, two or three substituents independently selected from the group consisting of hydroxyl, halo, C₁₋₄ alkyl, acylamino, oxo, —NO₂, —S(O)₂R²⁶, —CN, C₁₋₃ alkoxy, —CF₃, —OCF₃, —OCH₂CF₃, —C(O)—NH₂, aryl, cycloalkyl and heteroaryl; and
wherein said heteroaryl is optionally further substituted with C₁₋₄ alkyl or cycloalkyl; or
when R²⁰ and R²² are attached to a common nitrogen atom R²⁰ and R²² may join to form a heterocyclic or heteroaryl ring which is then optionally substituted with one, two or three substituents independently selected from the group consisting of hydroxyl, halo, C₁₋₄ alkyl, aralkyl, aryloxy, aralkyloxy, acylamino, —NO₂, —S(O)₂R²⁶, —CN, C₁₋₃ alkoxy, —CF₃, —OCF₃, aryl, heteroaryl and cycloalkyl; and
each R²⁶ is independently selected from the group consisting of hydrogen, C₁₋₄ alkyl, aryl and cycloalkyl; and
wherein the C₁₋₄ alkyl, aryl and cycloalkyl may be further substituted with from 1 to 3 substituents independently selected from the group consisting of hydroxyl, halo, C₁₋₄ alkoxy, —CF₃ and —OCF₃;
or a pharmaceutically acceptable salt, ester, hydrate, solvate, stereoisomer, mixture of stereoisomers, tautomer, polymorph and/or prodrug thereof.

In some embodiments, R² is —C₁₋₆ alkylene-R⁵.
In some embodiments, R⁵ is heteroaryl.
In some embodiments, R² is

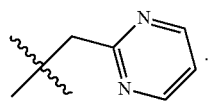 [SMILES: *Cc1ncccn1]

In some embodiments, n is 0 or 1;
R¹⁰ is —O—R²⁰ or C₁₋₄ alkyl;
wherein the alkyl is optionally substituted with three halo; and
R²⁰ is C₁₅ alkyl; and
wherein the alkyl is optionally substituted with one, two or three halo.
In some embodiments, n is 0 or 1; and R¹⁰ is 4-trifluoromethyl or 4-trifluoromethoxy.
In some embodiments, the compound is selected from the group consisting of:
4-(pyrimidin-2-ylmethyl)-7-((4-(trifluoromethoxy)phenyl)ethynyl)-3,4-dihydrobenzo[f][1,4]oxazepin-5(2H)-one (VIII-4);

7-(phenylethynyl)-4-(pyrimidin-2-ylmethyl)-3,4-dihydrobenzo[f][1,4]oxazepin-5(2H)-one (VIII-5); and
4-(pyrimidin-2-ylmethyl)-7-((4-(trifluoromethyl)phenyl)ethynyl)-3,4-dihydrobenzo[f][1,4]oxazepin-5(2H)-one (VIII-6);
or a pharmaceutically acceptable salt, ester, stereoisomer, mixture of stereoisomers or tautomer thereof.

In certain embodiments, the disclosure provides compounds of Formula IX:

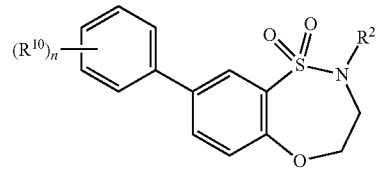

IX wherein:
n is 0, 1, 2, 3, 4 or 5;
each R¹⁰ is independently selected from the group consisting of halo, —NO₂, —CN, —SF₅, —Si(CH₃)₃, —O—R²⁰, —S—R²⁰, —C(O)—R²⁰, —C(O)—OR²⁰, —N(R²⁰)(R²²), —C(O)—N(R²⁰)(R²²), —N(R²⁰)—C(O)—R²², —N(R²⁰)—C(O)—OR²², —N(R²⁰)—S(O)₂—R²⁶, —S(O)₂—R²⁰, —O—S(O)₂—R²⁰, —S(O)₂—N(R²⁰)(R²²), C₁₋₆ alkyl, C₂₋₄ alkenyl, C₂₋₄ alkynyl, cycloalkyl, aryl, heteroaryl and heterocyclyl; and
wherein said C₁₋₆ alkyl, C₂₋₄ alkenyl, C₂₋₄ alkynyl, cycloalkyl, aryl, heteroaryl or heterocyclyl are optionally substituted with one, two or three substituents independently selected from the group consisting of halo, —NO₂, aryl, heterocyclyl, heteroaryl, C₁₋₆ alkyl, C₁₋₃ haloalkyl, cycloalkyl, —N(R²⁰)(R²²), —C(O)—R²⁰, —C(O)—OR²⁰, —C(O)—N(R²⁰)(R²²), —CN and —O—R²⁰;
R² is —C₁₋₆ alkylene-R⁵, -L-R⁵, alkylene-R⁵, —C₁₋₆ alkylene-L-R⁵ or —C₁₋₆ alkylene-L-C₁₋₆ alkylene-R⁵;
wherein each —C₁₋₆ alkylene is optionally substituted by one substituent independently selected from the group consisting of C₂₋₄ alkynyl, halo, —NO₂, —CN, —O—R²⁰, —N(R²⁰)(R²²), —C(O)—R²⁰, —C(O)—OR²⁶, —C(O)—N(R²⁰)(R²²), —N(R²⁰)—S(O)₂—R²⁰, cycloalkyl, aryl, heteroaryl or heterocyclyl; and
wherein said cycloalkyl, aryl, heteroaryl or heterocyclyl are optionally substituted with one, two or three substituents independently selected from the group consisting of C₁₋₆ alkyl, C₂₋₄ alkynyl, halo, —NO₂, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰;
L is —O—, —S—, —C(O)—, —NHS(O)₂—, —S(O)₂NH—, —C(O)NH— or —NHC(O)—, provided that when R² is -L-R⁵ or -L-C₁₋₆ alkylene-R⁵, then L is not —O—, —S—, —NHS(O)₂— or —NHC(O)—;
R⁵ is cycloalkyl, aryl, heteroaryl or heterocyclyl;
wherein said cycloalkyl, aryl, heteroaryl or heterocyclyl are optionally substituted with one, two or three substituents independently selected from the group consisting of C₁₋₆ alkyl, C₂₋₄ alkynyl, halo, —NO₂, cycloalkyl, aryl, heterocyclyl, heteroaryl, —N(R²⁰)(R²²), —N(R²⁰)—S(O)₂—R²⁰, —N(R²⁰)—C(O)—R²², —C(O)—R²⁰, —C(O)—OR²⁰, —C(O)—N(R²⁰)(R²²), —CN, oxo and —O—R²⁰;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —$N(R^{20})(R^{22})$, —$C(O)$—$R^{20}$, —$C(O)$—$OR^{20}$, —$C(O)$—$N(R^{20})(R^{22})$, —$S(O)_2$—$R^{20}$ and —O—$R^{20}$;

$R^{20}$ and $R^{22}$ are in each instance independently selected from the group consisting of hydrogen, $C_{1-6}$ alkyl, $C_{2-6}$ alkenyl, $C_{2-6}$ alkynyl, cycloalkyl, heterocyclyl, aryl and heteroaryl;

wherein the $C_{1-6}$ alkyl, $C_{2-6}$ alkenyl, $C_{2-6}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —$S(O)_2R^{26}$, —CN, $C_{1-3}$ alkoxy, —$CF_3$, —$OCF_3$, —$OCH_2CF_3$, —$C(O)$—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl;

wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, stereoisomer, mixture of stereoisomers or tautomer thereof.

In other embodiments, the disclosure provides compounds of Formula IX:

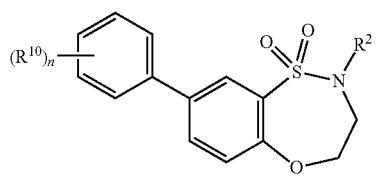

IX wherein:
n is 0, 1, 2 or 3:

each $R^{10}$ is independently selected from the group consisting of halo, —$NO_2$, —CN, —$SF_5$, —$Si(CH_3)_3$, —O—$R^{20}$, —S—$R^{20}$, —$C(O)$—$R^{20}$, —$C(O)$—$OR^{20}$, —$N(R^{20})(R^{22})$, —$C(O)$—$N(R^{20})(R^{22})$, —$N(R^{20})$—$C(O)$—$R^{22}$, —$N(R^{20})$—$C(O)$—$OR^{22}$, —$N(R^{20})$—$S(O)_2$—$R^{26}$, —$S(O)_2$—$R^{20}$, —O—$S(O)_2$—$R^{20}$, —$S(O)_2$—$N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$;

$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;

L is —O—, —S—, —$C(O)$—, —$NHS(O)_2$—, —$S(O)_2NH$—, —$C(O)NH$— or —$NHC(O)$—;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —$N(R^{20})(R^{22})$, —$N(R^{20})$—$S(O)_2$—$R^{20}$, —$N(R^{20})$—$C(O)$—$R^{22}$, —$C(O)$—$R^{20}$, —$C(O)$—$OR^{20}$, —$C(O)$—$N(R^{20})(R^{22})$, —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —$N(R^{20})(R^{22})$, —$C(O)$—$R^{20}$, —$C(O)$—$OR^{20}$, —$C(O)$—$N(R^{20})(R^{22})$, —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —$N(R^{20})(R^{22})$, —$C(O)$—$R^{20}$, —$C(O)$—$OR^{20}$, —$C(O)$—$N(R^{20})(R^{22})$, —$S(O)_2$—$R^{20}$ and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —$S(O)_2R^{26}$, —CN, $C_{1-3}$ alkoxy, —$CF_3$, —$OCF_3$, —$OCH_2CF_3$, —$C(O)$—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, mixture of stereoisomers, tautomer, polymorph and/or prodrug thereof.

In some embodiments, each —$C_{1-6}$ alkylene of $R^2$ is unsubstituted.

In some embodiments, $R^2$ is —$C_{1-6}$ alkylene-$R^5$.

In some embodiments, $R^2$ is not benzyl.

In some embodiments, $R^5$ is heteroaryl; wherein said heteroaryl is optionally further substituted with halo.

In some embodiments, $R^2$ is selected from the group consisting of

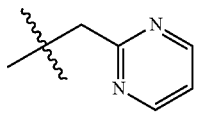 and 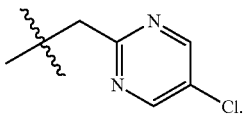

In some embodiments, $R^{10}$ is 4-trifluoromethyl.

In some embodiments, the compound is selected from the group consisting of:
2-((pyrimidin-2-yl)methyl)-8-(4-(trifluoromethyl)phenyl)-3,4-dihydro-2H-benzo[b][1,4,5]oxathiazepin-sulfone (IX-2); and
2-((5-chloropyrimidin-2-yl)methyl)-8-(4-(trifluoromethyl)phenyl)-3,4-dihydro-2H-benzo[b][1,4,5]oxathiazepin-sulfone (IX-3);

or a pharmaceutically acceptable salt, ester, stereoisomer, mixture of stereoisomers or tautomer thereof.

In certain embodiments, the disclosure provides compounds of Formula X:

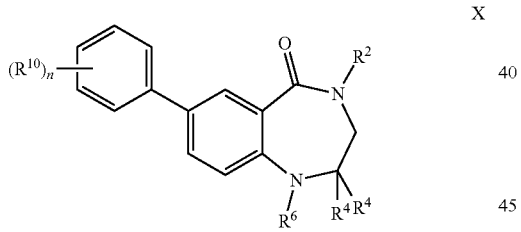

X wherein:

n is 0, 1, 2, 3, 4 or 5;

$R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—S(O)$_2$—$R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, $C_{1-3}$ haloalkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^2$ is —$C_{1-6}$ alkylene-$R^5$, -L-$R^5$, alkylene-$R^5$, —$C_{1-6}$ alkylene-L-$R^5$ or —$C_{1-6}$ alkylene-L-$C_{1-6}$ alkylene-$R^5$;

wherein each —$C_{1-6}$ alkylene is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—$OR^{26}$, —C(O)—N($R^{20}$)($R^{22}$), —N($R^{20}$)—S(O)$_2$—$R^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

L is —O—, —S—, —C(O)—, —NHS(O)$_2$—, —S(O)$_2$NH—, —C(O)NH— or —NHC(O)—, provided that when $R^2$ is -L-$R^5$ or -L-$C_{1-6}$ alkylene-$R^5$, then L is not —O—, —S—, —NHS(O)$_2$— or —NHC(O)—;

each $R^4$ is independently hydrogen, deuterium, $C_{1-15}$ alkyl, $C_{1-4}$ alkoxy, —C(O)—$OR^{26}$, —C(O)—N($R^{26}$)($R^{26}$), —N($R^{20}$)—S(O)$_2$—$R^{20}$, cycloalkyl, aryl, heteroaryl or heterocyclyl;

wherein said $C_{1-15}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

or two $R^4$ together with the carbon atom to which they are attached form an oxo;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—S(O)$_2$—$R^{20}$, —N($R^{20}$)—C(O)—$R^{22}$, —C(O)—$R^{20}$, —C(O)—$OR^{20}$, —C(O)—N($R^{20}$)($R^{22}$), —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —N($R^{20}$)

($R^{22}$), —C(O)—$R^{20}$, —C(O)—O$R^{20}$, —C(O)—N($R^{20}$)($R^{22}$), —CN, —S(O)$_2$—$R^{20}$ and —O—$R^{20}$;

$R^6$ is hydrogen, $C_{1-6}$ alkyl or cycloalkyl;
wherein said $C_{1-6}$ alkyl is optionally substituted with one, two or three substituents independently selected from the group consisting of halo, —NO$_2$, —N($R^{20}$)($R^{22}$), —C(O)—$R^{20}$, —C(O)—O$R^{20}$, —C(O)—N($R^{20}$)($R^{22}$), —CN and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;
wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —NO$_2$, —S(O)$_2$$R^{26}$, —CN, $C_{1-3}$ alkoxy, —CF$_3$, —OCF$_3$, —OCH$_2$CF$_3$, —C(O)—NH$_2$, aryl, cycloalkyl and heteroaryl; and
wherein said heteroaryl is optionally further substituted with $C_{1-4}$ alkyl or cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —NO$_2$, —S(O)$_2$$R^{26}$, —CN, $C_{1-3}$ alkoxy, —CF$_3$, —OCF$_3$, aryl, heteroaryl and cycloalkyl; and each $R^{26}$ is independently selected from the group consisting of hydrogen, $C_{1-4}$ alkyl, aryl and cycloalkyl; and
wherein the $C_{1-4}$ alkyl, aryl and cycloalkyl may be further substituted with from 1 to 3 substituents independently selected from the group consisting of hydroxyl, halo, $C_{1-4}$ alkoxy, —CF$_3$ and —OCF$_3$;

or a pharmaceutically acceptable salt, ester, stereoisomer, mixture of stereoisomers or tautomer thereof.

In other embodiments, the disclosure provides compounds of Formula X:

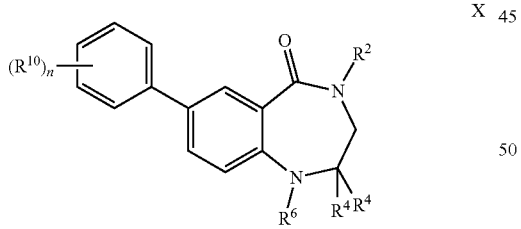

X wherein:
n is 0, 1, 2 or 3;
$R^{10}$ is independently selected from the group consisting of halo, —NO$_2$, —CN, —SF$_5$, —Si(CH$_3$)$_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—C(O)—O$R^{22}$, —N($R^{20}$)—S(O)$_2$—$R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, $C_{1-6}$ alkyl, cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$;

$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;

L is —O—, —S—, —C(O)—, —NHS(O)$_2$—, —S(O)$_2$NH—, —C(O)NH— or —NHC(O)—;

each $R^4$ is independently hydrogen, deuterium, $C_{1-15}$ alkyl, $C_{1-4}$ alkoxy, —C(O)—O$R^{26}$, —C(O)—N($R^{26}$)($R^{26}$), —N($R^{20}$)—S(O)$_2$—$R^{20}$, cycloalkyl, aryl, heteroaryl or heterocyclyl;
wherein said $C_{1-15}$ alkyl is optionally substituted with one, two or three substituents independently selected from the group consisting of halo, —NO$_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
wherein said cycloalkyl, aryl, heterocyclyl or heteroaryl are optionally further substituted with one, two or three substituents independently selected from the group consisting of halo, —NO$_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —NO$_2$, —N($R^{20}$)($R^{22}$), —C(O)—$R^{20}$, —C(O)—O$R^{20}$, —C(O)—N($R^{20}$)($R^{22}$), —CN and —O—$R^{20}$;

or two $R^4$ together with the carbon atom to which they are attached form an oxo;

$R^5$ is cycloalkyl, aryl, heteroaryl or heterocyclyl;
wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —NO$_2$, cycloalkyl, aryl, heterocyclyl, heteroaryl, —N($R^{20}$)($R^{22}$), —N($R^{20}$)—S(O)$_2$—$R^{20}$, —N($R^{20}$)—C(O)—$R^{22}$, —C(O)—$R^{20}$, —C(O)—O$R^{20}$, —C(O)—N($R^{20}$)($R^{22}$), —CN and —O—$R^{20}$;
wherein said $C_{1-6}$ alkyl, cycloalkyl, aryl, heterocyclyl or heteroaryl are optionally further substituted with one, two or three substituents independently selected from the group consisting of halo, —NO$_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
wherein said $C_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N($R^{20}$)($R^{22}$), —C(O)—$R^{20}$, —C(O)—O$R^{20}$, —C(O)—N($R^{20}$)($R^{22}$), —S(O)$_2$—$R^{20}$ and —O—$R^{20}$;

$R^6$ is hydrogen, $C_{1-15}$ alkyl, —C(O)—$R^{20}$, —C(O)—O$R^{26}$, cycloalkyl, aryl, heteroaryl or heterocyclyl;

wherein said $C_{1-15}$ alkyl is optionally substituted with one, two or three substituents independently selected from the group consisting of halo, $-NO_2$, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;

wherein said cycloalkyl, aryl, heterocyclyl or heteroaryl are optionally further substituted with one, two or three substituents independently selected from the group consisting of halo, $-NO_2$, $C_{1-6}$ alkyl, aralkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$; and wherein said $C_{1-6}$ alkyl, aralkyl, cycloalkyl, aryl, heterocyclyl or heteroaryl are optionally further substituted with one, two or three substituents independently selected from the group consisting of halo, $-NO_2$, $-N(R^{20})(R^{22})$, $-C(O)-R^{20}$, $-C(O)-OR^{20}$, $-C(O)-N(R^{20})(R^{22})$, $-CN$ and $-O-R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, $-NO_2$, $-S(O)_2R^{26}$, $-CN$, $C_{1-3}$ alkoxy, $-CF_3$, $-OCF_3$, $-OCH_2CF_3$, $-C(O)-NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, $-NO_2$, $-S(O)_2R^{26}$, $-CN$, $C_{1-3}$ alkoxy, $-CF_3$, $-OCF_3$, aryl, heteroaryl and cycloalkyl; and each $R^{26}$ is independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, $-CF_3$ and $-OCF_3$;

or a pharmaceutically acceptable salt, ester, hydrate, solvate, stereoisomer, mixture of stereoisomers, tautomer, polymorph and/or prodrug thereof.

In some embodiments, each $-C_{1-6}$ alkylene of $R^2$ is unsubstituted.

In some embodiments, $R^2$ is $-C_{1-6}$ alkylene-$R^5$.

In some embodiments, $R^5$ is aryl.

In some embodiments, $R^2$ is

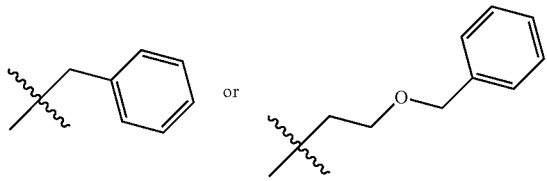

or

In some embodiments, $R^{10}$ is 4-trifluoromethyl or 4-trifluoromethoxy.

In some embodiments, each $R^4$ is independently hydrogen, deuterium or $C_{1-6}$ alkyl optionally substituted with heteroaryl, or two $R^4$ together with the carbon atom to which they are attached form an oxo.

In some embodiments, two $R^4$ together with the carbon atom to which they are attached form an oxo.

In some embodiments, $R^6$ is hydrogen or $C_{1-6}$ alkyl.

In some embodiments, $R^6$ is hydrogen or methyl.

In some embodiments, the compound is selected from the group consisting of:
4-(2-(benzyloxy)ethyl)-1-methyl-7-(4-(trifluoromethoxy)phenyl)-3,4-dihydro-1H-benzo[e][1,4]diazepine-2,5-dione (X-7);
4-benzyl-7-(4-(trifluoromethyl)phenyl)-3,4-dihydro-1H-benzo[e][1,4]diazepine-2,5-dione (X-8);
4-benzyl-1-methyl-7-(4-(trifluoromethyl)phenyl)-3,4-dihydro-1H-benzo[e][1,4]diazepine-2,5-dione (X-11); and
5-benzyl-8-(4-(trifluoromethyl)phenyl)-4H-benzo[f]imidazo[1,2-a][1,4]diazepin-6(5H)-one (X-12);
or a pharmaceutically acceptable salt, ester, stereoisomer, mixture of stereoisomers or tautomer thereof.

In certain embodiments, the disclosure provides compounds of Formula XII:

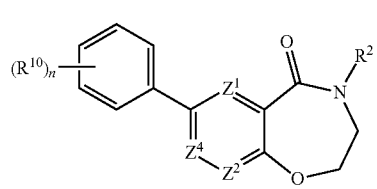

XII wherein:
$Z^1$ and $Z^2$ are each independently selected from the group consisting of $CR^7$ and N;
$Z^4$ is $CR^7$ or N; provided that only one of $Z^1$, $Z^2$ and $Z^4$ is N;
n is 0, 1, 2, 3, 4 or 5;
each $R^{10}$ is independently selected from the group consisting of halo, $-NO_2$, $-CN$, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $-N(R^{20})-C(O)-R^{22}$, $-N(R^{20})-C(O)-OR^{22}$, $-N(R^{20})-S(O)_2-R^{26}$, $-S(O)_2-R^{20}$, $-O-S(O)_2-R^{20}$, $-S(O)_2-N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, phenyl, heterocyclyl, heteroaryl, $C_{1-6}$ alkyl, $C_{1-3}$ haloalkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;

$R^2$ is $-C_{1-6}$ alkylene-$R^5$, -L-$R^5$, -L-$C_{1-6}$ alkylene-$R^5$, $-C_{1-6}$ alkylene-L-$R^5$ or $-C_{1-6}$ alkylene-L-$C_{1-6}$ alkylene-$R^5$;

wherein each $-C_{1-6}$ alkylene is optionally substituted by one substituent independently selected from the group consisting of $C_{2-4}$ alkynyl, halo, $-NO_2$, $-CN$, $-O-R^{20}$, $-N(R^{20})(R^{22})$, $-C(O)-R^{20}$, —C(O)—OR$^{26}$, —C(O)—N(R$^{20}$)(R$^{22}$), —N(R$^{20}$)—S(O)$_2$—R$^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

L is —O—, —S—, —C(O)—, —NHS(O)$_2$—, —S(O)$_2$NH—, —C(O)NH— or —NHC(O)—, provided that when R$^2$ is -L-R$^5$ or -L-C$_{1-6}$ alkylene-R$^5$, then L is not —O—, —S—, —NHS(O)$_2$— or —NHC(O)—;

R$^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN and —O—R$^{20}$;

wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, cycloalkyl, aryl, heterocyclyl or heteroaryl are optionally further substituted with one, two or three substituents independently selected from the group consisting of halo, aryl, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —S(O)$_2$—R$^{20}$ and —O—R$^{20}$;

R$^7$ is hydrogen, halo or C$_{1-6}$ alkyl;

R$^{20}$ and R$^{22}$ are in each instance independently selected from the group consisting of hydrogen, C$_{1-15}$ alkyl, C$_{2-15}$ alkenyl, C$_{2-15}$ alkynyl, cycloalkyl, heterocyclyl, aryl and heteroaryl;

wherein the C$_{1-15}$ alkyl, C$_{2-15}$ alkenyl, C$_{2-15}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, oxo, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and wherein said heteroaryl is optionally further substituted with C$_{1-4}$ alkyl or cycloalkyl; or when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and each R$^{26}$ is independently selected from the group consisting of hydrogen, C$_{1-4}$ alkyl, aryl and cycloalkyl; and wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;

or a pharmaceutically acceptable salt, ester, stereoisomer, mixture of stereoisomers or tautomer thereof.

In other embodiments, the disclosure provides compounds of Formula XII:

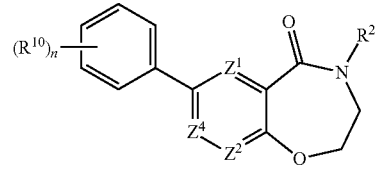

XII wherein:

Z$^1$ and Z$^2$ are each independently selected from the group consisting of CR$^7$ and N;

Z$^4$ is CR$^7$ or N; provided that only one of Z$^1$, Z$^2$ and Z$^4$ is N;

n is 0, 1, 2 or 3:

each R$^{10}$ is independently selected from the group consisting of halo, —NO$_2$, —CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^{20}$)—C(O)—OR$^{22}$, —N(R$^{20}$)—S(O)$_2$—R$^{26}$, —S(O)$_2$—R$^{20}$, —O—S(O)$_2$—R$^{20}$, —S(O)$_2$—N(R$^{20}$)(R$^{22}$), C$_{1-6}$ alkyl, C$_{2-4}$ alkenyl, C$_{2-4}$ alkynyl, cycloalkyl, aryl, heteroaryl and heterocyclyl; and wherein said C$_{1-6}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, C$_{1-6}$ alkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;

R$^2$ is —C$_{1-6}$ alkylene-R$^5$, -L-R$^5$, alkylene-R$^5$, —C$_{1-6}$ alkylene-L-R$^5$ or —C$_{1-6}$ alkylene-L-C$_{1-6}$ alkylene-R$^5$;

L is —O—, —S—, —C(O)—, —NHS(O)$_2$—, —S(O)$_2$NH—, —C(O)NH— or —NHC(O)—;

R$^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —N(R$^{20}$)—S(O)$_2$—R$^{20}$, —N(R$^{20}$)—C(O)—R$^{22}$, —C(O)—R$^{20}$, —C(O)—OR$^{20}$, —C(O)—N(R$^{20}$)(R$^{22}$), —CN and —O—R$^{20}$;

wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and wherein said C$_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —$N(R^{20})(R^{22})$, —$C(O)$—$R^{20}$, —$C(O)$—$OR^{20}$, —$C(O)$—$N(R^{20})(R^{22})$, —$S(O)_2$—$R^{20}$ and —$O$—$R^{20}$;

$R^7$ is hydrogen, halo or $C_{1-6}$ alkyl;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —$S(O)_2R^{26}$, —CN, $C_{1-3}$ alkoxy, —$CF_3$, —$OCF_3$, —$OCH_2CF_3$, —$C(O)$—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl; and
wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, mixture of stereoisomers, tautomer, polymorph and/or prodrug thereof.

In some embodiments, $R^2$ is —$C_{1-6}$ alkylene-$R^5$ or —$C_{1-6}$ alkylene-L-$C_{1-6}$ alkylene-$R^5$.

In some embodiments, each —$C_{1-6}$ alkylene of $R^2$ is unsubstituted.

In some embodiments, $R^5$ is cycloalkyl, aryl or heteroaryl; wherein said heteroaryl is optionally substituted with one, two or three substituents independently selected from the group consisting of $C_{1-6}$ alkyl, halo and —$O$—$R^{20}$.

In some embodiments, $R^2$ is

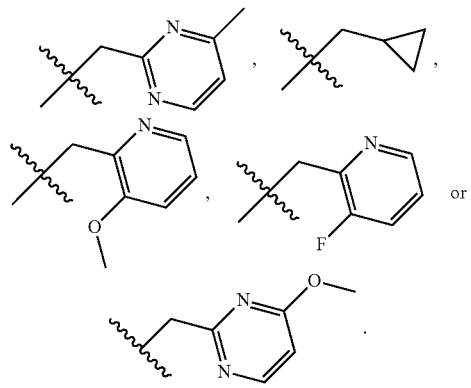

In some embodiments, n is 0 or 1;
$R^{10}$ is —$O$—$R^{20}$ or $C_{1-4}$ alkyl;
wherein the alkyl is optionally substituted with three halo; and
$R^{20}$ is $C_1$-$C_{15}$ alkyl; and
wherein the alkyl is optionally substituted with one, two or three halo.

In some embodiments, n is 0 or 1; and $R^{10}$ is 4-trifluoromethyl or 4-trifluoromethoxy.

In some embodiments, the compound is selected from the group consisting of:
4-benzyl-7-(4-(trifluoromethoxy)phenyl)-3,4-dihydropyrido[4,3-f][1,4]oxazepin-5(2H)-one (XII-1);
4-benzyl-7-(4-(trifluoromethoxy)phenyl)-3,4-dihydropyrido[2,3-f][1,4]oxazepin-5(2H)-one (XII-2);
4-benzyl-7-(4-(trifluoromethyl)phenyl)-3,4-dihydropyrido[2,3-f][1,4]oxazepin-5(2H)-one (XII-3);
4-(pyrimidin-2-ylmethyl)-7-(4-(trifluoromethoxy)phenyl)-3,4-dihydropyrido[4,3-f][1,4]oxazepin-5(2H)-one (XII-5);
4-((4-methylpyrimidin-2-yl)methyl)-7-(4-(trifluoromethoxy)phenyl)-3,4-dihydropyrido[4,3-f][1,4]oxazepin-5(2H)-one (XII-8);
4-(cyclopropylmethyl)-7-(4-(trifluoromethoxy)phenyl)-3,4-dihydropyrido[4,3-f][1,4]oxazepin-5(2H)-one (XII-9);
4-((3-methoxypyridin-2-yl)methyl)-7-(4-(trifluoromethoxy)phenyl)-3,4-dihydropyrido[4,3-f][1,4]oxazepin-5(2H)-one (XII-10);
4-((3-fluoropyridin-2-yl)methyl)-7-(4-(trifluoromethoxy)phenyl)-3,4-dihydropyrido[4,3-f][1,4]oxazepin-5(2H)-one (XII-11); and
4-((4-methoxypyrimidin-2-yl)methyl)-7-(4-(trifluoromethoxy)phenyl)-3,4-dihydropyrido[4,3-f][1,4]oxazepin-5(2H)-one (XII-14);
or a pharmaceutically acceptable salt, ester, stereoisomer, mixture of stereoisomers or tautomer thereof.

In certain embodiments, the disclosure provides compounds of Formula XIII:

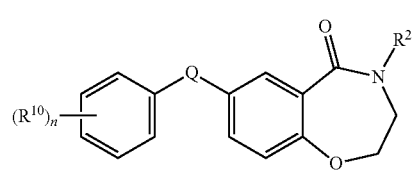

XIII wherein:
Q is a —$O$—$C_{0-2}$ alkylene- or —$NR^{11}$—$C_{0-2}$ alkylene-;
n is 1, 2, 3, 4 or 5;
$R^{10}$ is halo, —$NO_2$, —CN, —$SF_5$, —$Si(CH_3)_3$, —$O$—$R^{20}$, —$S$—$R^{20}$, —$C(O)$—$R^{20}$, —$C(O)$—$OR^{20}$, —$N(R^{20})(R^{22})$, —$C(O)$—$N(R^{20})(R^{22})$, —$N(R^{20})$—$C(O)$—$R^{22}$, —$N(R^{20})$—$C(O)$—$OR^{22}$, —$N(R^{20})$—$C(O)$—$OR^{22}$, —$N(R^{20})$—$S(O)_2$—$R^{26}$, —$S(O)_2$—$R^{20}$, —$O$—$S(O)_2$—$R^{20}$, —$S(O)_2$—$N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and
wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, aryl, heterocyclyl, heteroaryl, $C_{1-6}$ alkyl, $C_{1-3}$ haloalkyl, cycloalkyl, —$N(R^{20})$ ($R^{22}$), —C(O)—$R^{20}$, —C(O)—O$R^{20}$, —C(O)—N($R^{20}$)($R^{22}$), —CN and —O—$R^{20}$;

$R^2$ is —$C_{1-6}$ alkylene-$R^5$, -L-$R^5$, -L-$C_{1-6}$ alkylene-$R^5$, —$C_{1-6}$ alkylene-L-$R^5$ or —$C_{1-6}$ alkylene-L-$C_{1-6}$ alkylene-$R^5$;

wherein each —$C_{1-6}$ alkylene is optionally substituted by one substituent independently selected from the group consisting of $C_{2-4}$ alkynyl, halo, —$NO_2$, —CN, —O—$R^{20}$, —N($R^{20}$)($R^{22}$), —C(O)—$R^{20}$, —C(O)—O$R^{26}$, —C(O)—N($R^{20}$)($R^{22}$), —N($R^{20}$)—S(O)$_2$—$R^{20}$, cycloalkyl, aryl, heteroaryl or heterocyclyl; and wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;

L is —O—, —S—, —C(O)—, —NHS(O)$_2$—, —S(O)$_2$NH—, —C(O)NH— or —NHC(O)—, provided that when $R^2$ is -L-$R^5$ or -L-$C_{1-6}$ alkylene-$R^5$, then L is not —O—, —S—, —NHS(O)$_2$— or —NHC(O)—;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—S(O)$_2$—$R^{20}$, —N($R^{20}$)—C(O)—$R^{22}$, —C(O)—$R^{20}$, —C(O)—O$R^{20}$, —C(O)—N($R^{20}$)($R^{22}$), —CN, oxo and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —$NO_2$, —$CF_3$, —N($R^{20}$)($R^{22}$), —C(O)—$R^{20}$, —C(O)—O$R^{20}$, —C(O)—N($R^{20}$)($R^{22}$), —CN, —S(O)$_2$—$R^{20}$ and —O—$R^{20}$;

$R^{11}$ is hydrogen or $C_{1-4}$ alkyl;

$R^{20}$ and $R^{22}$ are in each instance independently selected from the group consisting of hydrogen, $C_{1-6}$ alkyl, $C_{2-6}$ alkenyl, $C_{2-6}$ alkynyl, cycloalkyl, heterocyclyl, aryl and heteroaryl;

wherein the $C_{1-6}$ alkyl, $C_{2-6}$ alkenyl, $C_{2-6}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, oxo, —$NO_2$, —S(O)$_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryloxy, aralkyloxy, acylamino, —$NO_2$, —S(O)$_2R^{26}$, —CN, $C_{1-3}$ alkoxy, —$CF_3$, —$OCF_3$, aryl, heteroaryl and cycloalkyl; and each $R^{26}$ is independently selected from the group consisting of hydrogen, $C_{1-4}$ alkyl, aryl and cycloalkyl;

wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, stereoisomer, mixture of stereoisomers or tautomer thereof.

In other embodiments, the disclosure provides compounds of Formula XIII:

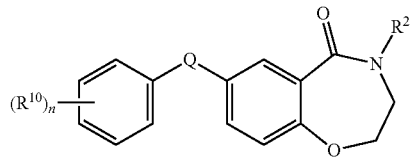

XIII wherein:

Q is a —O—$C_{0-2}$ alkylene- or —$NR^{11}$—$C_{0-2}$ alkylene-;

n is 1, 2 or 3;

$R^{10}$ is halo, —$NO_2$, —CN, —$SF_5$, —Si($CH_3$)$_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—C(O)—O$R^{22}$, —C(O)—O$R^{22}$, —N($R^{20}$)—S(O)$_2$— $R^{26}$, —S(O)$_2$—$R^{20}$, —O—S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$;

$R^2$ is —$C_{1-6}$ alkylene-$R^5$, -L-$R^5$, alkylene-$R^5$, —$C_{1-6}$ alkylene-L-$R^5$ or —$C_{1-6}$ alkylene-L-$C_{1-6}$ alkylene-$R^5$;

L is —O—, —S—, —C(O)—, —NHS(O)$_2$—, —S(O)$_2$NH—, —C(O)NH— or —NHC(O)—;

$R^5$ is cycloalkyl, aryl, heteroaryl or heterocyclyl;

wherein said cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —N($R^{20}$)—S(O)$_2$—$R^{20}$, —N($R^{20}$)—C(O)—$R^{22}$, —C(O)—$R^{20}$, —C(O)—O$R^{20}$, —C(O)—N($R^{20}$)($R^{22}$), —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, aryl, —NO₂, —CF₃, —N(R²⁰)(R²²), —C(O)—R²⁰, —C(O)—OR²⁰, —C(O)—N(R²⁰)(R²²), —S(O)₂—R²⁰ and —O—R²⁰;

R¹¹ is hydrogen or C₁₋₄ alkyl;

R²⁰ and R²² are in each instance independently selected from the group consisting of hydrogen, C₁₋₁₅ alkyl, C₂₋₁₅ alkenyl, C₂₋₁₅ alkynyl, cycloalkyl, heterocyclyl, aryl and heteroaryl;

wherein the C₁₋₁₅ alkyl, C₂₋₁₅ alkenyl, C₂₋₁₅ alkynyl, cycloalkyl, heterocyclyl, aryl and heteroaryl are optionally substituted with one, two or three substituents independently selected from the group consisting of hydroxyl, halo, C₁₋₄ alkyl, acylamino, oxo, —NO₂, —S(O)₂R²⁶, —CN, C₁₋₃ alkoxy, —CF₃, —OCF₃, —OCH₂CF₃, —C(O)—NH₂, aryl, cycloalkyl and heteroaryl; and wherein said heteroaryl is optionally further substituted with C₁₋₄ alkyl or cycloalkyl; or when R²⁰ and R²² are attached to a common nitrogen atom R²⁰ and R²² may join to form a heterocyclic or heteroaryl ring which is then optionally substituted with one, two or three substituents independently selected from the group consisting of hydroxyl, halo, C₁₋₄ alkyl, aralkyl, aryloxy, aralkyloxy, acylamino, —NO₂, —S(O)₂R²⁶, —CN, C₁₋₃ alkoxy, —CF₃, —OCF₃, aryl, heteroaryl and cycloalkyl; and each R²⁶ is independently selected from the group consisting of hydrogen, C₁₋₄ alkyl, aryl and cycloalkyl; and wherein the C₁₋₄ alkyl, aryl and cycloalkyl may be further substituted with from 1 to 3 substituents independently selected from the group consisting of hydroxyl, halo, C₁₋₄ alkoxy, —CF₃ and —OCF₃;

or a pharmaceutically acceptable salt, ester, hydrate, solvate, stereoisomer, mixture of stereoisomers, tautomer, polymorph and/or prodrug thereof.

In some embodiments, Q is a —O—, —NH— or —NR¹¹—.

In some embodiments, R¹¹ is methyl

In some embodiments, each —C₁₋₆ alkylene of R² is unsubstituted.

In some embodiments, R² is —C₁₋₆ alkylene-R⁵.

In some embodiments, R⁵ is heteroaryl.

In some embodiments, R² is

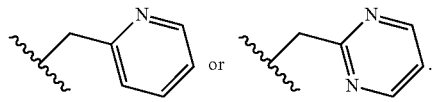 [SMILES: *Cc1ccccn1 ; *Cc1ncccn1]

In some embodiments, n is 1;

R¹⁰ is —O—R²⁰;

R²⁰ is C₁-C₁₅ alkyl; and wherein the alkyl is optionally substituted with one, two or three halo.

In some embodiments, R¹⁰ is 4-trifluoromethoxy.

In some embodiments, the compound is selected from the group consisting of:

4-(pyrimidin-2-ylmethyl)-7-(4-(trifluoromethoxy)phenylamino)-3,4-dihydrobenzo[f][1,4]oxazepin-5(2H)-one (XIII-1);

4-(pyrimidin-2-ylmethyl)-7-(4-(trifluoromethoxy)phenoxy)-3,4-dihydrobenzo[f][1,4]oxazepin-5(2H)-one (XIII-2);

4-(pyrimidin-2-ylmethyl)-7-(4-(trifluoromethyl)phenylamino)-3,4-dihydrobenzo[f][1,4]oxazepin-5(2H)-one (XIII-3);

4-(pyridin-2-ylmethyl)-7-(4-(trifluoromethoxy)phenylamino)-3,4-dihydrobenzo[f][1,4]oxazepin-5(2H)-one (XIII-4);

4-(pyridin-2-ylmethyl)-7-(4-(trifluoromethyl)phenylamino)-3,4-dihydrobenzo[f][1,4]oxazepin-5(2H)-one (XIII-6); and 7-(methyl(4-(trifluoromethoxy)phenyl)amino)-4-(pyrimidin-2-ylmethyl)-3,4-dihydrobenzo[f][1,4]oxazepin-5(2H)-one (XIII-10);

or a pharmaceutically acceptable salt, ester, stereoisomer, mixture of stereoisomers or tautomer thereof.

In certain alternative embodiments, the disclosure provides compounds of Formula IB:

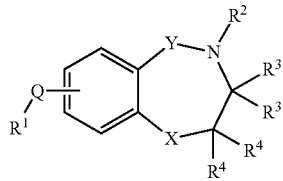

IB wherein:

R¹ is aryl, cycloalkenyl, heterocyclyl or heteroaryl;

wherein said aryl, cycloalkenyl, heterocyclyl or heteroaryl are optionally substituted with one, two or three substituents independently selected from the group consisting of halo, —NO₂, —CN, —SF₅, —Si(CH₃)₃, —O—R²⁰, —S—R²⁰, —C(O)—R²⁰, —C(O)—OR²⁰, —N(R²⁰)(R²²), —C(O)—N(R²⁰)(R²²), —N(R²⁰)—C(O)—R²², —N(R²⁰)—C(O)—OR²², —N(R²⁰)—S(O)₂—R²⁶, —S(O)₂—R²⁰, —S(O)₂—N(R²⁰)(R²²), C₁₋₆ alkyl, C₂₋₄ alkenyl, C₂₋₄ alkynyl, cycloalkyl, aryl, heteroaryl and heterocyclyl; and wherein said C₁₋₆ alkyl, C₂₋₄ alkenyl, C₂₋₄ alkynyl, cycloalkyl, aryl, heteroaryl or heterocyclyl are optionally substituted with one, two or three substituents independently selected from the group consisting of halo, —NO₂, phenyl, heterocyclyl, heteroaryl, C₁₋₆ alkyl, cycloalkyl, —N(R²⁰)(R²²), —C(O)—R²⁰, —C(O)—OR²⁰, —C(O)—N(R²⁰)(R²²), —CN and —O—R²⁰;

R² is hydrogen, C₁₋₁₅ alkyl, —C(O)—R²⁰, —C(O)—OR²⁶, —C(O)—N(R²⁶)(R²⁸), —N(R²⁰)—S(O)₂—R²⁰, cycloalkyl, aryl, heteroaryl or heterocyclyl;

wherein said C₁₋₁₅ alkyl, cycloalkyl, aryl, heteroaryl or heterocyclyl are optionally substituted with one, two or three substituents independently selected from the group consisting of C₁₋₆ alkyl, C₂₋₄ alkynyl, halo, —NO₂, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰;

wherein said C₁₋₆ alkyl, cycloalkyl, aryl, heterocyclyl or heteroaryl are optionally further substituted with one, two or three substituents independently selected from the group consisting of halo, —NO₂, C₁₋₆ alkyl, cycloalkyl, aryl, heterocyclyl, heteroaryl, —N(R²⁰)(R²²), —C(O)—R²⁰, —C(O)—OR²⁰, —C(O)—N(R²⁰)(R²²), —CN and —O—R²⁰; and wherein said C₁₋₆ alkyl, cycloalkyl, aryl, heterocyclyl or heteroaryl are optionally further substituted with one, two or three substituents independently selected from the group consisting of halo, —$NO_2$, —$CF_3$, —$N(R^{20})(R^{22})$, —C(O)—$R^{20}$, —C(O)—$OR^{20}$, —C(O)—$N(R^{20})(R^{22})$, —CN, —$S(O)_2$—$R^{20}$ and —O—$R^{20}$;

Q is a covalent bond or $C_2$ alkynylene;

Y is —C(O)—, —$CH_2$—, —$C(NR^5)$— or —$S(O)_2$—;

X is —O— or —$NR^6$—;

each $R^3$ is independently hydrogen, $C_{1-15}$ alkyl, cycloalkyl, aryl, heteroaryl or heterocyclyl;
  wherein said $C_{1-15}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$;
    wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and
    wherein said $C_{1-6}$ alkyl, aralkyl, cycloalkyl, aryl, heterocyclyl or heteroaryl, are optionally further substituted with one, two or three substituents independently selected from the group consisting of halo, —$NO_2$, —$N(R^{20})(R^{22})$, —C(O)—$R^{20}$, —C(O)—$OR^{20}$, —C(O)—$N(R^{20})(R^{22})$, —CN and —O—$R^{20}$;

or $R^2$ and one of $R^3$ can join together with the atom to which they are attached to form a heterocyclyl;
  wherein said heterocyclyl is optionally substituted with one, two or three substituents independently selected from the group consisting of $C_{1-15}$ alkyl, —O—$R^{20}$, —$N(R^{20})(R^{22})$, —$N(R^{20})$—C(O)—$OR^{20}$ and —C(O)—$OR^{20}$; and
    wherein said $C_{1-15}$ alkyl is optionally substituted with one, two or three substituents independently selected from the group consisting of halo and heteroaryl;

each $R^4$ is independently hydrogen, $C_{1-15}$ alkyl, $C_{1-4}$ alkoxy, —C(O)—$OR^{26}$, —C(O)—$N(R^{26})(R^{28})$, —$N(R^{20})$—$S(O)_2$—$R^{20}$, cycloalkyl, aryl, heteroaryl or heterocyclyl;
  wherein said $C_{1-15}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$;
    wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and
    wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —$N(R^{20})(R^{22})$, —C(O)—$R^{20}$, —C(O)—$OR^{20}$, —C(O)—$N(R^{20})(R^{22})$, —CN and —O—$R^{20}$;

or two $R^3$ or two $R^4$ together with the carbon atom to which they are attached form an oxo;

$R^5$ is hydrogen, $C_{1-15}$ alkyl, $C_{1-4}$ alkoxy, —C(O)—O—$R^{26}$, —C(O)—$N(R^{26})(R^{28})$, —$N(R^{20})$—$S(O)_2$—$R^{20}$, cycloalkyl, aryl, heteroaryl or heterocyclyl;
  wherein said $C_{1-15}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$;
    wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and
    wherein said $C_{1-6}$ alkyl, aralkyl, cycloalkyl, aryl, heterocyclyl or heteroaryl are optionally further substituted with one, two or three substituents independently selected from the group consisting of hydroxyl, halo, —$NO_2$, —$N(R^{20})(R^{22})$, —C(O)—$R^{20}$, —C(O)—$OR^{20}$, —C(O)—$N(R^{20})(R^{22})$, —CN and —O—$R^{20}$;

or $R^2$ and $R^5$ can join together with the atom to which they are attached to form a heterocyclyl or heteroaryl;
  wherein said heterocyclyl or heteroaryl is optionally substituted with one, two or three substituents independently selected from the group consisting of $C_{1-15}$ alkyl, cycloalkyl, heteroaryl, —O—$R^{20}$, —$N(R^{20})(R^{22})$, —$N(R^{20})$—C(O)—$OR^{20}$ and —C(O)—$OR^{20}$; and
    wherein said $C_{1-15}$ alkyl is optionally substituted with one, two or three substituents independently selected from the group consisting of halo and heteroaryl;

$R^6$ is hydrogen, $C_{1-15}$ alkyl, —C(O)—$R^{20}$, —C(O)—$OR^{26}$, cycloalkyl, aryl, heteroaryl or heterocyclyl;
  wherein said $C_{1-15}$ alkyl is optionally substituted with one, two or three substituents independently selected from the group consisting of halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$;
    wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and
    wherein said $C_{1-6}$ alkyl, aralkyl, cycloalkyl, aryl, heterocyclyl or heteroaryl are optionally further substituted with one, two or three substituents independently selected from the group consisting of halo, —$NO_2$, —$N(R^{20})(R^{22})$, —C(O)—$R^{20}$, —C(O)—$OR^{20}$, —C(O)—$N(R^{20})(R^{22})$, —CN and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;
  wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, —$NO_2$, —$S(O)_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and $R^{26}$ and $R^{28}$ are in each instance independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, mixture of stereoisomers, tautomer, polymorph and/or prodrug thereof.

In certain alternative embodiments, when Y is —C(O)—, X is —O—, each $R^4$ is hydrogen, $R^2$ and $R^3$ together with the atom to which they are attached form a piperazine which is optionally substituted with tert-butoxycarbonyl and Q is a bond, then $R^1$ is not unsubstituted phenyl or morpholinyl; and that when Y is —$S(O)_2$—, X is —O—, $R^2$ is benzyl, each $R^3$ is hydrogen, $Z^4$ is C-Q-$R^1$, Q is a bond and $R^1$ is aryl or heteroaryl, then both $R^4$ are hydrogen.

In certain alternative embodiments, the disclosure provides compounds of Formula IIA:

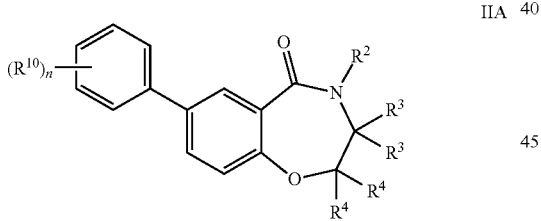

IIA wherein:

n is 0, 1, 2 or 3:

each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^2$)—C(O)—$OR^{22}$, —N($R^{20}$)—S(O)$_2$—$R^{26}$, —S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^2$ is hydrogen, $C_{1-15}$ alkyl, —C(O)—$R^{20}$, —C(O)—$OR^{26}$, —C(O)—N($R^{26}$)($R^{28}$), —N($R^{20}$)—S(O)$_2$—$R^{20}$, cycloalkyl, aryl, heteroaryl or heterocyclyl;

wherein said $C_{1-15}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, —$NO_2$, —$CF_3$, —N($R^{20}$)($R^{22}$), —C(O)—$R^{20}$, —C(O)—$OR^{20}$, —C(O)—N($R^{20}$)($R^{22}$), —S(O)$^2$—$R^{20}$ and —O—$R^{20}$;

each $R^3$ is independently hydrogen, $C_{1-15}$ alkyl, cycloalkyl, aryl, heteroaryl or heterocyclyl;

wherein said $C_{1-15}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;

wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl or heteroaryl, are optionally further substituted with one, two or three substituents independently selected from the group consisting of halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

or $R^2$ and one of $R^3$ can join together with the atom to which they are attached to form a heterocyclyl;

wherein said heterocyclyl is optionally substituted with one, two or three substituents independently selected from the group consisting of $C_{1-15}$ alkyl, —O—$R^{20}$, —N($R^{20}$)($R^{22}$), —N($R^{20}$)—C(O)—$OR^{20}$ and —C(O)—$OR^{20}$; and wherein said $C_{1-15}$ alkyl is optionally substituted with one, two or three substituents independently selected from the group consisting of halo and heteroaryl;

each $R^4$ is independently hydrogen, $C_{1-15}$ alkyl, $C_{1-4}$ alkoxy, —C(O)—$OR^{26}$, —C(O)—N($R^{26}$)($R^{28}$), —N($R^{20}$)—S(O)$_2$—$R^{20}$, cycloalkyl, aryl, heteroaryl or heterocyclyl;

wherein said $C_{1-15}$ alkyl is optionally substituted with one, two or three substituents independently selected from the group consisting of halo, —$NO_2$, cycloalkyl, aryl, heterocyclyl, heteroaryl, —N($R^{20}$)

($R^{22}$), —C(O)—$R^{20}$, —C(O)—$OR^{20}$, —C(O)—N($R^{20}$)($R^{22}$), —CN and —O—$R^{20}$;

wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, —$NO_2$, —$S(O)_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and $R^{26}$ and $R^{28}$ are in each instance independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, mixture of stereoisomers, tautomer, polymorph and/or prodrug thereof.

In some embodiments, $R^2$ is hydrogen or $C_{1-15}$ alkyl; wherein said alkyl is optionally substituted with one, two or three substituents independently selected from the group consisting of halo, aryl, heterocyclyl, heteroaryl, cycloalkyl and —O—$R^{20}$;

wherein said aryl, heterocyclyl or heteroaryl are optionally further substituted with one, two or three substituents independently selected from the group consisting of halo, $C_{1-6}$ alkyl, heterocyclyl, heteroaryl, cycloalkyl, —C(O)—$OR^{20}$, —CN and —O—$R^{20}$; and wherein said $C_{1-6}$ alkyl, or heteroaryl are optionally further substituted with one, two or three substituents independently selected from the group consisting of halo and —$CF_3$;

or $R^2$ and one of $R^3$ can join together with the atom to which they are attached to form a heterocyclyl;

wherein said heterocyclyl is optionally substituted with one, two or three substituents independently selected from the group consisting of $C_{1-15}$ alkyl, —N($R^{20}$)($R^{22}$) and —N($R^{20}$)—C(O)—$OR^{20}$; and wherein said $C_{1-15}$ alkyl is optionally substituted with one, two or three substituents independently selected from the group consisting of halo and heteroaryl; and $R^{20}$ and $R^{22}$ are in each instance independently selected from the group consisting of hydrogen, $C_1$-$C_{15}$ alkyl and heteroaryl.

In some embodiments, $R^2$ is hydrogen,

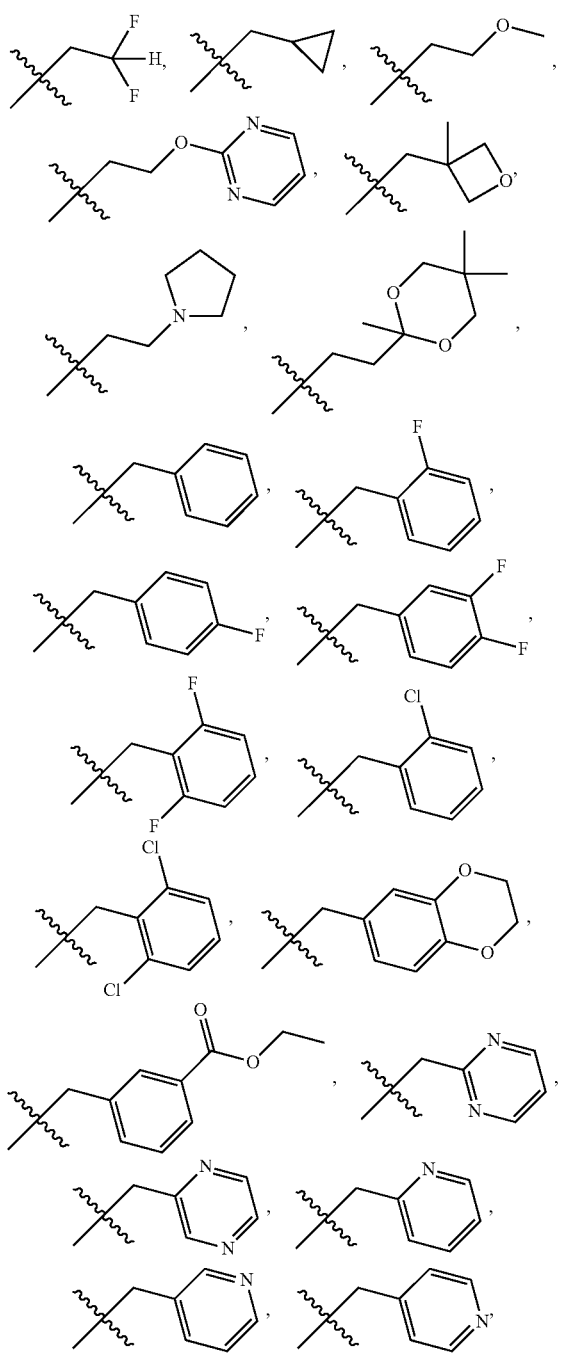

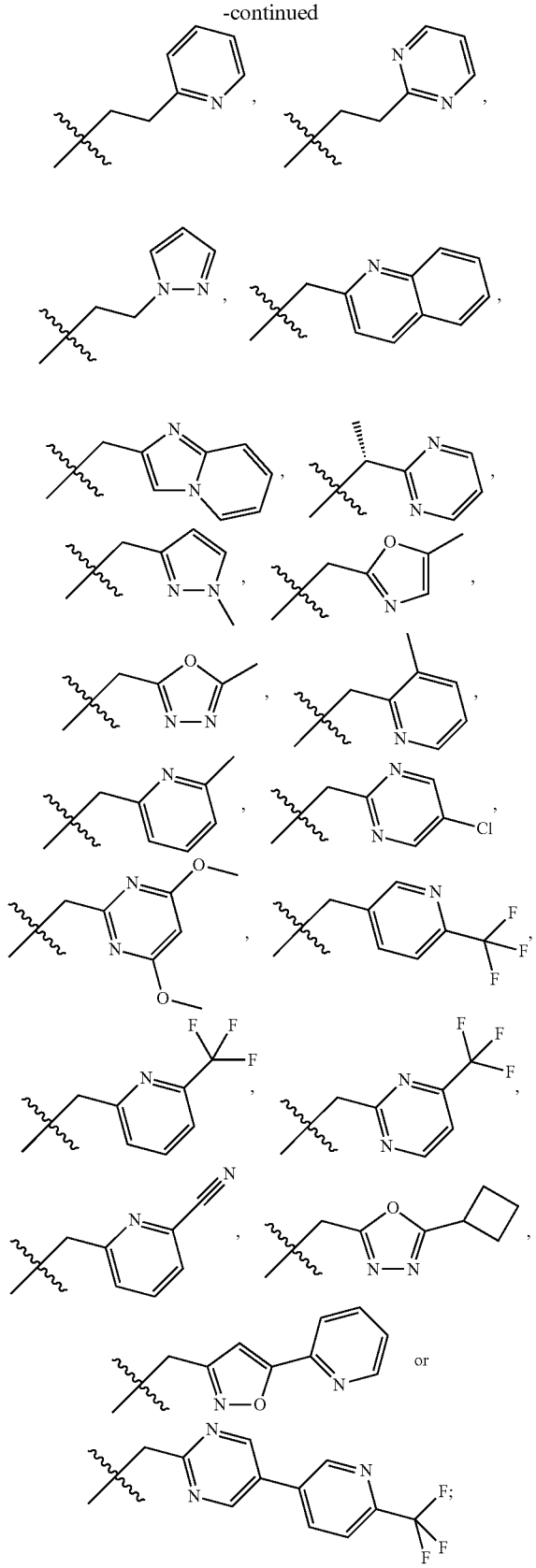

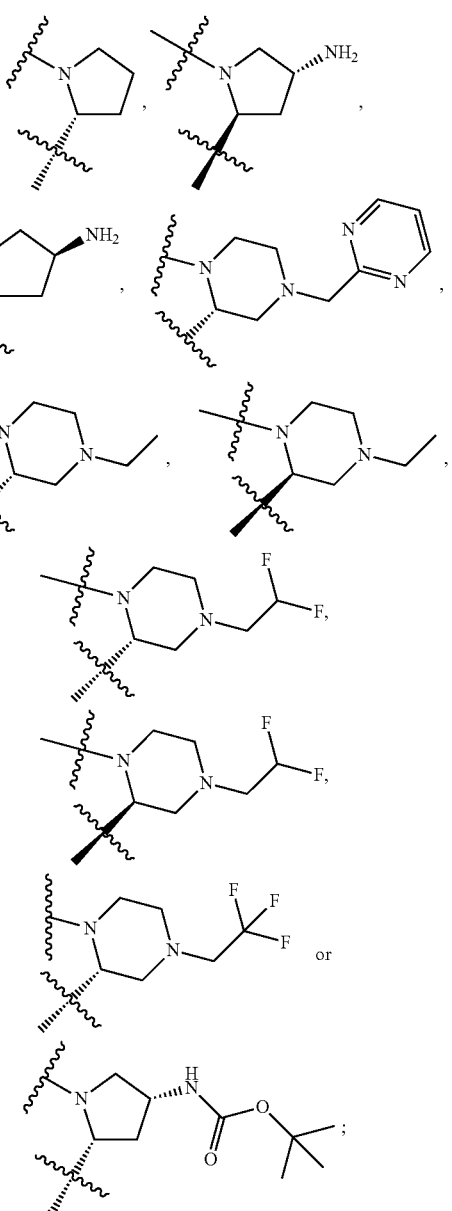

or a pharmaceutically acceptable salt, ester, hydrate, solvate, stereoisomer, mixture of stereoisomers, tautomer, polymorph and/or prodrug thereof.

In some embodiments, n is 1 or 2; and
each $R^{10}$ is independently selected from the group consisting of halo, —O—$R^{20}$, $C_{1-4}$ alkyl and cycloalkyl; and
wherein said alkyl is optionally substituted with one, two or three halo; and
$R^{20}$ is independently selected from the group consisting of $C_1$-$C_{15}$ alkyl and cycloalkyl; and
wherein the alkyl is optionally substituted with one, two or three halo.

In some embodiments, n is 1 or 2; and each $R^{10}$ is independently selected from the group consisting of 2-fluoro, 3-fluoro, 4-fluoro, 2-chloro, 4-chloro, 4-ethyl, 4-isopropyl, 4-tert-butyl, 4-trifluoromethyl, 4-cyclopropyl, 4-isobutoxy, 4-trifluoromethoxy, 4-(2,2,2-trifluoroethoxy) and 4-cyclopropoxy.

$R^2$ and one of $R^3$ together with the carbon atoms to which they are attached form a In some embodiments, each $R^3$ is independently hydrogen or $C_{1-15}$ alkyl;
  or $R^2$ and one of $R^3$ can join together with the atom to which they are attached to form a heterocyclyl;
    wherein said heterocyclyl is optionally substituted with one, two or three substituents independently selected from the group consisting of $C_{1-15}$ alkyl, —N($R^{20}$)($R^{22}$) and —N($R^{20}$)—C(O)—O$R^{20}$; and
      wherein said $C_{1-15}$ alkyl is optionally substituted with one, two or three substituents independently selected from the group consisting of halo and heteroaryl; and
  $R^{20}$ and $R^{22}$ are in each instance independently selected from the group consisting of hydrogen, $C_1$-$C_{15}$ alkyl and heteroaryl.

In some embodiments, each $R^3$ is independently hydrogen or $C_{1-15}$ alkyl.

In some embodiments, each $R^3$ is independently hydrogen, methyl or isopropyl.

In some embodiments, the compound is selected from the group consisting of
4-((3-methyloxetan-3-yl)methyl)-7-(4-(trifluoromethoxy)phenyl)-3,4-dihydrobenzo[f][1,4]oxazepin-5 (2H)-one;
4-(2-(pyrrolidin-1-yl)ethyl)-7-(4-(trifluoromethoxy)phenyl)-3,4-dihydrobenzo[f][1,4]oxazepin-5 (2H)-one;
4-((5-cyclobutyl-1,3,4-oxadiazol-2-yl)methyl)-7-(4-(trifluoromethoxy)phenyl)-3,4-dihydrobenzo[f][1,4]oxazepin-5 (2H)-one;
4-((2,3-dihydrobenzo[b][1,4]dioxin-6-yl)methyl)-7-(4-(trifluoromethoxy)phenyl)-3,4-dihydrobenzo[f][1,4]oxazepin-5 (2H)-one;
4-(2,2-difluoroethyl)-7-(4-(trifluoromethoxy)phenyl)-3,4-dihydrobenzo[f][1,4]oxazepin-5(2H)-one;
4-(quinolin-2-ylmethyl)-7-(4-(trifluoromethoxy)phenyl)-3,4-dihydrobenzo[f][1,4]oxazepin-5(2H)-one;
(R)-2-(pyrimidin-2-ylmethyl)-8-(4-(trifluoromethyl)phenyl)-3,4,12,12a-tetrahydro-1H-benzo[f]pyrazino[2,1-c][1,4]oxazepin-6(2H)-one;
4-(cyclopropylmethyl)-7-(4-(trifluoromethoxy)phenyl)-3,4-dihydrobenzo[f][1,4]oxazepin-5(2H)-one;
4-(2-methoxyethyl)-7-(4-(trifluoromethoxy)phenyl)-3,4-dihydrobenzo[f][1,4]oxazepin-5(2H)-one;
(S)-3-methyl-4-(pyrimidin-2-ylmethyl)-7-(4-(trifluoromethyl)phenyl)-3,4-dihydrobenzo[f][1,4]oxazepin-5 (2H)-one;
(R)-3-methyl-4-(pyrimidin-2-ylmethyl)-7-(4-(trifluoromethyl)phenyl)-3,4-dihydrobenzo[f][1,4]oxazepin-5 (2H)-one;
6-((5-oxo-7-(4-(trifluoromethoxy)phenyl)-2,3-dihydrobenzo[f][1,4]oxazepin-4(5H)-yl)methyl)picolinonitrile;
7-(4-(trifluoromethoxy)phenyl)-4-((6-(trifluoromethyl)pyridin-2-yl)methyl)-3,4-dihydrobenzo[f][1,4]oxazepin-5 (2H)-one;
7-(4-(trifluoromethoxy)phenyl)-4-((6-(trifluoromethyl)pyridin-3-yl)methyl)-3,4-dihydrobenzo[f][1,4]oxazepin-5 (2H)-one;
4-((6-methylpyridin-2-yl)methyl)-7-(4-(trifluoromethoxy)phenyl)-3,4-dihydrobenzo[f][1,4]oxazepin-5 (2H)-one;
(R)-3-methyl-7-(4-(trifluoromethyl)phenyl)-3,4-dihydrobenzo[f][1,4]oxazepin-5(2H)-one;
(2R,11aS)-2-amino-7-(4-(trifluoromethyl)phenyl)-2,3,11,11a-tetrahydrobenzo[f]pyrrolo[2,1-c][1,4]oxazepin-5 (1H)-one;
(R)-2-(2,2-difluoroethyl)-8-(4-(trifluoromethyl)phenyl)-3,4,12,12a-tetrahydro-1H-benzo[f]pyrazino[2,1-c][1,4]oxazepin-6(2H)-one;
(R)-2-ethyl-8-(4-(trifluoromethyl)phenyl)-3,4,12,12a-tetrahydro-1H-benzo[f]pyrazino[2,1-c][1,4]oxazepin-6(2H)-one;
(S)-2-(2,2-difluoroethyl)-8-(4-(trifluoromethyl)phenyl)-3,4,12,12a-tetrahydro-1H-benzo[f]pyrazino[2, 1-c][1,4]oxazepin-6(2H)-one;
(S)-2-ethyl-8-(4-(trifluoromethyl)phenyl)-3,4,12,12a-tetrahydro-1H-benzo[f]pyrazino[2, 1-c][1,4]oxazepin-6(2H)-one;
4-(pyrazin-2-ylmethyl)-7-(4-(trifluoromethoxy)phenyl)-3,4-dihydrobenzo[f][1,4]oxazepin-5 (2H)-one;
4-((5-methyloxazol-2-yl)methyl)-7-(4-(trifluoromethoxy)phenyl)-3,4-dihydrobenzo[f][1,4]oxazepin-5 (2H)-one;
7-(4-(trifluoromethoxy)phenyl)-4-(2-(2, 5,5-trimethyl-1,3-dioxan-2-yl)ethyl)-3,4-dihydrobenzo[f][1,4]oxazepin-5 (2H)-one;
tert-butyl (2R,11aR)-5-oxo-7-(4-(trifluoromethyl)phenyl)-1,2,3,5,11,11a-hexahydrobenzo[f]pyrrolo[2,1-c][1,4]oxazepin-2-ylcarbamate;
4-((5-(pyridin-2-yl)isoxazol-3-yl)methyl)-7-(4-(trifluoromethoxy)phenyl)-3,4-dihydrobenzo[f][1,4]oxazepin-5 (2H)-one;
4-((4, 6-dimethoxypyrimidin-2-yl)methyl)-7-(4-(trifluoromethoxy)phenyl)-3,4-dihydrobenzo[f][1,4]oxazepin-5 (2H)-one;
ethyl 3-((5-oxo-7-(4-(trifluoromethoxy)phenyl)-2,3-dihydrobenzo[f][1,4]oxazepin-4(5H)-yl)methyl)benzoate;
4-(2-(pyrimidin-2-yl)ethyl)-7-(4-(trifluoromethoxy)phenyl)-3,4-dihydrobenzo[f][1,4]oxazepin-5 (2H)-one;
4-(3,4-difluorobenzyl)-7-(4-(trifluoromethoxy)phenyl)-3,4-dihydrobenzo[f][1,4]oxazepin-5 (2H)-one;
4-methyl-7-(4-(trifluoromethoxy)phenyl)-3,4-dihydrobenzo[f][1,4]oxazepin-5(2H)-one;
4-(2-chlorobenzyl)-7-(4-(trifluoromethoxy)phenyl)-3,4-dihydrobenzo[f][1,4]oxazepin-5 (2H)-one;
4-(2, 6-dichlorobenzyl)-7-(4-(trifluoromethoxy)phenyl)-3,4-dihydrobenzo[f][1,4]oxazepin-5 (2H)-one;
4-(2,6-difluorobenzyl)-7-(4-(trifluoromethoxy)phenyl)-3,4-dihydrobenzo[f][1,4]oxazepin-5 (2H)-one;
4-(2-(1H-pyrazol-1-yl)ethyl)-7-(4-(trifluoromethoxy)phenyl)-3,4-dihydrobenzo[f][1,4]oxazepin-5 (2H)-one;
(2 S,11aS)-2-amino-7-(4-(trifluoromethyl)phenyl)-2,3,11,11a-tetrahydrobenzo[f]pyrrolo[2,1-c][1,4]oxazepin-5 (1H)-one;
4-(2-(pyridin-2-yl)ethyl)-7-(4-(trifluoromethoxy)phenyl)-3,4-dihydrobenzo[f][1,4]oxazepin-5 (2H)-one;
4-(2-fluorobenzyl)-7-(4-(trifluoromethoxy)phenyl)-3,4-dihydrobenzo[f][1,4]oxazepin-5 (2H)-one;
(R)-7-(4-(trifluoromethyl)phenyl)-2,3,11,11a-tetrahydrobenzo[f]pyrrolo[2,1-c][1,4]oxazepin-5(1H)-one;
4-(pyrimidin-2-ylmethyl)-7-(4-(trifluoromethyl)phenyl)-3,4-dihydrobenzo[f][1,4]oxazepin-5 (2H)-one;
4-(4-fluorobenzyl)-7-(4-(trifluoromethoxy)phenyl)-3,4-dihydrobenzo[f][1,4]oxazepin-5 (2H)-one;
4-((1-methyl-1H-pyrazol-3-yl)methyl)-7-(4-(trifluoromethoxy)phenyl)-3,4-dihydrobenzo[f][1,4]oxazepin-5 (2H)-one;
4-((5-chloropyrimidin-2-yl)methyl)-7-(4-(trifluoromethoxy)phenyl)-3,4-dihydrobenzo[f][1,4]oxazepin-5 (2H)-one;
4-(pyridin-4-ylmethyl)-7-(4-(trifluoromethoxy)phenyl)-3,4-dihydrobenzo[f][1,4]oxazepin-5 (2H)-one;
4-((5-cyclopropyl-1,3,4-oxadiazol-2-yl)methyl)-7-(4-(trifluoromethoxy)phenyl)-3,4-dihydrobenzo[f][1,4]oxazepin-5 (2H)-one;
4-(2-(pyrimidin-2-yloxy)ethyl)-7-(4-(trifluoromethoxy)phenyl)-3,4-dihydrobenzo[f][1,4]oxazepin-5 (2H)-one;

4-(pyridin-3-ylmethyl)-7-(4-(trifluoromethoxy)phenyl)-3,4-dihydrobenzo[f][1,4]oxazepin-5(2H)-one;

4-(pyridin-2-ylmethyl)-7-(4-(trifluoromethoxy)phenyl)-3,4-dihydrobenzo[f][1,4]oxazepin-5(2H)-one;

4-(pyrimidin-2-ylmethyl)-7-(4-(trifluoromethoxy)phenyl)-3,4-dihydrobenzo[f][1,4]oxazepin-5(2H)-one;

4-((3-methylpyridin-2-yl)methyl)-7-(4-(trifluoromethoxy)phenyl)-3,4-dihydrobenzo[f][1,4]oxazepin-5(2H)-one;

(S)-3-isopropyl-7-(4-(trifluoromethyl)phenyl)-3,4-dihydrobenzo[f][1,4]oxazepin-5(2H)-one;

(R)-2-(2,2,2-trifluoroethyl)-8-(4-(trifluoromethyl)phenyl)-3,4,12,12a-tetrahydro-1H-benzo[f]pyrazino[2,1-c][1,4]oxazepin-6(2H)-one;

4-(pyrimidin-2-ylmethyl)-7-p-tolyl-3,4-dihydrobenzo[f][1,4]oxazepin-5(2H)-one;

7-(4-chlorophenyl)-4-(pyrimidin-2-ylmethyl)-3,4-dihydrobenzo[f][1,4]oxazepin-5(2H)-one;

7-(4-isopropylphenyl)-4-(pyrimidin-2-ylmethyl)-3,4-dihydrobenzo[f][1,4]oxazepin-5(2H)-one;

7-(4-ethylphenyl)-4-(pyrimidin-2-ylmethyl)-3,4-dihydrobenzo[f][1,4]oxazepin-5(2H)-one;

7-(4-cyclopropylphenyl)-4-(pyrimidin-2-ylmethyl)-3,4-dihydrobenzo[f][1,4]oxazepin-5(2H)-one;

(R)-4-(1-(pyrimidin-2-yl)ethyl)-7-(4-(trifluoromethyl)phenyl)-3,4-dihydrobenzo[f][1,4]oxazepin-5(2H)-one;

7-(4-isobutoxyphenyl)-4-(pyrimidin-2-ylmethyl)-3,4-dihydrobenzo[f][1,4]oxazepin-5(2H)-one;

7-(4-tert-butylphenyl)-4-(pyrimidin-2-ylmethyl)-3,4-dihydrobenzo[f][1,4]oxazepin-5(2H)-one;

7-(4-cyclopropoxyphenyl)-4-(pyrimidin-2-ylmethyl)-3,4-dihydrobenzo[f][1,4]oxazepin-5(2H)-one;

7-(4-fluorophenyl)-4-(pyrimidin-2-ylmethyl)-3,4-dihydrobenzo[f][1,4]oxazepin-5(2H)-one;

7-(2-fluoro-4-(trifluoromethyl)phenyl)-4-(pyrimidin-2-ylmethyl)-3,4-dihydrobenzo[f][1,4]oxazepin-5 (2H)-one;

7-(3-fluoro-4-(2,2,2-trifluoroethoxy)phenyl)-4-(pyrimidin-2-ylmethyl)-3,4-dihydrobenzo[f][1,4]oxazepin-5 (2H)-one;

4-(pyrimidin-2-ylmethyl)-7-(4-(2,2,2-trifluoroethoxy)phenyl)-3,4-dihydrobenzo[f][1,4]oxazepin-5 (2H)-one;

7-(2-chloro-4-(trifluoromethyl)phenyl)-4-(pyrimidin-2-ylmethyl)-3,4-dihydrobenzo[f][1,4]oxazepin-5 (2H)-one;

7-(4-(trifluoromethoxy)phenyl)-4-((4-(trifluoromethyl)pyrimidin-2-yl)methyl)-3,4-dihydrobenzo[f][1,4]oxazepin-5 (2H)-one;

7-(4-(trifluoromethoxy)phenyl)-4-((5-(6-(trifluoromethyl)pyridin-3-yl)pyrimidin-2-yl)methyl)-3,4-dihydrobenzo[f][1,4]oxazepin-5 (2H)-one;

7-(4-chloro-2-fluorophenyl)-4-(pyrimidin-2-ylmethyl)-3,4-dihydrobenzo[f][1,4]oxazepin-5(2H)-one; and 4-(imidazo[1,2-a]pyridin-2-ylmethyl)-7-(4-(trifluoromethyl)phenyl)-3,4-dihydrobenzo[f][1,4]oxazepin-5 (2H)-one;

or a pharmaceutically acceptable salt, ester, hydrate, solvate, stereoisomer, mixture of stereoisomers, tautomer, polymorph and/or prodrug thereof.

In certain alternative embodiments, the disclosure provides compounds of Formula IIIA:

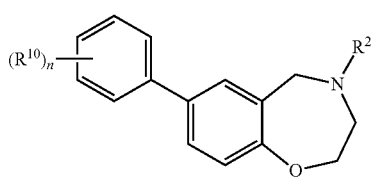

IIIA wherein:

n is 0, 1, 2 or 3:

each $R^{10}$ is independently selected from the group consisting of halo, $-NO_2$, $-CN$, $-SF_5$, $-Si(CH_3)_3$, $-O-R^{20}$, $-S-R^{20}$, $-C(O)-R^{20}$, $-C(O)-OR^{20}$, $-N(R^{20})(R^{22})$, $-C(O)-N(R^{20})(R^{22})$, $-N(R^{20})-C(O)-R^{22}$, $-N(R^{20})-C(O)-OR^{22}$, $-N(R^{20})-S(O)_2-R^{26}$, $-S(O)_2-R^{20}$, $-S(O)_2-N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, $-NO_2$, phenyl, heterocyclyl, heteroaryl, $C_{1-6}$ alkyl, cycloalkyl, $-N(R^{20})(R^{22})$, $-C(O)-R^{20}$, $-C(O)-OR^{20}$, $-C(O)-N(R^{20})(R^{22})$, $-CN$ and $-O-R^{20}$;

$R^2$ is hydrogen, $C_{1-15}$ alkyl, $-C(O)-R^{20}$, $-C(O)-OR^{26}$, $-C(O)-N(R^{26})(R^{28})$, $-N(R^{20})-S(O)_2-R^{20}$, cycloalkyl, aryl, heteroaryl or heterocyclyl;

wherein said $C_{1-15}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, $-NO_2$, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$;

wherein said $C_{1-6}$ alkyl, cycloalkyl, aryl, heterocyclyl or heteroaryl are optionally further substituted with one, two or three substituents independently selected from the group consisting of halo, $-NO_2$, $C_{1-6}$ alkyl, cycloalkyl, aryl, heterocyclyl, heteroaryl, $-N(R^{20})(R^{22})$, $-C(O)-R^{20}$, $-C(O)-OR^{20}$, $-C(O)-N(R^{20})(R^{22})$, $-CN$ and $-O-R^{20}$; and wherein said $C_{1-6}$ alkyl, cycloalkyl, aryl, heterocyclyl or heteroaryl are optionally further substituted with one, two or three substituents independently selected from the group consisting of halo, $-NO_2$, $-CF_3$, $-N(R^{20})(R^{22})$, $-C(O)-R^{20}$, $-C(O)-OR^{20}$, $-C(O)-N(R^{20})(R^{22})$, $-S(O)_2-R^{20}$ and $-O-R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, $-NO_2$, $-S(O)_2R^{26}$, $-CN$, $C_{1-3}$ alkoxy, $-CF_3$, $-OCF_3$, $-OCH_2CF_3$, $-C(O)-NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, $-NO_2$, $-S(O)_2R^{26}$, $-CN$, $C_{1-3}$ alkoxy, $-CF_3$, $-OCF_3$, aryl, heteroaryl and cycloalkyl; and $R^{26}$ and $R^{28}$ are in each instance independently selected from the group consisting of hydrogen, $C_{1-4}$ alkyl, aryl and cycloalkyl; and
wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;
or a pharmaceutically acceptable salt, ester, hydrate, solvate, stereoisomer, mixture of stereoisomers, tautomer, polymorph and/or prodrug thereof.

In some embodiments, $R^2$ is —C(O)—$R^{20}$; and
$R^{20}$ is heteroaryl.

In some embodiments, $R^2$ is

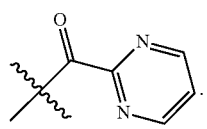

In some embodiments, n is 1; and
$R^{10}$ is —O—$R^{20}$; and
$R^{20}$ is $C_1$-$C_{15}$ alkyl; and
wherein the alkyl is optionally substituted with one, two or three halo.

In some embodiments, n is 1; and $R^{10}$ is 4-trifluoromethoxy.

In some embodiments, the compound is pyrimidin-2-yl(7-(4-(trifluoromethoxy)phenyl)-2,3-dihydrobenzo[f][1,4]oxazepin-4(5H)-yl)methanone
or a pharmaceutically acceptable salt, ester, hydrate, solvate, stereoisomer, mixture of stereoisomers, tautomer, polymorph and/or prodrug thereof.

In certain alternative embodiments, the disclosure provides compounds of Formula IV:

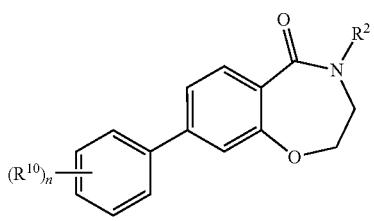

wherein:
n is 0, 1, 2 or 3:
each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —N($R^{20}$)($R^{22}$), —C(O)—N($R^{20}$)($R^{22}$), —N($R^{20}$)—C(O)—$R^{22}$, —N($R^{20}$)—C(O)—$OR^{22}$, —N($R^{20}$)—S(O)$_2$—$R^{26}$, —S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and
wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —N($R^{20}$)($R^{22}$), —C(O)—$R^{20}$, —C(O)—$OR^{20}$, —C(O)—N($R^{20}$)($R^{22}$), —CN and —O—$R^{20}$;

$R^2$ is hydrogen, $C_{1-15}$ alkyl, —C(O)—$R^{20}$, —C(O)—$OR^{26}$, —C(O)—N($R^{26}$)($R^{28}$), —N($R^{20}$)—S(O)$_2$—$R^{20}$, cycloalkyl, aryl, heteroaryl or heterocyclyl;
wherein said $C_{1-15}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$;
wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —N($R^{20}$)($R^{22}$), —C(O)—$R^{20}$, —C(O)—$OR^{20}$, —C(O)—N($R^{20}$)($R^{22}$), —CN and —O—$R^{20}$; and
wherein said $C_{1-6}$ alkyl, cycloalkyl, aryl, heterocyclyl or heteroaryl are optionally further substituted with one, two or three substituents independently selected from the group consisting of halo, —$NO_2$, —$CF_3$, —N($R^{20}$)($R^{22}$), —C(O)—$R^{20}$, —C(O)—$OR^{20}$, —C(O)—N($R^{20}$)($R^{22}$), —S(O)$_2$—$R^{20}$ and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;
wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, —$NO_2$, —S(O)$_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and
wherein said heteroaryl is optionally further substituted with $C_{1-4}$ alkyl or cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —$NO_2$, —S(O)$_2R^{26}$, —CN, $C_{1-3}$ alkoxy, —$CF_3$, —$OCF_3$, aryl, heteroaryl and cycloalkyl; and $R^{26}$ and $R^{28}$ are in each instance independently selected from the group consisting of hydrogen, $C_{1-4}$ alkyl, aryl and cycloalkyl; and
wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;
or a pharmaceutically acceptable salt, ester, hydrate, solvate, stereoisomer, mixture of stereoisomers, tautomer, polymorph and/or prodrug thereof.

In certain alternative embodiments, the disclosure provides compounds of Formula V:

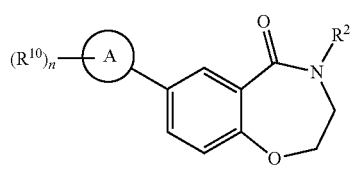

wherein:

A is cycloalkenyl;

n is 0, 1, 2 or 3:

each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —$N(R^{20})(R^{22})$, —C(O)—$N(R^{20})(R^{22})$, —$N(R^{20})$—C(O)—$R^{22}$, —$N(R^{20})$—C(O)—$OR^{22}$, —$N(R^{20})$—$S(O)_2$—$R^{26}$, —$S(O)_2$—$R^{20}$, —$S(O)_2$—$N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —$N(R^{20})(R^{22})$, —C(O)—$R^{20}$, —C(O)—$OR^{20}$, —C(O)—$N(R^{20})(R^{22})$, —CN and —O—$R^{20}$;

$R^2$ is hydrogen, $C_{1-15}$ alkyl, —C(O)—$R^{20}$, —C(O)—$OR^{26}$, —C(O)—$N(R^{26})(R^{28})$, —$N(R^{20})$—$S(O)_2$—$R^{20}$, cycloalkyl, aryl, heteroaryl or heterocyclyl;

wherein said $C_{1-15}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN, oxo and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, —$NO_2$, —$CF_3$, —$N(R^{20})(R^{22})$, —C(O)—$R^{20}$, —C(O)—$OR^{20}$, —C(O)—$N(R^{20})(R^{22})$, —$S(O)_2$—$R^{20}$ and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, —$NO_2$, —$S(O)_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and $R^{26}$ and $R^{28}$ are in each instance independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, mixture of stereoisomers, tautomer, polymorph and/or prodrug thereof.

In some embodiments, A is cyclohex-1-enyl.

In some embodiments, $R^2$ is $C_{1-15}$ alkyl;

wherein said alkyl is optionally substituted with heteroaryl.

In some embodiments, $R^2$ is

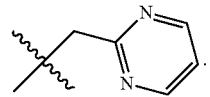 [SMILES: *Cc1ncccn1]

In some embodiments, n is 0 or 1; and $R^{10}$ is $C_{1-4}$ alkyl.

In some embodiments, A is cyclohex-1-enyl;

n is 0 or 1; and $R^{10}$ is 4-methyl or 4-tert-butyl.

In some embodiments, the compound is selected from the group consisting of 7-(4-tert-butylcyclohex-1-enyl)-4-(pyrimidin-2-ylmethyl)-3,4-dihydrobenzo[f][1,4]oxazepin-5(2H)-one;

7-cyclohexenyl-4-(pyrimidin-2-ylmethyl)-3,4-dihydrobenzo[f][1,4]oxazepin-5(2H)-one; and 7-(4-methylcyclohex-1-enyl)-4-(pyrimidin-2-ylmethyl)-3,4-dihydrobenzo[f][1,4]oxazepin-5(2H)-one;

or a pharmaceutically acceptable salt, ester, hydrate, solvate, stereoisomer, mixture of stereoisomers, tautomer, polymorph and/or prodrug thereof.

In certain alternative embodiments, the disclosure provides compounds of Formula VI:

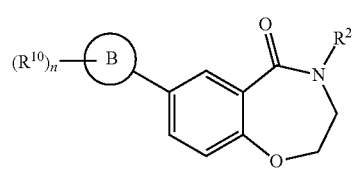

wherein:

B is heterocyclyl or heteroaryl;

n is 0, 1, 2 or 3:

each $R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —$N(R^{20})(R^{22})$, —C(O)—$N(R^{20})(R^{22})$, —$N(R^{20})$—C(O)—$R^{22}$, —$N(R^{20})$—C(O)—$OR^{22}$, —$N(R^{20})$—$S(O)_2$—$R^{26}$, —$S(O)_2$—$R^{20}$, —$S(O)_2$—$N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$;

$R^2$ is hydrogen, $C_{1-15}$ alkyl, —C(O)—$R^{20}$, —C(O)—O$R^{26}$, —C(O)—N($R^{26}$)($R^{28}$), —N($R^{20}$)—S(O)$_2$—$R^{20}$, cycloalkyl, aryl, heteroaryl or heterocyclyl;

wherein said $C_{1-15}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, —NO$_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN, oxo and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —NO$_2$, $C_{1-6}$ alkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, —NO$_2$, —CF$_3$, —N($R^{20}$)($R^{22}$), —C(O)—$R^{20}$, —C(O)—O$R^{20}$, —C(O)—N($R^{20}$)($R^{22}$), —S(O)$_2$—$R^{20}$ and —O—$R^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl; and wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, —NO$_2$, —S(O)$_2$$R^{26}$, —CN, $C_{1-3}$ alkoxy, —CF$_3$, —OCF$_3$, —OCH$_2$CF$_3$, —C(O)—NH$_2$, aryl, cycloalkyl and heteroaryl;

wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —NO$_2$, —S(O)$_2$$R^{26}$, —CN, $C_{1-3}$ alkoxy, —CF$_3$, —OCF$_3$, aryl, heteroaryl and cycloalkyl; and $R^{26}$ and $R^{28}$ are in each instance independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —CF$_3$ and —OCF$_3$;

or a pharmaceutically acceptable salt, ester, hydrate, solvate, stereoisomer, mixture of stereoisomers, tautomer, polymorph and/or prodrug thereof.

In some embodiments, B is heterocyclyl.
In some embodiments, B is 2-oxo-1,2-dihydropyridin-4-yl.
In some embodiments, B is heteroaryl.
In some embodiments, B is pyridin-4-yl.
In some embodiments, $R^2$ is $C_{1-15}$ alkyl;

wherein said alkyl is optionally substituted with heteroaryl.

In some embodiments, $R^2$ is

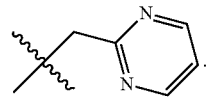 [SMILES: *Cc1ncccn1]

In some embodiments, n is 1;
$R^{10}$ is —O—$R^{20}$ or $C_{1-4}$ alkyl; and
$R^{20}$ is $C_1$-$C_{15}$ alkyl.
In some embodiments, B is 2-tert-butoxypyridin-4-yl.
In some embodiments, B is 1-methyl-2-oxo-1,2-dihydropyridin-4-yl.
In some embodiments, the compound is selected from the group consisting of 7-(2-tert-butoxypyridin-4-yl)-4-(pyridin-2-ylmethyl)-3,4-dihydrobenzo[f][1,4]oxazepin-5(2H)-one; and 7-(1-methyl-2-oxo-1,2-dihydropyridin-4-yl)-4-(pyridin-2-ylmethyl)-3,4-dihydrobenzo[f][1,4]oxazepin-5 (2H)-one;

or a pharmaceutically acceptable salt, ester, hydrate, solvate, stereoisomer, mixture of stereoisomers, tautomer, polymorph and/or prodrug thereof.

In certain alternative embodiments, the disclosure provides compounds of Formula VIIIA:

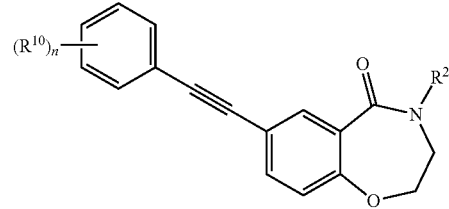

VIIIA wherein:
n is 0, 1, 2 or 3:
each $R^{10}$ is independently selected from the group consisting of halo, —NO$_2$, —CN, —SF$_5$, —Si(CH$_3$)$_3$, —O—$R^{20}$, —S—$R^{20}$, —C(O)—$R^{20}$, —C(O)—O$R^{20}$, —N($R^{20}$)($R^{22}$), —C(O)—N($R^{20}$)($R^{22}$), —N($R^{20}$)—C(O)—$R^{22}$, —N($R^{20}$)—C(O)—O$R^{22}$, —N($R^{20}$)—S(O)$_2$—$R^{26}$, —S(O)$_2$—$R^{20}$, —S(O)$_2$—N($R^{20}$)($R^{22}$), $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, $C_{1-6}$ alkyl, cycloalkyl, —N($R^{20}$)($R^{22}$), —C(O)—$R^{20}$, —C(O)—O$R^{20}$, —C(O)—N($R^{20}$)($R^{22}$), —CN and —O—$R^{20}$;

$R^2$ is hydrogen, $C_{1-15}$ alkyl, —C(O)—$R^{20}$, —C(O)—O$R^{26}$, —C(O)—N($R^{26}$)($R^{28}$), —N($R^{20}$)—S(O)$_2$—$R^{20}$, cycloalkyl, aryl, heteroaryl or heterocyclyl;

wherein said $C_{1-15}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, —NO$_2$, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN, oxo and —O—R$^{20}$;
  wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
    wherein said C$_{1-6}$ alkyl, cycloalkyl, aryl, heterocyclyl or heteroaryl are optionally further substituted with one, two or three substituents independently selected from the group consisting of halo, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —S(O)$_2$—R$^{20}$ and —O—R$^{20}$;
R$^{20}$ and R$^{22}$ are in each instance independently selected from the group consisting of hydrogen, C$_{1-15}$ alkyl, C$_{2-15}$ alkenyl, C$_{2-15}$ alkynyl, cycloalkyl, heterocyclyl, aryl and heteroaryl;
  wherein the C$_{1-15}$ alkyl, C$_{2-15}$ alkenyl, C$_{2-15}$ alkynyl, cycloalkyl, heterocyclyl, aryl and heteroaryl are optionally substituted with one, two or three substituents independently selected from the group consisting of hydroxyl, halo, C$_{1-4}$ alkyl, acylamino, —NO$_2$, —S(O)$_2$R$^{26}$, —CN, C$_{1-3}$ alkoxy, —CF$_3$, —OCF$_3$, —OCH$_2$CF$_3$, —C(O)—NH$_2$, aryl, cycloalkyl and heteroaryl; and
    wherein said heteroaryl is optionally further substituted with C$_{1-4}$ alkyl or cycloalkyl; or
when R$^{20}$ and R$^{22}$ are attached to a common nitrogen atom R$^{20}$ and R$^{22}$ may join to form a heterocyclic or heteroaryl ring which is then optionally substituted with one, two or three substituents independently selected from the group consisting of hydroxyl, halo, C$_{1-4}$ alkyl, aralkyl, aryl, aryloxy, aralkyloxy, acylamino, —NO$_2$, —S(O)$_2$R$^{26}$, —CN, C$_{1-3}$ alkoxy, —CF$_3$, —OCF$_3$, aryl, heteroaryl and cycloalkyl; and
R$^{26}$ and R$^{28}$ are in each instance independently selected from the group consisting of hydrogen, C$_{1-4}$ alkyl, aryl and cycloalkyl; and
  wherein the C$_{1-4}$ alkyl, aryl and cycloalkyl may be further substituted with from 1 to 3 substituents independently selected from the group consisting of hydroxyl, halo, C$_{1-4}$ alkoxy, —CF$_3$ and —OCF$_3$;
or a pharmaceutically acceptable salt, ester, hydrate, solvate, stereoisomer, mixture of stereoisomers, tautomer, polymorph and/or prodrug thereof.

In some embodiments, R$^2$ is C$_{1-15}$ alkyl;
wherein said alkyl is optionally substituted with heteroaryl.
In some embodiments, R$^2$ is

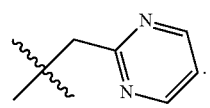 [SMILES: *Cc1ncccn1]

In some embodiments, n is 0 or 1;
R$^{10}$ is —O—R$^{20}$ or C$_{1-4}$ alkyl;
  wherein the alkyl is optionally substituted with three halo; and
  R$^{20}$ is C$_1$-C$_{15}$ alkyl; and
  wherein the alkyl is optionally substituted with one, two or three halo.
In some embodiments, n is 0 or 1; and R$^{10}$ is 4-trifluoromethyl or 4-trifluoromethoxy.

In some embodiments, the compound is selected from the group consisting of
4-(pyrimidin-2-ylmethyl)-7-((4-(trifluoromethoxy)phenyl)ethynyl)-3,4-dihydrobenzo[f][1,4]oxazepin-5(2H)-one;
7-(phenylethynyl)-4-(pyrimidin-2-ylmethyl)-3,4-dihydrobenzo[f][1,4]oxazepin-5(2H)-one; and
4-(pyrimidin-2-ylmethyl)-7-((4-(trifluoromethyl)phenyl)ethynyl)-3,4-dihydrobenzo[f][1,4]oxazepin-5(2H)-one;
or a pharmaceutically acceptable salt, ester, hydrate, solvate, stereoisomer, mixture of stereoisomers, tautomer, polymorph and/or prodrug thereof.

In certain alternative embodiments, the disclosure provides compounds of Formula IX:

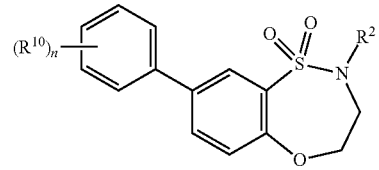

IX wherein:
n is 0, 1, 2 or 3:
each R$^{10}$ is independently selected from the group consisting of halo, —NO$_2$, —CN, —SF$_5$, —Si(CH$_3$)$_3$, —O—R$^{20}$, —S—R$^{20}$, —C(O)—R$^{20}$, —C(O)—OR$^{20}$, —N(R$^{20}$)(R$^{22}$), —C(O)—N(R$^{20}$)(R$^{22}$), —N(R$^{20}$)—C(O)—R$^{22}$, —N(R$^2$)—C(O)—OR$^{22}$, —N(R$^{20}$)—S(O)$_2$—R$^{26}$, —S(O)$_2$—R$^{20}$, —S(O)$_2$—N(R$^{20}$)(R$^{22}$), C$_{1-6}$ alkyl, C$_{2-4}$ alkenyl, C$_{2-4}$ alkynyl, cycloalkyl, aryl, heteroaryl and heterocyclyl; and
  wherein said C$_{1-6}$ alkyl, C$_{2-4}$ alkenyl, C$_{2-4}$ alkynyl, cycloalkyl, aryl, heteroaryl or heterocyclyl are optionally substituted with one, two or three substituents independently selected from the group consisting of halo, —NO$_2$, phenyl, heterocyclyl, heteroaryl, C$_{1-6}$ alkyl, cycloalkyl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$;
R$^2$ is hydrogen, C$_{1-15}$ alkyl, —C(O)—R$^{20}$, —C(O)—OR$^{26}$, —C(O)—N(R$^{26}$)(R$^{28}$), —N(R$^{20}$)—S(O)$_2$—R$^{20}$, cycloalkyl, aryl, heteroaryl or heterocyclyl;
  wherein said C$_{1-15}$ alkyl, cycloalkyl, aryl, heteroaryl or heterocyclyl are optionally substituted with one, two or three substituents independently selected from the group consisting of C$_{1-6}$ alkyl, C$_{2-4}$ alkynyl, halo, —NO$_2$, cycloalkyl, aryl, heterocyclyl, heteroaryl, —N(R$^{20}$)(R$^{22}$), —C(O)—R$^{20}$, —C(O)—OR$^{20}$; —C(O)—N(R$^{20}$)(R$^{22}$), —CN, oxo and —O—R$^{20}$;
    wherein said C$_{1-6}$ alkyl, cycloalkyl, aryl, heterocyclyl or heteroaryl are optionally further substituted with one, two or three substituents independently selected from the group consisting of halo, —NO$_2$, C$_{1-6}$ alkyl, cycloalkyl, aryl, heterocyclyl, heteroaryl, —N(R$^{20}$)(R$^{22}$), —C(O)—R$^{20}$, —C(O)—OR$^{20}$, —C(O)—N(R$^{20}$)(R$^{22}$), —CN and —O—R$^{20}$; and
    wherein said C$_{1-6}$ alkyl, cycloalkyl, aryl, heterocyclyl or heteroaryl are optionally further substituted with one, two or three substituents independently selected from the group consisting of halo, —NO$_2$, —CF$_3$, —N(R$^{20}$)(R$^{22}$), —C(O)—R$^{20}$, —C(O)—OR$^{20}$, —C(O)—N(R$^{20}$)(R$^{22}$), —S(O)$_2$—R$^{20}$ and —O—R$^{20}$;

$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;

wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, —$NO_2$, —$S(O)_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and wherein said heteroaryl is optionally further substituted with $C_{1-4}$ alkyl or cycloalkyl; or when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —$NO_2$, —$S(O)_2R^{26}$, —CN, $C_{1-3}$ alkoxy, —$CF_3$, —$OCF_3$, aryl, heteroaryl and cycloalkyl; and $R^{26}$ and $R^{28}$ are in each instance independently selected from the group consisting of hydrogen, $C_{1-4}$ alkyl, aryl and cycloalkyl; and wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;

or a pharmaceutically acceptable salt, ester, hydrate, solvate, stereoisomer, mixture of stereoisomers, tautomer, polymorph and/or prodrug thereof.

In some embodiments, $R^2$ is $C_{1-15}$ alkyl;

wherein said alkyl is optionally substituted with heteroaryl; and wherein said heteroaryl is optionally further substituted with halo.

In some embodiments, $R^2$ is selected from the group consisting of

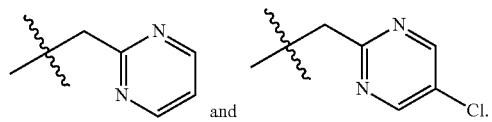 [SMILES: *Cc1ncccn1 ; *Cc1ncc(Cl)cn1]

In some embodiments, $R^{10}$ is 4-trifluoromethyl.

In some embodiments, the compound is selected from the group consisting of:

2-((pyrimidin-2-yl)methyl)-8-(4-(trifluoromethyl)phenyl)-3,4-dihydro-2H-benzo[b][1,4,5]oxathiazepin-sulfone; and 2-((5-chloropyrimidin-2-yl)methyl)-8-(4-(trifluoromethyl)phenyl)-3,4-dihydro-2H-benzo[b][1,4,5]oxathiazepin-sulfone;

or a pharmaceutically acceptable salt, ester, hydrate, solvate, stereoisomer, mixture of stereoisomers, tautomer, polymorph and/or prodrug thereof.

In certain alternative embodiments, the disclosure provides compounds of Formula X:

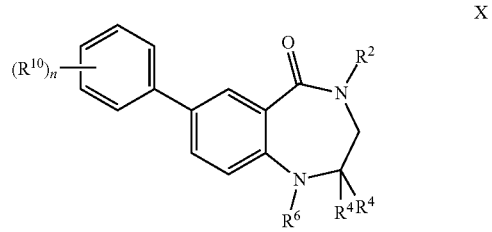

X wherein:

n is 0, 1, 2 or 3;

$R^{10}$ is independently selected from the group consisting of halo, —$NO_2$, —CN, —$SF_5$, —$Si(CH_3)_3$, —O—$R^{20}$, —S—$R^{20}$, —C(O)—$R^{20}$, —C(O)—$OR^{20}$, —$N(R^{20})(R^{22})$, —C(O)—$N(R^{20})(R^{22})$, —$N(R^{20})$—C(O)—$R^{22}$, —$N(R^{20})$—C(O)—$OR^{22}$, —$N(R^{20})$—$S(O)_2$—$R^{26}$, —$S(O)_2$—$R^{20}$, —$S(O)_2$—$N(R^{20})(R^{22})$, $C_{1-6}$ alkyl, $C_{2-4}$ alkenyl, $C_{2-4}$ alkynyl, cycloalkyl, aryl, heteroaryl and heterocyclyl; and wherein said $C_{1-6}$ alkyl, $C_{2-4}$ alkenyl, $C_{2-4}$ alkynyl, cycloalkyl, aryl, heteroaryl or heterocyclyl are optionally substituted with one, two or three substituents independently selected from the group consisting of halo, —$NO_2$, phenyl, heterocyclyl, heteroaryl, $C_{1-6}$ alkyl, cycloalkyl, —$N(R^{20})(R^{22})$, —C(O)—$R^{20}$, —C(O)—$OR^{20}$, —C(O)—$N(R^{20})(R^{22})$, —CN and —O—$R^{20}$;

$R^2$ is hydrogen, $C_{1-15}$ alkyl, —C(O)—$R^{20}$, —C(O)—$OR^{26}$, —C(O)—$N(R^{26})(R^{28})$, —$N(R^{20})$—$S(O)_2$—$R^{20}$, cycloalkyl, aryl, heteroaryl or heterocyclyl;

wherein said $C_{1-15}$ alkyl, cycloalkyl, aryl, heteroaryl or heterocyclyl are optionally substituted with one, two or three substituents independently selected from the group consisting of $C_{1-6}$ alkyl, $C_{2-4}$ alkynyl, halo, —$NO_2$, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN, oxo and —O—$R^{20}$;

wherein said $C_{1-6}$ alkyl, cycloalkyl, aryl, heterocyclyl or heteroaryl are optionally further substituted with one, two or three substituents independently selected from the group consisting of halo, —$NO_2$, $C_{1-6}$ alkyl, cycloalkyl, aryl, heterocyclyl, heteroaryl, —$N(R^{20})(R^{22})$, —C(O)—$R^{20}$, —C(O)—$OR^{20}$, —C(O)—$N(R^{20})(R^{22})$, —CN and —O—$R^{20}$; and wherein said $C_{1-6}$ alkyl, cycloalkyl, aryl, heterocyclyl or heteroaryl are optionally further substituted with one, two or three substituents independently selected from the group consisting of halo, —$NO_2$, —$CF_3$, —$N(R^{20})(R^{22})$, —C(O)—$R^{20}$, —C(O)—$OR^{20}$, —C(O)—$N(R^{20})(R^{22})$, —CN, —$S(O)_2$—$R^{20}$ and —O—$R^{20}$;

each $R^4$ is independently hydrogen, $C_{1-15}$ alkyl, $C_{1-4}$ alkoxy, —C(O)—$OR^{26}$, —C(O)—$N(R^{26})(R^{28})$, —$N(R^{20})$—$S(O)_2$—$R^{20}$, cycloalkyl, aryl, heteroaryl or heterocyclyl;

wherein said $C_{1-15}$ alkyl is optionally substituted with one, two or three substituents independently selected from the group consisting of halo, —$NO_2$, cycloalkyl, aryl, heterocyclyl, heteroaryl, —$N(R^{20})$ ($R^{22}$), —C(O)—$R^{20}$, —C(O)—O$R^{20}$, —C(O)—N($R^{20}$)($R^{22}$), —CN and —O—$R^{20}$;
  wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
  wherein said $C_{1-6}$ alkyl, aralkyl, cycloalkyl, aryl, heterocyclyl, heteroaryl, are optionally further substituted with one, two or three substituents independently selected from the group consisting of hydroxyl, halo, —$NO_2$, —N($R^{20}$)($R^{22}$), —C(O)—$R^{20}$, —C(O)—O$R^{20}$, —C(O)—N($R^{20}$)($R^{22}$), —CN and —O—$R^{20}$;
or two $R^4$ together with the carbon atom to which they are attached form an oxo;
$R^6$ is hydrogen, $C_{1-15}$ alkyl, —C(O)—$R^{20}$, —C(O)—O$R^{26}$, cycloalkyl, aryl, heteroaryl or heterocyclyl;
  wherein said $C_{1-15}$ alkyl is optionally substituted with one, two or three substituents independently selected from the group consisting of halo, —$NO_2$, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$;
  wherein said cycloalkyl, aryl, heterocyclyl or heteroaryl are optionally further substituted with one, two or three substituents independently selected from the group consisting of halo, —$NO_2$, $C_{1-6}$ alkyl, aralkyl, cycloalkyl, aryl, heterocyclyl, heteroaryl, —N($R^{20}$)($R^{22}$), —C(O)—$R^{20}$, —C(O)—O$R^{20}$, —C(O)—N($R^{20}$)($R^{22}$), —CN and —O—$R^{20}$; and
  wherein said $C_{1-6}$ alkyl, aralkyl, cycloalkyl, aryl, heterocyclyl or heteroaryl are optionally further substituted with one, two or three substituents independently selected from the group consisting of halo, —$NO_2$, —N($R^{20}$)($R^{22}$), —C(O)—$R^{20}$, —C(O)—O$R^{20}$, —C(O)—N($R^{20}$)($R^{22}$), —CN and —O—$R^{20}$;
$R^{20}$ and $R^{22}$ are in each instance independently selected from the group consisting of hydrogen, $C_{1-15}$ alkyl, $C_{2-15}$ alkenyl, $C_{2-15}$ alkynyl, cycloalkyl, heterocyclyl, aryl and heteroaryl;
  wherein the $C_{1-15}$ alkyl, $C_{2-15}$ alkenyl, $C_{2-15}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, —$NO_2$, —S(O)$_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and
    wherein said heteroaryl is optionally further substituted with $C_{1-4}$ alkyl or cycloalkyl; or
  when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —$NO_2$, —S(O)$_2R^{26}$, —CN, $C_{1-3}$ alkoxy, —$CF_3$, —$OCF_3$, aryl, heteroaryl and cycloalkyl; and
$R^{26}$ and $R^{28}$ are in each instance independently selected from the group consisting of hydrogen, $C_{1-4}$ alkyl, aryl and cycloalkyl; and
  wherein the $C_{1-4}$ alkyl, aryl and cycloalkyl may be further substituted with from 1 to 3 substituents independently selected from the group consisting of hydroxyl, halo, $C_{1-4}$ alkoxy, —$CF_3$ and —$OCF_3$;
or a pharmaceutically acceptable salt, ester, hydrate, solvate, stereoisomer, mixture of stereoisomers, tautomer, polymorph and/or prodrug thereof.

In some embodiments, $R^2$ is $C_{1-15}$ alkyl;
  wherein the alkyl is optionally substituted with aryl or —O—$R^{20}$; and
$R^{20}$ is $C_1$-$C_{15}$ alkyl;
  wherein the alkyl is optionally substituted with aryl.

In some embodiments, $R^2$ is

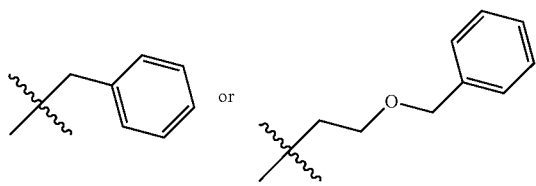

In some embodiments, $R^{10}$ is 4-trifluoromethyl or 4-trifluoromethoxy.

In some embodiments, two $R^4$ together with the carbon atom to which they are attached form an oxo.

In some embodiments, $R^6$ is hydrogen or $C_{1-15}$ alkyl.

In some embodiments, $R^6$ is hydrogen or methyl.

In some embodiments, the compound is selected from the group consisting of
4-(2-(benzyloxy)ethyl)-1-methyl-7-(4-(trifluoromethoxy)phenyl)-3,4-dihydro-1H-benzo[e][1,4]diazepine-2,5-dione; and
4-benzyl-7-(4-(trifluoromethyl)phenyl)-3,4-dihydro-1H-benzo[e][1,4]diazepine-2,5-dione;
or a pharmaceutically acceptable salt, ester, hydrate, solvate, stereoisomer, mixture of stereoisomers, tautomer, polymorph and/or prodrug thereof.

In some embodiments of Formula I and each of the other formulas disclosed herein, $R^{20}$ and $R^{22}$ are in each instance independently selected from the group consisting of hydrogen, $C_{1-6}$ alkyl, $C_{2-6}$ alkenyl, $C_{2-6}$ alkynyl, cycloalkyl, heterocyclyl, aryl and heteroaryl;
  wherein the $C_{1-6}$ alkyl, $C_{2-6}$ alkenyl, $C_{2-6}$ alkynyl, cycloalkyl, heterocyclyl, aryl and heteroaryl are optionally substituted with one, two or three substituents independently selected from the group consisting of hydroxyl, halo, $C_{1-4}$ alkyl, acylamino, —$NO_2$, —S(O)$_2R^{26}$, —CN, $C_{1-3}$ alkoxy, —$CF_3$, —$OCF_3$, —$OCH_2CF_3$, —C(O)—$NH_2$, aryl, cycloalkyl and heteroaryl; and
  wherein said heteroaryl is optionally further substituted with $C_{1-4}$ alkyl or cycloalkyl; or
when $R^{20}$ and $R^{22}$ are attached to a common nitrogen atom $R^{20}$ and $R^{22}$ may join to form a heterocyclic or heteroaryl ring which is then optionally substituted with one, two or three substituents independently selected from the group consisting of hydroxyl, halo, $C_{1-4}$ alkyl, aralkyl, aryl, aryloxy, aralkyloxy, acylamino, —$NO_2$, —S(O)$_2R^{26}$, —CN, $C_{1-3}$ alkoxy, —$CF_3$, —$OCF_3$, aryl, heteroaryl and cycloalkyl.

In certain embodiments, $R^{20}$ is hydrogen or $C_{1-6}$ alkyl; wherein the $C_{1-6}$ alkyl is optionally substituted with one, two or three halo.

In certain embodiments, $R^{20}$ is hydrogen. In other embodiments, $R^{20}$ is —$CF_3$.

4. Further Embodiments

In some embodiments, the compounds provided by the present disclosure are effective in the treatment of conditions or diseases known to respond to administration of late sodium channel blockers, including but not limited to cardiovascular diseases such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, compounds provided by the present disclosure which function as late sodium channel blockers may be used in the treatment of diseases affecting the neuromuscular system resulting in pain, itching, seizures, or paralysis, or in the treatment of diabetes or reduced insulin sensitivity, and disease states related to diabetes, such as diabetic peripheral neuropathy.

Certain compounds of the disclosure may also possess a sufficient activity in modulating neuronal sodium channels, i.e., $Na_v$. 1.1, 1.2, 1.3, 1.5, 1.7, and/or 1.8, and may have appropriate pharmacokinetic properties such that they may be active with regard to the central and/or peripheral nervous system. Consequently, some compounds of the disclosure may also be of use in the treatment of epilepsy or pain or itching or heachache of a neuropathic origin.

In one embodiment, this disclosure provides a method of treating a disease state in a mammal that is alleviable by treatment with an agent capable of reducing late sodium current, comprising administering to a mammal in need thereof a therapeutically effective dose of a compound of Formula I, IA, IB, II, IIA, IIB, III, IIIA, IV, V, VI, VIII, VIIIA, IX, X, XII or XIII or other formulas or compounds disclosed herein. In another embodiment, the disease state is a cardiovascular disease selected from one or more of atrial and ventricular arrhythmias, heart failure (including congestive heart failure, diastolic heart failure, systolic heart failure, acute heart failure), Prinzmetal's (variant) angina, stable and unstable angina, exercise induced angina, congestive heart disease, ischemia, recurrent ischemia, reperfusion injury, myocardial infarction, acute coronary syndrome, peripheral arterial disease, pulmonary hypertension, and intermittent claudication.

In another embodiment, the disease state is diabetes or diabetic peripheral neuropathy. In a further embodiment, the disease state results in one or more of neuropathic pain, epilepsy, heachache, seizures, or paralysis.

In one embodiment, this disclosure provides a method of treating diabetes in a mammal, comprising administering to a mammal in need thereof a therapeutically effective dose of a compound of Formula I, IA, IB, II, IIA, IIB, III, IIIA, IV, V, VI, VIII, VIIIA, IX, X, XII or XIII or other formulas or compounds disclosed herein. Diabetes mellitus is a disease characterized by hyperglycemia; altered metabolism of lipids, carbohydrates and proteins; and an increased risk of complications from vascular disease. Diabetes is an increasing public health problem, as it is associated with both increasing age and obesity.

There are two major types of diabetes mellitus: 1) Type I, also known as insulin dependent diabetes (IDDM) and 2) Type II, also known as insulin independent or non-insulin dependent diabetes (NIDDM). Both types of diabetes mellitus are due to insufficient amounts of circulating insulin and/or a decrease in the response of peripheral tissue to insulin.

Type I diabetes results from the body's failure to produce insulin, the hormone that "unlocks" the cells of the body, allowing glucose to enter and fuel them. The complications of Type I diabetes include heart disease and stroke; retinopathy (eye disease); kidney disease (nephropathy); neuropathy (nerve damage); as well as maintenance of good skin, foot and oral health.

Type II diabetes results from the body's inability to either produce enough insulin or the cells inability to use the insulin that is naturally produced by the body. The condition where the body is not able to optimally use insulin is called insulin resistance. Type II diabetes is often accompanied by high blood pressure and this may contribute to heart disease. In patients with type II diabetes mellitus, stress, infection, and medications (such as corticosteroids) can also lead to severely elevated blood sugar levels. Accompanied by dehydration, severe blood sugar elevation in patients with type II diabetes can lead to an increase in blood osmolality (hyperosmolar state). This condition can lead to coma.

It has been suggested that ranolazine (RANEXA®, a selective inhibitor of INaL) may be an antidiabetic agent that causes β-cell preservation and enhances insulin secretion in a glucose-dependent manner in diabetic mice (see, Y. Ning et al. J Pharmacol Exp Ther. 2011, 337(1), 50-8). Therefore it is contemplated that the compounds of Formula I, IA, IB, II, IIA, IIB, III, IIIA, IV, V, VI, VIII, VIIIA, IX, X, XII or XIII or other formulas or compounds disclosed herein can be used as antidiabetic agents for the treatment of diabetes.

5. Pharmaceutical Compositions and Administration

Compounds provided in accordance with the present disclosure are usually administered in the form of pharmaceutical compositions. This disclosure therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure.

Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Preferably, for parenteral administration, sterile injectable solutions are prepared containing a therapeutically effective amount, e.g., 0.1 to 700 mg, of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of compounds in accordance with the disclosure. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g, or alternatively, or 100 mg to 500 mg, of a compound described herein, and for parenteral administration, preferably from 0.1 mg to 700 mg, or alternatively, 0.1 mg to 100 mg, of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

Patients being treated by administration of the late sodium channel blockers of the disclosure often exhibit diseases or conditions that benefit from treatment with other therapeutic agents. These diseases or conditions can be of cardiovascular nature or can be related to pulmonary disorders, metabolic disorders, gastrointestinal disorders and the like. Additionally, some coronary patients being treated by administration of the late sodium channel blockers of the disclosure exhibit conditions that can benefit from treatment with therapeutic agents that are antibiotics, analgesics, and/or antidepressants and anti-anxiety agents.

Cardiovascular Agent Combination Therapy

Cardiovascular related diseases or conditions that can benefit from a combination treatment of the late sodium channel blockers of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the late sodium channel blockers of the disclosure with therapeutic agents suitable for treating cardiovascular related conditions allows enhancement in the standard of care therapy the patient is currently receiving. In some embodiments, the late sodium channel blockers of the disclosure are co-administered with ranolazine (RANEXA®).

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral®), atenolol (Tenormin®), betaxolol (Kerlone®), bisoprolol/hydrochlorothiazide (Ziac®), bisoprolol (Zebeta®), carteolol (Cartrol®), esmolol (Brevibloc®), labetalol (Normodyne®, Trandate®), metoprolol (Lopressor®, Toprol® XL), nadolol (Corgard®), propranolol (Inderal®), sotalol (Betapace®), and timolol (Blocadren®).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc®, Lotrel®), bepridil (Vascor®), diltiazem (Cardizem®, Tiazac®), felodipine (Plendil®), nifedipine (Adalat®, Procardia®), nimodipine (Nimotop®), nisoldipine (Sular®), verapamil (Calan®, Isoptin®, Verelan®), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn®), furosemide (Lasix®), bumetanide (Bumex®), spironolactone (Aldactone®), and eplerenone (Inspra®).

Angiotensin converting enzyme (ACE) inhibitors reduce the workload on the heart by expanding the blood vessels and decreasing resistance to blood flow. Examples of ACE inhibitors include benazepril (Lotensin®), captopril (Capoten®), enalapril (Vasotec®), fosinopril (Monopril®), lisinopril Zestril®), moexipril (Univasc®), perindopril (Aceon®), quinapril (Accupril®), ramipril (Altace®), and trandolapril (Mavik®).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (Plavix®), prasugrel (Effient®), dipyridamole, cilostazol, persantine sulfinpyrazone, dipyridamole, indomethacin, and glycoprotein 11b/111a inhibitors, such as abciximab, tirofiban, and eptifibatide (Integrelin®). Beta blockers and calcium channel blockers also have a platelet-inhibiting effect.

Anticoagulants prevent blood clots from growing larger and prevent the formation of new clots. Examples of anticoagulants include bivalirudin (Angiomax®), warfarin (Coumadin®), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest (see U.S. Patent Application Publication No. 2010/0056536 and U.S. Patent Application Publication No. 2011/0183990, the entirety of which are incorporated herein).

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopressor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril Zestril®); angiotensin-II receptor antagonists, such as candesartan (Atacand®), eprosartan (Teveten®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride®), diazoxide (Hyperstat® IV), hydralazine (Apresoline®), minoxidil (Loniten®), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip®), ciprofibrate (Modalim®), and statins, such as atorvastatin (Lipitor®), fluvastatin (Lescol®), lovastatin (Mevacor®, Altocor®), mevastatin, pitavastatin (Livalo®, Pitava®) pravastatin (Lipostat®), rosuvastatin (Crestor®), and simvastatin (Zocor®).

In this disclosure, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient a compound as disclosed herein (e.g., Formula I, IA, IB, II, IIA, IIB, III, IIIA, IV, V, VI, VIII, VIIIA, IX, X, XII or XIII) in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire®, Bricanyl®), albuterol (Proventir), salmeterol (Serevent®, Serevent Diskus®), theophylline, ipratropium bromide (Atrovent®), tiotropium (Spiriva®), methylprednisolone (Solu-Medrol®, Medrol®), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix®), lansoprazole (Prevacid®), esomeprazole (Nexium®), omeprazole (Prilosec®), rabeprazole; H2 blockers, such as cimetidine (Tagamet®), ranitidine (Zantac®), famotidine (Pepcid®), nizatidine (Axid®); prostaglandins, such as misoprostol (Cytotec®); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with a compound as disclosed herein (e.g., Formula I, IA, IB, II, IIA, IIB, III, IIIA, IV, V, VI, VIII, VIIIA, IX, X, XII or XIII).

Antibiotics

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil) (Duricef®), cephalexin (Keflex®), cephradine (Velosef®), cefaclor (Ceclor®), cefuroxime axtel (Ceftin®), cefprozil (Cefzil®), loracarbef (Lorabid®), cefixime (Suprax®), cefpodoxime proxetil (Vantin®), ceftibuten (Cedax®), cefdinir (Omnicef®), ceftriaxone (Rocephin®), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the late sodium channel blockers of the disclosure to treat neuropathic pain via inhibition of the $Na_V$ 1.7 and 1.8 sodium channels, combination with analgesics are particularly invisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft®, Lustral®, Apo-Sertral®, Asentra®, Gladem®, Serlift®, Stimuloton®; escitalopram (Lexapro®, Cipralex®); fluoxetine (Prozac® Sarafem® Fluctin® Fontex®, Prodep®, Fludep®, Lovan®); venlafaxine (Effexor® XR, Efexor®); citalopram (Celexa®, Cipramil®, Talohexane®); paroxetine (Paxil®, Seroxat®, Aropax®); trazodone (Desyrel®); amitriptyline (Elavil®); and bupropion (Wellbutrin®, Zyban®).

Accordingly, one aspect of the disclosure provides for a composition comprising the late sodium channel blockers of the disclosure and at least one therapeutic agent. In an alternative embodiment, the composition comprises the late sodium channel blockers of the disclosure and at least two therapeutic agents. In further alternative embodiments, the composition comprises the late sodium channel blockers of the disclosure and at least three therapeutic agents, the late sodium channel blockers of the disclosure and at least four therapeutic agents, or the late sodium channel blockers of the disclosure and at least five therapeutic agents.

The methods of combination therapy include co-administration of a single formulation containing the late sodium channel blockers of the disclosure and therapeutic agent or agents, essentially contemporaneous administration of more than one formulation comprising the late sodium channel blocker of the disclosure and therapeutic agent or agents, and consecutive administration of a late sodium channel blocker of the disclosure and therapeutic agent or agents, in any order, wherein preferably there is a time period where the late sodium channel blocker of the disclosure and therapeutic agent or agents simultaneously exert their therapeutic affect.

6. Synthesis of Example Compounds

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula I, IA, IB, II, IIA, IIB, III, IIIA, IV, V, VI, VIII, VIIIA, IX, X, XII or XIII or other formulas or compounds disclosed herein, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products.

Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I

The compounds of Formula I (and Formula IA, IB, II, IIA, IIB, III, IIIA, IV, V, VI, VIII, VIIIA, IX, X, XII or XIII) are typically prepared by first providing the molecular core 1-1 and then attaching the desired -Q-$R^1$ substituents using suitable coupling conditions (e.g., Suzuki coupling) and the desired —$R^2$ substituents using suitable substitution conditions. These processes are show below in Scheme 1 for the synthesis of a compound of Formula I, wherein -Q-$R^1$ is at either $Z^3$ or $Z^4$ in each of Formulas 1-1, 1-2, 1-3 and I shown in Scheme 1, wherein the bromo and/or -Q-$R^1$ is at either $Z^3$ or $Z^4$ in each of the Formulas shown in Scheme 1.

example dichlorobis(triphenylphosphine) palladium(II), at a temperature of about 120-170° C., for about 10 minutes to about 1 hour or at a lower temperature, i.e., 90-110° C. for 2 to 5 days. When the reaction is substantially complete, the product of Formula I is isolated by conventional means.

It will be appreciated that the $R^2$ substitutent can be modified or added either before (as shown in Scheme 1) or after the addition of the $R^1$ moiety. The $R^2$ moiety may be coupled to the core 1-1 under substitution reaction conditions with an appropriate reagent of formula LG-$R^2$ (where LG is a leaving group such as a halo, hydroxyl, alkoxy or the like) as shown in Scheme 1. Typical substitution reaction conditions include the presence of a base, such as ssium carbonate, sodium bicarbonate, triethylamine, and the like, in a polar aprotic solvent, such as N,N-dimethylformamide, and optionally an elevated temperature of about 100-150° C. or in a microwave. Also, in the case where the $R^2$ substituent contains a heteroaryl ring, the heteroaryl ring may be synthesized and cyclized before or after addition of the -Q-$R^1$ portion.

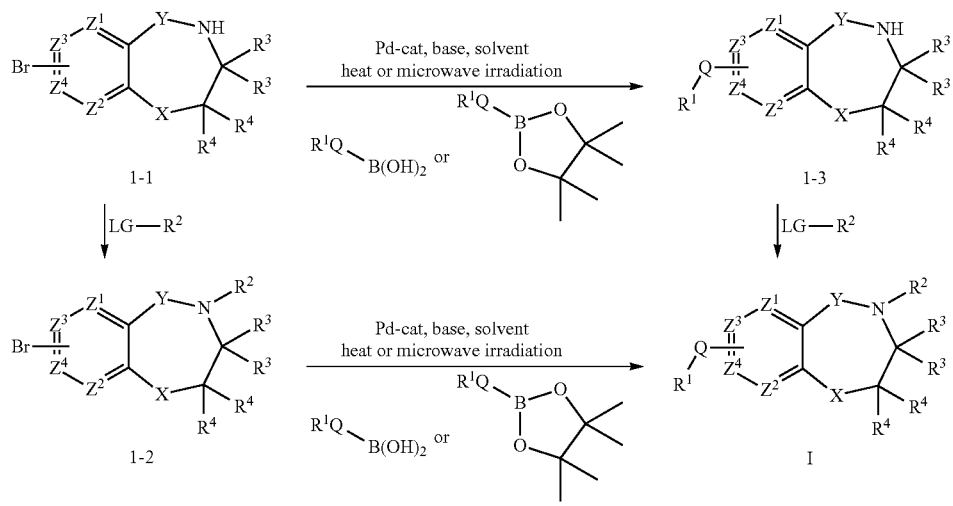

Scheme 1

In general, a halogenated compound of formula 1-1, in this case a brominated compound, is reacted with an appropriately substituted boronic acid derivative of formula $R^1$Q-B(OH)$_2$ or a boronic ester thereof, in an inert solvent, for example aqueous N,N-dimethylformamide, in the presence of a mild base, for example potassium carbonate or sodium bicarbonate. The reaction is typically conducted in the presence of a metal catalyst with an appropriate ligand, for Optional Core Synthesis In certain embodiments, the core may be synthesized before or after addition of the -Q-$R^1$ substituent (Scheme 2). For example, such alternative routes for the synthesis of 3,4-dihydrobenzo[f][1,4]oxazepin-5(2H)-one compounds of Formula 2-8 (i.e., Formula IA, II, IIA, IIB, IV, V, VI VIII, X, XII and XIII) are shown in Scheme 2, below, wherein the bromo and/or -Q-R$^1$ is at either Z$^3$ or Z$^4$ in each of the Formulas shown in Scheme 2.

pounds of Formula 2-4 can be isolated by conventional means. Compounds of Formula 2-4 are cyclized to afford

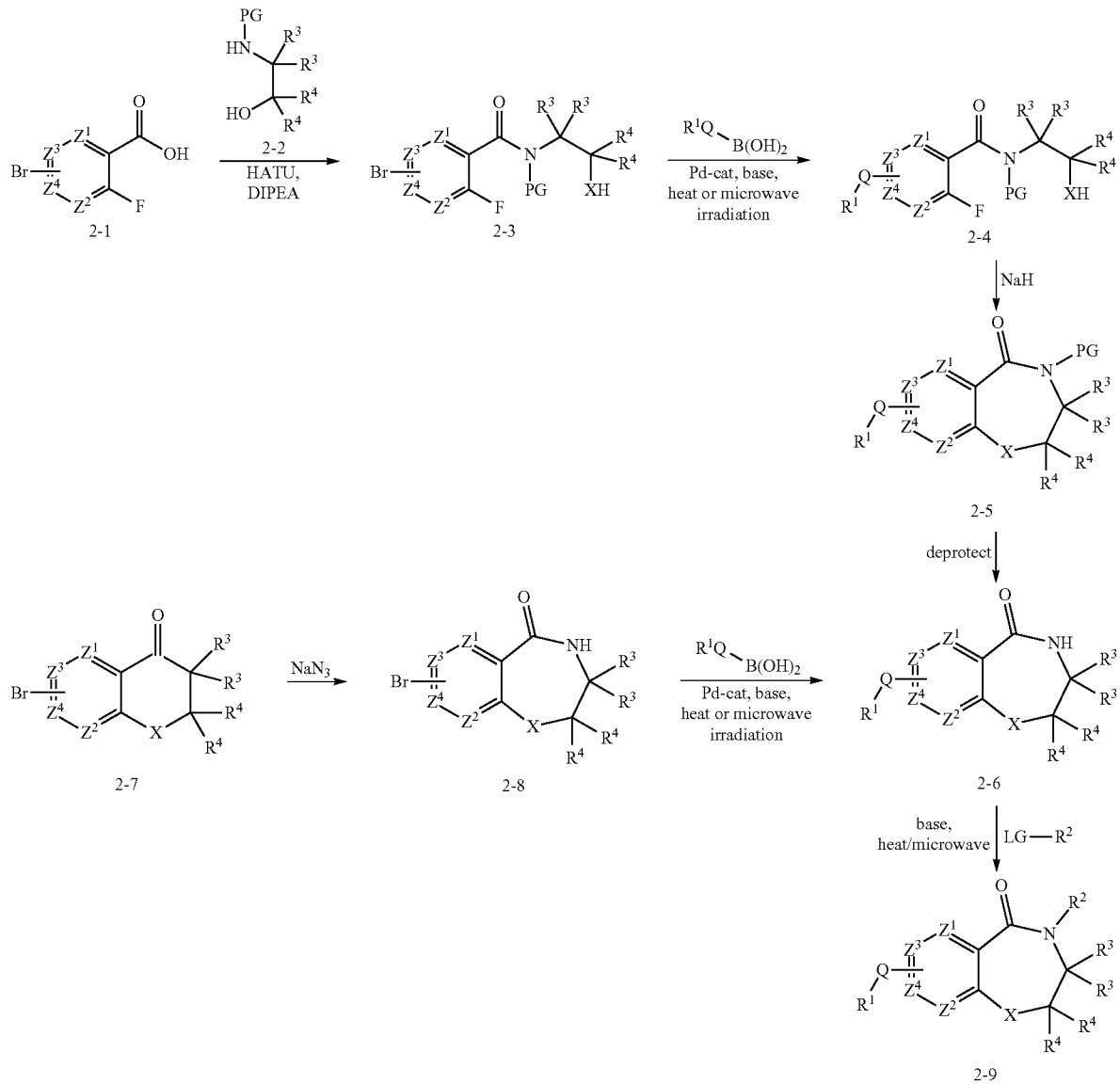

Scheme 2

In one embodiment, compounds of Formula 2-3 can be provided from compounds of Formula 2-1 via amide formation with a suitably protected 2-2, where PG is a protecting group, such as benzyl. Compounds of Formula 2-3 are coupled with an appropriately substituted boronic acid derivative of formula R$^1$Q-B(OH)$_2$ or a boronic ester thereof, under typical coupling reaction conditions. Typical coupling reaction conditions an inert solvent, for example aqueous N,N-dimethylformamide, in the presence of a mild base, for example potassium carbonate or sodium bicarbonate. The reaction is typically conducted in the presence of a metal catalyst with an appropriate ligand, for example dichlorobis(triphenylphosphine) palladium(II), at a temperature of about 120-170° C., for about 10 minutes to about 1 hour or at a lower temperature, i.e., 90-110° C. for 2 to 5 days. When the reaction is substantially complete, the comcompounds of Formula 2-5 using sodium hydride, in a suitable solvent, such as dimethylformamide. Deprotection under suitable conditions provides compounds of Formula 2-6.

In another embodiment, compounds of Formula 2-8 are prepared from commercially available compounds of Formula 2-7 using sodium azide. Compounds of Formula 2-6 can be obtained from compounds of Formula 2-8 via reaction with an appropriately substituted boronic acid derivative of formula R$^1$Q-B(OH)$_2$ or a boronic ester thereof, under typical coupling reaction conditions as described above.

The R$^2$ moiety may be coupled to compounds of Formula 2-6 under substitution reaction conditions with an appropriate reagent of formula LG-R$^2$ (where LG is a leaving group such as a halo, hydroxyl, alkoxy or the like) as shown in Scheme 1 to afford 3,4-dihydrobenzo[f][1,4]oxazepin-5(2H)-one compounds of Formula 2-9. Typical substitution reaction conditions include the presence of a base, such as ssium carbonate, sodium bicarbonate, triethylamine, and the like, in a polar aprotic solvent, such as N,N-dimethylformamide, and optionally an elevated temperature of about 100-150° C. or in a microwave.

2,3,4,5-Tetrahydrobenzo[f][1,4]oxazepine compounds of Formula 3-2 (i.e., Formula III and IIIA) are synthesized from compounds of Formula 2-6 as shown in Scheme 3, below, wherein -Q-$R^1$ is at either C7 or C8 in each of the Formulas shown in Scheme 2.

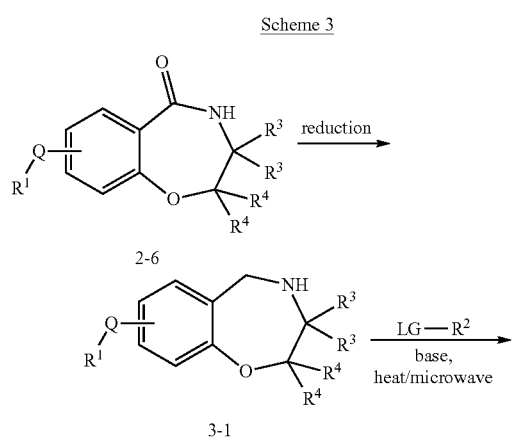

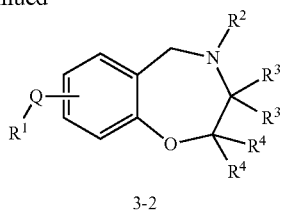

In one embodiment, compounds of Formula 3-1 can be provided from the reduction of compounds of Formula 2-6 via amide formation with a suitably protected 2-2, where PG is a protecting group, such as benzyl. The $R^2$ moiety may be coupled to compounds of Formula 2-6 under substitution reaction conditions with an appropriate reagent of formula LG-$R^2$ (where LG is a leaving group such as a halo, hydroxyl, alkoxy or the like) as shown in Scheme 1 to afford compounds of Formula 3-2.

Compounds of Formula 4-3 (i.e., Formula IX) are synthesized as shown in Scheme 4, below, wherein -Q-$R^1$ is at either C7 or C8 in each of the Formulas shown in Scheme 2.

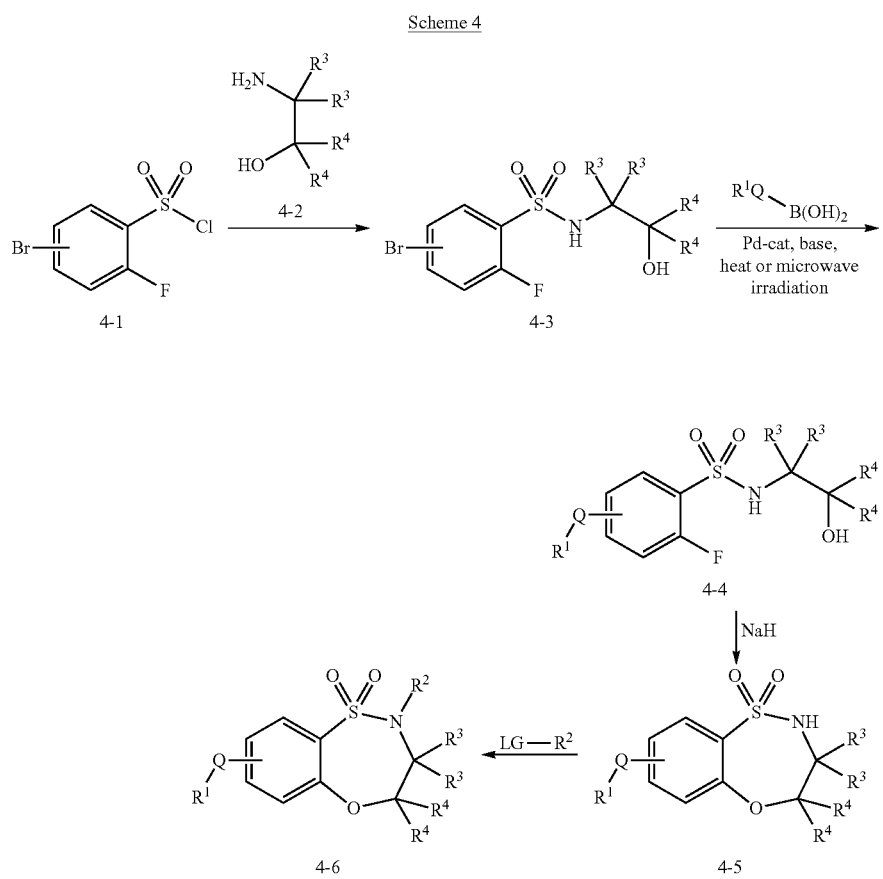

In one embodiment, compounds of Formula 4-3 can be provided from compounds of Formula 4-1 via sulfonamide formation with an amino alcohol 4-2. Compounds of Formula 4-3 are coupled with an appropriately substituted boronic acid derivative of formula R$^1$Q-B(OH)$_2$ or a boronic ester thereof, under typical coupling reaction conditions as discussed in Scheme 2. Compounds of Formula 4-4 are cyclized to afford compounds of Formula 5-5 using sodium hydride, in a suitable solvent, such as dimethylformamide.

The R$^2$ moiety may be coupled to compounds of Formula 4-5 under substitution reaction conditions with an appropriate reagent of formula LG-R$^2$ (where LG is a leaving group such as a halo, hydroxyl, alkoxy or the like) as shown in Scheme 1 to afford compounds of Formula 4-6. Typical substitution reaction conditions include the presence of a base, such as ssium carbonate, sodium bicarbonate, triethylamine, and the like, in a polar aprotic solvent, such as N,N-dimethylformamide, and optionally an elevated temperature of about 100-150° C. or in a microwave.

It will also be appreciated that the addition of any substituent may result in the production of a number of isomeric products any or all of which may be isolated and purified using conventional techniques.

EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

List of abbreviations and acronyms.

| Abbreviation | Meaning |
|---|---|
| ° C. | Degree Celcius |
| anal | Analytical |
| ATP | Adenosine-5'-triphosphate |
| ATX II | Anemonia sulcata toxin |
| ACN | Acetonitrile |
| CHO | Chinese hamster ovary |
| conc. | Concentrated |
| d | Doublet |
| DABCO | 1,4-Diazabicyclo[2.2.2]octane |
| dd | Doublet of doublets |
| DCM | Dichloromethane |
| DIPEA | N,N-diisopropylethylamine |
| DMF | Dimethylformamide |
| DMSO | Dimethylsulfoxide |
| dppf | 1,1'-Bis(diphenylphosphino)ferrocene |
| EA | Ethyl alcohol |
| ECF | Extracellular fluid |
| EDTA | Ethylenediaminetetraacetic acid |
| EGTA | Ethylene glycol tetraacetic acid |
| equiv/eq | Equivalents |
| ESI | Electrospray ionization |
| Ac | Acetate |
| Et | Ethyl |
| g | Grams |
| HEPES | (4-(2-Hydroxyethyl)-1-piperazineethanesulfonic acid) |
| HATU | 2-(7-Aza-1H-Benzotriazole-1-yl)-1,1,3,3-tetramethyluronium hexafluorophosphate |
| hERG | human Ether-à-go-go Related Gene |
| HPLC | High-performance liquid chromatography |

-continued

List of abbreviations and acronyms.

| Abbreviation | Meaning |
|---|---|
| h | Hours |
| Hz | Hertz |
| IC$_{50}$ | The half maximal inhibitory concentration |
| IMR-32 | Human neuroblastoma cell line |
| J | Coupling constant |
| Kg | Kilogram |
| kHz | Kilohertz |
| LCMS/LC-MS | Liquid chromatography-mass spectrometry |
| M | Molar |
| m | multiplet |
| m/z | mass-to-charge ratio |
| M+ | Mass peak |
| M + H | Mass peak plus hydrogen |
| Me | Methyl |
| mg | Milligram |
| MHz | Megahertz |
| min/m | Minute |
| ml/mL | Milliliter |
| mM | Millimolar |
| mmol | Millimole |
| nmol | Nanomole |
| mOsmol | Milliosmole |
| MRM | Magnetic Resonance Microscopy |
| MS | Mass spectroscopy |
| ms | Millisecond |
| mV | Millivolt |
| mw | Microwave |
| N | Normal |
| mol | Mole |
| NMR | Nuclear magnetic resonance |
| pA | Picoamps |
| Ph | Phenyl |
| prep | Preparative |
| q.s. | Quantity sufficient to achieve a stated function |
| Rf | Retention factor |
| RT/rt | Room temperature |
| s | Second |
| s | Singlet |
| SEM | Standard error of the mean |
| t | Triplet |
| TB | Tonic Block |
| TEA | Triethylamine |
| TFA | Trifluoroacetic acid |
| THF | Tetrahydrofuran |
| TLC | Thin layer chromatography |
| TTX | Tetrodotoxin |
| UDB | Use Dependent Block |
| WT | Wild type |
| δ | Chemical shift |
| μg | Microgram |
| μL/μl | Microliter |
| μM | Micromolar |
| μm | Micrometer |
| μmol | Micromole |

Example 1

7-(4-(trifluoromethoxy)phenyl)-3,4-dihydrobenzo[f][1,4]oxazepin-5(2H)-one (Compound II-74)

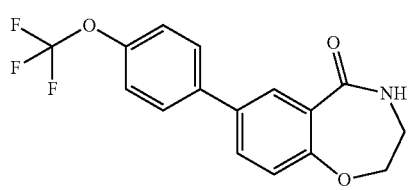

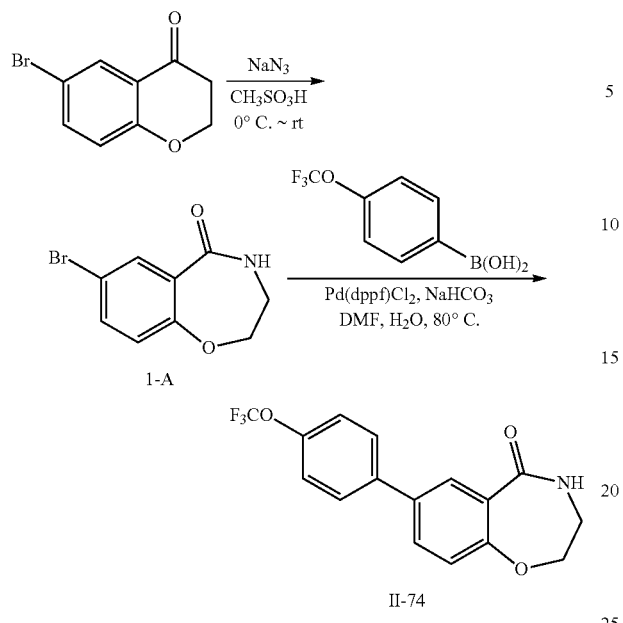

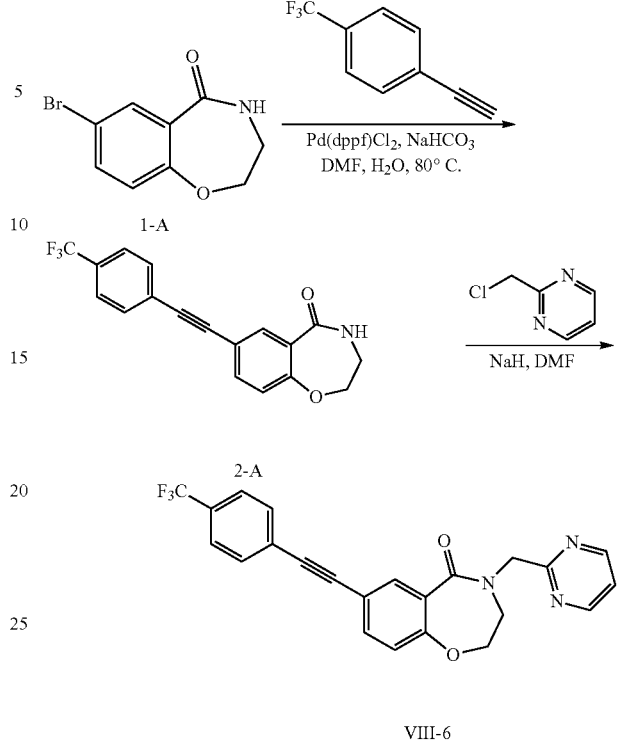

Commercially available 6-bromochroman-4-one (1.0 g, 3 mmol) was dissolved in 10 mL methanesulfonic acid. The solution was cooled using an ice bath and sodium azide (0.30 g, 4.5 mmol) was added over a period of 45 min. The mixture was stirred at RT for 16 h. The mixture was neutralized using conc. HCl. The resulting solid was filtered and washed with water to afford Compound 1-A as analytically pure sample.

For the Suzuki coupling reaction the following conditions were applied: To a suspension of Compound 1-A (1 eq), the substituted boronic acid or boronate ester (1.2 eq) and base sodium bicarbonate (3 eq) in solvent (DMF:water in the ratio of 4:1) was added palladium catalyst Pd(dppf)Cl$_2$ (10 mol %) and heated at 80° C. for 2-4 h. The reaction progress was followed by LC and after completion, the reaction mixture was filtered through celite, washed with ethyl acetate. The filtrate was concentrated the filtrate and purified by prep TLC/prep HPLC or column chromatography to afford Compound II-74.

Example 2

4-(pyrimidin-2-ylmethyl)-7-((4-(trifluoromethyl)phenyl)ethynyl)-3,4-dihydrobenzo[f][1,4]oxazepin-5(2H)-one (Compound VIII-6)

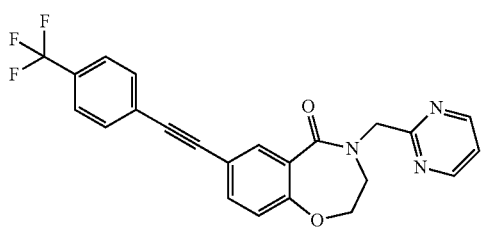

Compound 2-A was prepared from Compound 1-A according to Example 1 using 1-ethynyl-4-(trifluoromethyl)benzene in place of the boronic acid.

To a solution of 2-A (1 eq) in DMF was added the corresponding halide (1.3 eq). To the mixture was added sodium hydride (60% dispersion in oil, 2 mmol) and stirred at room temperature for 10 min, followed by heating at 80° C. for 24 h. The reaction mixture was quenched with water, extracted with ethyl acetate (100 mL). The organic layer was washed with water, brine and dried over sodium sulphate and concentrated And purified using prep TLC/prep HPLC or column chromatography to afford Compound VIII-6.

$^1$H-NMR (CDCl$_3$) δ 8.71 (d, 2H, J=4.4 Hz), 8.20 (d, 1H, J=2.4 Hz), 7.55-7.59 (m, 5H), 7.20 (t, 1H, J=4.8 Hz), 7.01 (d, 1H, J=8.4 Hz), 5.08 (s, 2H), 4.58 (t, 2H, J=4.6 Hz), 3.76 (t, 2H, J=5.0 Hz); MS m/z 424.1 (M+H).

Example 3

4-(pyridin-2-ylmethyl)-7-(4-(trifluoromethoxy)phenyl)-3,4-dihydrobenzo[f][1,4]oxazepin-5(2H)-one (Compound II-72)

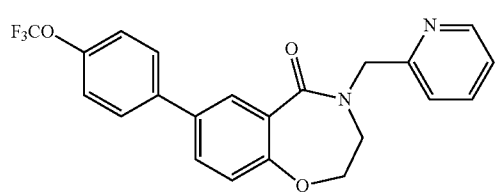 [SMILES: O=C1c2cc(-c3ccc(OC(F)(F)F)cc3)ccc2OCCN1Cc1ccccn1]

Compound II-72 was prepared according to Examples 1 and 2 using the appropriate starting materials. $^1$H-NMR (CDCl$_3$) δ 8.81 (d, 1H, J=5.6 Hz), 8.27 (t, 1H, J=7.8 Hz), 8.07 (d, 1H, J=8.4 Hz), 8.02 (d, 1H, J=2.4 Hz), 7.75 (t, 1H, J=6.4 Hz), 7.65 (dd, 1H, J=8.6, 2.6 Hz), 7.58 (dd, 2H, J=4.8, 2.8 Hz), 7.28 (d, 2H, J=8.4 Hz), 7.12 (d, 1H, J=8.4 Hz), 5.24 (s, 2H), 4.39 (t, 2H, J=5.0 Hz), 3.85 (t, 2H, J=5.0 Hz); MS m/z 415.1 (M+H).

Example 4

4-(pyridin-3-ylmethyl)-7-(4-(trifluoromethoxy)phenyl)-3,4-dihydrobenzo[f][1,4]oxazepin-5(2H)-one (Compound II-70)

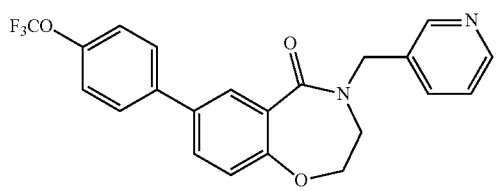 [SMILES: O=C1c2cc(-c3ccc(OC(F)(F)F)cc3)ccc2OCCN1Cc1cccnc1]

Compound II-70 was prepared according to Examples 1 and 2 using the appropriate starting materials. ¹H-NMR (CDCl₃) δ 9.00 (s, 1H), 8.75 (d, 1H, J=5.2 Hz), 8.47 (d, 1H, J=7.6 Hz), 8.05 (d, 1H, J=2.4 Hz), 7.83 (dd, 1H, J=7.8, 5.4 Hz), 7.66 (dd, 1H, J=8.8, 2.4 Hz), 7.60 (d, 2H, J=8.4 Hz), 7.28 (d, 2H, J=8.4 Hz), 7.13 (d, 1H, J=8.0 Hz), 4.99 (s, 2H), 4.37 (t, 2H, J=5.0 Hz), 3.67 (t, 2H, J=5.0 Hz); MS m/z 415.1 (M+H).

Example 5

4-(2-(pyrimidin-2-yloxy)ethyl)-7-(4-(trifluoromethoxy)phenyl)-3,4-dihydrobenzo[f][1,4]oxazepin-5(2H)-one (Compound II-69)

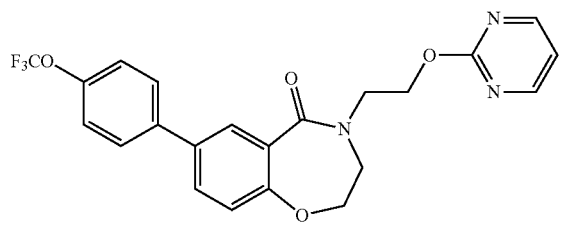 [SMILES: O=C1c2cc(-c3ccc(OC(F)(F)F)cc3)ccc2OCCN1CCOc1ncccn1]

Compound II-69 was prepared according to Examples 1 and 2 using the appropriate starting materials. ¹H-NMR (CDCl₃) δ 8.53 (d, 2H, J=4.8 Hz), 8.03 (d, 1H, J=2.4 Hz), 7.58-7.61 (m, 3H), 7.27 (d, 2H, J=5.2 Hz), 7.07 (d, 1H, J=8.0 Hz), 6.97 (t, 1H, J=4.8 Hz), 4.66 (t, 2H, J=4.8 Hz), 4.51 (t, 2H, J=5.2 Hz), 4.07 (t, 2H, J=5.0 Hz), 3.78 (t, 2H, J=5.0 Hz); MS m/z 468.0 (M+Na).

Example 6

4-(4-fluorobenzyl)-7-(4-(trifluoromethoxy)phenyl)-3,4-dihydrobenzo[f][1,4]oxazepin-5(2H)-one (Compound II-62)

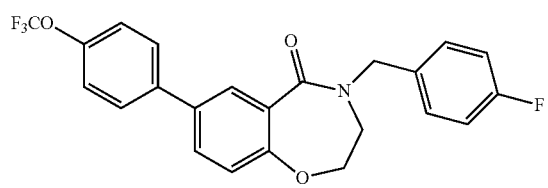 [SMILES: O=C1c2cc(-c3ccc(OC(F)(F)F)cc3)ccc2OCCN1Cc1ccc(F)cc1]

Compound II-62 was prepared according to Examples 1 and 2 using the appropriate starting materials. ¹H-NMR (CDCl₃) δ 8.10 (d, 1H, J=2.8 Hz), 7.60-7.63 (m, 3H), 7.35 (dd, 2H, J=8.4, 1.2 Hz), 7.28 (d, 2H, J=8.0 Hz), 7.03-7.09 (m, 3H), 4.82 (s, 2H), 4.22 (t, 2H, J=5.2 Hz), 3.51 (t, 2H, J=5.2 Hz); MS m/z 432.1 (M+H).

Example 7

4-(pyrimidin-2-ylmethyl)-7-(4-(trifluoromethyl)phenyl)-3,4-dihydrobenzo[f][1,4]oxazepin-5(2H)-one (Compound II-61)

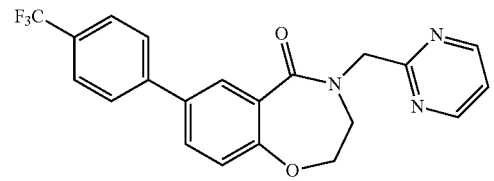 [SMILES: O=C1c2cc(-c3ccc(C(F)(F)F)cc3)ccc2OCCN1Cc1ncccn1]

Compound II-61 was prepared according to Examples 1 and 2 using the appropriate starting materials. ¹H-NMR (CDCl₃) δ 8.80 (d, 2H, J=5.2 Hz), 8.19 (d, 1H, J=2.8 Hz), 7.66-7.71 (m, 5H), 7.33 (t, 1H, J=5.0 Hz), 7.13 (d, 1H, J=8.4 Hz), 5.14 (s, 2H), 4.59 (t, 2H, J=4.8 Hz), 3.81 (t, 2H, J=5.0 Hz); MS m/z 400.1 (M+H).

Example 8

4-(2-fluorobenzyl)-7-(4-(trifluoromethoxy)phenyl)-3,4-dihydrobenzo[f][1,4]oxazepin-5(2H)-one (Compound II-57)

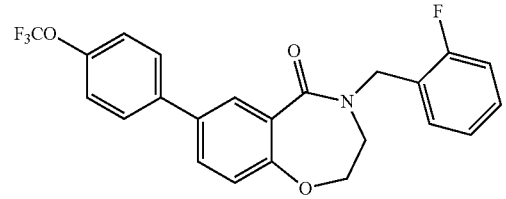 [SMILES: O=C1c2cc(-c3ccc(OC(F)(F)F)cc3)ccc2OCCN1Cc1ccccc1F]

Compound II-57 was prepared according to Examples 1 and 2 using the appropriate starting materials. ¹H-NMR (CDCl₃) δ 8.07 (d, 1H, J=2.4 Hz), 7.58-7.61 (m, 3H), 7.49-7.51 (m, 1H), 7.26-7.31 (m, 3H), 7.16 (t, 1H, J=7.6

Hz), 7.07-7.18 (m, 2H), 4.92 (s, 2H), 4.29 (t, 2H, J=4.8 Hz), 3.61 (t, 2H, J=5.0 Hz); MS m/z 432.1 (M+H).

Example 9

4-(2-(pyridin-2-yl)ethyl)-7-(4-(trifluoromethoxy)phenyl)-3,4-dihydrobenzo[f][1,4]oxazepin-5(2H)-one (Compound II-54)

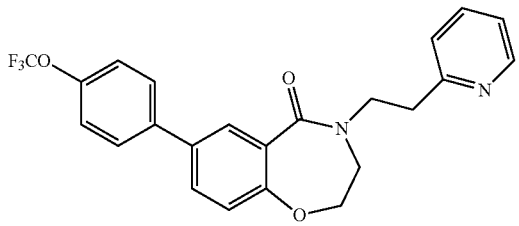

Compound II-54 was prepared according to Examples 1 and 2 using the appropriate starting materials. $^1$H-NMR (CDCl$_3$) δ 8.57 (d, 1H, J=4.8 Hz), 8.03 (d, 1H, J=2.4 Hz), 7.67-7.69 (m, 1H), 7.57-7.61 (m, 3H), 7.20-7.33 (m, 4H), 7.04 (d, 1H, J=8.8 Hz), 4.19 (t, 2H, J=4.8 Hz), 4.06 (t, 2H, J=7.4 Hz), 3.51 (t, 2H, J=5.0 Hz), 3.24 (t, 2H, J=6.8 Hz); MS m/z 429.1 (M+H).

Example 10

4-(2-(1H-pyrazol-1-yl)ethyl)-7-(4-(trifluoromethoxy)phenyl)-3,4-dihydrobenzo[f][1,4]oxazepin-5(2H)-one (Compound II-50)

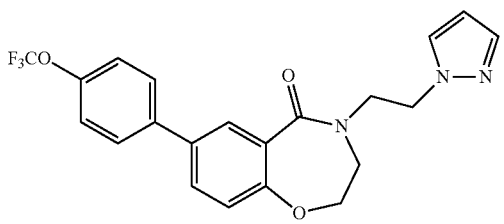 [SMILES: O=C1c2cc(-c3ccc(OC(F)(F)F)cc3)ccc2OCCN1CCn1cccn1]

Compound II-50 was prepared according to Examples 1 and 2 using the appropriate starting materials. $^1$H-NMR (CDCl$_3$) δ 8.02 (d, 1H, J=2.4 Hz), 7.58-7.64 (m, 4H), 7.47 (d, 1H, J=1.6 Hz), 7.28 (d, 2H, J=8.8 Hz), 7.04 (d, 1H, J=8.4 Hz), 6.30 (t, 1H, J=2.2 Hz), 4.55 (t, 2H, J=5.8 Hz), 4.11 (t, 2H, J=5.4 Hz), 3.96 (t, 2H, J=5.0 Hz), 3.28 (t, 2H, J=5.0 Hz); MS m/z 418.1 (M+H).

Example 11

4-(2,6-difluorobenzyl)-7-(4-(trifluoromethoxy)phenyl)-3,4-dihydrobenzo[f][1,4]oxazepin-5(2H)-one (Compound II-49)

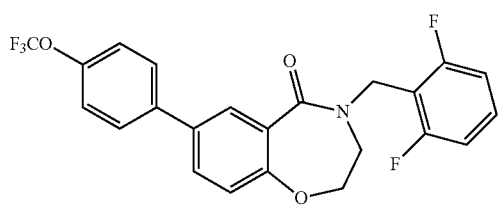 [SMILES: O=C1c2cc(-c3ccc(OC(F)(F)F)cc3)ccc2OCCN1Cc1c(F)cccc1F]

Compound II-49 was prepared according to Examples 1 and 2 using the appropriate starting materials. $^1$H-NMR (CDCl$_3$) δ 8.08 (d, 1H, J=2.4 Hz), 7.57-7.61 (m, 3H), 7.26-7.33 (m, 3H), 7.05 (d, 1H, J=8.4 Hz), 6.95 (t, 2H, J=8.0 Hz), 4.98 (s, 2H), 4.23 (t, 2H, J=4.8 Hz), 3.59 (t, 2H, J=4.8 Hz); MS m/z 450.1 (M+H).

Example 12

4-(2,6-dichlorobenzyl)-7-(4-(trifluoromethoxy)phenyl)-3,4-dihydrobenzo[f][1,4]oxazepin-5(2H)-one (Compound II-48)

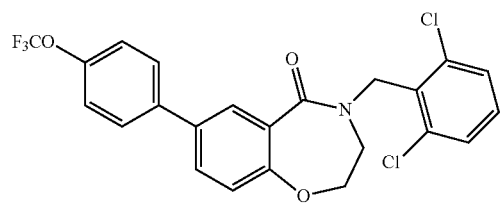 [SMILES: O=C1c2cc(-c3ccc(OC(F)(F)F)cc3)ccc2OCCN1Cc1c(Cl)cccc1Cl]

Compound II-48 was prepared according to Examples 1 and 2 using the appropriate starting materials. $^1$H-NMR (CDCl$_3$) δ 8.06 (d, 1H, J=2.4 Hz), 7.59-7.62 (m, 3H), 7.40 (d, 2H, J=8.0 Hz), 7.25-7.29 (m, 3H), 7.06 (d, 1H, J=8.4 Hz), 5.24 (s, 2H), 4.07 (t, 2H, J=5.0 Hz), 3.42 (t, 2H, J=5.2 Hz); MS m/z 483.0 (M+H).

Example 13

4-(2-chlorobenzyl)-7-(4-(trifluoromethoxy)phenyl)-3,4-dihydrobenzo[f][1,4]oxazepin-5(2H)-one (Compound II-47)

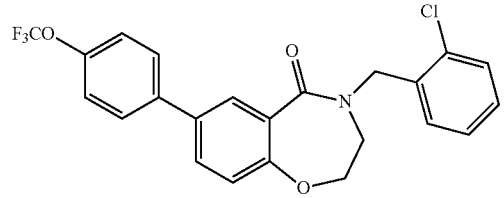 [SMILES: O=C1c2cc(-c3ccc(OC(F)(F)F)cc3)ccc2OCCN1Cc1ccccc1Cl]

Compound II-47 was prepared according to Examples 1 and 2 using the appropriate starting materials. $^1$H-NMR (CDCl$_3$) δ 8.10 (d, 1H, J=2.4 Hz), 7.60-7.64 (m, 3H), 7.47 (dd, 1H, J=7.0, 2.2 Hz), 7.41 (dd, 1H, J=7.4, 1.8 Hz), 7.26-7.30 (m, 4H), 7.09 (d, 1H, J=8.4 Hz), 5.01 (s, 2H), 4.28 (t, 2H, J=5.0 Hz), 3.58 (t, 2H, J=5.2 Hz); MS m/z 448.1 (M+H).

Example 14

7-(phenylethynyl)-4-(pyrimidin-2-ylmethyl)-3,4-dihydrobenzo[f][1,4]oxazepin-5(2H)-one (Compound VIII-5)

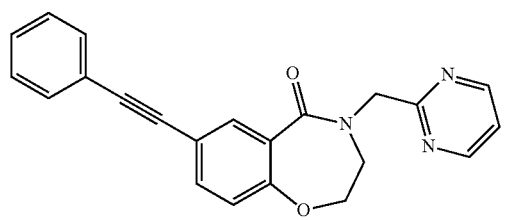 [SMILES: O=C1c2cc(C#Cc3ccccc3)ccc2OCCN1Cc1ncccn1]

Compound VIII-5 was prepared according to Example 2 using the appropriate starting materials. $^1$H-NMR (CD$_3$OD) δ 8.76 (d, 2H, J=4.8 Hz), 7.92 (d, 1H, J=2.4 Hz), 7.60 (dd, 1H, J=8.6, 1.8 Hz), 7.48-7.51 (m, 2H), 7.35-7.39 (m, 4H), 7.07 (d, 1H, J=8.8 Hz), 5.05 (s, 2H), 4.59 (t, 2H, J=4.8 Hz), 3.83 (t, 2H, J=4.8 Hz); MS m/z 356.1 (M+H).

Example 15

4-(pyrimidin-2-ylmethyl)-7-((4-(trifluoromethoxy)phenyl)ethynyl)-3,4-dihydrobenzo[f][1,4]oxazepin-5(2H)-one (Compound VIII-4)

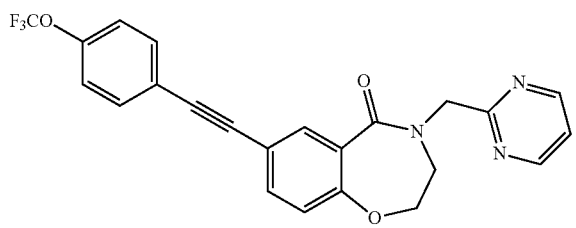 [SMILES: O=C1c2cc(C#Cc3ccc(OC(F)(F)F)cc3)ccc2OCCN1Cc1ncccn1]

Compound VIII-4 was prepared according to Example 2 using the appropriate starting materials. $^1$H-NMR (CD$_3$OD) δ 8.76 (d, 2H, J=7.2 Hz), 7.95 (d, 1H, J=2.4 Hz), 7.59-7.63 (m, 3H), 7.38 (t, 1H, J=5.0 Hz), 7.29 (d, 2H, J=8.4 Hz), 7.08 (d, 1H, J=8.8 Hz), 5.05 (s, 2H), 4.60 (t, 2H, J=5.0 Hz), 3.83 (t, 2H, J=4.8 Hz); MS m/z 440.1 (M+H).

Example 16

4-(2-(pyrimidin-2-yl)ethyl)-7-(4-(trifluoromethoxy)phenyl)-3,4-dihydrobenzo[f][1,4]oxazepin-5(2H)-one (Compound II-44)

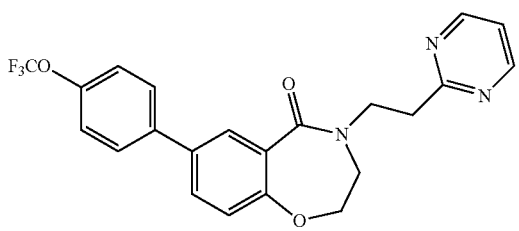 [SMILES: O=C1c2cc(-c3ccc(OC(F)(F)F)cc3)ccc2OCCN1CCc1ncccn1]

Compound II-44 was prepared according to Examples 1 and 2 using the appropriate starting materials. $^1$H-NMR (CDCl$_3$) δ 8.70 (d, 2H, J=5.2 Hz), 8.00 (d, 1H, J=2.4 Hz), 7.56-7.59 (m, 3H), 7.26 (d, 2H, J=8.4 Hz), 7.20 (t, 1H, J=5.2 Hz), 7.04 (d, 1H, J=8.8 Hz), 4.36 (t, 2H, J=5.0 Hz), 4.16 (t, 2H, J=7.0 Hz), 3.59 (t, 2H, J=5.0 Hz), 3.38 (t, 2H, J=6.0 Hz); MS m/z 430.1 (M+H).

Example 17

4-((4,6-dimethoxypyrimidin-2-yl)methyl)-7-(4-(trifluoromethoxy)phenyl)-3,4-dihydrobenzo[f][1,4]oxazepin-5(2H)-one (Compound II-42)

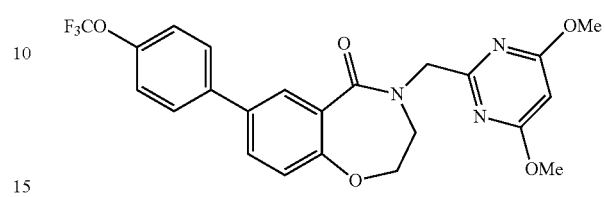

Compound II-42 was prepared according to Examples 1 and 2 using the appropriate starting materials. $^1$H-NMR (CD$_3$OD) δ 8.00 (d, 1H, J=2.4 Hz), 7.76 (dd, 1H, J=8.2, 2.6 Hz), 7.69 (dd, 2H, J=6.8, 2.0 Hz), 7.34 (d, 2H, J=8.0 Hz), 7.16 (d, 1H, J=8.8 Hz), 6.11 (s, 1H), 4.87 (s, 2H), 4.58 (t, 2H, J=5.0 Hz), 3.93 (s, 6H), 3.84 (t, 2H, J=5.2 Hz); MS m/z 476.1 (M+H).

Example 18

4-((5-methyloxazol-2-yl)methyl)-7-(4-(trifluoromethoxy)phenyl)-3,4-dihydrobenzo[f][1,4]oxazepin-5(2H)-one (Compound II-33)

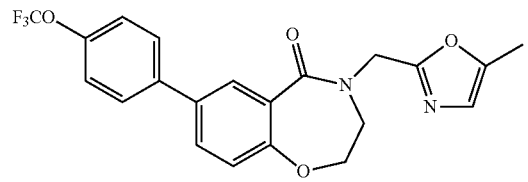 [SMILES: Cc1cnc(CN2CCOc3ccc(-c4ccc(OC(F)(F)F)cc4)cc3C2=O)o1]

Compound II-33 was prepared according to Examples 1 and 2 using the appropriate starting materials. $^1$H-NMR (CD$_3$OD) δ 8.00 (d, 1H, J=2.4 Hz), 7.77 (dd, 1H, J=8.4, 2.4 Hz), 7.71 (d, 2H, J=8.8 Hz), 7.34 (d, 2H, J=8.0 Hz), 7.15 (d, 1H, J=8.4 Hz), 6.81 (d, 1H, J=0.8 Hz), 4.93 (s, 2H), 4.43 (t, 2H, J=5.2 Hz), 3.76 (t, 2H, J=5.2 Hz), 2.34 (d, 3H, J=0.8 Hz); MS m/z 419.1 (M+H).

Example 19

4-(pyrazin-2-ylmethyl)-7-(4-(trifluoromethoxy)phenyl)-3,4-dihydrobenzo[f][1,4]oxazepin-5(2H)-one (Compound II-31)

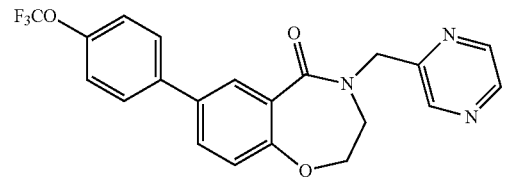 [SMILES: O=C1c2cc(-c3ccc(OC(F)(F)F)cc3)ccc2OCCN1Cc1cnccn1]

Compound II-31 was prepared according to Examples 1 and 2 using the appropriate starting materials. $^1$H-NMR (CD$_3$OD) δ 8.71 (d, 1H, J=0.8 Hz), 8.60 (t, 1H, J=2.0 Hz), 8.53 (d, 1H, J=2.4 Hz), 7.99 (d, 1H, J=2.4 Hz), 7.77 (dd, 1H, J=8.4, 2.4 Hz), 7.72 (dd, 2H, J=6.6, 2.2 Hz), 7.34 (d, 2H, J=8.0 Hz), 7.15 (d, 1H, J=8.4 Hz), 5.01 (s, 2H), 4.47 (t, 2H, J=5.2 Hz), 3.82 (t, 2H, J=5.0 Hz); MS m/z 416.1 (M+H).

Example 20

4-((6-methylpyridin-2-yl)methyl)-7-(4-(trifluoromethoxy)phenyl)-3,4-dihydrobenzo[f][1,4]oxazepin-5(2H)-one (Compound II-17)

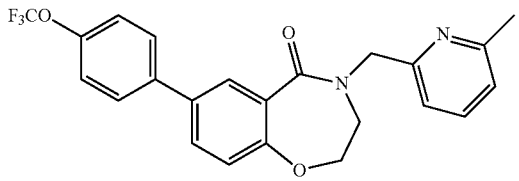 [SMILES: Cc1cccc(CN2CCOc3ccc(-c4ccc(OC(F)(F)F)cc4)cc3C2=O)n1]

Compound II-17 was prepared according to Examples 1 and 2 using the appropriate starting materials. $^1$H-NMR (CD$_3$OD) δ 8.28 (t, 1H, J=7.8 Hz), 8.00 (t, 1H, J=2.4 Hz), 7.81 (dd, 1H, J=8.2, 2.6 Hz), 7.68-7.73 (m, 4H), 7.35 (dd, 2H, J=8.6, 1.0 Hz), 7.20 (d, 1H, J=8.8 Hz), 5.09 (s, 2H), 4.50 (t, 2H, J=5.0 Hz), 3.86 (t, 2H, J=5.0 Hz), 2.77 (s, 3H); MS m/z 429.1 (M+H).

Example 21

7-(4-(trifluoromethoxy)phenyl)-4-((6-(trifluoromethyl)pyridin-2-yl)methyl)-3,4-dihydrobenzo[f][1,4]oxazepin-5(2H)-one (Compound II-15)

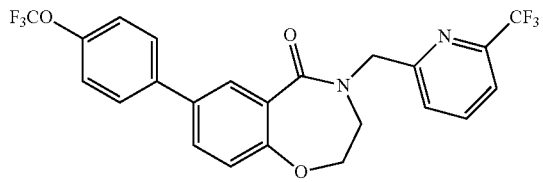

Compound II-15 was prepared according to Examples 1 and 2 using the appropriate starting materials. $^1$H-NMR (CD$_3$OD) δ 7.98-8.04 (m, 2H), 7.68-7.77 (m, 5H), 733 (d, 2H, J=8.0 Hz), 7.14 (d, 1H, J=8.4 Hz), 5.01 (s, 2H), 4.48 (t, 2H, J=5.2 Hz), 3.80 (t, 2H, J=5.2 Hz); MS m/z 483.1 (M+H).

Example 22

6-((5-oxo-7-(4-(trifluoromethoxy)phenyl)-2,3-dihydrobenzo[f][1,4]oxazepin-4(5H)-yl)methyl)picolinonitrile (Compound II-14)

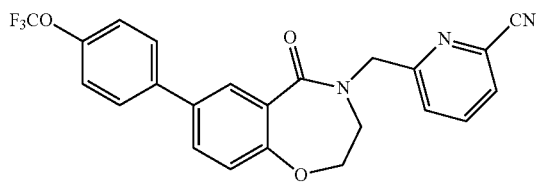 [SMILES: O=C1c2cc(-c3ccc(OC(F)(F)F)cc3)ccc2OCCN1Cc1cccc(C(F)(F)F)n1]

Compound II-14 was prepared according to Examples 1 and 2 using the appropriate starting materials. $^1$H-NMR (CD$_3$OD) δ 7.96-8.00 (m, 2H), 7.69-7.79 (m, 5H), 733 (d, 2H, J=8.0 Hz), 7.15 (d, 1H, J=8.4 Hz), 4.98 (s, 2H), 4.46 (t, 2H, J=5.2 Hz), 3.79 (t, 2H, J=5.0 Hz); MS m/z 440.1 (M+H).

Example 23

4-(cyclopropylmethyl)-7-(4-(trifluoromethoxy)phenyl)-3,4-dihydrobenzo[f][1,4]oxazepin-5(2H)-one (Compound II-10)

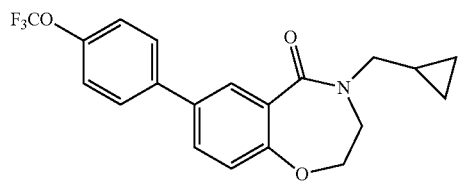 [SMILES: O=C1c2cc(-c3ccc(OC(F)(F)F)cc3)ccc2OCCN1CC1CC1]

Compound II-10 was prepared according to Examples 1 and 2 using the appropriate starting materials. $^1$H-NMR (CD$_3$OD) δ 7.92 (d, 1H, J=2.8 Hz), 7.69-7.75 (m, 3H), 7.34 (d, 2H, J=8.0 Hz), 7.13 (d, 1H, J=8.4 Hz), 4.48 (t, 2H, J=5.2 Hz), 3.70 (t, 2H, J=5.2 Hz), 3.53 (d, 2H, J=6.8 Hz), 1.13-1.18 (m, 1H), 0.57-0.61 (m, 2H), 0.35-0.40 (m, 2H); MS m/z 378.1 (M+H).

Example 24

4-(quinolin-2-ylmethyl)-7-(4-(trifluoromethoxy)phenyl)-3,4-dihydrobenzo[f][1,4]oxazepin-5(2H)-one (Compound II-7)

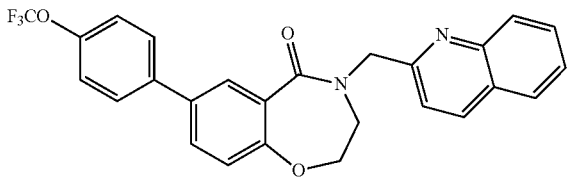 [SMILES: O=C1c2cc(-c3ccc(OC(F)(F)F)cc3)ccc2OCCN1Cc1ccc2ccccc2n1]

Compound II-7 was prepared according to Examples 1 and 2 using the appropriate starting materials. $^1$H-NMR (CD$_3$OD) δ 8.35 (d, 1H, J=8.8 Hz), 8.02-8.05 (m, 2H), 7.93 (d, 1H, J=7.6 Hz), 7.72-7.79 (m, 4H), 7.60 (d, 2H, J=8.4 Hz), 7.35 (d, 2H, J=8.0 Hz), 7.16 (d, 1H, J=8.8 Hz), 5.15 (s, 2H), 4.43 (t, 2H, J=5.2 Hz), 3.79 (t, 2H, J=5.0 Hz); MS m/z 465.1 (M+H).

Example 25

7-(3-fluoro-4-(trifluoromethyl)phenyl)-4-(pyrimidin-2-ylmethyl)-3,4-dihydrobenzo[f][1,4]oxazepin-5(2H)-one (Compound II-130)

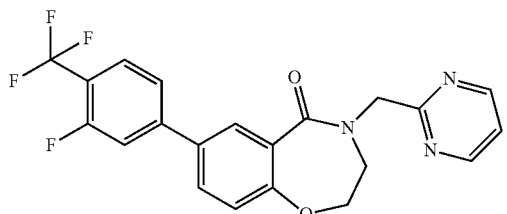

7-Bromo-3,4-dihydrobenzo[f][1,4]oxazepin-5(2H)-one (1.0 g, 4.13 mmol) was dissolved in DMF (10 ml) cooled down in a ice/water bath and treated with sodium hydride (60% dispersion) (363 mg, 9.08 mmol) portion wise. After 10 min a solution of 2-(chloromethyl)pyrimidine hydrochloride (813 mg, 4.96 mmol) in DMF (4 ml) was added, the reaction mixture warmed up to room temperature and quenched with 12 mL of water after it was complete. The reaction mixture was extracted with EtOAc and water and the organic phase was dried, evaporated and purified by silica gel chromatography (95% DCM/MeOH) to afford 7-bromo-4-(pyrimidin-2-ylmethyl)-3,4-dihydrobenzo[f][1,4]oxazepin-5(2H)-one.

Similar procedure to Example 1 for the synthesis of 7-(4,4,5,5-tetramethyl-1,3,2-dioxaborolan-2-yl)-3,4-dihydrobenzo[f][1,4]oxazepin-5(2H)-one was followed to obtain the title compound using instead of 7-bromo-3,4-dihydrobenzo[f][1,4]oxazepin-5(2H)-one.

A mixture of 7-bromo-4-(pyrimidin-2-ylmethyl)-3,4-dihydrobenzo[f][1,4]oxazepin-5(2H)-one (50 mg, 0.15 mmol), 2-(3-fluoro-4-(trifluoromethyl)phenyl)-4,4,5,5-tetramethyl-1,3,2-dioxaborolane (52 mg, 0.18 mmol), cesium carbonate (146 mg, 0.45 mmol), 1,1'-bis(diphenylphosphino)ferrocene]dichloropalladium (10 mg, 0.015 mmol) was dissolved in a degassed mixture of DMF and water 3/1.5 (4.5 mL). The mixture was heated in microwave at 85° C. for 40 min. The mixture was poured into EtOAc and washed with water and brine. The organic layer was collected, dried over sodium sulfate and loaded onto silica gel. A flash column (5% MeOH in EtOAc) and reverse phase chromatography gave 7-(3-fluoro-4-(trifluoromethyl)phenyl)-4-(pyrimidin-2-ylmethyl)-3,4-dihydrobenzo[f][1,4]oxazepin-5(2H)-one.

MS found for $C_{21}H_{15}F_4N_3O_2$ as $(M+H)^+$ 418.13. $^1$H NMR (400 MHz, DMSO-$d_6$): δ: 8.78 (d, J=4.0 Hz, 2H), 8.09 (d, J=2.0 Hz, 1H), 7.91 (dd, J=2.4, 8.0 Hz, 1H), 7.85-7.80 (m, 2H), 7.70 (d, J=8.4 Hz, 1H), 7.41 (t, J=4.8 Hz, 1H), 7.17 (d, J=8.4 Hz, 1H), 4.98 (s, 2H), 4.55 (t, J=4.8 Hz, 2H), 3.79 (t, J=4.8 Hz, 2H).

Example 26

7-(4-(difluoromethyl)phenyl)-4-(pyrimidin-2-ylmethyl)-3,4-dihydrobenzo[f][1,4]oxazepin-5(2H)-one (Compound II-124)

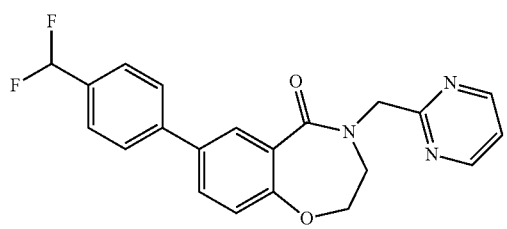 [SMILES: O=C1c2cc(-c3ccc(C(F)F)cc3)ccc2OCCN1Cc1ncccn1]

Compound II-124 was prepared according to Example 25 using 4-(difluoromethyl)phenylboronic acid. MS found for $C_{21}H_{17}F_2N_3O_2$ as $(M+H)^+$ 382.15. $^1$H NMR (400 MHz, DMSO-$d_6$): δ: 8.77 (d, J=4.8 Hz, 2H), 8.00 (d, J=2.4 Hz0, 1H), 7.84-7.77 (m, 4H), 7.63 (d, J=7.6 Hz, 2H), 7.40 (t, J=5.2 Hz, 1H), 7.15 (d, J=8.8 Hz, 1H), 7.06 (t, J=56.4 Hz, 1H), 4.98 (s, 2H), 4.52 (t, J=4.4 Hz, 2H), 3.77 (t, J=5.2 Hz, 2H).

Example 27

7-(4-cyclopentylphenyl)-4-(pyrimidin-2-ylmethyl)-3,4-dihydrobenzo[f][1,4]oxazepin-5(2H)-one (Compound II-120)

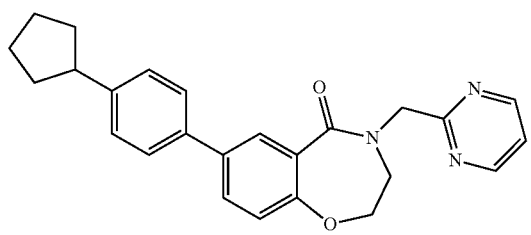 [SMILES: O=C1c2cc(-c3ccc(C4CCCC4)cc3)ccc2OCCN1Cc1ncccn1]

Compound II-120 was prepared according to Example 25 using 4-cyclopentylphenylboronic acid. MS found for $C_{25}H_{25}N_3O_2$ as $(M+H)^+$ 400.2. $^1$H NMR (400 MHz, DMSO-$d_6$): δ: 8.77 (d, J=4.8 Hz, 2H), 7.90 (d, J=2.4 Hz, 1H), 7.74 (dd, J=2.4, 8.8 Hz, 1H), 7.52 (d, J=8.4 Hz, 2H), 7.40 (t, J=4.8 Hz, 1H), 7.30 (d, J=8.0 Hz, 2H), 7.10 (d, J=8.8 Hz, 1H), 4.97 (s, 2H), 4.48 (t, J=4.4 Hz, 2H), 3.74 (t, J=5.2 Hz, 2H), 3.00-2.96 (m, 1H), 2.01-1.97 (m, 2H), 1.78-1.51 (m, 6H).

Example 28

7-(4-chloro-3-fluorophenyl)-4-(pyrimidin-2-ylmethyl)-3,4-dihydrobenzo[f][1,4]oxazepin-5(2H)-one (Compound II-131)

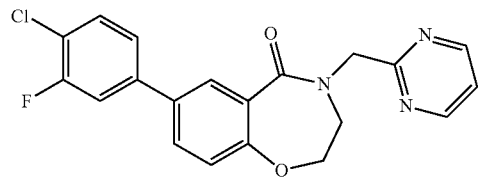 [SMILES: O=C1c2cc(-c3ccc(Cl)c(F)c3)ccc2OCCN1Cc1ncccn1]

Compound II-131 was prepared according to Example 25 using 4-chloro-3-fluorophenylboronic acid. MS found for C20H15ClFN3O2 as $(M+H)^+$ 384.09. $^1$H NMR (400 MHz, DMSO-$d_6$): δ: 8.78 (d, J=5.2 Hz, 2H), 7.99 (d, J=2.4 Hz0, 1H), 7.83 (dd, J=2.0-8.0 Hz, 1H), 7.72 (d, J=8.8 Hz, 1H), 7.62 (t, J=8.0 Hz, 1H), 7.51 (dd, J=1.2-8.4 Hz, 1H), 7.42 (t, J=4.8 Hz, 1H), 7.13 (d, J=8.0 Hz, 1H), 4.98 (s, 2H), 4.52 (t, J=4.8 Hz, 2H), 3.77 (t, J=4.8 Hz, 2H).

Example 29

7-(2-tert-butoxypyridin-4-yl)-4-(pyrimidin-2-ylmethyl)-3,4-dihydrobenzo[f][1,4]oxazepin-5(2H)-one (Compound VI-2)

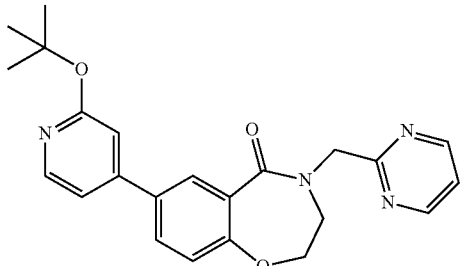

To a mixture of 4-promo-2-tert-butoxypyridine (1.0 g, 4.34 mmol), bis(pinacolato)diboron (1.32 g, 5.22 mmol), potassium acetate (1.28 g, 13.0 mmol), [1,1'-bis(diphenylphosphino)ferrocene]dichloropalladium methylene choloride complex (310 mg, 0.43 mmol) was suspended with degassed dioxane (15 mL) and heated at 85° C. for 60 min. The reaction mixture was diluted with EtOAc, washed with water and brine, dried (MgS(O)$_4$), filtered and concentrated. The concentrate was purified by flash chromatography on silica gel eluding with 33% percent ethyl acetate/hexanes to afford the compound 2-tert-butoxy-4-(4,4,5,5-tetramethyl-1,3,2-dioxaborolan-2-yl)pyridine.

Similar procedure as in Example 25 was followed to obtain the title compound using 2-tert-butoxy-4-(4,4,5,5-tetramethyl-1,3,2-dioxaborolan-2-yl)pyridine that was previously prepared.

MS found for $C_{23}H_{24}N_4O_3$ as $(M+H)^+$ 405.13. $^1$H NMR (400 MHz, DMSO-d$_6$): δ: 8.77 (d, J=4.8 Hz, 2H), 8.14 (d, J=5.6 Hz, 1H), 8.03 (d, J=2.4 Hz, 1H), 7.88 (dd, J=2.4-8.4 Hz, 1H), 7.40 (t, J=4.8 Hz, 1H), 7.18 (d, J=5.6 Hz, 1H), 7.12 (d, J=8.4 Hz, 1H), 6.89 (s, 1H), 4.97 (s, 2H), 4.53 (t, J=4.8 Hz, 2H), 3.77 (t, J=4.4 Hz, 2H), 1.54 (s, 9H).

Example 30

7-(5-methylthiophen-2-yl)-4-(pyrimidin-2-ylmethyl)-3,4-dihydrobenzo[f][1,4]oxazepin-5(2H)-one (Compound VI-20)

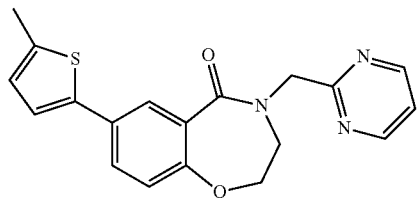 [SMILES: Cc1ccc(-c2ccc3c(c2)C(=O)N(Cc2ncccn2)CCO3)s1]

A mixture of 4-(pyrimidin-2-ylmethyl)-7-(4,4,5,5-tetramethyl-1,3,2-dioxaborolan-2-yl)-3,4-dihydrobenzo[f][1,4]oxazepin-5(2H)-one (50 mg, 0.13 mmol), 2-bromo-5-methylthiophene (28 mg, 0.156 mmol), cesium carbonate (128 mg, 0.39 mmol), 1,1'-Bis(diphenylphosphino)ferrocene]dichloropalladium (9 mg, 0.013 mmol) was dissolved in a degassed mixture of DMF and water 3/1.5 (4.5 ml). The mixture was heated in microwave at 85° C. for 40 min. The mixture was poured into EtOAc and washed with water and brine. The organic layer was collected, dried over sodium sulfate and loaded onto silica gel. A flash column (5% MeOH in EtOAc) and reverse phase chromatography gave 7-(5-methylthiophen-2-yl)-4-(pyrimidin-2-ylmethyl)-3,4-dihydrobenzo[f][1,4]oxazepin-5(2H)-one.

MS found for $C19H17N3O2S$ as $(M+H)^+$ 352.09. $^1$H NMR (400 MHz, DMSO-d$_6$): $^1$H-NMR (DMSO) δ: 8.70 (d, J=4.0 Hz, 2H), 7.80 (d, J=2.0 Hz, 1H), 7.68 (dd, J=2.0-8.4 Hz, 1H), 7.40 (t, J=4.8 Hz, 1H), 7.23 (d, J=3.2 Hz, 1H), 7.05 (d, J=8.4 Hz, 1H), 6.77 (d, J=2.8 Hz, 1H), 4.95 (s, 2H), 4.46 (t, J=4.8 Hz, 2H), 3.73 (t, J=4.8 Hz, 2H), 2.48 (s, 3H).

Example 31

1-(4-(5-oxo-4-(pyrimidin-2-ylmethyl)-2,3,4,5-tetrahydrobenzo[f][1,4]oxazepin-7-yl)phenyl)cyclopentanecarbonitrile (Compound II-122)

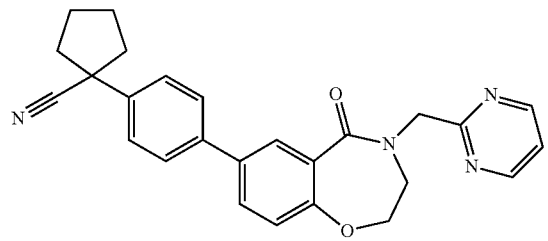 [SMILES: N#CC1(c2ccc(-c3ccc4c(c3)C(=O)N(Cc3ncccn3)CCO4)cc2)CCCC1]

To a solution of 2-(4-bromophenyl)acetonitrile (1.0 g, 5.10 mmol) and 1,4-dibromobutane (0.67 ml, 5.6 mmol) in THF (10 ml) was added potassium bis(trimethylsilyl) amide (2.23 g, 11.2 mmol) and tetra-n-butylammonium bromide (164 mg, 0.51 mmol). The mixture was stirred for 2 h and then quenched with 1N HCl. Ethyl acetate was added, the layers separated and the organic layer was washed with water and brine. Drying, solvent evaporation and flash chromatography (silica gel, 20% EtOAc/hexanes) gave 1-(4-bromophenyl)cyclopentanecarbonitrile.

Similar procedure as in Example 30 was followed to obtain the title compound using 1-(4-bromophenyl)cyclopentanecarbonitrile.

MS found for $C26H24N4O2$ as $(M+H)^+$ 425.21. $^1$H NMR (400 MHz, DMSO-d$_6$): $^1$H-NMR (DMSO) δ: 8.72 (d, J=4.0 Hz, 2H), 7.90 (d, J=2.4 Hz, 1H), 7.74 (dd, J=2.4-8.8 Hz, 1H), 7.63 (d, J=8.4 Hz, 2H), 7.50 (d, J=8.4 Hz, 2H), 7.35 (t, J=4.8 Hz, 1H), 7.08 (d, J=8.8 Hz, 1H), 4.92 (s, 2H), 4.45 (t, J=4.4 Hz, 2H), 3.71 (t, J=4.8 Hz, 2H), 2.37-2.34 (m, 2H), 2.05-2.02 (m, 2H), 1.85-1.83 (m, 4H).

Example 32

7-(4-ethoxyphenyl)-4-(pyrimidin-2-ylmethyl)-3,4-dihydrobenzo[f][1,4]oxazepin-5(2H)-one (Compound II-123)

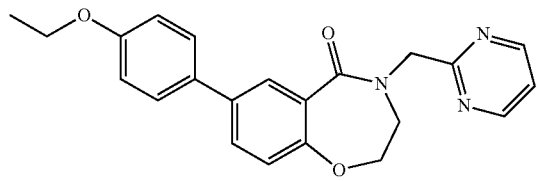 [SMILES: CCOc1ccc(-c2ccc3c(c2)C(=O)N(Cc2ncccn2)CCO3)cc1]

Compound II-123 was prepared according to Example 30 using 1-bromo-4-ethoxybenzene. MS found for $C22H21N3O3$ as $(M+H)^+$ 376.15. $^1$H NMR (400 MHz, DMSO-d$_6$): δ: 8.77 (d, J=5.2 Hz, 2H), 7.86 (d, J=2.4 Hz0, 1H), 7.71 (dd, J=2.8-8.4 Hz, 1H), 7.54 (d, J=8.8 Hz, 2H), 7.40 (t, J=4.8 Hz, 1H), 7.08 (d, J=8.0 Hz, 1H), 6.97 (d, J=8.4 Hz, 2H), 4.96 (s, 2H), 4.47 (t, J=4.8 Hz, 2H), 4.06-4.01 (m, 2H), 3.74 (t, J=4.4 Hz, 2H), 1.34-1.30 (m, 3H).

Example 33

7-(4-(difluoromethoxy)phenyl)-4-(pyrimidin-2-ylmethyl)-3,4-dihydrobenzo[f][1,4]oxazepin-5(2H)-one (Compound II-119)

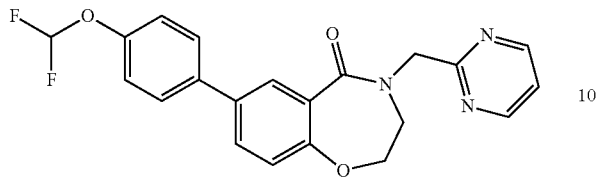

Compound II-119 was prepared according to Example 30 using 1-bromo-4-(difluoromethoxy)benzene. MS found for C21H17F2N3O3 as (M+H)+ 398.13. $^1$H NMR (400 MHz, DMSO-d$_6$): $^1$H-NMR (DMSO) δ: 8.77 (d, J=4.8 Hz, 2H), 7.92 (d, J=2.0 Hz0, 1H), 7.77 (dd, J=2.4-8.4 Hz, 1H), 7.68 (d, J=8.4 Hz, 2H), 7.40 (t, J=4.8 Hz, 1H), 7.26 (t, J=74.0 Hz, 2H), 7.23 (d, J=8.8 Hz, 1H), 7.12 (d, J=8.4 Hz, 1H), 4.97 (s, 2H), 4.50 (t, J=4.8 Hz, 2H), 3.75 (t, J=4.8 Hz, 2H).

Example 34

4-(4-fluorobenzyl)-7-(1-methyl-2-oxo-1,2-dihydropyridin-4-yl)-3,4-dihydrobenzo[f][1,4]oxazepin-5(2H)-one (Compound VI-22)

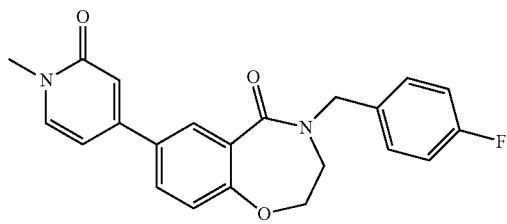 [SMILES: Cn1ccc(-c2ccc3c(c2)C(=O)N(Cc2ccc(F)cc2)CCO3)cc1=O]

Compound VI-22 was prepared according to Example 30 using 1-(chloromethyl)-4-fluorobenzene and 4-bromo-1-methylpyridin-2(1H)-one. MS found for C22H19FN2O3 as (M+H)+ 379.27 $^1$H NMR (400 MHz, DMSO-d$_6$): δ: 8.01 (d, J=2.4 Hz, 1H), 7.83 (dd, J=2.0-8.4 Hz, 1H), 7.75 (d, J=6.8 Hz, 1H), 7.42-7.38 (m, 2H), 7.17 (t, J=9.2 Hz, 2H), 7.10 (d, J=8.0 Hz, 1H), 6.63 (s, 1H), 6.56 (dd, J=2.0-7.2 Hz, 1H), 4.74 (s, 2H), 4.27 (t, J=4.8 Hz, 2H), 3.56 (t, J=4.8 Hz, 2H), 3.42 (s, 3H).

Example 35

7-(1-isopropyl-2-methyl-1H-imidazol-5-yl)-4-(pyrimidin-2-ylmethyl)-3,4-dihydrobenzo[f][1,4]oxazepin-5(2H)-one (Compound VI-23)

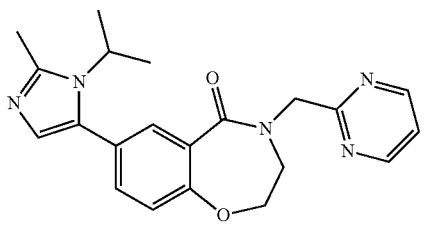 [SMILES: Cc1ncc(-c2ccc3c(c2)C(=O)N(Cc2ncccn2)CCO3)n1C(C)C]

Compound VI-23 was prepared according to Example 30 using 5-bromo-1-isopropyl-2-methyl-1H-imidazole. MS found for C21H23N5O2 as (M+H)+ 378.14 $^1$H NMR (400 MHz, DMSO-d$_6$): δ: 8.77 (d, J=4.8 Hz, 2H), 8.15 (s, 1H), 7.63 (d, J=2.0 Hz, 1H), 7.40 (t, J=4.8 Hz, 2H), 7.10 (d, J=8.0 Hz, 1H), 6.68 (s, 1H), 4.95 (s, 2H), 4.52 (t, J=4.8 Hz, 1H), 4.32-4.29 (s, 1H), 3.77 (t, J=4.8 Hz, 2H), 2.41 (s, 3H), 1.34 (d, J=6.8 Hz, 6H).

Example 36

7-(1-methyl-2-oxo-1,2-dihydropyridin-4-yl)-4-(pyrimidin-2-ylmethyl)-3,4-dihydrobenzo[f][1,4]oxazepin-5(2H)-one (Compound VI-13)

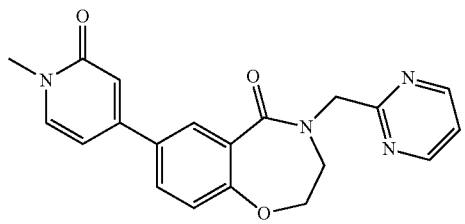 [SMILES: Cn1ccc(-c2ccc3c(c2)C(=O)N(Cc2ncccn2)CCO3)cc1=O]

A mixture of 7-(4,4,5,5-tetramethyl-1,3,2-dioxaborolan-2-yl)-3,4-dihydrobenzo[f][1,4]oxazepin-5(2H)-one (200 mg, 0.69 mmol), 4-bromo-1-methylpyridin-2(1H)-one (156 mg, 0.83 mmol), cesium carbonate (674 mg, 2.07 mmol), 1,1'-Bis(diphenylphosphino)ferrocene]dichloropalladium (49 mg, 0.069 mmol) was dissolved in a degassed mixture of DMF and water 3/1.5 (4.5 mL). The mixture was heated in microwave at 85° C. for 40 min. The mixture was poured into EtOAc and washed with water and brine. The organic layer was collected, dried over sodium sulfate and loaded onto silica gel. A flash column (5% MeOH in EtOAc) and reverse phase chromatography gave 7-(1-methyl-2-oxo-1,2-dihydropyridin-4-yl)-3,4-dihydrobenzo[f][1,4]oxazepin-5 (2H)-one.

7-(1-methyl-2-oxo-1,2-dihydropyridin-4-yl)-3,4-dihydrobenzo[f][1,4]oxazepin-5(2H)-one (50 mg, 0.185 mmol) was dissolved in DMF (3 mL) and cooled down in a ice/water bath and treated with sodium hydride (60% dispersion) (17 mg, 0.41 mmol) portion wise. After 10 min a solution of 2-(chloromethyl)pyrimidine hydrochloride (37 mg, 0.22 mmol) in DMF (2 mL) was added and the reaction mixture was warmed up to room temperature and quenched with 6 mL of water after it was complete. The reaction mixture was extracted with EtOAc and water and the organic phase was dried, evaporated and purified by silica gel chromatography (95% DCM/MeOH) and then purified by reverse phase chromatography to afford 7-(1-methyl-2-oxo-1,2-dihydropyridin-4-yl)-4-(pyrimidin-2-ylmethyl)-3,4-dihydrobenzo[f][1,4]oxazepin-5(2H)-one.

MS found for C20H18N4O3 as (M+H)+ 363.19. $^1$H NMR (400 MHz, DMSO-d$_6$) δ: 8.77 (d, J=5.2 Hz, 2H), 7.99 (d, J=2.8 Hz0, 1H), 7.83 (dd, J=2.4-8.4 Hz, 1H), 7.73 (d, J=7.2 Hz, 1H), 7.40 (t, J=5.2 Hz, 1H), 7.12 (d, J=8.8 Hz, 1H), 6.60 (d, J=1.6 Hz, 1H), 6.53 (dd, J=2.0-7.2 Hz, 1H), 4.97 (s, 2H), 4.54 (t, J=4.8 Hz, 2H), 3.77 (t, J=4.4 Hz, 2H), 3.42 (s, 3H).

Example 37

7-(1-methyl-2-oxo-1,2-dihydropyridin-4-yl)-4-(pyridin-2-ylmethyl)-3,4-dihydrobenzo[f][1,4]oxazepin-5(2H)-one (Compound VI-12)

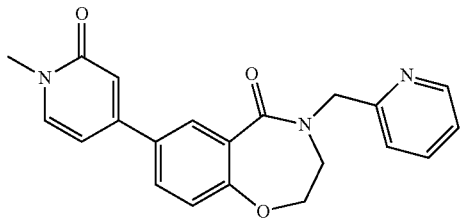 [SMILES: Cn1ccc(-c2ccc3c(c2)C(=O)N(Cc2ccccn2)CCO3)cc1=O]

Compound VI-12 was prepared according to Example 36 using 2-(chloromethyl)pyridine hydrochloride. MS found for C21H19N3O3 as (M+H)+ 362.18. ¹H NMR (400 MHz, DMSO-d₆): δ: 8.73 (s, 1H), 8.25 (s, 1H), 7.99 (s, 1H), 7.84-7.75 (m, 4H), 7.12 (d, J=8.0 Hz, 1H), 6.60-6.53 (m, 2H), 5.02 (s, 2H), 4.44 (s, 2H), 3.79 (s, 2H), 3.41 (s, 3H).

Example 38

7-(2-tert-butoxypyridin-4-yl)-4-(pyridin-2-ylmethyl)-3,4-dihydrobenzo[f][1,4]oxazepin-5(2H)-one (Compound VI-4)

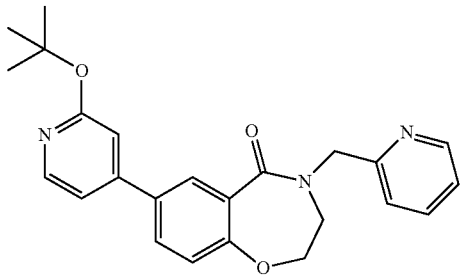

Compound VI-4 was prepared according to Example 36 using 7-bromo-3,4-dihydrobenzo[f][1,4]oxazepin-5(2H)-one, 2-tert-butoxy-4-(4,4,5,5-tetramethyl-1,3,2-dioxaborolan-2-yl)pyridine and 2-(chloromethyl)pyridine hydrochloride.

MS found for C24H25N3O3 as (M+H)+ 404.18. ¹H NMR (400 MHz, DMSO-d₆): δ: 8.52 (d, J=4.8 Hz, 1H), 8.15 (d, J=5.2 Hz, 1H), 8.03 (d, J=2.4 Hz, 1H), 7.87 (dd, J=2.0-8.0 Hz, 1H), 7.79-7.75 (m, 1H), 7.35 (d, J=8.0 Hz, 1H), 7.29 (dd, J=4.8-6.8 Hz, 1H), 7.21 (d, J=5.6 Hz, 1H), 7.12 (d, J=8.4 Hz, 1H), 6.91 (s, 1H), 4.85 (s, 2H), 4.39 (t, J=4.4 Hz, 2H), 3.69 (t, J=4.8 Hz, 2H), 1.54 (s, 9H).

Example 39

7-(2-oxo-1,2-dihydropyridin-4-yl)-4-(pyridin-2-ylmethyl)-3,4-dihydrobenzo[f][1,4]oxazepin-5(2H)-one (Compound VI-3)

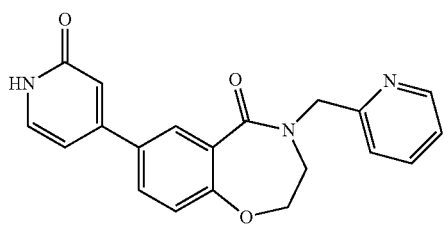 [SMILES: O=C1c2cc(-c3cc[nH]c(=O)c3)ccc2OCCN1Cc1ccccn1]

Compound VI-3 was generated after the acidic hydrolysis of Compound VI-4 with formic acid. MS found for C20H17N3O3 as (M+H)+ 348.13 ¹H NMR (400 MHz, DMSO-d₆): δ: 11.56 (s, 1H), 8.52 (d, J=4.8 Hz, 1H), 7.98 (d, J=2.4 Hz, 1H), 7.82-7.75 (m, 2H), 7.42 (d, J=6.8 Hz, 1H), 7.35 (d, J=7.6 Hz, 1H), 7.28 (dd, J=4.8-6.8 Hz, 1H), 7.11 (d, J=8.8 Hz, 1H), 6.53 (s, 1H), 6.47 (dd, J=1.6-6.4 Hz, 1H), 4.85 (s, 2H), 4.39 (t, J=4.4 Hz, 2H), 3.69 (t, J=4.4 Hz, 2H).

Example 40

4-(pyrimidin-2-ylmethyl)-7-(4-(trifluoromethoxy)phenyl)-3,4-dihydrobenzo[f][1,4]oxazepin-5(2H)-one (Compound II-73)

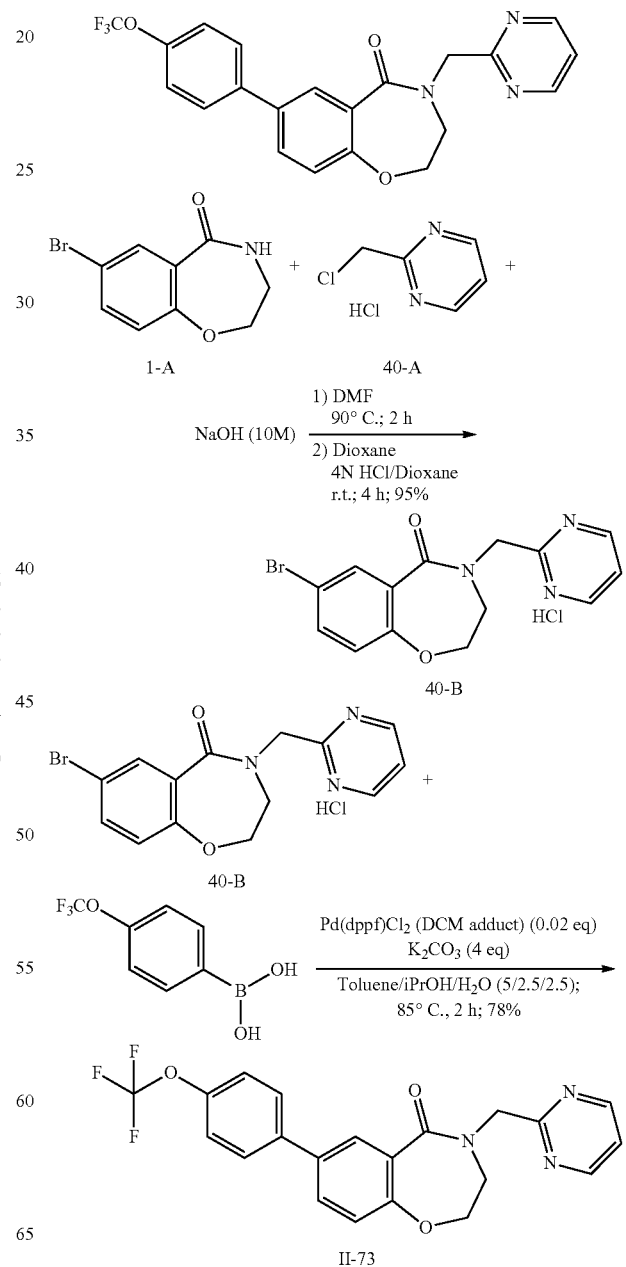

-continued

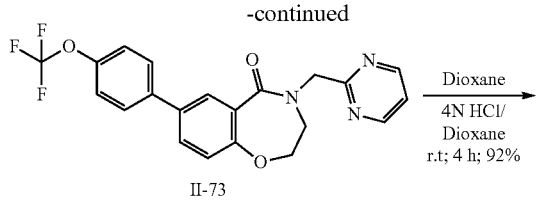

II-73

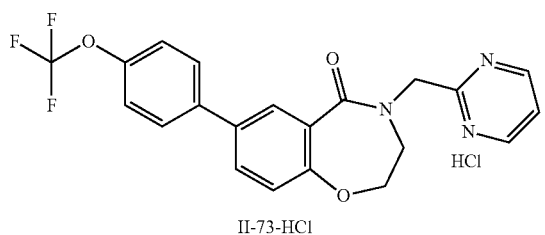

II-73-HCl

To a solution of Compound 1-A (20 g, 0.083 mol, 1 eq.) and Compound 40-A (25 g, 0.15 mol, 1.8 eq.) in DMF (150 mL), NaOH solution (20 mL, 10M, 5 eq.) was slowly added at room temperature (slightly exothermic) and stirred at r.t. for 10 min, followed by heating at 95° C. for 2 h. After cooling the reaction mixture, ethyl acetate (200 mL) was added and the organic layer was separated. The organics was washed with water (20 mL), brine, dried over sodium sulphate and concentrated.

The residue was dissolved in 1,4-dioxane (50 mL) and to this 4N HCl in dioxane (50 mL) and conc. HCl (2 mL) was added and stirred at room temperature for 4 h, filtered the precipitate, washed with ethyl acetate and dried. Compound 40-B obtained (30 g) was a light yellow solid.

To the bromide (15 g, 0.04 mol, 1 eq), boronic acid (12.5 g, 0.06 mol, 1.5 eq) and potassium carbonate (22 g, 0.16 mol, 4 eq) in a round bottom flask, solvent (150 mL, toluene/isopropano/water: 2/1/1) was added and stirred under nitrogen for 10 min. To the above solution the palladium catalyst (1 g, 0.012 mol, 0.02 eq) was added and heated at 85° C. for 2 h. The reaction mixture was diluted with ethyl acetate, separated the organic layer and filtered the organic layer through a plug of celite and silica gel and concentrated. Column purification on silica gel using ethyl acetate/hexane as eluent provided Compound II-73 (13 g).

To a solution of Compound II-73 (26 g) in 1,4-dioxane (25 mL), 4N HCl/dioxane (25 mL) was added followed by conc. HCl (2 mL) and stirred at room temperature for 4 h. Solvent was distilled off, dichloromethane was added and distilled off and to the residue, ethyl acetate (150 mL) was added and stirred at room temperature overnight and filtered the precipitate, washed with ethyl acetate, hexane and dried under vacuum. Compound II-73-HCl obtained (24.8 g) was a white solid.

$^1$H-NMR (CDCl$_3$) δ 8.72 (d, 2H, J=5.2 Hz), 8.17 (d, 1H, J=2.4 Hz), 7.59-7.63 (m, 3H), 7.26 (d, 2H, J=3.2 Hz), 7.22 (t, 1H, J=4.8 Hz), 7.10 (d, 1H, J=8.4 Hz), 5.10 (s, 2H), 4.56 (t, 2H, J=5.0 Hz), 3.77 (t, 2H, J=5.0 Hz); MS m/z 416.1 (M+H).

Example 41

7-(4-(trifluoromethyl)phenyl)-3,4-dihydrobenzo[f][1,4]oxazepin-5(2H)-one (Compound II-128)

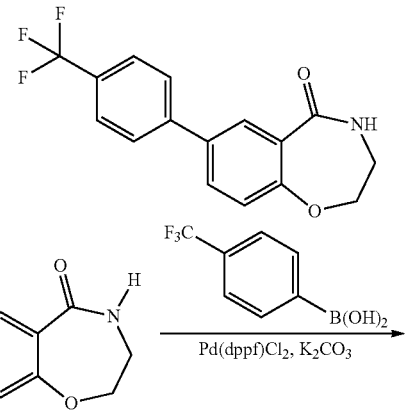

7-Bromo-3,4-dihydrobenzo[f][1,4]oxazepin-5(2H)-one (2.0 g), 4-trifluoromethoxyphenylboronic acid (2.2 g) and potassium carbonate (2.0 g) were combined in a mixture of toluene (20 mL), isopropanol (10 mL) and water (10 mL) and the resulting suspension was degassed with nitrogen. Palladium chloride dppf complex was added (0.42 g) and the reaction was heated overnight at 85° C. After cooling aqueous layer was discarded and the organic layer was diluted 2-fold with ethyl acetate, dried over MgS(O)$_4$ and concentrated. Recrystallization was conducted by dissolving in a minimum necessary amount of dichloromethane and crushing with excess hexane, resulting in 7-(4-(trifluoromethyl)phenyl)-3,4-dihydrobenzo[f][1,4]oxazepin-5(2H)-one as a grey solid (1.43 g).

$^1$H NMR: 8.42 (t, 1H); 8.12 (d, 1H); 7.86-7.76 (m, 5H); 7.13 (d, 1H); 4.38 (t, 2H); 3.37 (quartet, 2H).

Example 42

4-(imidazo[1,2-a]pyridin-2-ylmethyl)-7-(4-(trifluoromethyl)phenyl)-3,4-dihydrobenzo[f][1,4]oxazepin-5(2H)-one (Compound II-129)

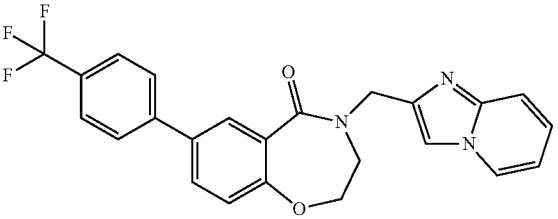

-continued

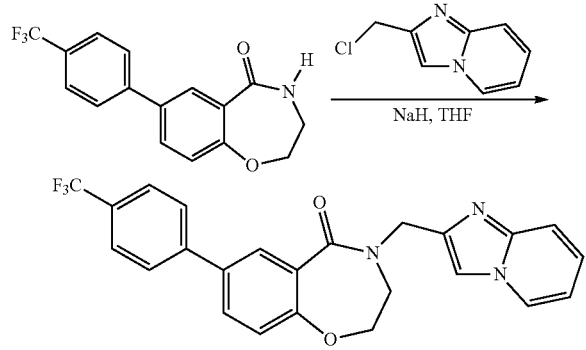

7-(4-(trifluoromethyl)phenyl)-3,4-dihydrobenzo[f][1,4]oxazepin-5(2H)-one (50 mg) was dissolved in dry THF and the NaH suspension (6 mg, 60% in oil) was added, followed shortly by 2-(chloromethyl)imidazo[1,2-a]pyridine (29 mg) and stirred overnight at room temperature. Worked up with ethyl acetate and pH 7 buffer organic layer dried over MgS(O)$_4$ and concentrated. Purification was conducted on normal phase (CH$_2$Cl$_2$/10% EtOH in ethyl acetate gradient) followed by reverse-phase (ACN/H$_2$O, 0.1% TFA). Resulting glassy solid was dissolved in dioxane, diluted 10-fold with 0.1N HCl and lyophilized resulting in 4-(imidazo[1,2-a]pyridin-2-ylmethyl)-7-(4-(trifluoromethyl)phenyl)-3,4-dihydrobenzo[f][1,4]oxazepin-5(2H)-one hydrochloride salt as a white solid (42.2 mg).

$^1$H NMR: 7.95 (s, 1H); 7.53 (d, 2H); 7.36 (m, 2H); 7.31 (d, 2H); 7.20 (d, 1H); 5.30 (s, 2H); 2.16 (s, 3H); $^{19}$F NMR: −58.36 (s); MS (ESI+): 391.0 (base peak, M+H$^+$); 803.2 (2M+Na$^+$).

Example 43

8-(4-(trifluoromethyl)phenyl)-3,4-dihydro-2H-benzo[b][1,4,5]oxathiazepin-sulfone (Compound IX-1)

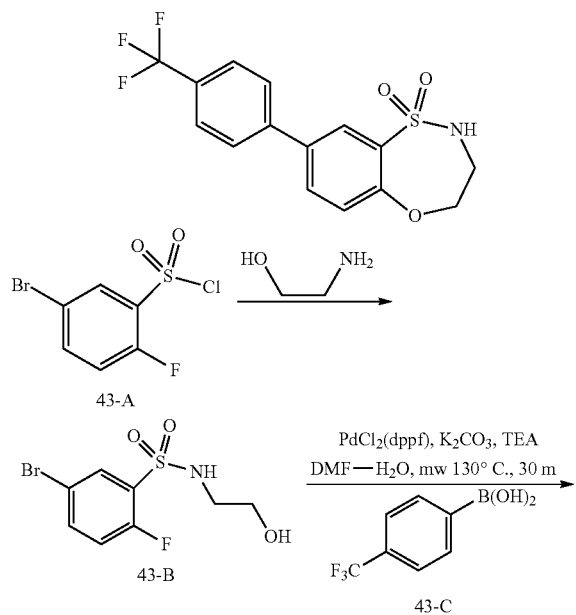

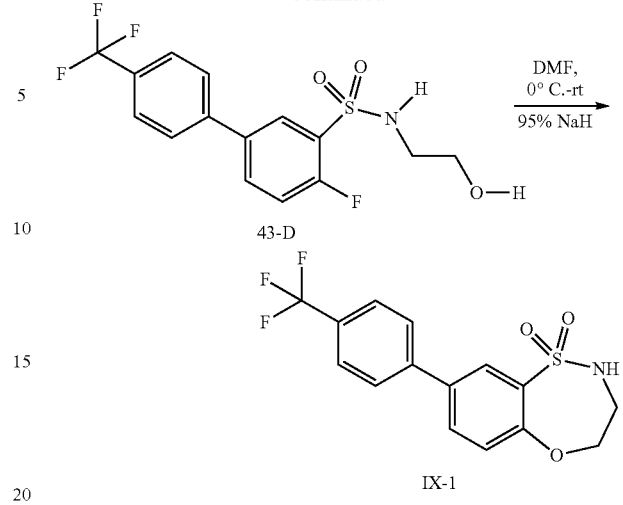

To a cooled (0° C.) solution of Compound 43-A (1.368 g, 5.0 mmol) in anhydrous THF (10 mL) was added dropwise 2-aminoethanol (1.833 g, 30.0 mmol) in THF (10 mL) with stir. After completion of addition, the reaction mixture was allowed to warm to room temperature overnight. The mixture was concentrated in vaccuo, taken up in EA-H$_2$O (100-50 mL), transferred to separation funnel, the aqueous layer was extracted with EA (50 mL×3), combined organic phase was washed with 0.1 N HCl (100 mL×2), dried, concentrated to give Compound 43-B (1.355 g). LCMS m/z 226.0 (M+H), 228.0 (M+H+2), anal HPLC>98%. It was used directly in the next step without further purification.

To a solution of Compound 43-B (920 mg, 3.11 mmol) and 4-trifluoromethylphenylboronic acid Compound 43-C (886 mg, 4.66 mmol) in DMF (6 mL) was added K$_2$CO$_3$ (1.932 g, 13.98 mmol), triethylamine (1 mL) and H$_2$O (1 mL). The reaction mixture was stirred for 5 min under an atmosphere of dry N$_2$. PdCl$_2$(dppf) (68 mg, 0.09 mmol) was added and the resulting mixture was heated at 130° C. for 30 min in a Biotage microwave. The reaction mixture was cooled, diluted with EtOAc (30 mL), filtered through a layer of celite, washed with 20% DMF in EtOAc (60 mL), combined filtrate concentrated in vaccuo. To the resulting slurry was added 1% MOH in CH$_2$Cl$_2$ (10 mL), filtered and the filtrate was subjected to Yamazen chromatography, eluting with a gradient of EtOAc in CH$_2$Cl$_2$ to afford the desired product Compound 43-D (823 mg, 2.26 mmol, 73%). LCMS m/z 364.1 (M+H), anal HPLC>92% in purity.

To a cooled (0° C.) solution of Compound 43-D (73 mg, 0.20 mmol) in anhydrous DMF (3 mL) was added 95% NaH (10 mg, 0.40 mmol) in 3 portions and the resulting mixture was allowed to warm to room temperature under an atmosphere of N$_2$ for 3 h. The reaction was quenched with solid NH$_4$Cl (159 mg, 3.0 mmol), then EtOAc-H$_2$O (30 mL and 10 mL) was added, transferred to a separation funnel. The aqueous layer was extracted with EtOAc (3×10 mL), combined organic phase dried (MgS(O)$_4$), concentrated. The crude mixture was subjected to Yamazen chromatography, eluting with a gradient of EtOAc in CH$_2$Cl$_2$ (0% to 25%) to afford Compound IX-1 (34 mg, 0.10 mmol, 50%).

LCMS m/z 344.0 (M+H), anal HPLC>96% in purity. $^1$H NMR (400 MHz; DMSO-d6) δ 7.97 (d, J=2.3 Hz, 1H); 7.93 (dd, J=8.3, 2.4 Hz, 1H); 7.90 (s, 1H); 7.85 (m, 4H); 7.35 (d, J=8.2 Hz, 1H); 4.14 (m, 2H); 3.47 (m, 2H). $^{19}$F NMR (400 MHz; DMSO-d6) δ −61.50 (s, 3F).

Example 44

2-((5-chloropyrimidin-2-yl)methyl)-8-(4-(trifluoromethyl)phenyl)-3,4-dihydro-2H-benzo[b][1,4,5]oxathiazepin-sulfone (Compound IX-3)

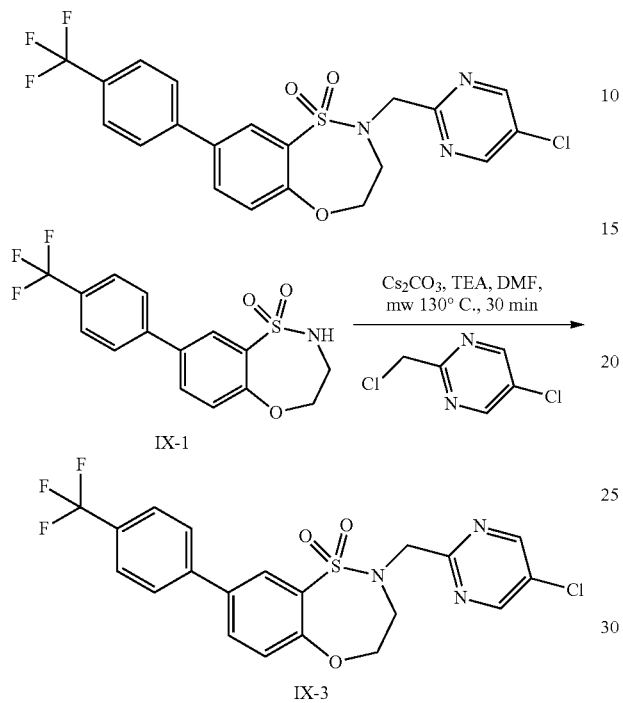

A mixture of chloromethyl-5-chloropyrimidine (82 mg, 0.50 mmol), Compound IX-1 (17 mg, 0.05 mmol), $K_2CO_3$ (169 mg, 1.22 mmol), triethylamine (0.5 mL) anhydrous DMF (3 mL) in a Biotage microwave vial was capped and irradiated at 130° C. for 30 min in a Biotage microwave. The reaction was cooled, taken up in EtOAc (30 mL), filtered through a silica gel plug and concentrated. The crude mixture was subjected to Gilson preparative HPLC, eluting with a gradient of ACN in $H_2O$ (5% to 95%) to afford Compound IX-3 (19 mg, 0.04 mmol, 80%).

LCMS m/z 470.0 (M+H), 472.0 (M+H+2), anal HPLC>98% in purity, $^1$H NMR (400 MHz; acetone-d6) 8.77 (s, 2H); 8.04 (d, J=2.3 Hz, 1H); 7.95 (m, 3H); 7.84 (d, J=8.4 Hz, 2H); 7.37 (d, J=8.4 Hz, 1H); 4.57 (s, 2H); 4.41 (m, 2H); 4.00 (m, 2H). $^{19}$F NMR (400 MHz; acetone-d6) −63.62 (s, 3F).

Example 45

8-(4-(trifluoromethoxy)phenyl)-3,4-dihydro-2H-benzo[b][1,4,5]oxathiazepin-sulfone (Compound IX-5)

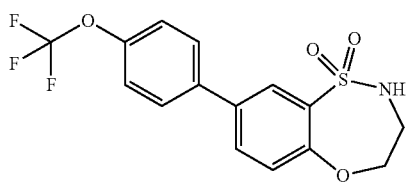 [SMILES: O=S1(=O)NCCOc2ccc(-c3ccc(OC(F)(F)F)cc3)cc21]

Compound IX-5 was prepared according to Example 44 using the appropriate starting materials [m/z 360.1, M+H].

Example 46

2-(2,2,2-trifluoroeth-1-yl)-8-(4-(trifluoromethyl)phenyl)-3,4-dihydro-2H-benzo[b][1,4,5]oxathiazepin-sulfone (Compound IX-4)

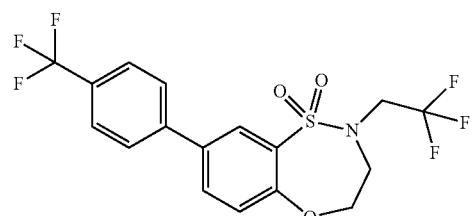

Compound IX-4 was prepared according to Example 44 using the appropriate starting materials [m/z 426.1, M+H].

Example 47

2-(2,2,2-trifluoroeth-1-yl)-8-(4-(trifluoromethoxy)phenyl)-3,4-dihydro-2H-benzo[b][1,4,5]oxathiazepin-sulfone (Compound IX-7)

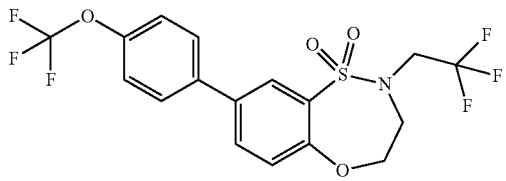 [SMILES: O=S1(=O)c2cc(-c3ccc(OC(F)(F)F)cc3)ccc2OCCN1CC(F)(F)F]

Compound IX-7 was prepared according to Example 44 using the appropriate starting materials.

Example 48

2-((pyrimidin-2-yl)methyl)-8-(4-(trifluoromethyl)phenyl)-3,4-dihydro-2H-benzo[b][1,4,5]oxathiazepin-sulfone (Compound IX-2)

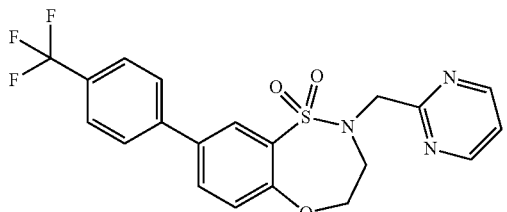

Compound IX-2 was prepared according to Example 44 using the appropriate starting materials [m/z 436.1, M+H].

Example 49

2-((pyrimidin-2-yl)methyl)-8-(4-(trifluoromethoxy)phenyl)-3,4-dihydro-2H-benzo[b][1,4,5]oxathiazepin-sulfone (Compound IX-6)

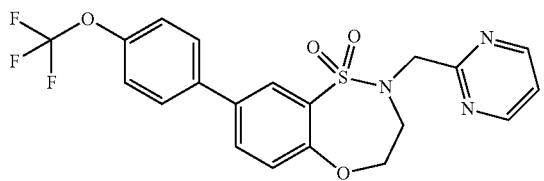 [SMILES: O=S1(=O)c2cc(-c3ccc(OC(F)(F)F)cc3)ccc2OCCN1Cc1ncccn1]

Compound IX-6 was prepared according to Example 44 using the appropriate starting materials.

Example 50

2-((5-cyclobutyl-1,3,4-oxadiazol-2-yl)methyl)-8-(4-(trifluoromethoxy)phenyl)-3,4-dihydro-2H-benzo[b][1,4,5]oxathiazepin-sulfone (Compound IX-8)

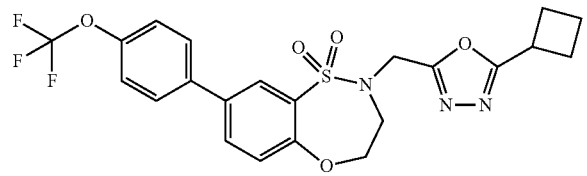 [SMILES: O=S1(=O)c2cc(-c3ccc(OC(F)(F)F)cc3)ccc2OCCN1Cc1nnc(C2CCC2)o1]

Compound IX-8 was prepared according to Example 44 using the appropriate starting materials.

Example 51

2-(cyclopropylmethyl)-8-(4-(trifluoromethyl)phenyl)-3,4-dihydro-2H-benzo[b][1,4,5]oxathiazepin-sulfone (Compound IX-9)

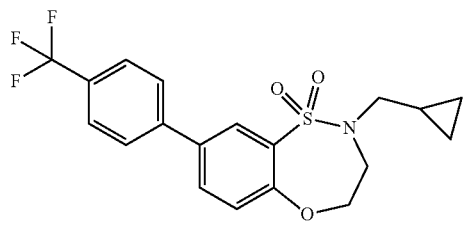 [SMILES: O=S1(=O)c2cc(-c3ccc(C(F)(F)F)cc3)ccc2OCCN1CC1CC1]

Compound IX-9 was prepared according to Example 44 using the appropriate starting materials.

Example 52

2-(2-methoxyeth-1-yl)-8-(4-(trifluoromethyl)phenyl)-3,4-dihydro-2H-benzo[b][1,4,5]oxathiazepin-sulfone (Compound IX-10)

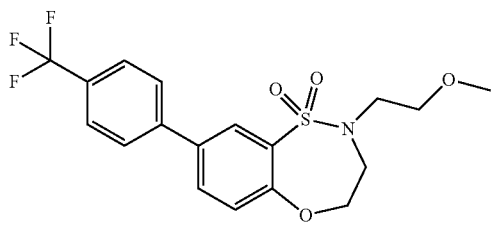 [SMILES: COCCN1CCOc2ccc(-c3ccc(C(F)(F)F)cc3)cc2S1(=O)=O]

Compound IX-10 was prepared according to Example 44 using the appropriate starting materials [m/z 402.1, M+H].

Example 53

4-((5-cyclobutyl-1,3,4-oxadiazol-2-yl)methyl)-7-(4-(trifluoromethoxy)phenyl)-3,4-dihydrobenzo[f][1,4]oxazepin-5(2H)-one (Compound II-4)

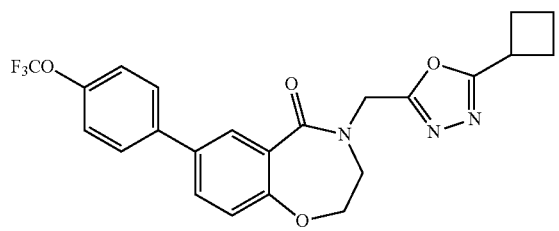 [SMILES: O=C1c2cc(-c3ccc(OC(F)(F)F)cc3)ccc2OCCN1Cc1nnc(C2CCC2)o1]

Compound II-4 was prepared according to the Examples disclosed herein using the appropriate starting materials. $^1$H-NMR (CD$_3$OD) δ 8.01 (d, 1H, J=2.0 Hz), 7.78 (dd, 1H, J=8.8, 2.4 Hz), 7.71 (d, 2H, J=8.4 Hz), 7.35 (d, 2H, J=8.0 Hz), 7.16 (d, 1H, J=8.8 Hz), 5.07 (s, 2H), 4.49 (t, 2H, J=5.0 Hz), 3.75-3.83 (m, 3H), 2.41-2.47 (m, 4H), 2.00-2.21 (m, 2H); MS m/z 460.1 (M+H).

Example 54

4-((3-methylpyridin-2-yl)methyl)-7-(4-(trifluoromethoxy)phenyl)-3,4-dihydrobenzo[f][1,4]oxazepin-5(2H)-one (Compound II-75)

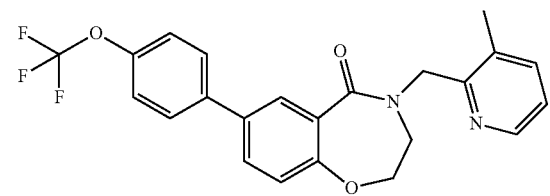 [SMILES: Cc1cccnc1CN1CCOc2ccc(-c3ccc(OC(F)(F)F)cc3)cc2C1=O]

Compound II-75 was prepared according to the Examples disclosed herein using the appropriate starting materials. $^1$H-NMR (CD$_3$OD) δ 8.35 (d, 1H, J=4.8 Hz), 8.00 (d, 1H, J=2.4 Hz), 7.70-7.77 (m, 3H), 7.66 (d, 1H, J=7.6 Hz), 7.35

(d, 1H, J=8.0 Hz), 7.26-7.29 (m, 2H), 7.13 (d, 1H, J=8.0 Hz), 5.01 (s, 2H), 4.25 (t, 2H, J=5.2 Hz), 3.68 (t, 2H, J=5.2 Hz), 2.43 (s, 3H); MS m/z 429.1 (M+H).

Example 55

7-(2-fluoro-4-(trifluoromethyl)phenyl)-4-(pyrimidin-2-ylmethyl)-3,4-dihydrobenzo[f][1,4]oxazepin-5(2H)-one (Compound II-105)

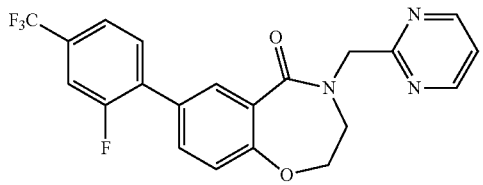 [SMILES: O=C1c2cc(-c3ccc(C(F)(F)F)cc3F)ccc2OCCN1Cc1ncccn1]

Compound II-105 was prepared according to the Examples disclosed herein using the appropriate starting materials. $^1$H-NMR (CD$_3$OD) δ 8.76 (d, 2H, J=4.8 Hz), 8.02 (s, 1H), 7.71-7.75 (m, 2H), 7.54-7.59 (m, 2H), 7.38 (t, 1H, J=4.8 Hz), 7.18 (d, 1H, J=8.4 Hz), 5.07 (s, 2H), 4.62 (t, 2H, J=4.8 Hz), 3.86 (t, 2H, J=4.8 Hz); MS m/z 418.1 (M+H).

Example 56

7-(2-chloro-4-(trifluoromethyl)phenyl)-4-(pyrimidin-2-ylmethyl)-3,4-dihydrobenzo[f][1,4]oxazepin-5(2H)-one (Compound II-110)

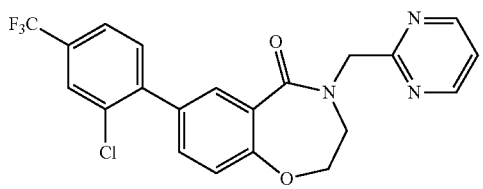 [SMILES: O=C1c2cc(-c3ccc(C(F)(F)F)cc3Cl)ccc2OCCN1Cc1ncccn1]

Compound II-110 was prepared according to the Examples disclosed herein using the appropriate starting materials. $^1$H-NMR (CD$_3$OD) δ 8.76 (d, 2H, J=4.8 Hz), 7.88 (d, 1H, J=2.4 Hz), 7.82 (s, 1H), 7.69 (d, 1H, J=7.6 Hz), 7.60-7.63 (m, 2H), 7.38 (t, 1H, J=5.0 Hz), 7.17 (d, 1H, J=8.0 Hz), 5.07 (s, 2H), 4.62 (t, 2H, J=4.8 Hz), 3.86 (t, 2H, J=4.8 Hz); MS m/z 434.0 (M+H).

Example 57

7-(4-(trifluoromethoxy)phenyl)-4-((4-(trifluoromethyl)pyrimidin-2-yl)methyl)-3,4-dihydrobenzo[f][1,4]oxazepin-5(2H)-one (Compound II-113)

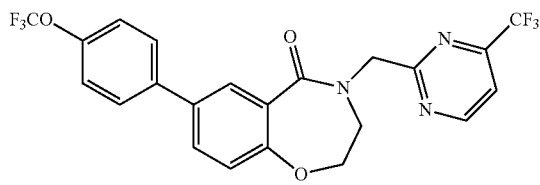 [SMILES: O=C1c2cc(-c3ccc(OC(F)(F)F)cc3)ccc2OCCN1Cc1nccc(C(F)(F)F)n1]

Compound II-113 was prepared according to the Examples disclosed herein using the appropriate starting materials. $^1$H-NMR (CD$_3$OD) δ 9.08 (d, 1H, J=5.2 Hz), 8.01 (d, 1H, J=2.0 Hz), 7.76-7.79 (m, 2H), 7.71 (d, 2H, J=9.2 Hz), 7.34 (d, 2H, J=8.0 Hz), 7.17 (d, 1H, J=8.4 Hz), 5.16 (s, 2H), 4.63 (t, 2H, J=5.0 Hz), 3.88 (t, 2H, J=4.8 Hz); MS m/z 484.1 (M+H).

Example 58

7-(4-(trifluoromethoxy)phenyl)-4-((3-(trifluoromethyl)pyridin-2-yl)methyl)-3,4-dihydrobenzo[f][1,4]oxazepin-5(2H)-one (Compound II-126)

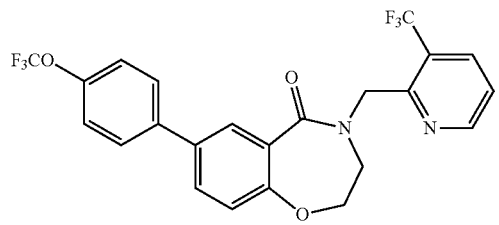 [SMILES: O=C1c2cc(-c3ccc(OC(F)(F)F)cc3)ccc2OCCN1Cc1ncccc1C(F)(F)F]

Compound II-126 was prepared according to the Examples disclosed herein using the appropriate starting materials. $^1$H-NMR (CD$_3$OD) δ 8.74 (d, 1H, J=5.2 Hz), 8.13 (d, 1H, J=7.6 Hz), 8.01 (d, 1H, J=6.4 Hz), 7.77 (dd, 1H, J=8.2, 2.2 Hz), 7.71 (d, 2H, J=8.4 Hz), 7.48 (dd, 1H, J=7.4, 5.0 Hz), 7.34 (d, 2H, J=8.4 Hz), 7.16 (d, 1H, J=8.8 Hz), 5.18 (s, 2H), 4.57 (t, 2H, J=4.8 Hz), 3.81 (t, 2H, J=5.2 Hz); MS m/z 483.1 (M+H).

Example 59

4-(oxazol-2-ylmethyl)-7-(4-(trifluoromethoxy)phenyl)-3,4-dihydrobenzo[f][1,4]oxazepin-5(2H)-one (Compound II-127)

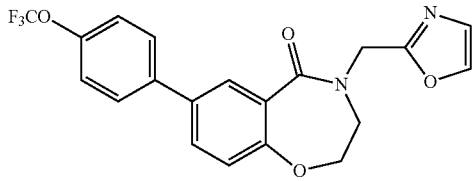 [SMILES: O=C1c2cc(-c3ccc(OC(F)(F)F)cc3)ccc2OCCN1Cc1ncco1]

Compound II-127 was prepared according to the Examples disclosed herein using the appropriate starting materials. $^1$H-NMR (CD$_3$OD) δ 8.00 (d, 1H, J=2.4 Hz), 7.92 (s, 1H), 7.77 (dd, 1H, J=8.6, 2.2 Hz), 7.72 (d, 2H, J=8.4 Hz), 7.35 (d, 2H, J=8.0 Hz), 7.14-7.17 (m, 2H), 4.99 (s, 2H), 4.44 (t, 2H, J=5.0 Hz), 3.78 (t, 2H, J=5.0 Hz); MS m/z 405.0 (M+H).

Example 60

4-(2-(benzyloxy)ethyl)-1-methyl-7-(4-(trifluoromethoxy)phenyl)-3,4-dihydro-1H-benzo[e][1,4]diazepine-2,5-dione (Compound X-7)

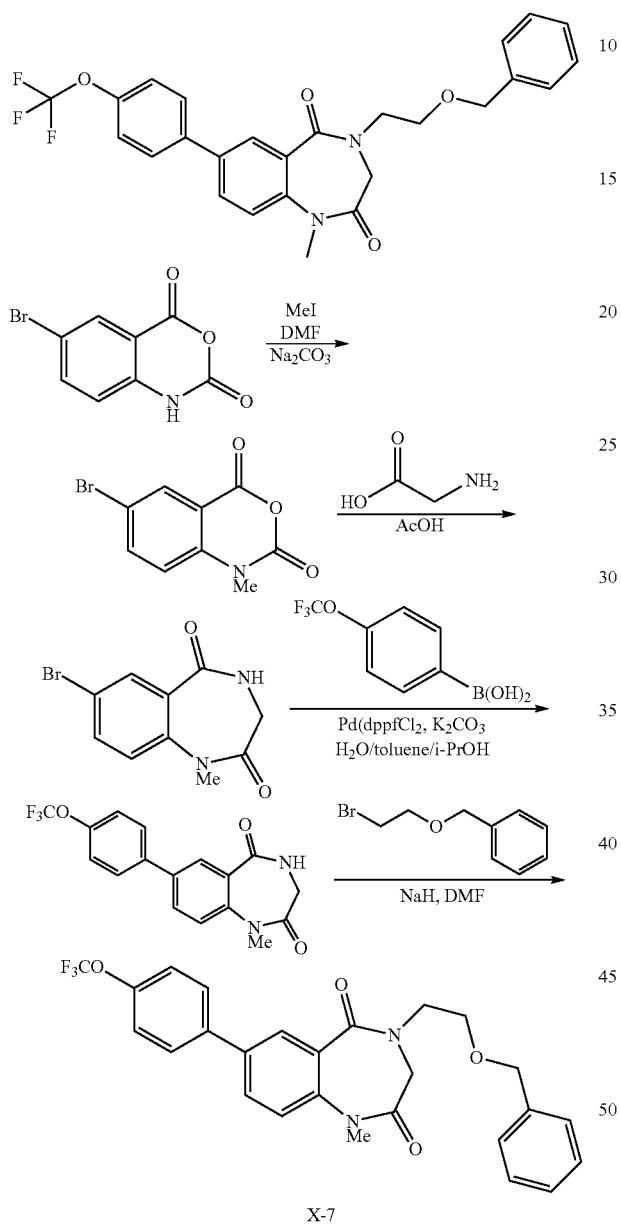

X-7

6-Bromo-1H-benzo[d][1,3]oxazine-2,4-dione (5.0 g, 20.66 mmol), iodomethane (1.94 mL, d=2.28, 4.4 g, 31.0 mmol, 1.5 equiv.) and Na$_2$CO$_3$ (4.38 g, 41.3 mmol, 2 equiv.) were placed in a round bottomed flask. To the flask were added DMF (40 mL) at ambient temperature. The mixture was stirred overnight at room temperature and then filtered through a glass filter. Obtained filtrate was diluted with water to form precipitates. The precipitates were dissolved in EtOAc and the solution was dried over MgS(O)4. The solvent was removed under reduced pressure. At this point, since the conversion was ~50%, K$_2$CO$_3$ (14.3 g, 103.3 mmol, 5 equiv.) and iodomethane (2.58 mL, d=2.28, 41.3 mmol, 2.0 equiv.) were added to the solution of the crude material in DMF. The mixture was heated at 30° C. so that the reaction can go to completion and then filtered through a glass filter. Obtained filtrate was diluted with water to form precipitates. Formed precipitates were filtered through a glass filter to give the desired product (6-bromo-1-methyl-1H-benzo[d][1,3]oxazine-2,4-dione). This was used for the subsequent step without further purification.

6-Bromo-1-methyl-1H-benzo[d][1,3]oxazine-2,4-dione (5.29 g, 20.66 mmol) and glycine (1.7 g, 22.73 mmol, 1.1 equiv.) were dissolved in AcOH (100 mL) in a round bottomed flask. The mixture was heated under reflux conditions for 2 hours. The mixture was purified by automated silica-gel column chromatography using EtOAc/hexane gradient as the eluent. The purification give the desired product (7-bromo-1-methyl-3,4-dihydro-1H-benzo[e][1,4]diazepine-2,5-dione, colorless powder, 446.7 mg).

7-Bromo-1-methyl-3,4-dihydro-1H-benzo[e][1,4]diazepine-2,5-dione (446.7 mg, 1.661 mmol), 4-trifluoromethoxyboronic acid (445.0 mg, 2.159 mmol, 1.3 equiv.) Pd(dppf)Cl$_2$·CH$_2$Cl$_2$ (120.0 mg, 0.166 mmol, 10 mol %) and K$_2$CO$_3$ (482.0 mg, 3.49 mmol, 2.1 equiv.) were dissolved in a mixed solvents, H$_2$O/toluene/i-PrOH (2.5 mL: 5 mL: 2.5 mL) in a 10 mL round bottomed flask under a nitrogen atmosphere. The mixture was heated at 60° C. for 64 h. The mixture was purified by automated silica-gel column chromatography using EtOAc/hexane gradient as the eluent. The purification give the desired product (1-methyl-7-(4-(trifluoromethoxy)phenyl)-3,4-dihydro-1H-benzo[e][1,4]diazepine-2,5-dione, 415.0 mg).

1-Methyl-7-(4-(trifluoromethoxy)phenyl)-3,4-dihydro-1H-benzo[e][1,4]diazepine-2,5-dione (50.0 mg, 0.143 mmol) and NaH (17 mg, 0.428 mmol, 3.0 equiv.) were placed in a 2-5 mL Smith process vial under a nitrogen atmosphere. To the vial was added DMF (5 mL) to observe hydrogen extlusion. And then ((2-bromoethoxy)methyl)benzene (45 μL, 0.285 mmol, d=0.135, 2 equiv.) was added at room temperature. After stirring for 50 min, the reaction was quenched with AcOH. Resulting mixture was directly injected to a preparative HPLC to give the desired product (4-(2-(benzyloxy)ethyl)-1-methyl-7-(4-(trifluoromethoxy)phenyl)-3,4-dihydro-1H-benzo[e][1,4]diazepine-2,5-dione, 42.7 mg) as a light yellow film.

LCMS (EI: 70 eV) 503 (M$^+$+Na), 486 (M$^+$+1).

Example 61

4-(pyrimidin-2-ylmethyl)-7-(4-(trifluoromethyl)phenyl)-3,4-dihydro-1H-benzo[e][1,4]diazepine-2,5-dione (Compound X-9)

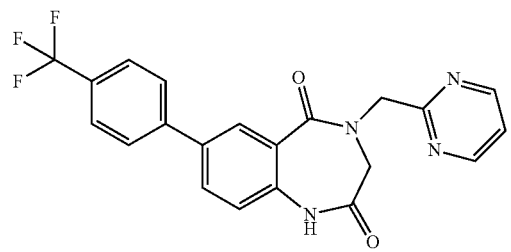

-continued

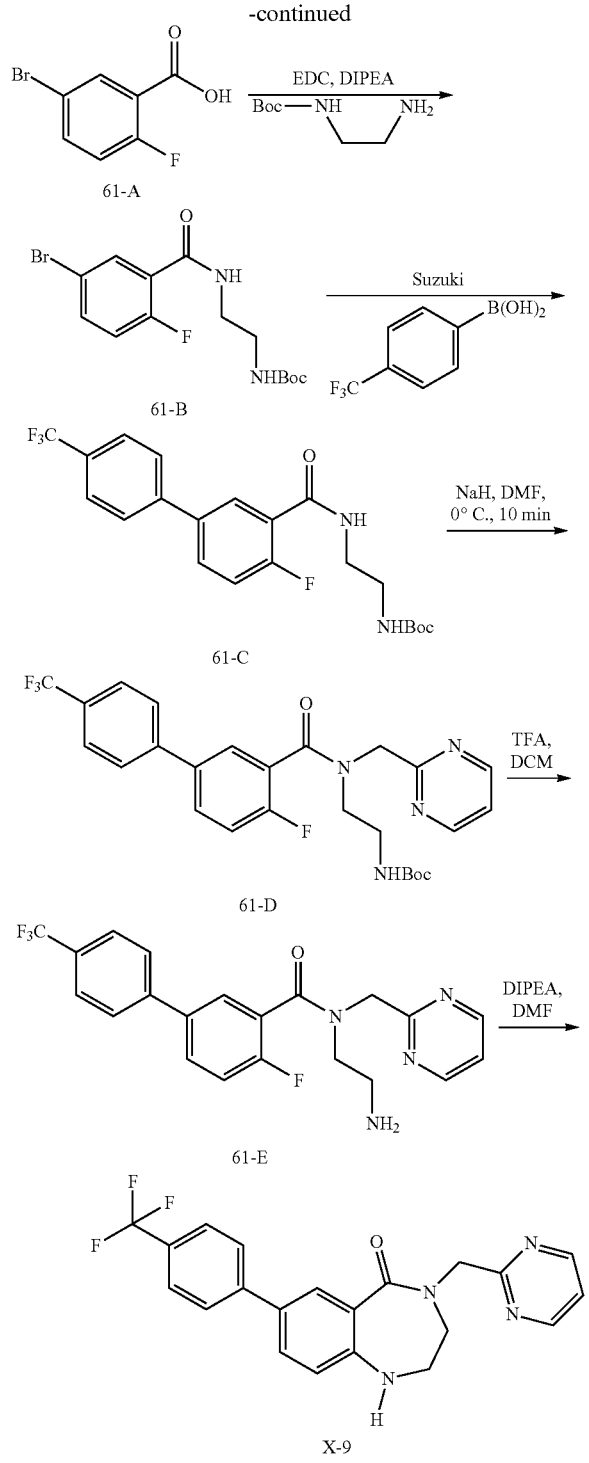

EaOAc/n-hexane to give compound 61-B (6.386 g, 17.67 mmol, 88%). LCMS m/z 362.0 (M+H), anal HPLC>90%. It was used directly in the next step without further purification.

Procedure to Compound 61-C Standard Suzuki coupling as described above, starting from compound 61-B (658 mg, 1.8 mmol), a pale yellow solid 61-D (610 mg, 1.4 mmol, 79%) was obtained using Yamazen chromatography eluting with EaOAc/n-hexane, LCMS m/z 327.1 (M-t-Butyl), 876.3 (2M+Na), it was used directly in the next step without further purification.

Procedure to Compound 61-D and 61-E To a anhydrous DMF (30 mL) solution of compound C (213 mg, 0.500 mmol) and chloromethyl pyrimidine HCl salt (248 mg, 1.50 mmol) was added slowly 95% NaH (65 mg, 2.7 mmol) and stirred 5 min. Another portion of 95% NaH (55 mg, 2.3 mmol) was added, stirred for 5 min. The crude mixture was quenched by 30% aqueous NH$_4$Cl (40 mL), extracted with EtOAc (3×100 mL), combined organic phase was washed with saturated NaHCO$_3$ (100 mL), brine (100 mL), dried, concentrated in vaccuo. Reverse-phase HPLC was used to obtain a yellow solid 61-D (75 mg, 0.14 mmol, 29%). LCMS m/z 519.2 (M+H). It was used directly in the next step without further purification.

To a solution of compound 61-D (70 mg, 0.13 mmol) in DCM (5.0 mL) was added TFA (2.0 mL) and stirred overnight. Then it was concentrated in vaccuo, only one single peak in LCMS as compound 61-E, m/z 419.1 (M+H), anal HPLC>95 in purity.

Procedure to compound X-9 To a anhydrous DMF solution (15 mL) of the above compound 61-E (54 mg, 0.13 mmol) was added Hunig's base (2 mL), capped in a Biotage microwave vial and subjected to microwave heating at 150° C. for 40 min. The reaction mixture was filtered, concentrated in vaccuo and subjected to Gilson preparative HPLC, eluting with a gradient of ACN in H$_2$O (5% to 95%) to afford X-9 (16 mg, 0.04 mmol, 31%). LCMS m/z 399.1 (M+H), anal HPLC>98% in purity.

Example 62

1-methyl-4-(pyrimidin-2-ylmethyl)-7-(4-(trifluoromethyl)phenyl)-3,4-dihydro-1H-benzo[e][1,4]diazepin-5(2H)-one (Compound X-10)

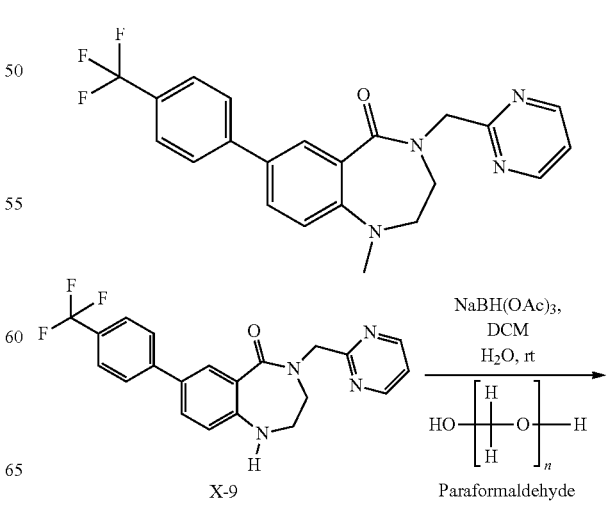

Procedure to 61-B To a mixture of compound 61-A (4.380 g, 20.0 mmol), N-Boc diamine (5.000 g, 31.2 mmol) and EDC (5.600 g, 38.74 mmol) in anhydrous CH$_2$Cl$_2$ (80 mL) was added dropwise Hunig's base (10 mL, 56.16 mmol) with stir. After completion of addition, the reaction mixture was concentrated in vaccuo, taken up in EA-H$_2$O (200-100 mL), transferred to separation funnel, the aqueous layer was extracted with EA (100 mL×3), combined organic phase was washed with 0.1 N HCl (100 mL×2), dried, concentrated, column chromatographed using Yamazen, eluting with

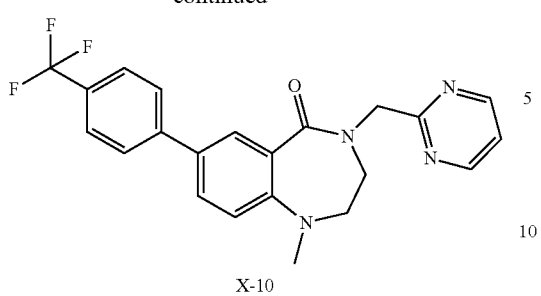

X-10

Procedure to compound X-10 To a anhydrous DCM solution (3 mL) of the compound X-9 (14 mg, 0.035 mmol) was added paraformaldehyde (0.5 mL) and H$_2$O (1 mL), stirred for 5 min, THF (1 mL) was added to help solubility. After 5 min, borohydride (63 mg, 0.31 mmol) was added, stirred for 30 min until the starting material disappeared in LCMS. The crude mixture was quenched by 30% aqueous NH$_4$Cl (10 mL), extracted with EtOAc (3×30 mL), combined organic phase was washed with saturated NaHCO$_3$ (30 mL), brine (30 mL), dried, concentrated in vaccuo. Reverse-phase HPLC was used to obtain a yellow solid X-10 (6 mg, 0.015 mmol, 42%). LCMS m/z 412.1 (M+H), anal HPLC>98%.

Example 63

4-((1-methyl-1H-imidazol-2-yl)methyl)-7-(4-(trif-luoromethoxy)phenyl)-3,4-dihydrobenzo[f][1,4]ox-azepin-5(2H)-one (Compound II-186)

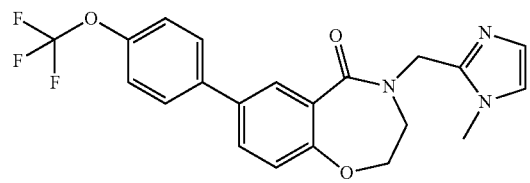

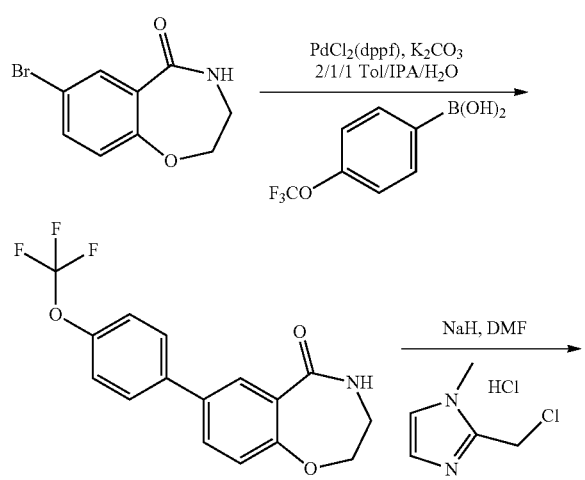

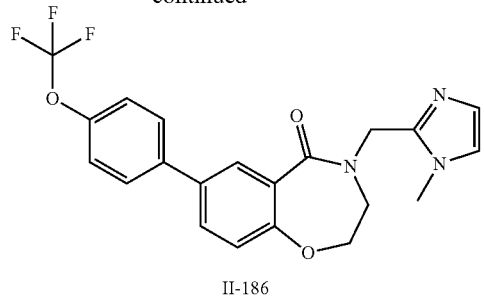

II-186

Compound II-186 was prepared according to the Examples disclosed herein using the appropriate starting materials. The Suzuki coupling was performed under standard conditioned explained in the other procedures using Pd(dppf)Cl$_2$.

Alkylation of the amide was performed using sodium hydride following the standard procedure to provide the final products.

Mass (M+H)$^+$ 418.1. $^1$H NMR (400 MHz; dmso-d$_6$) δ 7.93 (s, 1H); 7.75 (m, 3H); 7.58 (m, 2H); 7.42 (m, 2H); 4.86 (m, 2H); 4.18 (m, 2H); 3.75 (s, 3H); 3.65 (m, 2H). $^{19}$F NMR (400 MHz; DMSO-d6) δ −57.26 (s, 3F).

Example 64

4-(2-morpholinoethyl)-7-(4-(trifluoromethoxy)phe-nyl)-3,4-dihydrobenzo[f][1,4]oxazepin-5(2H)-one (Compound II-188)

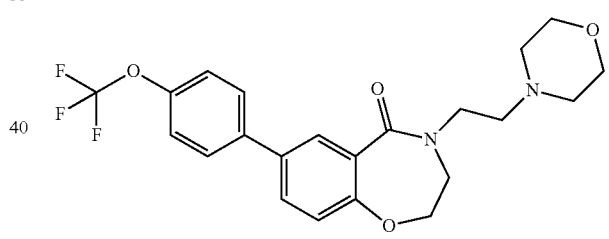

Compound II-188 was prepared according to the Examples disclosed herein using the appropriate starting materials. Mass (M+H)$^+$ 437.1.

Example 65

4-((5-methylpyrazin-2-yl)methyl)-7-(4-(trifluo-romethoxy)phenyl)-3,4-dihydrobenzo[f][1,4]oxaze-pin-5(2H)-one (Compound II-172)

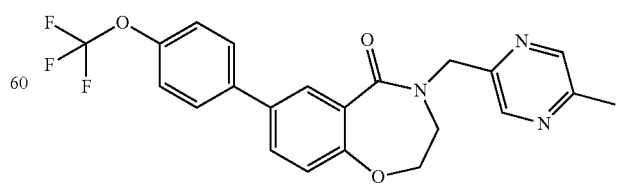

Compound II-172 was prepared according to the Examples disclosed herein using the appropriate starting materials. Mass (M+H)⁺ 430.1. ¹H NMR (400 MHz; DMSO-d6) δ 8.50 (m, 2H); 7.94 (s, 1H); 7.78 (m, 3H); 7.41 (d, J=8.5 Hz, 2H); 7.13 (d, J=8.1 Hz, 1H); 4.86 (s, 2H); 4.38 (m, 2H); 3.71 (m, 2H); 2.48 (s, 3H). ¹⁹F NMR (400 MHz; DMSO-d6) δ −57.26 (s, 3F).

Example 66

4-((6-methylpyrazin-2-yl)methyl)-7-(4-(trifluoromethoxy)phenyl)-3,4-dihydrobenzo[f][1,4]oxazepin-5(2H)-one (Compound II-175)

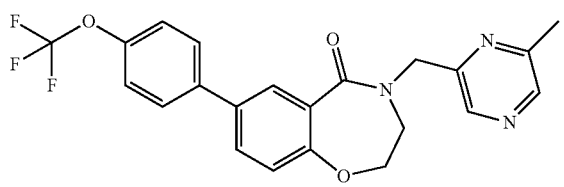 [SMILES: Cc1cncc(CN2CCOc3ccc(-c4ccc(OC(F)(F)F)cc4)cc3C2=O)n1]

Compound II-175 was prepared according to the Examples disclosed herein using the appropriate starting materials. Mass (M+H)⁺ 430.1 ¹H NMR (400 MHz; CD₃OD) δ 8.48 (s, 1H); 8.41 (s, 1H); 7.97 (s, 1H); 7.73 (m, 3H); 7.32 (d, J=8.6 Hz, 2H); 7.13 (d, J=8.6 Hz, 1H); 4.95 (s, 2H); 4.46 (m, 2H); 3.80 (m, 2H); 3.30 (s, 3H). ¹⁹F NMR (400 MHz; CD₃OD) δ −56.96 (s, 3F).

Example 67

4-((1-benzyl-1H-imidazol-2-yl)methyl)-7-(4-(trifluoromethoxy)phenyl)-3,4-dihydrobenzo[f][1,4]oxazepin-5(2H)-one (Compound II-187)

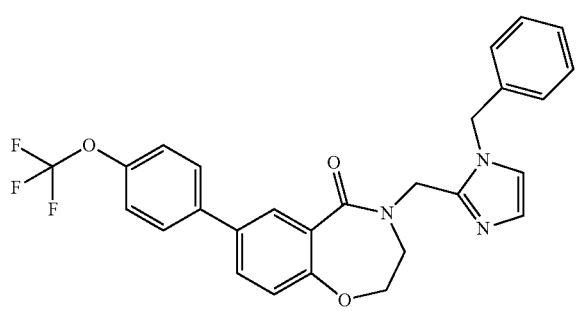 [SMILES: O=C1c2cc(-c3ccc(OC(F)(F)F)cc3)ccc2OCCN1Cc1nccn1Cc1ccccc1]

Compound II-187 was prepared according to the Examples disclosed herein using the appropriate starting materials. Mass (M+H)⁺ 494.1. ¹H NMR (400 MHz; dmso-d₆) δ 7.00-8.00 (m, 12H); 5.32 (s, 2H); 4.82 (s, 2H); 4.26 (m, 2H); 3.49 (m, 2H). ¹⁹F NMR (400 MHz; DMSO-d6) δ −57.25 (s, 3F).

Example 68

4-(imidazo[1,2-a]pyridin-2-ylmethyl)-7-(4-(trifluoromethoxy)phenyl)-3,4-dihydrobenzo[f][1,4]oxazepin-5(2H)-one (Compound II-189)

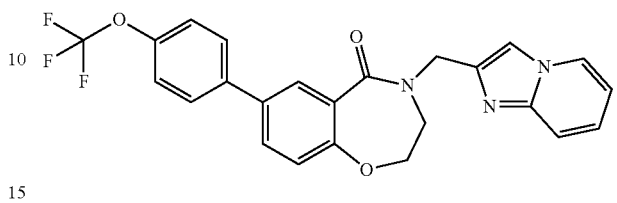

Compound II-189 was prepared according to the Examples disclosed herein using the appropriate starting materials. Mass (M+H)⁺ 454.1. ¹H NMR (400 MHz; dmso-d₆) δ 6.80-8.50 (m, 12H); 5.36 (s, 2H); 4.82 (m, 2H); 4.24 (m, 2H). ¹⁹F NMR (400 MHz; DMSO-d6) δ −57.38 (s, 3F).

Example 69 tert-butyl 2-(7-(4-(trifluoromethyl)phenyl)-2,3,4,5-tetrahydrobenzo[f][1,4]oxazepine-4-carbonyl)-5,6-dihydroimidazo[1,2-a]pyrazine-7(8H)-carboxylate (Compound III-40)

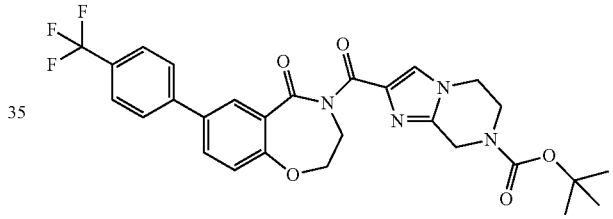

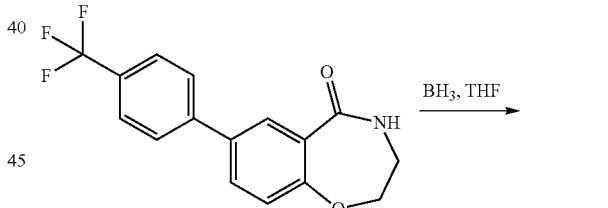

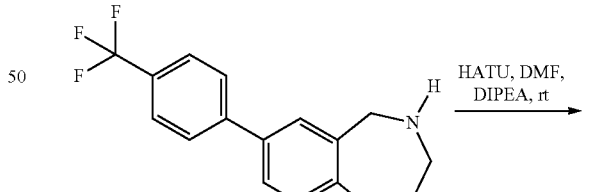

69-A

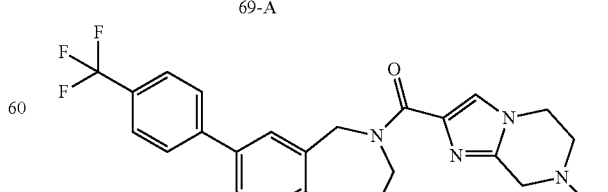

III-40

Decarboxylation of the amide was performed using 1M BH₃ in THF for 1-5 days following the standard procedure to provide amine 69-A. This was followed by a standard HATU catalyzed condensation reaction to afford Compound III-40. Mass (M+H)⁺ 543.2.

Example 70

(5,6,7,8-tetrahydroimidazo[1,2-a]pyrazin-2-yl)(7-(4-(trifluoromethyl)phenyl)-2,3-dihydrobenzo[f][1,4]oxazepin-4(5H)-yl)methanone (Compound III-42)

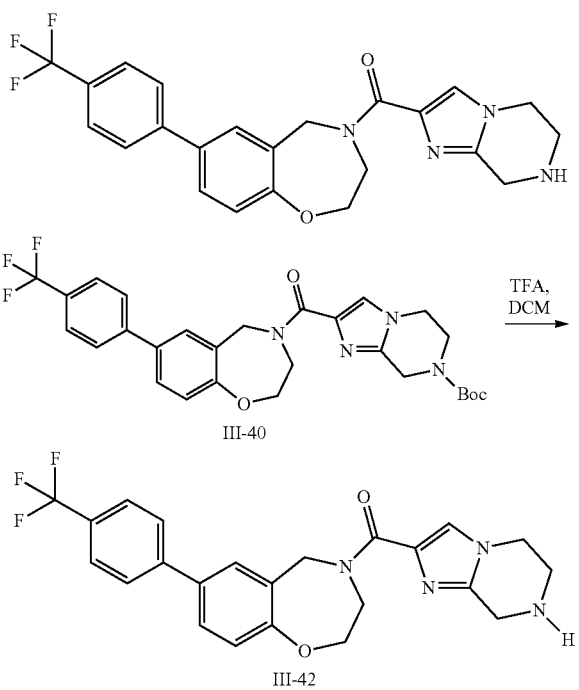

Compound III-40 was deprotected using TFA in dichloromethane in a standard procedure to give Compound III-42. Mass (M+H)⁺ 443.1.

Example 71

1-(2-(7-(4-(trifluoromethyl)phenyl)-2,3,4,5-tetrahydrobenzo[f][1,4]oxazepine-4-carbonyl)-5,6-dihydroimidazo[1,2-a]pyrazin-7(8H)-yl)ethanone (Compound III-48)

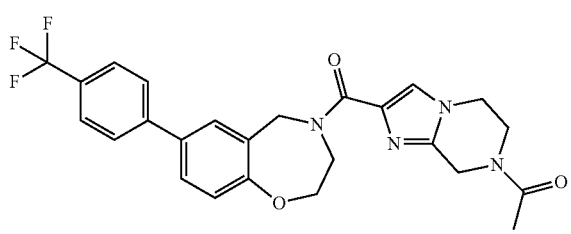

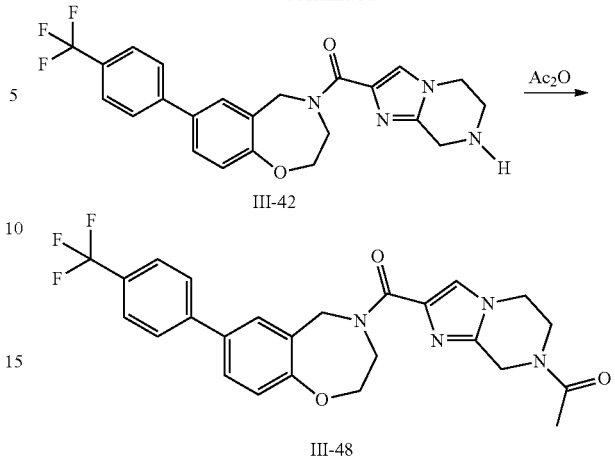

Standard acylation using acetic anhydride at room temperature of Compound III-42 afforded Compound III-48. Mass (M+H)⁺ 485.1.

Example 72

(1-methyl-1H-imidazol-5-yl)(7-(4-(trifluoromethyl)phenyl)-2,3-dihydrobenzo[f][1,4]oxazepin-4(5H)-yl)methanone (Compound III-32)

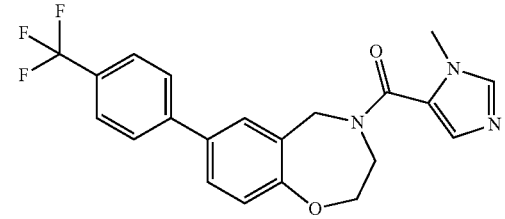 [SMILES: Cn1cncc1C(=O)N1CCOc2ccc(-c3ccc(C(F)(F)F)cc3)cc2C1]

Compound III-32 was prepared according to the Examples disclosed herein using the appropriate starting materials. Mass (M+H)⁺ 402.1.

Example 73

(1H-imidazol-2-yl)(7-(4-(trifluoromethyl)phenyl)-2,3-dihydrobenzo[f][1,4]oxazepin-4(5H)-yl)methanone (Compound III-33)

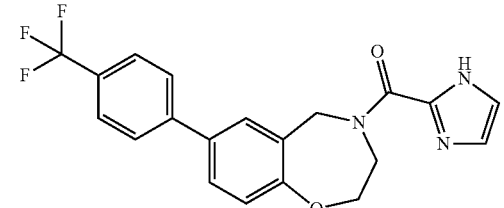

Compound III-33 was prepared according to the Examples disclosed herein using the appropriate starting materials. Mass (M+H)⁺ 388.1.

Example 74

(1-((1H-imidazol-1-yl)methyl)cyclopropyl)(7-(4-(trifluoromethyl)phenyl)-2,3-dihydrobenzo[f][1,4]oxazepin-4(5H)-yl)methanone (Compound III-34)

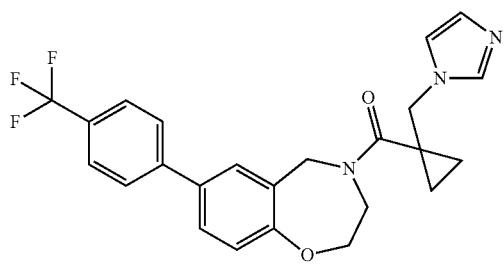 [SMILES: O=C(N1CCOc2ccc(-c3ccc(C(F)(F)F)cc3)cc2C1)C1(Cn2ccnc2)CC1]

Compound III-34 was prepared according to the Examples disclosed herein using the appropriate starting materials. Mass (M+H)+ 442.1.

Example 75

(1-methyl-1H-imidazol-2-yl)(7-(4-(trifluoromethyl)phenyl)-2,3-dihydrobenzo[f][1,4]oxazepin-4(5H)-yl)methanone (Compound III-37)

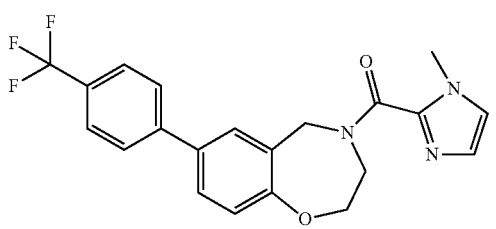 [SMILES: Cn1ccnc1C(=O)N1CCOc2ccc(-c3ccc(C(F)(F)F)cc3)cc2C1]

Compound III-37 was prepared according to the Examples disclosed herein using the appropriate starting materials. Mass (M+H)+ 402.1.

Example 76

(R)-tert-butyl 2-(7-(4-(trifluoromethyl)phenyl)-2,3,4,5-tetrahydrobenzo[f][1,4]oxazepine-4-carbonyl)pyrrolidine-1-carboxylate (Compound III-52)

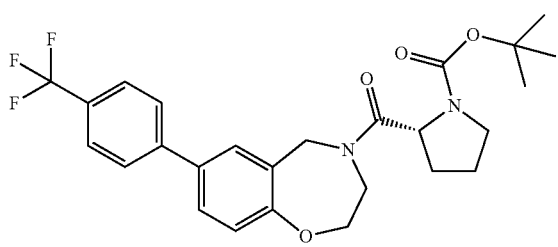 [SMILES: CC(C)(C)OC(=O)N1CCC[C@@H]1C(=O)N1CCOc2ccc(-c3ccc(C(F)(F)F)cc3)cc2C1]

Compound III-52 was prepared according to the Examples disclosed herein using the appropriate starting materials. Mass (M+H)+ 491.2.

Example 77

(1H-1,2,3-triazol-5-yl)(7-(4-(trifluoromethyl)phenyl)-2,3-dihydrobenzo[f][1,4]oxazepin-4(5H)-yl)methanone (Compound III-49)

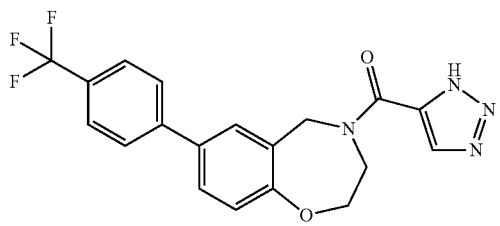 [SMILES: O=C(c1cnn[nH]1)N1CCOc2ccc(-c3ccc(C(F)(F)F)cc3)cc2C1]

Compound III-49 was prepared according to the Examples disclosed herein using the appropriate starting materials. Mass (M+H)+ 389.1.

Example 78

(1H-1,2,4-triazol-3-yl)(7-(4-(trifluoromethyl)phenyl)-2,3-dihydrobenzo[f][1,4]oxazepin-4(5H)-yl)methanone (Compound III-50)

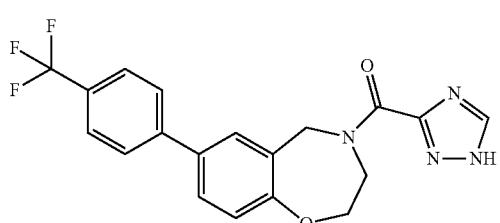

Compound III-50 was prepared according to the Examples disclosed herein using the appropriate starting materials. Mass (M+H)+ 389.1.

Example 79

(3-amino-1H-1,2,4-triazol-5-yl)(7-(4-(trifluoromethyl)phenyl)-2,3-dihydrobenzo[f][1,4]oxazepin-4(5H)-yl)methanone (Compound III-51)

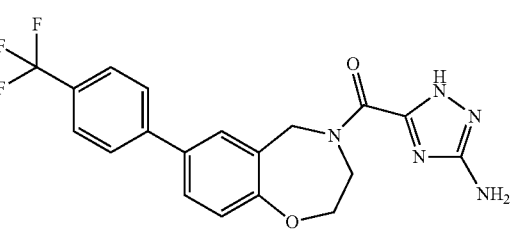

Compound III-51 was prepared according to the Examples disclosed herein using the appropriate starting materials. Mass (M+H)+ 404.1.

Example 80

(R)-pyrrolidin-2-yl(7-(4-(trifluoromethyl)phenyl)-2,3-dihydrobenzo[f][1,4]oxazepin-4(5H)-yl)methanone (Compound III-53)

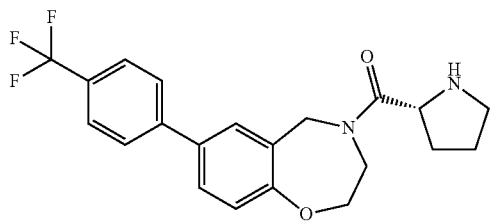 [SMILES: O=C([C@H]1CCCN1)N1CCOc2ccc(-c3ccc(C(F)(F)F)cc3)cc2C1]

Compound III-53 was prepared according to the Examples disclosed herein using the appropriate starting materials. Mass (M+H)⁺ 391.1.

Example 81

(1-phenyl-1H-1,2,3-triazol-5-yl)(7-(4-(trifluoromethyl)phenyl)-2,3-dihydrobenzo[f][1,4]oxazepin-4(5H)-yl)methanone (Compound III-54)

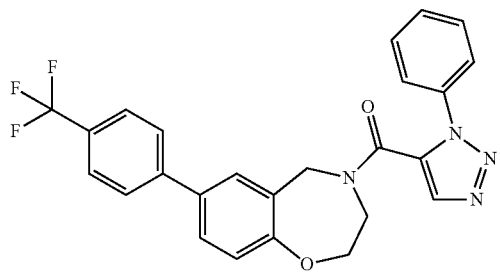 [SMILES: O=C(c1cnnn1-c1ccccc1)N1CCOc2ccc(-c3ccc(C(F)(F)F)cc3)cc2C1]

Compound III-54 was prepared according to the Examples disclosed herein using the appropriate starting materials.

Example 82

(R)-1-(2-(7-(4-(trifluoromethyl)phenyl)-2,3,4,5-tetrahydrobenzo[f][1,4]oxazepine-4-carbonyl)pyrrolidin-1-yl)ethanone (Compound III-55)

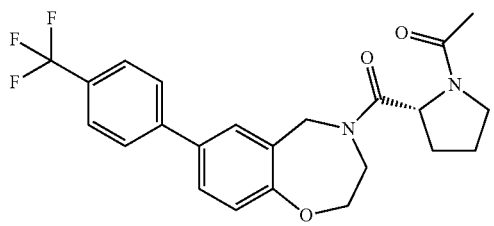 [SMILES: CC(=O)N1CCC[C@@H]1C(=O)N1CCOc2ccc(-c3ccc(C(F)(F)F)cc3)cc2C1]

Compound III-55 was prepared according to the Examples disclosed herein using the appropriate starting materials. Mass (M+H)⁺ 433.1.

Example 83

(1H-imidazol-2-yl)(7-(4-(trifluoromethoxy)phenyl)-2,3-dihydrobenzo[f][1,4]oxazepin-4(5H)-yl)methanone (Compound III-56)

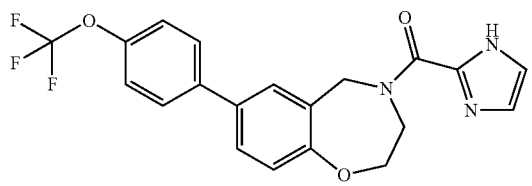 [SMILES: O=C(c1ncc[nH]1)N1CCOc2ccc(-c3ccc(OC(F)(F)F)cc3)cc2C1]

Compound III-56 was prepared according to the Examples disclosed herein using the appropriate starting materials. Mass (M+H)⁺ 404.1.

Example 84

(S)-4-benzyl-3-methyl-7-(4-(trifluoromethyl)phenyl)-3,4-dihydrobenzo[f][1,4]oxazepin-5(2H)-one (Compound II-132)

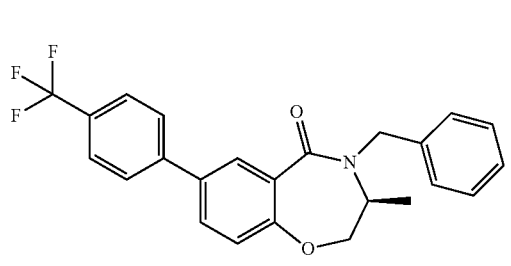

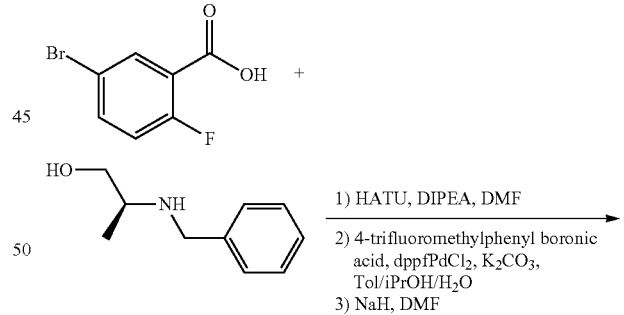

1) HATU, DIPEA, DMF
2) 4-trifluoromethylphenyl boronic acid, dppfPdCl₂, K₂CO₃, Tol/iPrOH/H₂O
3) NaH, DMF

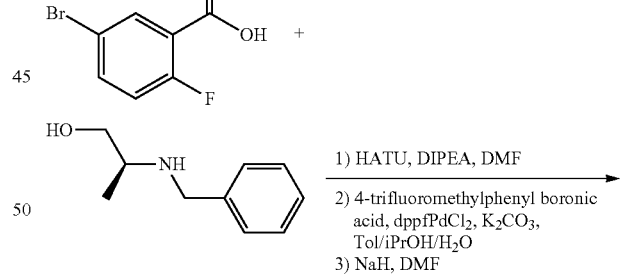

NBS, NMA, CHCl₃

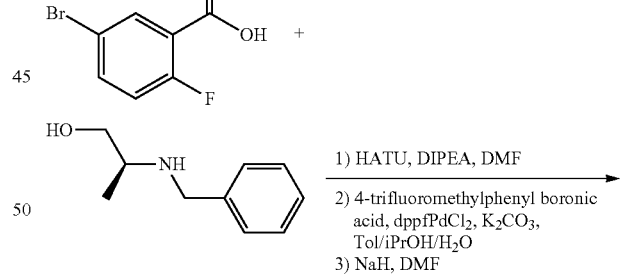

2-chloromethylpyrimidine
NaH, DMF

187
-continued

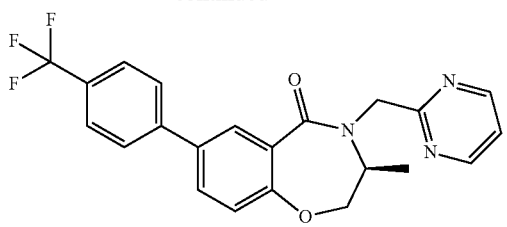

A solution of 5-bromo-2-fluorobenzoic acid (1 mmol), benzyl (S)-valinol (1 mmol), HATU (1 mmol) and diisopropylethylamine (3 mmol) in DMF (3 mL) was stirred at room temperature for 30 minutes. The reaction mixture was poured into a 1:1 solution of 1M HCl and brine and extracted with ethyl acetate. The organic layer was washed with saturated sodium bicarbonate solution and brine, dried and concentrated. The resided was taken up in a mixture of toluene, isopropanol and water (1 mL each) and added to a flask containing 4-trifluoromethylphenyl boronic acid (3 mmol), K$_2$CO$_3$ (3 mmol) and dppfPdCl$_2$ (40 mg) under nitrogen. The reaction mixture was stirred at 90° C. for 1 h. The organic layer was separated and concentrated before being purified by flash chromatography (rf=0.28 in 2:1 hexanes/ethyl acetate) to give a viscous oil. The product was dissolved in DMF (5 mL) and sodium hydride was added (5 mmol). The reaction mixture was stirred at room temperature for 40 minutes and was poured into a 1:1 solution of 1M HCl and brine and extracted with ethyl acetate. The organic layer was washed with saturated sodium bicarbonate solution and brine, dried and concentrated before being purified by flash chromatography (rf=0.59 in 2:1 hexanes/ethyl acetate) to give (S)-4-benzyl-3-methyl-7-(4-(trifluoromethyl)phenyl)-3,4-dihydrobenzo[f][1,4]oxazepin-5(2H)-one as an oil.

To a solution of the above product in chloroform was added NBS (2.5 equiv) and N-methylacetamide (10 mol %). The reaction was stirred for 18 hours at room temperature before being concentrated under vacuum. The residue was dissolved in ethyl acetate (10 mL) and 1M NaOH solution was added (10 mL). The mixture was stirred vigorously for 5 minutes and the organic layer was separated, washed with brine and concentrated. Flash chromatography (rf=0.10 in 2:1 hexanes/ethyl acetate) gave the debenzylated product.

To a solution of the above product (20 mg) and 2-chloromethylpyrimidine HCl salt (30 mg) in DMF was added sodium hydride (40 mg) and the reaction was stirred for 1 h at room temperature. The reaction mixture was quenched with 1M HCl and purified by preparative HPLC to give (S)-3-methyl-4-(pyrimidin-2-ylmethyl)-7-(4-(trifluoromethyl)phenyl)-3,4-dihydrobenzo[f][1,4]oxazepin-5(2H)-one TFA salt as a white powder.

188

Example 85

(2S,11aS)-2-amino-7-(4-(trifluoromethyl)phenyl)-2,3,11,11a-tetrahydrobenzo[f]pyrrolo[2,1-c][1,4]oxazepin-5(1H)-one (Compound II-51)

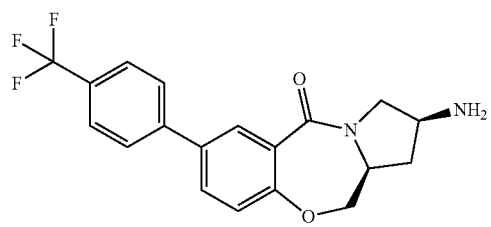 [SMILES: N[C@H]1C[C@H]2COc3ccc(-c4ccc(C(F)(F)F)cc4)cc3C(=O)N2C1]

Compound II-51 was prepared according to the Examples disclosed herein using the appropriate starting materials. C$_{19}$H$_{17}$F$_3$N$_2$O$_2$×TFA. 363.1 (M+1). $^1$H NMR (DMSO) δ 8.34 (d, J=2.8 Hz, 1H), 8.20 (br, 3H), 7.85 (m, 5H), 7.16 (d, J=8.4 Hz, 1H), 4.61 (d, J=12.0 Hz, 1H), 4.16 (m, 2H), 3.96 (m, 1H), 3.83 (br, 1H), 3.58 (m, 1H), 2.54 (m, 1H), 1.80 (m, 1H). $^{19}$F NMR (DMSO) δ −61.4 (s, 3F).

Example 86

(R)-2-(pyrimidin-2-ylmethyl)-8-(4-(trifluoromethyl)phenyl)-3,4,12,12a-tetrahydro-1H-benzo[f]pyrazino[2,1-c][1,4]oxazepin-6(2H)-one (Compound II-8)

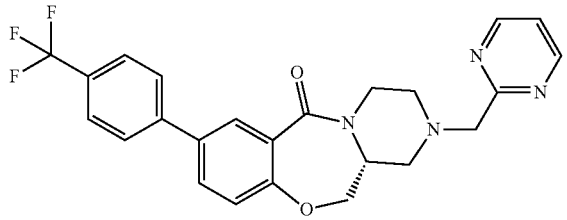 [SMILES: O=C1c2cc(-c3ccc(C(F)(F)F)cc3)ccc2OC[C@H]2CN(Cc3ncccn3)CCN12]

Compound II-8 was prepared according to the Examples disclosed herein using the appropriate starting materials. C$_{24}$H$_{21}$F$_3$N$_4$O$_2$×2-TFA. 455.1 (M+1).

Example 87

(S)-2-(pyrimidin-2-ylmethyl)-8-(4-(trifluoromethyl)phenyl)-3,4,12,12a-tetrahydro-1H-benzo[f]pyrazino[2,1-c][1,4]oxazepin-6(2H)-one (Compound II-9)

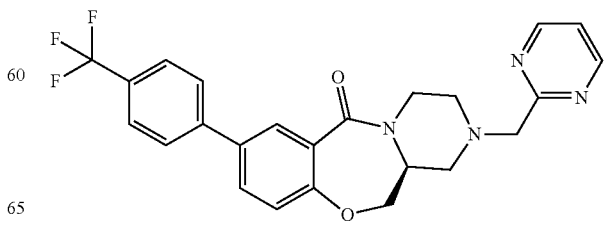

Compound II-9 was prepared according to the Examples disclosed herein using the appropriate starting materials. $C_{24}H_{21}F_3N_4O_2 \times 2$-TFA. 455.1 (M+1).

Example 88

(S)-3-methyl-4-(pyrimidin-2-ylmethyl)-7-(4-(trifluoromethyl)phenyl)-3,4-dihydrobenzo[f][1,4]oxazepin-5(2H)-one (Compound II-12)

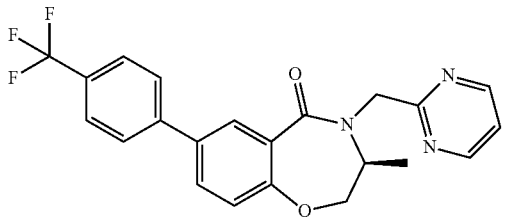 [SMILES: C[C@H]1COc2ccc(-c3ccc(C(F)(F)F)cc3)cc2C(=O)N1Cc1ncccn1]

Compound II-12 was prepared according to the Examples disclosed herein using the appropriate starting materials. $C_{22}H_{18}F_3N_3O_2 \times$TFA. 414.1 (M+1). $^1$H NMR (DMSO) δ 8.77 (d, J=5.2 Hz, 2H), 8.38 (d, J=2.4 Hz, 1H), 7.85 (m, 5H), 7.40 (t, J=5.0 Hz, 1H), 7.20 (d, J=8.4 Hz, 1H), 5.10 (J=17.0 Hz, 1H), 4.79 (d, J=17.0 Hz, 1H), 4.60 (m, 2H), 4.05 (m, 1H), 1.22 (d, J=6.8 Hz, 3H). $^{19}$F NMR (DMSO) δ −61.37 (s, 3F).

Example 89

(R)-3-methyl-4-(pyrimidin-2-ylmethyl)-7-(4-(trifluoromethyl)phenyl)-3,4-dihydrobenzo[f][1,4]oxazepin-5(2H)-one (Compound II-13)

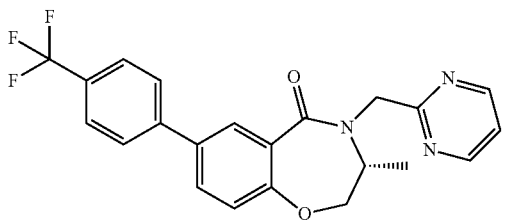 [SMILES: C[C@@H]1COc2ccc(-c3ccc(C(F)(F)F)cc3)cc2C(=O)N1Cc1ncccn1]

Compound II-13 was prepared according to the Examples disclosed herein using the appropriate starting materials. $C_{22}H_{18}F_3N_3O_2 \times$TFA. 414.1 (M+1). $^1$H NMR (DMSO) δ 8.77 (d, J=5.2 Hz, 2H), 8.38 (d, J=2.4 Hz, 1H), 7.85 (m, 5H), 7.40 (t, J=5.0 Hz, 1H), 7.20 (d, J=8.4 Hz, 1H), 5.10 (J=17.0 Hz, 1H), 4.79 (d, J=17.0 Hz, 1H), 4.60 (m, 2H), 4.05 (m, 1H), 1.22 (d, J=6.8 Hz, 3H). $^{19}$F NMR (DMSO) δ −61.37 (s, 3F).

Example 90

(S)-3-methyl-7-(4-(trifluoromethyl)phenyl)-3,4-dihydrobenzo[f][1,4]oxazepin-5(2H)-one (Compound II-18)

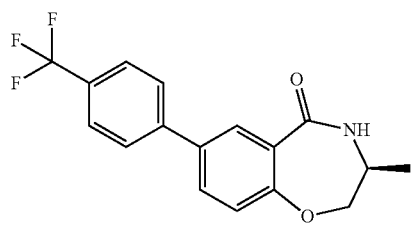 [SMILES: C[C@H]1COc2ccc(-c3ccc(C(F)(F)F)cc3)cc2C(=O)N1]

Compound II-18 was prepared according to the Examples disclosed herein using the appropriate starting materials. $C_{17}H_{14}F_3NO_2$. 322.1 (M+1). $^1$H NMR (DMSO) δ 8.41 (d, J=4.4 Hz, 1H), 8.20 (d, J=1.6 Hz, 1H), 7.85 (m, 5H), 7.16 (d, J=8.4 Hz, 1H), 4.22 (m, 2H), 3.68 (br, 1H), 1.15 (d, J=6.4 Hz, 3H).

Example 91

(R)-3-methyl-7-(4-(trifluoromethyl)phenyl)-3,4-dihydrobenzo[f][1,4]oxazepin-5(2H)-one (Compound II-19)

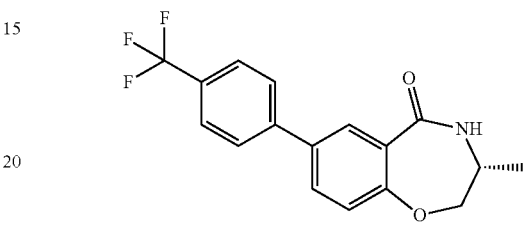

Compound II-19 was prepared according to the Examples disclosed herein using the appropriate starting materials. $C_{17}H_{14}F_3NO_2$. 322.1 (M+1). $^1$H NMR (DMSO) δ 8.41 (d, J=4.4 Hz, 1H), 8.20 (d, J=1.6 Hz, 1H), 7.85 (m, 5H), 7.16 (d, J=8.4 Hz, 1H), 4.22 (m, 2H), 3.68 (br, 1H), 1.15 (d, J=6.4 Hz, 3H).

Example 92

(2R,11aS)-2-amino-7-(4-(trifluoromethyl)phenyl)-2,3,11,11a-tetrahydrobenzo[f]pyrrolo[2,1-c][1,4]oxazepin-5(1H)-one (Compound II-21)

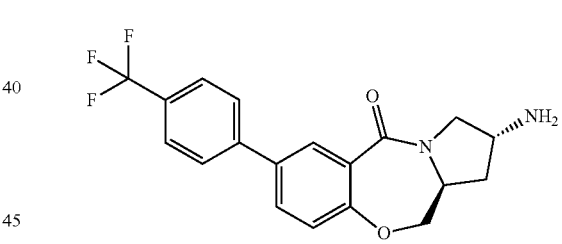

Compound II-21 was prepared according to the Examples disclosed herein using the appropriate starting materials. $C_{19}H_{17}F_3N_2O_2 \times$TFA. 363.1 (M+1).

Example 93

(R)-2-(2,2-difluoroethyl)-8-(4-(trifluoromethyl)phenyl)-3,4,12,12a-tetrahydro-1H-benzo[f]pyrazino[2,1-c][1,4]oxazepin-6(2H)-one (Compound II-22)

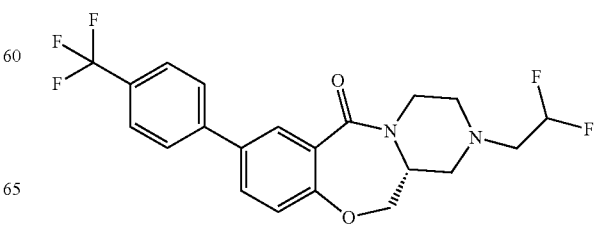

Compound II-22 was prepared according to the Examples disclosed herein using the appropriate starting materials. $C_{21}H_{19}F_5N_2O_2 \times TFA$. 427.1 (M+1). $^1H$ NMR (DMSO) δ 8.22 (d, J=2.4 Hz, 1H), 7.84 (m, 5H), 7.18 (d, J=8.4 Hz, 1H), 6.22 (tm, J=55.6 Hz, 1H), 4.53 (m, 1H), 4.27 (m, 1H), 3.97 (br, 2H), 3.62 (m, 1H), 2.90-2.60 (m, 6H). $^{19}F$ NMR (DMSO) δ −61.4 (s, 3F), −119.4 (dt, 55.6, 16.2 Hz, 2F).

Example 94

(R)-2-ethyl-8-(4-(trifluoromethyl)phenyl)-3,4,12,12a-tetrahydro-1H-benzo[f]pyrazino[2,1-c][1,4]oxazepin-6(2H)-one (Compound II-23)

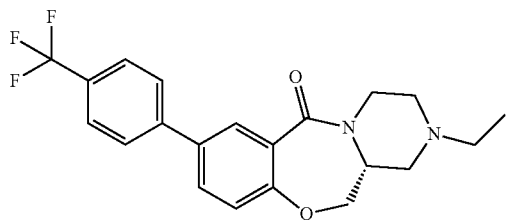 [SMILES: CCN1CCN2C(=O)c3cc(-c4ccc(C(F)(F)F)cc4)ccc3OC[C@H]2C1]

Compound II-23 was prepared according to the Examples disclosed herein using the appropriate starting materials. $C_{21}H_{21}F_3N_2O_2 \times TFA$. 391.1 (M+1).

Example 95

(S)-2-(2,2-difluoroethyl)-8-(4-(trifluoromethyl)phenyl)-3,4,12,12a-tetrahydro-1H-benzo[f]pyrazino[2,1-c][1,4]oxazepin-6(2H)-one (Compound II-24)

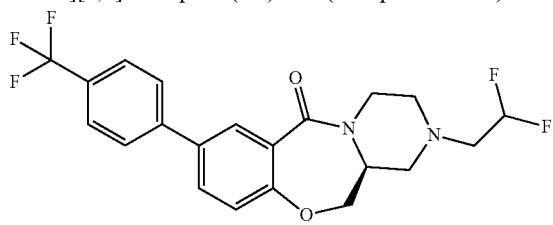

Compound II-24 was prepared according to the Examples disclosed herein using the appropriate starting materials. $C_{21}H_{19}F_5N_2O_2 \times TFA$. 427.1 (M+1). $^1H$ NMR (DMSO) δ 8.22 (d, J=2.4 Hz, 1H), 7.84 (m, 5H), 7.18 (d, J=8.4 Hz, 1H), 6.22 (tm, J=55.6 Hz, 1H), 4.53 (m, 1H), 4.27 (m, 1H), 3.97 (br, 2H), 3.62 (m, 1H), 2.90-2.60 (m, 6H). $^{19}F$ NMR (DMSO) δ −61.4 (s, 3F), −119.4 (dt, 55.6, 16.2 Hz, 2F).

Example 96

(S)-2-ethyl-8-(4-(trifluoromethyl)phenyl)-3,4,12,12a-tetrahydro-1H-benzo[f]pyrazino[2,1-c][1,4]oxazepin-6(2H)-one (Compound II-25)

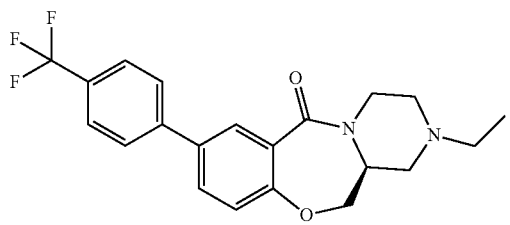 [SMILES: CCN1CCN2C(=O)c3cc(-c4ccc(C(F)(F)F)cc4)ccc3OC[C@@H]2C1]

Compound II-25 was prepared according to the Examples disclosed herein using the appropriate starting materials. $C_{21}H_{21}F_3N_2O_2 \times TFA$. 391.1 (M+1).

Example 97

(S)-3-isopropyl-7-(4-(trifluoromethyl)phenyl)-3,4-dihydrobenzo[f][1,4]oxazepin-5(2H)-one (Compound II-77)

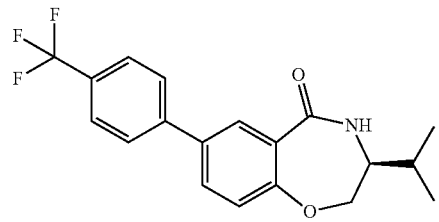 [SMILES: CC(C)[C@H]1COc2ccc(-c3ccc(C(F)(F)F)cc3)cc2C(=O)N1]

Compound II-77 was prepared according to the Examples disclosed herein using the appropriate starting materials. $C_{19}H_{18}F_3NO_2$. 350.1 (M+1).

Example 98

(R)-3-methyl-4-(pyridin-2-ylmethyl)-7-(4-(trifluoromethyl)phenyl)-3,4-dihydrobenzo[f][1,4]oxazepin-5(2H)-one (Compound II-80)

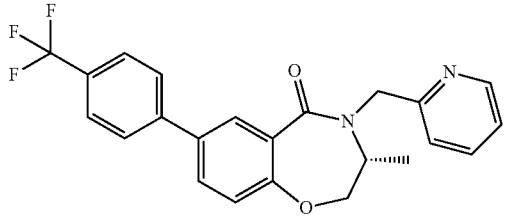 [SMILES: C[C@@H]1COc2ccc(-c3ccc(C(F)(F)F)cc3)cc2C(=O)N1Cc1ccccn1]

Compound II-80 was prepared according to the Examples disclosed herein using the appropriate starting materials. $C_{23}H_{19}F_3N_2O_2 \times TFA$. 413.1 (M+1).

Example 99

(S)-3-methyl-4-(pyridin-2-ylmethyl)-7-(4-(trifluoromethyl)phenyl)-3,4-dihydrobenzo[f][1,4]oxazepin-5(2H)-one (Compound II-81)

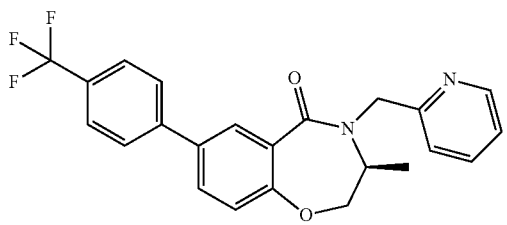 [SMILES: C[C@H]1COc2ccc(-c3ccc(C(F)(F)F)cc3)cc2C(=O)N1Cc1ccccn1]

Compound II-81 was prepared according to the Examples disclosed herein using the appropriate starting materials. $C_{23}H_{19}F_3N_2O_2 \times TFA$. 413.1 (M+1).

Example 100

4-(1-(pyridin-2-yl)ethyl)-7-(4-(trifluoromethyl)phenyl)-3,4-dihydrobenzo[f][1,4]oxazepin-5(2H)-one (Compound II-82)

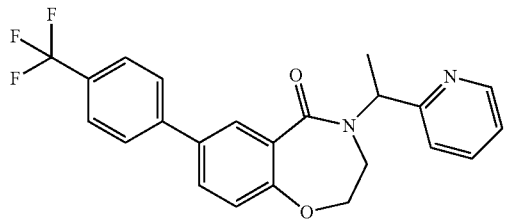 [SMILES: CC(c1ccccn1)N1CCOc2ccc(-c3ccc(C(F)(F)F)cc3)cc2C1=O]

Compound II-82 was prepared according to the Examples disclosed herein using the appropriate starting materials. $C_{22}H_{18}F_3N_3O_2 \times TFA$. 414.1 (M+1)

Example 101

(R)-2-(2,2,2-trifluoroethyl)-8-(4-(trifluoromethyl)phenyl)-3,4,12,12a-tetrahydro-1H-benzo[f]pyrazino[2,1-c][1,4]oxazepin-6(2H)-one (Compound II-83)

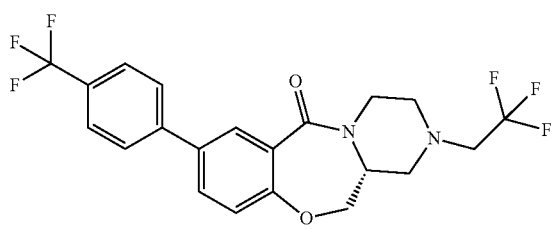 [SMILES: O=C1c2cc(-c3ccc(C(F)(F)F)cc3)ccc2OC[C@H]2CN(CC(F)(F)F)CCN12]

Compound II-83 was prepared according to the Examples disclosed herein using the appropriate starting materials. $C_{21}H_{18}F_6N_2O_2 \times TFA$. 445.1 (M+1)

Example 102

(R)-4-benzyl-2-methyl-7-(4-(trifluoromethyl)phenyl)-3,4-dihydrobenzo[f][1,4]oxazepin-5(2H)-one (Compound II-85)

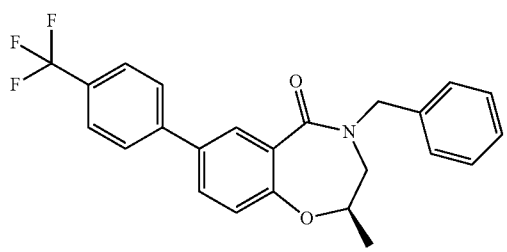 [SMILES: C[C@@H]1CN(Cc2ccccc2)C(=O)c2cc(-c3ccc(C(F)(F)F)cc3)ccc2O1]

Compound II-85 was prepared according to the Examples disclosed herein using the appropriate starting materials. $C_{24}H_{20}F_3NO_2$ 412.1 (M+1).

Example 103

(S)-4-benzyl-2-methyl-7-(4-(trifluoromethyl)phenyl)-3,4-dihydrobenzo[f][1,4]oxazepin-5(2H)-one (Compound II-86)

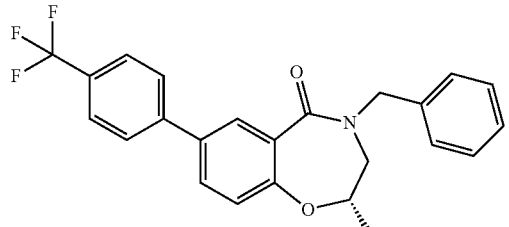

Compound II-86 was prepared according to the Examples disclosed herein using the appropriate starting materials. $C_{24}H_{20}F_3NO_2$ 412.1 (M+1).

Example 104

(S)-2-methyl-4-(pyrimidin-2-ylmethyl)-7-(4-(trifluoromethyl)phenyl)-3,4-dihydrobenzo[f][1,4]oxazepin-5(2H)-one (Compound II-101)

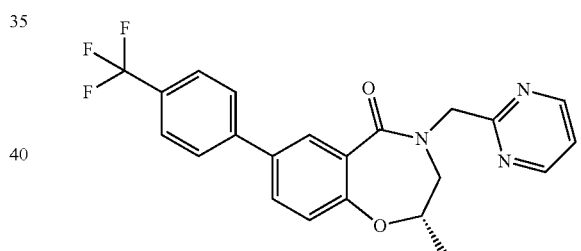

Compound II-101 was prepared according to the Examples disclosed herein using the appropriate starting materials. $C_{22}H_{18}F_3N_3O_2$. 414.1 (M+1)

Example 105

2-(pyridin-2-yl)-1-(7-(4-(trifluoromethyl)phenyl)-2,3-dihydrobenzo[f][1,4]oxazepin-4(5H)-yl)ethanone (Compound III-29)

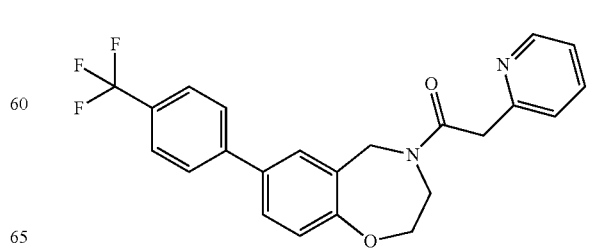

Compound III-29 was prepared according to the Examples disclosed herein using the appropriate starting materials. $C_{23}H_{19}F_3N_2O_2$. 413.1 (M+1).

Example 106

2-(pyrimidin-2-yl)-1-(7-(4-(trifluoromethyl)phenyl)-2,3-dihydrobenzo[f][1,4]oxazepin-4(5H)-yl)ethanone (Compound III-30)

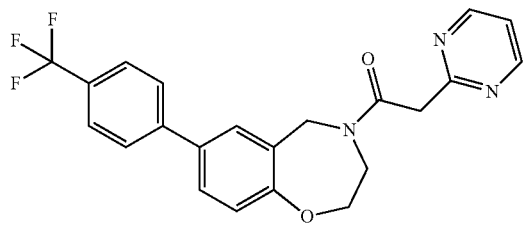 [SMILES: O=C(Cc1ncccn1)N1CCOc2ccc(-c3ccc(C(F)(F)F)cc3)cc2C1]

Compound III-30 was prepared according to the Examples disclosed herein using the appropriate starting materials. $C_{22}H_{18}F_3N_3O_2$. 414.1 (M+1).

Example 107

4-(5-oxo-4-(pyrimidin-2-ylmethyl)-2,3,4,5-tetrahydrobenzo[f][1,4]oxazepin-7-yl)phenyl trifluoromethanesulfonate (Compound II-171)

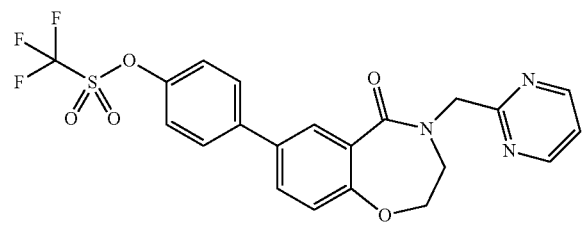 [SMILES: O=C1c2cc(-c3ccc(OS(=O)(=O)C(F)(F)F)cc3)ccc2OCCN1Cc1ncccn1]

Compound II-171 was prepared according to the Examples disclosed herein using the appropriate starting materials. $C_{21}H_{16}F_3N_3O_5S$. 480.1 (M+1).

Example 108

(R)-(2-methyl-7-(4-(trifluoromethoxy)phenyl)-2,3-dihydrobenzo[f][1,4]oxazepin-4(5H)-yl)(pyrimidin-2-yl)methanone (Compound III-38)

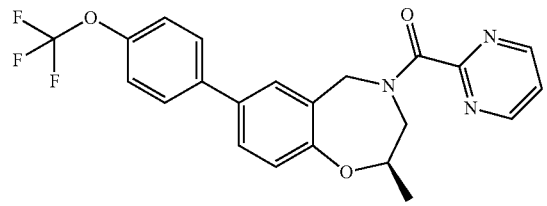 [SMILES: C[C@@H]1CN(C(=O)c2ncccn2)Cc2cc(-c3ccc(OC(F)(F)F)cc3)ccc2O1]

Compound III-38 was prepared according to the Examples disclosed herein using the appropriate starting materials. $C_{22}H_{18}F_3N_3O_3$. 430.1 (M+1).

Example 109

(S)-(2-methyl-7-(4-(trifluoromethoxy)phenyl)-2,3-dihydrobenzo[f][1,4]oxazepin-4(5H)-yl)(pyrimidin-2-yl)methanone (Compound III-39)

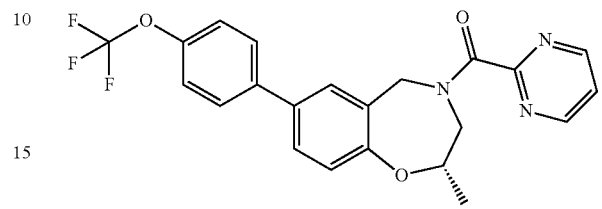

Compound III-39 was prepared according to the Examples disclosed herein using the appropriate starting materials. $C_{22}H_{18}F_3N_3O_3$. 430.1 (M+1).

Example 110

Phenyl(7-(4-(trifluoromethoxy)phenyl)-2,3-dihydrobenzo[f][1,4]oxazepin-4(5H)-yl)methanone (Compound III-4)

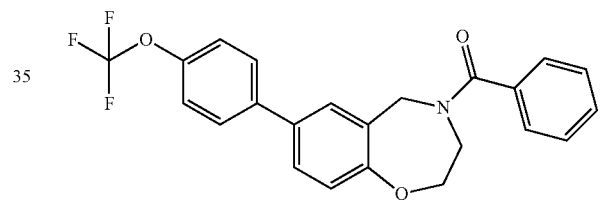

Compound III-4 was prepared according to the Examples disclosed herein using the appropriate starting materials. MS found for $C_{23}H_{18}F_3NO_3$ as $(M+H)^+$ 414.1.

Example 111

4-(pyrimidin-2-ylmethyl)-7-(4-(2,2,2-trifluoroethyl)phenyl)-3,4-dihydrobenzo[f][1,4]oxazepin-5(2H)-one (Compound II-150)

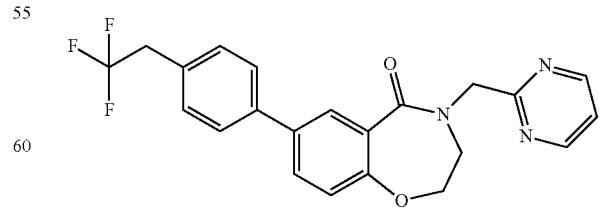

Compound II-150 was prepared according to the Examples disclosed herein using the appropriate starting materials. MS found for $C_{23}H_{18}F_3NO_3$ as $(M+H)^+$ 414.2.

Example 112

4-(pyridin-2-ylmethyl)-7-(4-(2,2,2-trifluoroethyl)phenyl)-3,4-dihydrobenzo[f][1,4]oxazepin-5(2H)-one (Compound II-151)

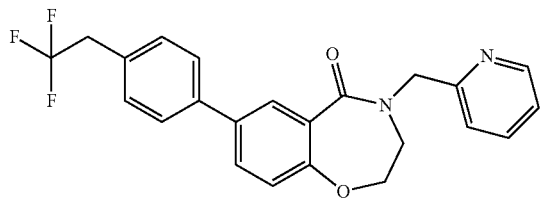 [SMILES: O=C1c2cc(-c3ccc(CC(F)(F)F)cc3)ccc2OCCN1Cc1ccccn1]

Compound was prepared according to the Examples disclosed herein using the appropriate starting materials. MS found for $C_{23}H_{19}F_3N_2O_2$ as $(M+H)^+$ 413.2 $^1$H NMR (400 MHz, dmso-d$_6$): δ: 8.54 (d, J=5.6 Hz, 1H), 7.96 (d, J=2.4 Hz, 1H), 7.80-7.76 (m, 2H); 7.67 (d, J=8.0 Hz, 1H), 7.42-7.28 (m, 4H); 7.14 (d, J=8.4 Hz, 1H); 4.86 (s, 2H), 4.38-4.36 (m, 2H), 3.72-3.64 (m, 4H).

Example 113

(1-methylcyclopropyl)(7-(4-(trifluoromethoxy)phenyl)-2,3-dihydrobenzo[f][1,4]oxazepin-4(5H)-yl)methanone (Compound III-10)

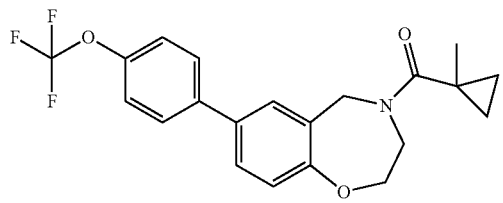 [SMILES: CC1(C(=O)N2CCOc3ccc(-c4ccc(OC(F)(F)F)cc4)cc3C2)CC1]

Compound III-10 was prepared according to the Examples disclosed herein using the appropriate starting materials. MS found for $C_{21}H_{20}F_3NO_3$ as $(M+H)^+$ 392.0.

Example 114

(3,3-difluorocyclobutyl)(7-(4-(trifluoromethoxy)phenyl)-2,3-dihydrobenzo[f][1,4]oxazepin-4(5H)-yl)methanone (Compound III-11)

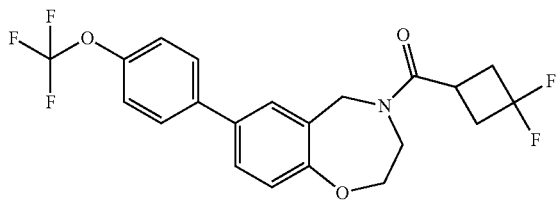 [SMILES: O=C(C1CC(F)(F)C1)N1CCOc2ccc(-c3ccc(OC(F)(F)F)cc3)cc2C1]

Compound III-11 was prepared according to the Examples disclosed herein using the appropriate starting materials. MS found for $C_{21}H_{18}F_5NO_3$ as $(M+H)^+$ 428.1.

Example 115

(1-methyl-1H-pyrazol-4-yl)(7-(4-(trifluoromethoxy)phenyl)-2,3-dihydrobenzo[f][1,4]oxazepin-4(5H)-yl)methanone (Compound III-12)

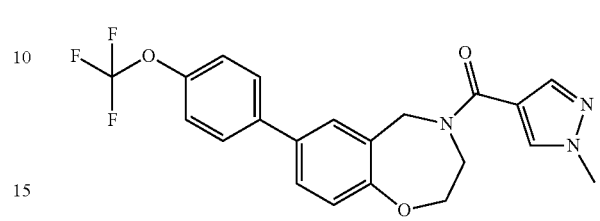

Compound III-12 was prepared according to the Examples disclosed herein using the appropriate starting materials. MS found for $C_{21}H_{18}F_3N_3O_3$ as $(M+H)^+$ 418.1. $^1$H NMR (400 MHz, dmso-d$_6$): δ: 8.03 (s, 1H), 7.73-7.41 (m, 7H); 7.03 (d, J=8.0 Hz, 1H), 4.82 (s, 2H), 4.26 (m, 2H); 4.00 (m, 2H); 383 (s, 3H).

Example 116

(1H-pyrazol-3-yl)(7-(4-(trifluoromethoxy)phenyl)-2,3-dihydrobenzo[f][1,4]oxazepin-4(5H)-yl)methanone (Compound III-15)

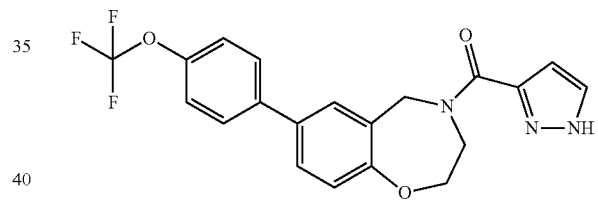

Compound III-15 was prepared according to the Examples disclosed herein using the appropriate starting materials. MS found for $C_{20}H_{16}F_3N_3O_3$ as $(M+H)^+$ 404.1.

Example 117

(1,5-dimethyl-1H-pyrazol-3-yl)(7-(4-(trifluoromethoxy)phenyl)-2,3-dihydrobenzo[f][1,4]oxazepin-4(5H)-yl)methanone (Compound III-58)

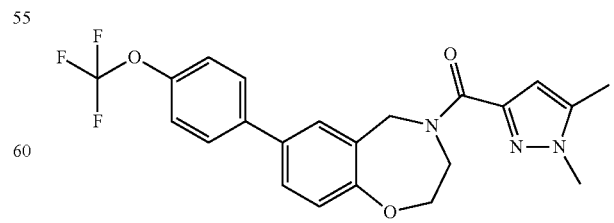

Compound III-58 was prepared according to the Examples disclosed herein using the appropriate starting materials. MS found for $C_{22}H_{20}F_3N_3O_3$ as $(M+H)^+$ 432.1

Example 118

Pyrazin-2-yl(7-(4-(trifluoromethoxy)phenyl)-2,3-dihydrobenzo[f][1,4]oxazepin-4(5H)-yl)methanone (Compound III-23)

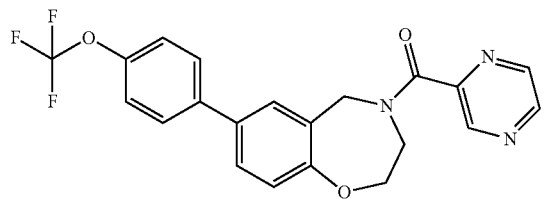 [SMILES: O=C(c1cnccn1)N1CCOc2ccc(-c3ccc(OC(F)(F)F)cc3)cc2C1]

Compound III-23 was prepared according to the Examples disclosed herein using the appropriate starting materials. MS found for $C_{21}H_{16}F_3N_3O_3$ as $(M+H)^+$ 416.1.

Example 119

Pyridazin-3-yl(7-(4-(trifluoromethoxy)phenyl)-2,3-dihydrobenzo[f][1,4]oxazepin-4(5H)-yl)methanone (Compound III-24)

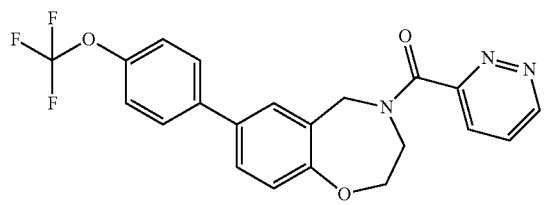 [SMILES: O=C(c1cccnn1)N1CCOc2ccc(-c3ccc(OC(F)(F)F)cc3)cc2C1]

Compound III-24 was prepared according to the Examples disclosed herein using the appropriate starting materials. MS found for $C_{16}H_{14}F_3NO_2$ as $(M+H)^+$ 310.1. MS found for $C_{21}H_{16}F_3N_3O_3$ as $(M+H)^+$ 416.1.

Example 120

4-(pyrimidin-2-ylmethyl)-7-p-tolyl-3,4-dihydrobenzo[f][1,4]oxazepin-5(2H)-one (Compound II-87)

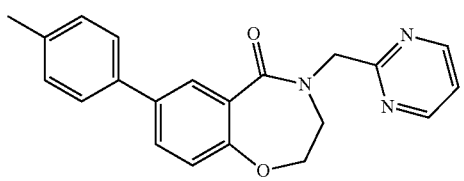 [SMILES: Cc1ccc(-c2ccc3c(c2)C(=O)N(Cc2ncccn2)CCO3)cc1]

Compound II-87 was prepared according to the Examples disclosed herein using the appropriate starting materials. MS found for $C_{21}H_{19}N_3O_2$ as $(M+H)^+$ 346.1 $^1$H NMR (400 MHz, dmso-d$_6$): δ: 8.77 (d, J=5.2 Hz, 2H), 7.90 (d, J=2.4 Hz, 1H), 7.75 (dd, J=2.4, 8.8 Hz, 1H), 7.52 (d, J=8.8 Hz, 2H), 7.40 (t, J=5.2 Hz, 1H), 7.25 (d, J=8.0 Hz, 2H), 7.42 (d, J=8.4 Hz, 1H), 4.96 (s, 2H), 4.49-4.47 (m, 2H), 3.75-3.73 (m, 2H), 2.31 (s, 3H).

Example 121

7-(4-chlorophenyl)-4-(pyrimidin-2-ylmethyl)-3,4-dihydrobenzo[f][1,4]oxazepin-5(2H)-one (Compound II-88)

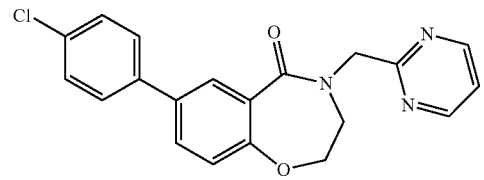 [SMILES: O=C1c2cc(-c3ccc(Cl)cc3)ccc2OCCN1Cc1ncccn1]

Compound II-88 was prepared according to the Examples disclosed herein using the appropriate starting materials. MS found for $C_{20}H_{16}N_3O_2Cl$ as $(M+H)^+$ 366.1 $^1$H NMR (400 MHz, dmso-d$_6$): δ: 8.77 (d, J=5.2 Hz, 2H), 7.94 (d, J=2.4 Hz, 1H), 7.79 (dd, J=2.4, 8.8 Hz, 1H), 7.67 (d, J=8.8 Hz, 2H), 7.49 (d, J=8.0 Hz, 2H), 7.40 (t, J=5.2 Hz, 1H), 7.13 (d, J=8.4 Hz, 1H), 4.97 (s, 2H), 4.51-4.49 (m, 2H), 3.77-3.74 (m, 2H).

Example 122

7-(4-isopropylphenyl)-4-(pyrimidin-2-ylmethyl)-3,4-dihydrobenzo[f][1,4]oxazepin-5(2H)-one (Compound II-89)

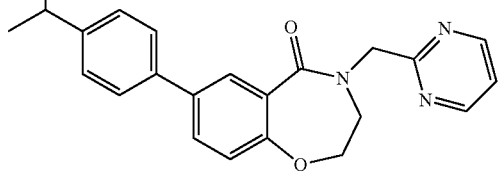

Compound II-89 was prepared according to the Examples disclosed herein using the appropriate starting materials. MS found for $C_{23}H_{23}N_3O_2$ as $(M+H)^+$ 374.1 $^1$H NMR (400 MHz, dmso-d$_6$): δ: 8.77 (d, J=5.2 Hz, 2H), 7.90 (d, J=2.4 Hz, 1H), 7.75 (dd, J=2.4, 8.8 Hz, 1H), 7.55 (d, J=8.8 Hz, 2H), 7.41 (t, J=5.2 Hz, 1H), 7.29 (d, J=8.0 Hz, 2H), 7.11 (d, J=8.4 Hz, 1H), 4.96 (s, 2H), 4.49-4.47 (m, 2H), 3.75-3.73 (m, 2H), 2.91 (m, 1H); 1.22 (d, J=7.2 Hz, 6H).

Example 123

7-(4-ethylphenyl)-4-(pyrimidin-2-ylmethyl)-3,4-dihydrobenzo[f][1,4]oxazepin-5(2H)-one (Compound II-91)

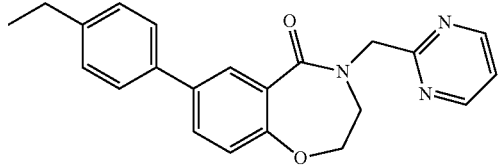 [SMILES: CCc1ccc(-c2ccc3c(c2)C(=O)N(Cc2ncccn2)CCO3)cc1]

Compound II-91 was prepared according to the Examples disclosed herein using the appropriate starting materials. MS found for $C_{22}H_{21}N_3O_2$ as $(M+H)^+$ 360.1 $^1H$ NMR (400 MHz, dmso-$d_6$): δ: 8.77 (d, J=5.2 Hz, 2H), 7.91 (d, J=2.4 Hz, 1H), 7.75 (dd, J=2.4, 8.8 Hz, 1H), 7.54 (d, J=8.8 Hz, 2H), 7.41 (t, J=5.2 Hz, 1H), 7.28 (d, J=8.0 Hz, 2H), 7.12 (d, J=8.4 Hz, 1H), 4.97 (s, 2H), 4.49-4.47 (m, 2H), 3.75-3.73 (m, 2H), 2.64 (q, J=7.6 Hz, 2H); 1.20 (d, J=7.6 Hz, 3H).

Example 124

7-(4-cyclopropylphenyl)-4-(pyrimidin-2-ylmethyl)-3,4-dihydrobenzo[f][1,4]oxazepin-5(2H)-one (Compound II-92)

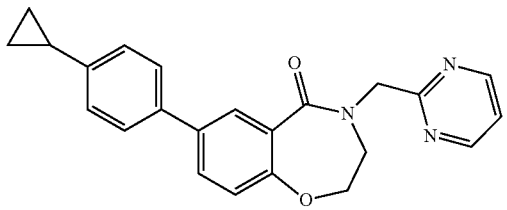 [SMILES: O=C1c2cc(-c3ccc(C4CC4)cc3)ccc2OCCN1Cc1ncccn1]

Compound II-92 was prepared according to the Examples disclosed herein using the appropriate starting materials. MS found for $C_{22}H_{21}N_3O_2$ as $(M+H)^+$ 372.1 $^1H$ NMR (400 MHz, dmso-$d_6$): δ: 8.77 (d, J=5.2 Hz, 2H), 7.88 (d, J=2.4 Hz, 1H), 7.74 (dd, J=2.4, 8.8 Hz, 1H), 7.50 (d, J=8.8 Hz, 2H), 7.41 (t, J=5.2 Hz, 1H), 7.14 (d, J=8.0 Hz, 2H), 7.10 (d, J=8.4 Hz, 1H), 4.96 (s, 2H), 4.49-4.47 (m, 2H), 3.75-3.73 (m, 2H), 1.94-1.89 (m, 1H); 0.97-0.93 (m, 2H); 0.70-0.66 (m, 2H).

Example 125

7-(4-methoxyphenyl)-4-(pyrimidin-2-ylmethyl)-3,4-dihydrobenzo[f][1,4]oxazepin-5(2H)-one (Compound II-94)

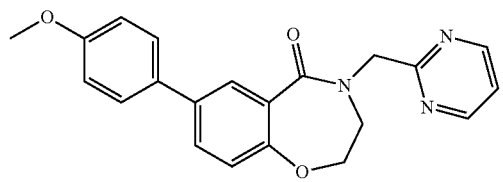 [SMILES: COc1ccc(-c2ccc3c(c2)C(=O)N(Cc2ncccn2)CCO3)cc1]

Compound II-94 was prepared according to the Examples disclosed herein using the appropriate starting materials. MS found for $C_{21}H_{19}N_3O_3$ as $(M+H)^+$ 362.1 $^1H$ NMR (400 MHz, dmso-$d_6$): δ: 8.78 (d, J=5.2 Hz, 2H), 7.86 (d, J=2.4 Hz, 1H), 7.72 (dd, J=2.4, 8.8 Hz, 1H), 7.56 (d, J=8.8 Hz, 2H), 7.41 (t, J=5.2 Hz, 1H), 7.10 (d, J=8.0 Hz, 2H), 7.00 (d, J=8.4 Hz, 1H), 4.97 (s, 2H), 4.48-4.45 (m, 2H), 3.76 (s, 3H); 3.74-3.72 (m, 2H).

Example 126

7-(4-isobutoxyphenyl)-4-(pyrimidin-2-ylmethyl)-3,4-dihydrobenzo[f][1,4]oxazepin-5(2H)-one (Compound II-97)

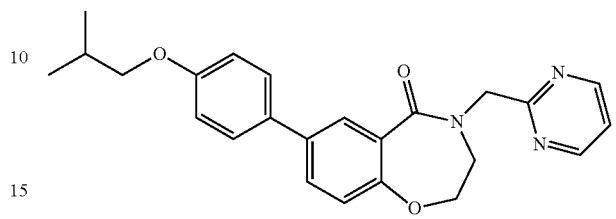

Compound II-97 was prepared according to the Examples disclosed herein using the appropriate starting materials. MS found for $C_{24}H_{25}N_3O_3$ as $(M+H)^+$ 404.1. $^1H$ NMR (400 MHz, dmso-$d_6$): δ: 8.78 (d, J=5.2 Hz, 2H), 7.85 (d, J=2.4 Hz, 1H), 7.72 (dd, J=2.4, 8.8 Hz, 1H), 7.54 (d, J=8.8 Hz, 2H), 7.41 (t, J=5.2 Hz, 1H), 7.10 (d, J=8.0 Hz, 2H), 6.99 (d, J=8.4 Hz, 1H), 4.97 (s, 2H), 4.48-4.46 (m, 2H), 3.76-3.72 (m, 4H); 2.03-1.97 (m, 1H); 0.97 (d, J=6.4 Hz, 6H).

Example 127

7-(4-tert-butylphenyl)-4-(pyrimidin-2-ylmethyl)-3,4-dihydrobenzo[f][1,4]oxazepin-5(2H)-one (Compound II-98)

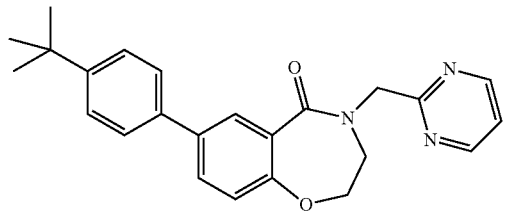 [SMILES: CC(C)(C)c1ccc(-c2ccc3c(c2)C(=O)N(Cc2ncccn2)CCO3)cc1]

Compound II-98 was prepared according to the Examples disclosed herein using the appropriate starting materials. MS found for $C_{24}H_{25}N_3O_3$ as $(M+H)^+$ 404.1 $^1H$ NMR (400 MHz, dmso-$d_6$): δ: 8.78 (d, J=5.2 Hz, 2H), 7.91 (d, J=2.4 Hz, 1H), 7.75 (dd, J=2.4, 8.8 Hz, 1H), 7.55 (d, J=8.8 Hz, 2H), 7.46 (d, J=8.0 Hz, 2H); 7.41 (t, J=5.2 Hz, 1H); 7.11 (d, J=8.4 Hz, 1H), 4.97 (s, 2H), 4.50-4.47 (m, 2H), 3.76-3.73 (m, 4H); 1.29 (s, 9H).

Example 128

7-(4-cyclopropoxyphenyl)-4-(pyrimidin-2-ylmethyl)-3,4-dihydrobenzo[f][1,4]oxazepin-5(2H)-one (Compound II-102)

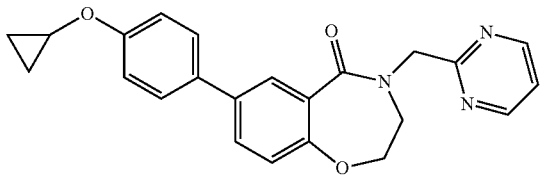 [SMILES: O=C1c2cc(-c3ccc(OC4CC4)cc3)ccc2OCCN1Cc1ncccn1]

Compound II-102 was prepared according to the Examples disclosed herein using the appropriate starting materials. MS found for $C_{23}H_{21}N_3O_3$ as $(M+H)^+$ 388.1 $^1$H NMR (400 MHz, dmso-$d_6$): δ: 8.78 (d, J=5.2 Hz, 2H), 7.86 (d, J=2.4 Hz, 1H), 7.72 (dd, J=2.4, 8.8 Hz, 1H), 7.57 (d, J=8.8 Hz, 2H), 7.41 (t, J=5.2 Hz, 1H); 7.46 (d, J=8.0 Hz, 2H), 7.11 (m, 3H), 4.97 (s, 2H), 4.48-4.46 (m, 2H), 3.87-3.86 (m, 1H); 3.84-3.74 (m, 2H); 0.80-0.75 (m, 2H); 0.67-0.65 (m, 2H).

Example 129

7-(4-chloro-2-fluorophenyl)-4-(pyrimidin-2-ylmethyl)-3,4-dihydrobenzo[f][1,4]oxazepin-5(2H)-one (Compound II-117)

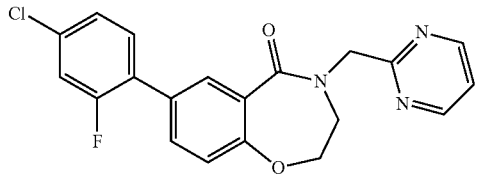 [SMILES: O=C1c2cc(-c3ccc(Cl)cc3F)ccc2OCCN1Cc1ncccn1]

Compound II-117 was prepared according to the Examples disclosed herein using the appropriate starting materials. MS found for $C_{20}H_{15}N_3O_2FCl$ as $(M+H)^+$ 384.1 $^1$H NMR (400 MHz, dmso-$d_6$): δ: 8.77 (d, J=5.2 Hz, 2H), 7.87 (d, J=2.4 Hz, 1H), 7.66 (dd, J=2.4, 8.8 Hz, 1H), 7.57-7.51 (m, 2H); 7.41-7.35 (m, 2H); 7.16 (d, J=8.0 Hz, 1H), 4.97 (s, 2H), 4.54-4.52 (m, 2H), 3.79-3.76 (m, 2H).

Example 130 pyrimidin-2-yl(7-(4-(trifluoromethoxy)phenyl)-2,3-dihydrobenzo[f][1,4]oxazepin-4(5H)-yl)methanone (Compound III-1)

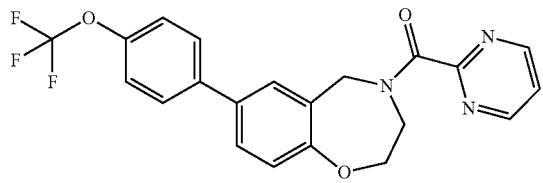 [SMILES: O=C(c1ncccn1)N1CCOc2ccc(-c3ccc(OC(F)(F)F)cc3)cc2C1]

To a solution of 7-(4-(trifluoromethoxy)phenyl)-3,4-dihydrobenzo[f][1,4]oxazepin-5(2H)-one (660 mgs, 2.0 mmol) in THF (6 mL), 1.0M Borane in THF (6.0 mL, 6.0 mmol) was added and the mixture was heated at 70° C. After 16 h, the mixture was cooled to rt and Methanol (22 mL) and 6.0M HCl (22 mL) was added and stirred at rt for 2 h. The reaction mixture was then concentrated and the solids formed were filtered and washed with ether and dried to give 7-(4-(trifluoromethoxy)phenyl)-2,3,4,5-tetrahydrobenzo[f][1,4]oxazepine as HCl salt. The above compound (100 mgs, 0.29 mmol), pyrimidine-2-carboxylic acid (47 mgs, 0.38 mmol), HATU (143 mgs, 0.38 mmol), in DMF (1 mL) was added NMM (0.1 mL, 0.86 mmol) and stirred at 60° C. for 30 min. The reaction mixture was then diluted with EtOAc and washed with NaHCO$_3$, brine and dried (MgS(O)$_4$). The mixture was the filtered, concentrated and chromatographed (SiO$_2$, 50% EtOAc/DCM) to provide the title compound.

MS found for $C_{21}H_{16}F_3N_3O_3$ as $(M+H)^+$ 415.9. $^1$H NMR (400 MHz, dmso-$d_6$): mixture of rotomers (~2:1): $^1$H-NMR (DMSO) of the major rotomer: δ 8.86 (d, J=5.2 Hz, 2H), 7.77 (d, J=8.8 Hz, 2H), 7.75 (m, 1H); 7.69-7.54 (m, 2H); 7.47-7.40 (m, 2H); 7.11 (d, J=8.0 Hz, 1H); 4.85 (s, 2H); 4.25-4.03 (m, 4H); 3.58-3.56 (m, 2H).

Example 131

7-cyclohexenyl-4-(pyrimidin-2-ylmethyl)-3,4-dihydrobenzo[f][1,4]oxazepin-5(2H)-one (Compound V-3)

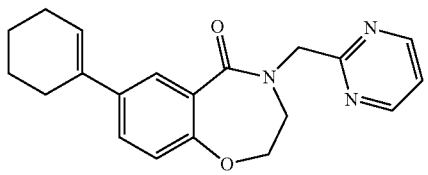 [SMILES: O=C1c2cc(C3=CCCCC3)ccc2OCCN1Cc1ncccn1]

Compound V-3 was prepared according to the Examples disclosed herein using the appropriate starting materials. MS found for $C_{20}H_{21}N_3O_2$ as $(M+H)^+$ 336.1.

Example 132

7-(4-methylcyclohex-1-enyl)-4-(pyrimidin-2-ylmethyl)-3,4-dihydrobenzo[f][1,4]oxazepin-5(2H)-one (Compound V-5)

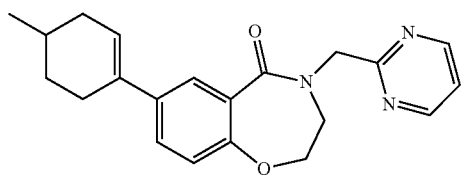 [SMILES: CC1CC=C(c2ccc3c(c2)C(=O)N(Cc2ncccn2)CCO3)CC1]

Compound V-5 was prepared according to the Examples disclosed herein using the appropriate starting materials. MS found for $C_{21}H_{23}N_3O_2$ as $(M+H)^+$ 350.1 $^1$H NMR (400 MHz, dmso-$d_6$): δ: 8.76 (d, J=5.2 Hz, 2H), 7.65 (d, J=2.4 Hz, 1H), 7.53 (dd, J=2.4, 8.4 Hz, 1H), 7.42-7.39 (m, 1H); 6.98 (d, J=84 Hz, 1H); 6.08 (m, 1H); 4.94 (s, 2H); 4.44-4.42 (m, 2H), 3.69-3.67 (m, 2H); 2.36-2.23 (m, 4H); 1.81-1.66 (m, 5H); 1.31-1.26 (m, 1H).

Example 133

7-(4-ethylcyclohex-1-enyl)-4-(pyrimidin-2-ylmethyl)-3,4-dihydrobenzo[f][1,4]oxazepin-5(2H)-one (Compound V-6)

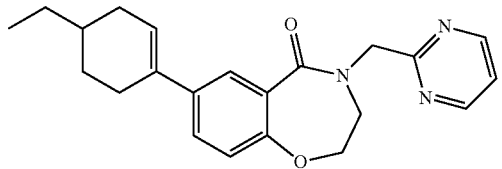 [SMILES: CCC1CC=C(c2ccc3c(c2)C(=O)N(Cc2ncccn2)CCO3)CC1]

205

Compound V-6 was prepared according to the Examples disclosed herein using the appropriate starting materials. MS found for $C_{22}H_{25}N_3O_2$ as $(M+H)^+$ 364.1 $^1H$ NMR (400 MHz, dmso-$d_6$): δ: 8.77 (d, J=5.2 Hz, 2H), 7.65 (d, J=2.4 Hz, 1H), 7.52 (dd, J=2.4, 8.4 Hz, 1H), 7.42-7.38 (m, 1H); 6.98 (d, J=8.4 Hz, 1H); 6.09 (m, 1H); 4.94 (s, 2H), 4.44-4.42 (m, 2H), 3.70-3.67 (m, 2H); 2.36-2.25 (m, 3H); 1.84-1.77 (m, 2H); 1.32-1.26 (m, 4H); 0.91-0.88 (m, 3H).

Example 134

(R)-7-(4-methylcyclohex-1-enyl)-4-(pyrimidin-2-ylmethyl)-3,4-dihydrobenzo[f][1,4]oxazepin-5(2H)-one (Compound V-8)

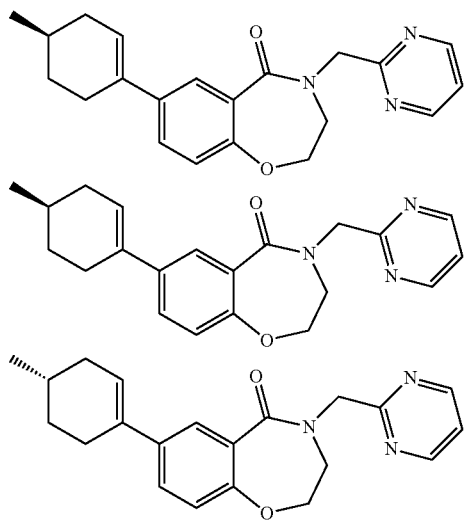

The racemic 7-(4-methylcyclohex-1-enyl)-4-(pyrimidin-2-ylmethyl)-3,4-dihydrobenzo[f][1,4]oxazepin-5(2H)-one was separted using chiral preparative HPLC to give pure enantiomers of Compound V-8 and Compound V-9.

R-enantiomer: MS found for $C_{21}H_{23}N_3O_2$ as $(M+H)^+$ 350.1

Example 135

(S)-7-(4-methylcyclohex-1-enyl)-4-(pyrimidin-2-ylmethyl)-3,4-dihydrobenzo[f][1,4]oxazepin-5(2H)-one (Compound V-9)

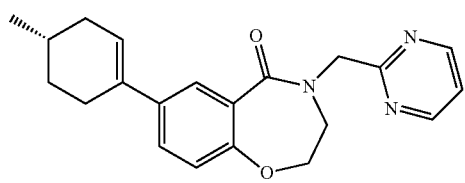 [SMILES: C[C@@H]1CC=C(c2ccc3c(c2)C(=O)N(Cc2ncccn2)CCO3)CC1]

Compound V-9 was prepared according to the Example above. S-enantiomer: MS found for $C_{21}H_{23}N_3O_2$ as $(M+H)^+$ 350.1

Example 136

3-(pyridin-2-ylmethyl)-7-(4-(trifluoromethoxy)phenyl)-3,4-dihydrobenzo[f][1,4]oxazepin-5(2H)-one (Compound II-142)

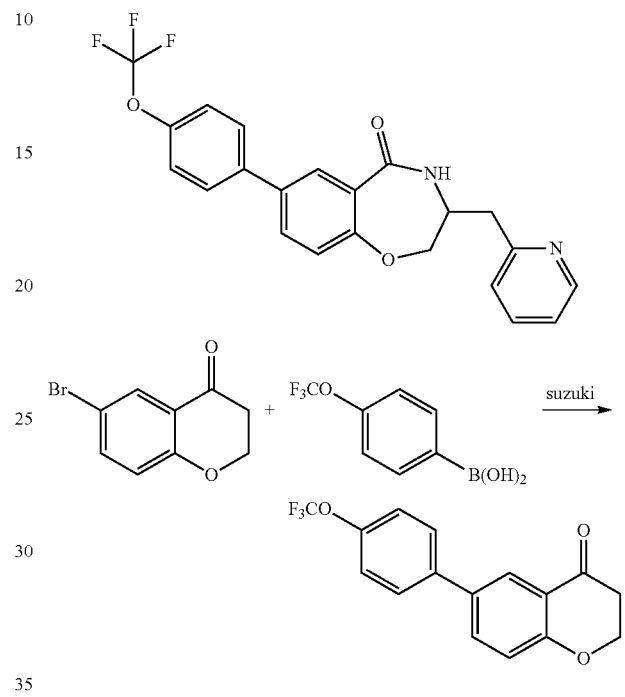

Synthesis of 6-(4-(trifluoromethoxy)phenyl)chroman-4-one. See previous Suzuki reaction conditions. m/z=309.0

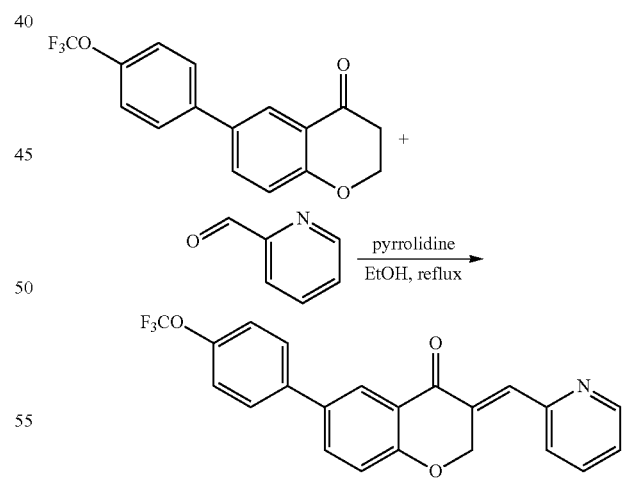

Synthesis of 3-(pyridin-2-ylmethylene)-6-(4-(trifluoromethoxy)phenyl)chroman-4-one. A solution of 400 mg 6-(4-(trifluoromethoxy)phenyl)chroman-4-one (1.3 mmol, 1.0 eq), 150 μL 2-pyridine carboxaldehyde (1.6 mmol, 1.2 eq) and 130 μL pyrrolidine (1.6 mmol, 1.2 eq) in 10 mL ethanol was refluxed 3 h. The reaction was concentrated and purified on silica gel column eluting with EA:Hex. 160 mg of a yellow solid was collected. m/z=398.0

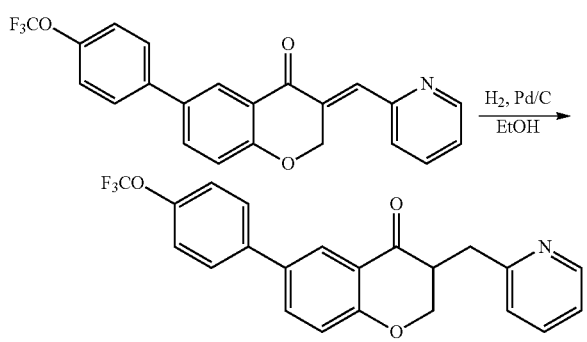

Synthesis of 3-(pyridin-2-ylmethyl)-6-(4-(trifluoromethoxy)phenyl)chroman-4-one. A solution of 150 mg 3-(pyridin-2-ylmethylene)-6-(4-(trifluoromethoxy)phenyl)chroman-4-one (0.38 mmol) in 20 mL EtOH with catalytic Pd/C was stirred under 1 atm of hydrogen gas for 16 h. The reaction was filtered through celite and the filtrate concentrated. The filtrate was purified on silica gel column eluting with EA:Hex. 85 mg of an off-white solid was collected. m/z=400.

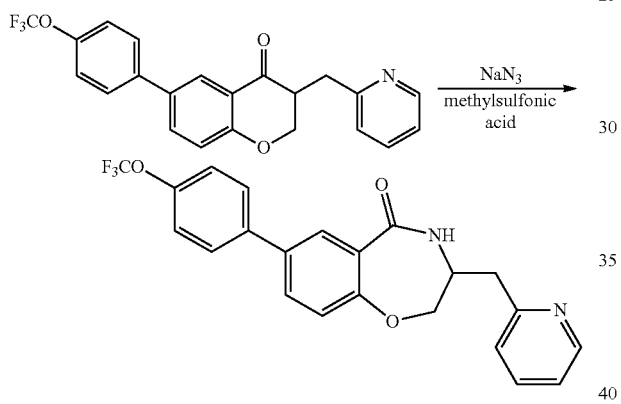

Synthesis of 3-(pyridin-2-ylmethyl)-7-(4-(trifluoromethoxy)phenyl)-3,4-dihydrobenzo[f][1,4]oxazepin-5(2H)-one. To a solution of 72 mg 3-(pyridin-2-ylmethyl)-6-(4-(trifluoromethoxy)phenyl)chroman-4-one (0.18 mmol) in 1 mL methylsulfonic acid 35 mg sodium azide (0.54 mmol) was added. After 1 h, reaction was diluted with 5 mL water and neutralized with addition of 1N NaOH solution. The precipitate was filter off to afford 65 mg off-white powder of product. m/z=415.0

Example 137

7-(4-(cyclobutylmethoxy)phenyl)-4-(pyrimidin-2-ylmethyl)-3,4-dihydrobenzo[f][1,4]oxazepin-5(2H)-one (Compound II-144)

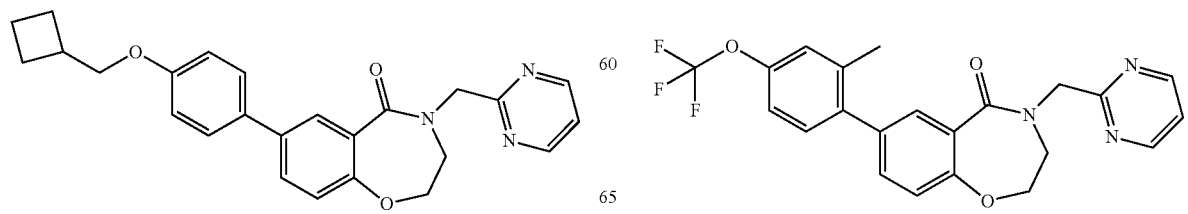

Compound II-144 was prepared according to example 25 using 2-(4-(cyclobutylmethoxy)phenyl)-4,4,5,5-tetramethyl-1,3,2-dioxaborolane. MS found for $C_{25}H_{25}N_3O_3$ as $(M+H)^+$ 416.22 $^1$H NMR (400 MHz, dmso-$d_6$): $^1$H-NMR (DMSO) δ: 8.78 (d, J=5.2 Hz, 2H), 7.86 (d, J=2.0 Hz, 1H), 7.72 (dd, J=2.4-8.4 Hz, 1H), 7.54 (d, J=8.4 Hz, 2H), 7.41 (t, J=5.2 Hz, 1H), 7.09 (d, J=8.4 Hz, 1H), 6.99 (d, J=8.8 Hz, 2H), 4.97 (s, 2H), 4.48 (t, J=4.4 Hz, 2H), 3.97 (d, J=6.8 Hz, 2H), 3.74 (t, J=4.8 Hz, 2H), 2.75-2.67 (m, 1H), 2.09-2.03 (m, 2H), 1.94-1.79 (m, 4H).

Example 138

4-(pyrimidin-2-ylmethyl)-7-(6-(2,2,2-trifluoroethyl)pyridin-3-yl)-3,4-dihydrobenzo[f][1,4]oxazepin-5(2H)-one (Compound VI-24)

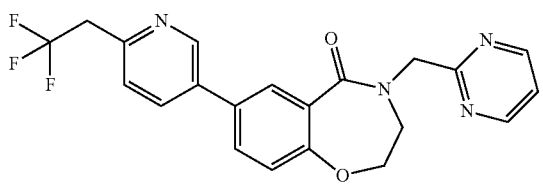 [SMILES: O=C1c2cc(-c3ccc(CC(F)(F)F)nc3)ccc2OCCN1Cc1ncccn1]

Compound VI-24 was prepared according to example 25 using 5-(4,4,5,5-tetramethyl-1,3,2-dioxaborolan-2-yl)-2-(2,2,2-trifluoroethyl)pyridine.

Example 139

7-(2-methyl-4-(trifluoromethyl)phenyl)-4-(pyrimidin-2-ylmethyl)-3,4-dihydrobenzo[f][1,4]oxazepin-5(2H)-one (Compound II-145)

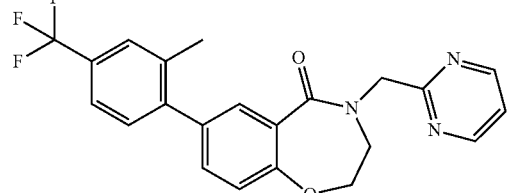

Compound II-145 was prepared according to example 25 using 2-methyl-4-(trifluoromethyl)phenylboronic acid. MS found for C22H18F3N3O2 as $(M+H)^+$ 414.32

Example 140

7-(2-methyl-4-(trifluoromethoxy)phenyl)-4-(pyrimidin-2-ylmethyl)-3,4-dihydrobenzo[f][1,4]oxazepin-5(2H)-one (Compound II-146)

Compound II-146 was prepared according to example 25 using 2-methyl-4-(trifluoromethoxy)phenylboronic acid. MS found for C22H18F3N3O3 as (M+H)+ 430.19 ¹H NMR (400 MHz, dmso-d₆): ¹H-NMR (DMSO) δ: 8.77 (d, J=5.2 Hz, 2H), 7.64 (d, J=2.4 Hz, 1H), 7.48 (dd, J=2.4-8.4 Hz, 1H), 7.40 (t, J=4.8 Hz, 1H), 7.31 (d, J=8.4 Hz, 2H), 7.23 (d, J=8.8 Hz, 1H), 7.11 (d, J=8.4 Hz, 1H), 4.96 (s, 2H), 4.52 (t, J=4.4 Hz, 2H), 3.78 (t, J=4.4 Hz, 2H), 2.25 (s, 3H).

Example 141

7-(4-(difluoromethyl)phenyl)-4-(pyridin-2-ylmethyl)-3,4-dihydrobenzo[f][1,4]oxazepin-5(2H)-one (Compound II-157)

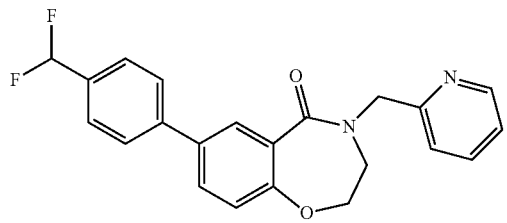 [SMILES: O=C1c2cc(-c3ccc(C(F)F)cc3)ccc2OCCN1Cc1ccccn1]

Compound II-157 was prepared according to example 25 using 4-(difluoromethyl)phenylboronic acid. MS found for C22H18F2N2O2 as (M+H)+ 381.20 ¹H NMR (400 MHz, dmso-d₆): ¹H-NMR (DMSO) δ: 8.54 (s, 1H), 8.02 (s, 1H), 7.85-7.80 (m, 4H), 7.65 (d, J=7.6 Hz, 2H), 7.38-7.31 (m, 2H), 7.16 (d, J=8.0 Hz, 1H), 7.08 (t, J=55.6 Hz, 1H), 4.87 (s, 2H), 4.40 (s, 2H), 3.71 (s, 2H).

Example 142

4-(pyridin-2-ylmethyl)-7-(2-(trifluoromethyl)pyridin-4-yl)-3,4-dihydrobenzo[f][1,4]oxazepin-5(2H)-one (Compound VI-25)

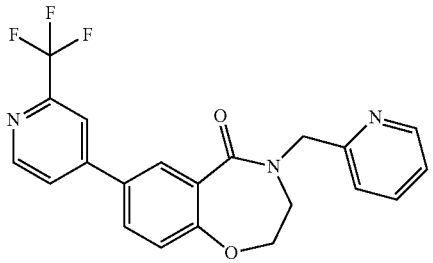 [SMILES: O=C1c2cc(-c3ccnc(C(F)(F)F)c3)ccc2OCCN1Cc1ccccn1]

Compound VI-25 was prepared according to example 25 using 4-(4,4,5,5-tetramethyl-1,3,2-dioxaborolan-2-yl)-2-(trifluoromethyl)pyridine.

Example 143

7-(4-chloro-3-fluorophenyl)-4-(pyridin-2-ylmethyl)-3,4-dihydrobenzo[f][1,4]oxazepin-5(2H)-one (Compound II-158)

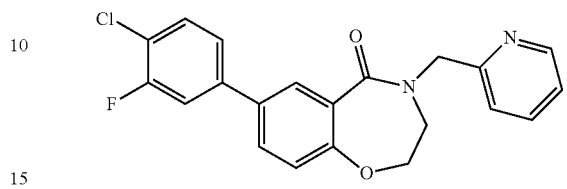

Compound II-158 was prepared according to example 25 using 4-chloro-3-fluorophenylboronic acid. MS found for C21H16ClFN2O2 as (M+H)+ 383.17 ¹H NMR (400 MHz, dmso-d₆): ¹H-NMR (DMSO) δ: 8.60 (d, J=4.8 Hz, 1H), 8.01 (d, J=7.2 Hz, 1H), 7.94 (d, J=2.4 Hz, 1H), 7.79 (dd, J=2.4-8.4 Hz, 1H), 7.69 (dd, J=2.0-10.8 Hz, 1H), 7.61-7.47 (m, 4H), 7.09 (d, J=8.4 Hz, 1H), 4.90 (s, 2H), 4.36 (t, J=4.8 Hz, 2H), 3.69 (t, J=4.8 Hz, 2H).

Example 144

7-(4-(difluoromethoxy)phenyl)-4-(pyridin-2-ylmethyl)-3,4-dihydrobenzo[f][1,4]oxazepin-5(2H)-one (Compound II-159)

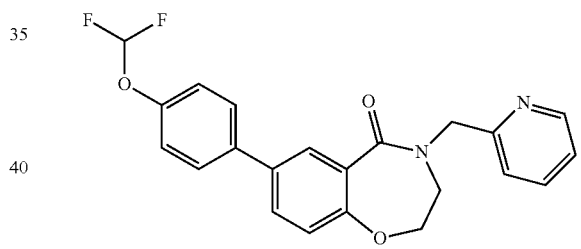

Compound II-159 was prepared according to example 25 using 2-(4-(difluoromethoxy)phenyl)-4,4,5,5-tetramethyl-1,3,2-dioxaborolane. MS found for C22H18F2N2O3 as (M+H)+ 397.22.

Example 145

4-(pyridin-2-ylmethyl)-7-(5-(trifluoromethyl)pyridin-2-yl)-3,4-dihydrobenzo[f][1,4]oxazepin-5(2H)-one (Compound VI-26)

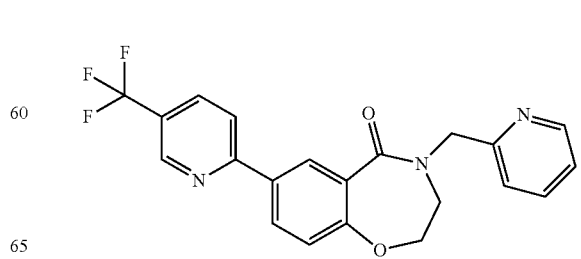

Compound VI-26 was prepared according to example 25 using 2-(4,4,5,5-tetramethyl-1,3,2-dioxaborolan-2-yl)-5-(trifluoromethyl)pyridine. MS found for C21H16F3N3O2 as (M+H)+ 400.21.

Example 146

7-(1-methyl-1H-pyrazol-4-yl)-4-(pyrimidin-2-ylmethyl)-3,4-dihydrobenzo[f][1,4]oxazepin-5(2H)-one (Compound VI-27)

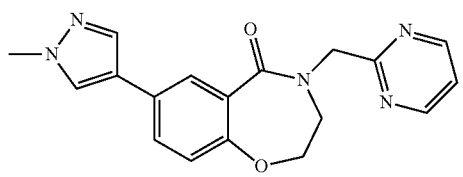 [SMILES: Cn1cc(-c2ccc3c(c2)C(=O)N(Cc2ncccn2)CCO3)cn1]

Compound VI-27 was prepared according to example 25 using 1-methyl-4-(4,4,5,5-tetramethyl-1,3,2-dioxaborolan-2-yl)-1H-pyrazole.

Example 147

7-(1-isopropyl-1H-pyrazol-4-yl)-4-(pyrimidin-2-ylmethyl)-3,4-dihydrobenzo[f][1,4]oxazepin-5(2H)-one (Compound VI-28)

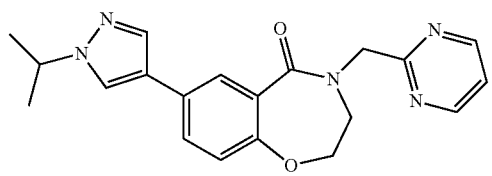 [SMILES: CC(C)n1cc(-c2ccc3c(c2)C(=O)N(Cc2ncccn2)CCO3)cn1]

Compound VI-28 was prepared according to example 25 using 1-isopropyl-4-(4,4, 5,5-tetramethyl-1,3,2-dioxaborolan-2-yl)-1H-pyrazole.

Example 148

7-(1-methyl-1H-pyrazol-3-yl)-4-(pyridin-2-ylmethyl)-3,4-dihydrobenzo[f][1,4]oxazepin-5(2H)-one (Compound VI-29)

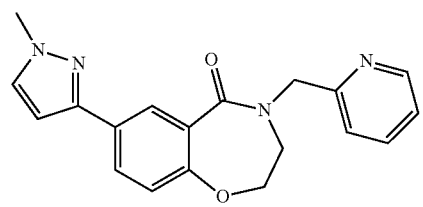 [SMILES: Cn1ccc(-c2ccc3c(c2)C(=O)N(Cc2ccccn2)CCO3)n1]

Compound VI-29 was prepared according to example 25 using 1-methyl-3-(4,4,5,5-tetramethyl-1,3,2-dioxaborolan-2-yl)-1H-pyrazole.

Example 149

7-(2-isopropylthiazol-4-yl)-4-(pyridin-2-ylmethyl)-3,4-dihydrobenzo[f][1,4]oxazepin-5(2H)-one (Compound VI-30)

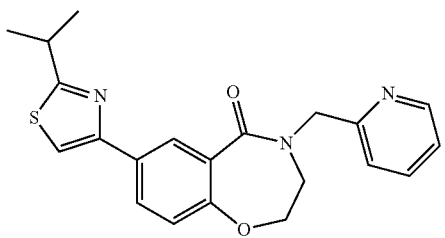 [SMILES: CC(C)c1nc(-c2ccc3c(c2)C(=O)N(Cc2ccccn2)CCO3)cs1]

Compound VI-30 was prepared according to example 25 using 2-isopropyl-4-(4,4,5,5-tetramethyl-1,3,2-dioxaborolan-2-yl)thiazole. MS found for C21H21N3O2S as (M+H)+ 380.20 $^1$H NMR (400 MHz, dmso-$d_6$): $^1$H-NMR (DMSO) δ: 8.53 (d, J=4.8 Hz, 1H), 8.26 (d, J=2.0 Hz, 1H), 8.01 (dd, J=2.0-8.8 Hz, 1H), 7.94 (s, 1H), 7.78 (t, J=7.2 Hz, 1H), 7.36-7.28 (m, 2H), 7.09 (d, J=8.0 Hz, 1H), 4.85 (s, 2H), 4.36 (t, J=4.4 Hz, 2H), 3.66 (t, J=4.8 Hz, 2H), 1.36 (d, J=6.8 Hz, 6H).

Example 150

4-(pyrimidin-2-ylmethyl)-7-(2,3,4-trifluorophenyl)-3,4-dihydrobenzo[f][1,4]oxazepin-5(2H)-one (Compound II-162)

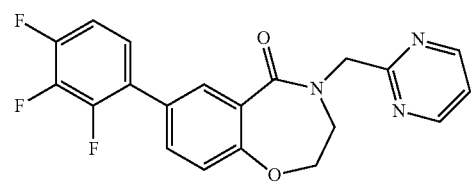 [SMILES: O=C1c2cc(-c3ccc(F)c(F)c3F)ccc2OCCN1Cc1ncccn1]

Compound II-162 was prepared according to example 25 using 2,3,4-trifluorophenylboronic acid. MS found for C20H14F3N3O2 as (M+H)+ 386.14.

Example 151

7-(3,4-difluorophenyl)-4-(pyrimidin-2-ylmethyl)-3,4-dihydrobenzo[f][1,4]oxazepin-5(2H)-one (Compound II-163)

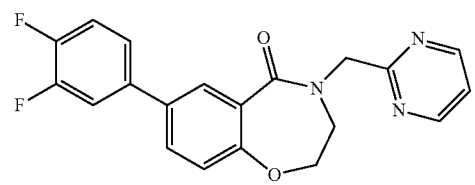 [SMILES: O=C1c2cc(-c3ccc(F)c(F)c3)ccc2OCCN1Cc1ncccn1]

Compound II-163 was prepared according to example 25 using 3,4-difluorophenylboronic acid. MS found for C20H15F2N3O2 as (M+H)+ 368.15.

Example 152

4-(pyridin-2-ylmethyl)-7-(5-(trifluoromethyl)thiophen-2-yl)-3,4-dihydrobenzo[f][1,4]oxazepin-5(2H)-one (Compound VI-31)

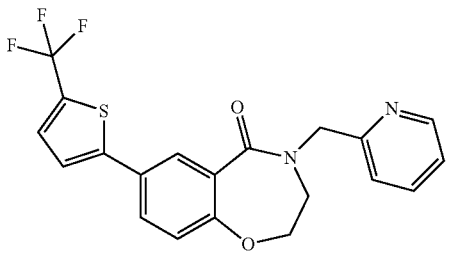 [SMILES: O=C1c2cc(-c3ccc(C(F)(F)F)s3)ccc2OCCN1Cc1ccccn1]

Compound VI-31 was prepared according to example 29 using 2-bromo-5-(trifluoromethyl)thiophene. MS found for C20H15F3N2O2S as (M+H)+ 405.16 $^1$H NMR (400 MHz, dmso-$d_6$): $^1$H-NMR (DMSO) δ: 8.53 (d, J=4.8 Hz, 1H), 8.02 (d, J=2.0 Hz, 1H), 7.87-7.71 (m, 3H), 7.59 (d, J=3.2 Hz, 1H), 7.37-7.28 (m, 2H), 7.13 (d, J=8.4 Hz, 1H), 4.85 (s, 2H), 4.40 (t, J=4.8 Hz, 2H), 3.70 (t, J=4.8 Hz, 2H).

Example 153

7-(5-cyclopropylthiophen-2-yl)-4-(pyridin-2-ylmethyl)-3,4-dihydrobenzo[f][1,4]oxazepin-5(2H)-one (Compound VI-32)

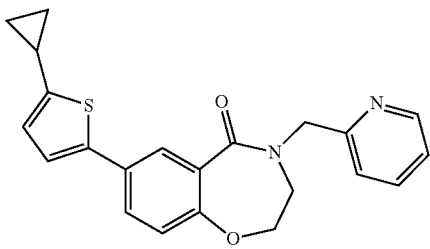 [SMILES: O=C1c2cc(-c3ccc(C4CC4)s3)ccc2OCCN1Cc1ccccn1]

Compound VI-32 was prepared according to example 29 using 2-bromo-5-cyclopropylthiophene. MS found for C22H20N2O2S as (M+H)+ 377.18 $^1$H NMR (400 MHz, dmso-$d_6$): $^1$H-NMR (DMSO) δ: 8.53 (d, J=4.8 Hz, 1H), 7.81-7.76 (m, 2H), 7.68 (dd, J=2.4-8.0 Hz, 1H), 7.36-7.24 (m, 3H), 7.04 (d, J=8.4 Hz, 1H), 6.80 (d, J=3.6 Hz, 1H), 4.84 (s, 2H), 4.34 (t, J=5.2 Hz, 2H), 3.66 (t, J=5.2 Hz, 2H), 2.14-2.10 (m, 1H), 1.02-0.97 (m, 2H), 0.71-0.67 (m, 2H).

Example 154

7-(2-methylthiazol-4-yl)-4-(pyridin-2-ylmethyl)-3,4-dihydrobenzo[f][1,4]oxazepin-5(2H)-one (Compound VI-33)

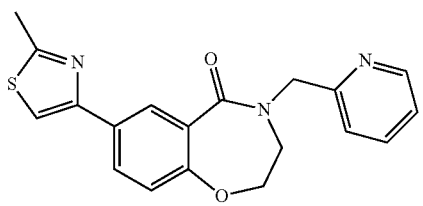 [SMILES: Cc1nc(-c2ccc3c(c2)C(=O)N(Cc2ccccn2)CCO3)cs1]

Compound VI-33 was prepared according to example 29 using 4-bromo-2-methylthiazole.

Example 155

4-benzyl-7-(4-(trifluoromethyl)phenyl)-3,4-dihydro-1H-benzo[e][1,4]diazepine-2,5-dione (Compound X-8)

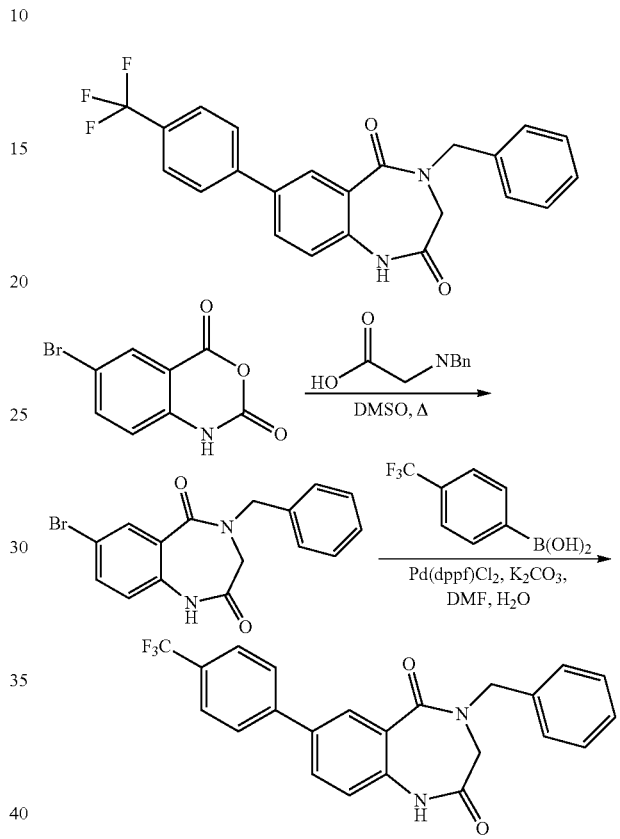

A mixture of 5-bromoisatoic anhydride (1 g, 4.13 mmol), N-benzylglycine (0.628 g, 4.13 mmol) and DMSO (3 mL) was heated in the microwave at 200° C. for one hour. After cooling, the mixture was diluted with water and the precipitate was filtered off, washed with water and dried, giving 4-benzyl-7-bromo-3,4-dihydro-1H-benzo[e][1,4]diazepine-2,5-dione (1.4 g, 98%) as an off-white powder.

4-Benzyl-7-bromo-3,4-dihydro-1H-benzo[e][1,4]diazepine-2,5-dione (1.4 g, 4.05 mmol) was combined with 4-(trifluoromethyl)phenylboronic acid (0.77 g, 4.05 mmol), potassium carbonate (1 g) and [1,1'-Bis(diphenylphosphino)ferrocene]dichloropalladium(II) (148 mg, 0.202 mmol) in 5 mL DMF. Water (3 mL) was added and the mixture was heated under nitrogen atmosphere at 80° C. for three hours. After cooling the mixture was diluted with ethyl acetate, washed with water and brine, dried with magnesium sulfate and evaporated. Purification by silica-gel chromatography (20-100% ethyl acetate in hexane) followed by recrystallization gave 4-benzyl-7-(4-(trifluoromethyl)phenyl)-3,4-dihydro-1H-benzo[e][1,4]diazepine-2,5-dione (1.25 g, 75%) as a white powder.

$^1$H-NMR (DMSO) δ: 10.61 (s, 1H), 8.13 (d, J=1.6 Hz, 1H), 7.92 (d, J=8.4 Hz, 3H), 7.11 (d, J=8.4 Hz, 2H), 7.36-7.25 (m, 5H), 7.22 (d, J=8.4 Hz, 1H), 4.79 (s, 2H), 3.92 (s, 2H). MS: 411 (MH+).

Example 156

4-benzyl-1-methyl-7-(4-(trifluoromethyl)phenyl)-3,4-dihydro-1H-benzo[e][1,4]diazepine-2,5-dione (Compound X-11)

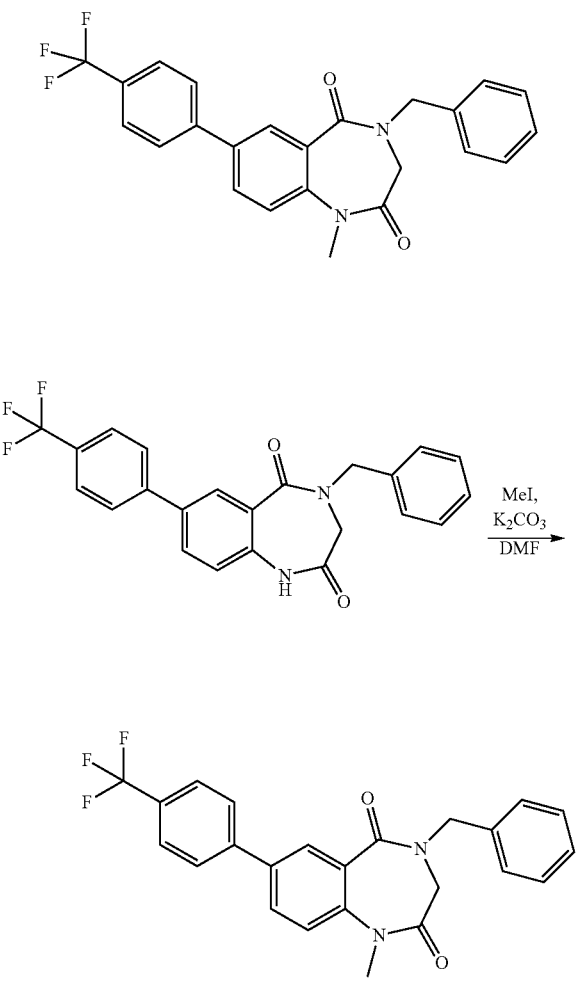

4-Benzyl-7-(4-(trifluoromethyl)phenyl)-3,4-dihydro-1H-benzo[e][1,4]diazepine-2,5-dione (9.80 mg, 0.024 mmol) and $K_2CO_3$ (10 mg, 0.072 mmol, 3.0 equiv.) were placed in a 0.5-2 mL Smith process vial under a nitrogen atmosphere. To the vial were added DMF (0.5 mL) and iodomethane (2.25 µL, 0.036 mmol, d=2.28 g/cm³, 1.5 equiv) at room temperature. After heating, stirred, at 60° C. for 2 hours, the reaction mixture was concentrated en vacuo. The resulting crude mixture was diluted with acetonitrile (1 mL), filtered through a syringe filter and injected into a preparative HPLC to give desired product (4-benzyl-1-methyl-7-(4-(trifluoromethyl)phenyl)-3,4-dihydro-1H-benzo[e][1,4]diazepine-2,5-dione, 1.8 mg) as a yellow film.

$^1$H-NMR (400 MHz; $CD_3CN$) δ 8.16 (d, 1H, J=2 Hz), 7.93 (dd, 1H, J=8.4 Hz, 2 Hz), 7.92 (d, 2H, J=7.8 Hz), 7.82 (d, 2H, J=7.8 Hz), 7.47 (d, 1H, J=8.4 Hz), 4.98 (d, 1H, J=15 Hz), 4.73 (d, 1H, J=15 Hz), 4.10 (d, 1H, J=15 Hz), 3.70 (d, 1H, J=15 Hz), 3.37 (s, 3H). $^{19}$F-NMR (400 MHz; $CD_3CN$) δ −63.96 (s, 3F). LCMS (EI: 70 eV) 447.1 (M++Na), 425.1 (M++1).

Example 157

(S)-3-(2-hydroxyethyl)-1-methyl-7-(4-(trifluoromethoxy)phenyl)-3,4-dihydro-1H-benzo[e][1,4]diazepine-2,5-dione (Compound X-1)

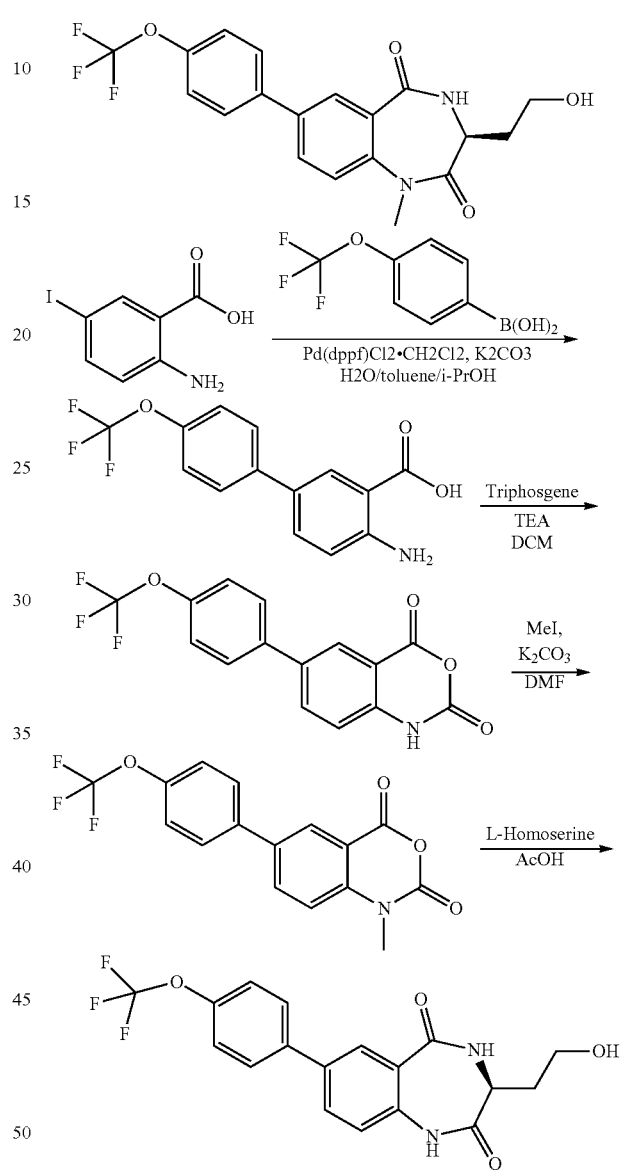

2-Amino-5-iodobenzoic acid (1.327 g, 5.05 mmol), 4-trifluoromethoxyboronic acid (1.455 g, 7.07 mmol, 1.4 equiv.), Pd(dppf)Cl₂·CH₂Cl₂ (183.0 mg, 0.252 mmol, 5 mol %) and $K_2CO_3$ (1.604 g, 11.61 mmol, 2.3 equiv.) were dissolved in a mixture of H2O/toluene/i-PrOH (2.5 mL: 5 mL: 2.5 mL) in a 10 mL Smith process vial equipped with a stir bar under a nitrogen atmosphere. The mixture was heated at 90° C. for 1 hour. After aqueous workup and removal of volatile solvents en vacuo, the mixture was purified by automated silica-gel column chromatography using an EtOAc/hexane gradient as the eluent. The purification gave the desired product (4-amino-4'-(trifluoromethoxy)biphenyl-3-carboxylic acid, 462.0 mg) as a colorless powder.

To a suspension of 4-amino-4'-(trifluoromethoxy)biphenyl-3-carboxylic acid (462.0 mg, 1.554 mmol) in $CH_2Cl_2$ (10 mL) in a round bottomed flask was added triethylamine (210 μL, 1.492 mmol, d=0.726 g/cm³, 0.96 equiv.). Flask was charged with nitrogen, cooled to 0° C. and a solution of triphosgene (148.0 mg, 0.497 mmol, 0.32 equiv.) in 2 mL DCM was added, followed by a solution of N,N-dimethyl-4-aminopyridine (30 mg, 0.246 mmol, 25 mol %) in CH$_2$Cl$_2$ (2 mL). Reaction mixture was allowed to stir 2 hours, then quenched with a small portion of 1N HCl. Reaction mixture with resulting precipitate was filtered through a disposable filter funnel and air-dried to give desired product (6-(4-(trifluoromethoxy)phenyl)-1H-benzo[d][1,3]oxazine-2,4-dione, 348.6 mg) as a colorless solid.

6-(4-(Trifluoromethoxy)phenyl)-1H-benzo[d][1,3]ox-azine-2,4-dione (348.6 mg, 1.077 mmol) and K$_2$CO$_3$ (228 mg, 2.153 mmol, 2 equiv.) were placed in a 0.5-2 mL Smith process vial. To the vial was added DMF (3 mL) and iodomethane (101 μL, d=2.28, 1.615 mmol, 1.5 equiv.) at ambient temperature. The mixture was stirred overnight at room temperature and then filtered through a disposable filter funnel. Obtained filtrate was diluted with water to form precipitates, which were collected on a disposable filter funnel and allowed to air-dry to give desired product (1-methyl-6-(4-(trifluoromethoxy)phenyl)-1H-benzo[d][1,3]oxazine-2,4-dione, 357.2 mg) as a colorless solid.

1-Methyl-6-(4-(trifluoromethoxy)phenyl)-1H-benzo[d][1,3]oxazine-2,4-dione (60 mg, 0.178 mmol) and L-homoserine (23.3 mg, 0.196 mmol, 1.1 equiv.) were added to a magnetically stirred 0.5-2 mL Smith process vial containing 0.75 mL glacial acetic acid. Reaction mixture was then heated for 2 hours at 130° C. Excess acetic acid was then removed en vacuo, residue was dissolved into a minimal amount of acetonitrile and purified by reverse-phase preparative HPLC to give the title compound (7.6 mg) following removal of solvent as a clear yellow film.

LCMS (EI: 70 eV) 459.1 (M++Na), 437.1 (M++1)

Example 158

1-methyl-7-(4-(trifluoromethoxy)phenyl)-3,4-dihydro-1H-benzo[e][1,4]diazepine-2,5-dione (Compound X-2)

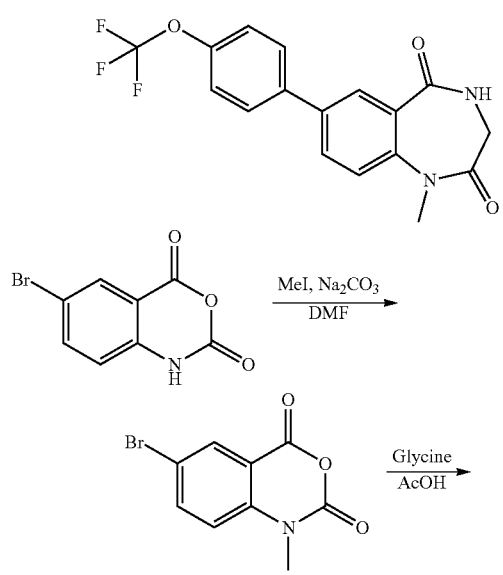

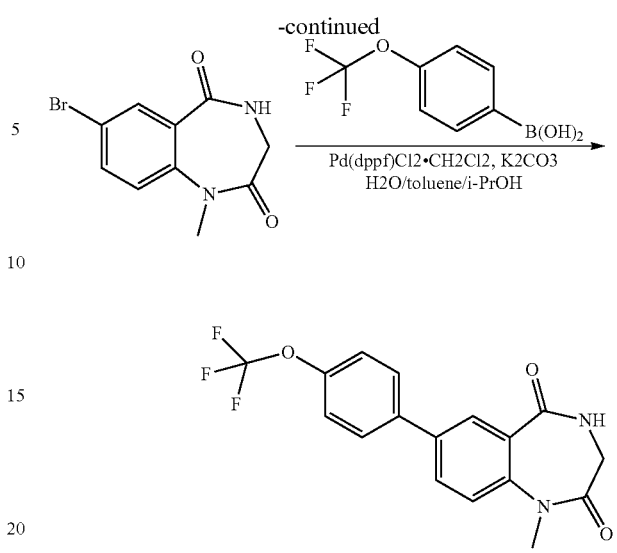

6-Bromo-1H-benzo[d][1,3]oxazine-2,4-dione (5.0 g, 20.66 mmol), iodomethane: (1.94 mL, d=2.28, 4.4 g, 31.0 mmol, 1.5 equiv.) and Na$_2$CO$_3$ (4.38 g, 41.3 mmol, 2 equiv.) were placed in a round bottomed flask. To the flask were added DMF (40 mL) at ambient temperature. The mixture was stirred overnight at room temperature and then filtered through a glass filter. Obtained filtrate was diluted with water to form precipitates. The precipitates were dissolved in EtOAc and the solution was dried over MgS(O)$_4$. The solvent was removed under reduced pressure. At this point, since the conversion was ~50%, K$_2$CO$_3$ (14.3 g, 103.3 mmol, 5 equiv.) and iodomethane (2.58 mL, d=2.28, 41.3 mmol, 2.0 equiv.) were added to the solution of the crude material in DMF. The mixture was heated at 30° C. so that the reaction can go to completion and then filtered through a glass filter. Obtained filtrate was diluted with water to form precipitates. Formed precipitates were filtered through a glass filter to give the desired product (6-bromo-1-methyl-1H-benzo[d][1,3]oxazine-2,4-dione). This was used for the subsequent step without further purification.

6-Bromo-1-methyl-1H-benzo[d][1,3]oxazine-2,4-dione (5.29 g, 20.66 mmol) and glycine (1.7 g, 22.73 mmol, 1.1 equiv.) were dissolved in AcOH (100 mL) in a round bottomed flask. The mixture was heated under reflux conditions for 2 hours. The mixture was purified by automated silica-gel column chromatography using EtOAc/hexane gradient as the eluent. The purification give the desired product (7-bromo-1-methyl-3,4 dihydro-1H-benzo[e][1,4]diazepine-2,5-dione, colorless powder, 446.7 mg).

7-Bromo-1-methyl-3,4-dihydro-1H-benzo[e][1,4]diazepine-2,5-dione (446.7 mg, 1.661 mmol), 4-trifluoromethoxyboronic acid (445.0 mg, 2.159 mmol, 1.3 equiv.) Pd(dppf)Cl$_2$.CH$_2$Cl$_2$ (120.0 mg, 0.166 mmol, 10 mol %) and K$_2$CO$_3$ (482.0 mg, 3.49 mmol, 2.1 equiv.) were dissolved in a mixture of H2O/toluene/i-PrOH (2.5 mL: 5 mL: 2.5 mL) in a 10 mL round bottomed flask under a nitrogen atmosphere. The mixture was heated at 60° C. for 64 hours. The mixture was purified by automated silica-gel column chromatography using EtOAc/hexane gradient as the eluent. Evaporation of solvent en vacuo gave the title compound (415.0 mg) as a white powder.

LCMS (EI: 70 eV) 373.1 (M++Na), 351.1 (M++1)

Example 159

1-methyl-4-(pyrimidin-2-ylmethyl)-7-(4-(trifluoromethoxy)phenyl)-3,4-dihydro-1H-benzo[e][1,4]diazepine-2,5-dione (Compound X-3)

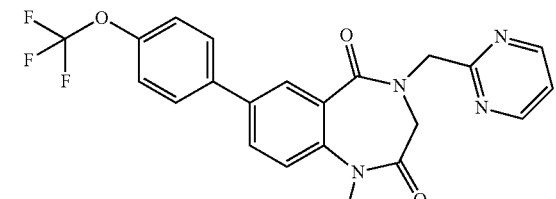

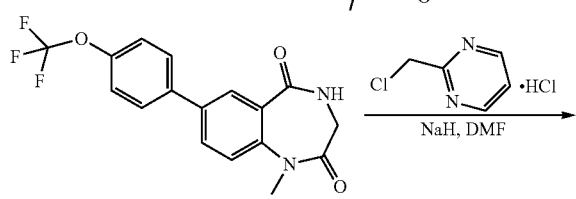

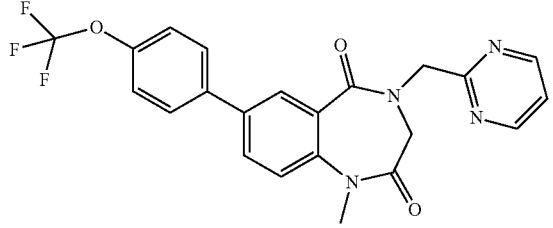

1-Methyl-7-(4-(trifluoromethoxy)phenyl)-3,4-dihydro-1H-benzo[e][1,4]diazepine-2,5-dione (22.9 mg, 0.065 mmol) and NaH (15.6 mg, 0.650 mmol, 10.0 equiv.) were placed in a 0.5-2 mL Smith process vial. To the vial was added DMF (0.5 mL) followed by 2-(chloromethyl)pyrimidine hydrochloride (53.9 mg, 0.327 mmol, 5 equiv.) was added at room temperature. After stirring for 50 min, reaction was quenched with AcOH. Resulting mixture was filtered and purified via preparative reverse phase HPLC to give the title compound (2.2 mg) as a clear yellow film.

LCMS (EI: 70 eV) 443.1 (M++1)

Example 160

1-methyl-4-(pyridin-2-ylmethyl)-7-(4-(trifluoromethoxy)phenyl)-3,4-dihydro-1H-benzo[e][1,4]diazepine-2,5-dione (Compound X-4)

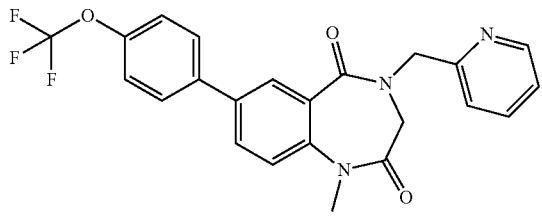 [SMILES: CN1C(=O)CN(Cc2ccccn2)C(=O)c2cc(-c3ccc(OC(F)(F)F)cc3)ccc21]

Compound X-4 was prepared according to the above example using the appropriate starting materials.

Example 161

4-(4-(1H-pyrazol-1-yl)benzyl)-1-methyl-7-(4-(trifluoromethoxy)phenyl)-3,4-dihydro-1H-benzo[e][1,4]diazepine-2,5-dione (Compound X-6)

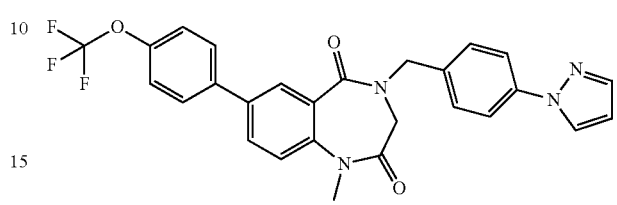

Compound X-6 was prepared according to the above example using the appropriate starting materials.

Example 162

1-(4-methoxybenzyl)-7-(4-(trifluoromethoxy)phenyl)-3,4-dihydro-1H-benzo[e][1,4]diazepine-2,5-dione (Compound X-5)

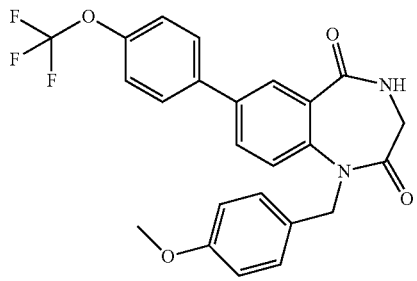

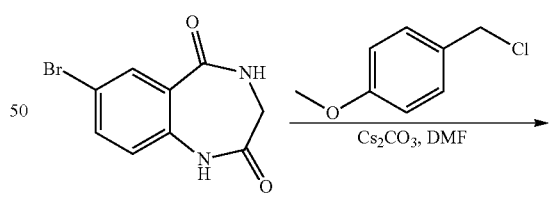

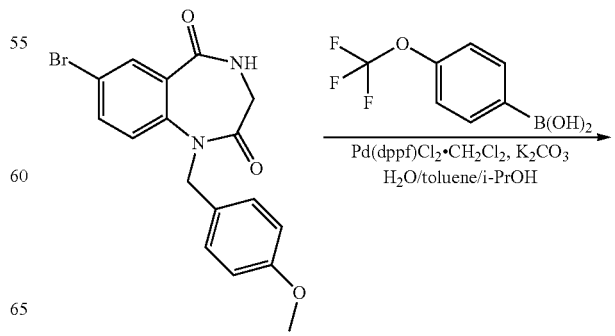

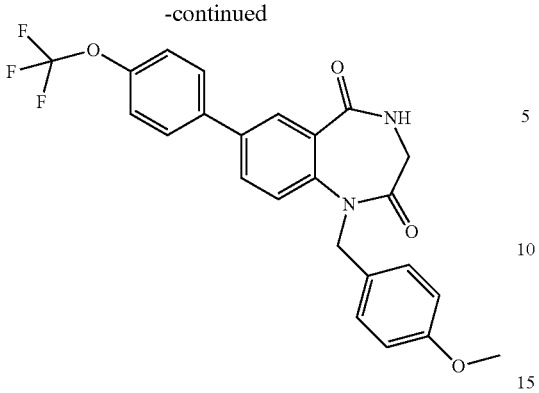

7-Bromo-3,4-dihydro-1H-benzo[e][1,4]diazepine-2,5-dione (510.0 mg, 2 mmol) and Cs$_2$CO$_3$ (1.955 mg, 6 mmol, 3 equiv.) were placed in a round bottomed flask. To the reaction vessel was added DMF (10 mL) and 4-methoxybenzyl chloride (273 μL, 1.615 mmol, d=1.15 g/mL, 1 equiv.) at ambient temperature. The mixture was stirred overnight at room temperature and then filtered through a disposable filter funnel. Resulting filtrate was concentrated en vacuo and purified by automated silica-gel column chromatography using an EtOAc/hexane gradient as the eluent to give the desired product (7-bromo-1-(4-methoxybenzyl)-3,4-dihydro-1H-benzo[e][1,4]diazepine-2,5-dione, 378.3 mg) as a colorless solid.

7-Bromo-1-methyl-3,4-dihydro-1H-benzo[e][1,4]diazepine-2,5-dione (375.0 mg, 1.007 mmol), 4-trifluoromethoxyboronic acid (270.0 mg, 1.31 mmol, 1.3 equiv.) Pd(dppf)Cl$_2$.CH$_2$Cl$_2$ (72.9.0 mg, 0.101 mmol, 10 mol %) and K$_2$CO$_3$ (292.0 mg, 2.116 mmol, 2.1 equiv.) were dissolved in a mixture of H$_2$O/toluene/i-PrOH (1.25 mL: 2.5 mL: 1.25 mL) in a 2-5 mL Smith process vial equipped with a stir bar under a nitrogen atmosphere. The mixture was heated at 50° C. for 17 hours. After aqueous workup and removal of volatile solvents en vacuo, the mixture was purified by automated silica-gel column chromatography using an EtOAc/hexane gradient as the eluent. The purification gave the title compound (419 mg) as a colorless powder.

LCMS (EI: 70 eV) 479.1 (M++Na), 457.1 (M++1)

Example 163

4-benzyl-7-(4-(trifluoromethoxy)phenyl)-3,4-dihydropyrido[4,3-f][1,4]oxazepin-5(2H)-one (Compound XII-1)

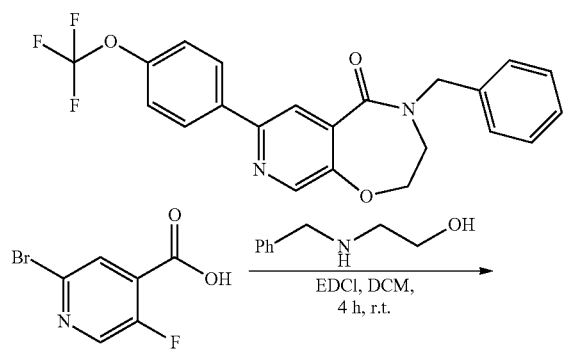

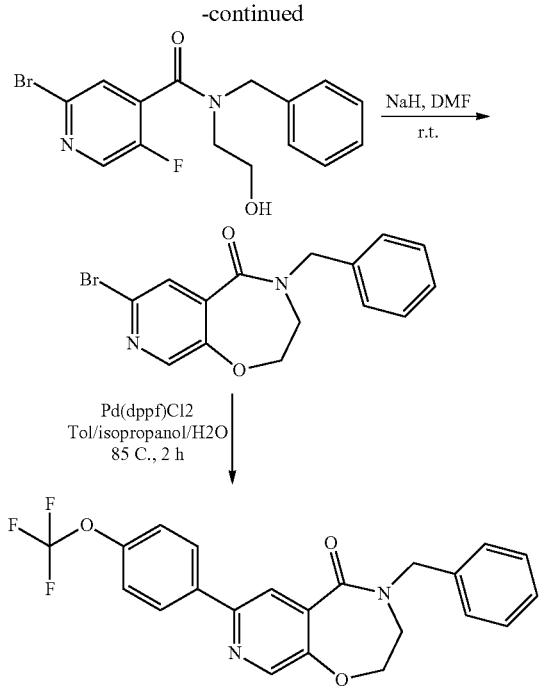

To 2-bromo-5-fluoroisonicotinic acid (5 g, 22.72 mmol) benzyl amino ethanol (4.20 g, 27.27 mmol, 1.2 eq) was added in the presence of EDCI (5.2 g, 27.27 mmol, 1.2 eq) in dichloromethane (100 mL) and stirred at room temperature for 4 h. The reaction mixture was diluted with dichloromethane, washed with water, brine, dried over sodium sulfate and concentrated (5.0 g). The residue (5.0 g, 14.16 mmol) was cyclized by dissolving in DMF (20 mL), sodium hydride (1.2 g, 28 mmol) was added and stirred at room temperature for 2 h. The reaction mixture was neutralized with dil. HCl and extracted with ethyl acetate, washed with water, brine, dried over sodium sulfate and concentrated. Purified by flash chromatography furnished 4.4 g of the cyclized product.

The Suzuki coupling was performed under standard conditioned explained in the other procedures using Pd(dppf) Cl$_2$. Mass (M+H)$^+$ 415.1. CDCl$_3$: 8.46 (S, 1H), 8.28 (S, 1H), 8.05 (d, J=8.8 Hz, 2H), 7.42-7.32 (m, 5H), 7.30 (d, J=8.0 Hz, 2H), 4.86 (s, 2H), 4.31 (t, J=4 Hz, 2H), 3.57 (t, J=4 Hz, 2H)

Example 164

4-(cyclopropylmethyl)-7-(4-(trifluoromethoxy)phenyl)-3,4-dihydropyrido[4,3-f][1,4]oxazepin-5(2H)-one (Compound XII-9)

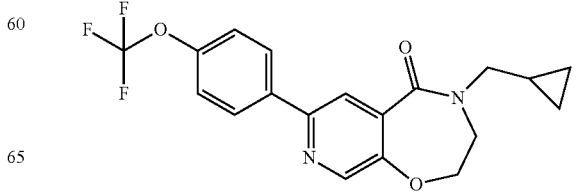

-continued

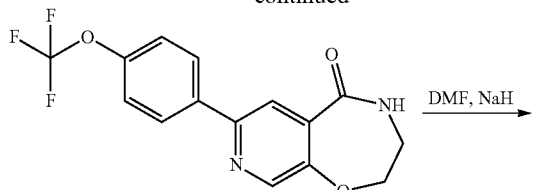

XII-4

DMF, NaH

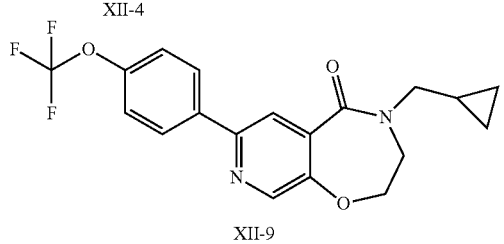

XII-9

Alkylation of the amide was performed using sodium hydride following the standard procedure to provide Compound XII-9. Mass (M+H)+ 379.0.

Example 165

4-(pyrimidin-2-ylmethyl)-7-(4-(trifluoromethoxy)phenyl)-3,4-dihydropyrido[4,3-f][1,4]oxazepin-5(2H)-one (Compound XII-5)

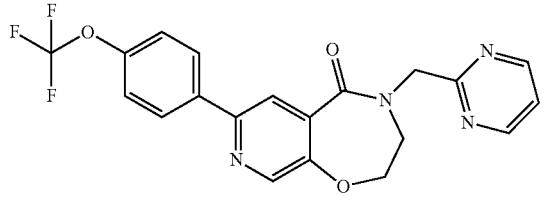 [SMILES: O=C1c2cc(-c3ccc(OC(F)(F)F)cc3)ncc2OCCN1Cc1ncccn1]

Compound XII-5 was prepared according to the Examples disclosed herein using the appropriate starting materials. Mass (M+H)+ 417.0.

Example 166

4-((3-methoxypyridin-2-yl)methyl)-7-(4-(trifluoromethoxy)phenyl)-3,4-dihydropyrido[4,3-f][1,4]oxazepin-5(2H)-one (Compound XII-10)

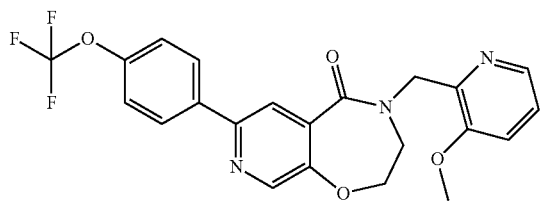 [SMILES: COc1cccnc1CN1CCOc2cnc(-c3ccc(OC(F)(F)F)cc3)cc2C1=O]

Compound XII-10 was prepared according to the Examples disclosed herein using the appropriate starting materials. Mass (M+H)+ 446.1. CDCl$_3$: 8.55 (s, 1H), 8.41 (s, 1H), 8.22 (s, 1H), 7.97 (d, J=8.2 Hz, 2H), 7.61 (d, J=2.8 Hz, 2H), 7.30 (d, J=8.4 Hz, 2H), 5.12 (s, 2H), 4.55 (t, J=4 Hz, 2H), 4.03 (s, 3H), 3.89 (t, J=4 Hz, 2 h).

Example 167

4-((4-methylpyrimidin-2-yl)methyl)-7-(4-(trifluoromethoxy)phenyl)-3,4-dihydropyrido[4,3-f][1,4]oxazepin-5(2H)-one (Compound XII-8)

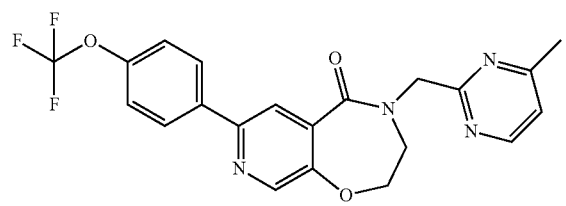 [SMILES: Cc1ccnc(CN2CCOc3cnc(-c4ccc(OC(F)(F)F)cc4)cc3C2=O)n1]

Compound XII-8 was prepared according to the Examples disclosed herein using the appropriate starting materials. Mass (M+H)+ 431.1. CDCl$_3$: 8.54 (d, J=4.8 Hz, 1H), 8.50 (s, 1H), 8.32 (s, 1H), 80.2 (d, J=8.8 Hz, 2H), 7.29 (d, J=83.4 Hz, 2H), 7.08 (d, J=5.2 Hz, 1H), 5.05 (s, 2H), 4.72 (t, J=4.4 Hz, 2H), 3.83 (t, J=4.4 Hz, 2H), 2.52 (s, 3H).

Example 168

4-((3-fluoropyridin-2-yl)methyl)-7-(4-(trifluoromethoxy)phenyl)-3,4-dihydropyrido[4,3-f][1,4]oxazepin-5(2H)-one (Compound XII-11)

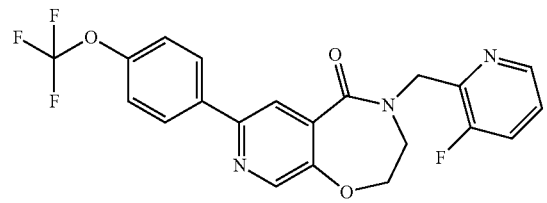 [SMILES: O=C1c2cc(-c3ccc(OC(F)(F)F)cc3)ncc2OCCN1Cc1ncccc1F]

Compound XII-11 was prepared according to the Examples disclosed herein using the appropriate starting materials. Mass (M+H)+ 434.0. CDCl$_3$: 8.42 (s, 1H), 8.30 (d, J=4.4 Hz, 1H), 8.23 (s, 1H), 7.96 (d, J=8.4 Hz, 2H), 7.37 (t, J=8.4 Hz, 1H), 7.22 (d, J=8 Hz, 2H), 7.21 (d, J=8.4 Hz, 1H), 4.99 (s, 2H), 4.53 (t, J=4.4 Hz, 2H), 3.78 (t, J=4 Hz, 2H).

Example 169

4-((4-methoxypyrimidin-2-yl)methyl)-7-(4-(trifluoromethoxy)phenyl)-3,4-dihydropyrido[4,3-f][1,4]oxazepin-5(2H)-one (Compound XII-14)

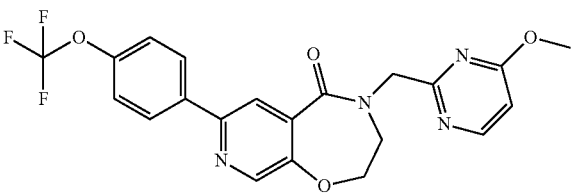 [SMILES: COc1ccnc(CN2CCOc3cnc(-c4ccc(OC(F)(F)F)cc4)cc3C2=O)n1]

Compound XII-14 was prepared according to the Examples disclosed herein using the appropriate starting materials. Mass (M+H)+ 447.1.

Example 170

4-benzyl-9-fluoro-7-(4-(trifluoromethoxy)phenyl)-3,4-dihydrobenzo[f][1,4]oxazepin-5(2H)-one (Compound II-165)

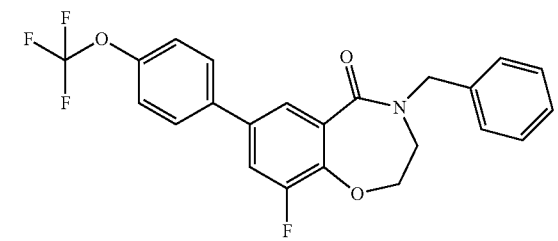

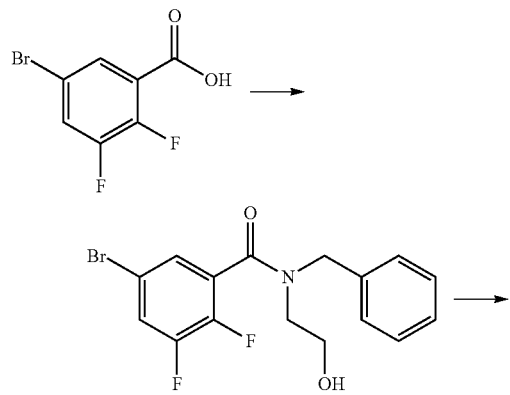

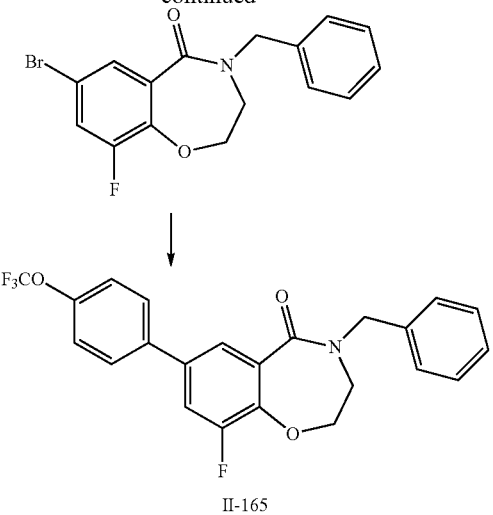

Compound II-165 was prepared according to the Examples disclosed herein using the appropriate starting materials. Mass (M+H)$^+$ 432.1. CDCl$_3$:7.80 (s, 1H), 7.53 (d, J=8.8 Hz, 2H), 7.37 (dd, J1=2.4 Hz, J2=11.2 Hz, 1H), 7.31 (d, J=4 Hz, 2H), 7.29-7.20 (m, 5H), 4.79 (s, 2H), 4.21 (t, J=5.2 Hz, 2H), 3.47 (t, J=5.2 Hz, 2H).

Example 171

4-benzyl-9-fluoro-7-(4-(trifluoromethyl)phenyl)-3,4-dihydrobenzo[f][1,4]oxazepin-5(2H)-one (Compound II-166)

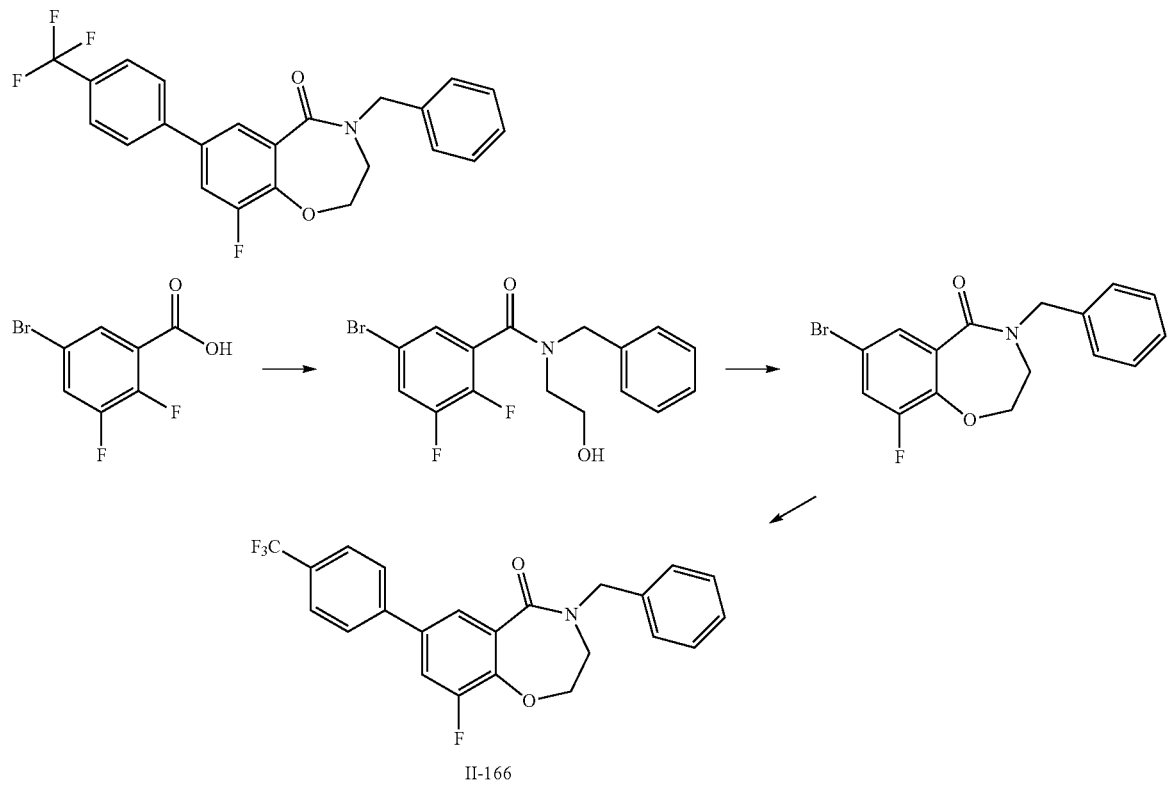

Compound II-166 was prepared according to the Examples disclosed herein using the appropriate starting materials. Mass (M+H)+ 416.1. CDCl₃:7.87 (s, 1H), 7.63 (s, 4H), 7.42 (dd, J1=1.6 Hz, J2=10.8 Hz, 1H), 7.32-7.24 (m, 5H), 4.79 (s, 2H), 4.22 (t, J=5.2 Hz, 2H), 3.48 (t, J=5.2 Hz, 2H).

Example 172

4-benzyl-8-fluoro-7-(4-(trifluoromethoxy)phenyl)-3,4-dihydrobenzo[f][1,4]oxazepin-5(2H)-one (Compound II-167)

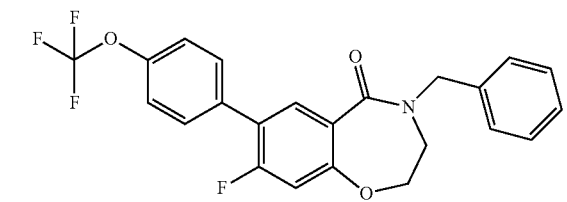

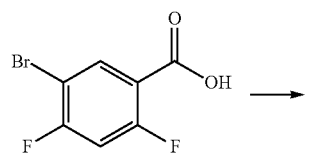

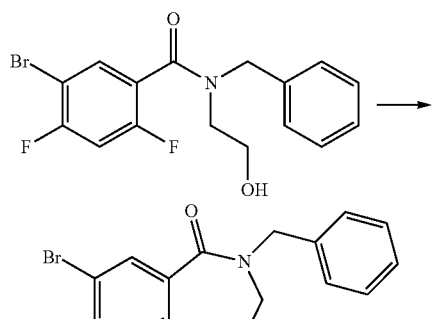

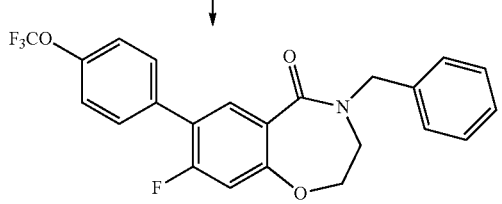

II-167

Compound II-167 was prepared according to the Examples disclosed herein using the appropriate starting materials. Mass (M+H)+ 432.1. CDCl₃:8.07 (d, J=9.2 Hz, 1H), 7.58 (d, J=7.6 Hz, 2 h), 7.40-7.32 (m, 5H), 7.28 (d, J=8.4 Hz, 2H), 6.81 (d, J=11.2 Hz, 1H), 4.84 (s, 2H), 4.24 (t, J=4.8 Hz, 2H), 3.54 (t, J=4.8 Hz, 2H).

Example 173

4-benzyl-8-fluoro-7-(4-(trifluoromethyl)phenyl)-3,4-dihydrobenzo[f][1,4]oxazepin-5(2H)-one (Compound II-168)

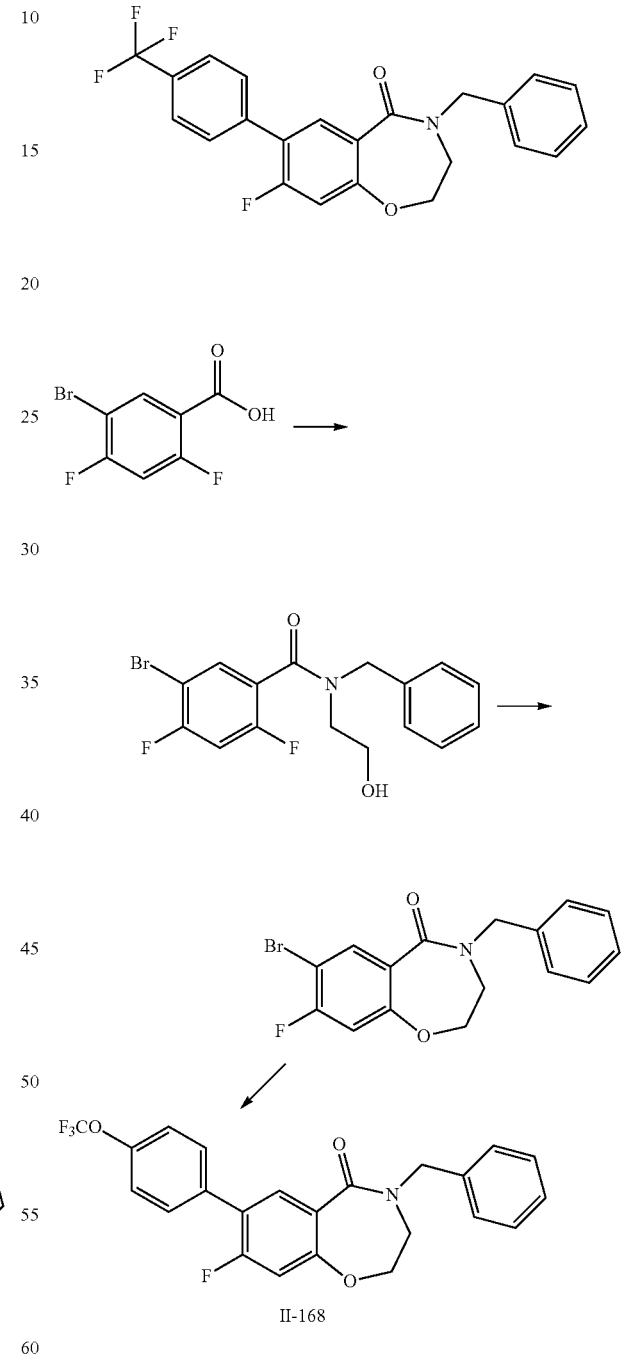

II-168

Compound II-168 was prepared according to the Examples disclosed herein using the appropriate starting materials. Mass (M+H)+ 416.1. CDCl₃:8.11 (d, J=9.2 Hz, 1H), 7.74-7.64 (m, 4H), 7.40-7.30 (m, 5H), 6.83 (d, J=11.6 Hz, 1H), 4.85 (s, 2H), 4.26 (t, J=4.8 Hz, 2H), 3.56 (t, J=4.8 Hz, 2H).

Example 174

4-benzyl-7-(4-(trifluoromethoxy)phenyl)-3,4-dihydropyrido[2,3-f][1,4]oxazepin-5(2H)-one (Compound XII-2)

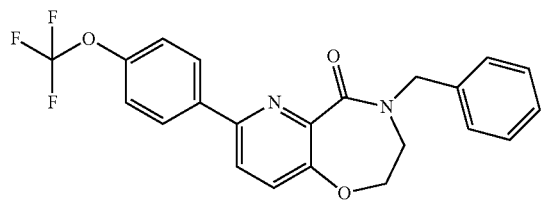

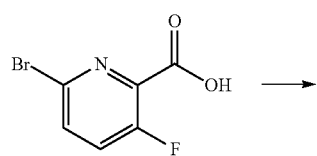

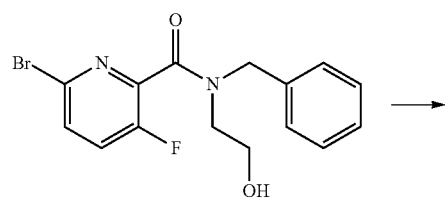

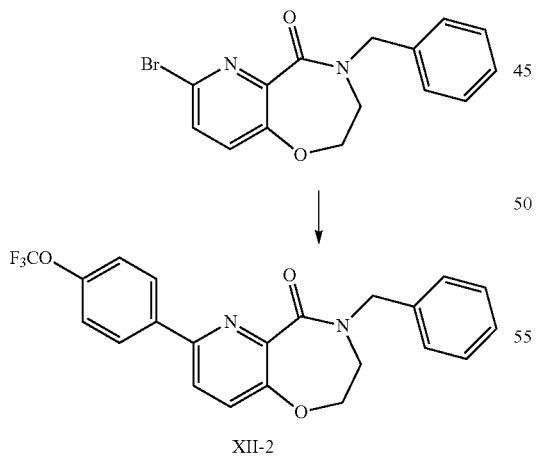

XII-2

Example 175

4-benzyl-7-(4-(trifluoromethyl)phenyl)-3,4-dihydropyrido[2,3-f][1,4]oxazepin-5(2H)-one (Compound XII-3)

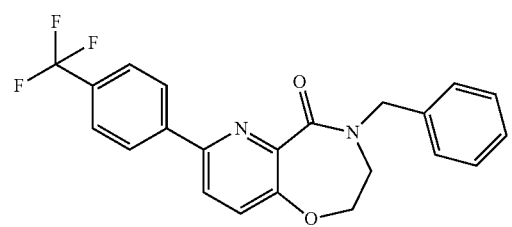

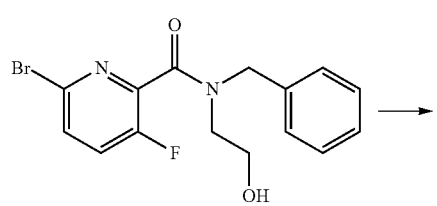

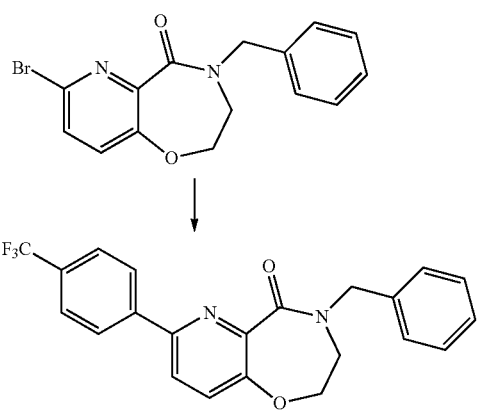

XII-3

Compound XII-2 was prepared according to the Examples disclosed herein using the appropriate starting materials. Mass (M+H)$^+$ 415.1. CDCl$_3$: 8.09 (d, J=8.4 Hz, 2H), 7.79 (d, J=8.8 Hz, 1H), 7.46 (d, J=8.8 Hz, 1H), 7.44-7.32 (m, 5H), 7.30 (d, J=8 Hz, 2H), 4.91 (s, 2H), 4.18 (t, J=5.2 Hz, 2H), (t, J=5.2 Hz, 2H).

Compound XII-3 was prepared according to the Examples disclosed herein using the appropriate starting materials. Mass (M+H)$^+$ 399.1. CDCl$_3$: 8.18 (d, J=8.4 Hz, 2H), 7.84 (d, J=8.4 Hz, 1H), 7.71 (d, J=8 Hz, 2H), 7.48 (d, J=8 Hz, 1H), 7.46-7.30 (m, 5H), 4.91 (s, 2H), 4.20 (t, J=5.2 Hz, 2H), 3.54 (t, J=5.2 Hz, 2H).

Example 176

4-(pyrimidin-2-ylmethyl)-7-(4-(trifluoromethoxy)phenyl)-3,4-dihydropyrido[2,3-f][1,4]oxazepin-5(2H)-one (Compound XII-6)

Example 177

4-(pyrimidin-2-ylmethyl)-7-(4-(trifluoromethyl)phenyl)-3,4-dihydropyrido[2,3-f][1,4]oxazepin-5(2H)-one (Compound XII-7)

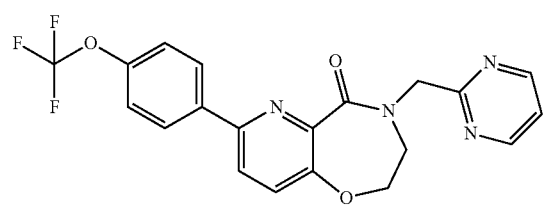

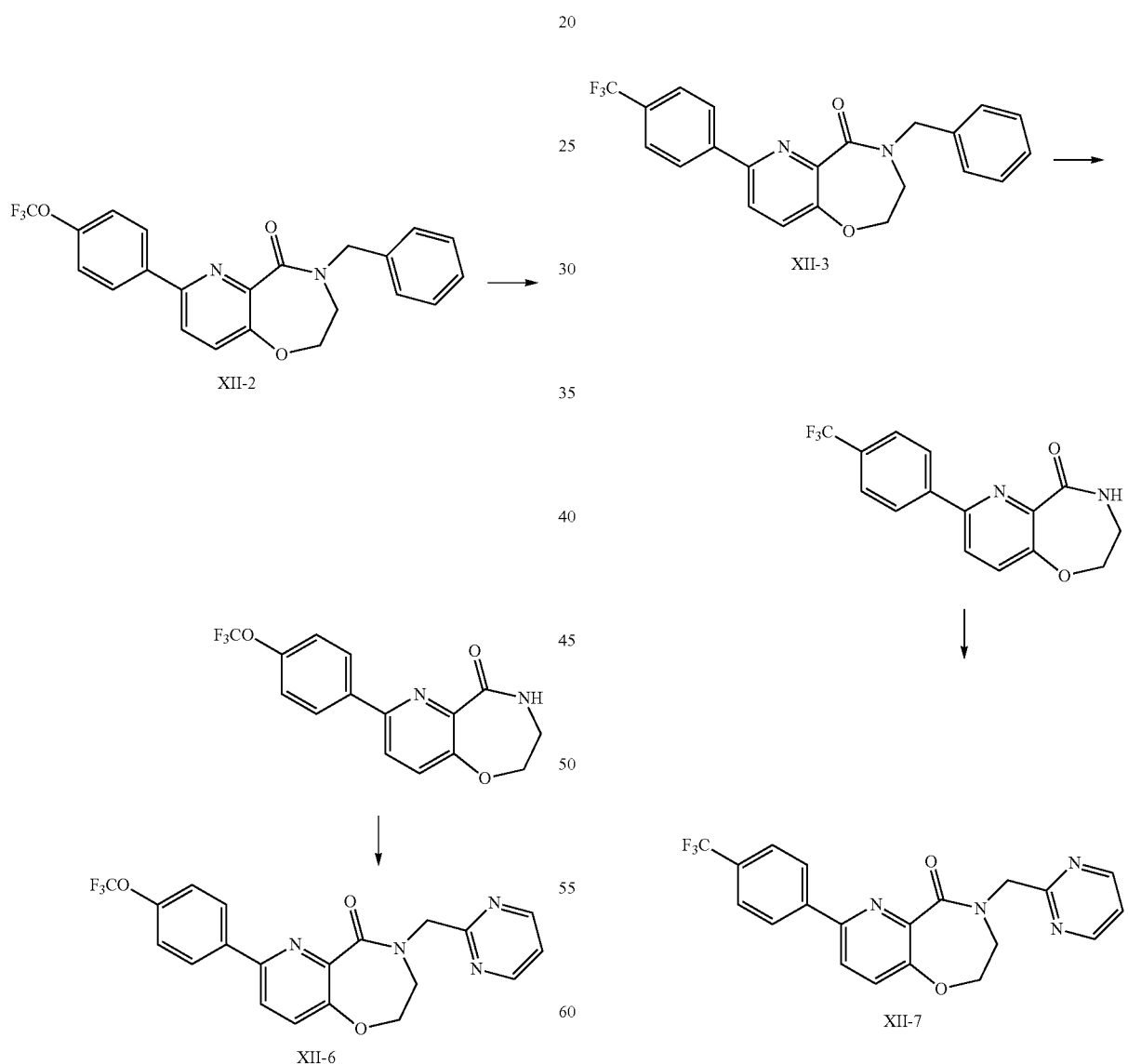

Compound XII-6 was prepared according to the Examples disclosed herein using the appropriate starting materials. Mass (M+H)$^+$ 417.0.

Compound XII-7 was prepared according to the Examples disclosed herein using the appropriate starting materials. Mass (M+H)$^+$ 401.0.

Example 178

2,2,3,3-tetradeutero-4-(pyrimidin-2-ylmethyl)-7-(4-(trifluoromethoxy)phenyl)-3,4-dihydrobenzo[f][1,4]oxazepin-5(2H)-one (Compound II-174)

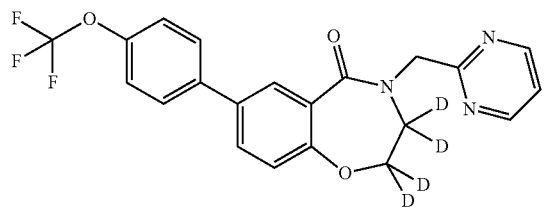

Step 1

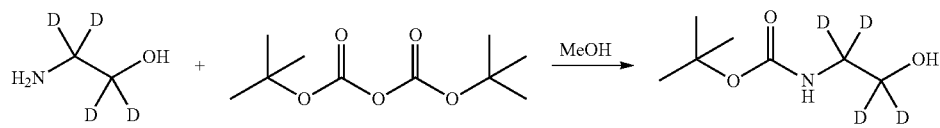

Step 2

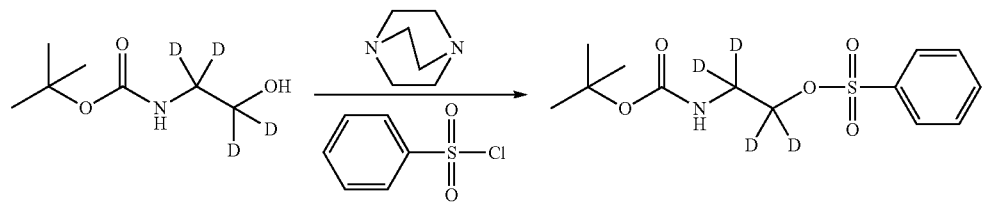

Step 3

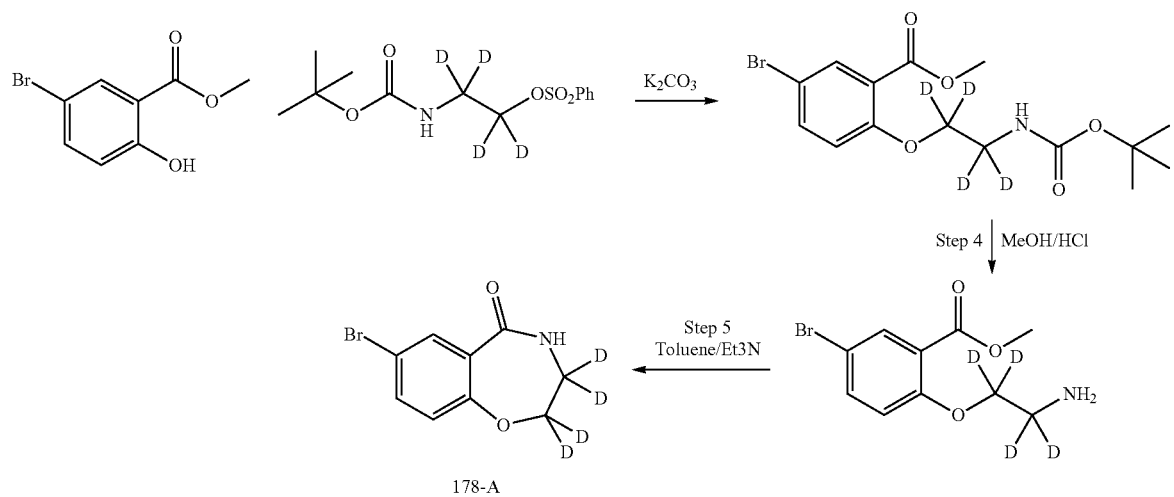

178-A

Step 1: To a solution of 2-aminoethanol (2.0 g, 30 mmol) in methanol (50 mL) at 0° C., Boc₂O (6.0 g, 27 mmol) was added slowly and the reaction mixture was stirred at r.t. for 2 h. Concentrate the reaction mixture to remove methanol, the residue was dissolved in ethyl acetate, the organic layer was washed with brine, dried over sodium sulfate and concentrated to get the Boc protected amino ethanol (5.0 g) and used directly for the next reaction.

Step 2: To a solution of DABCO (5 g, 45 mmol) in toluene (50 mL), N-Boc-2-aminoethanol (5 g, 30 mmol) in toluene was added at room temperature. The reaction mixture was cooled to 0° C. and benzenesulfonyl chloride (5.8 g, 33 mmol) was added slowly and stirred at room temperature for 2 h. Water was added to the reaction mixture, adjust the pH of the mixture to 2-3 by adding 6N HCl. The organic layer was separated, washed with water, sodium bicarbonate, water and brine. Dried over sodium sulfate and concentrated to get an oily product (6.0 g, 70% yield from two steps) which was used directly for the next step.

Step 3: To a solution of protected aminoethanol (6 g, 19.5 mmol) in DMF (20 mL) methyl 5-bromo-2-hydroxybenzoate (3 g, 13 mmol) was added followed by potassium carbonate (3.58 g, 26 mmol) and heated the mixture at 70° C. for 4 h. Solvent was distilled off, the residue was treated with ethyl acetate. The organic layer was washed with water, brine and concentrated to give an oily product (4 g, 81%) and is used for the next step.

Step 4: To the above oily product in methanol (10 mL) at room temperature HCl in methanol (2 ml in 10 mL) was added and heated at 70° C. for 2 h. Solvent was distilled off, the residue was treated with ether, filtered the precipitate. The product obtained (2.5 g, 85%) is used for the cyclization step.

Step 5: To the above product (2.5 g, 9 mmol) in toluene (10 mL), triethylamine (4 ml, 36 mmol) was added and heated at 105° C. for 48 h, until the LC-MS no starting material. The reaction mixture was cooled, diluted with methylene chloride, separated the organic layer. Add water to the organic layer and treated with 6N HCl, to adjust the pH 2. The organics were washed with water, brine and dried and concentrated. The residue was treated with dichloromethane and hexane and filtered the product 178-A (2.0 g, 90% yield).

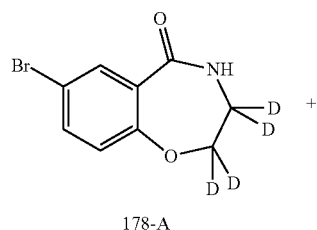
178-A

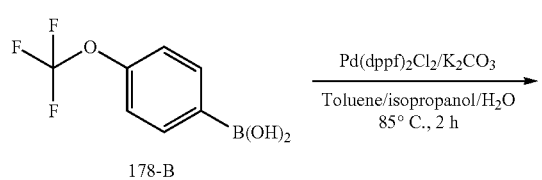
178-B

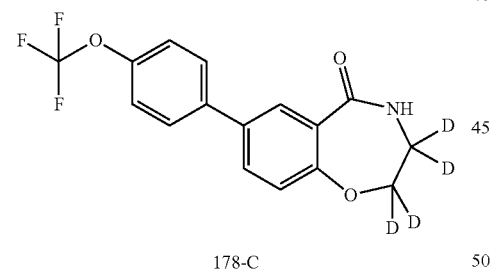
178-C

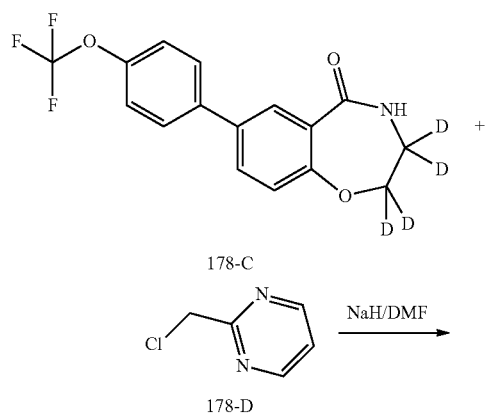
178-C
178-D

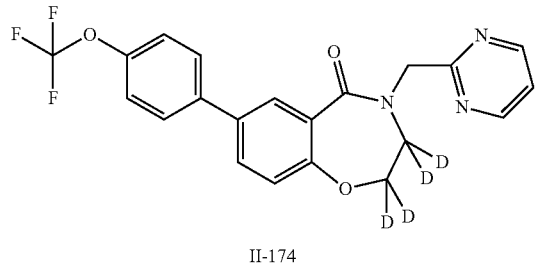
II-174

Suzuki: To the bromide 178-A (2 g, 8.16 mmol, 1 eq), boronic acid 178-B (2.5 g, 12.2 mmol, 1.5 eq) and potassium carbonate (3.4 g, 24.48 mol, 3 eq) in a round bottom flask, solvent (60 mL, toluene/isopropano/water: 2/1/1) was added and stirred under nitrogen for 10 min. To the above solution the palladium catalyst Pd(dppf)Cl$_2$ (142 mg, 0.16 mmol, 0.02 eq) was added and heated at 85° C. for 2 h. The reaction mixture was diluted with ethyl acetate, separated the organic layer and filtered the organic layer through a plug of celite and silica gel and concentrated. Column purification on silica gel using ethyl acetate/hexane as eluent provided 178-C (2 g, 75% yield).

Alkylation: To a solution of 178-C (2 g, 6.12 mmol, 1 eq.) chloromethyl pyrimidine 178-D (1.5 g, 9.17 mmol, 1.5 eq.) in DMF (10 mL), NaH (60% dispersion in oil) (600 mg, 25 mmol, 4 eq.) was slowly added at room temperature (slightly exothermic) and stirred at r.t. for 30 min. The reaction mixture was treated with few drops of HCl, diluted the reaction mixture with ethyl acetate and treated with water. The organic layer was separated, washed with brine, dried and concentrated. Column purification on silica gel using ethyl acetate/hexane as eluent provided Compound II-174 (1.8 g, 70% yield). Mass (M+H)$^+$ 420.1. CDCl$_3$:8.65 (d, J=5.2 Hz, 2H), 8.10 (s, 1H), 7.58-7.50 (m, 3H), 7.18 (d, J=8 Hz, 2H), 7.14 (t, J=5.2 Hz, 1H), 7.02 (d, J=8.4 Hz, 1H), 5.02 (s, 2H).

Example 179

4-((3-methyloxetan-3-yl)methyl)-7-(4-(trifluoromethoxy)phenyl)-3,4-dihydrobenzo[f][1,4]oxazepin-5(2H)-one (Compound II-1)

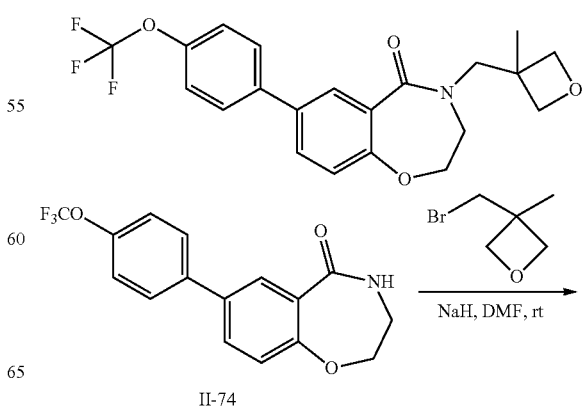
II-74

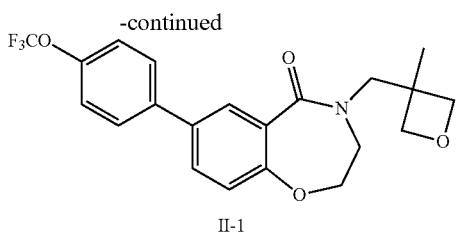

4-((3-Methyloxetan-3-yl)methyl)-7-(4-(trifluoromethoxy)phenyl)-3,4-dihydrobenzo[f][1,4]oxazepin-5(2H)-one was prepared according to Example 25 using 3-(bromomethyl)-3methyloxetane.

$^1$H-NMR (400 MHz, DMSO) 1.305 (s, 3H), 3.618-3.643 (m, 2H), 3.750 (s, 2H), 4.183-4.198 (d, 2H, J=6 Hz), 4.346-4.322 (t, 2H, J, =4.8 Hz), 4.563-4.577 (d, 2H, J, =5.6 Hz), 7.109-7.131 (d, 1H, J=8.8 Hz), 7.413-7.433 (s, 2H, J=8 Hz), 7.752-7.786 (m, 3H), 7.878-7.883 (d, 1H, J=2 Hz), MS m/z 407.1 (MH$^+$).

Example 180

4-((3-((2-oxopyrrolidin-1-yl)methyl)oxetan-3-yl)methyl)-7-(4-(trifluoromethoxy)phenyl)-3,4-dihydrobenzo[f][1,4]oxazepin-5(2H)-one (Compound II-108)

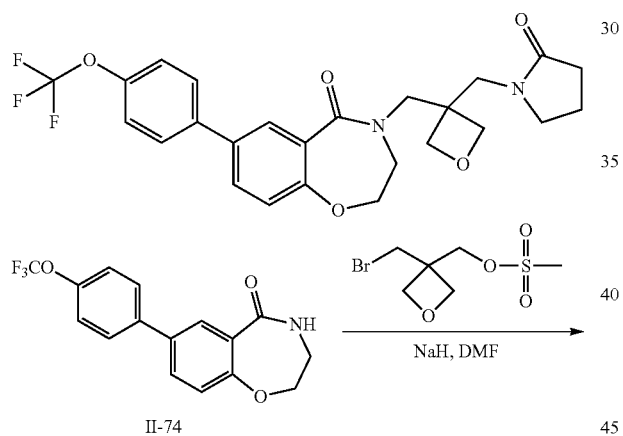

Compound 180-A and Compound II-108 was prepared according to Example 25 using (3-(bromomethyl)oxetan-3-yl)methyl methanesulfonate.

Example 181

4-(2-(2-oxopyrrolidin-1-yl)ethyl)-7-(4-(trifluoromethoxy)phenyl)-3,4-dihydrobenzo[f][1,4]oxazepin-5(2H)-one (Compound II-116)

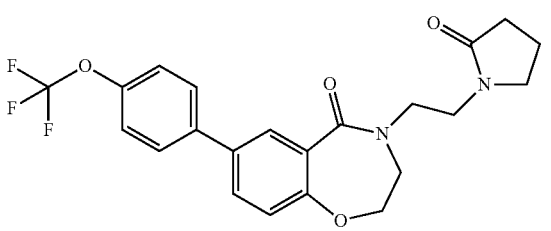

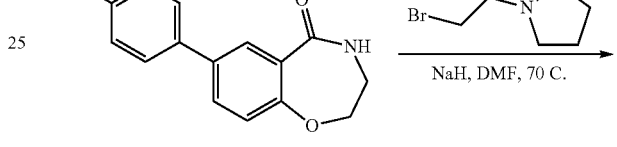

Compound II-116 was prepared according to Example 25 using 1-(2-bromoethyl)pyrrolidin-2-one.

Example 182

7-(2-methoxypyrimidin-5-yl)-4-(pyrimidin-2-ylmethyl)-3,4-dihydrobenzo[f][1,4]oxazepin-5(2H)-one (Compound VI-7)

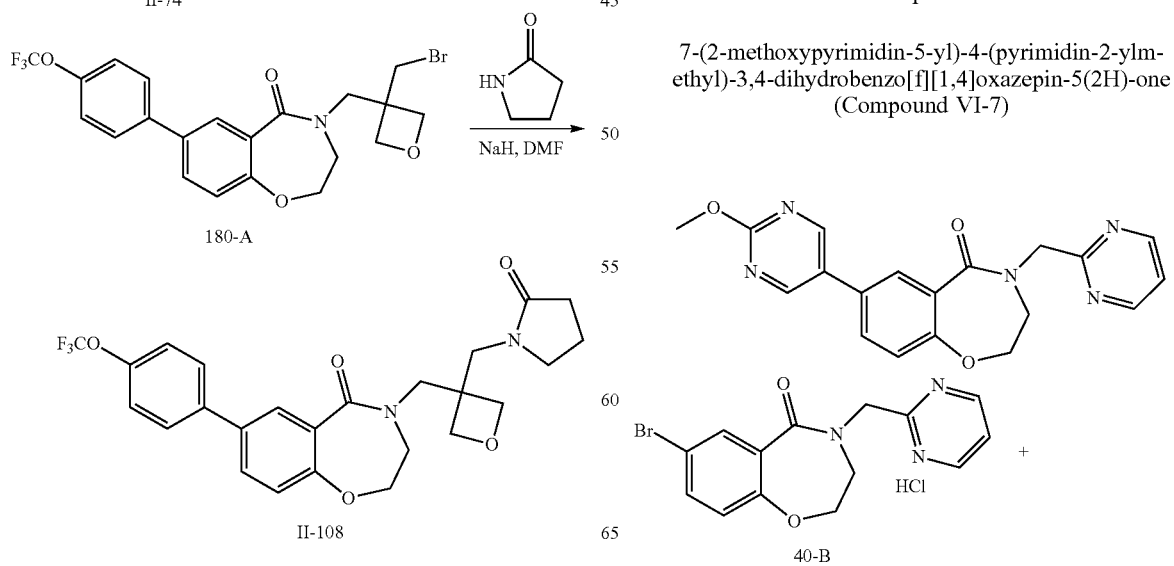

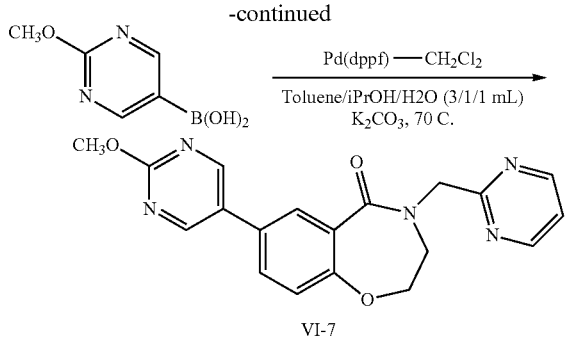

40-B (0.405 mmol), potassium carbonate (111 mmol) and Palladium chloride dppf catalyst (0.05 mmol) were combined in a mixture of toluene (3 mL), isopropanol (1 mL) and water (1 mL). The resulting suspension was heated at 85 degrees for 2 hours. The reaction mixture was concentrated down and diluted with ethyl acetate and filtered through celite. The filtrate was washed with water. The organic layer was purified by prep HPLC and prep TLC to afford Compound VI-7.

Example 183

1-(4-(5-oxo-4-(pyrimidin-2-ylmethyl)-2,3,4,5-tetrahydrobenzo[f][1,4]oxazepin-7-yl)phenyl)cyclopropanecarbonitrile (Compound II-109)

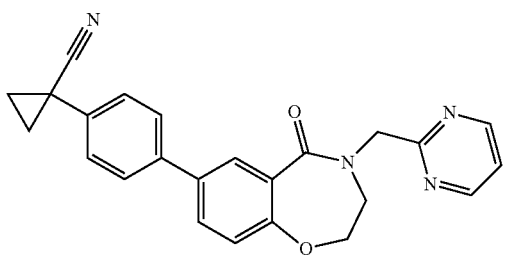 [SMILES: N#CC1(c2ccc(-c3ccc4c(c3)C(=O)N(Cc3ncccn3)CCO4)cc2)CC1]

Compound II-109 was prepared according to the Examples disclosed herein using the appropriate starting materials.

Example 184

N-(2-(5-oxo-4-(pyrimidin-2-ylmethyl)-2,3,4,5-tetrahydrobenzo[f][1,4]oxazepin-7-yl)-5-(trifluoromethoxy)phenyl)acetamide (Compound II-111)

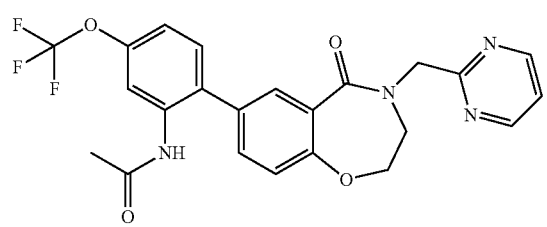 [SMILES: CC(=O)Nc1cc(OC(F)(F)F)ccc1-c1ccc2c(c1)C(=O)N(Cc1ncccn1)CCO2]

Compound II-111 was prepared according to the Examples disclosed herein using the appropriate starting materials.

Example 185

7-(2-(4-methylpiperazin-1-yl)pyrimidin-5-yl)-4-(pyrimidin-2-ylmethyl)-3,4-dihydrobenzo[f][1,4]oxazepin-5(2H)-one (Compound VI-14)

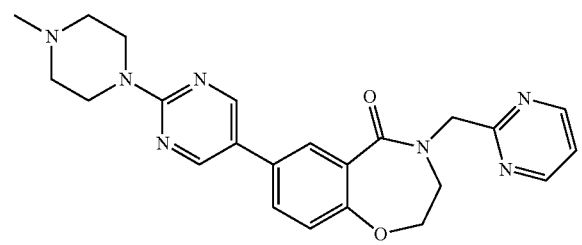 [SMILES: CN1CCN(c2ncc(-c3ccc4c(c3)C(=O)N(Cc3ncccn3)CCO4)cn2)CC1]

Compound VI-14 was prepared according to the Examples disclosed herein using the appropriate starting materials. MS m/z 432.2 (M+).

Example 186

4-(pyrimidin-2-ylmethyl)-7-(2-(2,2,2-trifluoroethylamino)pyrimidin-5-yl)-3,4-dihydrobenzo[f][1,4]oxazepin-5(2H)-one (Compound VI-15)

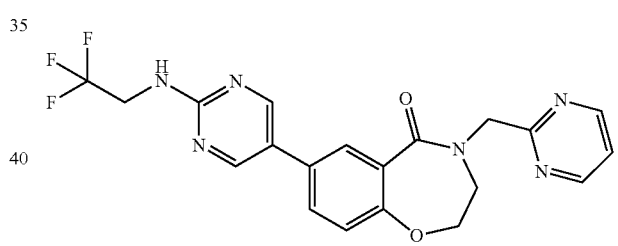

Compound VI-15 was prepared according to the Examples disclosed herein using the appropriate starting materials.

Example 187

7-(6-morpholinopyridin-3-yl)-4-(pyrimidin-2-ylmethyl)-3,4-dihydrobenzo[f][1,4]oxazepin-5(2H)-one (Compound VI-16)

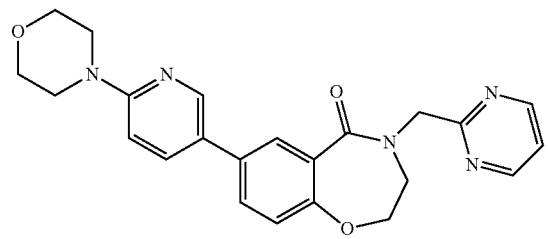 [SMILES: O=C1c2cc(-c3ccc(N4CCOCC4)nc3)ccc2OCCN1Cc1ncccn1]

Compound VI-16 was prepared according to the Examples disclosed herein using the appropriate starting materials.

Example 188

N-(2-(5-oxo-7-(4-(trifluoromethoxy)phenyl)-2,3-dihydrobenzo[f][1,4]oxazepin-4(5H)-yl)ethyl)ethanesulfonamide (Compound II-178)

II-74

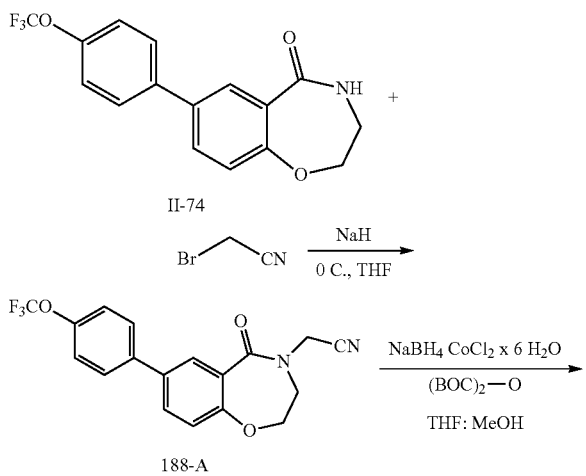

188-A

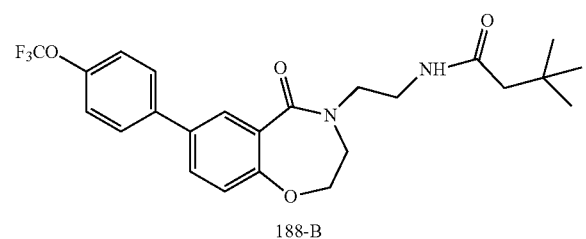

188-B

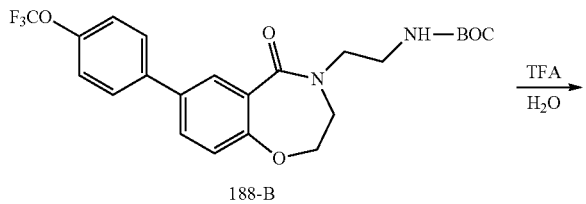

188-B

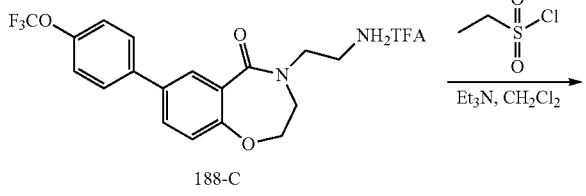

188-C

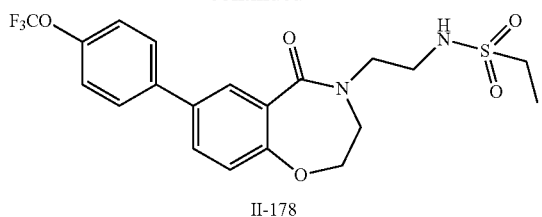

II-178

II-74 (1.04 mmol) and NaH (3.13 mmol) was stirred in THF (6 mL) at 0 degrees under nitrogen. Bromoacetonitrile was added dropwise. The resulting reaction mixture was allowed to slowly warm up to room temperature over the period of 2 hours after which time the reaction mixture was quenched with water and then extracted with dichloromethane. The organic layer was purified by prep HPLC to afford 188-A.

188-A (0.635 mmol) was dissolved in a mixture of THF:MeOH (4:6 mL). To this was added cobalt chloride (2.49 mmol) and di-tert-butyldicarbonate (1.26 mmol) under nitrogen follow by addition of sodium borohydride (0.762 mmol). The resulting mixture was stirred at ambient temperature overnight. The mixture was filtered through celite and washed with 9:1 mixture of MeOH/H$_2$O. The filtrate was washed with saturated NaHCO$_3$ and then extracted with ethyl acetate. The organic layer was dried over Na$_2$S(O)$_4$ and concentrated down to afford 188-B as an oil which was used without further purifications to make 188-C.

188-B (200 mg) was combined with TFA (9 mL) and H$_2$O (1 mL) and stirred under nitrogen for 2 hours. The reaction mixture was concentrated and used without further purifications to make Compound II-178.

A solution of 188-C (25 mg) in dicholoromethane (3 mL) was chilled in an ice bath. To this was added triethylamine (0.1 mL) followed by ethanesulfonyl chloride (0.05 mL). The reaction mixture was stirred under cold conditions for 2 hours after which it was quenched with water. The mixture was extracted with dichloromethane and purified by prep HPLC to afford Compound II-178. MS m/z 459.1 (M$^+$).

Example 189

N-(2-(5-oxo-7-(4-(trifluoromethoxy)phenyl)-2,3-dihydrobenzo[f][1,4]oxazepin-4(5H)-yl)ethyl)cyclopropanesulfonamide (Compound II-179)

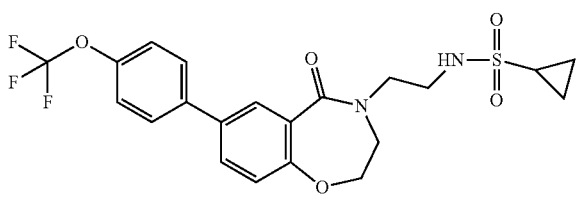 [SMILES: O=C1c2cc(-c3ccc(OC(F)(F)F)cc3)ccc2OCCN1CCNS(=O)(=O)C1CC1]

Compound II-179 was prepared according to the Examples disclosed herein using the appropriate starting materials. MS m/z 471.1 (M$^+$).

Example 190

4-fluoro-N-(2-(5-oxo-7-(4-(trifluoromethoxy)phenyl)-2,3-dihydrobenzo[f][1,4]oxazepin-4(5H)-yl)ethyl)benzenesulfonamide (Compound II-181)

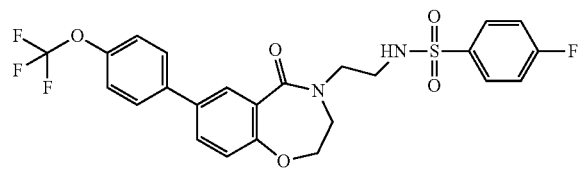 [SMILES: O=C1c2cc(-c3ccc(OC(F)(F)F)cc3)ccc2OCCN1CCNS(=O)(=O)c1ccc(F)cc1]

Compound II-181 was prepared according to the Examples disclosed herein using the appropriate starting materials. MS m/z 525.1 (M+).

Example 191

N-(2-(5-oxo-7-(4-(trifluoromethoxy)phenyl)-2,3-dihydrobenzo[f][1,4]oxazepin-4(5H)-yl)ethyl)cyclopentanesulfonamide (Compound II-183)

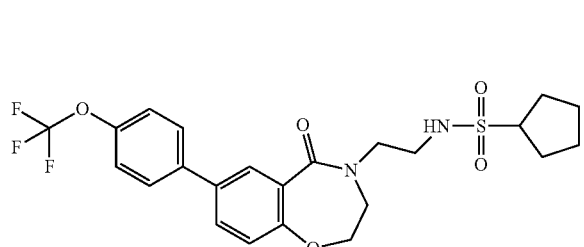

Compound II-183 was prepared according to the Examples disclosed herein using the appropriate starting materials. MS m/z 499.1 (M+).

Example 192

1-methyl-N-(2-(5-oxo-7-(4-(trifluoromethoxy)phenyl)-2,3-dihydrobenzo[f][1,4]oxazepin-4(5H)-yl)ethyl)-1H-imidazole-2-sulfonamide (Compound II-184)

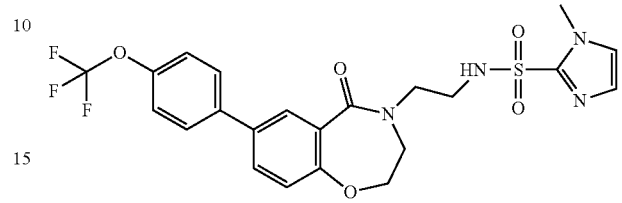

Compound II-184 was prepared according to the Examples disclosed herein using the appropriate starting materials. MS m/z 511.1 (M+).

Example 193

N-(2-(5-oxo-7-(4-(trifluoromethoxy)phenyl)-2,3-dihydrobenzo[f][1,4]oxazepin-4(5H)-yl)ethyl)benzenesulfonamide (Compound II-177)

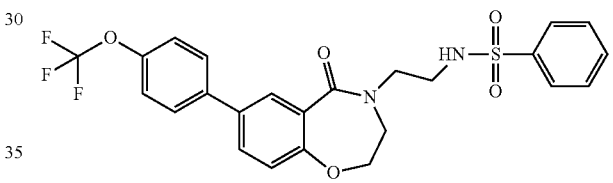

Compound II-177 was prepared according to the Examples disclosed herein using the appropriate starting materials. MS m/z 507.1 (M+).

Example 194

N-methyl-N-(2-(5-oxo-7-(4-(trifluoromethoxy)phenyl)-2,3-dihydrobenzo[f][1,4]oxazepin-4(5H)-yl)ethyl)benzenesulfonamide (Compound II-182)

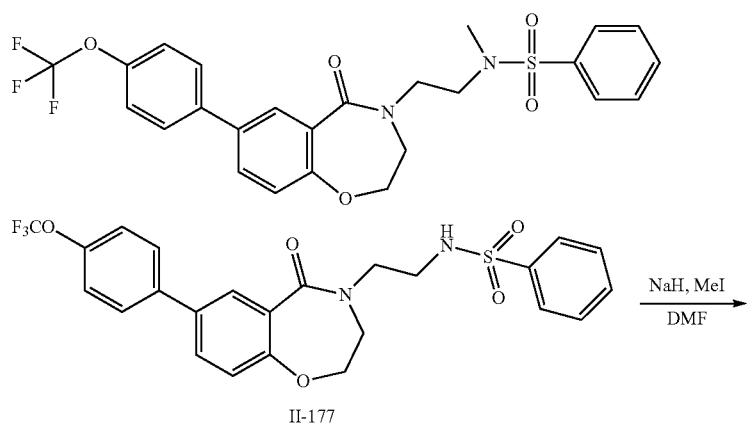

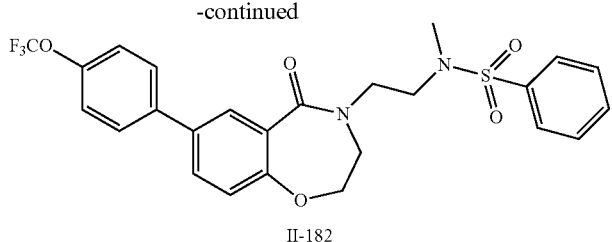
II-182
Compound II-182 was prepared according to Example 25 using iodomethane and Compound II-177.
Example 195
N-(2-(5-oxo-7-(4-(trifluoromethoxy)phenyl)-2,3-dihydrobenzo[f][1,4]oxazepin-4(5H)-yl)ethyl)-2-(pyrimidin-2-yl)acetamide (Compound II-185)
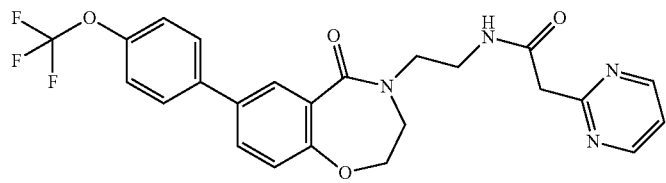
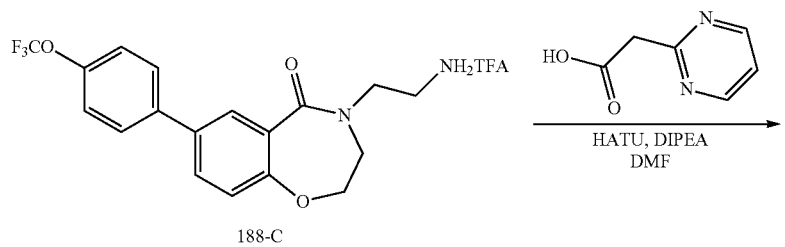
188-C
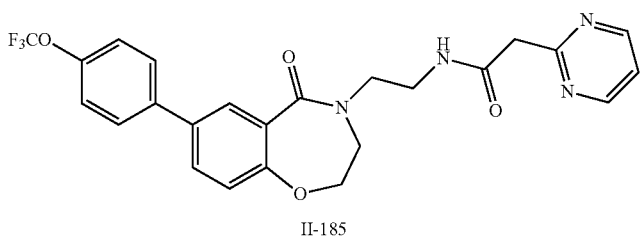
II-185

188-C (0.054 mmol) was dissolved in DMF (3 mL) follow by addition of HATU and DIPEA. The resulting mixture was stirred at room temperature for 3 hours after which water was added and extracted with dichloromethane. The organic was purified by prep HPLC to afford Compound II-185.

Example 196

4-((5-cyclopropyl-1,3,4-oxadiazol-2-yl)methyl)-7-(4-(trifluoromethoxy)phenyl)-3,4-dihydrobenzo[f][1,4]oxazepin-5(2H)-one (Compound II-68)

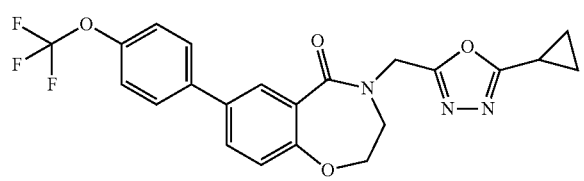 [SMILES: O=C1c2cc(-c3ccc(OC(F)(F)F)cc3)ccc2OCCN1Cc1nnc(C2CC2)o1]

Compound II-68 was prepared according to the Examples disclosed herein using the appropriate starting materials. MS m/z 446.1 (M+H).

Example 197

4-(pyridin-4-ylmethyl)-7-(4-(trifluoromethoxy)phenyl)-3,4-dihydrobenzo[f][1,4]oxazepin-5(2H)-one (Compound II-67)

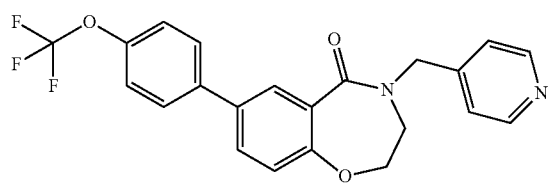 [SMILES: O=C1c2cc(-c3ccc(OC(F)(F)F)cc3)ccc2OCCN1Cc1ccncc1]

Compound II-67 was prepared according to the Examples disclosed herein using the appropriate starting materials. MS m/z 415.1 (M+H).

Example 198

4-((5-chloropyrimidin-2-yl)methyl)-7-(4-(trifluoromethoxy)phenyl)-3,4-dihydrobenzo[f][1,4]oxazepin-5(2H)-one (Compound II-65)

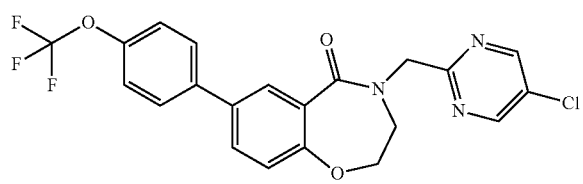 [SMILES: O=C1c2cc(-c3ccc(OC(F)(F)F)cc3)ccc2OCCN1Cc1ncc(Cl)cn1]

Compound II-65 was prepared according to the Examples disclosed herein using the appropriate starting materials. MS m/z 450.0 (M+H).

Example 199

4-((1-methyl-1H-pyrazol-3-yl)methyl)-7-(4-(trifluoromethoxy)phenyl)-3,4-dihydrobenzo[f][1,4]oxazepin-5(2H)-one (Compound II-64)

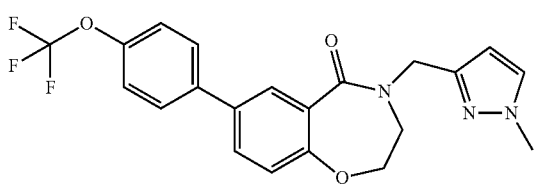 [SMILES: Cn1ccc(CN2CCOc3ccc(-c4ccc(OC(F)(F)F)cc4)cc3C2=O)n1]

Compound II-64 was prepared according to the Examples disclosed herein using the appropriate starting materials. MS m/z 418.1 (M+H).

Example 200

4-methyl-7-(4-(trifluoromethoxy)phenyl)-3,4-dihydrobenzo[f][1,4]oxazepin-5(2H)-one (Compound II-46)

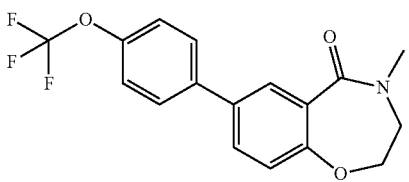 [SMILES: CN1CCOc2ccc(-c3ccc(OC(F)(F)F)cc3)cc2C1=O]

Compound II-46 was prepared according to the Examples disclosed herein using the appropriate starting materials. MS m/z 338.1 (M+H).

Example 201

4-(3,4-difluorobenzyl)-7-(4-(trifluoromethoxy)phenyl)-3,4-dihydrobenzo[f][1,4]oxazepin-5(2H)-one (Compound II-45)

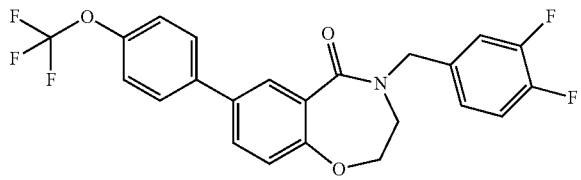 [SMILES: O=C1c2cc(-c3ccc(OC(F)(F)F)cc3)ccc2OCCN1Cc1ccc(F)c(F)c1]

Compound II-45 was prepared according to the Examples disclosed herein using the appropriate starting materials. MS m/z 450.1 (M+H).

Example 202

4-((5-(pyridin-2-yl)isoxazol-3-yl)methyl)-7-(4-(trifluoromethoxy)phenyl)-3,4-dihydrobenzo[f][1,4]oxazepin-5(2H)-one (Compound II-41)

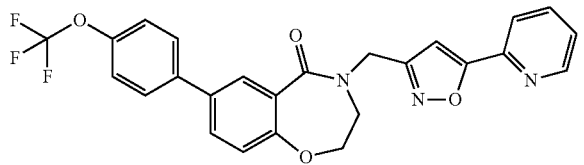 [SMILES: O=C1c2cc(-c3ccc(OC(F)(F)F)cc3)ccc2OCCN1Cc1cc(-c2ccccn2)on1]

Compound II-41 was prepared according to the Examples disclosed herein using the appropriate starting materials. MS m/z 482.1 (M+H).

Example 203

7-(4-(trifluoromethoxy)phenyl)-4-((6-(trifluoromethyl)pyridin-3-yl)methyl)-3,4-dihydrobenzo[f][1,4]oxazepin-5(2H)-one (Compound II-16)

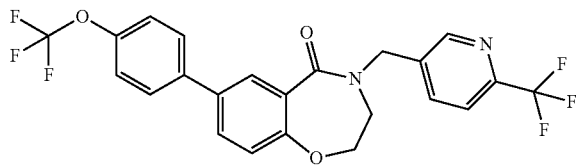 [SMILES: O=C1c2cc(-c3ccc(OC(F)(F)F)cc3)ccc2OCCN1Cc1ccc(C(F)(F)F)nc1]

Compound II-16 was prepared according to the Examples disclosed herein using the appropriate starting materials. MS m/z 483.1 (M+H).

Example 204

4-(2-methoxyethyl)-7-(4-(trifluoromethoxy)phenyl)-3,4-dihydrobenzo[f][1,4]oxazepin-5(2H)-one (Compound II-11)

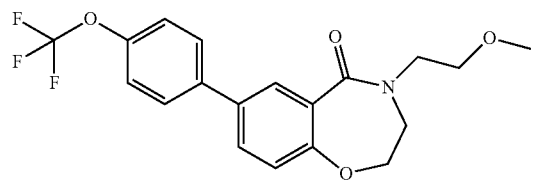 [SMILES: COCCN1CCOc2ccc(-c3ccc(OC(F)(F)F)cc3)cc2C1=O]

Compound II-11 was prepared according to the Examples disclosed herein using the appropriate starting materials. MS m/z 382.1 (M+H).

Example 205

4-(2,2-difluoroethyl)-7-(4-(trifluoromethoxy)phenyl)-3,4-dihydrobenzo[f][1,4]oxazepin-5(2H)-one (Compound II-6)

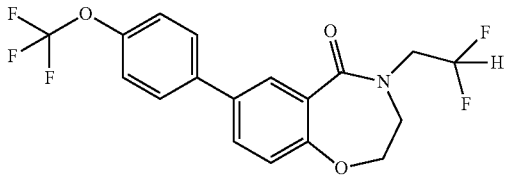 [SMILES: O=C1c2cc(-c3ccc(OC(F)(F)F)cc3)ccc2OCCN1CC(F)F]

Compound II-6 was prepared according to the Examples disclosed herein using the appropriate starting materials. MS m/z 388.1 (M+H).

Example 206

4-((2,3-dihydrobenzo[b][1,4]dioxin-6-yl)methyl)-7-(4-(trifluoromethoxy)phenyl)-3,4-dihydrobenzo[f][1,4]oxazepin-5(2H)-one (Compound II-5)

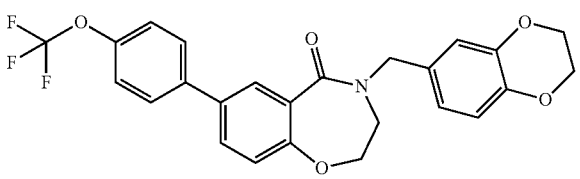 [SMILES: O=C1c2cc(-c3ccc(OC(F)(F)F)cc3)ccc2OCCN1Cc1ccc2c(c1)OCCO2]

Compound II-5 was prepared according to the Examples disclosed herein using the appropriate starting materials. MS m/z 472.1 (M+H).

Example 207

7-(4-fluorophenyl)-4-(pyrimidin-2-ylmethyl)-3,4-dihydrobenzo[f][1,4]oxazepin-5(2H)-one (Compound II-104)

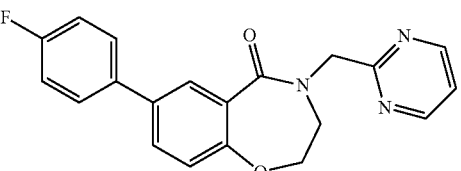

Compound II-104 was prepared according to the Examples disclosed herein using the appropriate starting materials. MS m/z 350.1 (M+H).

Example 208

7-(3-fluoro-4-(2,2,2-trifluoroethoxy)phenyl)-4-(pyrimidin-2-ylmethyl)-3,4-dihydrobenzo[f][1,4]oxazepin-5(2H)-one (Compound II-106)

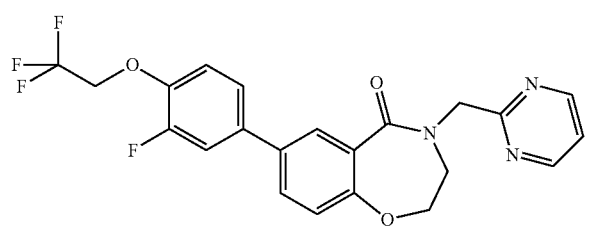 [SMILES: O=C1c2cc(-c3ccc(OCC(F)(F)F)c(F)c3)ccc2OCCN1Cc1ncccn1]

Compound II-106 was prepared according to the Examples disclosed herein using the appropriate starting materials. MS m/z 448.1 (M+H).

Example 209

4-(pyrimidin-2-ylmethyl)-7-(4-(2,2,2-trifluoroethoxy)phenyl)-3,4-dihydrobenzo[f][1,4]oxazepin-5(2H)-one (Compound II-107)

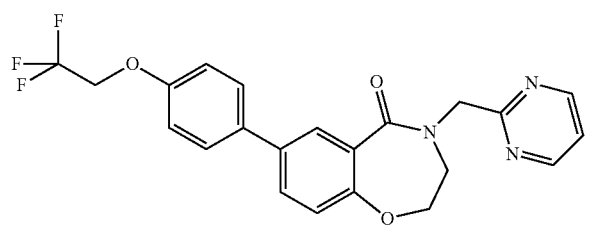 [SMILES: O=C1c2cc(-c3ccc(OCC(F)(F)F)cc3)ccc2OCCN1Cc1ncccn1]

Compound II-107 was prepared according to the Examples disclosed herein using the appropriate starting materials. MS m/z 430.1 (M+H).

Example 210

7-(4-(trifluoromethoxy)phenyl)-4-((5-(6-(trifluoromethyl)pyridin-3-yl)pyrimidin-2-yl)methyl)-3,4-dihydrobenzo[f][1,4]oxazepin-5(2H)-one (Compound II-115)

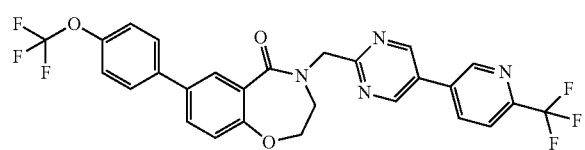 [SMILES: O=C1c2cc(-c3ccc(OC(F)(F)F)cc3)ccc2OCCN1Cc1ncc(-c2ccc(C(F)(F)F)nc2)cn1]

Compound II-115 was prepared according to the Examples disclosed herein using the appropriate starting materials. MS m/z 561.1 (M+H).

Example 211

4-((4-(pyrrolidin-1-yl)pyrimidin-2-yl)methyl)-7-(4-(trifluoromethoxy)phenyl)-3,4-dihydrobenzo[f][1,4]oxazepin-5(2H)-one (Compound II-125)

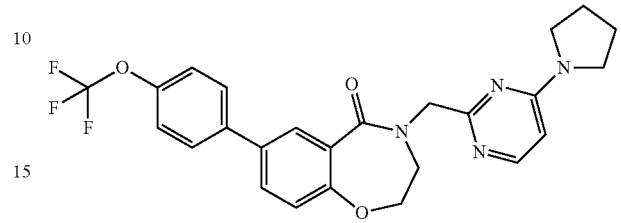

Compound II-125 was prepared according to the Examples disclosed herein using the appropriate starting materials. MS m/z 485.1 (M+H).

Example 212

4-((4-morpholinopyrimidin-2-yl)methyl)-7-(4-(trifluoromethoxy)phenyl)-3,4-dihydrobenzo[f][1,4]oxazepin-5(2H)-one (Compound II-133)

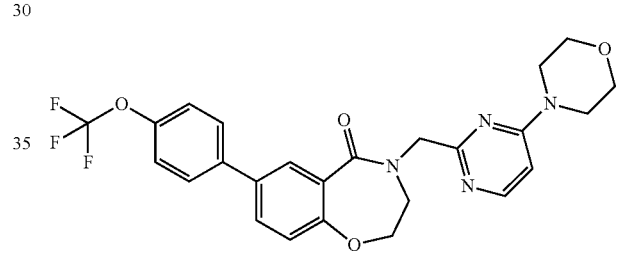

Compound II-133 was prepared according to the Examples disclosed herein using the appropriate starting materials. MS m/z 501.1 (M+H).

Example 213

4-benzyl-7-(4-(trifluoromethoxy)phenyl)-3,4-dihydrobenzo[f][1,4]oxazepin-5(2H)-one (Compound II-134)

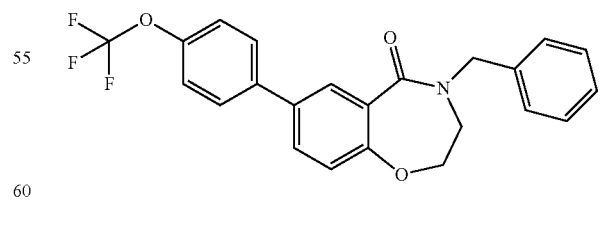

Compound II-134 was prepared according to the Examples disclosed herein using the appropriate starting materials. $^1$H-NMR (CD$_3$OD) δ 8.01 (d, 1H, J=2.4 Hz), 7.72-7.78 (m, 3H), 7.31-7.42 (m, 7H), 7.14 (d, 1H, J=8.0 Hz), 4.85 (s, 2H), 4.25 (t, 2H, J=5.0 Hz), 3.60 (t, 2H, J=5.4 Hz); MS m/z 414.1 (M+H).

Example 214

4-((4-methoxypyrimidin-2-yl)methyl)-7-(4-(trifluoromethoxy)phenyl)-3,4-dihydrobenzo[f][1,4]oxazepin-5(2H)-one (Compound II-137)

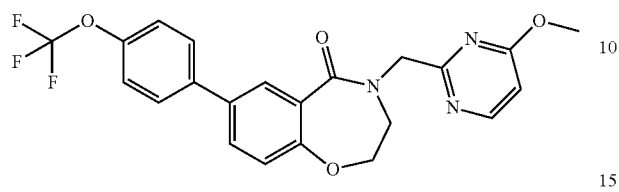

Compound II-137 was prepared according to the Examples disclosed herein using the appropriate starting materials. $^1$H-NMR (CD$_3$OD) δ 8.41 (d, 1H, J=6.0 Hz), 8.01 (d, 1H, J=2.4 Hz), 7.77 (dd, 1H, J=8.8, 2.4 Hz), 7.71 (d, 2H, J=8.4 Hz), 7.35 (d, 2H, J=8.0 Hz), 7.17 (d, 1H, J=8.0 Hz), 6.75 (d, 1H, J=6.0 Hz), 4.97 (s, 2H), 4.58 (t, 2H, J=4.8 Hz), 3.95 (s, 3H), 3.84 (t, 2H, J=5.2 Hz); MS m/z 446.1 (M+H).

Example 215

4-((4-methylpyrimidin-2-yl)methyl)-7-(4-(trifluoromethoxy)phenyl)-3,4-dihydrobenzo[f][1,4]oxazepin-5(2H)-one (Compound II-138)

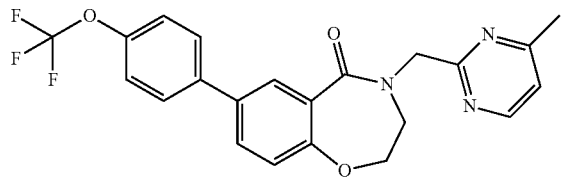 [SMILES: Cc1ccnc(CN2CCOc3ccc(-c4ccc(OC(F)(F)F)cc4)cc3C2=O)n1]

Compound II-138 was prepared according to the Examples disclosed herein using the appropriate starting materials. $^1$H-NMR (CD$_3$OD) δ 8.59 (d, 1H, J=5.2 Hz), 8.02 (d, 1H, J=2.4 Hz), 7.76 (dd, 1H, J=8.4, 2.4 Hz), 7.71 (d, 2H, J=8.4 Hz), 7.34 (d, 2H, J=8.0 Hz), 7.28 (d, 1H, J=5.2 Hz), 7.16 (d, 1H, J=8.4 Hz), 5.03 (s, 2H), 4.59 (t, 2H, J=5.0 Hz), 3.83 (t, 2H, J=5.0 Hz)), 2.53 (s, 3H); MS m/z 430.1 (M+H).

Example 216

4-((4-(piperidin-1-yl)pyrimidin-2-yl)methyl)-7-(4-(trifluoromethoxy)phenyl)-3,4-dihydrobenzo[f][1,4]oxazepin-5(2H)-one (Compound II-139)

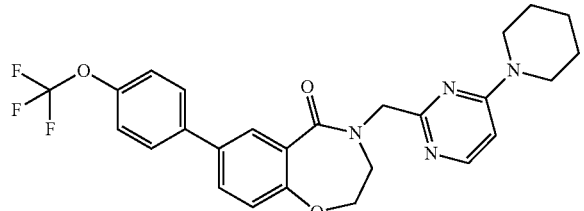

Compound II-139 was prepared according to the Examples disclosed herein using the appropriate starting materials. $^1$H-NMR (CD$_3$OD) δ 8.10 (d, 1H, J=7.2 Hz), 7.98 (d, 1H, J=2.4 Hz), 7.81 (dd, 1H, J=8.4, 2.4 Hz), 7.71 (d, 2H, J=9.2 Hz), 7.35 (d, 2H, J=8.0 Hz), 7.20 (d, 1H, J=8.8 Hz), 7.01 (d, 1H, J=7.6 Hz), 4.91 (s, 2H), 4.56 (t, 2H, J=5.0 Hz), 4.01 (br, 2H), 3.88 (t, 2H, J=4.8 Hz)), 3.73 (br, 2H), 1.59-1.73 (m, 6H); MS m/z 499.2 (M+H).

Example 217

4-((4-(dimethylamino)pyrimidin-2-yl)methyl)-7-(4-(trifluoromethoxy)phenyl)-3,4-dihydrobenzo[f][1,4]oxazepin-5(2H)-one (Compound II-140)

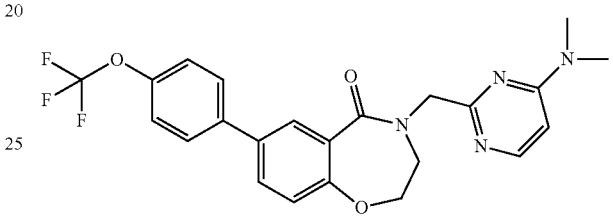

Compound II-140 was prepared according to the Examples disclosed herein using the appropriate starting materials. $^1$H-NMR (CD$_3$OD) δ 8.14 (d, 1H, J=7.2 Hz), 7.99 (d, 1H, J=2.4 Hz), 7.81 (dd, 1H, J=8.0, 2.4 Hz), 7.70 (d, 2H, J=9.2 Hz), 7.35 (d, 2H, J=8.4 Hz), 7.19 (d, 1H, J=8.4 Hz), 6.93 (d, 1H, J=7.2 Hz), 4.93 (s, 2H), 4.59 (t, 2H, J=5.0 Hz), 3.90 (t, 2H, J=5.0 Hz)), 3.30 (s, 6H); MS m/z 459.1 (M+H).

Example 218

4-benzyl-7-(4-(trifluoromethyl)phenyl)-3,4-dihydrobenzo[f][1,4]oxazepin-5(2H)-one (Compound II-141)

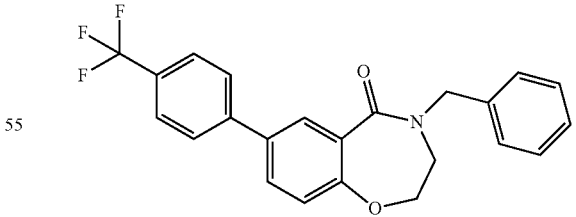

Compound II-141 was prepared according to the Examples disclosed herein using the appropriate starting materials. $^1$H-NMR (CD$_3$OD) δ 8.08 (d, 1H, J=2.4 Hz), 7.79-7.84 (m, 3H), 7.74 (d, 2H, J=8.4 Hz), 7.29-7.41 (m, 5H), 7.15 (d, 1H, J=8.4 Hz), 4.86 (s, 2H), 4.26 (t, 2H, J=5.2 Hz), 3.60 (t, 2H, J=5.2 Hz); MS m/z 398.1 (M+H).

Example 219

4-((3-methoxypyridin-2-yl)methyl)-7-(4-(trifluoromethoxy)phenyl)-3,4-dihydrobenzo[f][1,4]oxazepin-5(2H)-one (Compound II-143)

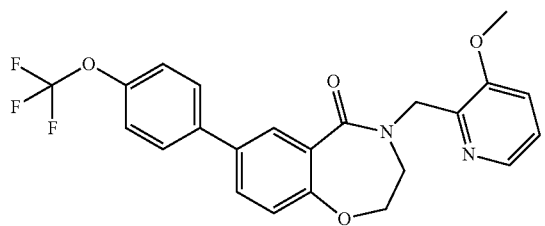 [SMILES: COc1cccnc1CN1CCOc2ccc(-c3ccc(OC(F)(F)F)cc3)cc2C1=O]

Compound II-143 was prepared according to the Examples disclosed herein using the appropriate starting materials. $^1$H-NMR (CD$_3$OD) δ 8.23 (d, 1H, J=5.6 Hz), 8.00 (d, 1H, J=2.8 Hz), 7.92 (d, 1H, J=8.4 Hz), 7.77 (dd, 1H, J=8.4, 2.4 Hz), 7.68-7.71 (m, 3H), 7.34 (d, 2H, J=8.0 Hz), 7.15 (d, 1H, J=8.8 Hz), 5.03 (s, 2H), 4.45 (t, 2H, J=4.8 Hz), 4.05 (s, 3H), 3.82 (t, 2H, J=5.0 Hz); MS m/z 445.1 (M+H).

Example 220

4-((1-(difluoromethyl)-1H-pyrazol-3-yl)methyl)-7-(4-(trifluoromethoxy)phenyl)-3,4-dihydrobenzo[f][1,4]oxazepin-5(2H)-one (Compound II-147)

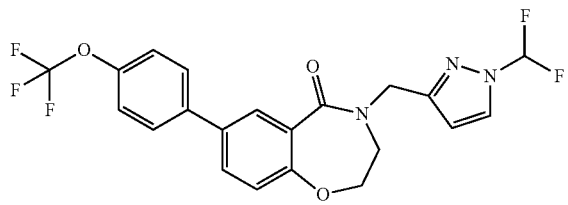 [SMILES: O=C1c2cc(-c3ccc(OC(F)(F)F)cc3)ccc2OCCN1Cc1ccn(C(F)F)n1]

Compound II-147 was prepared according to the Examples disclosed herein using the appropriate starting materials. $^1$H-NMR (CD$_3$OD) δ 8.01 (dd, 2H, J=9.4, 2.6 Hz), 7.76 (dd, 1H, J=8.2, 2.6 Hz), 7.72 (d, 2H, J=8.8 Hz), 7.73-7.76 (m, 2H), 7.13 (d, 1H, J=8.4 Hz), 6.54 (d, 1H, J=2.4 Hz), 4.88 (s, 2H), 4.35 (t, 2H, J=5.0 Hz), 3.69 (t, 2H, J=5.0 Hz); MS m/z 454.0 (M+H).

Example 221

7-(4-(trifluoromethoxy)phenyl)-4-((3-(trifluoromethyl)-1H-pyrazol-1-yl)methyl)-3,4-dihydrobenzo[f][1,4]oxazepin-5(2H)-one (Compound II-148)

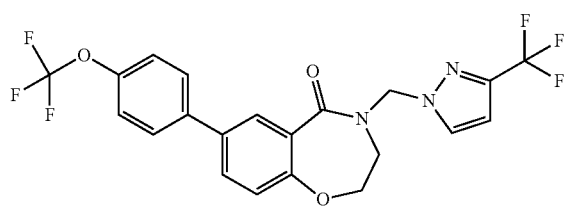 [SMILES: O=C1c2cc(-c3ccc(OC(F)(F)F)cc3)ccc2OCCN1Cn1ccc(C(F)(F)F)n1]

Compound II-148 was prepared according to the Examples disclosed herein using the appropriate starting materials. MS m/z 494.0 (M+Na).

Example 222

4-((1-cyclopentyl-1H-pyrazol-3-yl)methyl)-7-(4-(trifluoromethoxy)phenyl)-3,4-dihydrobenzo[f][1,4]oxazepin-5(2H)-one (Compound II-152)

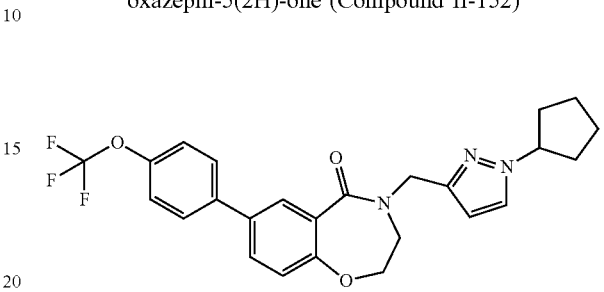

Compound II-152 was prepared according to the Examples disclosed herein using the appropriate starting materials. MS m/z 472.1 (M+H).

Example 223

4-((1-ethyl-1H-pyrazol-3-yl)methyl)-7-(4-(trifluoromethoxy)phenyl)-3,4-dihydrobenzo[f][1,4]oxazepin-5(2H)-one (Compound II-153)

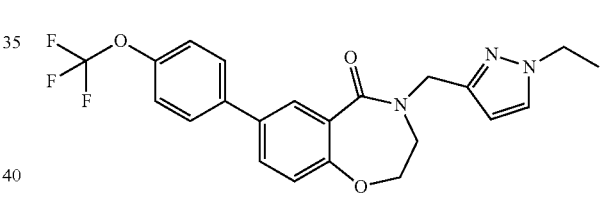

Compound II-153 was prepared according to the Examples disclosed herein using the appropriate starting materials. $^1$H-NMR (CD$_3$OD) δ 7.99 (d, 1H, J=2.4 Hz), 7.71-7.76 (m, 3H), 7.61 (d, 1H, J=2.4 Hz), 7.35 (d, 2H, J=8.0 Hz), 7.12 (d, 1H, J=8.4 Hz), 6.31 (d, 1H, J=2.4 Hz), 4.82 (s, 2H), 4.29 (t, 2H, J=5.0 Hz), 4.17 (q, 2H, J=7.2 Hz), 3.64 (t, 2H, J=7.4 Hz), 1.45 (t, 3H, J=7.4 Hz); MS m/z 432.1 (M+H).

Example 224

4-((1-methyl-1H-imidazol-4-yl)methyl)-7-(4-(trifluoromethoxy)phenyl)-3,4-dihydrobenzo[f][1,4]oxazepin-5(2H)-one (Compound II-154)

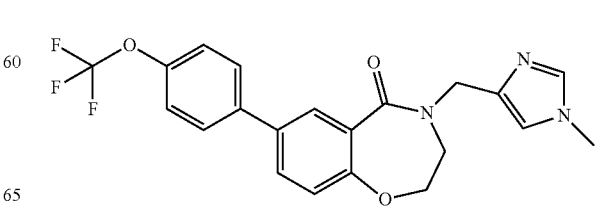

Compound II-154 was prepared according to the Examples disclosed herein using the appropriate starting materials. MS m/z 418.1 (M+H).

Example 225

4-((4-methyl-1H-pyrazol-1-yl)methyl)-7-(4-(trifluoromethoxy)phenyl)-3,4-dihydrobenzo[f][1,4]oxazepin-5(2H)-one (Compound II-155)

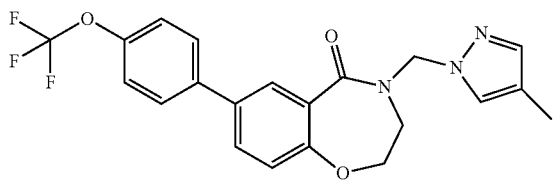 [SMILES: Cc1cnn(CN2CCOc3ccc(-c4ccc(OC(F)(F)F)cc4)cc3C2=O)c1]

Compound II-155 was prepared according to the Examples disclosed herein using the appropriate starting materials. $^1$H-NMR (CD$_3$OD) δ 7.98 (d, 1H, J=2.4 Hz), 7.76 (dd, 1H, J=8.2, 2.6 Hz), 7.71 (d, 2H, J=8.4 Hz), 7.61 (s, 1H), 7.34-7.37 (m, 3H), 7.11 (d, 1H, J=8.8 Hz), 5.83 (s, 2H), 4.21 (t, 2H, J=5.0 Hz), 3.76 (t, 2H, J=5.0 Hz), 2.09 (s, 3H); MS m/z 418.1 (M+H).

Example 226

4-((4-chloro-1H-pyrazol-1-yl)methyl)-7-(4-(trifluoromethoxy)phenyl)-3,4-dihydrobenzo[f][1,4]oxazepin-5(2H)-one (Compound II-156)

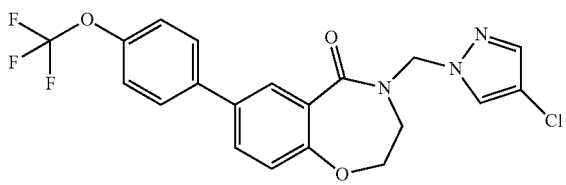 [SMILES: O=C1c2cc(-c3ccc(OC(F)(F)F)cc3)ccc2OCCN1Cn1cc(Cl)cn1]

Compound II-156 was prepared according to the Examples disclosed herein using the appropriate starting materials. $^1$H-NMR (CD$_3$OD) δ 7.99 (d, 1H, J=2.4 Hz), 7.91 (s, 1H), 7.77 (dd, 1H, J=8.4, 2.4 Hz), 7.71 (d, 2H, J=8.8 Hz), 7.52 (s, 1H), 7.35 (d, 2H, J=8.0 Hz), 7.13 (d, 1H, J=8.8 Hz), 5.85 (s, 2H), 4.29 (t, 2H, J=5.0 Hz), 3.81 (t, 2H, J=5.2 Hz); MS m/z 438.0 (M+H).

Example 227

4-((1-methyl-1H-pyrazol-4-yl)methyl)-7-(4-(trifluoromethoxy)phenyl)-3,4-dihydrobenzo[f][1,4]oxazepin-5(2H)-one (Compound II-160)

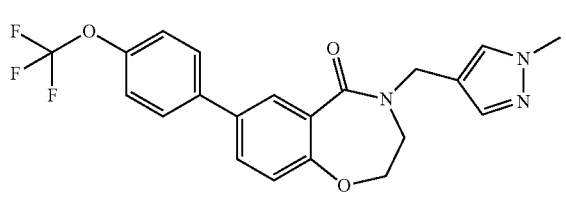 [SMILES: Cn1cc(CN2CCOc3ccc(-c4ccc(OC(F)(F)F)cc4)cc3C2=O)cn1]

Compound II-160 was prepared according to the Examples disclosed herein using the appropriate starting materials. $^1$H-NMR (CD$_3$OD) δ 7.98 (d, 1H, J=2.8 Hz), 7.67-7.76 (m, 4H), 7.53 (s, 1H), 7.35 (d, 2H, J=8.0 Hz), 7.12 (d, 1H, J=8.0 Hz), 4.69 (s, 2H), 4.31 (t, 2H, J=5.2 Hz), 3.87 (s, 3H), 3.62 (t, 2H, J=5.0 Hz); MS m/z 418.1 (M+H).

Example 228

4-((3-fluoropyridin-2-yl)methyl)-7-(4-(trifluoromethoxy)phenyl)-3,4-dihydrobenzo[f][1,4]oxazepin-5(2H)-one (Compound II-164)

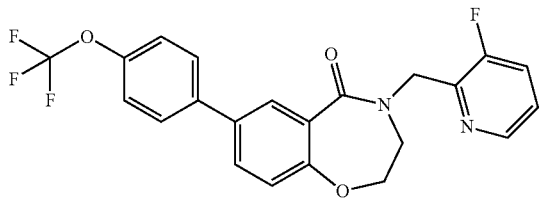 [SMILES: O=C1c2cc(-c3ccc(OC(F)(F)F)cc3)ccc2OCCN1Cc1ncccc1F]

Compound II-164 was prepared according to the Examples disclosed herein using the appropriate starting materials. $^1$H-NMR (CD$_3$OD) δ 8.37 (d, 1H, J=4.8 Hz), 8.00 (d, 1H, J=2.4 Hz), 7.76 (dd, 1H, J=8.0, 2.4 Hz), 7.72 (d, 2H, J=8.8 Hz), 7.61 (t, 1H, J=9.2 Hz), 7.38-7.42 (m, 1H), 7.34 (d, 2H, J=8.0 Hz), 7.14 (d, 1H, J=8.0 Hz), 5.07 (s, 2H), 4.45 (t, 2H, J=4.8 Hz), 3.78 (t, 2H, J=4.8 Hz); MS m/z 433.1 (M+H).

Example 229

7-(4-chloro-3-fluorophenyl)-4-((3-fluoropyridin-2-yl)methyl)-3,4-dihydrobenzo[f][1,4]oxazepin-5(2H)-one (Compound II-169)

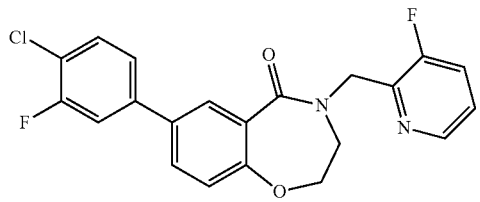 [SMILES: O=C1c2cc(-c3ccc(Cl)c(F)c3)ccc2OCCN1Cc1ncccc1F]

Compound II-169 was prepared according to the Examples disclosed herein using the appropriate starting materials. $^1$H-NMR (CD$_3$OD) δ 8.35 (d, 1H, J=5.2 Hz), 8.00 (s, 1H), 7.76 (d, 1H, J=8.4 Hz), 7.61 (t, 1H, J=9.2 Hz), 7.51-7.55 (m, 2H), 7.38-7.46 (m, 2H), 7.14 (d, 1H, J=8.0 Hz), 5.07 (s, 2H), 4.46 (t, 2H, J=4.8 Hz), 3.78 (t, 2H, J=4.8 Hz); MS m/z 401.1 (M+H).

Example 230

7-(2-fluoro-4-(trifluoromethyl)phenyl)-4-((3-fluoropyridin-2-yl)methyl)-3,4-dihydrobenzo[f][1,4]oxazepin-5(2H)-one (Compound II-170)

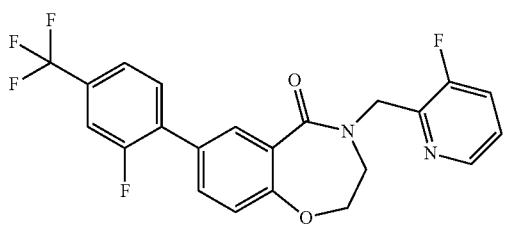 [SMILES: O=C1c2cc(-c3ccc(C(F)(F)F)cc3F)ccc2OCCN1Cc1ncccc1F]

Compound II-170 was prepared according to the Examples disclosed herein using the appropriate starting materials. ¹H-NMR (CD₃OD) δ 8.37 (d, 1H, J=4.8 Hz), 7.99 (s, 1H), 7.70-7.74 (m, 2H), 7.53-7.63 (m, 3H), 7.38-7.42 (m, 1H), 7.17 (d, 1H, J=8.4 Hz), 5.07 (s, 2H), 4.49 (t, 2H, J=5.0 Hz), 3.80 (t, 2H, J=4.8 Hz); MS m/z 435.1 (M+H).

Example 231

4-((3-fluoropyridin-2-yl)methyl)-7-(4-(trifluoromethyl)phenyl)-3,4-dihydrobenzo[f][1,4]oxazepin-5(2H)-one (Compound II-176)

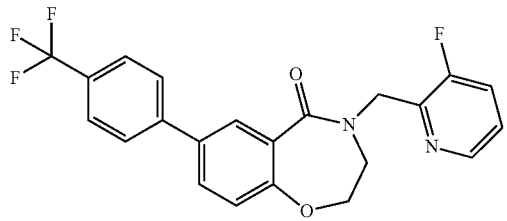 [SMILES: O=C1c2cc(-c3ccc(C(F)(F)F)cc3)ccc2OCCN1Cc1ncccc1F]

Compound II-176 was prepared according to the Examples disclosed herein using the appropriate starting materials. ¹H-NMR (CD₃OD) δ 8.36 (d, 1H, J=4.4 Hz), 8.06 (s, 1H), 7.71-7.81 (m, 3H), 7.72 (d, 2H, J=8.0 Hz), 7.60 (t, 1H, J=9.0 Hz), 7.37-7.41 (m, 1H), 7.15 (d, 1H, J=8.4 Hz), 5.06 (s, 2H), 4.46 (t, 2H, J=5.0 Hz), 3.78 (t, 2H, J=4.8 Hz); MS m/z 417.1 (M+H).

Example 232

4-(pyrimidin-2-ylmethyl)-7-(4-(trifluoromethoxy)phenylamino)-3,4-dihydrobenzo[f][1,4]oxazepin-5(2H)-one (Compound XIII-1)

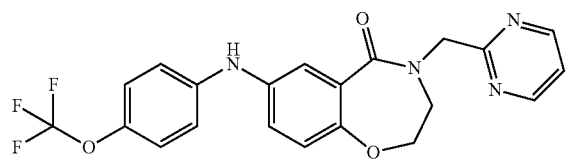 [SMILES: O=C1c2cc(Nc3ccc(OC(F)(F)F)cc3)ccc2OCCN1Cc1ncccn1]

Compound XIII-1 was prepared according to the Examples disclosed herein using the appropriate starting materials. MS m/z 431.1 (M+H).

Example 233

4-(pyrimidin-2-ylmethyl)-7-(4-(trifluoromethoxy)phenoxy)-3,4-dihydrobenzo[f][1,4]oxazepin-5(2H)-one (Compound XIII-2)

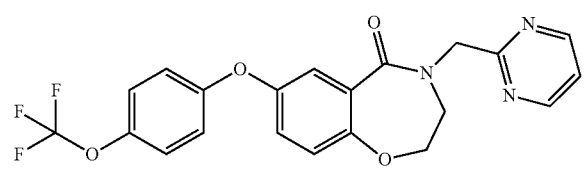

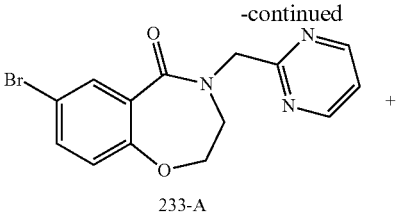

233-A

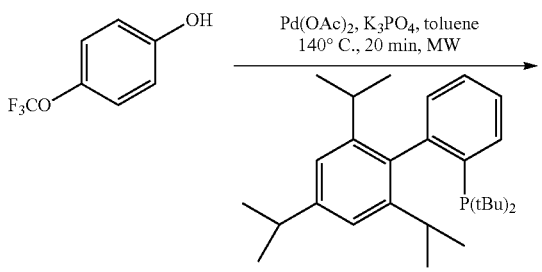

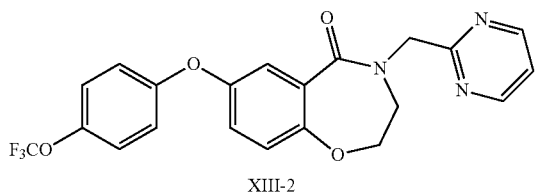

XIII-2

233-A (70 mg, 0.21 mmol), 4-(trifluoromethoxy)phenol (45 mg, 0.252 mmol), K₃PO₄ (134 mg, 0.63 mmol), Pd(OAc)₂ (3%) and di-tert-butyl(2'4'6'-triisopropylbiphenyl-2-yl)phosphine (6%) in toluene (3.5 mL) were put onto microwave at 140° C. for 20 min. The reaction mixture was diluted with EtOAC, filtered through ceilite and washed with EtOAc. The filtrate was concentrated and purified by HPLC followed by prep-TLC (EtOAc) to afford Compound XIII-2 (1.8 mg). MS m/z 432.1 (M+H).

Example 234

4-(pyrimidin-2-ylmethyl)-7-(4-(trifluoromethyl)phenylamino)-3,4-dihydrobenzo[f][1,4]oxazepin-5(2H)-one (Compound XIII-3)

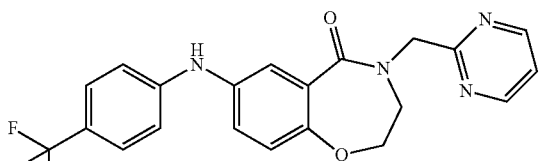

Compound XIII-3 was prepared according to the Examples disclosed herein using the appropriate starting materials. MS m/z 415.1 (M+H).

Example 235

4-(pyridin-2-ylmethyl)-7-(4-(trifluoromethoxy)phenylamino)-3,4-dihydrobenzo[f][1,4]oxazepin-5(2H)-one (Compound XIII-4)

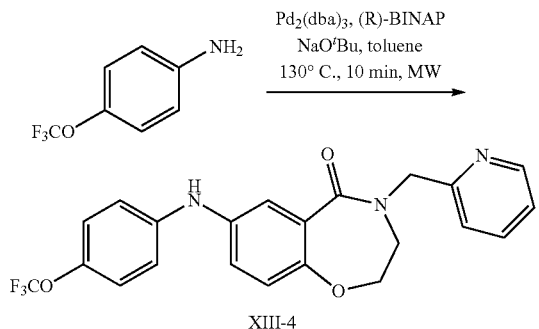

235-A (70 mg, 0.21 mmol), 4-(trifluoromethoxy)aniline (45 mg, 0.252 mmol), NaO$^t$Bu (40 mg, 0.42 mmol), Pd$_2$(dba)$_3$ (3%) and (R)-BINAP (6%) in toluene (3.5 mL) were put onto microwave at 130° C. for 10 min. The reaction mixture was diluted with EtOAC, filtered through ceilite and washed with EtOAc. The filtrate was concentrated and purified by HPLC to afford Compound XIII-4 (22.8 mg).

$^1$H-NMR (CD$_3$OD) δ 8.66 (d, 1H, J=5.2 Hz), 8.23 (t, 1H, J=8.0 Hz), 7.78 (d, 1H, J=8.0 Hz), 7.68 (t, 1H, J=6.4 Hz), 7.41 (s, 1H), 7.22-7.40 (m, 1H), 7.06-7.13 (m, 4H), 7.01 (d, 1H, J=8.8 Hz), 5.04 (s, 2H), 4.33 (t, 2H, J=5.0 Hz), 3.74 (t, 2H, J=5.4 Hz); MS m/z 430.1 (M+H).

Example 236

4-(pyridin-2-ylmethyl)-7-(4-(trifluoromethyl)phenylamino)-3,4-dihydrobenzo[f][1,4]oxazepin-5(2H)-one (Compound XIII-6)

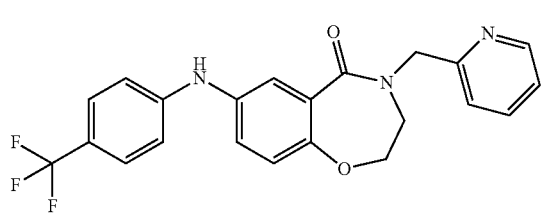 [SMILES: O=C1c2cc(Nc3ccc(C(F)(F)F)cc3)ccc2OCCN1Cc1ccccn1]

Compound XIII-6 was prepared according to the Examples disclosed herein using the appropriate starting materials. $^1$H-NMR (CD$_3$OD) δ 8.52 (d, 1H, J=5.2 Hz), 7.84 (t, 1H, J=7.6 Hz), 7.44-7.50 (m, 4H), 7.29-7.36 (m, 2H), 7.10 (d, 2H, J=8.0 Hz), 7.03 (d, 1H, J=8.8 Hz), 4.94 (s, 2H), 4.29 (t, 2H, J=5.2 Hz), 3.68 (t, 2H, J=5.6 Hz); MS m/z 414.1 (M+H).

Example 237

7-(methyl(4-(trifluoromethoxy)phenyl)amino)-4-(pyrimidin-2-ylmethyl)-3,4-dihydrobenzo[f][1,4]oxazepin-5(2H)-one (Compound XIII-10)

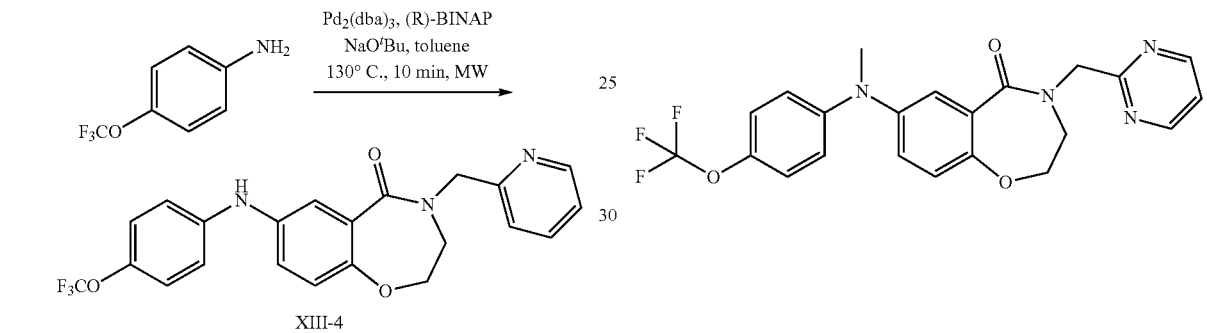

Compound XIII-10 was prepared according to the Examples disclosed herein using the appropriate starting materials. MS m/z 445.1 (M+H).

Example 238

7-(methyl(4-(trifluoromethoxy)phenyl)amino)-4-(pyridin-2-ylmethyl)-3,4-dihydrobenzo[f][1,4]oxazepin-5(2H)-one (Compound XIII-12)

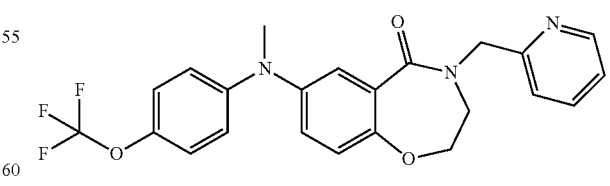

Compound XIII-12 was prepared according to the Examples disclosed herein using the appropriate starting materials. MS m/z 444.1 (M+H).

Example 239
5-benzyl-8-(4-(trifluoromethyl)phenyl)-4H-benzo[f]imidazo[1,2-a][1,4]diazepin-6(5H)-one (Compound X-12)
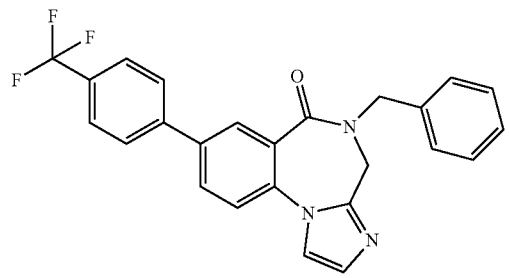
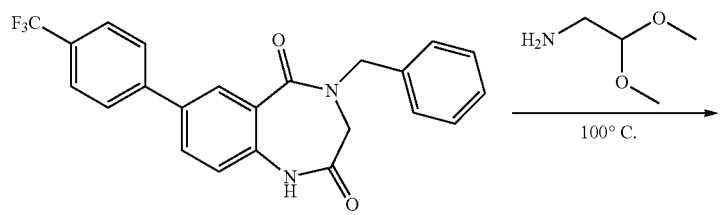
239-A
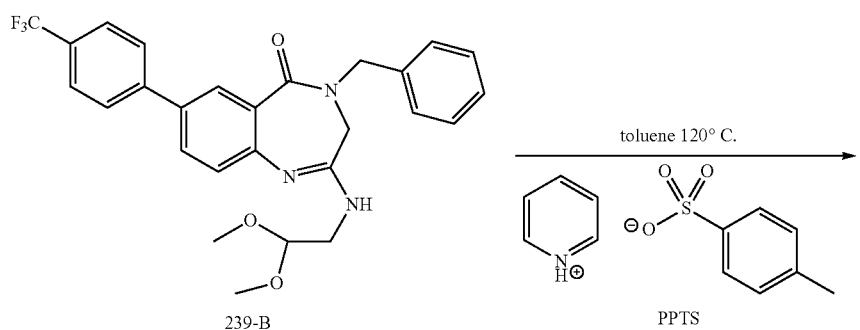
239-B
X-12

239-A (0.100 g, 0.244 mmol), 2, 2-dimethoxyethanamine (1 mL, 9.3 mmol) were mixed together, the resulting mixture was stirred at 100° C. for 4 hours. When the reaction was cooled down, Water was added dropwise until precipitation was finished. The precipitates were collected by filtration and washed with water to afford 239-B (0.111 g, 92%), MS m/z: 498 (M+H)+.

239-B (0.104 g, 0.209 mmol), PPTS (0.525 g, 2.09 mmol) were added to Toluene (5 mL). The resulting mixture was stirred at 120° C. overnight, concentrated and purified by preparative HPLC to afford Compound X-12 (0.013 g, 14%). MS m/z: 434 (MH+).

Example 240

N-(2-(5-oxo-7-(4-(trifluoromethoxy)phenyl)-2,3-dihydrobenzo[f][1,4]oxazepin-4(5H)-yl)ethyl)pyrimidine-2-carboxamide (Compound II-192)

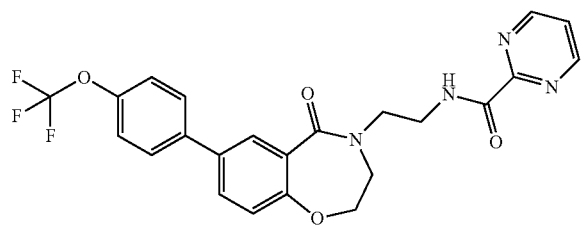

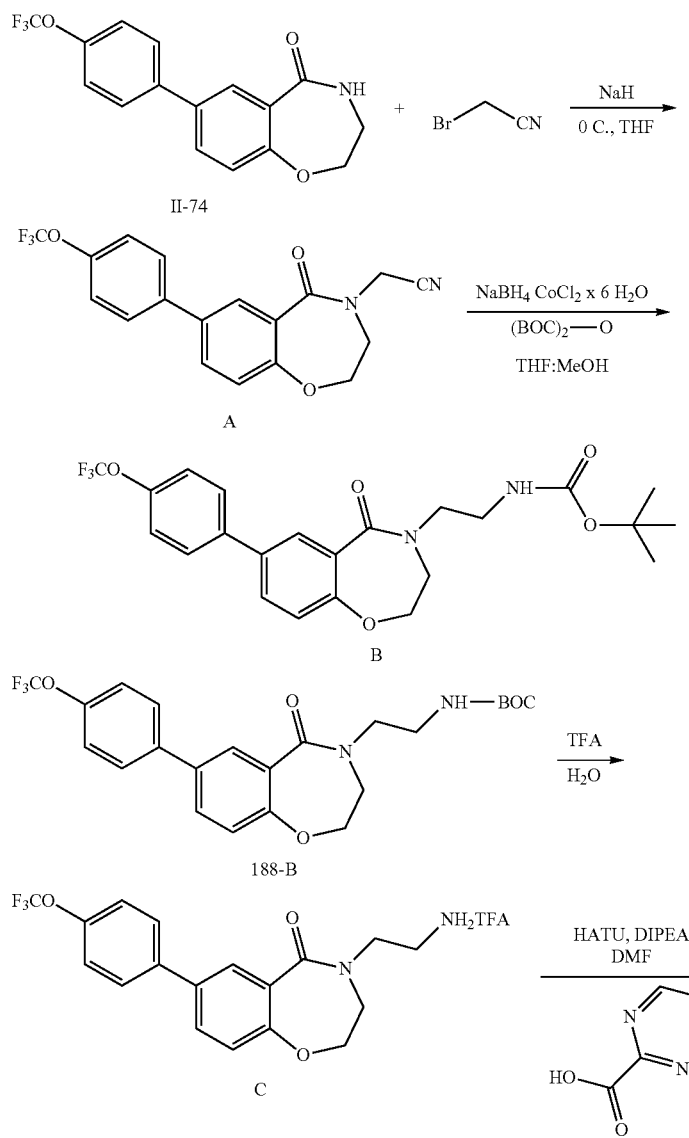

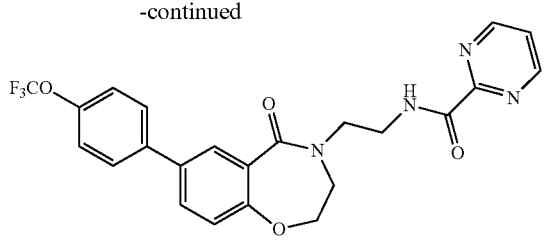

Compound II-192 was prepared according to Examples 188 and 195 disclosed herein using the appropriate starting materials. MS m/z 473.1 (M+).

Example 241

7-(5-cyclopropylthiophen-2-yl)-4-(pyrimidin-2-ylmethyl)-3,4-dihydrobenzo[f][1,4]oxazepin-5(2H)-one (Compound VI-36)

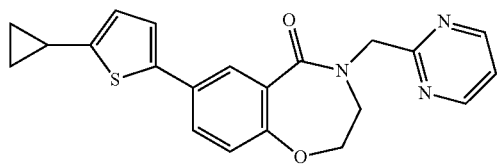 [SMILES: O=C1c2cc(-c3ccc(C4CC4)s3)ccc2OCCN1Cc1ncccn1]

Compound VI-36 was prepared according to the Examples disclosed herein using the appropriate starting materials. $^1$H-NMR (DMSO) δ 8.77 (d, 2H, J=5.2 Hz), 7.79 (d, 1H, J=2.4 Hz), 7.68 (dd, 1H, J=8.2, 2.6 Hz), 7.40 (t, 1H, J=5.0 Hz), 7.22 (d, 1H, J=3.2 Hz), 7.04 (d, 1H, J=8.8 Hz), 6.78-6.79 (m, 1H), 4.95 (s, 2H), 4.47 (t, 2H, J=5.0 Hz), 3.73 (t, 2H, J=5.0 Hz), 2.07-2.13 (m, 1H), 0.96-1.00 (m, 2H), 0.66-0.70 (m, 2H); MS m/z 378 (M+H).

Example 242

4-(pyrimidin-2-ylmethyl)-7-(5-(trifluoromethyl)thiophen-2-yl)-3,4-dihydrobenzo[f][1,4]oxazepin-5(2H)-one (Compound VI-37)

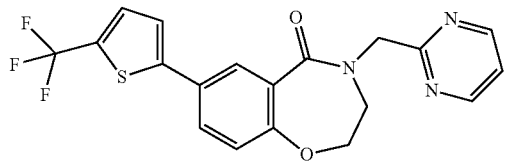 [SMILES: O=C1c2cc(-c3ccc(C(F)(F)F)s3)ccc2OCCN1Cc1ncccn1]

Compound VI-37 was prepared according to the Examples disclosed herein using the appropriate starting materials. $^1$H-NMR (DMSO) δ 8.70 (d, 2H, J=5.2 Hz), 7.72 (d, 1H, J=2.4 Hz), 7.61 (dd, 1H, J=8.2, 2.6 Hz), 7.30 (t, 1H, J=5.0 Hz), 7.12 (d, 1H, J=3.2 Hz), 7.01 (d, 1H, J=8.8 Hz), 6.72-6.75 (m, 1H), 4.91 (s, 2H), 4.42 (t, 2H, J=5.0 Hz), 3.71 (t, 2H, J=5.0 Hz), 2.07-2.11 (m, 1H), 0.94-1.1 (m, 2H), 0.64-0.69 (m, 2H); MS m/z 406 (M+H).

Example 243

4-(pyrimidin-2-ylmethyl)-7-(4-(trifluoromethyl)phenethyl)-3,4-dihydrobenzo[f][1,4]oxazepin-5(2H)-one (Compound VIII-8)

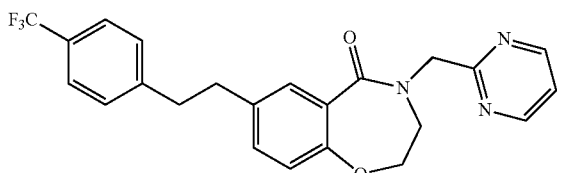

Compound VIII-8 was prepared according to the Examples disclosed herein using the appropriate starting materials. $^1$H-NMR (CD$_3$OD) δ 8.74 (d, 2H, J=4.8 Hz), 7.51-7.54 (m, 3H), 7.33-7.37 (m, 3H), 7.26 (dd, 1H, J=8.2, 2.2 Hz), 6.94 (d, 1H, J=8.0 Hz), 5.02 (s, 2H), 4.45 (t, 2H, J=5.2 Hz), 3.72 (t, 2H, J=5.2 Hz), 2.91-3.00 (m, 4H); MS m/z 428.1 (M+H).

Example 244

4-((3-fluoropyridin-2-yl)methyl)-7-(4-(trifluoromethyl)phenethyl)-3,4-dihydrobenzo[f][1,4]oxazepin-5(2H)-one (Compound VIII-9)

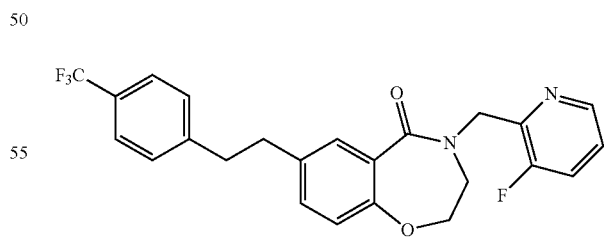

Compound VIII-9 was prepared according to the Examples disclosed herein using the appropriate starting materials. $^1$H-NMR (CD$_3$OD) δ 8.34 (d, 1H, J=5.2 Hz), 7.50-7.60 (m, 4H), 7.33-7.40 (m, 3H), 7.25 (dd, 1H, J=8.4, 2.4 Hz), 6.92 (d, 1H, J=8.0 Hz), 5.01 (d, 2H, J=1.6 Hz), 4.32 (t, 2H, J=5.2 Hz), 3.66 (t, 2H, J=5.2 Hz), 2.90-3.00 (m, 4H); MS m/z 445.1 (M+H).

Example 245

7-(4-(4-fluorophenoxy)phenyl)-4-(pyrimidin-2-ylmethyl)-3,4-dihydrobenzo[f][1,4]oxazepin-5(2H)-one (Compound II-193)

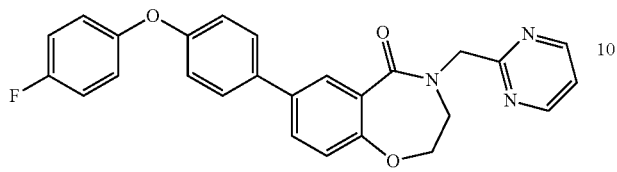

Compound II-193 was prepared according to the Examples disclosed herein using the appropriate starting materials. $^1$H-NMR (CD$_3$OD) δ 8.77 (d, 2H, J=5.2 Hz), 7.97 (d, 1H, J=2.0 Hz), 7.73 (dd, 1H, J=8.8, 2.4 Hz), 7.61 (dd, 2H, J=6.8, 2.0 Hz), 7.38 (t, 1H, J=4.8 Hz), 7.02-7.14 (m, 7H), 5.07 (s, 2H), 4.56 (t, 2H, J=5.0 Hz), 3.82 (t, 2H, J=5.0 Hz); MS m/z 442.1 (M+H).

Example 246

7-(4-phenoxyphenyl)-4-(pyrimidin-2-ylmethyl)-3,4-dihydrobenzo[f][1,4]oxazepin-5(2H)-one (Compound II-194)

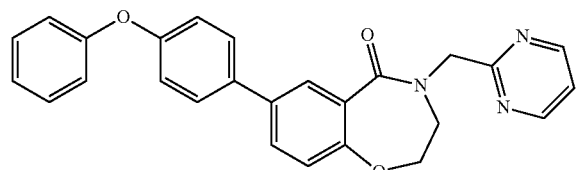

Compound II-194 was prepared according to the Examples disclosed herein using the appropriate starting materials. $^1$H-NMR (CD$_3$OD) δ 8.77 (d, 2H, J=5.2 Hz), 7.97 (d, 1H, J=2.4 Hz), 7.74 (dd, 1H, J=8.6, 2.6 Hz), 7.61 (dd, 2H, J=6.8, 2.4 Hz), 7.35-7.39 (m, 3H), 7.10-7.15 (m, 2H), 7.01-7.06 (m, 4H), 5.07 (s, 2H), 4.56 (t, 2H, J=5.2 Hz), 3.82 (t, 2H, J=5.0 Hz); MS m/z 424.1 (M+H).

Example 247

7-(3-phenoxyphenyl)-4-(pyrimidin-2-ylmethyl)-3,4-dihydrobenzo[f][1,4]oxazepin-5(2H)-one (Compound II-195)

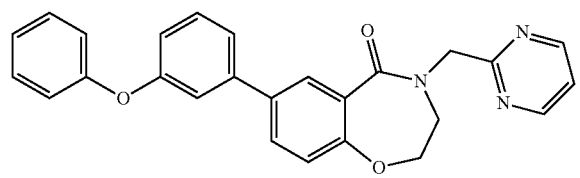 [SMILES: O=C1c2cc(-c3cccc(Oc4ccccc4)c3)ccc2OCCN1Cc1ncccn1]

Compound II-195 was prepared according to the Examples disclosed herein using the appropriate starting materials. $^1$H-NMR (CD$_3$OD) δ 8.76 (d, 2H, J=5.2 Hz), 7.96 (d, 1H, J=2.4 Hz), 7.71 (dd, 1H, J=8.2, 2.6 Hz), 7.34-7.44 (m, 5H), 7.23 (t, 1H, J=2.0 Hz), 7.10-7.14 (m, 2H), 7.02-7.04 (m, 2H), 6.93-6.96 (m, 1H), 5.06 (s, 2H), 4.56 (t, 2H, J=5.0 Hz), 3.81 (t, 2H, J=5.2 Hz); MS m/z 424.1 (M+H).

Example 248

(E)-4-benzyl-7-(4-(trifluoromethyl)styryl)-3,4-dihydrobenzo[f][1,4]oxazepin-5(2H)-one (Compound VIII-10)

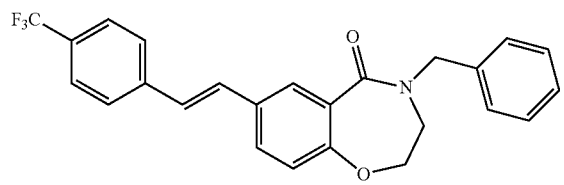 [SMILES: O=C1c2cc(/C=C/c3ccc(C(F)(F)F)cc3)ccc2OCCN1Cc1ccccc1]

Compound VIII-10 was prepared according to the Examples disclosed herein using the appropriate starting materials. MS m/z 424.1 (M+H).

Example 249

4-benzyl-7-(4-(trifluoromethyl)phenethyl)-3,4-dihydrobenzo[f][1,4]oxazepin-5(2H)-one (Compound VIII-11)

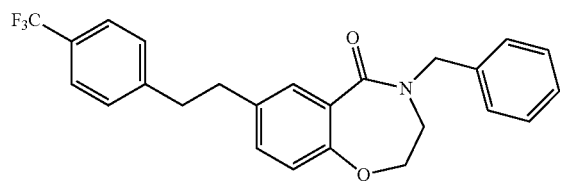 [SMILES: O=C1c2cc(CCc3ccc(C(F)(F)F)cc3)ccc2OCCN1Cc1ccccc1]

Compound VIII-11 was prepared according to the Examples disclosed herein using the appropriate starting materials. $^1$H-NMR (CD$_3$OD) δ 7.53-7.54 (m, 3H), 7.26-7.37 (m, 8H), 6.93 (d, 1H, J=8.0 Hz), 4.82 (s, 2H), 4.16 (t, 2H, J=5.2 Hz), 3.49 (t, 2H, J=5.2 Hz), 2.95-3.02 (m, 4H); MS m/z 426.1 (M+H).

Example 250

4-(3-(azetidin-1-ylsulfonyl)propyl)-7-(4-(trifluoromethoxy)phenyl)-3,4-dihydrobenzo[f][1,4]oxazepin-5(2H)-one (Compound II-191)

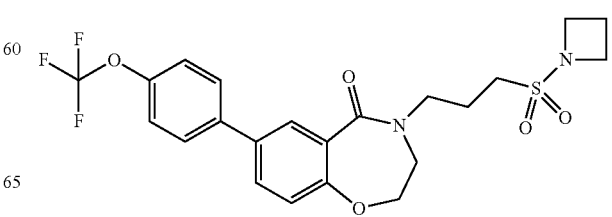

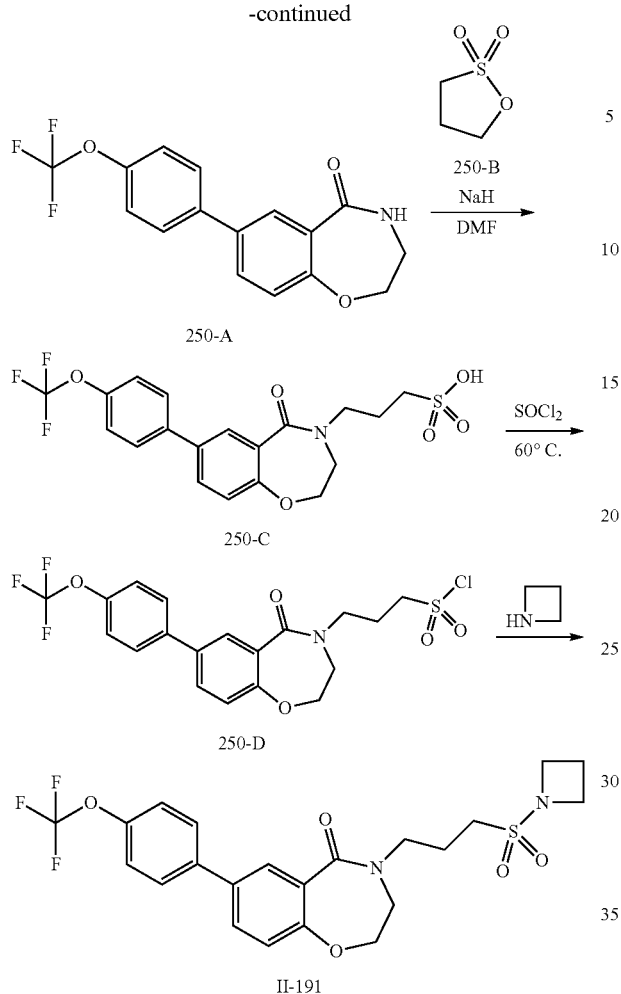

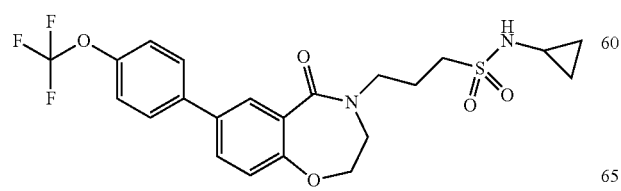

Compound 250-C was synthesized from Compound 250-A and sultone 250-B following general alkylation procedures. Compound 250-C (84 mg, 0.19 mmol) was treated with thionyl chloride at 60° C. overnight. The resulting mixture was concentrated to afford crude Compound 250-D which was treated with a solution of azetidine (26 μL, 2 eq) and triethylamine (250 μL) in DCM, the resulting mixture was stirred at room temperature for several hours, concentrated and purified with HPLC to afford Compound II-191 (42 mg). MS m/z: 485 (MH$^+$).

Example 251

N-cyclopropyl-3-(5-oxo-7-(4-(trifluoromethoxy)phenyl)-2,3-dihydrobenzo[f][1,4]oxazepin-4(5H)-yl)propane-1-sulfonamide (Compound II-190)

Compound II-190 was prepared according to the Examples disclosed herein using the appropriate starting materials. MS m/z: 485 (MH$^+$)

The following compounds were prepared according to the Examples disclosed herein using the appropriate starting materials:

4-(2,2,2-trifluoroethyl)-7-(4-(trifluoromethoxy)phenyl)-3,4-dihydrobenzo[f][1,4]oxazepin-5(2H)-one (Compound II-2) MS m/z 406.0 (M+H)

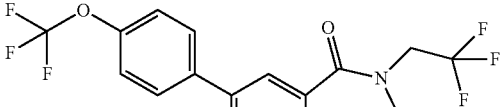

4-(2-(pyrrolidin-1-yl)ethyl)-7-(4-(trifluoromethoxy)phenyl)-3,4-dihydrobenzo[f][1,4]oxazepin-5(2H)-one (Compound II-3) MS m/z 421.1 (M+H)

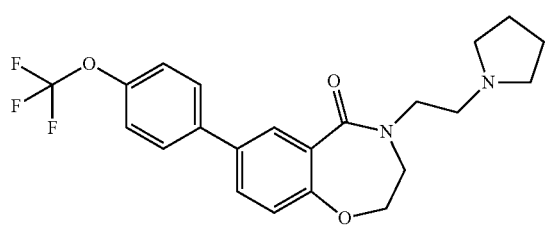 [SMILES: O=C1c2cc(-c3ccc(OC(F)(F)F)cc3)ccc2OCCN1CCN1CCCC1]

(2S,11aR)-2-amino-7-(4-(trifluoromethyl)phenyl)-2,3,11,11a-tetrahydrobenzo[f]pyrrolo[2,1-c][1,4]oxazepin-5(1H)-one (Compound II-20) MS m/z: 363 (MH$^+$)

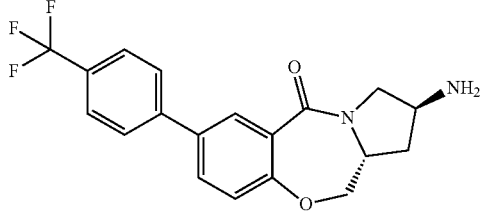 [SMILES: N[C@H]1C[C@@H]2COc3ccc(-c4ccc(C(F)(F)F)cc4)cc3C(=O)N2C1]

(R)-8-(4-(trifluoromethyl)phenyl)-3,4,12,12a-tetrahydro-1H-benzo[f]pyrazino[2,1-c][1,4]oxazepin-6(2H)-one (Compound II-26) MS m/z: 363 (MH$^+$)

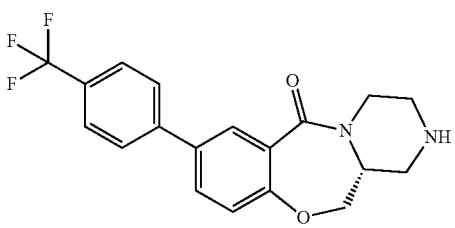 [SMILES: O=C1c2cc(-c3ccc(C(F)(F)F)cc3)ccc2OC[C@H]2CNCCN12]

273

(R)-tert-butyl 6-oxo-8-(4-(trifluoromethyl)phenyl)-3,4,12,12a-tetrahydro-1H-benzo[f]pyrazino[2,1-c][1,4]oxazepine-2(6H)-carboxylate (Compound II-27) MS m/z: 463 (MH⁺)

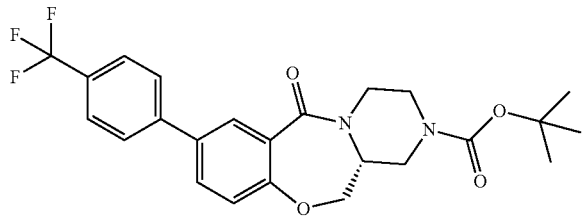 [SMILES: CC(C)(C)OC(=O)N1CCN2C(=O)c3cc(-c4ccc(C(F)(F)F)cc4)ccc3OC[C@H]2C1]

(S)-8-(4-(trifluoromethyl)phenyl)-3,4,12,12a-tetrahydro-1H-benzo[f]pyrazino[2,1-c][1,4]oxazepin-6(2H)-one (Compound II-28) MS m/z: 363 (MH⁺)

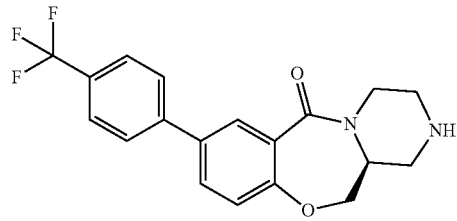 [SMILES: O=C1c2cc(-c3ccc(C(F)(F)F)cc3)ccc2OC[C@@H]2CNCCN12]

(S)-tert-butyl 6-oxo-8-(4-(trifluoromethyl)phenyl)-3,4,12,12a-tetrahydro-1H-benzo[f]pyrazino[2,1-c][1,4]oxazepine-2(6H)-carboxylate (Compound II-29) MS m/z: 463 (MH⁺)

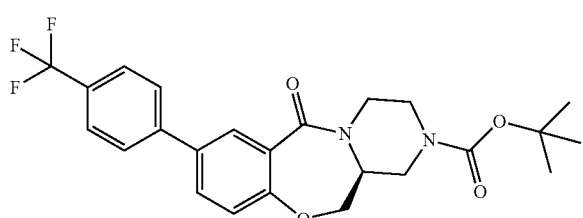

(2R,11aR)-2-(pyrimidin-2-ylamino)-7-(4-(trifluoromethyl)phenyl)-2,3,11,11a-tetrahydrobenzo[f]pyrrolo[2,1-c][1,4]oxazepin-5(1H)-one (Compound II-30) MS m/z: 441 (MH⁺)

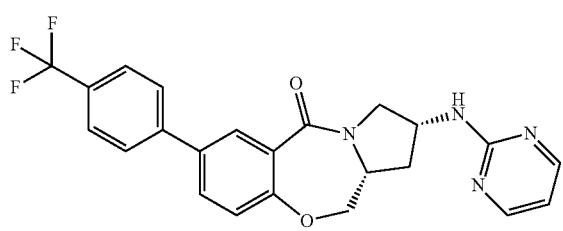 [SMILES: O=C1c2cc(-c3ccc(C(F)(F)F)cc3)ccc2OC[C@H]2C[C@@H](Nc3ncccn3)CN12]

274

4-((1-phenyl-5-(trifluoromethyl)-1H-pyrazol-4-yl)methyl)-7-(4-(trifluoromethoxy)phenyl)-3,4-dihydrobenzo[f][1,4]oxazepin-5(2H)-one (Compound II-32) MS m/z 548.1 (M+H)

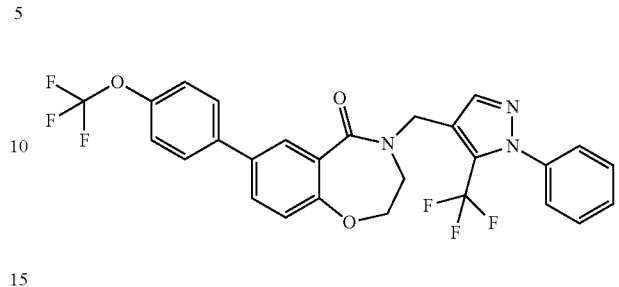

(2S,11aS)-2-(pyrimidin-2-ylamino)-7-(4-(trifluoromethyl)phenyl)-2,3,11,11a-tetrahydrobenzo[f]pyrrolo[2,1-c][1,4]oxazepin-5(1H)-one (Compound II-34) MS m/z: 441 (MH⁺)

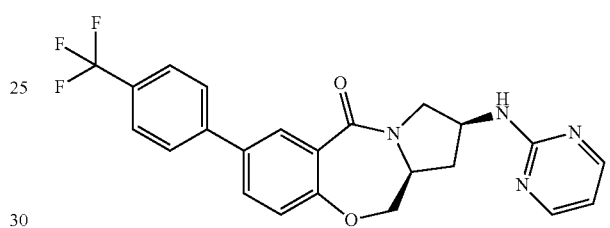

7-(4-(trifluoromethoxy)phenyl)-4-(2-(2,5,5-trimethyl-1,3-dioxan-2-yl)ethyl)-3,4-dihydrobenzo[f][1,4]oxazepin-5(2H)-one (Compound II-35) m/z: 480.1 (MH⁺)

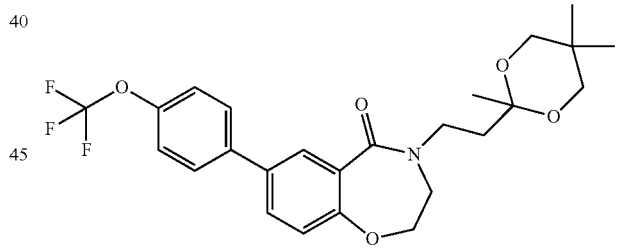

(2R,11aR)-2-(diethylamino)-7-(4-(trifluoromethyl)phenyl)-2,3,11,11a-tetrahydrobenzo[f]pyrrolo[2,1-c][1,4]oxazepin-5(1H)-one (Compound II-36) MS m/z: 419 (MH⁺)

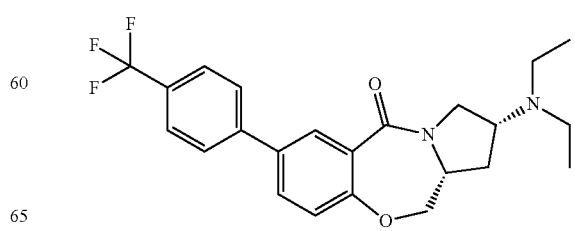

| 275 | 276 |
|---|---|
| (2S,11aS)-2-(diethylamino)-7-(4-(trifluoromethyl)phenyl)-2,3,11,11a-tetrahydrobenzo[f]pyrrolo[2,1-c][1,4]oxazepin-5(1H)-one (Compound II-37) MS m/z: 419 (MH⁺) | ethyl 3-((5-oxo-7-(4-(trifluoromethoxy)phenyl)-2,3-dihydrobenzo[f][1,4]oxazepin-4(5H)-yl)methyl)benzoate (Compound II-43) m/z: 486.1 (MH⁺) |

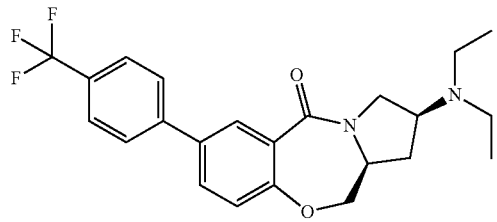 [SMILES: CCN(CC)[C@H]1C[C@H]2COc3ccc(-c4ccc(C(F)(F)F)cc4)cc3C(=O)N2C1]

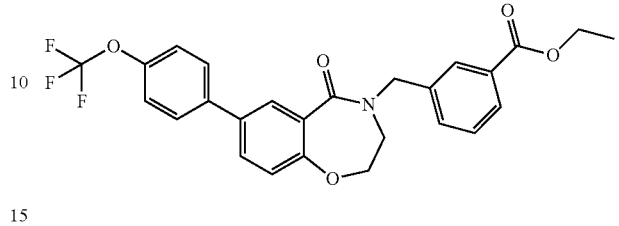

(2R,11aR)-2-amino-7-(4-(trifluoromethyl)phenyl)-2,3,11,11a-tetrahydrobenzo[f]pyrrolo[2,1-c][1,4]oxazepin-5(1H)-one (Compound II-38) MS m/z: 363 (MH⁺)

tert-butyl (2S,11aS)-5-oxo-7-(4-(trifluoromethyl)phenyl)-1,2,3,5,11,11a-hexahydrobenzo[f]pyrrolo[2,1-c][1,4]oxazepin-2-ylcarbamate (Compound II-52) MS m/z: 463 (MH⁺)

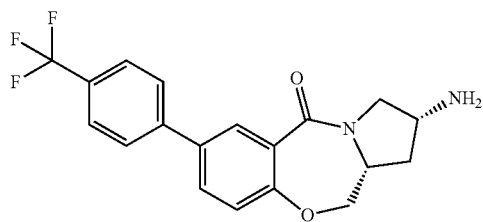 [SMILES: N[C@@H]1C[C@@H]2COc3ccc(-c4ccc(C(F)(F)F)cc4)cc3C(=O)N2C1]

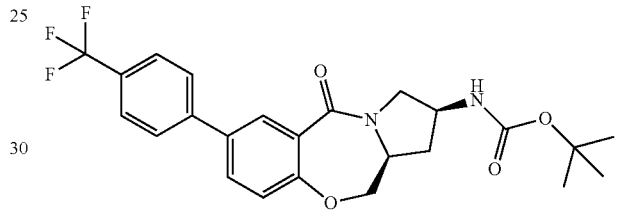

tert-butyl (2R,11aR)-5-oxo-7-(4-(trifluoromethyl)phenyl)-1,2,3,5,11,11a-hexahydrobenzo[f]pyrrolo[2,1-c][1,4]oxazepin-2-ylcarbamate (Compound II-39) MS m/z: 463 (MH⁺)

4-((3-cyclopropyl-1-methyl-1H-pyrazol-5-yl)methyl)-7-(4-(trifluoromethoxy)phenyl)-3,4-dihydrobenzo[f][1,4]oxazepin-5(2H)-one (Compound II-53) MS m/z 458.1 (M+H)

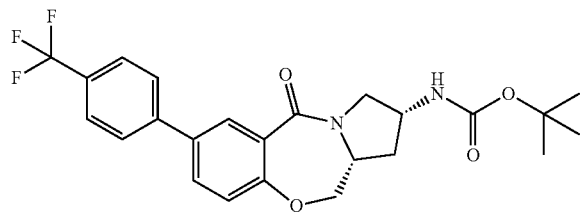 [SMILES: CC(C)(C)OC(=O)N[C@@H]1C[C@@H]2COc3ccc(-c4ccc(C(F)(F)F)cc4)cc3C(=O)N2C1]

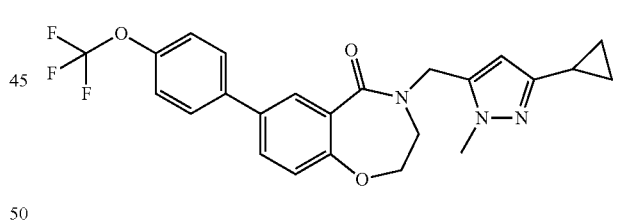

4-((5-(pyrimidin-2-yl)isoxazol-3-yl)methyl)-7-(4-(trifluoromethoxy)phenyl)-3,4-dihydrobenzo[f][1,4]oxazepin-5(2H)-one (Compound II-40) MS m/z 483.1 (M+H)

4-(4-(trifluoromethoxy)benzyl)-7-(4-(trifluoromethoxy)phenyl)-3,4-dihydrobenzo[f][1,4]oxazepin-5(2H)-one (Compound II-55) MS m/z 498.1 (M+H)

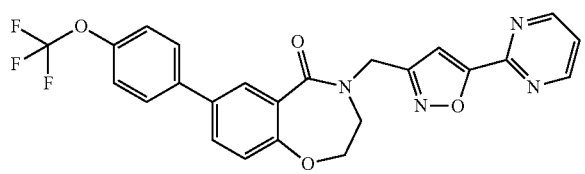

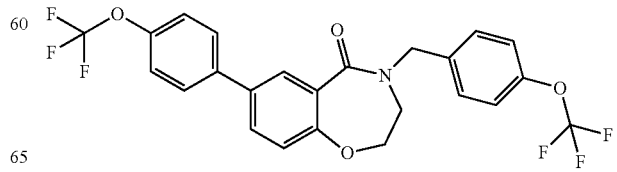

7-(4-(trifluoromethoxy)phenyl)-4-(4-(trifluoromethyl)benzyl)-3,4-dihydrobenzo[f][1,4]oxazepin-5(2H)-one (Compound II-56) MS m/z 482.1 (M+H)

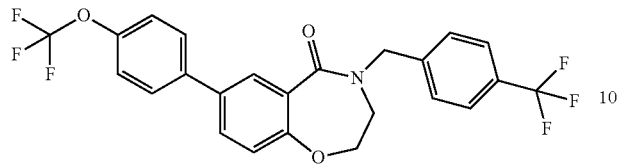

(2R,11aS)-2-hydroxy-7-(4-(trifluoromethyl)phenyl)-2,3,11,11a-tetrahydrobenzo[f]pyrrolo[2,1-c][1,4]oxazepin-5(1H)-one (Compound II-58) MS m/z: 364 (MH+)

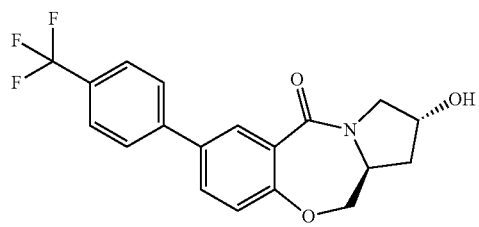 [SMILES: O=C1c2cc(-c3ccc(C(F)(F)F)cc3)ccc2OC[C@@H]2C[C@@H](O)CN12]

(R)-7-(4-(trifluoromethyl)phenyl)-2,3,11,11a-tetrahydrobenzo[f]pyrrolo[2,1-c][1,4]oxazepin-5(1H)-one (Compound II-59) MS m/z 348 (MH+)

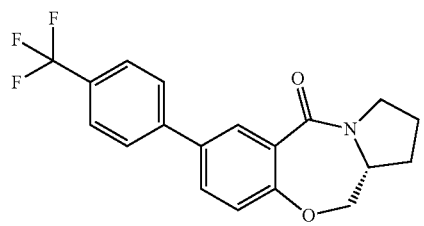 [SMILES: O=C1c2cc(-c3ccc(C(F)(F)F)cc3)ccc2OC[C@H]2CCCN12]

(S)-7-(4-(trifluoromethyl)phenyl)-2,3,11,11a-tetrahydrobenzo[f]pyrrolo[2,1-c][1,4]oxazepin-5(1H)-one (Compound II-60) MS m/z: 348 (MH+)

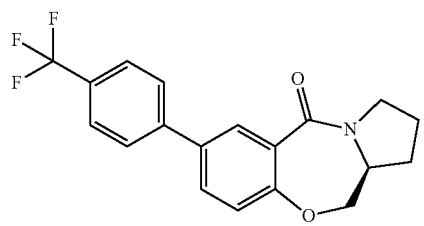 [SMILES: O=C1c2cc(-c3ccc(C(F)(F)F)cc3)ccc2OC[C@@H]2CCCN12]

8-(4-(trifluoromethyl)phenyl)-3,4,12,12a-tetrahydrobenzo[f][1,4]oxazino[3,4-c][1,4]oxazepin-6(1H)-one (Compound II-63) MS m/z: 364 (MH+)

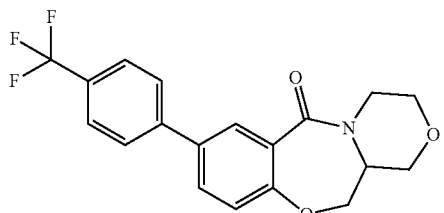

2-(2-(5-oxo-7-(4-(trifluoromethoxy)phenyl)-2,3-dihydrobenzo[f][1,4]oxazepin-4(5H)-yl)ethoxy)pyrimidine-4-carbonitrile (Compound II-66) MS m/z 471.1 (M+H)

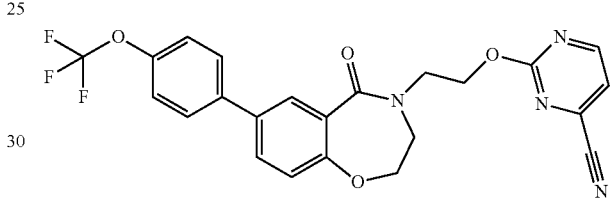

4-(2-hydroxyethyl)-7-(4-(trifluoromethoxy)phenyl)-3,4-dihydrobenzo[f][1,4]oxazepin-5(2H)-one (Compound II-71) MS m/z 368.1 (M+H)

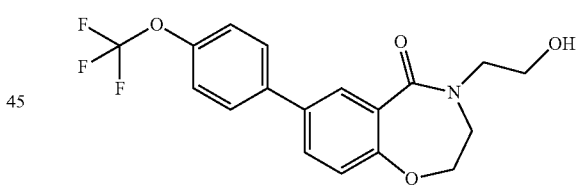

(R)-3-isopropyl-7-(4-(trifluoromethyl)phenyl)-3,4-dihydrobenzo[f][1,4]oxazepin-5(2H)-one (Compound II-76) MS m/z 349 (MH+)

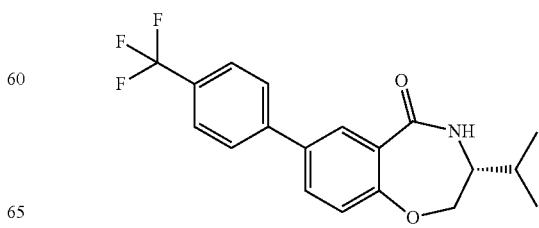

(R)-3-isopropyl-4-(pyrimidin-2-ylmethyl)-7-(4-(trifluoromethyl)phenyl)-3,4-dihydrobenzo[f][1,4]oxazepin-5(2H)-one (Compound II-78) MS m/z: 442 (MH⁺)

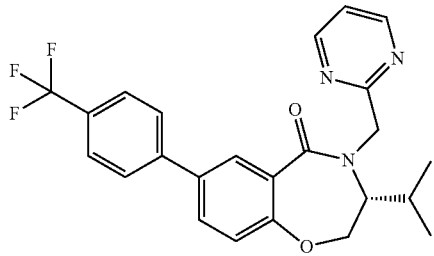 [SMILES: CC(C)[C@@H]1COc2ccc(-c3ccc(C(F)(F)F)cc3)cc2C(=O)N1Cc1ncccn1]

(S)-3-isopropyl-4-(pyrimidin-2-ylmethyl)-7-(4-(trifluoromethyl)phenyl)-3,4-dihydrobenzo[f][1,4]oxazepin-5(2H)-one (Compound II-79) MS m/z: 442 (MH⁺)

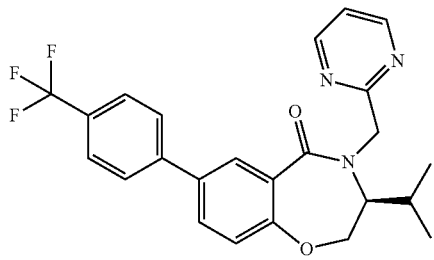 [SMILES: CC(C)[C@H]1COc2ccc(-c3ccc(C(F)(F)F)cc3)cc2C(=O)N1Cc1ncccn1]

(S)-2-(2,2,2-trifluoroethyl)-8-(4-(trifluoromethyl)phenyl)-3,4,12,12a-tetrahydro-1H-benzo[f]pyrazino[2,1-c][1,4]oxazepin-6(2H)-one (Compound II-84) m/z: 445 (MH⁺)

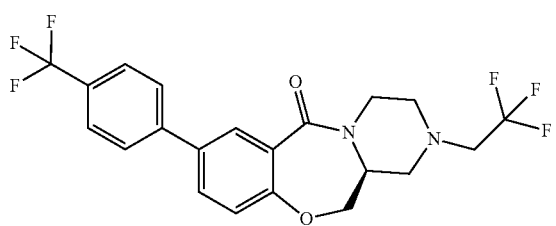 [SMILES: O=C1c2cc(-c3ccc(C(F)(F)F)cc3)ccc2OC[C@@H]2CN(CC(F)(F)F)CCN12]

7-(4-morpholinophenyl)-4-(pyrimidin-2-ylmethyl)-3,4-dihydrobenzo[f][1,4]oxazepin-5(2H)-one (Compound II-90) m/z: 417.2 (MH⁺)

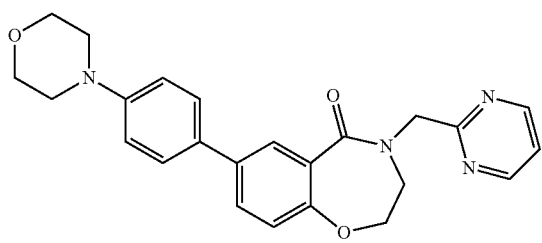 [SMILES: O=C1c2cc(-c3ccc(N4CCOCC4)cc3)ccc2OCCN1Cc1ncccn1]

7-(4-(methylsulfonyl)phenyl)-4-(pyrimidin-2-ylmethyl)-3,4-dihydrobenzo[f][1,4]oxazepin-5(2H)-one (Compound II-93) m/z: 410.0 (MH⁺)

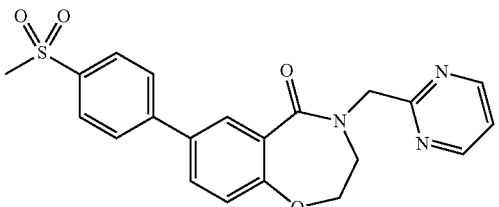

(R)-4-(1-(pyrimidin-2-yl)ethyl)-7-(4-(trifluoromethyl)phenyl)-3,4-dihydrobenzo[f][1,4]oxazepin-5(2H)-one (Compound II-95) m/z: 414 (MH⁺)

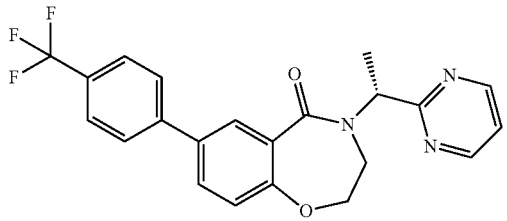 [SMILES: C[C@H](c1ncccn1)N1CCOc2ccc(-c3ccc(C(F)(F)F)cc3)cc2C1=O]

(S)-4-(1-(pyrimidin-2-yl)ethyl)-7-(4-(trifluoromethyl)phenyl)-3,4-dihydrobenzo[f][1,4]oxazepin-5(2H)-one (Compound II-96) m/z: 414 (MH⁺)

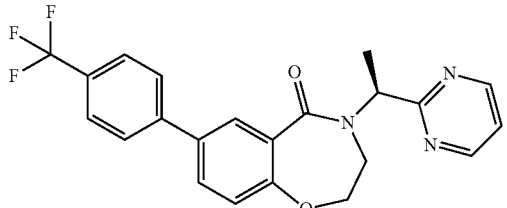

7-(4-tert-butoxyphenyl)-4-(pyrimidin-2-ylmethyl)-3,4-dihydrobenzo[f][1,4]oxazepin-5(2H)-one (Compound II-99) m/z: 404.5 (MH⁺)

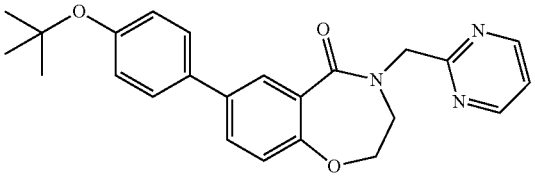 [SMILES: CC(C)(C)Oc1ccc(-c2ccc3c(c2)C(=O)N(Cc2ncccn2)CCO3)cc1]

281

(R)-2-methyl-4-(pyrimidin-2-ylmethyl)-7-(4-(trifluoromethyl)phenyl)-3,4-dihydrobenzo[f][1,4]oxazepin-5(2H)-one (Compound II-100) m/z: 414 (MH$^+$)

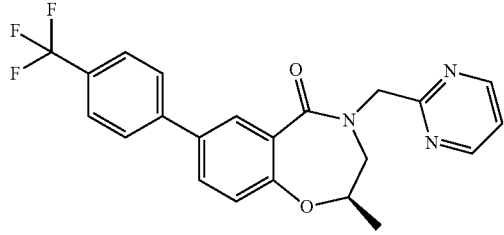 [SMILES: C[C@@H]1CN(Cc2ncccn2)C(=O)c2cc(-c3ccc(C(F)(F)F)cc3)ccc2O1]

tert-butyl 4-(5-oxo-4-(pyrimidin-2-ylmethyl)-2,3,4,5-tetrahydrobenzo[f][1,4]oxazepin-7-yl)phenylcarbamate (Compound II-103) m/z: 447.1 (MH$^+$)

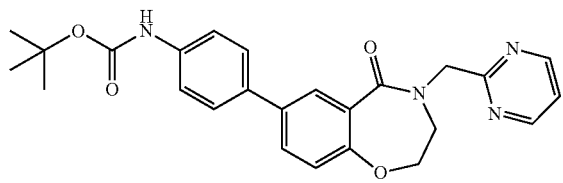 [SMILES: CC(C)(C)OC(=O)Nc1ccc(-c2ccc3c(c2)C(=O)N(Cc2ncccn2)CCO3)cc1]

N-(4-(5-oxo-4-(pyrimidin-2-ylmethyl)-2,3,4,5-tetrahydrobenzo[f][1,4]oxazepin-7-yl)phenyl)cyclopropanecarboxamide (Compound II-112) m/z: 415.2 (MH$^+$)

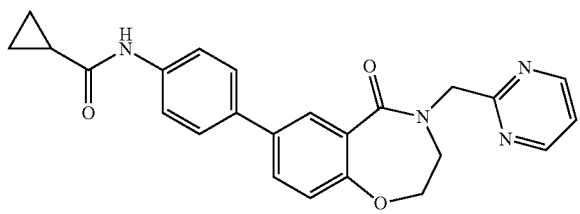 [SMILES: O=C(Nc1ccc(-c2ccc3c(c2)C(=O)N(Cc2ncccn2)CCO3)cc1)C1CC1]

4-((5-(pyridin-3-yl)pyrimidin-2-yl)methyl)-7-(4-(trifluoromethoxy)phenyl)-3,4-dihydrobenzo[f][1,4]oxazepin-5(2H)-one (Compound II-114) MS m/z 493.1 (M+H)

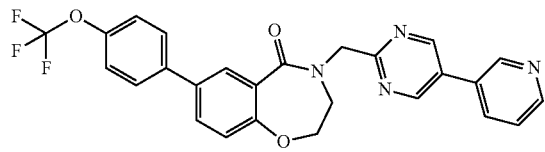 [SMILES: O=C1c2cc(-c3ccc(OC(F)(F)F)cc3)ccc2OCCN1Cc1ncc(-c2cccnc2)cn1]

282

7-(4-(2-hydroxypropan-2-yl)phenyl)-4-(pyrimidin-2-ylmethyl)-3,4-dihydrobenzo[f][1,4]oxazepin-5(2H)-one (Compound II-118) m/z: 390.2 (MH$^+$)

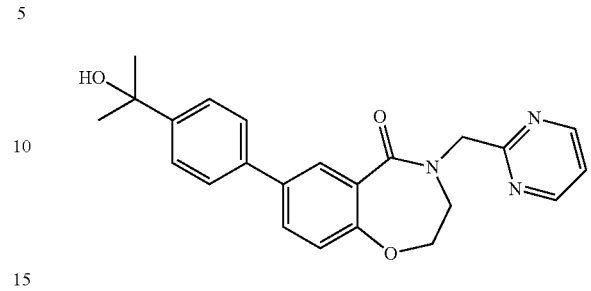

4-(pyrimidin-2-ylmethyl)-7-(4-(2,2,2-trifluoroacetyl)phenyl)-3,4-dihydrobenzo[f][1,4]oxazepin-5(2H)-one (Compound II-121) m/z: 428.2 (MH$^+$)

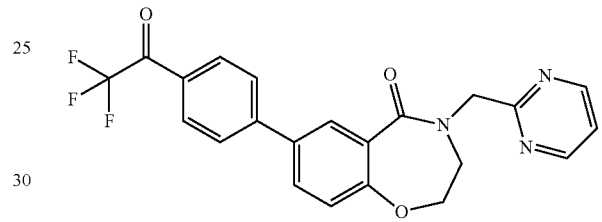

4-(pyrimidin-2-ylmethyl)-8-(4-(trifluoromethoxy)phenyl)-3,4-dihydrobenzo[f][1,4]oxazepin-5(2H)-one (Compound IV-1) MS m/z 416.0 (M+H)

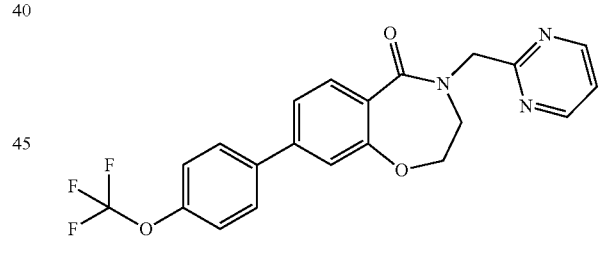

4-(pyridin-2-ylmethyl)-8-(4-(trifluoromethoxy)phenyl)-3,4-dihydrobenzo[f][1,4]oxazepin-5(2H)-one (Compound IV-2) MS m/z 415.1 (M+H)

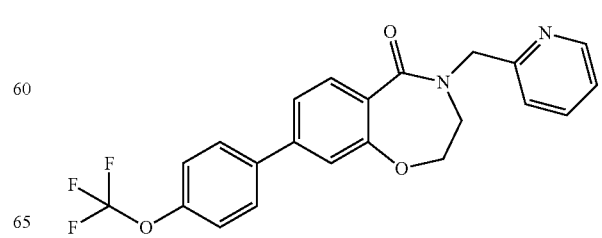

4-(pyridin-2-ylmethyl)-8-(3-(trifluoromethyl)phenyl)-3,4-dihydrobenzo[f][1,4]oxazepin-5(2H)-one (Compound IV-3) MS m/z 399.1 (M+H)

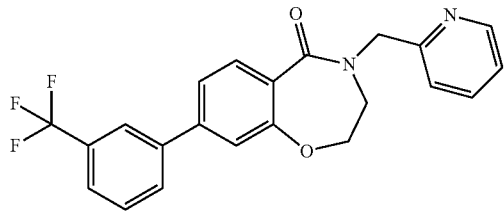 [SMILES: O=C1c2ccc(-c3cccc(C(F)(F)F)c3)cc2OCCN1Cc1ccccn1]

4-(pyrimidin-2-ylmethyl)-8-(3-(trifluoromethyl)phenyl)-3,4-dihydrobenzo[f][1,4]oxazepin-5(2H)-one (Compound IV-4) MS m/z 400.1 (M+H)

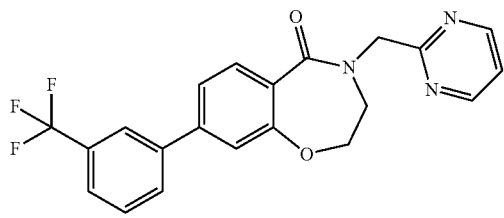 [SMILES: O=C1c2ccc(-c3cccc(C(F)(F)F)c3)cc2OCCN1Cc1ncccn1]

4-(pyrimidin-2-ylmethyl)-8-(4-(trifluoromethyl)phenyl)-3,4-dihydrobenzo[f][1,4]oxazepin-5(2H)-one (Compound IV-5) MS m/z 400.1 (M+H)

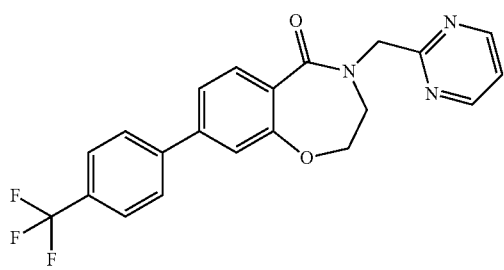

4-(pyridin-2-ylmethyl)-8-(3-(trifluoromethoxy)phenyl)-3,4-dihydrobenzo[f][1,4]oxazepin-5(2H)-one (Compound IV-6) MS m/z 415.1 (M+H)

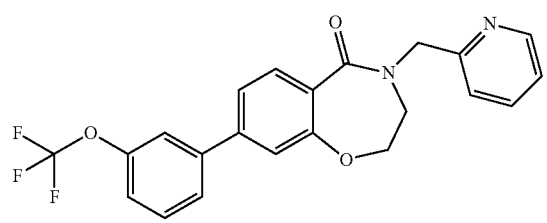 [SMILES: O=C1c2ccc(-c3cccc(OC(F)(F)F)c3)cc2OCCN1Cc1ncccn1]

4-(pyrimidin-2-ylmethyl)-8-(3-(trifluoromethoxy)phenyl)-3,4-dihydrobenzo[f][1,4]oxazepin-5(2H)-one (Compound IV-7) MS m/z 416.1 (M+H)

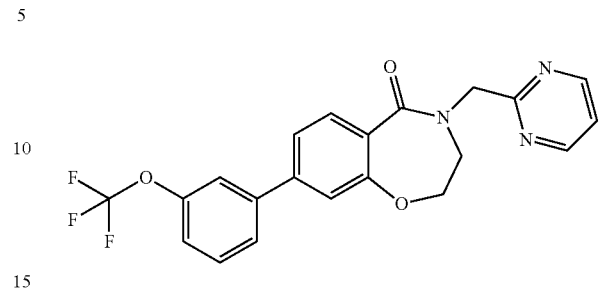

4-(pyridin-2-ylmethyl)-8-(4-(trifluoromethyl)phenyl)-3,4-dihydrobenzo[f][1,4]oxazepin-5(2H)-one (Compound IV-8) MS m/z 399.1 (M+H)

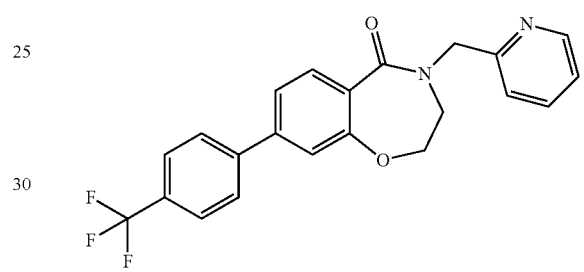

7-(4-tert-butylcyclohex-1-enyl)-4-(pyrimidin-2-ylmethyl)-3,4-dihydrobenzo[f][1,4]oxazepin-5(2H)-one (Compound V-1) m/z: 392.2 (MH$^+$)

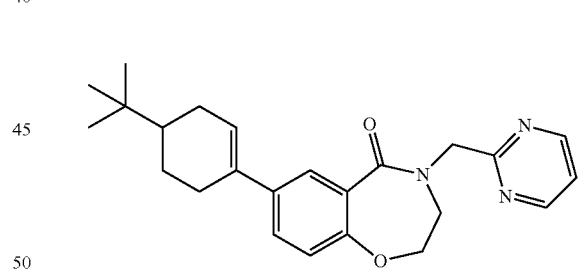

7-cyclopentenyl-4-(pyrimidin-2-ylmethyl)-3,4-dihydrobenzo[f][1,4]oxazepin-5(2H)-one (Compound V-2) m/z: 322.1 (MH$^+$)

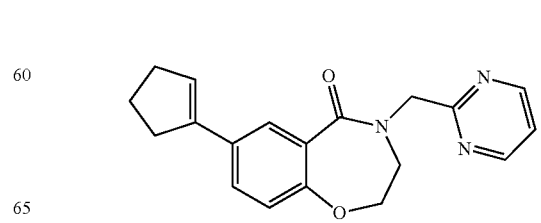

7-(4,4-dimethylcyclohex-1-enyl)-4-(pyrimidin-2-ylmethyl)-3,4-dihydrobenzo[f][1,4]oxazepin-5(2H)-one (Compound V-4) m/z: 364.2 (MH+)

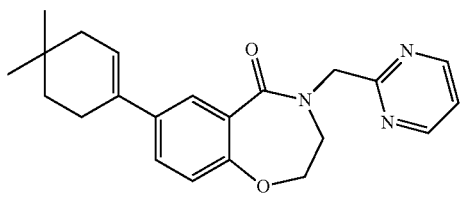 [SMILES: CC1(C)CC=C(c2ccc3c(c2)C(=O)N(Cc2ncccn2)CCO3)CC1]

7-(bicyclo[3.1.1]hept-2-en-3-yl)-4-(pyrimidin-2-ylmethyl)-3,4-dihydrobenzo[f][1,4]oxazepin-5(2H)-one (Compound V-7) m/z: 348.1 (MH+)

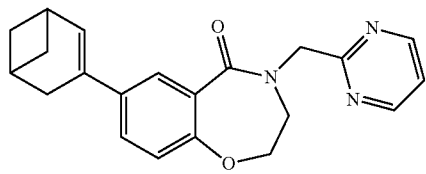 [SMILES: O=C1c2cc(C3=CC4CC(C3)C4)ccc2OCCN1Cc1ncccn1]

7-(2-oxo-1,2-dihydropyridin-4-yl)-4-(pyrimidin-2-ylmethyl)-3,4-dihydrobenzo[f][1,4]oxazepin-5(2H)-one (Compound VI-1) m/z: 349.1 (MH+)

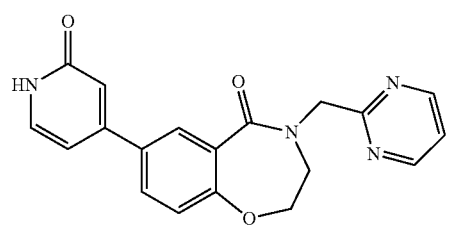 [SMILES: O=C1c2cc(-c3cc[nH]c(=O)c3)ccc2OCCN1Cc1ncccn1]

tert-butyl 4-(5-oxo-4-(pyrimidin-2-ylmethyl)-2,3,4,5-tetrahydrobenzo[f][1,4]oxazepin-7-yl)-5,6-dihydropyridine-1(2H)-carboxylate (Compound VI-5) m/z: 436.9 (MH+)

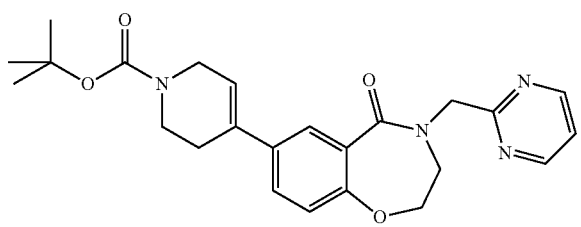 [SMILES: CC(C)(C)OC(=O)N1CC=C(c2ccc3c(c2)C(=O)N(Cc2ncccn2)CCO3)CC1]

4-(pyrimidin-2-ylmethyl)-7-(6-(2,2,2-trifluoroethoxy)pyridin-3-yl)-3,4-dihydrobenzo[f][1,4]oxazepin-5(2H)-one (Compound VI-6) MS m/z 431.1 (M+H)

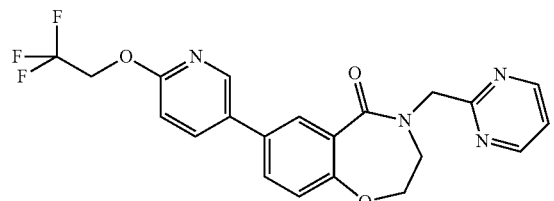

4-(pyrimidin-2-ylmethyl)-7-(6-(trifluoromethyl)pyridin-3-yl)-3,4-dihydrobenzo[f][1,4]oxazepin-5(2H)-one (Compound VI-8) MS m/z 401.1 (M+H)

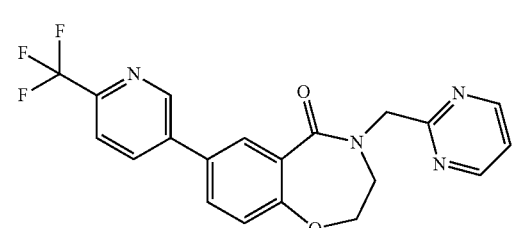

7-(6-fluoropyridin-3-yl)-4-(pyrimidin-2-ylmethyl)-3,4-dihydrobenzo[f][1,4]oxazepin-5(2H)-one (Compound VI-9) MS m/z 351.1 (M+H)

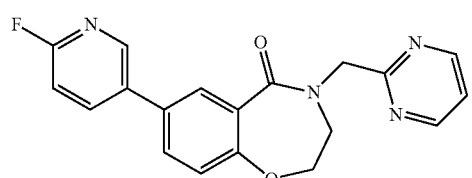

4-(pyrimidin-2-ylmethyl)-7-(2-(pyrrolidin-1-yl)pyrimidin-5-yl)-3,4-dihydrobenzo[f][1,4]oxazepin-5(2H)-one (Compound VI-10) MS m/z 403.1 (M+H)

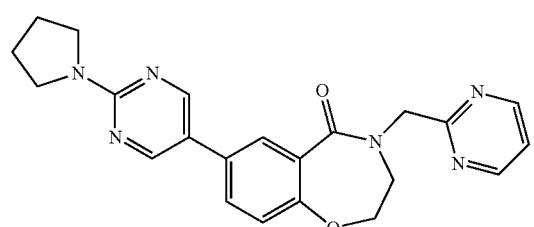

7-(2-(piperidin-1-yl)pyrimidin-5-yl)-4-(pyrimidin-2-ylmethyl)-3,4-dihydrobenzo[f][1,4]oxazepin-5(2H)-one (Compound VI-11) MS m/z 417.1 (M+H)

7-(cyclopropylethynyl)-4-(pyrimidin-2-ylmethyl)-3,4-dihydrobenzo[f][1,4]oxazepin-5(2H)-one (Compound VIII-1) m/z: 320.2 (MH⁺)

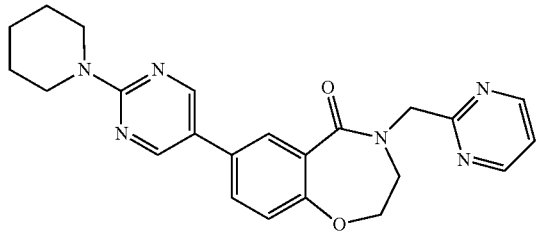 [SMILES: O=C1c2cc(-c3cnc(N4CCCCC4)nc3)ccc2OCCN1Cc1ncccn1]

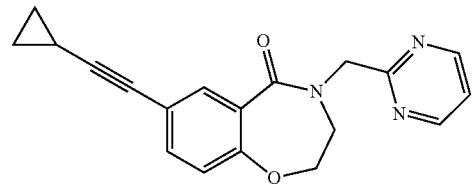

7-(1-(cyclopropanecarbonyl)-1,2,3,6-tetrahydropyridin-4-yl)-4-(pyrimidin-2-ylmethyl)-3,4-dihydrobenzo[f][1,4]oxazepin-5(2H)-one (Compound VI-17) m/z: 405.2 (MH⁺)

7-(3,3-dimethylbut-1-ynyl)-4-(pyrimidin-2-ylmethyl)-3,4-dihydrobenzo[f][1,4]oxazepin-5(2H)-one (Compound VIII-2) m/z: 336.1 (MH⁺)

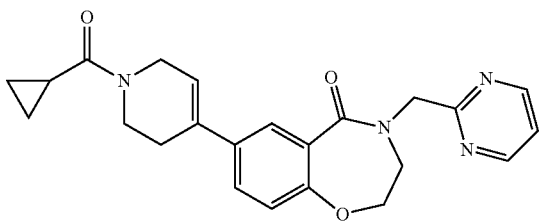 [SMILES: O=C1c2cc(C3=CCN(C(=O)C4CC4)CC3)ccc2OCCN1Cc1ncccn1]

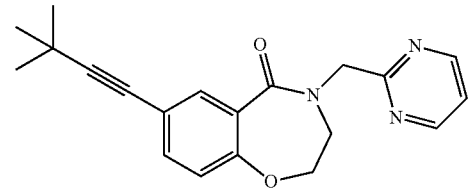

7-(pyrimidin-2-yl)-4-(pyrimidin-2-ylmethyl)-3,4-dihydrobenzo[f][1,4]oxazepin-5(2H)-one (Compound VI-18) MS m/z 334.1 (M+H)

7-((1-methyl-1H-imidazol-5-yl)ethynyl)-4-(pyrimidin-2-ylmethyl)-3,4-dihydrobenzo[f][1,4]oxazepin-5(2H)-one (Compound VIII-3) m/z: 360.2 (MH⁺)

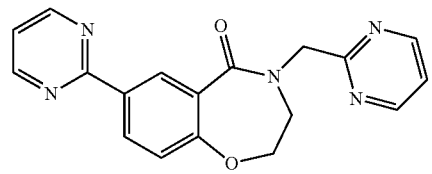 [SMILES: O=C1c2cc(-c3ncccn3)ccc2OCCN1Cc1ncccn1]

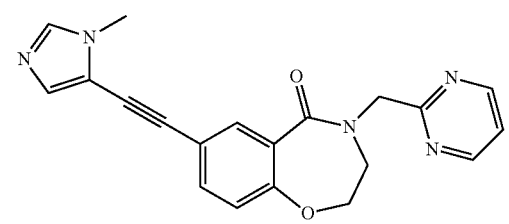

4-(pyrimidin-2-ylmethyl)-7-(5-(trifluoromethyl)pyrimidin-2-yl)-3,4-dihydrobenzo[f][1,4]oxazepin-5(2H)-one (Compound VI-19) MS m/z 402.1 (M+H)

4-(imidazo[1,2-a]pyridin-2-ylmethyl)-7-(4-(trifluoromethyl)phenyl)-3,4-dihydrobenzo[f][1,4]oxazepin-5(2H)-one (Compound II-135) m/z: 438.1 (MH⁺)

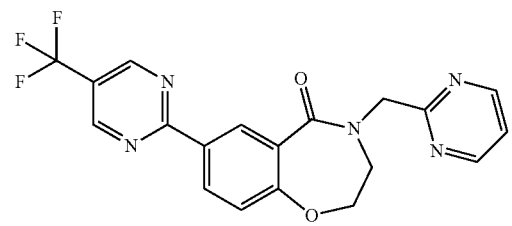 [SMILES: O=C1c2cc(-c3ncc(C(F)(F)F)cn3)ccc2OCCN1Cc1ncccn1]

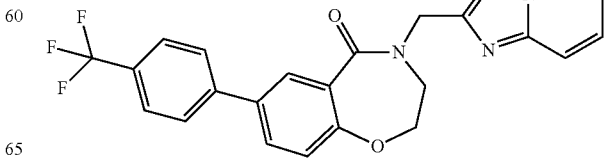

7-(3-fluoro-4-(trifluoromethyl)phenyl)-4-(pyrimidin-2-ylmethyl)-3,4-dihydrobenzo[f][1,4]oxazepin-5(2H)-one (Compound II-136) m/z: 418.1 (MH⁺)

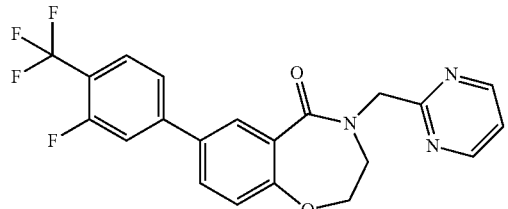

4-(pyrimidin-2-ylmethyl)-7-(4-(2,2,2-trifluoroethyl)phenyl)-3,4-dihydrobenzo[f][1,4]oxazepin-5(2H)-one (Compound II-150) m/z: 459.2 (MH⁺)

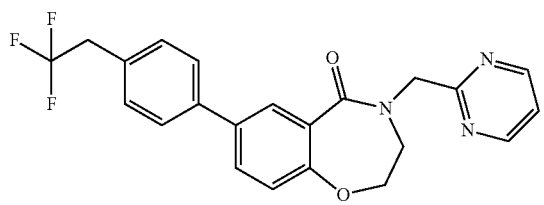 [SMILES: O=C1c2cc(-c3ccc(CC(F)(F)F)cc3)ccc2OCCN1Cc1ncccn1]

4-(pyridin-2-ylmethyl)-7-(4-(2,2,2-trifluoroethyl)phenyl)-3,4-dihydrobenzo[f][1,4]oxazepin-5(2H)-one (Compound II-151) m/z: 458.2 (MH⁺)

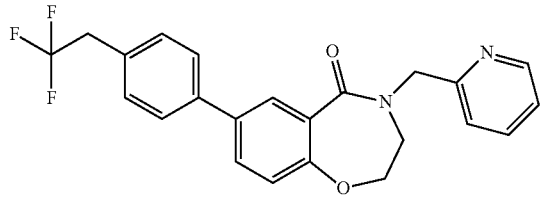

cyclopropyl(7-(4-(trifluoromethoxy)phenyl)-2,3-dihydrobenzo[f][1,4]oxazepin-4(5H)-yl)methanone (Compound III-8) m/z: 378 (MH⁺)

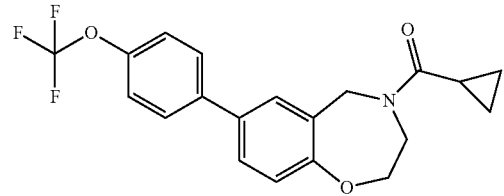 [SMILES: O=C(C1CC1)N1CCOc2ccc(-c3ccc(OC(F)(F)F)cc3)cc2C1]

(1H-pyrazol-4-yl)(7-(4-(trifluoromethoxy)phenyl)-2,3-dihydrobenzo[f][1,4]oxazepin-4(5H)-yl)methanone (Compound III-13) m/z: 404 (MH⁺)

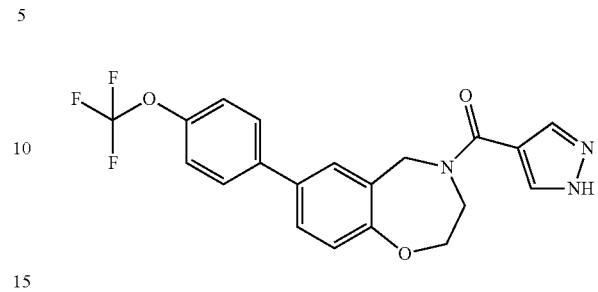

(3,5-dimethyl-1H-pyrazol-4-yl)(7-(4-(trifluoromethoxy)phenyl)-2,3-dihydrobenzo[f][1,4]oxazepin-4(5H)-yl)methanone (Compound III-14) m/z: 432.2 (MH⁺)

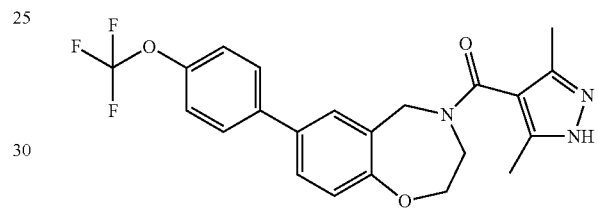

(1-methyl-3-(trifluoromethyl)-1H-pyrazol-4-yl)(7-(4-(trifluoromethoxy)phenyl)-2,3-dihydrobenzo[f][1,4]oxazepin-4(5H)-yl)methanone (Compound III-16) m/z: 486.1 (MH⁺)

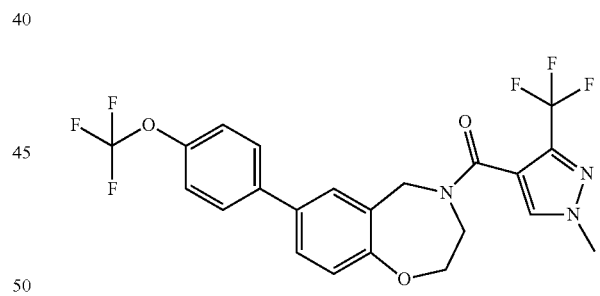

(3-methyl-1H-pyrazol-4-yl)(7-(4-(trifluoromethoxy)phenyl)-2,3-dihydrobenzo[f][1,4]oxazepin-4(5H)-yl)methanone (Compound III-17) m/z: 418.2 (MH⁺)

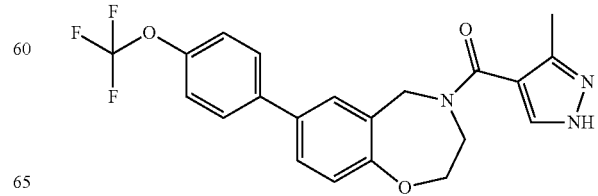

291

1-morpholino-2-(7-(4-(trifluoromethyl)phenyl)-2,3-dihydrobenzo[f][1,4]oxazepin-4(5H)-yl)ethanone (Compound III-28) m/z: 421 (MH⁺)

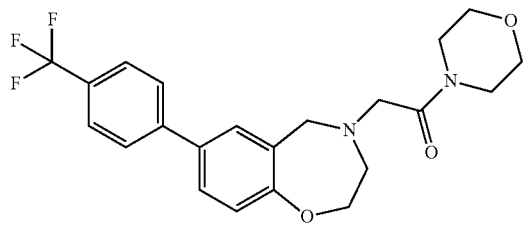 [SMILES: O=C(CN1CCOc2ccc(-c3ccc(C(F)(F)F)cc3)cc2C1)N1CCOCC1]

4-(pyrimidin-2-ylmethyl)-7-(pyrrolidin-1-yl)-3,4-dihydrobenzo[f][1,4]oxazepin-5(2H)-one (Compound VI-34) MS m/z 325.1 (M+H)

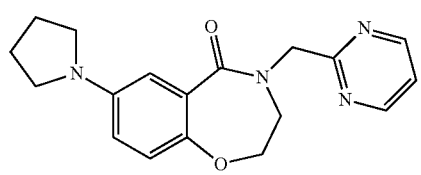 [SMILES: O=C1c2cc(N3CCCC3)ccc2OCCN1Cc1ncccn1]

4-(pyridin-2-ylmethyl)-7-(pyrrolidin-1-yl)-3,4-dihydrobenzo[f][1,4]oxazepin-5(2H)-one (Compound VI-35) MS m/z 324.1 (M+H)

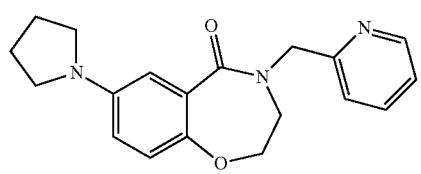 [SMILES: O=C1c2cc(N3CCCC3)ccc2OCCN1Cc1ccccn1]

4-benzyl-7-(4-(trifluoromethoxy)phenyl)-3,4-dihydropyrido[3,2-f][1,4]oxazepin-5(2H)-one (Compound XII-12) MS m/z 415.1 (M+H)

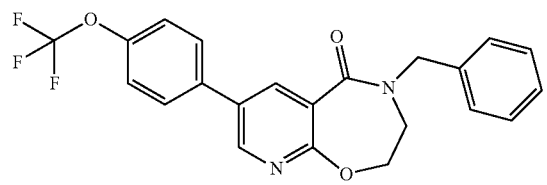 [SMILES: O=C1c2cc(-c3ccc(OC(F)(F)F)cc3)cnc2OCCN1Cc1ccccc1]

292

4-(pyrimidin-2-ylmethyl)-7-(4-(trifluoromethoxy)phenyl)-3,4-dihydropyrido[3,2-f][1,4]oxazepin-5(2H)-one (Compound XII-13) MS m/z 417.1 (M+H)

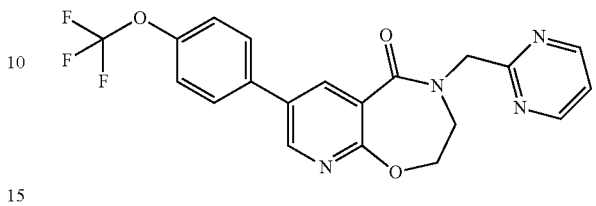

4-(pyridin-2-ylmethyl)-7-(4-(trifluoromethoxy)phenoxy)-3,4-dihydrobenzo[f][1,4]oxazepin-5(2H)-one (Compound XIII-5) MS m/z 431.1 (M+H)

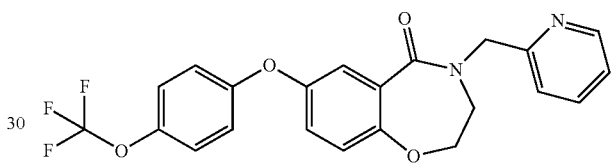

N-(5-oxo-4-(pyridin-2-ylmethyl)-2,3,4,5-tetrahydrobenzo[f][1,4]oxazepin-7-yl)benzamide (Compound XIII-7) MS m/z 374.1 (M+H)

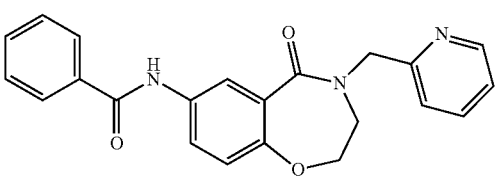 [SMILES: O=C(Nc1ccc2c(c1)C(=O)N(Cc1ccccn1)CCO2)c1ccccc1]

4-(pyridin-2-ylmethyl)-7-(4-(trifluoromethyl)phenoxy)-3,4-dihydrobenzo[f][1,4]oxazepin-5(2H)-one (Compound XIII-8) MS m/z 415.1 (M+H)

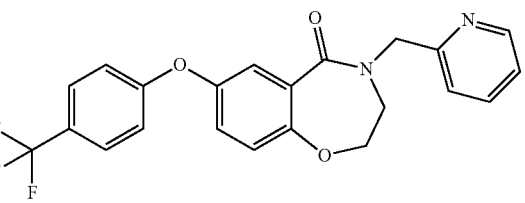

4-(pyrimidin-2-ylmethyl)-7-(4-(trifluoromethoxy)
benzylamino)-3,4-dihydrobenzo[f][1,4]oxazepin-5
(2H)-one (Compound XIII-9) MS m/z 445.1
(M+H)

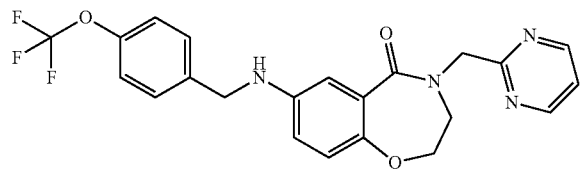 [SMILES: O=C1c2cc(NCc3ccc(OC(F)(F)F)cc3)ccc2OCCN1Cc1ncccn1]

4-(pyridin-2-ylmethyl)-7-(4-(trifluoromethoxy)ben-
zylamino)-3,4-dihydrobenzo[f][1,4]oxazepin-5(2H)-
one (Compound XIII-11) MS m/z 444.1 (M+H)

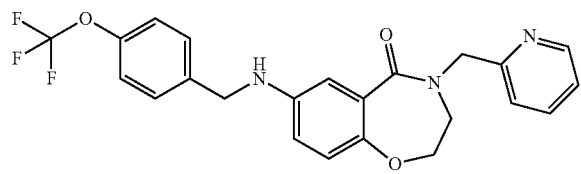 [SMILES: O=C1c2cc(NCc3ccc(OC(F)(F)F)cc3)ccc2OCCN1Cc1ccccn1]

N-(5-oxo-4-(pyridin-2-ylmethyl)-2,3,4,5-tetrahyd-
robenzo[f][1,4]oxazepin-7-yl)-4-(trifluoromethyl)
benzamide (Compound XIII-13) MS m/z 442.1
(M+H)

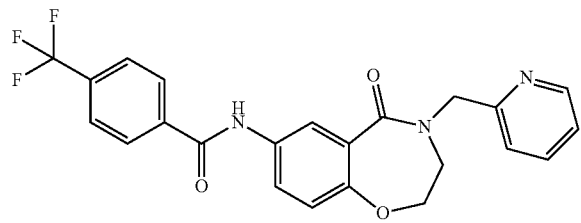 [SMILES: O=C(Nc1ccc2c(c1)C(=O)N(Cc1ccccn1)CCO2)c1ccc(C(F)(F)F)cc1]

7a-(7-(4-(trifluoromethoxy)phenyl)-2,3,4,5-tetrahyd-
robenzo[f][1,4]oxazepine-4-carbonyl)tetrahydro-1H-
pyrrolizin-3(2H)-one (Compound III-59) MS m/z
461.4 (M+H)

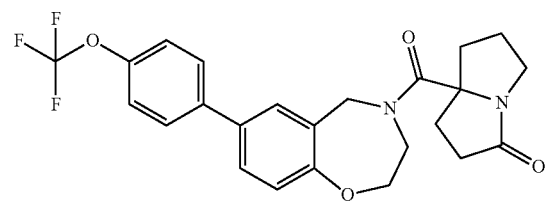 [SMILES: O=C1CCC2(C(=O)N3CCOc4ccc(-c5ccc(OC(F)(F)F)cc5)cc4C3)CCCN12]

N-(5-oxo-4-(pyridin-2-ylmethyl)-2,3,4,5-tetrahyd-
robenzo[f][1,4]oxazepin-7-yl)-4-(trifluoromethoxy)
benzamide (Compound XIII-14) MS m/z 458.1
(M+H)

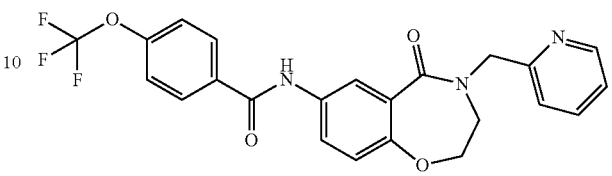

4-(pyridin-2-ylmethyl)-7-(4-(trifluoromethyl)phen-
ethyl)-3,4-dihydrobenzo[f][1,4]oxazepin-5(2H)-one
(Compound VIII-7) MS m/z 427.4 (M+H)

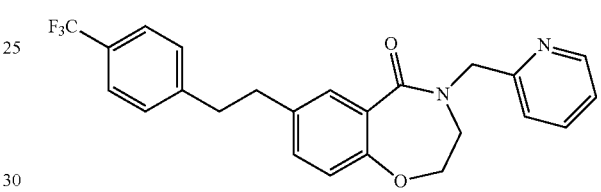

Example 252

Hard gelatin capsules containing the following ingredi-
ents are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Example 253

A tablet Formula Is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 254

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Example 255

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Example 256

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 257

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Example 258

A subcutaneous formulation may be prepared as follows:

| Ingredient | Quantity |
| --- | --- |
| Active Ingredient | 5.0 mg |
| Corn Oil | 1.0 mL |

Example 259

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Example 260

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients and water then added q.s. 100 g.

Example 261

Sustained Release Composition

| Ingredient | Weight Range % |
|---|---|
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this disclosure are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Example 262

Activity testing is conducted in the Examples below using methods described herein and those well known in the art.
Sodium Current Screening Assays:
The late sodium current (Late INa) and peak sodium current (Peak INa) assays are performed on an automated electrophysiology platform, QPatch 16× (Sophion Bioscience, Copenhagen, Denmark), which uses the whole cell patch clamp technique to measure currents through the cell membrane of up to 16 cells at a time. The assay uses an HEK293 (human embryonic kidney) cell line heterologously expressing the wild-type human cardiac sodium channel, hNa$_v$1.5, purchased from Millipore (Billerica, Mass.). No beta subunits were coexpressed with the Na channel alpha subunit. Cells are maintained with standard tissue culture procedures and stable channel expression is maintained with 400 μg/mL Geneticin in the culture medium. Cells isolated for use on QPatch are incubated for 5 minutes in Detachin 1×(Genlantis, San Diego, USA) at 37° C. to ensure that 80-90% of the cells are single and not part of a cell cluster. Experiments are carried out at 23-25° C.

For both the Late INa and Peak INa assays, series resistance compensation is set to 100% and series resistance and whole-cell compensation are performed automatically. Currents are digitized at 25 kHz and low-pass filtered at 12 kHz and 10 kHz for the late and peak INa assays, respectively. Currents through open sodium channels are automatically recorded and stored in the Sophion Bioscience Oracle database (Sophion Bioscience, Copenhagen, Denmark). Analysis is performed using QPatch Assay and database software and data are compiled in Excel.

Compound stocks are routinely made by the Gilead Sample Bank in plastic vials to 10 mM in dimethyl sulfoxide (DMSO). In some cases, when compounds are not soluble in DMSO, they are made in 100% ethanol. Stocks are sonicated as necessary. The extracellular solution for screening Late INa is composed of: 140 mM NaCl, 4 mM KCl, 1.8 mM CaCl$_2$, 0.75 mM MgCl$_2$ and 5 mM HEPES with pH adjusted to 7.4 using NaOH. The intracellular solution used to perfuse the inside of the cells for both the Late INa and Peak INa assays contains: 120 mM CsF, 20 mM CsCl, 5 mM EGTA, 5 mM HEPES and pH adjusted to 7.4 with CsOH. Compounds are diluted in extracellular solution to 1 μM in glass vials and then transferred to glass well plates before robotic addition to the cells. The 0 mM Na extracellular solution (0Na-ECF) used at the end of each experiment for the Late INa and Peak INa assays to measure baseline current contains: 140 mM N-methyl-D-glucamine; 4 mM KCl; 1.8 mM CaCl$_2$; 0.75 mM MgCl$_2$; 5 mM HEPES and pH was adjusted to 7.4 with HCl.
Late INa Screening Assay:
For the Late INa assay, sodium channels are activated every 10 seconds (0.1 Hz) by depolarizing the cell membrane to −20 mV for 250 milliseconds (ms) from a holding potential of −120 mV. In response to a −20 mV voltage step, typical hNa$_v$1.5 sodium currents activate rapidly to a peak negative current and then inactivate nearly completely within 3-4 ms.

Compounds were tested to determine their activity in blocking the late sodium current. Late INa was generated by adding 10 μM Tefluthrin (pyrethroid) to the extracellular solution while recording Na currents. To confirm the block of late $I_{Na}$ observed using the automated screening method, a second late $I_{Na}$ enhancer (ATX-II) and the manual patch clamp method were used. ATX-II and tefluthrin occupy distinct, non-overlapping binding sites and modify Na$^+$ channel function differently to increase late $I_{Na}$. Compounds tested have been found generally to inhibit the enhanced late $I_{Na}$ caused by either late $I_{Na}$ enhancer. For the purposes of the screening, late INa is defined as the mean current between 225 ms and 250 ms after stepping to −20 mV to activate Na channels. After establishing the whole cell recording configuration, late INa activator is added to each well 4 times over a 16-17 minute period so that the late component of the Na current reaches a stable value. Compounds were then added (typically at 1 in the presence of the late INa activator, with 3 additions over the course of 7 or 8 minutes. Measurements were made at the end of exposure to the third compound addition and values were normalized to the current level when all Na+ was removed from the extracellular solution after two additions of 0Na-ECF.

Results are reported as percent block of late INa. When tested in the assay disclosed above with 10 µM Tefluthrin activating late INa, for example Compounds 11-105 inhibited (or reduced) the late sodium current by 45% (see Table 1 for additional compound data). The inhibition of Late INa of the cardiac isoform hNa$_v$ 1.5 support the use of the compounds of this disclosure to treat atrial arrhythmias, ventricular arrhythmias, heart failure (including congestive heart failure, diastolic heart failure, systolic heart failure, acute heart failure), Prinzmetal's (variant) angina, stable angina, unstable angina, exercise induced angina, congestive heart disease, ischemia, recurrent ischemia, reperfusion injury, myocardial infarction, acute coronary syndrome, peripheral arterial disease, pulmonary hypertension and intermittent claudication.

Peak INa Screening Assay:

Compounds were also evaluated for their effect in several other assays, including their effect on Peak INa. Good separation between the concentrations of test compound to reduce late and peak $I_{Na}$ is beneficial to enable separation of the desired effect to reduce late $I_{Na}$ induced electrical and mechanical dysfunction from the undesired effect to reduce peak $I_{Na}$, which can lead to slowing or block of conduction of electrical excitation in the heart. It is contemplated that the compounds of Formula I avoid significant block of peak INa. Since the peak INa in the cells used herein can be very large, introducing artifacts in the recording, the concentration of Na+ in the bath can be reduced to 20 mM and a nonpermeant cation added to compensate for the Na+ that was removed to maintain the osmolarity and ionic strength of the solution (see solution details below). Analysis of peak INa generally requires correction for rundown before determining the % block of peak current by the tested compound.

A separate Peak INa screening assay was developed to allow assessment of the effect of compounds on peak INa at both low and high stimulation frequencies in order to identify compounds that are highly selective for block of late INa but do not block peak INa. A low stimulation frequency of 0.1 Hz was used to determine the effect of the test compound when the channel spent most of the time in the resting (closed) state and provides information about Tonic Block (TB). A higher stimulation frequency (3 Hz) was used to measure block of the channel when it spent more time in the activated and inactivated states and provided a measure of Use-Dependent Block (UDB). Use-dependent block refers to the accumulation of block with increased frequency of channel activation. Block of cardiac peak $I_{Na}$ by compounds of this disclosure is increased with an increase in the frequency of stimulation from 0.1 to 1-5 Hz (frequencies encountered either in the normal heart or during tachycardia). It is therefore expected that reduction of peak $I_{Na}$ by compounds of this disclosure will be greater at high heart rates, such as those during tachyarrhythmias, than at normal heart rates. As a consequence, compounds of this disclosure may reduce Na+ and Ca$^{2+}$ overload due to late INa and abnormal electrical activity and electrical conduction in myocardium that is arrhythmic, especially during ischemia.

The −100 mV holding potential and the 3 Hz stimulation frequency were chosen so that the benchmark compound would have a small but detectable effect under experimental conditions, allowing for direct comparison of new compounds with the benchmark. The extracellular solution for screening Peak INa is composed of: 20 mM NaCl, 120 mM N-methyl-D glucamine, 4 mM KCl, 1.8 mM CaCl$_2$, 0.75 mM MgCl$_2$ and 5 mM HEPES with pH adjusted to 7.4 using HCl. The intracellular solution used for the Peak INa assay is the same as outlined for the Late INa assay (see above).

For the peak INa assay, Na+ channels were activated by depolarizing the cell membrane to 0 mV for 20 ms from a holding potential of −100 mV. After establishing the whole cell recording configuration, channels were stimulated to open with low frequency stimulation (0.1 Hz) for 7 minutes so that the recording can be monetered and the extent to which the recording has stabilized can be assessed. After this stabilization period the stimulation frequency was increased to 3 Hz for 2 minutes and then returned to 0.1 Hz. Since 3 Hz stimulation causes a small decrease in the peak current even in the absence of compound, this internal control was used for each cell, when no compound is present, to correct the results from 3 Hz stimulation when compound is present. Following 3 Hz stimulation under control conditions, the cell is allowed to recover for 200 seconds before compound is added. The test compound tested at 1 or 3 µM (depending on the % block of late INa at 1 µM) was added 3 times at 60 second intervals, while stimulating the channels to open at 0.1 Hz to monitor the progression of TB. After the third compound addition, a 320 second wait period was imposed to allow for equilibration before the second period of 3 Hz stimulation begins. TB was measured before the second period of 3 Hz stimulation. Both TB and UDB were analyzed by incorporating rundown correction for the peak INa and UDB as calculated by compensating for the small use-dependent effect of the stimulation protocol on peak INa in the absence of compound. Compound II-105 exhibited peak INa TB of 9% and peak INa UDB of 11%, both measured at 1 µM.

The above data demonstrates the selectivity of Compound II-105 to block late INa compared to peak INa (45% versus 9% for peak INa TB; and 45% versus 11% for peak INa UDB) and suggests that Compound II-105 should show minimal to no effects on conduction through the heart (which is driven by peak INa) at concentrations that effectively block late INa.

hERG Screening Assay:

Compounds were also tested for their effect to block the hERG K+ channel. At least a 3-5-fold separation, preferably 10 fold separation, of IC$_{50}$ values for compounds to inhibit late $I_{Na}$ (more potent) and hERG (less potent) indicates that a compound is unlikely to cause QT prolongation and/or proarrhythmic effects at concentrations needed to reduce late $I_{Na}$.

Compounds were screened to test their activity in blocking the hERG potassium channel at AVIVA Biosciences (San Deigo, Calif., USA). The hERG channel is heterologously expressed in a CHO (Chinese Hamster Ovary) cell line. Cells were maintained with standard tissue culture procedures and stable channel expression was maintained with 500 µg/mL G418 in the culture medium. Cells were harvested for testing on the PatchXpress 7000A automated patch clamp with Accumax (Innovative Cell Technologies, San Diego, Calif.) to isolate single cells.

The following solutions were used for electrophysiological recordings. The external solution contained: 2 mM CaCl$_2$; 2 mM MgCl$_2$; 4 mM KCl; 150 mM NaCl; 10 mM Glucose; 10 mM HEPES (pH 7.4 with 1M NaOH; osmolarity, ~310 mOsm). The internal solution contained: 140 mM KCl, 10 mM MgCl$_2$, 6 mM EGTA, 5 mM HEPES, 5 mM ATP (pH adjusted to 7.25 with KOH; osmolarity, ~295 mOsm).

hERG channels were activated when the voltage was first stepped to −50 mV for 300 ms from the −80 mV holding potential and then stepped to +20 mV for 5 seconds. At +20 mV the channels open and then largely inactivate, so the currents are relatively small. Upon returning to −50 mV from +20 mV, hERG currents transiently become much larger as inactivation is rapidly removed and then the channel closes. The first step to −50 mV for 300 ms was used as a baseline for measuring the peak amplitude during the step to −50 mV after channel activation. The peak tail current at −50 mV was measured both under control conditions and after addition of compound, each cell serving as its own control.

All compounds were prepared as 10 mM DMSO stocks in glass vials. Stock solutions were mixed by vigorous vortexing and sonication for about 2 minutes at room temperature. For testing, compounds were diluted in glass vials using an intermediate dilution step in pure DMSO and then further diluted to working concentrations in external solution. Dilutions were prepared no longer than 20 minutes before use.

For the electrophysiological recordings, after achieving the whole-cell configuration, cells were monitored for 90 seconds to assess stability and washed with external solution for 66 seconds. The voltage protocol described above was then applied to the cells every 12 seconds and throughout the whole procedure. Only cells with stable recording parameters and meeting specified health criteria were allowed to enter the compound addition procedure.

External solution containing 0.1% DMSO (vehicle) was applied to the cells first to establish the control peak current amplitude. After allowing the current to stabilize for 3 to 5 minutes, 1 μM and then 10 μM test compounds were applied. Each compound concentration was added 4 times and cells were kept in test solution until the effect of the compound reached steady state or for a maximum of 12 minutes. After addition of test compound, a positive control (1 μM Cisapride) was added and must block >95% of the current for the experiment to be considered valid. Washout in the external solution compartment was performed until the recovery of the current reached steady state. Data were analyzed using DataXpress software and its associated SQL server database, Clampfit (Molecular Devices, Inc., Sunnyvale, USA) and Origin 7 (Originlab Corp.) When tested in the assay disclosed above, Compound II-105 inhibited (or reduced) the activity of the hERG potassium channel by <10% at 1 μM (see Table 1 for additional compound data).

Compounds were tested using the above described assay methods. Data are obtained by testing the listed compounds at 1 μM concentration in the late and peak INa assays (and other concentrations as needed) and at 1 μM and 10 μM for the hERG channel assay.

TABLE 1

Late $I_{Na}$ Assay results

| No. | Late $I_{Na}$ 1 μM | Peak TB 1 μM | Peak UDB 1 μM |
|---|---|---|---|
| II-1 | 25 | | |
| II-3 | 15 | | |
| II-4 | 30 | | |
| II-5 | 26 | | |
| II-6 | 16 | | |
| II-7 | 34 | | |
| II-8 | 21 | | |
| II-10 | 43 | 9 | 2 |
| II-11 | 23 | | |
| II-12 | 21 | | |
| II-13 | 18 | | |
| II-14 | 47 | 7 | 6 |
| II-15 | 48 | 8 | 8 |
| II-16 | 19 | | |
| II-17 | 59 | 47 | 46 |
| II-19 | 21 | | |
| II-21 | 18 | | |
| II-22 | 30 | | |
| II-23 | 25 | | |
| II-24 | 23 | | |
| II-25 | 25 | | |
| II-31 | 51 | 9 | 8 |
| II-33 | 46 | 10 | 13 |
| II-35 | 25 | | |
| II-39 | 16 | | |
| II-41 | 17 | | |
| II-42 | 34 | | |
| II-43 | 23 | | |
| II-44 | 39 | | |
| II-45 | 27 | | |
| II-46 | 25 | | |
| II-47 | 60 | 13 | 45 |
| II-48 | 47 | 13 | 53 |
| II-49 | 63 | 28 | 44 |
| II-50 | 48 | 5 | 19 |
| II-51 | 20 | | |
| II-54 | 51 | 13 | 20 |
| II-57 | 55 | 50 | 41 |
| II-59 | 15 | | |
| II-61 | 41 | | |
| II-62 | 49 | 10 | 14 |
| II-64 | 55 | 12 | 19 |
| II-65 | 19 | | |
| II-67 | 22 | | |
| II-68 | 17 | | |
| II-69 | 33 | | |
| II-70 | 37 | | |
| II-71 | 12 | | |
| II-72 | 60 | 22 | 34 |
| II-73 | 42 | | |
| II-74 | 12 | | |
| II-75 | 68 | 45 | 59 |
| II-77 | 21 | | |
| II-83 | 31 | | |
| II-87 | 22 | | |
| II-88 | 41 | | |
| II-89 | 28 | | |
| II-91 | 54 | 8 | 11 |
| II-92 | 34 | | |
| II-95 | 19 | | |
| II-97 | 36 | | |
| II-98 | 39 | | |
| II-102 | 21 | | |
| II-104 | 21 | | |
| II-105 | 45 | 9 | 11 |
| II-106 | 18 | | |
| II-107 | 18 | | |
| II-110 | 35 | | |
| II-113 | 27 | | |
| II-115 | 21 | | |
| II-117 | 37 | | |
| II-122 | 19 | | |
| II-123 | 21 | | |
| II-124 | 17 | | |
| II-129 | 33 | | |
| II-133 | 23 | | |
| II-134 | 69 | 38 | 34 |
| II-135 | 32 | | |
| II-136 | 30 | | |
| II-137 | 54 | 28 | 26 |
| II-138 | 47 | 16 | 23 |
| II-139 | 31 | | |
| II-140 | 32 | | |
| II-141 | 73 | 40 | 40 |
| II-142 | 19 | | |

TABLE 1-continued

Late I$_{Na}$ Assay results

| No. | Late I$_{Na}$ 1 µM | Peak TB 1 µM | Peak UDB 1 µM |
|---|---|---|---|
| II-143 | 65 | | |
| II-144 | 68 | 34 | 41 |
| II-145 | 19 | | |
| II-146 | 36 | | |
| II-147 | 54 | 13 | 6 |
| II-148 | 17 | | |
| II-150 | 27 | | |
| II-151 | 51 | 13 | 14 |
| II-152 | 23 | | |
| II-153 | 56 | 15 | 13 |
| II-154 | 25 | | |
| II-155 | 38 | 13 | 11 |
| II-156 | 48 | 23 | 13 |
| II-157 | 43 | 13 | 16 |
| II-158 | 58 | 34 | 26 |
| II-159 | 28 | | |
| II-160 | 48 | | |
| II-162 | 20 | | |
| II-163 | 28 | | |
| II-164 | 75 | | |
| II-165 | 56 | 15 | 30 |
| II-166 | 53 | 20 | 34 |
| II-167 | 56 | 20 | 25 |
| II-168 | 44 | 36 | 47 |
| II-169 | 65 | 23 | 23 |
| II-170 | 66 | 36 | 31 |
| II-171 | 24 | | |
| II-172 | 33 | | |
| II-174 | 48 | 7 | 18 |
| II-175 | 53 | 21 | 16 |
| II-176 | 68 | 45 | 44 |
| II-177 | 22 | | |
| II-178 | 19 | | |
| II-179 | 21 | | |
| II-186 | 55 | 20 | 30 |
| II-187 | 62 | 9 | 21 |
| II-189 | 53 | 23 | 28 |
| II-190 | 18 | | |
| II-191 | 25 | | |
| II-192 | 15 | | |
| II-193 | 70 | | |
| II-194 | 63 | | |
| II-195 | 66 | | |
| III-1 | 33 | | |
| III-4 | 35 | | |
| III-10 | 29 | | |
| III-11 | 20 | | |
| III-12 | 39 | 10 | 17 |
| III-15 | 50 | 19 | 18 |
| III-23 | 26 | | |
| III-24 | 17 | | |
| III-29 | 48 | 11 | 14 |
| III-30 | 16 | | |
| III-32 | 22 | | |
| III-33 | 37 | | |
| III-37 | 41 | | |
| III-38 | 28 | | |
| III-40 | 22 | | |
| III-50 | 24 | | |
| III-58 | 26 | | |
| IV-4 | 14 | | |
| V-1 | 24 | | |
| V-3 | 23 | | |
| V-5 | 49 | 5 | 5 |
| VI-4 | 36 | | |
| VI-11 | 19 | | |
| VI-26 | 28 | | |
| VI-30 | 40 | | |
| VI-31 | 61 | 50 | 42 |
| VI-32 | 66 | 28 | 26 |
| VI-36 | 47 | | |
| VI-37 | 48 | | |
| VIII-4 | 61 | 12 | 19 |
| VIII-5 | 32 | | |
| VIII-6 | 38 | | |
| VIII-7 | 59 | | |
| VIII-8 | 47 | | |
| VIII-9 | 50 | | |
| VIII-10 | 25 | | |
| VIII-11 | 42 | | |
| IX-2 | 22 | | |
| IX-3 | 27 | | |
| X-8 | 50 | 6 | 10 |
| X-11 | 48 | 17 | 20 |
| X-12 | 26 | | |
| XII-1 | 53 | 25 | 21 |
| XII-2 | 57 | 45 | 64 |
| XII-3 | 44 | 51 | 79 |
| XII-5 | 25 | | |
| XII-8 | 36 | | |
| XII-9 | 22 | | |
| XII-10 | 45 | 13 | 20 |
| XII-11 | 55 | 25 | 24 |
| XII-14 | 26 | | |
| XIII-1 | 16 | | |
| XIII-2 | 19 | | |
| XIII-3 | 17 | | |
| XIII-4 | 51 | 8 | 9 |
| XIII-6 | 60 | 8 | 8 |
| XIII-10 | 22 | | |

The assay results shown in the above table establishes that compounds tested showed activity as modulators of late sodium current, for example by inhibiting (or reducing) the late sodium current.

In some embodiments the effects of a compound of Formula I are specific for the late sodium current and show little or no activity with respect to one or more other ion channels. Thus, in some embodiments, a compound having an activity of reducing late sodium current will also exhibit little or no activity with regard to the peak sodium current. In particular embodiments, a compound having an activity of reducing late sodium current will also exhibit little or no activity with regard to the hERG potassium channel.

Table 2 is a summary comparing compound II-73 and ranolazine ability to block late and peak hNa$_v$ 1.5 Na$^+$ current and hERG K$^+$ current. The data in Table 2 were obtained in similar but not necessarily contemporaneous experiments.

TABLE 2

| | IC$_{50}$ µM | | | IC$_{50}$ Ratio (fold) | |
|---|---|---|---|---|---|
| | Late INa | Peak INa | hERG | Peak INa/ Late INa | hERG/ Late INa |
| II-73 | 0.6 ± 0.1 | 52 ± 5 | 5.7 ± 0.6 | 87 | 10 |
| Ranolazine | 6.7 ± 1.4 | 428 ± 33 | 13.4 ± 0.5 | 64 | 2 |

The above data suggests that the compound of Example II-73 exhibits comparable or improved properties with respect to the tested parameters.

L-Type Ca2+ Channel Assay—ChanTest:

Selected compounds were screened for block of the cardiac L-type Ca$^{2+}$ channel (hCav1.2, encoded by the human CACNA1C gene and coexpressed with the beta 2 subunit, encoded by the human CACNB2 gene and alpha2delta1, encoded by the CACNA2D1 gene). The Ca$^{2+}$ channel is heterologously expressed in a CHO (Chinese Hamster Ovary) cell line. Cells are maintained following standard tissue culture procedures and stable channel expression is maintained with appropriate selection antibiotics in the culture medium. Cells are harvested for testing on the PatchXpress automated patch clamp (Model 7000A, Molecular Devices, Sunnyvale, Calif.) by washing twice with Hank's Balanced Salt Solution, treating the cells with trypsin and re-suspending cells in culture medium ($4\text{-}6\times10^6$ cells in 20 mL). Cells in suspension are allowed to recover for 10 minutes in a tissue culture incubator set at 37° C. in a humidified 95% air, 5% $CO_2$ atmosphere.

The following solutions are used for electrophysiological recordings. The external solution contains (mM): 137 NaCl, 4 KCl, 1.8 $CaCl_2$, 1 $MgCl_2$, 10 Glucose, 10 HEPES (pH 7.4 with NaOH). The internal solution contains (mM): 130 Cs Aspartate, 5 $MgCl_2$, 10 EGTA, 4 ATP, 0.5 GTP, 10 HEPES, (pH adjusted to 7.2 with N-methyl-D-glucamine).

Vehicle is applied to naïve cells (n≥2, where n=the number cells), for a 5-10 minute exposure interval. Each solution exchange is performed in quadruplicate. At the end of each experiment, a saturating concentration of nifedipine (10 µM) is added to block hCav1.2 current. Leak current is digitally subtracted from the total membrane current record.

Test compound stock solutions are prepared by addition of dimethyl sulfoxide (DMSO) and stored frozen. Each test compound DMSO stock is sonicated (Model 2510/5510, Branson Ultrasonics, Danbury, Conn.), at ambient room temperature for at least 20 minutes to facilitate dissolution. Test compound concentrations are prepared fresh daily by diluting stock solutions into the standard extracellular physiological saline solution (see above). The maximum percent of DMSO added with compound is 0.1%. All test compound and control solutions are placed in a glass-lined 96-well compound plate before loading on PatchXpress.

Two concentrations (1, 10 µM) of each test compound are applied at five (5) minute intervals via disposable polyethylene micropipette tips to naïve cells (n≥2, where n=the number cells/concentration). Each test compound concentration is added to the cell in quadruplicate. Total duration of exposure to each test compound concentration is 5 minutes.

Onset and steady state block of hCav1.2 ($\alpha1C/\beta2/\alpha2\delta$) channels is measured using a stimulus voltage pattern consisting of a depolarizing test pulse (duration, 200 ms; amplitude, 10 mV) at 10 s intervals from a −80 mV holding potential. Peak current is measured during a step to 10 mV.

When tested in the assay disclosed above, Compound II-73 blocked the hCav1.2 late current by 14% and peak current by 32% at 1 µM concentration. At 10 µM concentration the compound II-73 blocked the hCav1.2 late current by 47% and the peak current by 79%.

Example 263

Compounds of this disclosure that block cardiac late $I_{Na}$ may also mediate UDB of other $Na^+$ channel isoforms including the major $Na^+$ channel isoforms in peripheral nervous system pain fibers, $Na_v1.7$ and 1.8. Compounds of this disclosure that block these channels may also be useful to decrease neuropathic pain.

In particular embodiments, a compound will exhibit a high selectivity for the late sodium current modulatory activity as compared to the activity in one or more other ion channels. The selectivity of a compound may be determined by determining the percentage reduction in late sodium current due to the compound, as measured by the assay described above. The percentage reduction in one other ion channel activity, such as the hERG potassium channel, due to the compound is determined as described above. The selectivity is determined by taking the ratio of (percentage reduction in late sodium current) to (percentage reduction in one other ion channel activity). The assays conducted to measure activities in this regard should be performed as described above, with the compound at a concentration of 10 µM (or at the upper limit of solubility, if less). In particular embodiments, the selectivity of a compound of the disclosure will be at least 5:1, e.g. at least 6:1, at least 7:1, at least 8:1, at least 9:1, at least 10:1, at least 12:1, at least 15:1, at least 20:1, or at least 25:1, when comparing the percentage reduction in late sodium current versus percentage reduction of one of the peak sodium current, the hERG potassium channel current. Selectivity data can be calculated based on the values provided in the Examples above.

Evidence supports a role for the tetrodotoxin-sensitive $Na_v1.7$ in the pathogenesis of pain. In this assay, using whole-cell patch-clamp technique, the effects of compounds of the disclosure on $hNa_v1.7$ ($hNa_v1.7+\beta1$ subunits) peak $Na^+$ current ($I_{Na}$) are tested as described previously (Rajamani et al, 2009). Cells are continuously maintained using MEM (Gibco-Invitrogen, Carlsbad, Calif.) supplemented with 10% heat inactivated fetal bovine serum, 1% penicillin-streptomycin, 600 µg/mL geneticin (Gibco-Invitrogen), 2 µg/mL blastocydin (Calbiochem, NJ, USA), and are incubated at 37° C. in an atmosphere of 5% $CO_2$ in air. For recording hNav1.7 $I_{Na}$, HEK293 cells are superfused with an extracellular solution containing (in mM): 140 NaCl, 3KCl, 10 HEPES, 10 glucose, 1 $MgCl_2$, 1 $CaCl_2$, pH 7.4 (with NaOH). Patch pipettes are filled with an internal solution containing (in mM): 140 CsF, 10 NaCl, 1 EGTA, 10 HEPES, pH 7.3 (with CsOH).

Whole-cell $I_{Na}$ are recorded as described previously (Rajamani et al, 2009) using an Axopatch 200B amplifier (Molecular Devices, Sunnyvale, USA). Signals are filtered at 5 kHz and sampled at 20 kHz. Patch pipettes are formed using borosilicate glass (World Precision Instruments, Sarasota, USA) using a micropipette puller (Dagan Corporation, Minneapolis, USA). The offset potential is zeroed before the pipette is attached to the cell and the voltages are not corrected for the liquid junction potential. In all recordings, 75-80% of the series resistance compensation will be achieved, thus yielding a maximum voltage error of ~5 mV and leak currents are cancelled by P/4 subtraction. pCLAMP 10.0 software (Molecular Devices) will be used to generate voltage clamp protocols and acquire data. The membrane potential is held at −100 or −120 mV and the cell dialyzed with the pipette solution for 5-7 minutes before current is recorded, to avoid time-dependent shifts in $Na^+$ channel gating within the first several minutes after patch rupture. In all experiments, the temperature of experimental solutions will be maintained at 20±1° C. using a CL-100 bipolar temperature controller (Warner Instruments, Hamden, USA).

Data are analyzed using Clampfit and Microcal Origin (MicroCal, Northampton, USA) software.

When tested in the assay disclosed above, Compound II-73 blocked the $hNa_v$ 1.7 sodium channel isoform with $IC_{50}$ of 5.2 µM at a frequency of 10 Hz. Compound II-73 blocked the $hNa_v$ 1.8 sodium channel isoform with a $IC_{50}$ of >10 µM at a 10 Hz frequency. At higher frequency of 25 Hz, compound II-73 blocked both $hNa_v$ 1.7 and $hNa_v$ 1.8 isoforms with $IC_{50}$ of 1.1 and 1.5 µM respectively. The inhibition of either $hNa_v$ 1.7 and $hNa_v$ 1.8 isoforms or the inhibition of both channels when stimulated at these frequencies support the use of compounds of this disclosure to decrease neuropathic pain.

Example 264

Expression of Human Na$_V$1.1 cDNA

All experiments with human Na$_V$1.1 are conducted as described (Kahlig, et al., PNAS, 105: 9799-9804). Briefly, expression of hNav1.1 is achieved by transient transfection using Qiagen Superfect reagent (5.5 µg of DNA is transfected at a plasmid mass ratio of 10:1:1 for $\alpha_1$:$\beta_1$:$\beta_2$). The human $\beta_1$ and $\beta_2$ cDNAs are cloned into plasmids containing the marker genes DsRed (DsRed-IRES2-h$\beta_1$) or eGFP (eGFP-IRES2-h$\beta_2$) flanking an internal ribosome entry site (IRES).

Electrophysiology

Whole-cell voltage-clamp recordings are used to measure the biophysical properties of WT and mutant Na$_V$1.1 channels, as described previously (Kahlig, 2008). For recording hNav1.1 I$_{Na}$, HEK293 cells are superfused with solution containing (in mM): 145 NaCl, 4 KCl, 1.8 CaCl$_2$, 1 MgCl$_2$, 10 dextrose, 10 HEPES, with a pH of 7.35 and osmolarity of 310 mOsmol/kg. The pipette solution contains (in mM): 110 CsF, 10 NaF, 20 CsCl, 2 EGTA, 10 HEPES, with a pH of 7.35 with an osmolarity of 300 mOsmol/kg. Cells are allowed to stabilize for 10 min after establishment of the whole-cell configuration before current is measured. Series resistance is compensated 90% to assure that the command potential is reached within microseconds with a voltage error<2 mV. Leak currents are subtracted by using an online P/4 procedure and all currents are low-pass Bessel filtered at 5 kHz and digitized at 50 kHz.

For use-dependent studies, cells are stimulated with depolarizing pulse trains (−10 mV, 5 ms, 300 pulses, 10 and 25 Hz) from a holding potential of −120 mV. Currents are then normalized to the peak current recorded in response to the first pulse in each frequency train. For tonic block studies, peak and persistent (late) currents are evaluated in response to a 200 ms depolarization to −10 mV (0.2 Hz) following digital subtraction of currents recorded in the presence and absence of 0.5 µM tetrodotoxin (TTX). The sodium current termed Late INa in the periphery is commonly called persistent INa in the CNS. Persistent current is calculated during the final 10 ms of the 200 ms step. Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM.

In Vitro Pharmacology

A stock solution of 10 mM compound of Formula I is prepared in 0.1 M HCl or DMSO. A fresh dilution of the compound of Formula I in the bath solution is prepared every experimental day and the pH is readjusted to 7.35 as necessary. The final DMSO concentration was kept at 0.1% in all solutions. Direct application of the perfusion solution to the clamped cell is achieved using the Perfusion Pencil system (Automate, Berkeley, Calif.). Direct cell perfusion is driven by gravity at a flow rate of 350 µL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion. Where appropriate, concentration inhibition curves are fit with the Hill equation: $I/I_{max}=1/[1+10^{\wedge}(\log IC_{50}-I)*k]$, where IC$_{50}$ is the concentration that produces half inhibition and k is the Hill slope factor.

Solutions containing the compounds of the disclosure are perfused for three minutes prior to current recordings to allow equilibrium (tonic) drug block. Tonic block of peak current is measured from this steady-state condition. Use-dependent block of peak current is measured during pulse number 300 of the pulse train, (−10 mV, 5 ms, 300 pulses, 10 Hz) from a holding potential of −120 mV. Two sequential pulse train stimulations are averaged to obtain mean current traces for each recording condition.

In Vivo Pharmacology

Jugular vein cannulated male Sprague Dawley rats (250-350 g, Charles River Laboratories, Hollister, Calif.) are used to study brain penetration of the compounds of the disclosure in vivo. Animal use is approved by the Institutional Animal Care and Use Committee, Gilead Sciences. Three rats per group are infused intravenously with the compound of the disclosure in saline at 85.5 µg/kg/min. After 1, 2.5 or 5 h the animals are sacrificed for plasma and brain collection, and concentrations of the compound of the disclosure are measured by liquid chromatography coupled with tandem mass spectrometry (LC-MS/MS). Brain tissue is homogenated in 1% 2N HCl acidified 5% sodium fluoride (final homogenate is diluted 3-fold). Plasma and brain homogenate samples (50 µl) are precipitated along with deuterated D3-Formula I as an internal standard, vortexed and centrifuged. The supernatant (50 µL) is transferred and diluted with water (450 µl) prior to injection (10 µl). High performance liquid chromatography was performed using a Shimadzu LC-10AD liquid chromatograph and a Luna C18(2), 3 µm, 20×2.0 mm column with a mobile phase consisting of water containing 0.1% formic acid (solution A) and acetonitrile (solution B) carried out under isocratic conditions (75% solution A, 25% solution B; flow rate 0.300 ml/min). Mass spectrometric analyses are performed using an API3000 mass spectrometer (Applied Biosystems, Foster City, Calif.) operating in positive ion mode with MRM transition 428.1>98. Brain-to-plasma ratios are calculated for each sample as ng compound/g brain divided by ng compound/ml plasma.

Example 265

Expression of Human Na$_V$1.2 cDNA

Wild-type (WT) cDNA stably transfected in Chinese hamster ovary (CHO) cells is used to record I$_{Na}$. Unless otherwise noted, all reagents are purchased from Sigma-Aldrich (St Louis, Mo., U.S.A.).

Electrophysiology

Whole-cell voltage-clamp recordings are used to measure the biophysical properties of WT. Briefly, the pipette solution consists of (in mM) 110 CsF, 10 NaF, 20 CsCl, 2 EGTA, 10 HEPES, with a pH of 7.35 and osmolarity of 300 mOsmol/kg. The bath (control) solution contains in (mM): 145 NaCl, 4 KCl, 1.8 CaCl$_2$, 1 MgCl$_2$, 10 dextrose, 10 HEPES, with a pH of 7.35 and osmolarity of 310 mOsmol/kg. Cells are allowed to stabilize for 10 min after establishment of the whole-cell configuration before current is measured. Series resistance is compensated 90% to assure that the command potential is reached within microseconds with a voltage error<2 mV. Leak currents are subtracted by using an online P/4 procedure and all currents are low-pass Bessel filtered at 5 kHz and digitized at 50 kHz.

For clarity, representative ramp currents are low pass filtered off-line at 50 Hz. Specific voltage-clamp protocols assessing channel activation, fast inactivation and availability during repetitive stimulation are used. Results are presented as mean±SEM.

Tonic block of peak current is measured using a step to −10 mV (20 ms) from a holding potential of −120 mV (0.2

Hz). Use-dependent block of peak current is measured during pulse number 300 of a pulse train (−10 mV, 5 ms, 300 pulses, 10 Hz or 25 Hz) from a holding potential of −120 mV. Two sequential pulse train stimulations are averaged to obtain mean current traces for each recording condition, which are then used for offline subtraction and analysis.

For use-dependent studies, cells are stimulated with depolarizing pulse trains (−10 mV, 5 ms, 300 pulses, 10 and 25 Hz) from a holding potential of −120 mV. Currents are then normalized to the peak current recorded in response to the first pulse in each frequency train. For tonic block studies, peak current is evaluated in response to a 20 ms depolarization to −10 mV (0.2 Hz). Data analysis is performed using Clampfit 9.2 (Axon Instruments, Union City, Calif., U.S.A), Excel 2002 (Microsoft, Seattle, Wash., U.S.A.), and OriginPro 7.0 (OriginLab, Northampton, Mass., U.S.A) software. Results are presented as mean±SEM.

In Vitro Pharmacology

A stock solution of 10 mM compound of Formula I is prepared in 0.1 M HCl or DMSO. A fresh dilution of the compound of Formula I in the bath solution is prepared every experimental day and the pH is readjusted to 7.35 as necessary. The final DMSO concentration was kept at 0.1% in all solutions. Direct application of the perfusion solution to the clamped cell is achieved using the Perfusion Pencil system (Automate, Berkeley, Calif.). Direct cell perfusion is driven by gravity at a flow rate of 350 μL/min using a 250 micron tip. This system sequesters the clamped cell within a perfusion stream and enables complete solution exchange within 1 second. The clamped cell is perfused continuously starting immediately after establishing the whole-cell configuration. Control currents are measured during control solution perfusion.

Solutions are perfused for three minutes prior to current recordings to allow equilibrium (tonic) drug block. Tonic block of peak currents is measured from this steady-state condition. Three sequential current traces are averaged to obtain a mean current for each recording. The mean current traces are utilized for offline analysis. Use-dependent block of peak current is measured during pulse number 300 of the pulse train, (−10 mV, 5 ms, 300 pulses, 10 Hz) from a holding potential of −120 mV. Two sequential pulse train stimulations are averaged to obtain mean current traces for each recording condition, which are then used for offline subtraction and analysis Where appropriate, concentration inhibition curves are fit with the Hill equation: $I/I_{max}=1/[1+10^{(\log IC_{50}-I)*k}]$, where $IC_{50}$ is the concentration that produces half inhibition and k is the Hill slope factor.

Results

Using the above methods it may be demonstrated that the compounds of the disclosure are selective for inhibiting cardiac Late Ina current without inhibiting peak and low frequency currents of brain isoforms NaV 1.1 and 1.2. The compounds of the disclosure may inhibit the very high frequency firing of $Na_v1.1$ and $Na_v1.2$ or demonstrate voltage dependent block of mutant $Na_v1.1$ and $Na_v1.2$ observed with epilepsy patients. In addition compounds of this disclosure may show activity for inhibition of a panel of $Na_v1.1$ mutant channels associated with the epilepsy and headache (migraine) syndromes GEFS+, SMEI and FHM3 suggesting the ability of the compounds of the disclosure to preferentially block the abnormal increased persistent current carried by these mutant channels. disclosure When tested in the assay disclosed above for $hNa_v$ 1.1 and $hNa_v$ 1.2 sodium channel isoforms, Compound II-73 blocked the $hNa_v$ 1.1 sodium channel peak INa with $IC_{50}$ value of >100 μM at a frequency of 10 Hz and the $hNa_v$ 1.2 sodium channel isoform peak INa with $IC_{50}$ value of >30 μM at the same frequency. At higher frequency of 25 Hz the compound II-73 blocked both $hNa_v$ 1.1 and $hNa_v$ 1.2 isoforms with $IC_{50}$ of 3.4 μM and 10.1 μM respectively. The inhibition of either $hNa_v$ 1.1 and $hNa_v$ 1.2 isoforms or the inhibition of both channels when stimulated at these frequencies support the use of compounds of this disclosure to treat patients with epilepsy.

TABLE 3

Late $I_{Na}$ Assay results

| No. | Late $I_{Na}$* | NAV1.1* UDB-10HZ | NAV1.2* UDB-10HZ | hERG | RHEART MAPD90_ATX* |
|---|---|---|---|---|---|
| II-7 | 34 | 0 | 13 | | −10 |
| II-10 | 43 | −4 | 9 | | |
| II-14 | 47 | 16 | 19 | | |
| II-17 | 59 | | | <10 | |
| II-22 | 30 | 3 | 15 | 16 | |
| II-42 | 34 | 2 | 12 | | −27 |
| II-46 | 25 | 2 | 16 | | |
| II-61 | 41 | 9 | 25 | <10 | −62 |
| II-73 | 42 | 10 | 19 | 18 | −56 |
| II-75 | 68 | 35 | 52 | | |
| II-83 | 31 | −2 | 10 | 21 | |
| II-88 | 41 | −10 | −1 | 26 | −69 |
| II-91 | 54 | −9 | −3 | | |
| II-98 | 39 | −1 | −8 | <10 | −50 |
| II-105 | 45 | −17 | 1 | <10 | |
| II-110 | 35 | −4 | −2 | 26 | |
| II-117 | 37 | −11 | −18 | <10 | |
| II-129 | 33 | 8 | 7 | 17 | −49 |
| II-138 | 47 | 21 | 40 | | |
| II-143 | 65 | 29 | 44 | | |
| II-156 | 48 | | | | −23 |
| III-1 | 33 | −1 | −3 | <10 | −47 |
| V-5 | 49 | −18 | 3 | | |
| VIII-4 | 61 | 5 | 18 | 30 | −25 |
| VIII-6 | 38 | 6 | 20 | <10 | −49 |
| X-8 | 50 | −12 | −14 | <10 | |
| XII-1 | 53 | −1 | −4 | | |
| XII-8 | 36 | 11 | 11 | | −34 |

*% Inhibition at 1 uM

Example 266

Ischemia-Induced ST Segment Elevation in Anesthetized Rabbits

This study was undertaken to determine the anti-ischemic effects of compounds of the present disclosure in an in vivo rabbit model.

Methods:

Female New Zealand rabbits (3.0-4.0 kg) were purchased from Western Oregon Rabbitry. Animals were housed on a 12-h light and dark cycle and received standard laboratory chow and water. All experiments were performed in accordance with the Guide for the Care and Use of Laboratory Animals published by The National Research Council and with the experimental protocol approved by the Institutional Animal Care Committee of Gilead Sciences, Inc.

Rabbits were anesthetized with ketamine (35 mg/kg) and xylazine (5 mg/kg) intramuscular injection (im). A tracheotomy was performed and the trachea was intubated with an endotracheal tube. The animal was ventilated with room air supplemented with oxygen using a pressure control animal ventilator (Kent Scientific Corp., Torrington, Conn.) at a respiratory rate of 40 strokes/min and peak inspiration pressure of 10 $mmH_2O$, which was adjusted to keep blood gases and pH within the physiological range (iSTAT clinic analyzer, Heska Corp.; Waukesha, Wis.). The left femoral artery was cannulated for the measurement of blood pressure (BP). Blood samples were also withdrawn from femoral artery. The right external jugular vein was cannulated for drug/vehicle administration. Needle electrodes were inserted subcutaneously into the limbs for recording of the surface electrocardiogram (ECG). The heart was exposed via an incision in the $4^{th}$ intercostal space ($4^{th}$ and/or $5^{th}$ ribs were cut for a clear surgical vision). The chest was opened and a pericardial cradle was formed using 4 retractors. A coronary artery occluder, comprised of a snare made of 5 cm PE-10 tubing with a 6-0 Prolene polypropylene suture in it, was placed loosely around the left anterior descending artery (LAD) at its origin. Two unipolar electrodes, made with teflon coated silver wire attached to a small patch of filter paper, were attached on the surface of the ischemic and normal regions of the left ventricle to record epicardial electrocardiogram. Reference electrodes were placed in the open incision of the neck. The body temperature of the animal was monitored via a rectal thermometer and maintained at 37-40° C. by adjusting the surface temperature of the surgical table. Regional ischemia (15 min) was induced by ligating the LAD followed by 15 min of reperfusion caused by releasing the ligation. The heart was excised at the end of the experiment and the LAD was re-ligated. The ischemic area was visualized by perfusing the heart with 1% Evans blue in saline and calculated as a percentage of total ventricular weight. Rabbits with ischemic area less than 10% or larger than 25% were excluded from the analysis. Animals were randomly assigned to vehicle and test compound groups. Test compounds was dissolved in 5% NMP, 30% PG, 45% PEG 400 and 20% de-ionized water ($dH_2O$). Test compound was given as an iv bolus at 0.1, 0.2 and 0.4 mg/kg. After 30 min of dosing, the heart was subjected to 15 min of ischemia followed by 15 min of reperfusion.

Results:

The compound of Example II-61 dose-dependently prevented the ischemia-induced ST elevation. The area under curve (AUC) for the ST segment height was reduced (vs. control) by 38% and 88% at 0.28 and 0.52 μM plasma concentration of compound of Example II-61. At the plasma concentration levels studied, compound of Example II-61 had no significant effect on blood pressure (BP), heart rate (HR) and ECG intervals prior to the ischemia. The data suggests the compound of Example II-61 prevents ischemia-induced myocardial electrical dysfunction in a dose-dependent manner.

Similarly, compound of Example II-73 dose-dependently prevented the ischemia-induced ST elevation. The area under curve (AUC) for the ST segment height was reduced (vs. control) by 55% and 93% at 0.25 and 0.5 μM respective plasma concentration of compound of Example II-73. At the plasma concentration levels studied, compound of Example II-73 had no significant effect on blood pressure (BP), heart rate (HR) and ECG intervals prior to the ischemia. The data suggests the compound of Example II-73 prevents ischemia-induced myocardial electrical dysfunction in a dose-dependent manner.

What is claimed is:

1. A compound of formula:

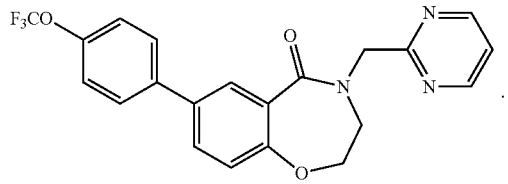 [SMILES: O=C1c2cc(-c3ccc(OC(F)(F)F)cc3)ccc2OCCN1Cc1ncccn1]

2. A pharmaceutical composition comprising a compound of formula:

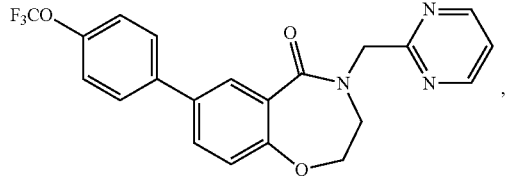 [SMILES: O=C1c2cc(-c3ccc(OC(F)(F)F)cc3)ccc2OCCN1Cc1ncccn1]

and a pharmaceutically acceptable carrier.

* * * * *